US011891426B2

(12) United States Patent
Lobb et al.

(10) Patent No.: US 11,891,426 B2
(45) Date of Patent: Feb. 6, 2024

(54) CD19 VARIANTS

(71) Applicants: Aleta Biotherapeutics Inc., Natick, MA (US); Regents of The University of Minnesota, Minneapolis, MN (US)

(72) Inventors: Roy Lobb, Wellesley, MA (US); Paul Rennert, Holliston, MA (US); Benjamin Hackel, Edina, MN (US); Justin Klesmith, Roseville, MN (US)

(73) Assignees: Aleta Biotherapeutics Inc., Natick, MA (US); Regents of The University of Minnesota, Minneapolis, MN (US)

( * ) Notice: Subject to any disclaimer, the term of this patent is extended or adjusted under 35 U.S.C. 154(b) by 69 days.

(21) Appl. No.: 16/954,002

(22) PCT Filed: Dec. 14, 2018

(86) PCT No.: PCT/US2018/065835
§ 371 (c)(1),
(2) Date: Jun. 15, 2020

(87) PCT Pub. No.: WO2019/118918
PCT Pub. Date: Jun. 20, 2019

(65) Prior Publication Data
US 2021/0079060 A1   Mar. 18, 2021

Related U.S. Application Data

(60) Provisional application No. 62/599,211, filed on Dec. 15, 2017.

(51) Int. Cl.
| | |
|---|---|
| *C07K 14/705* | (2006.01) |
| *C07K 16/32* | (2006.01) |
| *A61K 38/17* | (2006.01) |
| *A61K 39/395* | (2006.01) |
| *A61K 45/06* | (2006.01) |
| *A61K 39/00* | (2006.01) |

(52) U.S. Cl.
CPC .... *C07K 14/70503* (2013.01); *A61K 38/1774* (2013.01); *A61K 39/39558* (2013.01); *A61K 45/06* (2013.01); *C07K 16/32* (2013.01); *A61K 2039/505* (2013.01); *C07K 2317/622* (2013.01); *C07K 2319/33* (2013.01)

(58) Field of Classification Search
CPC .............. C07K 14/70503; C07K 16/32; C07K 2317/622; C07K 2319/33; C07K 14/7051; C07K 2317/34; C07K 2319/03; C07K 16/2803; C07K 16/2863; C07K 16/2887; C07K 2317/22; C07K 2319/00; C07K 16/2851; C07K 14/70596; A61K 38/1774; A61K 39/39558; A61K 45/06; A61K 2039/505; A61K 39/0011; A61K 39/001112; A61K 2039/5156; A61K 2039/5158; A61K 38/00; A61K 39/0008; A61P 35/00
See application file for complete search history.

(56) References Cited

U.S. PATENT DOCUMENTS

| | | | |
|---|---|---|---|
| 5,798,208 A | 8/1998 | Crea | |
| 5,830,650 A | 11/1998 | Crea | |
| 6,180,370 B1 | 1/2001 | Queen et al. | |
| 6,300,065 B1 | 10/2001 | Kieke et al. | |
| 6,423,538 B1 | 7/2002 | Wittrup et al. | |
| 6,649,340 B1 | 11/2003 | Crea | |
| 8,394,411 B2 | 3/2013 | Roberts et al. | |
| 8,470,528 B2 | 6/2013 | Pasqualini et al. | |
| 8,513,390 B2 | 8/2013 | Stagliano et al. | |
| 9,120,853 B2 | 9/2015 | Lowman et al. | |
| 10,508,143 B1* | 12/2019 | Lobb | C07K 14/7051 |
| 10,669,349 B2* | 6/2020 | Lobb | C07K 14/70596 |
| 2003/0036092 A1 | 2/2003 | Iverson et al. | |
| 2003/0100023 A1 | 5/2003 | Iverson et al. | |
| 2004/0072740 A1 | 4/2004 | Iverson et al. | |
| 2005/0136428 A1 | 6/2005 | Crea | |
| 2015/0183875 A1 | 7/2015 | Cobbold et al. | |
| 2021/0130494 A1* | 5/2021 | Lobb | C07K 16/32 |

FOREIGN PATENT DOCUMENTS

| | | |
|---|---|---|
| WO | WO-92/22324 A1 | 12/1992 |
| WO | WO-98/37186 A1 | 8/1998 |
| WO | WO-98/46645 A2 | 10/1998 |
| WO | WO-2008/022152 A2 | 2/2008 |
| WO | WO-2017/031353 A1 | 2/2017 |
| WO | WO-2017/055328 A1 | 4/2017 |
| WO | WO-2017/075533 | 5/2017 |
| WO | WO-2017/075537 A1 | 5/2017 |
| WO | WO-2018/161017 A1 | 9/2018 |
| WO | WO-2019/118918 A1 | 6/2019 |

OTHER PUBLICATIONS

De Oliveira, A CD19/Fc fusion protein for detection of anti-CD19 chimeric antigen receptors, 2013, Journal of Translational Medicine, vol. 11 (Year: 2013).*
Tedder et al (1989) (Isolation of cDNAs encoding the CD19 antigen of human and mouse B lymphocytes. A new member of the immunoglobulin superfamily, J Immunol Jul. 15, 1989, 143 (2) 712-717). (Year: 1989).*
Ackerman, M. et al., Highly avid magnetic bead capture: an efficient selection method for de novo protein engineering utilizing yeast surface display, Biotechnol. Prog, 25:774-783 (2009).
Adler, M. J. et al., Therapeutic antibodies against cancer, Hematol. Oncol. Clin. North Am., 26(3):447-81 (2012).

(Continued)

*Primary Examiner* — Laura B Goddard
*Assistant Examiner* — Sarah A Alsomairy
(74) *Attorney, Agent, or Firm* — Choate, Hall & Stewart LLP; Brenda Herschbach Jarrell; Rolando Medina

(57) ABSTRACT

CD19 variants, methods of identifying CD19 variants, and methods of using such CD19 variants, e.g., for treating cancer, are described.

10 Claims, 60 Drawing Sheets

Specification includes a Sequence Listing.

(56) References Cited

OTHER PUBLICATIONS

Ahmad, S. et al., Probing protein stability and proteolytic resistance by loop scanning: A comprehensive mutational analysis, Protein Science, 21:433-446 (2012).

Boder, E. T. and Wittrup, K. D., Yeast surface display for screening combinatorial polypeptide libraries, Nat Biotechnol, 15(6):553-557 (1997).

Chao, G. et al., Isolating and engineering human antibodies using yeast surface display, Nat. Protoc, 1(2):755-768 (2006).

Cooper, S. et al., Predicting protein structures with a multiplayer online game, Nature, 466(7307):756-760 (2010).

Cull, M. G. et al., Screening for receptor ligands using large libraries of peptides linked to the C terminus of the lac repressor, Proc Natl Acad Sci, 89(5):1865-1869 (1992).

Czerkinsky, C. C. et. al., A solid-phase enzyme-linked immunospot (ELISPOT) assay for enumeration of specific antibody-secreting cells, J Immunol Methods, 65(1-2):109-21 (1983).

Desnoyers, L. R. et al., Tumor-specific activation of an EGFR-targeting probody enhances therapeutic index, Science Translational Medicine, 5(207):207-144 (2013).

Dreher, M. L. et al., Colony assays for antibody fragments expressed in bacteria, J. Immunol. Methods, 139(2):197-205 (1991).

Fuchs, P. et al., Targeting recombinant antibodies to the surface of Escherichia coli: fusion to a peptidoglycan associated lipoprotein, Biotechnology, 9(12):1369-1372 (1991).

Grabherr, R. and Ernst, W., The baculovirus expression system as a tool for generating diversity by viral surface display, Comb. Chem. High Throughput. Screen., 4(2):185-192 (2001).

Guachalla, L. M. et al., Multiple Modes of Action of a Monoclonal Antibody against Multidrug-Resistant Escherichia coli Sequence Type 131-H 30, Antimicrob. Agents Chemother, 61(11):e01428-17 (2017).

Hackel, B. J. et al., Stability and CDR Composition Biases Enrich Binder Functionality Landscapes, J. Mol. Biol., 401(1):84-96 (2010).

Hajitou, A. et al., A hybrid vector for ligand-directed tumor targeting and molecular imaging, Cell, 125(12):358-398 (2006).

Hung, C. et al., Ovarian cancer gene therapy using HPV-16 pseudovirion carrying the HSV-tk gene, PLoS One, 7(7):e40983 (2012).

International Search Report for PCT/US18/65835 (CD19 Variants, filed Dec. 14, 2018), issued by ISA/US, 5 pages (dated May 28, 2019).

Kang, A. S. et al., Linkage of recognition and replication functions by assembling combinatorial antibody Fab libraries along phage surfaces, Proc Natl Acad Sci, 88(10):4363-4366 (1991).

Kines, R. C., HUman papillomavirus capsids preferentially bind and infect tumor cells, Int J Cell, 138(4):901-911 (2016).

Klesmith, J. R. et al., Retargeting CD19 Chimeric Antigen Receptor T Cells via Engineered CD19-Fusion Proteins, Molecular Pharmaceutics, 16:3544-3558 (2019).

Kügler, M. et al., Stabilization and humanization of a single-chain Fv antibody fragment Specific for human lymphocyte antigen CD19 by designed point mutations and CDR-grafting onto a human framework, Protein Engineering, Design & Selection, 22(3):135-147 (2009).

Lei, S. H. et al., Characterization of the Erwinia carotovora pelB Gene and Its Product Pectate Lyasem J. Bacteriol.m 169(9):4379 (1987).

Li, G. N. et al., Monoclonal antibody-related drugs for cancer therapy, Drug Discov. Ther., 7(5):178-84 (2013).

Maude, S. L. et al., CD19-targeted chimeric antigen receptor T-cell therapy for acute lymphoblastic leukemia, Blood, 125(26):4017-4024 (2015).

Rennert, P. Impact fusion proteins redirect CAR19 T cell cytotoxicity to diverse tumor antigens, Aleta Biotherapeutics, pp. 1-29.

Roberts, R. W. and Szostak, J. W., RNA-peptide fusions for the in vitro selection of peptides and proteins, Proc Natl Acad Sci, 94(23):12297-12302 (1997).

Sayers, J. R. et al., 5'-3' exonucleases in phosphorothioate-based oligonucleotide-directed mutagenesis, Nucleic Acids Res., 16:791-802 (1988).

Schaffitzel, C. et al., Ribosome display: an in vitro method for selection and evolution of antibodies from libraries, J. Immunol. Methods, 231(1-2):119-135 (1999).

Scott, A.M. et al, Monoclonal antibodies in cancer therapy, Cancer Immun., 12:14 (2012).

Sliwkowski, M. X. et al., Antibody therapeutics in cancer, Science, 341:1192-1198 (2013).

Soding, J. et al., The HHpred interactive server for protein homology detection and structure prediction, Nucl. Acid Res., 33:244-248 (2005).

Storek, K. M. et al., Monoclonal antibody targeting the ?-barrel assembly machine of Escherichia coli is bactericidal, PNAS, 115(14):3692-3697 (2018).

Svendsen, P. et al., Antibody-Directed Glucocorticoid Targeting to CD163 in M2-type Macrophages Attenuates Fructose-Induced Liver Inflammatory Changes, Mol. Ther.: Methods & Clin. Dev., 4:50-61 (2017).

Tedder, T. F. et al., CD19: a promising B cell target for rheumatoid arthritis, Nat. Rev. Rheumatol., 5(10):572-577 (2009).

Teplyakov, A. et al., Crystal structure of B-cell co-receptor CD19 in complex with antibody B43 reveals an unexpected fold, Proteins, 86(5):495-500 (2018).

Traxlmayr, M. W. and Obinger, C., Directed evolution of proteins for increased stability and expression using yeast display, Archives of Biochemistry and Biophysics, 526:174-180 (2012).

Van Zelm, M. C. et al., Antibody deficiency due to a missense mutation in CD19 demonstrates the importance of the conserved tryptophan 41 in immunoglobulin superfamily domain formation, Human Molecular Genetics, 20(9):1854-1863 (2011).

Wang, K. et al., CD19: a biomarker for B cell development, lymphoma diagnosis and therapy, Exp. Hematol. Oncol., 1(1):36 (2012).

Webb, B. and Sali, A., Comparative Protein Structure Modeling Using Modeller, Curr. Protoc. Bioinforma. 5.6.1-32 (2014).

Wiersma, V. R. et al., C-type lectin-like molecule-1 (CLL1)-targeted Trail augments the tumoricidal activity of granulocytes and potentiates therapeutic antibody-dependent cell-mediated cytotoxicity, Mabs, 7(2):321-30 (2015).

Woldring, D. R. et al., High-Throughput Ligand Discovery Reveals a Sitewise Gradient of Diversity in Broadly Evolved Hydrophilic Fibronectin Domains, PLoS One, 10(9):e0138956 (2015).

Wrenbeck, E. E. et al., Plasmid-based one-pot saturation mutagenesis, Nat. Methods, 13:928-930 (2016).

Written Opinion for PCT/US18/65835 (CD19 Variants, filed Dec. 14, 2018), issued by ISA/US, 12 pages (dated May 28, 2019).

Zhou, C. et al., Pharmacokinetics and pharmacodynamics of DSTA4637A: A novel Thiomab™ antibody antibiotic conjugate against Staphylococcus aureus in mice, mAbs 8(8):1612-1619 (2016).

Zhou, L. J. et al., Structure and domain organization of the CD19 antigen of human, mouse, and guinea pig B lymphocytes. Conservation of the extensive cytoplasmic domain., J Immunol., 147:1424-1432 (1991).

Laurent, E. et al., Directed Evolution of Stabilized Monomeric CD19 for Monovalent CAR Interaction Studies and Monitoring of CAR-T Cell Patients, ACS Synthetic Biology, 10(5):1184-1198 (2021).

* cited by examiner

| Site 1 | Site 2 | Site 3 |
|---|---|---|
| L5 | V7 | V9 |
| A15 | L17 | - |
| N14 | V16 | Q18 |
| Q29 | L31 | W33 |
| R35 | S37 | L39 |
| P41 | L43 | L45 |
| L45 | L47 | L49 |
| L52 | I54 | M56 |
| L59 | I61 | L63 |
| W62 | F64 | F66 |
| I65 | N67 | S69 |
| V68 | M72 | - |
| Y76 | C78 | P80 |
| K86 | W88 | P90 |
| W92 | V94 | V96 |
| L161 | N162 | Q163 |
| Q167 | L169 | M171 |
| S175 | L177 | L179 |
| L193 | W195 | H197 |
| L206 | S208 | E210 |
| L207 | L209 | L211 |
| D219 | W221 | M223 |
| E224 | G226 | L228 |
| T225 | L227 | L229 |
| G238 | Y240 | - |
| L247 | M249 | F251 |
| L253 | I255 | T256 |

FIG. 2

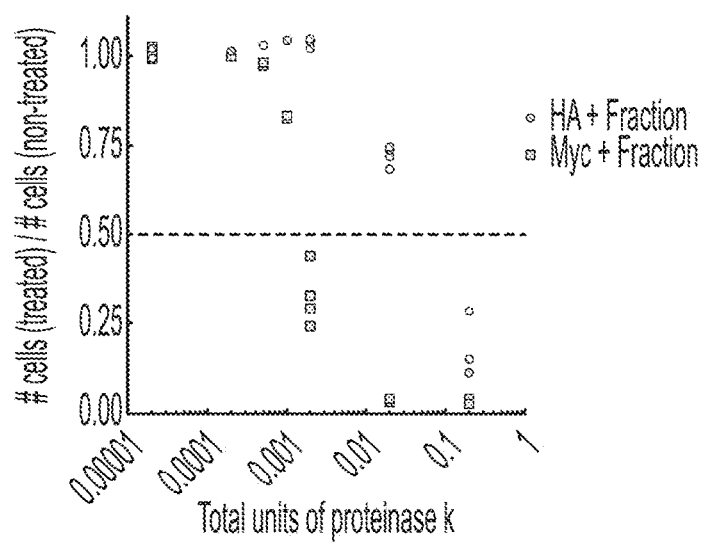 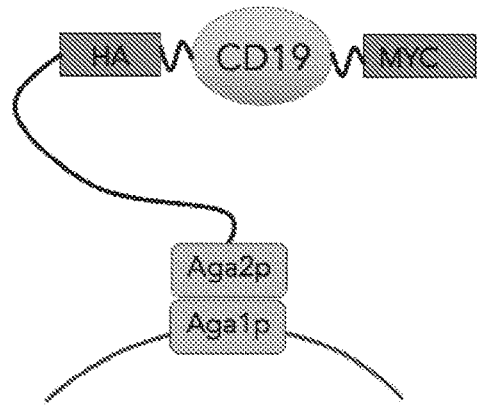
FIG. 5A
FIG. 5B

| Codons | Wild-Type | Design1 | Design2 | Design3 | Design4 | Cons/5th |
|---|---|---|---|---|---|---|
| 14,16,18 | NVQ | TAW | EWP | DWR | TVP | TWP |
| 29,31,33 | QLW | SVW | EVW | | | |
| 45,47,49 | LLL | YLV | AFQ | VFR | VFG | VFV |
| 52,54,56 | LIM | LVI | LVV | GGV | | MVV |
| 59,61,63 | LIL | NVL | GVA | GTV | DLT | DIV |
| 62,64,66 | WFF | SVS | GVR | SRR | GVP | SVR |
| 167,169,171 | QLM | RMV | | | | RLV |
| 219,221,223 | DWM | DWT | EIW | EVT | EID | EWT |
| 224,226,228 | EGL | GRF | GDV | GSV | GSM | GRV |
| 240,243 | YH | WH | WS | | | |
| 247,249,251 | LMF | VTF | RIY | VTY | | TIF |
| 253,255,256 | LIT | LVK | LVI | LVR | LVV | |
| 261,262,264,265 | LWWL | SKTK | KASD | SATP | SATK | LKWL |

| Location | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 225 | 228 | 240 | 243 | 247 | 249 | 251 | 255 | 256 | 261 | 262 | 264 | 265 |
|---|---|---|---|---|---|---|---|---|---|---|---|---|---|---|---|---|---|---|---|---|---|---|---|---|---|---|---|---|---|---|---|---|---|---|---|---|---|
| WT | N | V | Q | Q | L | L | L | L | I | M | L | I | L | W | F | F | Q | L | M | D | W | M | E | G | L | Y | H | L | M | F | I | T | L | W | W | L |
| Design 1 | T | A | W | S | V | Y | L | V | L | V | I | N | V | L | S | V | S | R | M | V | D | W | T | G | R | F | W | H | V | T | F | V | K | S | K | T | K |
| Design 2 | E | W | P | E | V | A | F | Q | L | V | V | G | V | A | G | V | R |   |   |   | E | I | W | G | D | V | W | S | R | I | Y | V | I | K | A | S | D |
| Design 3 |   |   |   |   |   |   |   |   |   |   |   |   |   |   |   |   |   |   |   |   |   |   |   |   |   |   |   |   |   |   |   |   |   |   |   |   |   |
| Design 4 | T | V | P |   |   | V | F | G |   |   |   | D | L | T | G | V | P |   |   |   | E | I | D | G | S | M |   |   | T | I | F |   | V | S | A | T | K |
| Design 5/C | T | W | P |   |   | V | F | V | M | V | V | D | I | V | S | V | R | R | L | V | E | W | T | G | R | V |   |   | T | I | F |   |   | L | K | W | L |

PPF (top)

| | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 225 | 228 | 240 | 243 | 247 | 249 | 251 | 255 | 256 | 261 | 262 | 264 | 265 |
|---|---|---|---|---|---|---|---|---|---|---|---|---|---|---|---|---|---|---|---|---|---|---|---|---|---|---|---|---|---|---|---|---|---|---|---|---|---|
| JRK6 | N | V | Q | Q | L | Y | L | V | M | V | V | L | I | L | S | V | S | Q | L | M | D | W | T | E | G | M | W | Y | L | M | F | V | V | S | K | T | K |
| JRK5 | T | V | P | S | V | L | L | L | L | V | M | D | I | V | S | V | R | R | L | V | D | W | T | G | R | F | Y | H |   |   |   | I | T | S | K | T | K |
| JRK3 | N | V | Q | E | V | V | F | V | L | I | M | L | I | L | G | V | R | Q | L | M | E | W | T | G | R | V | W | S | V | T | F | V |   | S | K | T | K |
| JRK4 | T | W | P | Q | L | V | F | V | L | V | I | L | I | L | G | V | R | R | M | V | E | W | T | G | R | V | W | H | R | I | Y | V | K | S | A | T | K |
| JRK7 | T | V | P | E | V | L | L | L | L | V | I | N | V | L | S | V | R | R | L | V | D | W | T | G | R | V | Y | H | R | I | Y | I | T | S | A | T | K |
| JRK20 | E | W | P | Q | L | V | F | V | L | V | V | N | V | L | S | V | S | R | M | V | D | W | T | G | R | F | Y | H | L | M | F | V | K | S | A | T | K |
| JRK21 | N | V | Q | S | V | V | F | V | L | V | M | D | I | V | S | V | S | R | M | V | D | W | T | G | R | V | Y | H | L | M | F | V | I | S | K | T | P |
| JRK22 | E | W | P | Q | L | V | F | V | L | V | V | N | V | L | S | V | S | R | M | V | D | W | T | G | R | F | Y | H | L | M | F | V | K | S | A | T | K |
| JRK23 | N | V | Q | Q | L | A | F | Q | L | V | V | G | V | A | G | V | R | R | M | V | E | W | T | G | R | I | W | S | R | I | Y | V | I | S | A | T | K |
| JRK24 | T | W | P | E | V | L | L | L | L | V | I | N | V | L | G | V | R | R | L | V | D | W | M | G | S | M | Y | H | V | T | F | V | K | S | A | T | K |

PPF (#2)

| | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 225 | 228 | 240 | 243 | 247 | 249 | 251 | 255 | 256 | 261 | 262 | 264 | 265 |
|---|---|---|---|---|---|---|---|---|---|---|---|---|---|---|---|---|---|---|---|---|---|---|---|---|---|---|---|---|---|---|---|---|---|---|---|---|---|
| JRK8 | E | W | P | Q | L |   |   |   | L | I | M | N | V | L | S | V | G | R | M | V | E | W | T | G | R | V | W | Y | R | I | Y | V | V |   |   |   |   |
| JRK9 | E | W | P | Q | L | A | F | Q | L | V | V | L | I | L | G | V | R | R | L | V | x | x | x | x | x | x | x | x | x | x | x | x | x | x | x | x | x |
| JRK10 | T | V | P | S | V | V | F | V | M | V | M | G | V | A | G | V | R | R | M | V | E | W | T | G | R | F | W | S | R | I | Y | V | K | S | A | T | K |
| JRK12 |   |   |   | Q | L | L | L | L | L | V | V | D | I | V | S | V | R | R | M | V | E | W | T | G | R | V | W | H | L | M | F | V | I |   |   |   |   |
| JRK11 | N | V | Q | S | V | L | L | L | M | V | V | G | V | A | S | V | S | R | L | V | D | W | M |   |   |   | W | H | R | I | Y | V | K | S | A | T | K |
| JRK25 | E | W | P | E | L | L | L | V | L | V | I | L | I | L | G | V | P | R | M | V | x | x | x | x | x | x | x | x | x | x | x | x | x | x | x | x | x |
| JRK26 | T | W | P | E | V | Y | L | V | L | I | I | N | V | L | G | V | S | R | L | V | E | I | W | E | G | L | W | H | L | M | F | V | V |   |   |   |   |
| JRK27 | N | V | Q | S | V | L | L | L | M | V | V | N | V | L | S | V | R | x | L | V | x | x | x | x | x | x | x | x | x | x | x | x | x | x | x | x | x |
| JRK29 | N | V | Q | Q | L | V | F | V | L | V | I | G | V | A | W | F | F | R | M | V | E | I | W | G | R | L | Y | H | V | T | F | V | K |   |   |   |   |

Additional Protease Sort

| | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 225 | 228 | 240 | 243 | 247 | 249 | 251 | 255 | 256 | 261 | 262 | 264 | 265 |
|---|---|---|---|---|---|---|---|---|---|---|---|---|---|---|---|---|---|---|---|---|---|---|---|---|---|---|---|---|---|---|---|---|---|---|---|---|---|
| JRK5 | N | V | Q | E | V | V | F | V | L | I | M | D | I | V | S | V | R | R | L | V | D | W | T | E | G | L | W | S | L | M | F | V | V | S | A | T | K |
| JRK4 | T | V | P | S | V | V | F | Q | L | V | V | D | I | V | S | V | R | R | M | V | D | W | T | E | G | V | W | P | R | I | Y | V | K | S | A | T | K |
| JRK6 | T | W | P | E | V | V | F | V | M | V | V | N | V | L | S | V | S | R | L | V | D | W | T | G | R | V | Y | S | V | T | F | V | A |   |   |   |   |
| JRK2 | N | V | Q | Q | L | L | L | L | L | V | M | D | I | V | S | V | R | R | M | V | D | W | M | G | S | M | W | S | L | M | F | V | I |   |   |   |   |
| JRK3 | N | V | Q | S | V | A | F | Q | L | V | V | L | I | L | G | V | R | R | M | V | E | I | W | G | D | V | W | H | V | T | F | V | I | S | A | T | K |
| JRK1 | N | V | Q | S | V | A | F | Q | L | V | V | L | I | L | G | V | R | R | M | V | E | I | W | G | D | V | W | H | V | T | F | V | I | S | A | T | K |
| Enrich | N | V | Q | Q | L | L | L | V | L | V | I | N | I | L | G | V | S | R | M | V | D | W | T | E | R | F | Y | L | M | F | V | K | S | A | T | K |

FIG. 11

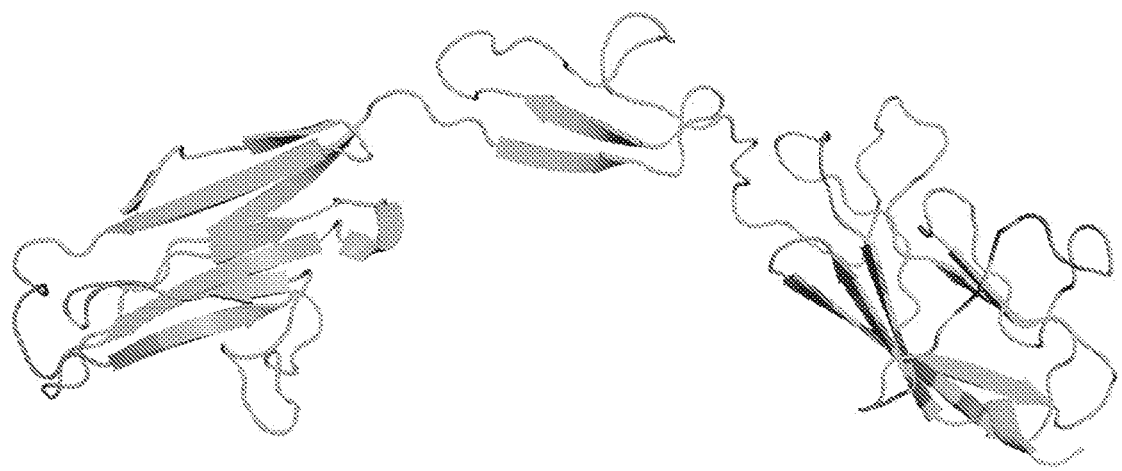

FIG. 12A

| Domain 1 Loop | | | Domain 2 Loop | | | Domain 2 Sheet | | |
|---|---|---|---|---|---|---|---|---|
| Site | WT | Div. 1 | Div. 2 | Site | WT | Div. 1 | Div. 2 | |
| 23 | T | SANTDYPH | Full | 186 | D | SANTDYPH | Full | 194 | S | SANTDYPH | 16 (-CGRW) |
| 24 | S | SANTDYPH | Full | 187 | S | SANTDYPH | Full | 196 | T | TISNAVDG | 16 (-CGRW) |
| 25 | D | SANTDYPH | Full | 188 | V | VILMATSF | Full | 198 | V | VILMATSF | 16 (-CGRW) |
| 26 | G | GAST | GASTNDIV | 189 | S | SANTDYPH | Full | 204 | K | KNRSEDG | 16 (-CGRW) |
| 27 | P | PSA | PSAYNTDH | 190 | R | RKTGEAMV | Full | 206 | L | VILMATSF | 16 (-CGRW) |
| 28 | T | SANTDYPH | Full | 191 | G | GAST | GASTNDIV | 208 | S | SANTDYPH | 16 (-CGRW) |
| 29 | Q | QEKDNH | Full | 192 | P | PSA | PSAYNTDH | 239 | K | KTRNSIM | 16 (-CGRW) |
| 30 | Q | QEKDNH | Full | | | | | 241 | Y | YHFLDINV | 16 (-CGRW) |
| | | | | 209 | L | LIVSAT | Full | 243 | H | HYNILFDV | 16 (-CGRW) |
| 56 | M | VILMATSF | Full | 210 | E | QEKDNH | Full | 248 | T | SANTDYPH | 16 (-CGRW) |
| 57 | R | GAST | GASTNDIV | 224 | E | EGAQRPVL | Full | 250 | S | SANTDYPH | 16 (-CGRW) |
| 58 | P | PSA | PSAYNTDH | 225 | T | SANTDYPH | Full | 252 | H | SANTDYPH | 16 (-CGRW) |
| 59 | L | VILMATSF | Full | | | | | 254 | E | EQ only | EQ |
| 60 | A | GASNTDIV | Full | 243 | H | SANTDYPH | Full | | | | |
| | | | | 244 | R | RHNSDG | Full | | | | |
| 82 | P | PLSFAVIT | Full | 245 | G | GASTND | GASTNDIV | | | | |
| 83 | P | PSA | PSAYNTDH | 246 | N | SANTDYPH | Full | | | | |
| 84 | S | SANTDYPH | Full | 247 | L | LWSTMR | Full | | | | |
| 85 | E | QEKDNH | Full | | | | | | | | |
| 86 | K | QEKDNH | Full | | | | | | | | |

| Location | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 226 | 228 | 240 | 246 | 247 | 249 | 251 | 255 | 256 | 261 | 262 | 264 | 265 |
|---|---|---|---|---|---|---|---|---|---|---|---|---|---|---|---|---|---|---|---|---|---|---|---|---|---|---|---|---|---|---|---|---|---|---|---|---|---|
| WT | N | V | Q | Q | L | L | L | L | L | I | M | L | I | L | W | F | F | Q | L | M | D | W | M | E | G | L | Y | H | L | M | F | I | T | L | W | W | L |
| Design 1 | T | A | W | S | V | Y | L | V | L | V | I | N | V | L | S | V | S | R | M | V | D | W | T | G | R | F | W | H | V | T | F | V | K | S | K | T | K |
| Design 2 | E | W | P | E | V | A | F | Q | L | V | V | G | V | A | G | V | R |  |  |  | E | I | W | G | D | V | W | S | R | I | Y | V | I | K | A | S | D |
| Design 3 |  |  |  |  |  |  |  |  |  |  |  |  |  |  |  |  |  |  |  |  |  |  |  |  |  |  |  |  |  |  |  |  |  |  |  |  |  |
| Design 4 | T | V | P |  |  | V | F | G |  |  |  | D | L | T | G | V | P |  |  |  | E | I | D | G | S | M |  |  |  |  |  | V | V | S | A | T | K |
| Design 5C | T | W | P |  |  | V | F | V | M | V | V | D | I | V | S | V | R | R | L | V | E | W | T | G | R | V |  |  | T | I | F |  |  | L | K | W | L |

| | 14 | 16 | 18 | 29 | 31 | 45 | 47 | 49 | 52 | 54 | 56 | 59 | 61 | 63 | 62 | 64 | 66 | 167 | 169 | 171 | 219 | 221 | 223 | 224 | 226 | 228 | 240 | 246 | 247 | 249 | 251 | 255 | 256 | 261 | 262 | 264 | 265 | |
|---|---|---|---|---|---|---|---|---|---|---|---|---|---|---|---|---|---|---|---|---|---|---|---|---|---|---|---|---|---|---|---|---|---|---|---|---|---|---|
| scFv1 | N | V | Q | E | V | L | L | L | M | V | V | D | L | T | W | F | F | R | L | V | E | W | M | G | R | F | W | S | L | M | F | V | K |   |   |   |   | |
| scFv2 | T | V | Q | Q | L | V | F | G | L | I | M | L | I | L | G | V | P | R | M | V | E | W | T | G | R | F | W | H | L | M | F | V | V |   |   |   |   | |
| scFv3 | T | A | W | E | V | V | F | G | L | I | M | D | I | V | S | V | R | Q | L | M | E | I | W | E | G | L | x | x | x | x | x | x | x | x | x | x | x | S166I |
| JRK1 | T | A | W | S | V | Y | L | V | M | V | M | D | I | V | S | V | S | Q | L | M | D | W | T | G | R | V | W | H | R | I | Y | V | K |   |   |   |   | |
| JRK3 | N | V | Q | Q | L | L | L | L |   |   |   | N | V | L | S | V | R | R | M | V | E | I | W | E | G | L | W | H | L | M | F | V | I | K | A | S | D | G48V |
| JRK4 | N | V | Q | Q | L | Y | L | V | L | G | I | L | I | L | S | V | S | R | L | V | E | I | D | E | G | L | W | Y |   |   |   | V | T | F | V | I |   | |
| JRK6 | T | A | W | E | V | L | L | L | L | V | V | L | I | L | G | V | P | R | M | V | D | W | M | G | V | R | F | W | H | L | M | F | V | T | K | A | S | D |
| JRK8 | T | W | P | Q | L | V | F | G | L | V | I |   | D | I | F | S | V | R | R | L | V | D | W | T | G | R | V | W | S |   |   |   |   |   |   |   |   | |
| JRK5 | T | A | W | Q | L | Y | L | V | M | V | V | N | V | L | S | V | S | R | M | V | D | W | M | E | G | V | W | H |   |   |   | I | T |   |   |   |   | |
| JRK2 | T | A | W | Q | L | L | L | L | M | V | M | G | V | A | S | V | R | M | V | D | W | M | G | S | I | Y | H | L | M | F | V | V | K | A | S | D |   | |
| JRK7 |   |   |   | Q | L | L | L | L | L | V | I | N | V | L | G | V | P | R | L | V | x | x | x | x | x | x | x | x | x | x | x | x | x | x | x | x | x | |
| Enrich | T | A | W | Q | L | L | L | L | M | V | M | N | I | L | S | V | S | R | M | V | D | W | M | E | G | L | W | Y | L | M | F | V | K |   |   |   |   | |

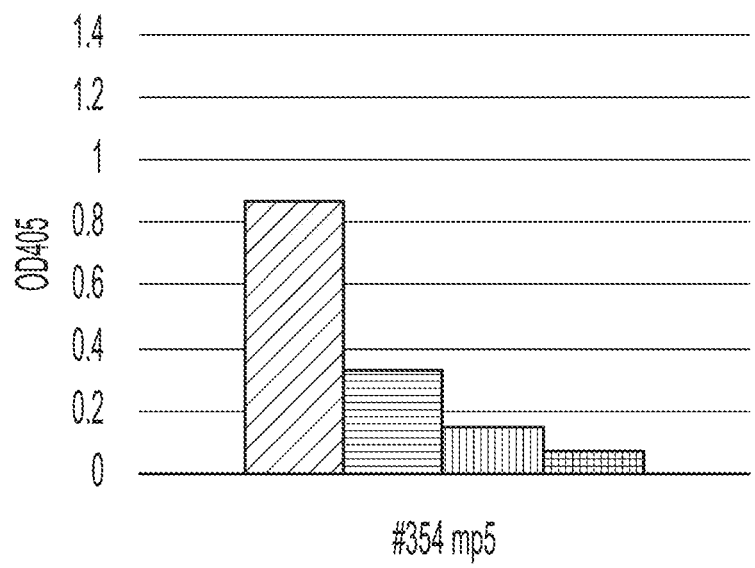
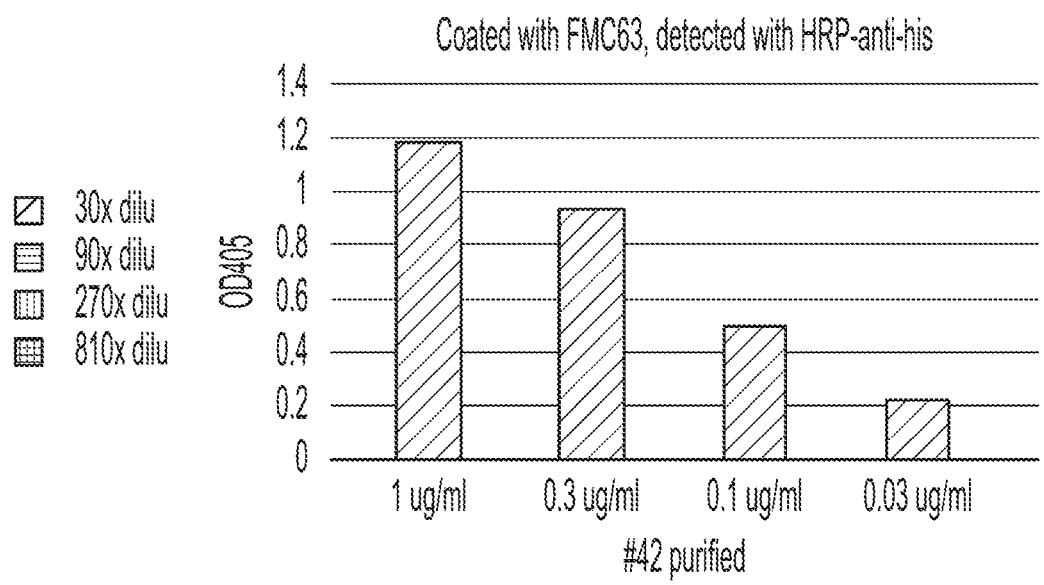
FIG. 26

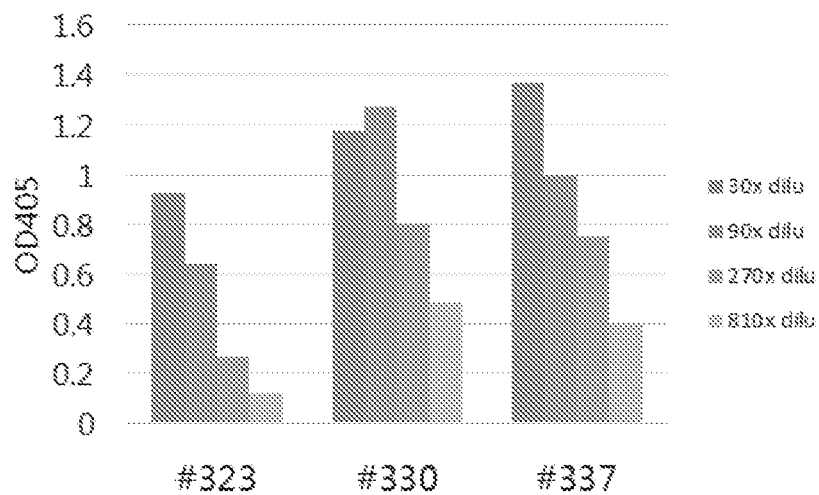
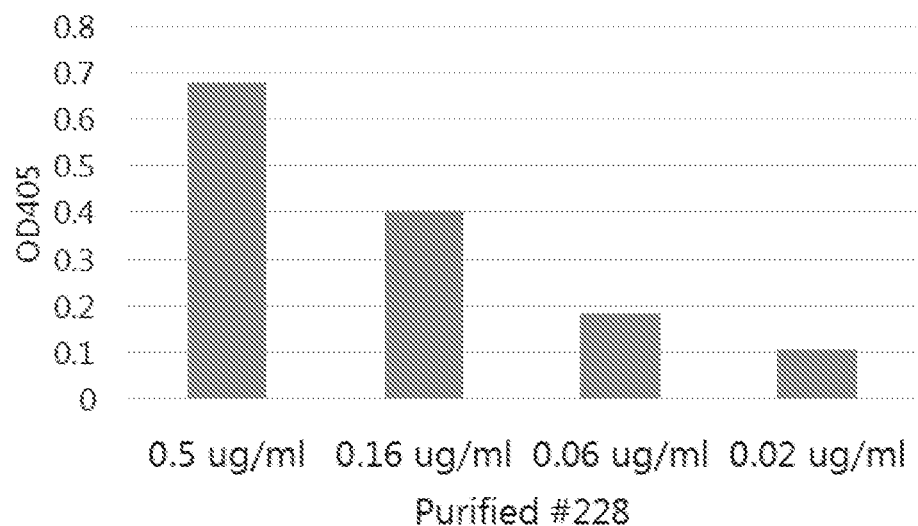
FIG. 39

|  | ug/ml | Average % Binding | STD | Average MFI | STD |
|---|---|---|---|---|---|
| 186 purified | 7.5 | 61.2% | 4.4% | 3887.8 | 46.4 |
|  | 2.5 | 55.9% | 3.8% | 3741.9 | 122.7 |
|  | 0.83 | 39.9% | 1.0% | 3514.2 | 155.8 |
|  | 0.28 | 20.6% | 0.7% | 3266.0 | 55.8 |
|  | 0.09 | 8.8% | 0.8% | 2997.2 | 7.9 |
|  | 0.03 | 4.0% | 0.1% | 3812.8 | 561.0 |
|  | 0.01 | 2.5% | 0.2% | 9689.7 |  |
|  | 0.003 | 2.0% | 0.0% | 3956.8 |  |
| 330 (5/8/18) | 9 | 97.1% | 0.2% | 12170.5 | 647.8 |
|  | 3 | 96.6% | 0.1% | 11354.2 | 234.3 |
|  | 1.00 | 96.4% | 0.2% | 10827.7 | 164.2 |
|  | 0.33 | 93.7% | 0.1% | 7995.3 | 149.7 |
|  | 0.11 | 80.9% | 1.3% | 4660.6 | 115.9 |
|  | 0.04 | 41.4% | 6.9% | 3345.2 | 204.8 |
|  | 0.01 | 10.1% | 2.3% | 3148.4 | 19.8 |
|  | 0.004 | 3.6% | 0.2% | 3007.9 | 307.1 |
| 357 (8/13/18) | 13 | 92.1% | 0.2% | 7212.0 | 0.3 |
|  | 4.333333 | 92.2% | 0.1% | 7030.3 | 27.1 |
|  | 1.44 | 91.5% | 0.1% | 6945.7 | 222.7 |
|  | 0.48 | 88.6% | 3.5% | 6558.2 | 704.2 |
|  | 0.16 | 77.9% | 8.4% | 5444.9 | 123.8 |
|  | 0.05 | 50.1% | 5.0% | 3757.7 | 128.4 |
|  | 0.02 | 14.0% | 4.6% | 3071.8 | 110.2 |
|  | 0.006 | 4.4% | 0.5% | 3287.7 |  |
|  | 0 | 1.3% |  | 2998.0 |  |

FIG. 46A

| | ng/ml | Average RLU | STD | Average % | STD |
|---|---|---|---|---|---|
| | 1200 | 66093.2 | 7419.3 | 83.8 | 1.8 |
| | 400.0 | 44660.4 | 14166.8 | 89.1 | 3.5 |
| | 133.3 | 54256.7 | 46775.2 | 86.7 | 11.5 |
| 330 | 44.4 | 129207.6 | 57157.7 | 68.3 | 14.0 |
| (5/8/18) | 14.8 | 324746.0 | 7448.7 | 20.4 | 1.8 |
| | 4.9 | 370792.0 | 67899.2 | 9.1 | 16.6 |
| | 1.65 | 427140.5 | 9129.5 | -4.7 | 2.2 |
| | 0.55 | 377745.5 | 98995.7 | 7.4 | 24.3 |
| | 0.18 | 398022.0 | | 2.5 | |
| | | | | | |
| | 2300 | 77736.9 | 28956.6 | 81.0 | 7.1 |
| | 766.7 | 72935.6 | 66400.6 | 82.1 | 16.3 |
| | 255.6 | 33640.1 | 6795.2 | 91.8 | 1.7 |
| 357 | 85.2 | 57505.2 | 10690.1 | 85.9 | 2.6 |
| (8/13/18) | 28.4 | 76753.2 | 20010.0 | 81.2 | 4.9 |
| | 9.5 | 192162.8 | 119407.6 | 52.9 | 29.3 |
| | 3.16 | 320800.7 | 15553.9 | 21.4 | 3.8 |
| | 1.05 | 306601.3 | 44678.0 | 24.9 | 10.9 |
| | 0.35 | 354933.0 | 75680.2 | 13.0 | 18.5 |
| | | | | | |
| | 1000 | 136864.0 | | 66.5 | |
| | 333.3 | 122285.0 | | 70.0 | |
| | 111.1 | 352193.0 | | 13.7 | |
| | 37.0 | 193153.0 | | 52.7 | |
| 186 | 12.3 | 323003.0 | | 20.9 | |
| | 4.1 | 308092.0 | | 24.5 | |
| | 1.37 | 340880.0 | | 16.5 | |
| | 0.46 | 382458.0 | | 6.3 | |
| | 0.15 | 354552.0 | | 13.1 | |
| | NB | 408097.5 | 41427.3 | 0.0 | 10.2 |
| | U937 | 730155.3 | 75416.6 | | |

FIG. 47A

CD19 VARIANTS

CROSS REFERENCE TO RELATED APPLICATIONS

This application claims priority to U.S. Provisional Patent Application No. 62/599,211 filed Dec. 15, 2017 the entire contents of which is hereby incorporated by reference.

BACKGROUND

B-lymphocyte antigen CD19, also known as CD19 (Cluster of Differentiation 19), is a protein that in humans is encoded by the CD19 gene. CD19 is the target of various immunotherapies, including CD19 CAR T-cells.

SUMMARY

The present disclosure provides methods of identifying CD19 variants having particular functional attributes, such as ability to bind anti-CD19 antibodies and/or improved stability. Accordingly, in some aspects, the disclosure provides methods of identifying a stable CD19 variant, the method comprising: a) obtaining or providing a plurality of CD19 polypeptides, each CD19 polypeptide having one or more amino acid substitutions of the amino acid sequence of SEQ ID NO:2; b) determining if a CD19 polypeptide of the plurality is bound by an anti-CD19 antibody or fragment thereof; c) determining if a CD19 polypeptide of the plurality is more resistant to protease cleavage relative to a polypeptide comprising the amino acid sequence of SEQ ID NO:2; and/or d) determining if a CD19 polypeptide of the plurality is more thermally stable relative to a polypeptide comprising the amino acid sequence of SEQ ID NO:2; wherein a CD19 polypeptide is a stable CD19 variant if the polypeptide (i) is bound by an anti-CD19 antibody or fragment thereof, (ii) is more resistant to protease cleavage relative to the polypeptide comprising the amino acid sequence of SEQ ID NO:2, and/or (iii) is more thermally stable relative to the polypeptide comprising the amino acid sequence of SEQ ID NO:2. In some embodiments, the anti-CD19 antibody is FMC63 or 4G7.

In some embodiments, the plurality of CD19 polypeptides comprise one or more amino acid substitutions at positions 2, 3, 7, 8, 9, 10, 11, 12, 13, 14, 15, 16, 18, 20, 22, 25, 28, 29, 30, 31, 32, 33, 34, 38, 39, 45, 47, 49, 52, 53, 54, 55, 56, 57, 58, 59, 61, 62, 63, 64, 66, 68, 70, 72, 84, 90, 93, 94, 99, 100, 105, 108, 111, 113, 114, 115, 122, 123, 124, 125, 127, 130, 131, 132, 135, 138, 139, 140, 141, 142, 143, 144, 145, 146, 148, 149, 154, 167, 169, 171, 185, 189, 193, 194, 196, 198, 202, 204, 206, 207, 209, 211, 212, 213, 215, 216, 217, 219, 220, 221, 222, 223, 224, 225, 226, 228, 229, 230, 232, 235, 240, 243, 247, 249, 250, 251, 252, 253, 255, 256, 257, 258, 259, 260, 261, 262, 264, 265, 269, or 271 of SEQ ID NO:2. In some embodiments, the plurality of CD19 polypeptides comprise amino acid substitutions at one or more of the following sets of amino acid positions of SEQ ID NO:2: 5/7/9; 14/16/18; 29/31; 29/31/33; 35/37/39; 45/47/49; 52/54/56; 59/61/63; 62/64/66; 76/78/80; 86/88/90; 167/169/171; 175/177/179; 193/195/197; 206/208/210; 207/209/211; 219/221/223; 240/243; 224/226/228; 247/249/251; 253/255/256; 255/256; or 261/262/264/265.

In other aspects, the disclosure provides CD19 variants, fusion proteins comprising CD19 variants, nucleic acids encoding CD19 variants (or fusion proteins), and cellular therapeutics encoding such CD19 variants or fusion proteins. Such compositions are useful for treatment of cancer and/or for initiating or modulating immune responses.

In some embodiments, a CD19 variant has a measured level of stability that is at least 20%, 40%, 60%, 80%, 100%, 120%, 140%, 160%, 180%, 200%, 250%, 300%, 400%, or 500%, greater than that of a polypeptide comprising the amino acid sequence of SEQ ID NO:2. In some embodiments, a CD19 variant is more resistant to protease cleavage relative to a polypeptide comprising the amino acid sequence of SEQ ID NO:2. In some embodiments, a CD19 variant is more thermally stable relative to a polypeptide comprising the amino acid sequence of SEQ ID NO:2.

In some embodiments, the CD19 variant comprises one or more amino acid substitutions of SEQ ID NO:2 listed in Table 1A, Table 1B, Table 2A, Table 2B, Table 3, Table 6, FIG. 8B, FIG. 11, FIG. 12B, FIG. 14A, FIG. 14B, FIG. 14C, FIG. 14D, or FIG. 15B.

In some embodiments, the CD19 variant comprises amino acid substitutions at one or more of the following sets of amino acid positions of SEQ ID NO:2: 5/7/9; 14/16/18; 29/31; 29/31/33; 35/37/39; 45/47/49; 52/54/56; 59/61/63; 62/64/66; 76/78/80; 86/88/90; 167/169/171; 175/177/179; 193/195/197; 206/208/210; 207/209/211; 219/221/223; 240/243; 224/226/228; 247/249/251; 253/255/256; 255/256; or 261/262/264/265. In some embodiments, the amino acid substitutions comprise substitutions shown in Table 1B, Table 2B, Table 3, Table 6, FIG. 8B, FIG. 11, FIG. 14A, FIG. 14B, FIG. 14C, FIG. 14D, or FIG. 15B.

In some embodiments, the CD19 variant binds an anti-CD19 antibody. In some embodiments, the CD19 variant binds a tumor antigen. In some embodiments, a tumor antigen is MART-1/MelanA (MART-I), gp100 (Pmel 17), tyrosinase, TRP-1, TRP-2, MAGE-1, MAGE-3, BAGE, GAGE-1, GAGE-2, p15, CEA, p53, Ras, HER-2/neu, BCR-ABL, E2A-PRL, H4-RET, IGH-IGK, MYL-RAR, Epstein Barr virus antigens EBVA, human papillomavirus (HPV) antigen E6 or E7, TSP-180, MAGE-4, MAGE-5, MAGE-6, RAGE, NY-ESO, erbB, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, MUC16, IL13Rα2, FRα, VEGFR2, Lewis Y, FAP, EphA2, CEACAM5, EGFR, CA6, CA9, GPNMB, EGP1, FOLR1, endothelial receptor, STEAP1, SLC44A4, Nectin-4, AGS-16, guanalyl cyclase C, MUC-1, CFC1B, integrin alpha 3 chain (of a3b1, a laminin receptor chain), TPS, CD19, CD20, CD22, CD30, CD72, CD180, CD171 (L1CAM), CD123, CD133, CD138, CD37, CD70, CD79a, CD79b, CD56, CD74, CD166, CD71, CLL-1/CLEC12A, ROR1, Glypican 3 (GPC3), Mesothelin, CD33/IL3Ra, c-Met, PSCA, PSMA, Glycolipid F77, EGFRvIII, BCMA, GD-2, MY-ESO-1, or MAGE A3.

In some embodiments the present disclosure provides a fusion protein comprising (a) an antibody or scaffold polypeptide, or antigen binding fragment thereof, that binds an antigen, and (b) a CD19 variant. In some embodiments, the antigen is an antigen associated with an autoimmune disorder. In some embodiments, the antigen is an infectious agent antigen. In some embodiments, the antibody or scaffold polypeptide, or antigen binding fragment thereof, comprises an scFv or VHH or Type III fibronectin domain. In some embodiments, the CD19 variant is fused to the C-terminus or N-terminus of a light chain of an antibody of fragment. In some embodiments, the CD19 variant is fused to the C-terminus or N-terminus of a heavy chain of an antibody of fragment. In some embodiments, the CD19 variant is fused to the C-terminus of a light chain of an antibody of fragment.

In some embodiments, the VHH comprises the amino acid sequence of any one of SEQ ID Nos:203-225, or a fragment thereof. In some embodiments, the VHH comprises a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHHGAS depicted in each of SEQ ID Nos:203-225. In some embodiments, the VHH comprises a portion (e.g., a CLL-1 binding portion) of the amino acid sequence of any one of SEQ ID Nos:203-225, wherein the portion lacks all of the C-terminal amino acids TSGPGGQGAEQKLISEEDLGAHHHHHHGAS depicted in each of SEQ ID Nos:203-225. In some embodiments, the VHH comprises a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHHGAS depicted in each of SEQ ID Nos:203-225, and wherein the portion lacks one or more (e.g., 1, 2, 3, 4, 5, or more), additional amino acids. In some embodiments, the VHH comprises a portion (e.g., a CLL-1 binding portion) of the amino acid sequence of any one of SEQ ID Nos:203-225, wherein the portion lacks all of the C-terminal amino acids TSGPGGQGAEQKLISEEDLGAHHHHHHGAS depicted in each of SEQ ID Nos:203-225, and wherein the portion lacks one or more (e.g., 1, 2, 3, 4, 5, or more), additional amino acids. In some embodiments, the VHH comprises an amino acid sequence that is at least 85%, 90%, 91%, 92%, 93%, 94%, 95%, 96%, 97%, 98%, 99%, or 100% identical to a portion of the amino acid sequence of any one of SEQ ID Nos:203-225, wherein the portion lacks one or more of the C-terminal amino acids TSGPGGQGAEQKLISEEDLGAHHHHHHGAS depicted in each of SEQ ID Nos:203-225. In some embodiments, the VHH comprises an amino acid sequence that is at least 85%, 90%, 91%, 92%, 93%, 94%, 95%, 96%, 97%, 98%, 99%, or 100% identical to a portion of the amino acid sequence of any one of SEQ ID Nos:203-225, wherein the portion lacks all of the C-terminal amino acids TSGPGGQGAEQKLISEEDLGAHHHHHHGAS depicted in each of SEQ ID Nos:203-225. In some embodiments, the VHH comprises an amino acid sequence that is at least 85%, 90%, 91%, 92%, 93%, 94%, 95%, 96%, 97%, 98%, 99%, or 100% identical to a portion of the amino acid sequence of any one of SEQ ID Nos:203-225, wherein the portion lacks one or more of the C-terminal amino acids TSGPGGQGAEQKLISEEDLGAHHHHHHGAS depicted in each of SEQ ID Nos:203-225, and wherein the portion lacks one or more (e.g., 1, 2, 3, 4, 5, or more), additional amino acids. In some embodiments, the VHH comprises an amino acid sequence that is at least 85%, 90%, 91%, 92%, 93%, 94%, 95%, 96%, 97%, 98%, 99%, or 100% identical to a portion of the amino acid sequence of any one of SEQ ID Nos:203-225, wherein the portion lacks all of the C-terminal amino acids TSGPGGQ-GAEQKLISEEDLGAHHHHHHGAS depicted in each of SEQ ID Nos:203-225, and wherein the portion lacks one or more (e.g., 1, 2, 3, 4, 5, or more), additional amino acids.

In some embodiments, the VHH comprises at least one CDR (e.g., CDR1, CDR2, and/or CDR3) depicted in any one of SEQ ID Nos:203-225. In some embodiments, the VHH comprises at least one CDR that is at least 85%, 90%, 91%, 92%, 93%, 94%, 95%, 96%, 97%, 98%, 99%, or 100% identical to a CDR (e.g., CDR1, CDR2, and/or CDR3) depicted in any one of SEQ ID Nos:203-225. In some embodiments, the VHH comprises CDR1, CDR2, and/or CDR3 of any one of Groups 1-13 depicted in Table 5A and/or Table 5B. In some embodiments, the VHH comprises (i) CDR1 and CDR2; (ii) CDR2 and CDR3; (iii) CDR1 and CDR3; or (iv) CDR1, CDR2, and CDR3 of any one of Groups 1-13 depicted in Table 5A and/or Table 5B. In some embodiments, the VHH comprises CDR1, CDR2, and CDR3 of Group 1; CDR1, CDR2, and CDR3 of Group 2; CDR1, CDR2, and CDR3 of Group 3; CDR1, CDR2, and CDR3 of Group 4; CDR1, CDR2, and CDR3 of Group 5; CDR1, CDR2, and CDR3 of Group 6; CDR1, CDR2, and CDR3 of Group 7; CDR1, CDR2, and CDR3 of Group 8; CDR1, CDR2, and CDR3 of Group 9; CDR1, CDR2, and CDR3 of Group 10; or CDR1, CDR2, and CDR3 of Group 13, depicted in Table 5A and/or Table 5B.

In some embodiments, the present disclosure provides a nucleic acid encoding a fusion protein described herein. In some embodiments, the present disclosure provides a nucleic acid encoding a fusion protein comprising (a) an antibody or scaffold polypeptide, or antigen binding fragment thereof, that binds an antigen, and (b) a CD19 variant. In some embodiments, the present disclosure provides a cell comprising a nucleic acid encoding a fusion protein comprising (a) an antibody or scaffold polypeptide, or antigen binding fragment thereof, that binds an antigen, and (b) a CD19 variant. In some embodiments, the present disclosure provides an adenoviral vector, adeno-associated viral (AAV) vector, or a chimeric AAV/phage (AAVP) vector, comprising a nucleic acid encoding a fusion protein comprising (a) an antibody or scaffold polypeptide, or antigen binding fragment thereof, that binds an antigen, and (b) a CD19 variant. In some embodiments, the present disclosure provides an oncolytic viral vector comprising a nucleic acid encoding a fusion protein comprising (a) an antibody or scaffold polypeptide, or antigen binding fragment thereof, that binds an antigen, and (b) a CD19 variant. In some embodiments, an oncolytic viral vector is an autonomous parvoviral vector, myxoma viral vector, paramyxoviral vector, reoviral vector, picornaviral vector, vaccinia viral vector, adenoviral vector, herpes simplex viral vector, or a vesicular stomatitis viral vector.

In some embodiments, the present disclosure provides a cell comprising a vector, comprising a nucleic acid encoding a fusion protein comprising (a) an antibody or scaffold polypeptide, or antigen binding fragment thereof, that binds an antigen, and (b) a CD19 variant. In some embodiments this cell is a tumor cells.

In some embodiments, the present disclosure provides a lentiviral or retroviral vector comprising a nucleic acid encoding a fusion protein comprising (a) an antibody or scaffold polypeptide, or antigen binding fragment thereof, that binds an antigen, and (b) a CD19 variant. In some embodiments, the lentiviral or retroviral vector further comprises a nucleic acid encoding a CAR.

In some embodiments, the present disclosure provides a cell comprising a lentiviral or retroviral vector comprising a nucleic acid encoding a fusion protein comprising (a) an antibody or scaffold polypeptide, or antigen binding fragment thereof, that binds an antigen, and (b) a CD19 variant. In some embodiments the cell is a T cell.

In some embodiments, the present disclosure provides a method of treating a subject having a tumor, comprising administering to the subject a fusion protein comprising (a) an antibody or scaffold polypeptide, or antigen binding fragment thereof, that binds an antigen, and (b) a CD19 variant, a cell comprising a vector encoding a fusion protein comprising (a) an antibody or scaffold polypeptide, or antigen binding fragment thereof, that binds an antigen, and (b) a CD19 variant, or a vector comprising a nucleic acid encoding a fusion protein comprising (a) an antibody or scaffold polypeptide, or antigen binding fragment thereof, that binds an antigen, and (b) a CD19 variant. In some embodiments, the method of treatment further comprises administering an antibody, an antibody drug conjugate, or a CAR-T cell to the subject, wherein the antibody, the antibody drug conjugate, or the CAR-T cell binds the CD19 variant.

In some embodiments, the present disclosure provides a method of identifying a stable CD19 variant, the method comprising: a) obtaining a plurality of CD19 polypeptides, each CD19 polypeptide having one or more amino acid substitutions of the amino acid sequence of SEQ ID NO:2; b) determining if a CD19 polypeptide of the plurality is bound by an anti-CD19 antibody or fragment thereof; c) determining if a CD19 polypeptide of the plurality is more resistant to protease cleavage relative to a polypeptide comprising the amino acid sequence of SEQ ID NO:2; and/or d) determining if a CD19 polypeptide of the plurality is more thermally stable relative to a polypeptide comprising the amino acid sequence of SEQ ID NO:2; wherein a CD19 polypeptide is a stable CD19 variant if the polypeptide (i) is bound by the anti-CD19 antibody or fragment thereof, (ii) is more resistant to protease cleavage relative to the polypeptide comprising the amino acid sequence of SEQ ID NO:2, and/or (iii) is more thermally stable relative to the polypeptide comprising the amino acid sequence of SEQ ID NO:2. In some embodiments the anti-CD19 antibody is FMC63 or 4G7. In some embodiments, the plurality of CD19 polypeptides comprise one or more amino acid substitutions at positions 2, 3, 7, 8, 9, 10, 11, 12, 13, 14, 15, 16, 18, 20, 22, 25, 28, 29, 30, 31, 32, 33, 34, 38, 39, 45, 47, 49, 52, 53, 54, 55, 56, 57, 58, 59, 61, 62, 63, 64, 66, 68, 70, 72, 84, 90, 93, 94, 99, 100, 105, 108, 111, 113, 114, 115, 122, 123, 124, 125, 127, 130, 131, 132, 135, 138, 139, 140, 141, 142, 143, 144, 145, 146, 148, 149, 154, 167, 169, 171, 185, 189, 193, 194, 196, 198, 202, 204, 206, 207, 209, 211, 212, 213, 215, 216, 217, 219, 220, 221, 222, 223, 224, 225, 226, 228, 229, 230, 232, 235, 240, 243, 247, 249, 250, 251, 252, 253, 255, 256, 257, 258, 259, 260, 261, 262, 264, 265, 269, or 271 of SEQ ID NO:2. In some embodiments, the plurality of CD19 polypeptides comprise amino acid substitutions at one or more of the following sets of amino acid positions of SEQ ID NO:2: 5/7/9; 14/16/18; 29/31; 29/31/33; 35/37/39; 45/47/49; 52/54/56; 59/61/63; 62/64/66; 76/78/80; 86/88/90; 167/169/171; 175/177/179; 193/195/197; 206/208/210; 207/209/211; 219/221/223; 240/243; 224/226/228; 247/249/251; 253/255/256; 255/256; or 261/262/264/265.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The figures of the drawings are for illustration purposes only, not for limitation.

FIG. 2 is a table showing triplet library design. Two or three amino acids were simultaneously diversified in 27 different combinations. The sites were selected based on potential structural importance as determined by homology modeling (FIG. 1) and non-polarity.

FIG. 5A is a graph depicting proteinase K cleavage of yeast-displayed wild-type CD19. Yeast displaying wild-type CD19 were incubated with the indicated amount of proteinase K in PBSA at 37° C. for 10 min. Yeast were washed, and the N-terminal HA and C-terminal MYC epitopes were labeled with antibodies and evaluated by flow cytometry. 0.002 and 0.02 units of proteinase K provided CD19 cleavage while maintaining Aga2p-HA display. FIG. 5B is a schematic of yeast-displayed CD19 with epitopes indicated.

(FIG. 10B). Yeast were washed and the N-terminal HA and C-terminal MYC epitopes were labeled with antibodies an evaluated by flow cytometry.

FIG. 12A is a ribbon diagram of the extracellular domain of CD19 highlighting potential regions for diversity to generate binding ligands. Orange: Ig domain 1 loops; blue: Ig domain 2 loops; red: Ig domain 2 sheet. FIG. 12B depicts tables of exemplary diversity designs. The homology model was determined as follows. The 258 residue amino acid sequence of CD19 comprising the N-terminal domain, domain linker, and C-terminal domain was submitted to HHPred (Riding et al., Nucleic Acids Res. 33:244-248 (2005)) using the default parameters. HHPpred makemodel was then used to make a model for MODELLER (Eswar et al., Curr. Protoc. Bioinforma. 5.6.1-32 (2006) doi:10.1002/0471250953.bi0506s4711) using the automatically pick best template option. The optimal single template (1qz1) was selected for MODELLER (Note: the option for selecting the multiple optimal templates also output a structure similar to 1qz1). The output structure was then refined in Foldit (Cooper et al, Nature 466:756-760 (2010)) standalone by side-chain repacking, and full-structure minimization.

FIG. 14C depicts further sequence analysis of CD19/anti-HER2 scFv variants from multi-mutant library; mutants that emerged from selections for FMC63 binding and HER2 binding were sequenced. Amino acids at the diversified positions are indicated for numerous clones.

FIG. 15B depicts sequence analysis of CD19/anti-HER2 scFv variants from multi-mutant library; mutants that emerged from selections for FMC63 binding and HER2 binding were sequenced. Amino acids at the diversified positions are indicated for numerous clones.

FIG. 26 depicts detection of secreted bispecific fusion proteins comprising a CD19 variant protein.

FIG. 39 depicts the titers of various CD19 mutant-VHH/Clec12A and VHH/Clec12A-CD19 mutant constructs.

FIG. 40 depicts the binding of various CD19 mutant-VHH/Clec12A and VHH/Clec12A-CD19 mutant constructs to CLEC12a.

FIG. 41 depicts the binding of various CD19 mutant-VHH/Clec12A and VHH/Clec12A-CD19 mutant constructs to CLEC12a.

FIGS. 46A and 46B depict binding EC50s for a bispecific construct comprising the VH and VL domains of Construct #186, an anti-CLEC12a VHH (clone 2H3), and a CD19 mutant.

FIGS. 47A and 47B depict killing of CLEC12a positive cells by CAR19 due to bridging by a bispecific construct comprising the VH and VL domains of Construct #186, an anti-CLEC12a VHH (clone 2H3), and a CD19 mutant.

Figure 1A:
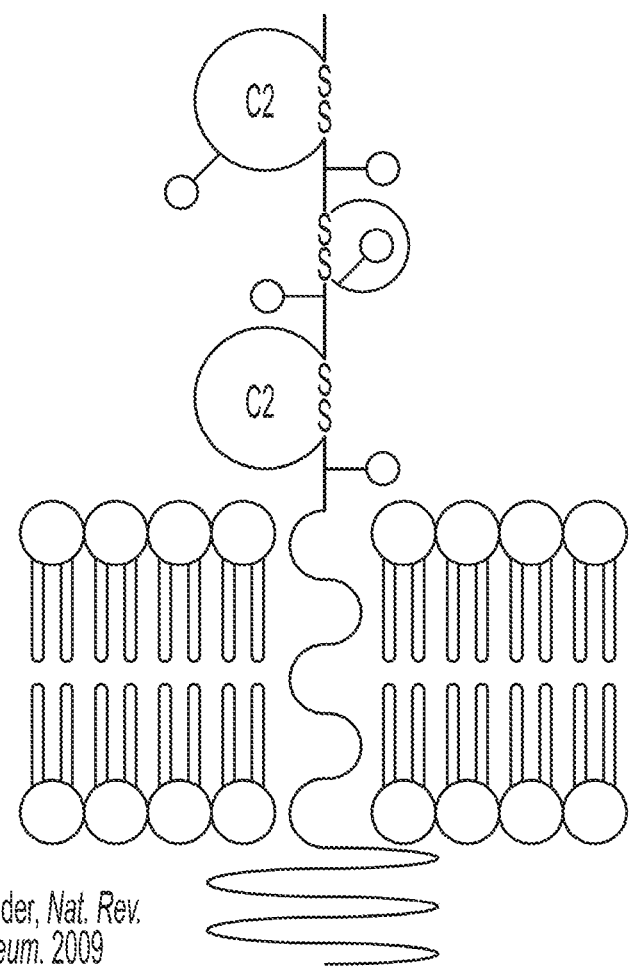
FIG. 1A is a schematic of the CD19 protein (reproduced from Tedder, Nat. Rev. Rheumatol. 5:572-577 (2009)).

FIG. 49 depicts killing of U937 and NALM6 cells by cells infected with a lentiviral vector encoding a fusion protein comprising CAR19; CD19; and an anti-CLEC12a scFv.

FIG. 50 depicts titration of mab 3B10 against CD19 or peptide expressed on yeast.

DEFINITIONS

In order for the present invention to be more readily understood, certain terms are first defined below. Additional definitions for the following terms and other terms are set forth throughout the specification.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (including by intratracheal instillation), transdermal, vaginal and vitreal. In some embodiments, administration may be intratumoral or peritumoral. In some embodiments, administration may involve intermittent dosing. In some embodiments, administration may involve continuous dosing (e.g., perfusion) for at least a selected period of time.

Adoptive cell therapy: As used herein, "adoptive cell therapy" or "ACT" involves the transfer of immune cells with antitumour activity into cancer patients. In some embodiments, ACT is a treatment approach that involves the use of lymphocytes with antitumour activity, the in vitro expansion of these cells to large numbers and their infusion into a cancer-bearing host.

Affinity: As used herein, the term "affinity" refers to the characteristics of a binding interaction between an antigen binding moiety (e.g., an antibody described herein) and an antigen target (e.g., CLL-1) and that indicates the strength of the binding interaction. In some embodiments, the measure of affinity is expressed as a dissociation constant ($K_D$). In some embodiments, an antigen binding moiety has a high affinity for an antigen target (e.g., a $K_D$ of less than about $10^{-7}$ M, less than about $10^{-8}$ M, or less than about $10^{-9}$ M).

Amelioration: As used herein, "amelioration" refers to prevention, reduction and/or palliation of a state, or improvement of the state of a subject. Amelioration includes, but does not require, complete recovery or complete prevention of a disease, disorder or condition.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are composed of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are fully human, or are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present disclosure is in a format selected from, but not limited to, intact IgG, IgE and IgM, bi- or multi-specific antibodies (e.g., Zybodies®, etc), single chain Fvs, polypeptide-Fc fusions, Fabs, camelid antibodies, masked antibodies (e.g., Probodies®), Small Modular ImmunoPharmaceuticals ("SMIPs™"), single chain or Tandem diabodies (TandAb®), Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc.), or other pendant group (e.g., polyethylene glycol, etc.)).

Antibody Fragment: As used herein, an "antibody fragment" includes a portion of an intact antibody, such as, for example, the antigen-binding or variable region of an antibody. Examples of antibody fragments include Fab, Fab', F(ab')$_2$, and Fv fragments; triabodies; tetrabodies; linear antibodies; single-chain antibody molecules; and multi-specific antibodies formed from antibody fragments. For example, antibody fragments include isolated fragments, "Fv" fragments (consisting of the variable regions of the heavy and light chains), recombinant single chain polypeptide molecules in which light and heavy chain variable regions are connected by a peptide linker ("scFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')$_2$ fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Antigen: The term "antigen", as used herein, refers to an agent that elicits an immune response; and/or an agent that binds to a T cell receptor (e.g., when presented by an MHC molecule) or to an antibody or antibody fragment. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer (e.g., other than a nucleic acid or amino acid polymer)) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source), or alternatively may exist on or in a cell. In some embodiments, an antigen is a recombinant antigen.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myeloid leukemias, myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Domain: The term "domain" is used herein to refer to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecular (e.g., a small molecule, carbohydrate, a lipid, a nucleic acid, or a polypeptide). In some embodiments, a domain is a section of a polypeptide; in some such embodiments, a domain is characterized by a particular structural element (e.g., a particular amino acid sequence or sequence motif, $\alpha$-helix character, $\beta$-sheet character, coiled-coil character, random coil character, etc), and/or by a particular functional feature (e.g., binding activity, enzymatic activity, folding activity, signaling activity, etc).

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fusion protein: As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Identity: As used herein, the term "identity" refers to the overall relatedness between nucleic acid molecules (e.g., DNA molecules and/or RNA molecules) and/or between polypeptides. In some embodiments, nucleic acids or polypeptides are considered to be "substantially identical" to one another if their sequences are at least 25%, 30%, 35%, 40%, 45%, 50%, 55%, 60%, 65%, 70%, 75%, 80%, 85%, 90%, 95%, 96%, 97%, 98%, or 99% identical. Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 75%, at least 80%, at least 85%, at least 90%, at least 95%, at least 96%, at least 97%, at least 98%, at least 99%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller, 1989, which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immunoglobulin single variable domain: The term "immunoglobulin single variable domain" or "single variable domain", as used herein, means an immunoglobulin variable domain which is capable of specifically binding to an epitope of the antigen without pairing with an additional variable immunoglobulin domain. One example of immunoglobulin single variable domains in the meaning of the present invention is "domain antibody", such as the immunoglobulin single variable domains VH and VL (VH domains and VL domains). Another example of immunoglobulin single variable domains is a "VHH domain" (or simply "VHH") from camelids, as described herein.

Immunoglobulin variable domain: The term "immunoglobulin variable domain" or "variable domain", as used herein, means an immunoglobulin domain that is or includes four "framework regions" (referred to in the art and herein as "framework region 1" or "FR1"; as "framework region 2" or "FR2"; as "framework region 3" or "FR3"; and as "framework region 4" or "FR4", respectively); which framework regions are interrupted by three "complementarity determining regions" or "CDRs" (referred to in the art and herein as "complementarity determining region 1" or "CDR1"; as "complementarity determining region 2" or "CDR2"; and as "complementarity determining region 3" or "CDR3", respectively). In some embodiments, the general structure or sequence of an immunoglobulin variable domain can be indicated as follows: FR1-CDR1-FR2-CDR2-FR3-CDR3-FR4.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein.

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, cancer. In some embodiments, the subject is a human.

$K_a$: As used herein, "$K_a$" refers to an association rate of a particular antigen binding moiety and an antigen target to form an antigen binding moiety/antigen target complex.

$K_d$: As used herein, "$K_d$" refers to a dissociation rate of a particular antigen binding moiety/antigen target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Linker: As used herein, the term "linker" refers to, e.g., in a fusion protein, an amino acid sequence of an appropriate length other than that appearing at a particular position in the natural protein and is generally designed to be flexible and/or to interpose a structure, such as an a-helix, between two protein moieties. In general, a linker allows two or more domains of a fusion protein to retain 50%, 55%, 60%, 65%, 70%, 75%, 80%, 85%, 90%, 95% or more of the biological activity of each of the domains. A linker may also be referred to as a spacer. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. A variety of different linker elements that can appropriately be used when engineering polypeptides (e.g., fusion polypeptides) known in the art (see, e.g., Holliger, P., et al. (1993) Proc. Natl. Acad. Sci. USA 90:6444-6448; Poljak, R. J., et al. (1994) Structure 2: 1121-1123)).

Nucleic acid: As used herein, "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Operably linked: As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Peptide: The term "peptide" as used herein refers to a polypeptide that is typically relatively short, for example having a length of less than about 100 amino acids, less than about 50 amino acids, less than 20 amino acids, or less than 10 amino acids.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Promoter: As used herein, a "promoter" is a DNA sequence recognized by the synthetic machinery of the cell, or introduced synthetic machinery, required to initiate the specific transcription of a polynucleotide sequence. A "constitutive" promoter is a nucleotide sequence which, when operably linked with a polynucleotide that encodes or specifies a gene product, causes the gene product to be produced in a cell under most or all physiological conditions of the cell. An "inducible" promoter is a nucleotide sequence that, when operably linked with a polynucleotide that encodes or specifies a gene product, causes the gene product to be produced in a cell substantially only when a promoter-specific inducer is present in the cell.

Protein: As used herein, the term "protein", refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

Reference: As used herein, "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Selective binding: As used herein, "selective binding", "selectively binds" "specific binding", or "specifically binds" refers, with respect to an antigen binding moiety and an antigen target, preferential association of an antigen binding moiety to an antigen target and not to an entity that is not the antigen target. A certain degree of non-specific binding may occur between an antigen binding moiety and a non-target. In some embodiments, an antigen binding moiety selectively binds an antigen target if binding between the antigen binding moiety and the antigen target is greater than 2-fold, greater than 5-fold, greater than 10-fold, or greater than 100-fold as compared with binding of the antigen binding moiety and a non-target. In some embodiments, an antigen binding moiety selectively binds an antigen target if the binding affinity is less than about $10^{-5}$M, less than about $10^{-6}$M, less than about $10^{-7}$M, less than about $10^{-8}$M, or less than about $10^{-9}$M.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Suffering from: An individual who is "suffering from" a disease, disorder, or condition (e.g., cancer) has been diagnosed with and/or exhibits one or more symptoms of the disease, disorder, or condition.

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a cellular therapeutic described herein (e.g., an immune cell comprising or consisting of an antigen binding receptor encoded by an and an inducible expression construct as described herein).

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, "therapeutically effective amount"

refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in one or more pro-angiogenic markers, an increase in anti-angiogenic markers, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Transduction: As used herein, "transduction" is the process whereby a nucleic acid is introduced into a cell by a viral vector. In some embodiments, transduction describes viral vector mediated introduction of nucleic acid sequences into lymphocytes for the production of cell therapeutics.

Transformation: As used herein, "transformation" refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. Viral vector mediated transformation can be referred to as "transduction". In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Treatment: As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Tumor infiltrating lymphocyte: As used herein, the term "tumor-infiltrating lymphocytes" refers to white blood cells of a subject afflicted with a cancer (such as melanoma), that have left the blood stream and have migrated into a tumor. In some embodiments, tumor-infiltrating lymphocytes have tumor specificity.

Variant: As used herein, the term "variant" refers to an entity that shows significant structural identity with a reference entity but differs structurally from the reference entity in the presence or level of one or more chemical moieties as compared with the reference entity. The terms "variant" and "mutant" are used interchangeably herein. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. A polypeptide may have a characteristic sequence element comprised of a plurality of amino acids having designated positions relative to one another in linear or three-dimensional space and/or contributing to a particular biological function. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, a reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced or an increased level of one or more biological activities as compared with the reference polypeptide. In many embodiments, a polypeptide is considered to be a "variant" of a parent or reference polypeptide if the polypeptide has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

Vector: As used herein, "vector" refers to a nucleic acid molecule capable of transporting another nucleic acid to which it is associated. In some embodiments, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION

Among other things, the present disclosure provides methods of identifying CD19 variants, and compositions including such CD19 variants. Scaffold based binding proteins are known for their potential to bind specific antigen targets, e.g., similar to antibodies. Some scaffold binding proteins include a stable framework core, and putative antigen binding regions can tolerate multiple substitutions. Thus, a scaffold framework core can be synthetically engineered from which a library of different sequence variants can be built upon. Sequence diversity typically exists at exterior surfaces of proteins, such as loop structures or other exterior surfaces that can serve as potential antigen binding regions. The present disclosure involves screening and identifying CD19 variants exhibiting antigen binding and/or stability.

CD19

CD19 is a 95 kDa type I transmembrane glycoprotein that is used as a biomarker of B cell development (Wang et al., Exp. Hematol. Oncol. 1:36 (2012)). CD19 expression in lymphoma and leukemia has made it an effective therapeutic target, especially for chimeric antigen receptor (CAR) T cell therapy (Maude et al., Blood 125:4017-4024 (2015)). Based on CD19's uniquely efficacious performance in CAR-T cell therapy, therapeutic approaches have been described that involve "converting" CD19⁻ tumors into CD19⁺ tumors using antibody-CD19 fusions or CD19 variants engineered to bind directly to tumor biomarkers (see, e.g., WO2017/075537 and WO2017/075533). In these contexts, the structural integrity—including proper folding, presentation of biological epitopes, and stability—of the CD19 extracellular region may be important to performance of the molecular therapy.

Figure 1B:
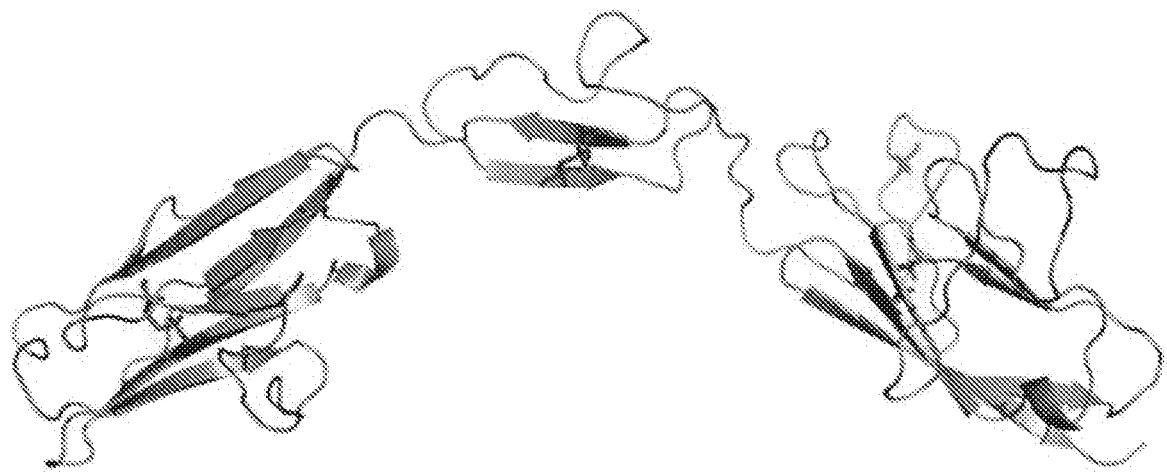
FIG. 1B is a ribbon diagram of the structure of the extracellular portion of CD19 predicted by the HHPred server (Soding et al., Nucl. Acid Res. 33:244-248 (2005)).

The extracellular region of CD19 was hypothesized to contain two C2-like immunoglobulin domains (see, e.g., Wang et al., Exp. Hematol. Oncol. 1:36 (2012); Tedder et al., Nat. Rev. Rheumatol. 5:572-577 (2009)). This is supported by homology modeling (Soding et al., Nucleic Acids Res. 33:244-248 (2005)) (see FIG. 1). However, a recently published structure demonstrated that CD19 does not include C2-like immunoglobulin domains (Teplyakov et al., Proteins 86:495-500 (2018)).

The nucleotide sequence of human CD19, as well as nucleotide sequences of specific domains of CD19, are known (see Genbank Accession No. M84371.1). For example, the nucleotide sequence encoding the extracellular domain of CD19 is:

```
                                          (SEQ ID NO: 1)
CCCGAGGAACCTCTAGTGGTGAAGGTGGAAGAGGGAGATAACGCTGTGCT

GCAGTGCCTCAAGGGGACCTCAGATGGCCCCACTCAGCAGCTGACCTGGT

CTCGGGAGTCCCCGCTTAAACCCTTCTTAAAACTCAGCCTGGGGCTGCCA

GGCCTGGGAATCCACATGAGGCCCCTGGCCATCTGGCTTTTCATCTTCAA

CGTCTCTCAACAGATGGGGGGCTTCTACCTGTGCCAGCCGGGGCCCCCCT

CTGAGAAGGCCTGGCAGCCTGGCTGGACAGTCAATGTGGAGGGCAGCGGG

GAGCTGTTCCGGTGGAATGTTTCGGACCTAGGTGGCCTGGGCTGTGGCCT

GAAGAACAGGTCCTCAGAGGGCCCCAGCTCCCCTTCCGGGAAGCTCATGA

GCCCCAAGCTGTATGTGTGGGCCAAAGACCGCCCTGAGATCTGGGAGGGA

GAGCCTCCGTGTCTCCCACCGAGGGACAGCCTGAACCAGAGCCTCAGCCA

GGACCTCACCATGGCCCTGGCTCCACACTCTGGCTGTCCTGTGGGGTAC

CCCCTGACTCTGTGTCCAGGGGCCCCCTCTCCTGGACCCATGTGCACCCC

AAGGGGCCTAAGTCATTGCTGAGCCTAGAGCTGAAGGACGATCGCCCGGC

CAGAGATATGTGGGTAATGGAGACGGGTCTGTTGTTGCCCCGGGCCACAG

CTCAAGACGCTGGAAAGTATTATTGTCACCGTGGCAACCTGACCATGTCA

TTCCACCTGGAGATCACTGCTCGGCCAGTACTATGGCACTGGCTGCTGAG

GACTGGTGGCTGGAAG.
```

The amino acid sequence of the extracellular domain of CD19 is:

```
                                          (SEQ ID NO: 2)
PEEPLVVKVEEGDNAVLQCLKGTSDGPTQQLTWSRESPLKPFLKLSLGLP

GLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHP

KGPKSLLSLELKDDRPARDMWVMETGLLLPRATAQDAGKYYCHRGNLTMS

FHLEITARPVLWHWLLRTGGWK.
```

As discussed herein, the disclosure provides CD19 variants. In some embodiments, a CD19 variant is or includes a full length CD19 polypeptide, or a portion thereof, that includes one or more amino acid substitutions described herein. In some embodiments, a CD19 variant is or includes a CD19 extracellular domain, or a portion thereof, that includes one or more amino acid substitutions described herein. In some embodiments, a CD19 variant is or includes one or both CD19 C2-like Ig domains (or a portion of one or both Ig domains), one or both of which includes one or more amino acid substitutions described herein. In some embodiments, a CD19 variant is or includes a CD19 extracellular domain lacking one or more amino acids at the C-terminus and including both C2-like Ig domains, and includes one or more amino acid substitutions described herein. In some embodiments, a CD19 variant is or includes a CD19 extracellular domain lacking 1, 2, 3, 4, 5, 6, 7, 8, 9, 10, 11, 12, 13, 14, 15, or more amino acids at the C-terminus and including both C2-like Ig domains, and includes one or more amino acid substitutions described herein.

Methods of Identifying CD19 Variants

CD19 variants can be identified by screening variants (e.g., a library of variants) having specific targeted extracellular domain substitutions. It is believed that using such an approach, overall CD19 stability can be maximized while minimizing non-immunogenic substitutions. Additionally, the size of a library of CD19 variants can be tailored such that the overall diversity can be screened in one or more systems. Thus, in some embodiments, the extracellular domain (ECD) of CD19, and/or one or both of the C2-like Ig domains including loops or sheets described by Teplyakov et al., Proteins 86:495-500 (2018) are used as scaffolds for mutagenesis, and CD19 variants (e.g., CD19 or a portion thereof (e.g., ECD, one or both C2-like Ig domains, one or more loops described by Teplyakov et al., Proteins 86:495-500 (2018), and/or a portion thereof) that include one or more mutations can be screened and selected based on expression and/or based on one or more functional characteristics described herein (e.g., binding to an anti-CD19 antibody, binding to a target antigen, and/or stability).

To provide variant nucleic acid sequences that encode CD19 variants, a number of methods known in the art may be utilized. In some embodiments, a screening procedure is used that enables identification and/or isolation of nucleic acids that encode CD19 variants that bind an anti-CD19 antibody and/or bind a particular antigen. Exemplary methods include a so-called biopanning step, known from technologies such as phage display (Kang, A. S. et al. 1991. Proc Natl Acad Sci USA 88, 4363-4366), ribosome display (Schaffitzel, C. et al. 1999. J. Immunol. Methods 231, 119-135), DNA display (Cull, M. G. et al. 1992. Proc Natl Acad Sci USA 89, 1865-1869), RNA-peptide display (Roberts, R. W., Szostak, J. W., 1997. Proc Natl Acad Sci USA 94, 12297-12302), covalent display (WO 98/37186), bacterial surface display (Fuchs, P. et al. 1991. Biotechnology 9, 1369-1372), yeast surface display (Boder, E. T., Wittrup, K. D., 1997. Nat Biotechnol 15, 553-557) and eukaryotic virus display (Grabherr, R., Ernst, W., 2001. Comb. Chem. High Throughput. Screen. 4, 185-192). FACS and magnetic bead sorting are also applicable for enrichment (panning) purposes using labeled anti-CD19 antibody or labeled antigen. Immunodetection assays such as ELISA (Dreher, M. L. et al. 1991. J. Immunol. Methods 139, 197-205) and ELISPOT (Czerkinsky, C. C. et. al. 1983. J Immunol Methods. 65, 109-21) can also be used either following a biopanning step or alone.

Libraries

In some embodiments, CD19 variants are generated for screening by synthesizing individual oligonucleotides that encode a defined region of CD19 (e.g., ECD or portion thereof) and have no more than one codon for the predetermined amino acid. This can be accomplished, e.g., by incorporating at each codon position within the oligonucleotide either a codon required for synthesis of a wild-type polypeptide or a codon for the predetermined amino acid (see, e.g., U.S. Publication No. 20050136428). In another embodiment, walk-through mutagenesis (WTM) can be used (see e.g., U.S. Pat. Nos. 6,649,340; 5,830,650; and 5,798,208). WTM allows multiple mutations to be made with a minimum number of oligonucleotides, which can be produced individually, in batches, using, e.g., doping techniques, and then mixed or pooled as desired.

A mixture of oligonucleotides for generation of a library can be synthesized by known methods. Synthesized polynucleotides can be inserted into a suitable vector using standard genetic engineering techniques. By means of an appropriate vector (including, e.g., phage vectors, plasmids) the genes can be introduced into a cell-free extract, phage, prokaryotic cell, or eukaryotic cell suitable for expression of the fibronectin binding domain molecules.

In some embodiments, CD19 nucleic acid sequences are introduced into a single stranded plasmid. For example, a gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R. et al., Nucleic Acids Res. 16: 791-802 (1988)). Polymerase chain reaction (PCR) methodology can also be used to incorporate polynucleotides into a gene.

The size of a library can vary depending upon the targeted region of CD19 (e.g., CD19 ECD or portion thereof) and the amount of sequence diversity desired. In some embodiments, a library is designed to contain fewer than $10^{15}$, $10^{14}$, $10^{13}$, $10^{12}$, $10^{11}$, $10^{10}$, $10^9$, $10^8$, $10^7$, or $10^6$ CD19 variants. In some embodiments, libraries may be attached to a solid support, such as a microchip, and preferably arrayed, using art recognized techniques.

In some embodiments, CD19 variants can be identified having better antigen binding properties and/or improved chemo-physical properties, such as solubility or stability. In some embodiments, an identified CD19 variant is subjected to affinity maturation to increase the affinity/avidity of the binding molecule to a target antigen.

Expression and Screening

Libraries of polynucleotides generated by any of the above techniques or other suitable techniques can be expressed and screened to identify CD19 variants having desired structure and/or activity. Expression of the CD19 variants can be carried out using cell-free extracts (and e.g., ribosome display), phage display, prokaryotic cells, or eukaryotic cells (e.g., yeast display). In some embodiments, a microbial expression and display system is used to express and screen CD19 variant libraries. Typically, CD19 polypeptide or portion thereof described herein is joined by a linker peptide to another surface molecule creating a fusion protein.

In some embodiments, polynucleotides are engineered to serve as templates that can be expressed in a cell free extract. Vectors and extracts as described, for example in U.S. Pat. Nos. 5,324,637; 5,492,817; 5,665,563, can be used. Ribosome display and other cell-free techniques for linking a polynucleotide (i.e., a genotype) to a polypeptide (i.e., a phenotype) can be used (see, e.g., U.S. Pat. Nos. 6,348,315; 6,261,804; 6,258,558).

In some embodiments, polynucleotides are expressed in an E. coli expression system (see, e.g., Pluckthun et al., Meth. Enzymol. 178:476-515 (1989); Skerra et al., Biotechnology 9:273-278 (1991)), and CD19 variants are expressed for secretion in the medium and/or in the cytoplasm of the bacteria (see, e.g., Better et al., Meth. Enzymol. 178:476 (1989)). In some embodiments, CD19 variants are attached to the 3' end of a sequence encoding a signal sequence, such as the ompA, phoA or pelB signal sequence (see, e.g., Lei et al., J. Bacteriol. 169:4379 (1987)).

In some embodiments, CD19 variants are expressed on the membrane surface of a prokaryote, e.g., E. coli, using a secretion signal and lipidation moiety as described, e.g., in US20040072740A1; US20030100023A1; and US20030036092A1.

In another embodiment, polynucleotides are expressed in eukaryotic cells (e.g., yeast) using, for example, yeast display as described, e.g., in U.S. Pat. Nos. 6,423,538; 6,331, 391; and 6,300,065. The yeast display system utilizes the a-agglutinin yeast adhesion receptor to display proteins on the cell surface. CD19 variant libraries are expressed as fusion partners with the Aga2 proteinA, and a library of CD19 variants can be transfected into a recipient yeast host using standard techniques. In some embodiments, a linker described herein is included between a CD19 polypeptide (or portion) and Aga2 protein A. Expressed fusion proteins are secreted from the cell and become disulfide linked to the Aga1 protein, which is attached to the yeast cell wall (see Invitrogen, pYD1 Yeast Display product literature). Yeast cells can then be screened and separated using known methods, such as flow cytometry and fluorescence-activated cell sorting (FACS) or magnetic beads.

Higher eukaryotic cells for expression of CD19 variants can also be used, such as mammalian cells, for example myeloma cells (e.g., NS/0 cells), hybridoma cells, HEK-293 cells, or Chinese hamster ovary (CHO) cells. CD19 variants can be designed to be expressed into the culture medium, or expressed on the surface of such a cell.

Screening of expressed CD19 variants can be accomplished by any appropriate means. For example, binding activity can be evaluated by standard immunoassay and/or affinity chromatography. Binding activity can also be assayed in vitro using, e.g., a Biacore instrument. In some embodiments, a CD19 variant is identified that that binds to a target (e.g., a target antigen described herein) at a level that is at least 20%, 40%, 60%, 80%, 100%, 120%, 140%, 160%, 180%, 200%, 250%, 300%, 400%, 500% or more, greater than that of a wild-type CD19.

In some embodiments, stability of CD19 variants can be assessed using known techniques, such as measuring protein level following exposure to elevated temperatures and/or measuring protein level following enzymatic and/or chemical treatment. In some embodiments, a CD19 variant is identified as having a measured protein level, following exposure to elevated temperature, enzymatic, and/or chemical treatment, that is at least 3%, 5%, 7%, 9%, 10%, 15%, 20%, 40%, 60%, 80%, 100%, 120%, 140%, 160%, 180%, 200%, 250%, 300%, 400%, 500% or more, greater than that of a wild-type CD19 exposed to the same conditions. For example, a CD19 variant can have a melting temperature that is about 0.5, 1, 1.5, 2, 2.5, 3, 3.5, 4, 4.5, 5, 6, 7, 8, 9, or 10 degrees Celsius, higher than a corresponding melting temperature of a wild-type CD19 exposed to the same conditions.

In exemplary methods described herein, CD19 variants are identified that demonstrate a threshold level of stability and/or an improved level of stability (e.g., relative to wild-type CD19 or another CD19 variant). For example, a nucleotide sequence encoding CD19 ECD can be systematically mutagenized to create a first CD19 mutant library, which can be screened for CD19 variants demonstrating stability. In some embodiments, a second library (a "sub-library") can be created from nucleotide sequences encoding stable CD19 variants identified from the first CD19 mutant library, which can also be screened for CD19 variants demonstrating stability. CD19 variants exhibiting stability (e.g., identified from the first and/or the second library) can be used in one or more compositions and/or methods described herein. Additionally or alternatively, CD19 variants exhibiting stability (e.g., identified from the first and/or the second library) can be further screened for ability to bind a particular antigen, e.g., an antigen described herein. For example, a nucleotide sequence encoding a stable CD19 variant having one or more amino acid mutations relative to wild-type CD19 can be systematically mutagenized (i.e., at codons encoding amino acids other than those identified as imparting stability) to create a new library that can be subsequently screened for stable CD19 variants that bind a particular antigen, e.g., an antigen described herein.

Antigens

In some embodiments, a CD19 variant is identified to selectively bind to any target antigen. Exemplary target antigens include, e.g., MART-1/MelanA (MART-I), gp100 (Pmel 17), tyrosinase, TRP-1, TRP-2, MAGE-1, MAGE-3, BAGE, GAGE-1, GAGE-2, p15, CEA, p53, Ras, HER-2/neu, BCR-ABL, E2A-PRL, H4-RET, IGH-IGK, MYL-RAR, Epstein Barr virus antigens EBVA, human papillomavirus (HPV) antigen E6 or E7, TSP-180, MAGE-4, MAGE-5, MAGE-6, RAGE, NY-ESO, erbB, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, MUC16, IL13Rα2, FRα, VEGFR2, Lewis Y, FAP, EphA2, CEACAM5, EGFR, CA6, CA9, GPNMB, EGP1, FOLR1, endothelial receptor, STEAP1, SLC44A4, Nectin-4, AGS-16, guanalyl cyclase C, MUC-1, CFC1B, integrin alpha 3 chain (of a3b1, a laminin receptor chain), TPS, CD19, CD20, CD22, CD30, CD72, CD180, CD171 (L1CAM), CD123, CD133, CD138, CD37, CD70, CD79a, CD79b, CD56, CD74, CD166, CD71, CLL-1/CLEC12A, ROR1, Glypican 3 (GPC3), Mesothelin, CD33/IL3Ra, c-Met, PSCA, PSMA, Glycolipid F77, EGFRvIII, BCMA, GD-2, MY-ESO-1, or MAGE A3.

Exemplary CD19 Variants

Using methods described herein, CD19 variants were identified that demonstrated a level of stability that was increased relative to wild-type CD19. Thus, in some embodiments, a CD19 variant includes one or more of the amino acid substitutions of SEQ ID NO:2 listed in Table 1A, Table 1B, Table 2A, Table 2B, Table 3, Table 6, FIG. 8B, FIG. 11, FIG. 12B, FIG. 14A-FIG. 14D, or FIG. 15B.

In some embodiments, a CD19 variant includes an amino acid substitution at one or more of the following amino acid positions of SEQ ID NO:2: 2, 3, 7, 8, 9, 10, 11, 12, 13, 14, 15, 16, 18, 20, 22, 25, 28, 29, 30, 31, 32, 33, 34, 38, 39, 45, 47, 49, 52, 53, 54, 55, 56, 57, 58, 59, 61, 62, 63, 64, 66, 68, 70, 72, 84, 90, 93, 94, 99, 100, 105, 108, 111, 113, 114, 115, 122, 123, 124, 125, 127, 130, 131, 132, 135, 138, 139, 140, 141, 142, 143, 144, 145, 146, 148, 149, 154, 167, 169, 171, 185, 189, 193, 194, 196, 198, 202, 204, 206, 207, 209, 211, 212, 213, 215, 216, 217, 219, 220, 221, 222, 223, 224, 225, 226, 228, 229, 230, 232, 235, 240, 243, 247, 249, 250, 251, 252, 253, 255, 256, 257, 258, 259, 260, 261, 262, 264, 265, 269, or 271. Exemplary amino acid substitutions at these positions are shown in Table 1A, Table 2A, Table 3, Table 6, FIG. 11, FIG. 12B, FIG. 14A-FIG. 14D, or FIG. 15B.

In some embodiments, a CD19 variant includes one or more of the following amino acid substitutions at one or more of the following positions, as shown in Table 6:

TABLE 6

| Position of SEQ ID NO: 2 | Amino Acid Substitution ("*" denotes deletion) |
|---|---|
| 1 | F or I |
| 5 | V |
| 10 | M, R, Q, T, N, F, K, H, L, A, I, W, V, or Y |
| 13 | Q |
| 14 | T or D |
| 16 | F, W, Y, L, or M |
| 18 | P or L |
| 20 | G, P, D, S, N, or A |
| 21 | G or P |
| 23 | P, V, or R |
| 25 | L |
| 28 | D or Y |
| 29 | E |
| 30 | E |
| 31 | I, V, N, or M |
| 32 | E |
| 36 | D or G |
| 37 | D |
| 39 | N, D, E, H, S, T, or Q |
| 41 | G |
| 45 | Y or V |
| 47 | F, W, M, G, or T |
| 49 | A, C, or V |
| 52 | V |
| 53 | A |
| 54 | C or M |
| 55 | F, L, V, M, Y, A, P, or W |
| 56 | V, I, L, Q or F |
| 57 | T, G, E, D, S, A, N, or Q |
| 59 | N, G, E, S, D, K, H, T, Q, A, R, M, V, W, or P |
| 60 | G |
| 61 | T |
| 62 | D, E, T, S, R, M, or Q |
| 63 | T, V, or A |
| 64 | T, V, G, A, R, E, S, Q, K, I, H, M, or Y |
| 66 | H, K, R, T, A, Q, S, P, G, or N |
| 70 | C, H, or A |
| 71 | D, S, or E |
| 79 | Y |
| 81 | P |
| 84 | M |
| 85 | A |
| 86 | D |
| 87 | N, G, H, F, or K |
| 89 | Y |
| 91 | A |
| 95 | S |
| 110 | K |
| 112 | D, N, H, or E |
| 113 | K or Y |
| 116 | N or Q |
| 126 | H |
| 129 | H |
| 130 | P or H |
| 132 | N or R |
| 133 | D or K |
| 139 | Y, T, or F |
| 140 | H |
| 141 | K, M, or N |
| 146 | Q or V |
| 147 | L, R, M, Q, or K |
| 152 | I, L, or V |

TABLE 6-continued

| Position of SEQ ID NO: 2 | Amino Acid Substitution ("*" denotes deletion) |
|---|---|
| 157 | D |
| 158 | N |
| 159 | H or P |
| 160 | L |
| 161 | D, N, or S |
| 162 | H |
| 167 | R or K |
| 171 | V or I |
| 177 | A |
| 178 | K, A, R, G, S, M, E, V, or N |
| 179 | I |
| 183 | I |
| 187 | A |
| 192 | W |
| 196 | L, M, V, I, or W |
| 197 | W |
| 199 | H |
| 201 | H or R |
| 205 | Q, V, L, D, A, or T |
| 208 | F or T |
| 210 | W |
| 212 | S, F, A, T, L, M, G, C, V, W, or P |
| 214 | * |
| 215 | Y, W, M, or A |
| 216 | H |
| 217 | Q, M, or L |
| 219 | E or I |
| 221 | V, I, or Y |
| 223 | T, D, W, N, S, Y, M, or F |
| 224 | D or G |
| 225 | D, N, S, or E |
| 226 | T, S, A, Q, M, Y, K, N, or E |
| 227 | I |
| 228 | V, M, or T |
| 231 | N or H |
| 232 | V |
| 234 | K, Q, R, M, or P |
| 235 | A or F |
| 239 | M or L |
| 240 | W |
| 243 | T, K, S, Q, M, or R |
| 247 | T or R |
| 250 | E or A |
| 252 | K, Q, I, V, E, or R |
| 253 | F |
| 254 | W |
| 255 | V |
| 256 | K |
| 257 | K, R, P, Q, or H |
| 258 | K |
| 259 | * |
| 260 | K, R, N, S, G, T, P, Y, or * |
| 261 | K, N, T, Q, W, R, S, A, G, P, H, or * |
| 262 | D, H, R, P, E, S, Q, N, T, A, K, N, I, M, Y, or G |
| 263 | K, P, R, or N |
| 264 | K, N, T, D, H, Q, G, S, P, R, E, A, or Y |
| 265 | P, K, G, R, or D |
| 266 | N, K, S, R, E, H, Q, G, D, A, or P |
| 268 | W, M, L, K, R, Q, or G |
| 269 | I, V, L, M, F, R, K, W, or T |
| 270 | N, P, or Q |
| 271 | K, H, or Q |

In some embodiments, a CD19 variant includes amino acid substitutions at one or more of the following sets of amino acid positions of SEQ ID NO:2: 5/7/9; 14/16/18; 29/31; 29/31/33; 35/37/39; 45/47/49; 52/54/56; 59/61/63; 62/64/66; 76/78/80; 86/88/90; 167/169/171; 175/177/179; 193/195/197; 206/208/210; 207/209/211; 219/221/223; 240/243; 224/226/228; 247/249/251; 253/255/256; 255/256; or 261/262/264/265. Exemplary amino acid substitutions at these sets of positions are shown in Table 1B, Table 2B, Table 3, Table 6, FIG. 8B, FIG. 11, FIG. 14A, FIG. 14B, FIG. 14C, FIG. 14D, or FIG. 15B.

Additional CD19 variants can be identified using methods of the disclosure.

Methods of Using CD19 Variants

Fusion Proteins

WO2017/075537 and WO2017/075533 describe, in part, fusion proteins comprising or consisting of an antigen-binding protein (e.g., an antibody or fragment, or a scaffold polypeptide or fragment) and CD19, or a fragment thereof, or expression constructs encoding such fusion proteins. A CD19 variant described herein, or a CD19 variant identified using a method of the disclosure, can be included in any CD19-based construct described in WO2017/075537 and WO2017/075533. As described in WO2017/075537 and WO2017/075533, such constructs are useful for the treatment of cancer.

Accordingly, in some embodiments, a CD19 variant described herein is included as part of a fusion protein, e.g., a fusion protein that includes a CD19 variant and an antibody, antibody fragment, scaffold polypeptide, or scaffold polypeptide fragment described herein. In some embodiments, a fusion protein is or includes a CD19 variant fused to the amino (N) terminus of another protein, for example, a CD19 variant fused to the amino (N) terminus of an antigen binding protein (e.g., antibody or antibody fragment, or a scaffold polypeptide or fragment described herein). In some embodiments, a fusion protein is or includes a CD19 variant fused to the amino terminus of a light chain of an antibody, or a fragment thereof. In some embodiments, a fusion protein is or includes a CD19 variant fused to the amino terminus of a heavy chain of an antibody, or portion thereof. In some embodiments, a CD19 variant fusion protein includes a linker described herein.

In some embodiments, a fusion protein is or includes a CD19 variant fused to the carboxyl (C) terminus of another protein, for example, a CD19 variant fused to the carboxyl (C) terminus of an antigen binding protein (e.g., antibody or antibody fragment, or a scaffold polypeptide or fragment described herein). In some embodiments, a fusion protein is or includes a CD19 variant fused to the carboxyl terminus of a light chain of an antibody, or a fragment thereof. In some embodiments, a fusion protein is or includes a CD19 variant fused to the carboxyl terminus of a heavy chain of an antibody, or portion thereof.

In other embodiments, the disclosure includes a constitutive or inducible expression construct as described in WO2017/075537 and WO2017/075533, which expression construct comprises a nucleic acid sequence that includes at least a promoter operably linked to a nucleotide sequence encoding a CD19 variant fusion protein described herein.

Antibodies

As described herein, in some embodiments, the disclosure provides fusion proteins including a CD19 variant and an antibody, or a fragment thereof. Any antibody can be included in such fusion proteins. In some embodiments, an antibody is an anti-tumor antibody. Various review articles have been published that describe useful anti-tumor antibodies (see, for example, Adler et al., Hematol. Oncol. Clin. North Am. 26:447-81 (2012); Li et al., Drug Discov. Ther. 7:178-84 (2013); Scott et al., Cancer Immun. 12:14 (2012); and Sliwkowski et al., Science 341:1192-1198 (2013)). Table 4 presents a non-comprehensive list of certain human polypeptide antigens targeted by known, available antibody agents, and notes certain cancer indications for which the antibody agents have been proposed to be useful.

TABLE 4

| Human Antigen | Antibody (commercial or scientific name) | Cancer indication |
| --- | --- | --- |
| CD2 | Siplizumab | Non-Hodgkin's Lymphoma |
| CD3 | UCHT1 | Peripheral or Cutaneous T-cell |
| CD4 | HuMax-CD4 | Lymphoma |
| CD19 | SAR3419, MEDI-551 | Diffuse Large B-cell Lymphoma |
| CD19 and CD3 or CD22 | Bispecific antibodies such as Blinatumomab, DT2219ARL | Non-Hodgkin's Lymphoma |
| CD20 | Rituximab, Veltuzumab, Tositumomab, Ofatumumab, Ibritumomab, Obinutuzumab, | B cell malignancies (Non-Hodgkin's lymphoma, Chronic lymphocytic leukemia) |
| CD22 (SIGLEC2) | Inotuzumab, tetraxetan, CAT-8015, DCDT2980S, Bectumomab | Chemotherapy-resistant hairy cell leukemia, Hodgkin's lymphoma |
| CD30 | Brentuximab vedotin | |
| CD33 | Gemtuzumab ozogamicin (Mylotarg) | Acute myeloid leukemia |
| CD37 | TRU-016 | Chronic lymphocytic leukemia |
| CD38 | Daratumumab | Multiple myeloma, hematological tumors |
| CD40 | Lucatumumab | Non-Hodgkin's lymphoma |
| CD52 | Alemtuzumab (Campath) | Chronic lymphocytic leukemia |
| CD56 (NCAM1) | Lorvotuzumab | Small Cell Lung Cancer |
| CD66e (CEA) | Labetuzumab | Breast, colon and lung tumors |
| CD70 | SGN-75 | Non-Hodgkin's lymphoma |
| CD74 | Milatuzumab | Non-Hodgkin's lymphoma |
| CD138 (SYND1) | BT062 | Multiple Myeloma |
| CD152 (CTLA-4) | Ipilimumab | Metastatic melanoma |
| CD221 (IGF1R) | AVE1642, IMC-A12, MK-0646, R150, CP 751871 | Glioma, lung, breast, head and neck, prostate and thyroid cancer |
| CD254 (RANKL) | Denosumab | Breast and prostate carcinoma |
| CD261 (TRAILR1) | Mapatumumab | Colon, lung and pancreas tumors and haematological malignancies |
| CD262 (TRAILR2) | HGS-ETR2, CS-1008 | |
| CD326 (Epcam) | Edrecolomab, 17-1A, IGN101, Catumaxomab, Adecatumumab | Colon and rectal cancer, malignant ascites, epithelial tumors (breast, colon, lung) |
| CD309 (VEGFR2) | IM-2C6, CDP791 | Epithelium-derived solid tumors |
| CD319 (SLAMF7) | HuLuc63 | Multiple myeloma |

TABLE 4-continued

| Human Antigen | Antibody (commercial or scientific name) | Cancer indication |
|---|---|---|
| CD340 (HER2) | Trastuzumab, Pertuzumab, Ado-trastuzumab emtansine | Breast cancer |
| CAIX (CA9) | cG250 | Renal cell carcinoma |
| EGFR (c-erbB) | Cetuximab, Panitumumab, nimotuzumab and 806 | Solid tumors including glioma, lung, breast, colon, and head and neck tumors |
| EPHA3 (HEK) | KB004, IIIA4 | Lung, kidney and colon tumors, melanoma, glioma and haematological malignancies |
| Episialin | Epitumomab | Epithelial ovarian tumors |
| FAP | Sibrotuzumab and F19 | Colon, breast, lung, pancreas, and head and neck tumors |
| HLA-DR beta | Apolizumab | Chronic lymphocytic leukemia, non-Hodkin's lymphoma |
| FOLR-1 | Farletuzumab | Ovarian tumors |
| 5T4 | Anatumomab | Non-small cell lung cancer |
| GD3/GD2 | 3F8, ch14.18, KW-2871 | Neuroectodermal and epithelial tumors |
| gpA33 | huA33 | Colorectal carcinoma |
| GPNMB | Glembatumumab | Breast cancer |
| HER3 (ERBB3) | MM-121 | Breast, colon, lung, ovarian, and prostate tumors |
| Integrin αVβ3 | Etaracizumab | Tumor vasculature |
| Integrin α5β1 | Volociximab | Tumor vasculature |
| Lewis-Y antigen | hu3S193, IgN311 | Breast, colon, lung and prostate tumors |
| MET (HGFR) | AMG 102, METMAB, SCH900105 | Breast, ovary and lung tumors |
| Mucin-1/CanAg | Pemtumomab, oregovomab, Cantuzumab | Breast, colon, lung and ovarian tumors |
| PSMA | ADC, J591 | Prostate Cancer |
| Phosphatidylserine | Bavituximab | Solid tumors |
| TAG-72 | Minretumomab | Breast, colon and lung tumors |
| Tenascin | 81C6 | Glioma, breast and prostate tumours |
| VEGF | Bevacizumab | Tumour vasculature |

In some embodiments, a fusion protein described herein includes a CD19 variant and an antibody or fragment thereof including, e.g., intact IgG, IgE or IgM, bi- or multi-specific antibodies (e.g., Zybodies®, etc), single chain Fvs, polypeptide-Fc fusions, Fabs, camelid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®.

In some instances, a CD19 variant described herein can be placed (e.g., fused) on the C-terminus and/or N-terminus of an antibody (or fragment) described herein. For example, a CD19 variant can be fused to the C-terminus and/or N-terminus of a light chain or portion (e.g., VL); and/or to the C-terminus and/or N-terminus of a heavy chain or portion (e.g., VH). In some embodiments, a CD19 variant described herein can be placed (e.g., fused) within an antibody (or fragment) or between antibody domains (e.g., scFvs) described herein. For example, a fusion protein can include an anti-EGFR scFv, an anti-Her2 scFv and a mutant CD19, in various configurations. Such fusion partners can exist within such fusion proteins in various configurations, e.g., anti-EGFR scFv/CD19 mutant/anti-Her2 scFv; anti-Her2scFv/CD19 mutant/anti-EGFR scFv; CD19 mutant/anti-EGFR scFv/anti-Her2 scFv; CD19 mutant/anti-Her2 scFv/anti-EGFR scFv; anti-EGFR scFv/anti-Her2 scFv/CD19 mutant; and/or anti-Her2 scFv/anti-EGFR scFv/CD19 mutant.

In some embodiments, an antibody targets an antigen described herein. For example, in some embodiments, an antibody targets PD-1, TIM-3, LAG-3, IDO, A2AR, TGF-beta, CD47, or another protein involved in an immunosuppressive pathway. Exemplary, nonlimiting fusion proteins can include an anti-PD1 scFv; anti-PD-L1 scFv; anti-CD39 scFv; or anti-CD73 scFv.

In some embodiments, an antibody targets one or more infectious agents. For example, an antibody can target CD163 (see, e.g., Svendsen et al., Mol. Ther.: Methods & Clin. Dev. 4:50-61 (2017)). In some embodiments, an antibody targets bacteria, such as bacterial O25b antigen (see, e.g., Guachalla et al., Antimicrob. Agents Chemother. 61:e01428-17 (2017)); one or more components of the (β-barrel assembly machine (BAM), e.g., BamA, BamB, BamC, BamD, or BamE (e.g., MAB1 antibody) (see, e.g., Storek et al., PNAS 115:3692-3697 (2018)); or *S. aureus* (e.g., an anti-*S. aureus* antibody described in Zhou et al., mAbs 8:1612-1619 (2016)).

Antibodies or fragments can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using methods described in, e.g., Morrison, 1985, Science 229: 1202, and humanized antibodies by methods described in, e.g., U.S. Pat. No. 6,180,370.

Single Domain Antibodies

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art known, or any future single domain antibodies. Single domain antibodies may be derived from any species including, but not limited to mouse, human, camel, llama, goat, rabbit, bovine. According to one aspect of the disclosure, a single domain antibody as used herein is a naturally occurring single domain antibody known as heavy chain antibody devoid of light chains. Such single domain antibodies are disclosed in, e.g., WO 94/04678. Such variable domains derived from a heavy chain antibody naturally devoid of light chain is referred to herein as a "VHH" or "nanobody". Such a VHH molecule can be derived from antibodies raised in Camelidae species, for example in camel, dromedary, llama, vicuna, alpaca and guanaco. Other species besides Camelidae (e.g., Homo sapiens) may produce heavy chain antibodies naturally devoid of light chain; such VHHs are within the scope of the disclosure.

The amino acid residues of VHH domains from Camelids are numbered according to the general numbering for VH domains given by Kabat et al., "Sequence of proteins of immunological interest", US Public Health Services, NIH (Bethesda, MD), Publication No 91-3242 (1991); see also Riechmann et al., J. Immunol. Methods 231:25-38 (1999). According to this numbering, FR1 comprises the amino acid residues at positions 1-30, CDR1 comprises the amino acid residues at positions 31-35, FR2 comprises the amino acids at positions 36-49, CDR2 comprises the amino acid residues at positions 50-65, FR3 comprises the amino acid residues at positions 66-94, CDR3 comprises the amino acid residues at positions 95-102, and FR4 comprises the amino acid residues at positions 103-113.

It should be noted, however (as is well known in the art for VH domains and for VHH domains), that the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present disclosure, claims and figures, the numbering according to Kabat and applied to VHH domains as described above will be followed, unless indicated otherwise.

Anti-CLL-1 Single Domain Antibodies

Human C-type lectin-like molecule-1 (CLL-1), also known as MICL or CLEC12A, is a type II transmembrane glycoprotein and member of the large family of C-type lectin-like receptors involved in immune regulation. CLL-1 has previously been identified from myeloid-derived cells. The intracellular domain of CLL-1 contains an immunotyrosine-based inhibition motif (ITIM) and a YXXM motif. Phosphorylation of ITIM-containing receptors on a variety of cells results in inhibition of activation pathways through recruitment of protein tyrosine phosphatases SHP-1, SHP-2 and SHIP. The YXXM motif has a potential SH2 domain-binding site for the p85 subunit of PI-3 kinase, 13 which has been implicated in cellular activation pathways, revealing a potential dual role of CLL-1 as an inhibitory and activating molecule on myeloid cells. Indeed, association of CLL-1 with SHP-1 and SHP-2 has been demonstrated experimentally in transfected and myeloid-derived cell lines.

In some embodiments, the disclosure provides fusion proteins that include a CLL-1 binding antibody that is or includes a VHH having the amino acid sequence of any one of SEQ ID Nos:203-225, or a fragment thereof (e.g., a CLL-1 binding fragment thereof). As indicated in the listing of sequences provided herein, each of SEQ ID Nos:203-225 includes VHH amino acids at the N-terminus, and the following amino acids at the C-terminus: (i) a linker of 9 amino acids (TSGPGGQGA), (ii) a myc-tag (EQKLISEEDL), (iii) a linker of 2 amino acids (GA), (iv) a hexa-histidine tag (HHHHHH), and (v) an additional 3 amino acids (GAS). Thus, in some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks one or more of (i)-(v) (and/or lacks a portion of one or more of (i)-(v)). In some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHH-GAS depicted in each of SEQ ID Nos:203-225. In some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks all of the C-terminal amino acids TSGPGGQ-GAEQKLISEEDLGAHHHHHHGAS depicted in each of SEQ ID Nos:203-225.

In some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks one or more of (i)-(v) (and/or lacks a portion of one or more of (i)-(v)), and wherein the portion lacks one or more (e.g., 1, 2, 3, 4, 5, or more), additional amino acids (i.e., other than an amino acid included in (i)-(v)). In some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHH-GAS depicted in each of SEQ ID Nos:203-225, and wherein the portion lacks one or more (e.g., 1, 2, 3, 4, 5, or more), additional amino acids. In some embodiments, the disclosure provides fusion proteins that include an antibody that is or includes a VHH having a portion (e.g., a CLL-1 binding portion) of the amino acid sequence of any one of SEQ ID Nos:203-225, wherein the portion lacks all of the C-terminal amino acids TSGPGGQGAEQKLISEEDLGAHHHHHH-GAS depicted in each of SEQ ID Nos:203-225, and wherein the portion lacks one or more (e.g., 1, 2, 3, 4, 5, or more), additional amino acids.

In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks one or more of (i)-(v) (and/or lacks a portion of one or more of (i)-(v)). In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHHGAS depicted in each of SEQ ID Nos:203-225. In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks all of the C-terminal amino acids TSGPGGQGAEQKLISEED-LGAHHHHHHGAS depicted in each of SEQ ID Nos:203-225.

In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks one or more of (i)-(v) (and/or lacks a portion of one or more of (i)-(v)), and wherein the portion lacks one or more (e.g., 1, 2, 3, 4, 5, or more), additional amino acids (i.e., other than an amino acid included in (i)-(v)). In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks one or more of the C-terminal amino acids TSGPGGQGAEQKLISEEDLGAHHHHHH-GAS depicted in each of SEQ ID Nos:203-225, and wherein the portion lacks one or more (e.g., 1, 2, 3, 4, 5, or more), additional amino acids. In some embodiments, the disclosure provides fusion proteins that include an antibody that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:203-225, wherein the portion lacks all of the C-terminal amino acids TSGPGGQGAEQKLISEEDL-GAHHHHHHGAS depicted in each of SEQ ID Nos:203-225, and wherein the portion lacks one or more (e.g., 1, 2, 3, 4, 5, or more), additional amino acids.

In some embodiments, the disclosure provides fusion proteins that include an antibody that is or includes a VHH comprising at least one CDR (e.g., CDR1, CDR2, and/or CDR3) depicted in any one of SEQ ID Nos:203-225. In some embodiments, the disclosure provides fusion proteins that include an antibody that is or includes a VHH comprising a portion of at least one CDR (e.g., CDR1, CDR2, and/or CDR3) depicted in any one of SEQ ID Nos:203-225, wherein the portion lacks 1, 2, 3, 4, 5, or more amino acids of a CDR depicted in any one of SEQ ID Nos:203-225. In some embodiments, the disclosure provides fusion proteins that include an antibody that is or includes a VHH comprising at least one CDR that is at least 85%, 90%, 91%, 92%, 93%, 94%, 95%, 96%, 97%, 98%, 99%, or 100% identical to a CDR (e.g., CDR1, CDR2, and/or CDR3) depicted in any one of SEQ ID Nos:203-225. In some embodiments, the disclosure provides fusion proteins that include an antibody that is or includes a VHH comprising an amino acid sequence that is at least 85%, 90%, 91%, 92%, 93%, 94%, 95%, 96%, 97%, 98%, 99%, or 100% identical to a portion of at least one CDR (e.g., CDR1, CDR2, and/or CDR3) depicted in any one of SEQ ID Nos:203-225, wherein the portion lacks 1, 2, 3, 4, 5, or more amino acids of a CDR depicted in any one of SEQ ID Nos:203-225.

In some embodiments, the disclosure provides fusion proteins that include an antibody that is or includes a VHH comprising CDR1, CDR2, and/or CDR3 of any one of Groups 1-13 depicted in Table 5A and/or Table 5B. In some embodiments, the disclosure provides fusion proteins that include an antibody that is or includes a VHH comprising (i) CDR1 and CDR2; (ii) CDR2 and CDR3; (iii) CDR1 and CDR3; or (iv) CDR1, CDR2, and CDR3 of any one of Groups 1-13 depicted in Table 5A and/or Table 5B (e.g., wherein the CDRs are from one particular Group, or wherein the CDRs are selected from two or more different Groups). In some embodiments, the disclosure provides an antibody that is or includes a VHH comprising CDR1, CDR2, and CDR3 of Group 1; CDR1, CDR2, and CDR3 of Group 2; CDR1, CDR2, and CDR3 of Group 3; CDR1, CDR2, and CDR3 of Group 4; CDR1, CDR2, and CDR3 of Group 5; CDR1, CDR2, and CDR3 of Group 6; CDR1, CDR2, and CDR3 of Group 7; CDR1, CDR2, and CDR3 of Group 8; CDR1, CDR2, and CDR3 of Group 9; CDR1, CDR2, and CDR3 of Group 10; CDR1, CDR2, and CDR3 of Group 11; CDR1, CDR2, and CDR3 of Group 12; or CDR1, CDR2, and CDR3 of Group 13, as depicted in Table 5A and/or Table 5B.

TABLE 5A

| Group | CDR1 | CDR2 | CDR3 |
|---|---|---|---|
| 1 | CAASGSIFAINEI | VAACASDGNTY | DANSRGNYY |
| 2 | CVVSGDTRSI | VAACASDGNTY | DANSRGNYY |
| 3 | CVASGSIRSI | VAACASDGNTY | DANSRGNYY |
| 4 | CAASGFTFNSYA | WVSDINSGGGSTN | ATELRGSDYYRGPIREYAY |
| 5 | CAASGLTFSNYA | AINWSGGTTD | AASYRLRITVVVTPDEYHY |
| 6 | CAASGFAFDDYA | WVSSISWNGGGTY | VKLVDSGWYSAYDY |
| 7 | CVVSGATSNVNA | LVAAISSGGSTS | AAQDWATEGYEYDY |
| 8 | CVVSGTMFSGKD | VATVSSDGGTD | HFLWGRHY |
| 9 | CVASGNDISGSA | VAVDAPRERPF | GPSLRTFHGREWYRPPWFTS |

TABLE 5A-continued

| Group | CDR1 | CDR2 | CDR3 |
|---|---|---|---|
| 10 | CAASGSIFSINA | VAVVSRFGETT | NARIRGNYGSRIDY |
| 11 | CVVSGNMLDLNT | LVAALGISTY | ARDYNFES |
| 12 | GSDRSINV | ITSGGTT | KADTRWGGMY |
| 13 | GRTIDNGA | INWSGGAT | ASRRGVDLRRNSYEYDY |

TABLE 5B

CDRs as identified based on IMGT numbering and ANARCI software (http://opig.stats.ox.ac.uk/webapps/sabdab-sabpred/ANARCI.php)

| Group | CDR1 | CDR2 | CDR3 |
|---|---|---|---|
| 1 | GSIFAINEINL | CASDGNT | DANSRGNYY |
| 2 | GDTRSINL | CASDGNT | DANSRGNYY |
| 3 | GSIRSINV | CASDGNT | DANSRGNYY |
| 4 | GFTFNSYA | INSGGGST | ATELRGSDYYRGPIREYAY |
| 5 | GLTFSNYA | INWSGGTT | AASYRLRITVVVTPDEYHY |
| 6 | GFAFDDYA | ISWNGGGT | VKLVDSGWYSAYDY |
| 7 | GATSNVNA | ISSGGST | AAQDWATEGYEYDY |
| 8 | GTMFSGKD | VSSDGGT | HFLWGRHY |
| 9 | GNDISGSA | VDAPRERP | GPSLRTFHGREWYRPPWFTS |
| 10 | GSIFSINA | VSRFGET | NARIRGNYGSRIDY |
| 11 | GNMLDLNT | LGIST | ARDYNFES |
| 12 | GSDRSINV | ITSGGTT | KADTRWGGMY |
| 13 | GRTIDNGA | INWSGGAT | ASRRGVDLRRNSYEYDY |

As will be understood by those of skill in the art, any such CDR sequence may be readily combined, e.g., using molecular biology techniques, with any other antibody sequences or domains provided herein or otherwise known in the art, including any framework regions, CDRs, or constant domains, or portions thereof as disclosed herein or otherwise known in the art, as may be present in an antibody or binding molecule of any format as disclosed herein or otherwise known in the art.

In some embodiments, the disclosure provides fusion proteins that include one or more anti-CLEC12a antibodies (or portions thereof), and one or more CD19 mutants described herein. For example, a fusion protein can include an anti-Clec12a scFv, a mutant CD19, and an anti-Clec12a VHH in various configurations. In another example, distinct anti-Clec12a VHH can be combined with mutant CD19 in various configurations. In another example, distinct anti-Clec12a VHH can be combined with scFv or VHH targeting one or more antigens present on myeloid leukemic cells, along with mutant CD19, in various configurations.

The binding properties of an antibody described herein to an antigen (e.g., CLL-1) can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and an antigen (e.g., CLL-1) can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of an antibody to an antigen (e.g., CLL-1). Such data can be used to compare different molecules. Information from SPR can also be used to develop structure-activity relationships (SAR). Variant amino acids at given positions can be identified that correlate with particular binding parameters, e.g., high affinity.

In certain embodiments, an antibody described herein exhibits high affinity for binding an antigen (e.g., CLL-1). In various embodiments, $K_D$ of an antibody as described herein for an antigen (e.g., CLL-1) is less than about $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$ M. In certain instances, $K_D$ of an antibody as described herein for an antigen (e.g., CLL-1) is between 0.001 and 1 nM, e.g., 0.001 nM, 0.005 nM, 0.01 nM, 0.05 nM, 0.1 nM, 0.5 nM, or 1 nM.

Scaffold Polypeptides

In some embodiments, the disclosure provides fusion proteins including a CD19 variant described herein and a scaffold polypeptide (or fragment thereof). A scaffold polypeptide (or fragment) can be selected to bind, e.g., to a tumor antigen (e.g., a tumor antigen described herein). Such scaffold polypeptides (or fragments) include, e.g., fibronectin domain (e.g., a Type III fibronectin domain), a DARPin, an adhiron, a lipocalin/anticalin, protein A, an affibody, thioredoxin, etc. For example, a fusion protein can be or include a Type III fibronectin domain-CD19 variant fusion protein.

Masked Constructs

In some embodiments, the disclosure includes a masked version of an antigen-binding protein described herein (e.g., antibody described herein). In some embodiments, a fusion protein of the disclosure includes a masked version of an antibody or antibody fragment described herein (e.g., a Probody® as described in, e.g., Sandersjoo et al. Cell. Mol. Life Sci. (2015) 72:1405-1415; US 2015/0183875; U.S. Pat. Nos. 8,513,390; and 9,120,853). In some embodiments, a masked construct comprises an antibody, or fragment thereof, a masking moiety, a cleavable moiety, and/or a linker.

In some embodiments, a masked construct comprises an antigen-binding protein (e.g., antibody, or fragment thereof) and a masking moiety. In some embodiments, a masking moiety is an amino acid sequence coupled to the antigen-binding protein, and positioned such that it reduces the protein's ability to specifically bind its target ("masking" the antigen-binding protein). In some embodiments, a masking moiety is coupled to the antigen-binding protein by way of a linker. In some embodiments, specific binding of a masked antigen-binding protein, to its target is reduced or inhibited, as compared to the specific binding of an "unmasked" antigen-binding protein, or as compared to the specific binding of the parental antigen-binding protein, to the target. In some embodiments, a masked antigen-binding protein demonstrates no measurable binding or substantially no measurable binding to the target, and/or demonstrates no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding to the target, as compared to the binding of an unmasked antigen-binding protein, or as compared to the binding of the parental antigen-binding protein to the target, e.g., for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater, e.g., when measured in vivo or in a Target Displacement in vitro immunoabsorbent assay (described in U.S. Pat. No. 8,513,390).

In some embodiments, specific binding of a masked antigen-binding protein to its target is reduced or inhibited, as compared to specific binding of the unmasked antigen-binding protein, or as compared to the specific binding of the parental antigen-binding protein to the target. The $K_d$ of the masked antigen-binding protein towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1,000-10,000,000, 10,000-100,000, 10,000-1,000,000, 10,000-10,000,000, 100,000-1,000,000, or 100,000-10,000,000 times greater than that of the unmasked antigen-binding protein, or than that of the parental antigen-binding protein. Conversely, the binding affinity of the masked antigen-binding protein towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than that of the unmasked antigen-binding protein, or than that of the parental antigen-binding protein.

Masking moieties are known in the art and include, e.g., known binding partners of antibodies, or fragments thereof. In some embodiments, a masking moiety is an amino acid sequence at the N-terminus, at the C-terminus, and/or at an internal site (e.g., an antigen binding loop) of the antigen-binding protein. In some embodiments, a masking moiety is or includes one or more pairs of cysteine residues, e.g., resulting in formation of a disulfide bond between cysteine pairs. In some such embodiments, disulfide bonds result in a conformationally constrained structure, which can be "unmasked" by cleavage of the disulfide bond by, e.g., a reducing agent. Exemplary masking moieties are described in, e.g., Sandersjoo et al. Cell. Mol. Life Sci. (2015) 72:1405-1415; US 2015/0183875; U.S. Pat. Nos. 8,513,390; and 9,120,853.

Cellular Therapeutics

In some embodiments, a nucleotide sequence encoding a CD19 variant described herein, or encoding a fusion protein comprising or consisting of a CD19 variant described herein, can be introduced into a cellular therapeutic. In some embodiments, a cellular therapeutic can be produced from an immune cell, e.g., a cell useful in or capable of use in adoptive cell therapy. In some embodiments, a cellular therapeutic is produced from a cell type selected from a group consisting of TILs, T-cells, CD8⁺ cells, CD4⁺ cells, NK-cells, delta-gamma T-cells, regulatory T-cells or peripheral blood mononuclear cells. As used herein "tumor-infiltrating lymphocytes" or TILs refer to white blood cells that have left the bloodstream and migrated into a tumor. Lymphocytes can be divided into three groups including B cells, T cells and natural killer cells. As used herein "T-cells" refers to CD3⁺ cells, including CD4⁺ helper cells, CD8⁺ cytotoxic T-cells and delta-gamma T cells.

In certain embodiments a cellular therapeutic is produced by genetically modifying (e.g., transforming) a cell, e.g., an immune cell, with a nucleic acid encoding a CD19 variant described herein, or a fusion protein comprising or consisting of a CD19 variant described herein. In some embodiments, such nucleic acid is included in a recombinant expression vector. The recombinant expression vector can comprise any type of nucleotides, including, but not limited to DNA and RNA, which can be single-stranded or double-stranded, synthesized or obtained in part from natural sources, and which can contain natural, non-natural or altered nucleotides. A recombinant expression vector can comprise naturally-occurring or non-naturally-occurring internucleotide linkages, or both types of linkages.

A recombinant expression vector can be any suitable recombinant expression vector. Suitable vectors include those designed for propagation and expansion or for expression or both, such as plasmids and viruses. For example, a vector can be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors useful in the context of the disclosure include pBI01, pBI101.2, pBI101.3, pBI121 and pBIN19 (Clontech). Examples of animal expression vectors useful in the context of the disclosure include pcDNA, pEUK-C1, pMAM, and pMAMneo (Clontech).

In some embodiments, a recombinant expression vector is a viral vector. Suitable viral vectors include, without limitation, retroviral vectors, alphaviral, vaccinial, adenoviral, adeno-associated viral, herpes viral, and fowl pox viral vectors, and preferably have a native or engineered capacity to transform an immune cell (e.g., T cell).

In ex-vivo applications such as cell therapy, gamma retroviral vectors, derived from murine leukemia virus (MLV), were developed first and are still used. Lentiviral vectors, based on human immunodeficiency virus (HIV), are widely used. The general strategy in designing lentiviral vectors is based on the deletion and alteration of the native viral sequences to prevent the generation of replication-competent viruses. Thus, the lentivirus components are segregated into three or four different plasmid constructs with the goal of preventing the possibility of complete recombination to a fully replication competent lentivirus (RCL). The viral vector genome contains at a minimum the transgene expression cassette, the long terminal repeats (LTRs), and the packaging signal. In most cases, three additional plasmids provide the factors required for virus production and packaging (e.g., gag, pol, env). The promoter-enhancer region from the 3' LTR is also deleted, preventing transcription from this region and subsequent viral replication (termed a self-inactivating vector; SIN). The essential steps of ex-vivo cell transformation or transduction involve cell isolation and culture of the desired cell type to allow the selection, expansion, and differentiation either before or after the cell has been transduced with a viral vector. In the case of hematopoietic cells, most of these steps are performed in a closed system using single-use blood collection and processing bags. For CAR T cell therapy, patient blood cells are harvested, and the desired T cell populations are selected and grown to the required levels. They are then transduced with a viral vector carrying the desired gene cassette, followed by CAR T cell expansion to the billion-cell level. Lentiviral vectors have been shown to transduce T cells efficiently and are, therefore, the preferred vector for introducing CAR into patient target cells. Expanded cells are then reintroduced into the patient.

In some embodiments a chimeric antigen receptor (CAR) that recognizes CD19 protein is expressed by a vector that has transduced a T cell. In some embodiments a CAR that recognizes CD19 protein is expressed, and a fusion protein is expressed, by a vector that has transduced a T cell. In some embodiments two vectors are used to transduce the T cell, one that expresses the CAR and one that expresses a fusion protein.

Recombinant expression vectors can be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

A recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the recombinant expression vectors include, for instance, neomycin/G418 resistance genes, puromycin resistance genes, hygromycin resistance genes, histidinol resistance genes, tetracycline resistance genes, and ampicillin resistance genes.

Vectors useful in the context of the disclosure can be "naked" nucleic acid vectors (i.e., vectors having little or no proteins, sugars, and/or lipids encapsulating them), or vectors complexed with other molecules. Other molecules that can be suitably combined with the vectors include without limitation viral coats, cationic lipids, liposomes, polyamines, gold particles, and targeting moieties such as ligands, receptors, or antibodies that target cellular molecules.

Vector DNA can be introduced into a cell, e.g., an immune cell (e.g., a T cell), via conventional transformation or transfection techniques. As used herein, the terms "transformation" and "transfection" and "transduction" are intended to refer to a variety of art-recognized techniques for introducing foreign nucleic acid (e.g., DNA) into a cell, including calcium phosphate or calcium chloride co-precipitation, DEAE-dextran-mediated transfection, lipofection, gene gun, or electroporation.

In some embodiments, a cell e.g., an immune cell (e.g., a T cell) is transduced with an integrating vector that expresses a chimeric antigen receptor (CAR) or specific T cell receptor (TCR). In some embodiments, the integrating expression vector is a lentiviral vector or a retroviral vector. In some embodiments, an expression construct is introduced using transposon technology. In some embodiments, an expression construct is introduced using electroporation, for example, of messenger RNA (mRNA). In some embodiments, the integrating vector expresses multiple elements, for example a CAR sequence and one or more additional elements. In some embodiments, additional elements include, but are not limited to fusion proteins, antibodies or fragments thereof, natural proteins, cytokines, and peptides. In some embodiments, the CAR sequence is separated from the additional element or elements by a cleavable element, for example a P2A or T2A sequence. In some embodiments, for example, an expressed product comprises a CAR19 sequence; a 2A cleavable sequence; CD19 or a domain, or variant thereof; additional element 1; additional element 2. In some embodiments, for example, an expressed product comprises CD19 or a domain, or variant thereof; additional element 1; additional element 2; a 2A cleavable sequence; and a CAR19 sequence. In some embodiments, for example, an expressed product comprises a CAR19 sequence; a 2A cleavable sequence; additional element 1; additional element 2; and CD19 or a domain, or variant thereof. In some embodiments, for example, an expressed product comprises additional element 1; CD19 or a domain, or variant thereof; additional element 2; a 2A cleavable sequence; and a CAR19 sequence.

Protein Therapeutics

In some aspects, CD19 variants, or fusion proteins comprising or consisting of CD19 variants, described herein can be produced and used as therapeutics instead of, or in addition to, being produced by a cellular therapeutic described herein. Such polypeptides can be included in a composition, e.g., a pharmaceutical composition, and used as a protein therapeutic. For example, a protein therapeutic that includes a CD19 variant can be administered in combination with a cellular therapeutic, e.g., CAR-T cell or ADC, that targets CD19.

A variety of methods of making polypeptides are known in the art and can be used to make a polypeptide to be included in a protein therapeutic. For example, a polypeptide can be recombinantly produced by utilizing a host cell system engineered to express a nucleic acid encoding the polypeptide. Recombinant expression of a gene can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and transfected cells can then be cultured by conventional techniques to produce polypeptide.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the *E. coli* expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by inclusion of appropriate transcription enhancer elements, transcription terminators, etc. (see, e.g., Bittner et al., 1987, Methods in Enzymol. 153:516-544).

In addition, a host cell strain can be chosen that modulates expression of inserted sequences, or modifies and processes the gene product in the specific fashion desired. Different host cells have characteristic and specific mechanisms for post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, e.g., BALB/c mouse myeloma line (NS0/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a protein described herein has been produced by recombinant expression, it may be purified by any method known in the art for purification, for example, by chromatography (e.g., ion exchange, affinity, and sizing column chromatography), centrifugation, differential solubility, or by any other standard technique for purification of proteins. For example, an antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a polypeptide can be fused to heterologous polypeptide sequences to facilitate purification. Alternatively or additionally, a polypeptide or fusion protein can be partially or fully prepared by chemical synthesis.

Viral Delivery

In some embodiments, a nucleic acid encoding a fusion protein described herein (e.g., a CD19 variant fusion protein described herein) can be introduced in a viral vector. In some embodiments, such a viral vector can be used to introduce a fusion protein into a cancer cell (e.g., a tumor cell). Introduction of such fusion protein can increase susceptibility to a subject's immune system and/or one or more additional therapeutic agents (see, e.g., WO2017/075533).

Vector Design

A nucleic acid sequence encoding a CD19 variant fusion protein described herein can be cloned into a number of types of vectors. For example, a nucleic acid can be cloned into a plasmid, a phagemid, a phage derivative, an animal virus, and a cosmid. Other vectors can include expression vectors, replication vectors, probe generation vectors, sequencing vectors, and viral vectors. In other examples, the vector can be a foamy viral (FV) vector, a type of retroviral vector made from spumavirus. Viral vector design and technology is well known in the art as described in Sambrook et al, (Molecular Cloning: A Laboratory Manual, 2001), and in other virology and molecular biology manuals.

Viral Transduction

Viruses are highly efficient at nucleic acid delivery to specific cell types, while often avoiding detection by the infected host immune system. These features make certain viruses attractive candidates as vehicles for introduction of cellular therapy targets into cancer cells, e.g., solid tumor cells. A number of viral based systems have been developed for gene transfer into mammalian cells. Examples of viral vectors include, but are not limited to, retroviruses, adenoviruses, adeno-associated viruses, herpes viruses, lentiviruses, poxviruses, herpes simplex 1 virus, herpes virus, oncoviruses (e.g., murine leukemia viruses), and the like. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Lentiviral and Retroviral transduction can be enhanced by the addition of polybrene (SantaCruz sc-134220; Millipore TR-1003-G; Sigma 107689), a cationic polymer (also known as hexamehtrine bromide) that is used to increase the efficiency of the retrovirus transduction.

For example, retroviruses provide a platform for gene delivery systems. Retroviruses are enveloped viruses that belong to the viral family Retroviridae. Once in a host's cell, the virus replicates by using a viral reverse transcriptase enzyme to transcribe its RNA into DNA. The retroviral DNA replicates as part of the host genome, and is referred to as a provirus. A selected gene can be inserted into a vector and packaged in retroviral particles using techniques known in the art. The recombinant virus can then be isolated and delivered to cells of the subject in vivo. A number of retroviral systems are known in the art, (see, e.g., U.S. Pat. Nos. 5,994,136, 6,165,782, and 6,428,953).

Retroviruses include the genus of Alpharetrovirus (e.g., avian leukosis virus), the genus of Betaretrovirus; (e.g., mouse mammary tumor virus) the genus of Deltaretrovirus (e.g., bovine leukemia virus and human T-lymphotropic virus), the genus of Epsilonretrovirus (e.g., Walleye dermal sarcoma virus), and the genus of Lentivirus. In some embodiments, a retrovirus is a lentivirus a genus of viruses of the Retroviridae family, e.g., characterized by a long incubation period. Lentiviruses are unique among the retroviruses in being able to infect non-dividing cells; they can deliver a significant amount of genetic information into the DNA of the host cell, so can be used as an efficient gene delivery vector. In some examples, a lentivirus can be, but not limited to, human immunodeficiency viruses (HIV-1 and HIV-2), simian immunodeficiency virus (S1V), feline immunodeficiency virus (FIV), equine infections anemia (EIA), and visna virus. Vectors derived from lentiviruses offer the means to achieve significant levels of gene transfer in vivo.

In some embodiments, a vector is an adenovirus vector. Adenoviruses are a large family of viruses containing double stranded DNA. They replicate the DNA of the host cell, while using a host's cell machinery to synthesize viral RNA DNA and proteins. Adenoviruses are known in the art to affect both replicating and non-replicating cells, to accommodate large transgenes, and to code for proteins without integrating into the host cell genome.

In some embodiments, an AAVP vector is used. An AAVP vector is a hybrid of prokaryotic-eukaryotic vectors, which are chimeras of genetic cis-elements of recombinant adeno-associated virus and phage. An AAVP combines selected elements of both phage and AAV vector systems, providing a vector that is simple to produce in bacteria and can exhibit little or no packaging limit, while allowing infection of mammalian cells combined with integration into the host chromosome. Vectors containing many of the appropriate elements are commercially available, and can be further modified by standard methodologies to include the necessary sequences. Among other things, AAVPs do not require helper viruses or trans-acting factors. In addition, the native tropism of AAV for mammalian cells is eliminated since there is not AAV capsid formation. Other methods and details are in U.S. Pat. No. 8,470,528 and Hajitou A. et al., Cell, 125: 358-398.

In some embodiments, a human papilloma (HPV) pseudovirus is used. DNA plasmids can be packaged into papillomavirus L1 and L2 capsid protein to generate pseudovirion that can efficiently deliver DNA. The encapsulation can protect the DNA from nucleases and provides a targeted delivery with a high level of stability. Many of the safety concerns associated with the use of viral vectors can be mitigated with an HPV pseudovirus. Other methods and examples are in Hung, C., et al., Plos One, 7:7(e40983); 2012, U.S. Pat. No. 8,394,411, and Kines, R., et al Int J of Cancer, 2015.

In some embodiments, an oncolytic virus is used. Oncolytic virus therapy can selectively replicate the virus in cancer cells, and can subsequently spread within a tumor, e.g., without affecting normal tissue. Alternatively, an oncolytic virus can preferentially infect and kill cells without causing damage to normal tissues. Oncolytic viruses can also effectively induce immune responses to themselves as well as to the infected tumor cell. Typically, oncolytic viruses fall into two classes: (I) viruses that naturally replicate preferentially in cancer cells and are nonpathogenic in humans. Exemplary class (I) oncolytic viruses include autonomous parvoviruses, myxoma virus (poxvirus), Newcastle disease virus (NDV; paramyxovirus), reovirus, and Seneca valley virus (picornavirus). A second class (II), includes viruses that are genetically manipulated for use as vaccine vectors, including measles virus (paramyxovirus), poliovirus (picornavirus), and vaccinia virus (poxvirus). Additionally, oncolytic viruses may include those genetically engineered with mutations/deletions in genes required for replication in normal but not in cancer cells including adenovirus, herpes simplex virus, and vesicular stomatitis virus. Oncolytic viruses can be used as a viral transduction method due to their low probability of genetic resistance because they can target multiple pathways and replicate in a tumor-selective method. The viral dose within a tumor can increase over time due to in situ viral amplification (as compared to small molecule therapies which decrease with time), and safety features can be built in (i.e., drug and immune sensitivity).

Administration

Certain embodiments of the disclosure include methods of administering to a subject a cellular therapeutic described herein (or a population thereof), a protein therapeutic described herein, a composition comprising a cellular therapeutic, and/or a composition comprising a protein therapeutic, e.g., in an amount effective to treat a subject. In some embodiments, the method effectively treats cancer in the subject.

In some embodiments a cellular therapeutic comprises an autologous cell that is administered into the same subject from which an immune cell was obtained. Alternatively, an immune cell is obtained from a subject and is transformed, e.g., transduced, with an expression construct described herein, to obtain a cellular therapeutic that is allogenically transferred into another subject.

In some embodiments, a cellular therapeutic is autologous to a subject, and the subject can be immunologically naive, immunized, diseased, or in another condition prior to isolation of an immune cell from the subject.

In some embodiments, additional steps can be performed prior to administration to a subject. For instance, a cellular therapeutic can be expanded in vitro after contacting (e.g., transducing or transfecting) an immune cell with an expression construct described herein, but prior to the administration to a subject. In vitro expansion can proceed for 1 day or more, e.g., 2 days or more, 3 days or more, 4 days or more, 6 days or more, or 8 days or more, prior to the administration to a subject. Alternatively, or in addition, in vitro expansion can proceed for 21 days or less, e.g., 18 days or less, 16 days or less, 14 days or less, 10 days or less, 7 days or less, or 5 days or less, prior to administration to a subject. For example, in vitro expansion can proceed for 1-7 days, 2-10 days, 3-5 days, or 8-14 days prior to the administration to a subject.

In some embodiments, during in vitro expansion, a cellular therapeutic can be stimulated with an antigen (e.g., a TCR antigen). Antigen specific expansion optionally can be supplemented with expansion under conditions that non-specifically stimulate lymphocyte proliferation such as, for example, anti-CD3 antibody, anti-Tac antibody, anti-CD28 antibody, or phytohemagglutinin (PHA). The expanded cellular therapeutic can be directly administered into a subject or can be frozen for future use, i.e., for subsequent administrations to a subject.

In some embodiments, a cellular therapeutic is treated ex vivo with interleukin-2 (IL-2) prior to infusion into a cancer patient, and the cancer patient is treated with IL-2 after infusion. Furthermore, in some embodiments, a cancer patient can undergo preparative lymphodepletion—the temporary ablation of the immune system—prior to administration of a cellular therapeutic. A combination of IL-2 treatment and preparative lymphodepletion can enhance persistence of a cellular therapeutic.

In some embodiments, a cellular therapeutic is transduced or transfected with a nucleic acid encoding a cytokine, which nucleic acid can be engineered to provide for constitutive, regulatable, or temporally-controlled expression of the cytokine. Suitable cytokines include, for example, cytokines which act to enhance the survival of T lymphocytes during the contraction phase, which can facilitate the formation and survival of memory T lymphocytes.

In certain embodiments, a cellular therapeutic is administered prior to, substantially simultaneously with, or after the administration of another therapeutic agent, such as a cancer therapeutic agent. The cancer therapeutic agent can be, e.g., a chemotherapeutic agent, a biological agent, or radiation treatment. In some embodiments, a subject receiving a cellular therapeutic is not administered a treatment which is sufficient to cause a depletion of immune cells, such as lymphodepleting chemotherapy or radiation therapy.

A cellular therapeutic described herein can be formed as a composition, e.g., a cellular therapeutic and a pharmaceutically acceptable carrier. In certain embodiments, a composition is a pharmaceutical composition comprising at least one cellular therapeutic described herein and a pharmaceutically acceptable carrier, diluent, and/or excipient. Pharmaceutically acceptable carriers described herein, for example, vehicles, adjuvants, excipients, and diluents, are well-known and readily available to those skilled in the art. Preferably, the pharmaceutically acceptable carrier is chemically inert to the active agent(s), e.g., a cellular therapeutic, and does not elicit any detrimental side effects or toxicity under the conditions of use.

A composition can be formulated for administration by any suitable route, such as, for example, intravenous, intratumoral, intraarterial, intramuscular, intraperitoneal, intrathecal, epidural, and/or subcutaneous administration routes. Preferably, the composition is formulated for a parenteral route of administration.

A composition suitable for parenteral administration can be an aqueous or nonaqueous, isotonic sterile injection solution, which can contain anti-oxidants, buffers, bacteriostats, and solutes, for example, that render the composition isotonic with the blood of the intended recipient. An aqueous or nonaqueous sterile suspension can contain one or more suspending agents, solubilizers, thickening agents, stabilizers, and preservatives.

Dosage administered to a subject, particularly a human, will vary with the particular embodiment, the composition employed, the method of administration, and the particular site and subject being treated. However, a dose should be sufficient to provide a therapeutic response. A clinician skilled in the art can determine the therapeutically effective amount of a composition to be administered to a human or other subject in order to treat or prevent a particular medical condition. The precise amount of the composition required to be therapeutically effective will depend upon numerous factors, e.g., such as the specific activity of the cellular therapeutic, and the route of administration, the amount of available antigen or antigens on tumor cells (e.g., as a consequence of tumor bulk or extent of tumor burder) and/or on normal cells, in addition to many subject-specific considerations, which are within those of skill in the art. In some embodiments, the appropriate dose for a cellular therapeutic for a particular cancer indication or indications can be defined in a dose-escalation clinical trial.

Any suitable number cellular therapeutic cells can be administered to a subject. While a single cellular therapeutic cell described herein is capable of expanding and providing a therapeutic benefit, in some embodiments, $10^2$ or more, e.g., $10^3$ or more, $10^4$ or more, $10^5$ or more, or $10^8$ or more, cellular therapeutic cells are administered. Alternatively, or additionally $10^{12}$ or less, e.g., $10^{11}$ or less, $10^9$ or less, $10^7$ or less, or $10^5$ or less, cellular therapeutic cells described herein are administered to a subject. In some embodiments, $10^2$-$10^5$, $10^4$-$10^7$, $10^3$-$10^9$, or $10^5$-$10^{10}$ cellular therapeutic cells described herein are administered.

A dose of a cellular therapeutic described herein can be administered to a mammal at one time or in a series of subdoses administered over a suitable period of time, e.g., on a daily, semi-weekly, weekly, bi-weekly, semi-monthly, bi-monthly, semi-annual, or annual basis, as needed. A dosage unit comprising an effective amount of a cellular therapeutic may be administered in a single daily dose, or the total daily dosage may be administered in two, three, four, or more divided doses administered daily, as needed.

A polypeptide described herein can be incorporated into a pharmaceutical composition (e.g., for use as a protein therapeutic). Pharmaceutical compositions comprising a polypeptide can be formulated by methods known to those skilled in the art (see, e.g., Remington's Pharmaceutical Sciences pp. 1447-1676 (Alfonso R. Gennaro, ed., 19th ed. 1995)). Pharmaceutical composition can be administered parenterally in the form of an injectable formulation comprising a sterile solution or suspension in water or another pharmaceutically acceptable liquid. For example, a pharmaceutical composition can be formulated by suitably combining a polypeptide with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the subject. A single dose of a pharmaceutical composition containing a polypeptide can be selected from a range of 0.001 to 1000 mg/kg of body weight. On the other hand, a dose can be selected in the range of 0.001 to 100000 mg/body weight, but the present disclosure is not limited to such ranges. Dose and method of administration can vary depending on the weight, age, condition, and the like of the subject, and can be suitably selected as needed by those skilled in the art.

Tumors

The present disclosure provides technologies useful in the treatment of any tumor. In some embodiments, a tumor is or comprises a hematologic malignancy, including but not limited to, acute lymphoblastic leukemia, acute myeloid leukemia, chronic lymphocytic leukemia, chronic myelogenous leukemia, hairy cell leukemia, AIDS-related lymphoma, Hodgkin lymphoma, non-Hodgkin lymphoma, Langerhans cell histiocytosis, multiple myeloma, or myeloproliferative neoplasms.

In some embodiments, a tumor is or comprises a solid tumor, including but not limited to breast carcinoma, a squamous cell carcinoma, a colon cancer, a head and neck cancer, ovarian cancer, a lung cancer, mesothelioma, a genitourinary cancer, a rectal cancer, a gastric cancer, or an esophageal cancer.

In some particular embodiments, a tumor is or comprises an advanced tumor, and/or a refractory tumor. In some embodiments, a tumor is characterized as advanced when certain pathologies are observed in a tumor (e.g., in a tissue sample, such as a biopsy sample, obtained from a tumor) and/or when cancer patients with such tumors are typically considered not to be candidates for conventional chemotherapy. In some embodiments, pathologies characterizing tumors as advanced can include tumor size, altered expression of genetic markers, invasion of adjacent organs and/or lymph nodes by tumor cells. In some embodiments, a tumor is characterized as refractory when patients having such a tumor are resistant to one or more known therapeutic modalities (e.g., one or more conventional chemotherapy regimens) and/or when a particular patient has demonstrated resistance (e.g., lack of responsiveness) to one or more such known therapeutic modalities.

Combination Therapy

In some embodiments, a cellular therapeutic and/or a protein therapeutic is administered in combination with a second cellular therapeutic, an antibody-drug conjugate, an antibody, and/or a polypeptide. In some embodiments, the extent of tumor targeting and/or killing by a second cellular therapeutic (e.g., CAR-T cell) is higher (e.g., additive or synergistic) than a level observed or measured in the absence of combined therapy with a cellular therapeutic or a protein therapeutic described herein.

A pharmaceutical composition comprising a cellular therapeutic and/or a protein therapeutic described herein can optionally contain, and/or be administered in combination with, one or more additional therapeutic agents, such as a cancer therapeutic agent, e.g., a chemotherapeutic agent or a biological agent. Examples of chemotherapeutic agents that can be used in combination with a cellular therapeutic described herein include platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., tamoxifen, raloxifene, leuprolide, bicaluatmide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

Examples of biological agents that can be used in the compositions and methods described herein include monoclonal antibodies (e.g., rituximab, cetuximab, panetumumab, tositumomab, trastuzumab, alemtuzumab, gemtuzumab ozogamicin, bevacizumab, catumaxomab, denosumab, obinutuzumab, ofatumumab, ramucirumab, pertuzumab, ipilimumab, nivolumab, nimotuzumab, lambrolizumab, pidilizumab, siltuximab, BMS-936559, RG7446/MPDL3280A, MEDI4736, tremelimumab, or others listed in Table 1 herein), enzymes (e.g., L-asparaginase), cytokines (e.g., interferons and interleukins), growth factors (e.g., colony stimulating factors and erythropoietin), cancer vaccines, gene therapy vectors, or any combination thereof.

In some embodiments, treatment methods described herein are performed on subjects for which other treatments of the medical condition have failed or have had less success in treatment through other means. Additionally, the treatment methods described herein can be performed in conjunction with one or more additional treatments of the medical condition. For instance, the method can comprise administering a cancer regimen, e.g., nonmyeloablative chemotherapy, surgery, hormone therapy, and/or radiation, prior to, substantially simultaneously with, or after the administration of a cellular therapeutic and/or a protein therapeutic described herein, or composition thereof. In certain embodiments, a subject to which a cellular therapeutic and/or a protein therapeutic described herein is administered can also be treated with antibiotics and/or one or more additional pharmaceutical agents.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

Exemplary amino acid and nucleotide sequences of the disclosure are listed in the following Table:

| Amino Acid SEQ ID NO: | Nucleotide SEQ ID NO: | Name | Construct# |
|---|---|---|---|
| — | 1 | Nucleotide sequence of human CD19 (extracellular domain) | — |
| 2 | — | Amino acid sequence of human CD19 (extracellular domain) | — |
| 3 | 58 | CD19 ECD N term mutant#1-EGFR Fn3 | #227 |
| 4 | 59 | CD19 ECD N term mutant#2-EGFR Fn3 | #228 |
| 5 | 60 | CD19 ECD N term mutant#3-EGFR Fn3 | #229 |
| 6 | 61 | CD19 ECD N term mutant#-EGFR Fn3 | #230 |
| 7 | 62 | CD19 D1 + 2-EGFR Fn3 | #160 |
| 8 | 63 | CD19 ECD N term mutant #2-Trastuzumab scFv | #311 |
| 9 | 64 | CD19 D1 + 2-Trastuzumab scFv (VH/VL) | #42 |
| 10 | 65 | Trastuzumab scFv-CD19 D1 + 2 C term mutant #2 | #263 |
| 11 | 66 | Trastuzumab scFv-CD19 D1 + 2 C term mutant #7 | #264 |
| 12 | 67 | Trastuzumab scFv-CD19 D1 + 2 C term mutant #11 | #265 |
| 13 | 68 | anti-CD20 scFv-CD19 D1 + 2 C term mutant #2 | #302 |
| 14 | 69 | CD19 D1 + 2-anti-CD20 scFv (VH/VL) | #83 |
| 15 | 70 | Cetuximab scFv-CD19 D1 + 2 C term mutant #2 | #307 |
| 16 | 71 | Cetuximab scFv-CD19 D1 + 2 C term mutant #11 | #308 |
| 17 | 72 | Masked Cetuximab scFv-CD19 D1 + 2 C term mutant #2 | #309 |
| 18 | 73 | Masked Cetuximab scFv-CD19 D1 + 2 C term mutant #11 | #310 |
| 19 | 74 | Masked Cetuximab scFv-CD19 D1 + 2 C term mutant #2-Trastuzumab scFv | #354 |
| 20 | 75 | Trastuzumab light chain-CD19 D1 + 2 C term mutant #2 | #375 |
| 21 | 76 | Trastuzumab heavy chain | #376 |
| 22 | 77 | Rituximab light chain-CD19 D1 + 2 C term mutant #2 | #377 |
| 23 | 78 | Rituximab heavy chain | #378 |
| 24 | 79 | Trastuzumab heavy chain with N297A glycosylation mutation | #393 |
| 25 | 80 | Rituximab heavy chain with N297A glycosylation mutation | #394 |
| 26 | 81 | CD19 ECD N term mutant #2-G4Sx4-anti CLEC12a VHH 1B12-His | #321 |
| 27 | 82 | anti-CLEC12a VHH 2H3-CD19 D1 + 2 C term mutant #2 | #330 |
| 28 | 83 | anti-CLEC12a VHH 1812-G4Sx4-CD19 D1 + 2 C term mutant #2-His | #327 |
| 29 | 84 | anti-CLEC12a VHH 1B1-G4Sx4-CD19 D1 + 2 C term mutant #2-His | #338 |
| 30 | 85 | anti-CLEC12a VHH 1A10-CD19 D1 + 2 C term mutant #2 | #337 |
| 31 | 86 | CD19 D1 + 2 N term mutant #2-Trastuzumab scFv | #340 |
| 32 | 87 | CD19 ECD N term mutant #2-anti-CD20 scFv | #283 |

-continued

| Amino Acid SEQ ID NO: | Nucleotide SEQ ID NO: | Name | Construct# |
|---|---|---|---|
| 33 | 88 | CD19 ECD N term mutant#2-CD20 Fn3 | #232 |
| 34 | 89 | CD19 ECD N term mutant#4-CD20 Fn3 | #234 |
| 35 | 90 | Trastuzumab scFv-CD19 ECD N term Hackel mutant #2 | #235 |
| 36 | 91 | LY2875358 heavy chain | #7 |
| 37 | 92 | LY2875358 light chain-CD19 D1 + 2 | #38 |
| 38 | 93 | Trastuzumab scFv (VH/VL)-CD19 D1 + 2 | #40 |
| 39 | 94 | CD19 mutant #2-G4Sx4-anti CLEC12a VHH 1G6-myc-His | #289 |
| 40 | 95 | CD19 mutant #2-G4Sx4-anti CLEC12a VHH 1H1-His | #290 |
| 41 | 96 | CD19 mutant #2-G4Sx4-anti CLEC12a VHH 2F3-myc-His | #291 |
| 42 | 97 | CD19 mutant #2-G4Sx4-anti CLEC12a VHH 2H3-myc-His | #292 |
| 43 | 98 | CD19 mutant #2-G4Sx4-anti CLEC12a VHH 2F5-myc-His | #293 |
| 44 | 99 | CD19 mutant #2-G4Sx4-anti CLEC12a VHH 1B11 myc His | #320 |
| 45 | 100 | CD19 mutant #2-G4Sx4-anti CLEC12a VHH 2C2-His | #323 |
| 46 | 101 | anti CLEC12a VHH 1H1-G4Sx4-CD19 C-term mutant #2-His | #328 |
| 47 | 102 | anti CLEC12a VHH 2F5-G4Sx4-CD19 C-term mutant #2-His | #329 |
| 48 | 103 | anti CLEC12a VHH 2C2-G4Sx4-CD19 C-term mutant #2-His | #331 |
| 49 | 104 | CD19 mutant #2-G4Sx4-anti CLEC12a VHH 1A10-His | #333 |
| 50 | 105 | CD19 mutant #2-G4Sx4-anti CLEC12a VHH 1B1-His | #334 |
| 51 | 106 | CD19 mutant #2-G4Sx4-anti CLEC12a VHH 2C8-His | #335 |
| 52 | 107 | CD19 domains 1 + 2-G4Sx4 Wiersma anti CLL1 VH-G4Sx4-VL-His | #186 |
| 53 | 108 | CLEC12a scFv (#186)-G4S-CLEC12aVHH (2H3)-G4S-CD19 (#330) | #357 |
| 54 | 109 | lentiviral vector encoding CAR19 as a P2A fusion with construct #186 | #221 |
| 55 | 110 | lentiviral vector encoding CAR19 as a P2A fusion with CD19-anti-HER2 scFv | #142 |
| 56 | 111 | lentiviral vector encoding CAR19 as a P2A fusion with CD19-G4S-anti-BCMA scFv (VH-linker-VL)-his | #173 |
| 57 | 112 | lentiviral vector encoding CAR19 as a P2A fusion with CD19-G4S-anti-CD20 leu16 scFv (VH-linker-VL)-his | #174 |

The disclosure is further illustrated by the following examples. The examples are provided for illustrative purposes only and are not to be construed as limiting the scope or content of the disclosure in any way.

EXAMPLES

Example 1

CD19 Combinatorial Library

An extracellular domain of CD19 (hereafter referred to as CD19; SEQ ID NO:2) with improved structural integrity was identified from combinatorial libraries via selections using yeast surface display (Boder et al., Nat. Biotechnol. 15: 553-557 (1997)) and fluorescence-activated cell sorting (Chao et al., Nat. Protoc. 1:755-768 (2006)). Two combinatorial libraries were created. In the first library, every amino acid was independently diversified to all twenty canonical amino acids; i.e., all single-residue mutations were included. The lone exceptions were L165 and S166, which were excluded from diversification, and S164, which was diversified to 15 amino acids using an NNC degenerate codon, both as a requirement of including a nicking endonuclease recognition DNA sequence within the protein-encoding gene sequence. In the second library, select combinations of two or three amino acids were simultaneously mutated to identify additive and synergistic mutations (FIG. 2).

Mutant CD19 genes were generated using nicking mutagenesis (Wrenbeck et al., Nat. Methods 13:928-930 (2016)) with NNK codons at each diversified site, introduced into a pCT-Aga2p-CD19-MYC yeast display vector, and transformed into yeast. The single and triple mutation libraries were split into three and two pools, respectively, based on the location of their diversification to enable their mutations to be identified via Illumina deep sequencing (which is incapable of efficiently sequencing the entire CD19 gene in one read). Single 1 corresponds to sites 1P to 92W of SEQ ID NO:2. Single 2 corresponds to sites 93T to 156P of SEQ ID NO:2. Single 3 corresponds to sites 157P to 272K of SEQ ID NO:2. Triple 1 corresponds to sets in domain 1 (first 15 rows in FIG. 2), and Triple 2 corresponds to sets in domain 2 (latter 12 rows in FIG. 2). $10^5$ to $10^6$ unique ligation transformants were obtained for each library, which provided 29-98 fold oversampling of possible sequences in singlet libraries and 1.1-2.4 fold oversampling of triplet libraries.

CD19 variants were identified from each library via three modes of selection: (1) ability to bind conformationally-dependent antibodies FMC63 and 4G7; (2) resistance to cleavage upon exposure to Proteinase K; and (3) extent of yeast surface display upon induction under thermal stress (37° C.), as described in Examples 2-4.

Example 2

Antibody Binding

Figure 3:
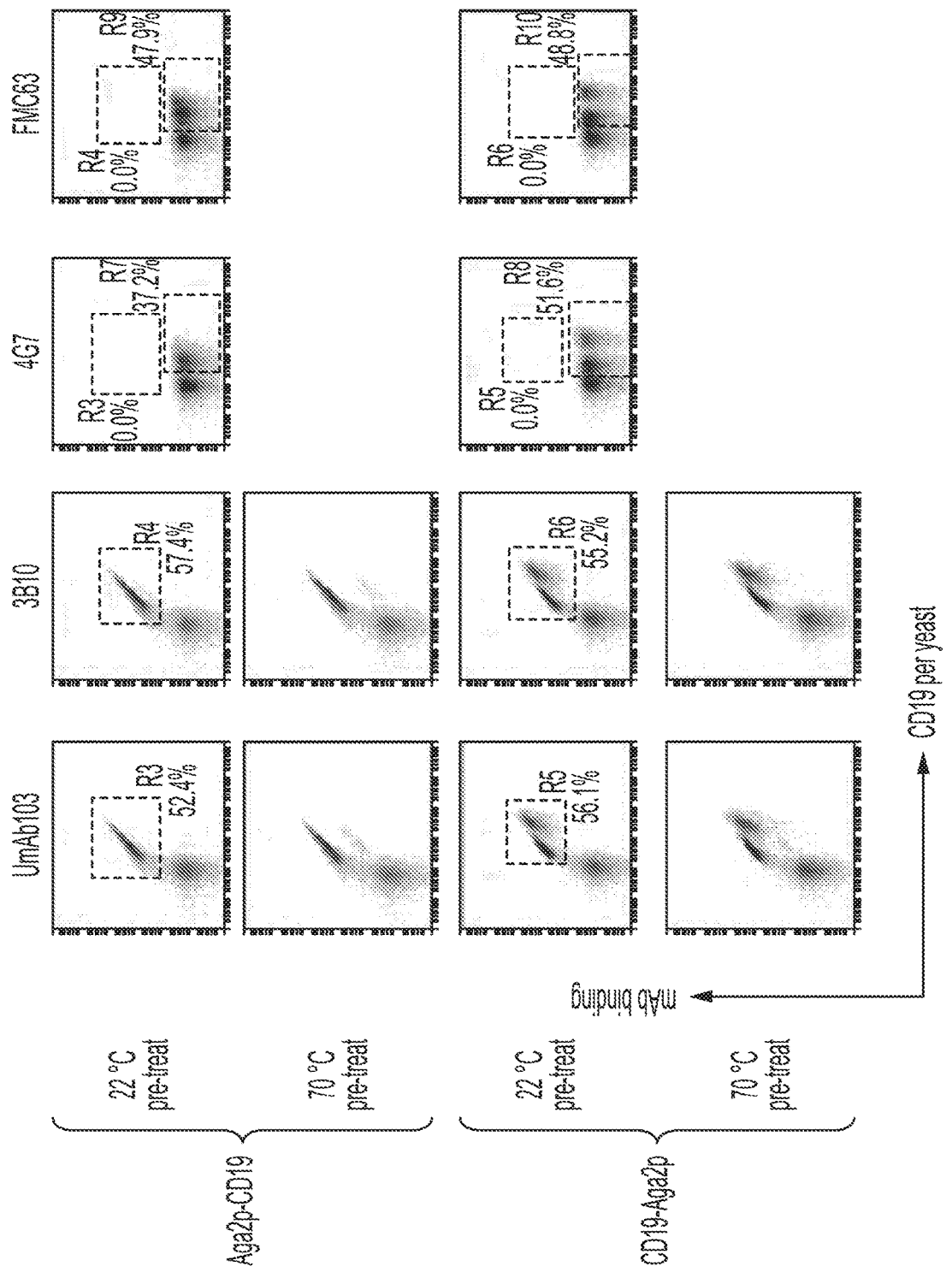
FIG. 3 depicts analysis of antibody binding to yeast-displayed wild-type CD19 by flow cytometry. Yeast were induced to display CD19 as a C-terminal (upper) or N-terminal (lower) fusion to Aga2p. Yeast with displayed CD19 were maintained at room temperature or incubated at 70° C. for 30 minutes, then chilled and labeled with the indicated antibody and an anti-cMYC antibody to detect full-length CD19 display. Binding was detected with secondary antibodies via flow cytometry.

Antibodies FMC63 and 4G7 were shown to bind wild-type CD19 produced in mammalian cell culture but not yeast-displayed wild-type CD19 (FIG. 3). In contrast, antibodies UmAb103 and 3B10 did effectively bind yeast-displayed wild-type CD19 (FIG. 3). Notably, UmAb103 and 3B10 were able to bind yeast-displayed wild-type CD19 even after elevated thermal treatment of CD19 (FIG. 3). These results suggest that UmAb103 and 3B10 bind non-conformational epitopes, which are readily presented on yeast-displayed wild-type CD19, whereas FMC63 and 4G7 bind epitopes that are not appropriately recapitulated on the yeast-displayed version of wild-type CD19.

Figure 4:
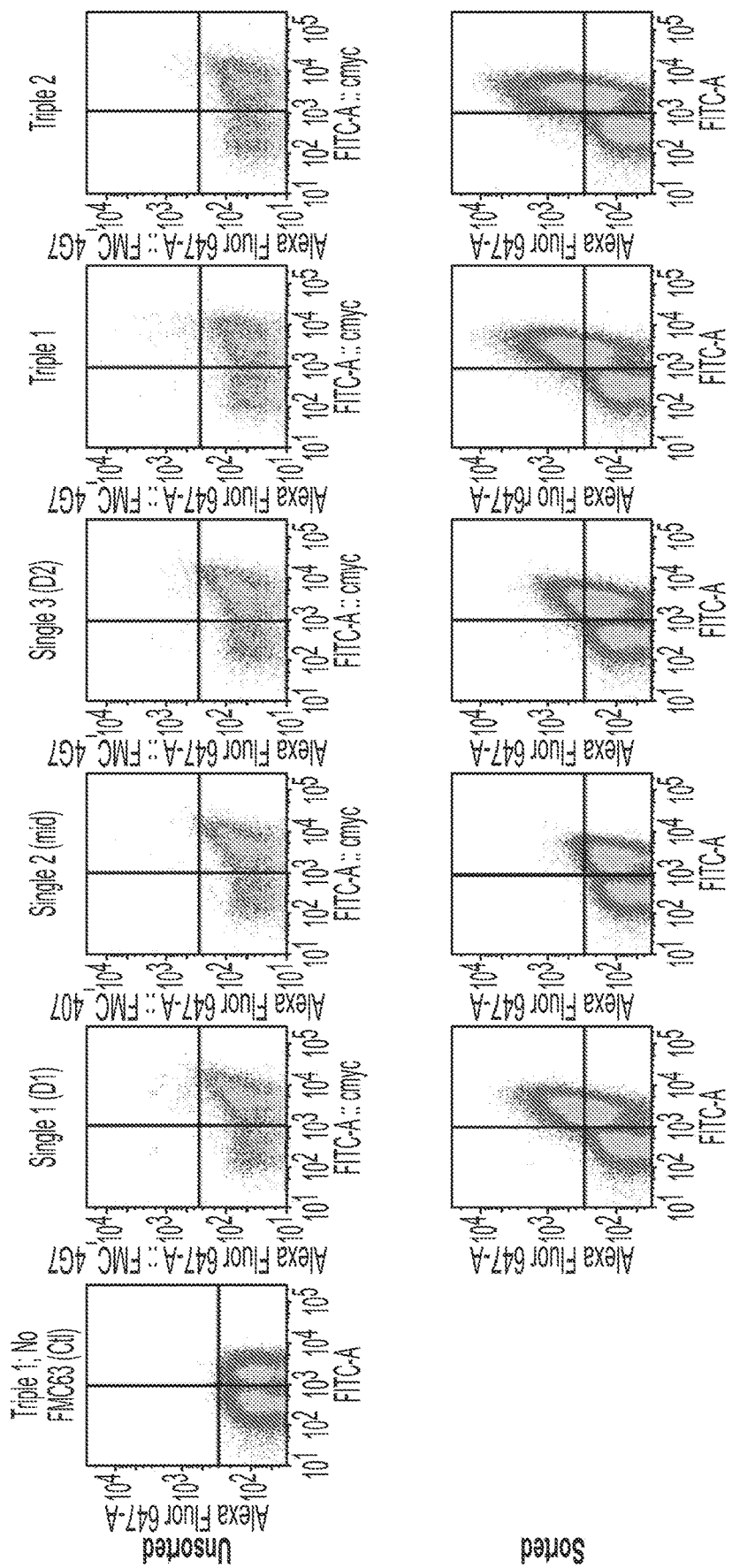
FIG. 4 depicts analysis of CD19 variants evolved to bind antibodies FMC63 by flow cytometry. Yeast displaying the indicated combinatorial library (unsorted or enriched for FMC63 binding) were incubated with FMC63 and FITC-conjugated anti-cMYC antibody (to label the C-terminal epitope to indicate full-length CD19) followed by anti-mouse-AlexaFluor647 and evaluated by flow cytometry.
Figure 6:
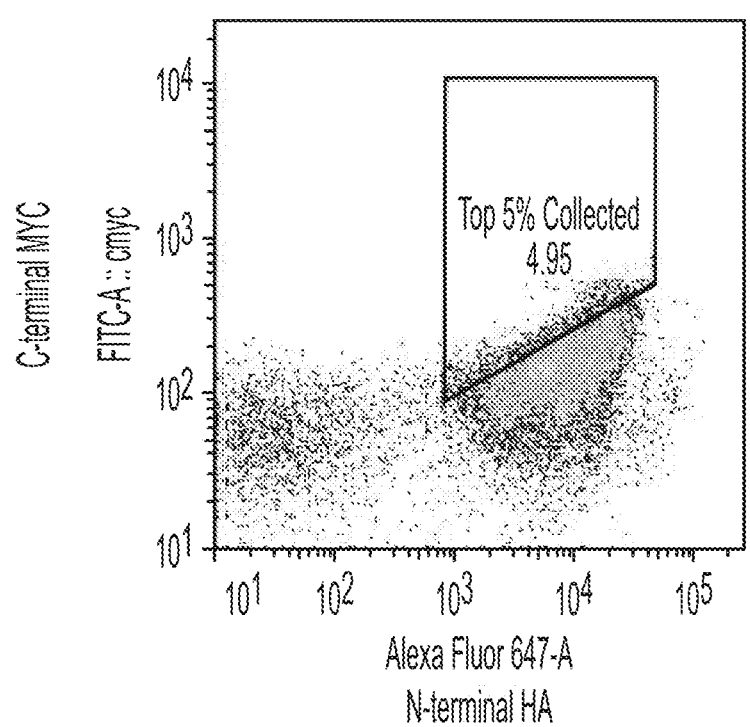
FIG. 6 depicts analysis of selection of improved CD19 variants by flow cytometry. Yeast displaying CD19 libraries were incubated with the 0.002 units proteinase K in PBSA for 10 min. at 37° C. Yeast were washed, and the N-terminal HA and C-terminal MYC epitopes were labeled with antibodies and evaluated by flow cytometry. Variants with the highest MYC/HA ratio were collected.

Thus, CD19 variants that regain binding to FMC63 and/or 4G7 were identified as structurally improved CD19 variants. Functional mutants were rare, but present, in the unsorted libraries (FIG. 4). Flow cytometric sorting isolated these improved variants (FIG. 4), which were identified via Illumina MiSeq deep sequencing. Statistical analysis revealed variants that were significantly enriched (Table 1A and Table 1B).

TABLE 1A

Single mutants with improved binding to FMC63 and 4G7: Single Mutants

| FMC63 Binding | | | | 4G7 Binding | | | |
|---|---|---|---|---|---|---|---|
| Location | WT | Mutation | Score | Location | WT | Mutation | Score |
| 264 | W | N | 9. ± 1.3 | 59 | L | N | 13.5 ± 2.9 |
| 262 | W | D | 8.3 ± .8 | 59 | L | G | 10.6 ± .3 |
| 262 | W | K | 8.2 ± .7 | 59 | L | E | 10.6 ± .5 |
| 264 | W | S | 7.6 ± .5 | 59 | L | D | 10.9 ± .8 |
| 262 | W | R | 7.4 ± .3 | 59 | L | S | 10.1 ± .4 |
| 264 | W | P | 8.6 ± 1.5 | 62 | W | E | 10. ± .7 |
| 228 | L | V | 7.4 ± .4 | 57 | R | D | 10.1 ± .9 |
| 264 | W | K | 8. ± 1. | 57 | R | T | 9.6 ± .6 |
| 264 | W | G | 7.2 ± .3 | 59 | L | H | 9.6 ± .6 |
| 260 | V | K | 7.5 ± .7 | 16 | V | F | 9.8 ± 1. |
| 262 | W | P | 7.4 ± .7 | 62 | W | D | 10.8 ± 2. |
| 226 | G | T | 7.3 ± .6 | 64 | F | V | 8.9 ± .4 |
| 262 | W | S | 7. ± .3 | 57 | R | S | 8.8 ± .4 |
| 264 | W | Q | 7.4 ± .8 | 56 | M | I | 8.8 ± .5 |

TABLE 1A-continued

Single mutants with improved binding to FMC63 and 4G7: Single Mutants

| FMC63 Binding | | | | 4G7 Binding | | | |
|---|---|---|---|---|---|---|---|
| Location | WT | Mutation | Score | Location | WT | Mutation | Score |
| 262 | W | E | 6.9 ± .3 | 31 | L | I | 8.9 ± .6 |
| 264 | W | R | 6.9 ± .3 | 59 | L | K | 9.5 ± 1.3 |
| 260 | V | R | 6.7 ± .3 | 64 | F | G | 8.4 ± .2 |
| 262 | W | A | 6.9 ± .5 | 39 | L | D | 8.5 ± .5 |
| 264 | W | T | 7.2 ± .8 | 59 | L | Q | 8.5 ± .5 |
| 223 | M | T | 6.7 ± .4 | 59 | L | T | 8.8 ± .9 |
| 243 | H | T | 7.1 ± .9 | 57 | R | G | 8.1 ± .2 |
| 262 | W | Q | 6.8 ± .6 | 20 | L | G | 8.1 ± .2 |
| 212 | K | S | 6.8 ± .6 | 14 | N | T | 8.3 ± .5 |
| 262 | W | G | 6.4 ± .2 | 45 | L | Y | 9. ± 1.2 |
| 59 | L | G | 6.5 ± .3 | 64 | F | T | 8.8 ± 1.3 |
| 232 | A | V | 6.3 ± .2 | 57 | R | E | 8.2 ± .7 |
| 240 | Y | W | 6.3 ± .3 | 66 | F | R | 7.8 ± .3 |
| 16 | V | F | 7. ± 1. | 66 | F | K | 8.2 ± .8 |
| 215 | R | W | 7.1 ± 1.1 | 18 | Q | P | 7.6 ± .5 |
| 255 | I | V | 6.4 ± .4 | 55 | H | F | 8.2 ± 1.3 |
| 269 | G | I | 6.7 ± .8 | 64 | F | A | 7.2 ± .4 |
| 59 | L | S | 6.4 ± .4 | 16 | V | Y | 8.2 ± 1.5 |
| 59 | L | E | 6.3 ± .5 | 55 | H | L | 7.1 ± .5 |
| 262 | W | H | 6.7 ± 1. | 59 | L | A | 7.1 ± .5 |
| 226 | G | S | 6.1 ± .4 | 56 | M | V | 6.8 ± .3 |
| 264 | W | A | 6.3 ± .5 | 57 | R | N | 8.3 ± 2.1 |
| 64 | F | G | 6. ± .2 | 20 | L | P | 6.5 ± .3 |
| 66 | F | R | 6. ± .3 | 31 | L | V | 6.2 ± .3 |
| 269 | G | L | 6.1 ± .4 | 55 | H | Y | 6.4 ± .5 |
| 62 | W | E | 6.4 ± .7 | 64 | F | E | 6.4 ± .6 |
| 16 | V | W | 6.7 ± 1. | 262 | W | D | 6.6 ± .8 |
| 257 | A | R | 6.1 ± .5 | 262 | W | K | 6.5 ± .7 |
| 264 | W | D | 6.2 ± .6 | 55 | H | V | 6.1 ± .3 |
| 261 | L | K | 6.2 ± .6 | 262 | W | R | 5.9 ± .3 |
| 64 | F | V | 6. ± .4 | 264 | W | K | 6.6 ± 1. |
| 257 | A | K | 6.1 ± .5 | 66 | F | A | 6. ± .4 |
| 260 | V | S | 5.8 ± .3 | 64 | F | Q | 6.1 ± .6 |
| 212 | K | A | 6.1 ± .6 | 262 | W | S | 5.8 ± .3 |
| 57 | R | G | 5.7 ± .2 | 262 | W | P | 6. ± .7 |
| 20 | L | G | 5.7 ± .2 | 66 | F | T | 6.2 ± .8 |

TABLE 1B

Triple mutants with improved binding to FMC63 and 4G7: Triple Mutants

| FMC63 Binding | | | | 4G7 Binding | | | |
|---|---|---|---|---|---|---|---|
| Location | WT | Mutations | Score | Location | WT | Mutations | Score |
| 62, 64, 66 | W, F, F | S, V, S | 15.4 ± 2.8 | 224, 226, 228 | E, G, L | D, N, F | 12.2 ± 2.4 |
| 62, 64, 66 | W, F, F | G, V, R | 14.1 ± 1.9 | 224, 226, 228 | E, G, L | G, S, M | 13. ± 3.3 |
| 62, 64, 66 | W, F, F | S, R, R | 13.7 ± 1.9 | 224, 226, 228 | E, G, L | G, R, I | 11.6 ± 1.9 |
| 62, 64, 66 | W, F, F | T, V, P | 16.6 ± 5.5 | 224, 226, 228 | E, G, L | G, S, L | 12.9 ± 3.3 |
| 224, 226, 228 | E, G, L | G, R, F | 12.8 ± 1.7 | 224, 226, 228 | E, G, L | G, T, V | 11.9 ± 2.4 |
| 62, 64, 66 | W, F, F | S, R, S | 13.2 ± 2.1 | 224, 226, 228 | E, G, L | E, A, I | 12.8 ± 3.3 |
| 62, 64, 66 | W, F, F | E, R, P | 16.5 ± 5.5 | 224, 226, 228 | E, G, L | E, N, V | 11.3 ± 1.9 |
| 62, 64, 66 | W, F, F | E, W, R | 14.2 ± 3.2 | 224, 226, 228 | E, G, L | G, A, T | 11.6 ± 2.4 |
| 62, 64, 66 | W, F, F | E, V, V | 13.4 ± 2.5 | 224, 226, 228 | E, G, L | G, E, V | 10.2 ± .9 |
| 224, 226, 228 | E, G, L | G, E, I | 14.3 ± 3.4 | 224, 226, 228 | E, G, L | G, A, V | 10. ± .8 |
| 62, 64, 66 | W, F, F | D, L, P | 16.3 ± 5.5 | 224, 226, 228 | E, G, L | G, R, Y | 11.5 ± 2.4 |
| 224, 226, 228 | E, G, L | G, D, V | 12. ± 1.2 | 224, 226, 228 | E, G, L | G, T, I | 10.2 ± 1.1 |
| 62, 64, 66 | W, F, F | A, R, L | 13.1 ± 2.3 | 224, 226, 228 | E, G, L | E, R, V | 10.5 ± 1.4 |
| 62, 64, 66 | W, F, F | W, S, S | 14. ± 3.2 | 224, 226, 228 | E, G, L | G, D, V | 10.3 ± 1.2 |
| 62, 64, 66 | W, F, F | T, R, Q | 16.3 ± 5.5 | 224, 226, 228 | E, G, L | G, R, F | 10.6 ± 1.7 |
| 62, 64, 66 | W, F, F | R, V, R | 12.3 ± 1.6 | 224, 226, 228 | E, G, L | E, S, V | 9.9 ± 1. |
| 59, 61, 63 | L, I, L | N, V, L | 13.9 ± 3.2 | 224, 226, 228 | E, G, L | G, R, V | 9.8 ± .9 |
| 62, 64, 66 | W, F, F | E, E, V | 16.2 ± 5.5 | 224, 226, 228 | E, G, L | G, R, L | 9.6 ± .7 |
| 62, 64, 66 | W, F, F | Y, S, R | 13.7 ± 3.2 | 224, 226, 228 | E, G, L | D, A, W | 12.2 ± 3.3 |
| 62, 64, 66 | W, F, F | D, V, M | 16. ± 5.6 | 219, 221, 223 | D, W, M | E, I, W | 12.2 ± 3.3 |
| 62, 64, 66 | W, F, F | W, V, A | 13.7 ± 3.2 | 224, 226, 228 | E, G, L | G, T, E | 10.4 ± 1.7 |
| 62, 64, 66 | W, F, F | T, V, F | 13.6 ± 3.2 | 224, 226, 228 | E, G, L | D, A, V | 12.1 ± 3.3 |
| 224, 226, 228 | E, G, L | E, E, V | 11.6 ± 1.2 | 224, 226, 228 | E, G, L | G, S, V | 9.8 ± 1.1 |

TABLE 1B-continued

| Triple mutants with improved binding to FMC63 and 4G7: Triple Mutants | | | | | | | |
|---|---|---|---|---|---|---|---|
| FMC63 Binding | | | | 4G7 Binding | | | |
| Location | WT | Mutations | Score | Location | WT | Mutations | Score |
| 62, 64, 66 | W, F, F | R, A, F | 15.9 ± 5.6 | 224, 226, 228 | E, G, L | G, N, L | 10.3 ± 1.7 |
| 224, 226, 228 | E, G, L | G, S, M | 13.8 ± 3.4 | 224, 226, 228 | E, G, L | G, G, I | 9.8 ± 1.1 |
| 224, 226, 228 | E, G, L | D, V, V | 13.8 ± 3.4 | 224, 226, 228 | E, G, L | G, V, V | 9.6 ± 1. |
| 62, 64, 66 | W, F, F | E, C, S | 12.6 ± 2.3 | 224, 226, 228 | E, G, L | G, D, L | 9.8 ± 1.3 |
| 62, 64, 66 | W, F, F | E, R, R | 12.4 ± 2.1 | 224, 226, 228 | E, G, L | G, R, M | 9.7 ± 1.2 |
| 62, 64, 66 | W, F, F | D, V, R | 12.6 ± 2.3 | 224, 226, 228 | E, G, L | G, N, T | 11.9 ± 3.3 |
| 224, 226, 228 | E, G, L | G, A, T | 12.7 ± 2.4 | 224, 226, 228 | E, G, L | G, E, H | 9.8 ± 1.4 |
| 62, 64, 66 | W, F, F | S, V, A | 13.5 ± 3.2 | 224, 226, 228 | E, G, L | D, R, L | 9.9 ± 1.5 |
| 224, 226, 228 | E, G, L | G, V, V | 11.2 ± 1. | 224, 226, 228 | E, G, L | G, D, C | 11.6 ± 3.3 |
| 62, 64, 66 | W, F, F | T, A, S | 15.7 ± 5.6 | 224, 226, 228 | E, G, L | E, T, V | 10. ± 1.7 |
| 62, 64, 66 | W, F, F | H, F, R | 12.4 ± 2.3 | 224, 226, 228 | E, G, L | G, E, I | 11.6 ± 3.3 |
| 224, 226, 228 | E, G, L | G, R, V | 11. ± .9 | 224, 226, 228 | E, G, L | G, A, H | 11.6 ± 3.3 |
| 62, 64, 66 | W, F, F | T, V, R | 12.2 ± 2.1 | 224, 226, 228 | E, G, L | G, E, R | 9.1 ± 1. |
| 62, 64, 66 | W, F, F | T, M, S | 15.7 ± 5.6 | 224, 226, 228 | E, G, L | D, L, I | 9.4 ± 1.3 |
| 224, 226, 228 | E, G, L | G, S, V | 11.2 ± 1.1 | 224, 226, 228 | E, G, L | G, Y, V | 11.4 ± 3.3 |
| 62, 64, 66 | W, F, F | S, V, R | 11.8 ± 1.7 | 224, 226, 228 | E, G, L | G, M, V | 11.4 ± 3.3 |
| 62, 64, 66 | W, F, F | H, V, S | 14. ± 4. | 224, 226, 228 | E, G, L | G, S, I | 11.3 ± 3.3 |
| 224, 226, 228 | E, G, L | G, G, I | 11.2 ± 1.2 | 224, 226, 228 | E, G, L | G, K, M | 11.3 ± 3.3 |
| 59, 61, 63 | L, I, L | N, I, I | 15.6 ± 5.6 | 224, 226, 228 | E, G, L | G, S, G | 8.7 ± .8 |
| 62, 64, 66 | W, F, F | S, F, N | 15.6 ± 5.6 | 224, 226, 228 | E, G, L | D, L, V | 11.2 ± 3.3 |
| 62, 64, 66 | W, F, F | N, L, P | 15.6 ± 5.6 | 224, 226, 228 | E, G, L | G, C, V | 9. ± 1.1 |
| 62, 64, 66 | W, F, F | D, V, S | 13.3 ± 3.2 | 224, 226, 228 | E, G, L | G, E, W | 9. ± 1.1 |
| 224, 226, 228 | E, G, L | G, A, V | 10.8 ± .8 | 224, 226, 228 | E, G, L | G, Q, M | 11.2 ± 3.3 |
| 62, 64, 66 | W, F, F | W, T, A | 13.9 ± 4. | 224, 226, 228 | E, G, L | D, Y, T | 9.7 ± 1.9 |
| 62, 64, 66 | W, F, F | D, A, S | 15.5 ± 5.6 | 219, 221, 223 | D, W, M | E, V, N | 11.1 ± 3.3 |
| 224, 226, 228 | E, G, L | G, R, I | 12. ± 2. | 224, 226, 228 | E, G, L | G, A, M | 8.9 ± 1.2 |
| 62, 64, 66 | W, F, F | G, V, K | 12.3 ± 2.3 | 219, 221, 223 | D, W, M | E, I, D | 9.6 ± 1.9 |

Example 3

Protease Resistance

Treatment of yeast-displayed wild-type CD19 with Proteinase K resulted in partial cleavage of the protein, dependent upon time of incubation, protease concentration, and CD19 stability. This can be readily measured by reduction in C-terminal MYC epitope signal while relatively maintaining N-terminal HA epitope signal (FIG. 5). The single- and triple-mutant combinatorial libraries were sorted to identify mutants with improved resistance to Proteinase K cleavage (FIG. 6). Illumina MiSeq deep sequencing revealed isolated improved variants (Table 2A and Table 2B).

TABLE 2A

| Single mutants with improved resistance to proteolysis Single Mutants | | | | | | | |
|---|---|---|---|---|---|---|---|
| Protease Stability-High | | | | Protease Stability-Low | | | |
| Location | WT | Mutation | Score | Location | WT | Mutation | Score |
| 132 | L | Q | 9.9 ± 2.1 | 149 | E | Y | 9.5 ± 3. |
| 261 | L | F | 9.7 ± 2.9 | 141 | A | I | 9.3 ± 3. |
| 149 | E | Y | 9. ± 3. | 209 | L | T | 7.5 ± 2.1 |
| 127 | S | Q | 8.1 ± 2.1 | 113 | L | C | 7.5 ± 2.2 |
| 130 | G | Q | 8.1 ± 2.1 | 9 | V | N | 7.8 ± 3. |
| 211 | L | T | 7.9 ± 2.1 | 122 | S | N | 6.1 ± 1.5 |
| 225 | T | Y | 8.7 ± 2.9 | 217 | A | W | 6.4 ± 1.7 |
| 209 | L | T | 7.9 ± 2.1 | 252 | H | M | 7.5 ± 3. |
| 140 | W | H | 7.6 ± 2.2 | 196 | T | M | 7.4 ± 3. |
| 125 | P | N | 6.5 ± 1.5 | 58 | P | Q | 7.4 ± 3. |
| 100 | G | D | 5.7 ± .9 | 72 | M | E | 7.4 ± 3. |
| 223 | M | F | 7.6 ± 3. | 258 | R | Y | 6.4 ± 2.1 |
| 250 | S | N | 7.6 ± 3. | 70 | Q | T | 7.2 ± 3. |
| 198 | V | Y | 6.3 ± 1.8 | 220 | M | C | 5.7 ± 1.5 |

TABLE 2A-continued

| Single mutants with improved resistance to proteolysis Single Mutants | | | | | | | |
|---|---|---|---|---|---|---|---|
| Protease Stability-High | | | | Protease Stability-Low | | | |
| Location | WT | Mutation | Score | Location | WT | Mutation | Score |
| 108 | S | H | 5.7 ± 1.3 | 256 | T | D | 6.3 ± 2.1 |
| 217 | A | W | 6.1 ± 1.8 | 235 | Q | Y | 7.1 ± 3. |
| 193 | L | Q | 5.4 ± 1.2 | 257 | A | I | 7.1 ± 3. |
| 54 | I | K | 5.9 ± 1.7 | 261 | L | T | 7.1 ± 3. |
| 123 | E | Y | 4.9 ± 1. | 13 | D | M | 7.1 ± 3. |
| 256 | T | D | 6.1 ± 2.2 | 32 | T | H | 7.1 ± 3. |
| 262 | W | K | 6.1 ± 2.2 | 53 | G | K | 7.1 ± 3. |
| 141 | A | Y | 5.2 ± 1.2 | 54 | I | K | 5.8 ± 1.7 |
| 143 | D | M | 4.6 ± .6 | 11 | E | F | 5.5 ± 1.5 |
| 130 | G | D | 4.9 ± 1. | 194 | S | I | 5.7 ± 1.8 |
| 143 | D | N | 4.9 ± 1. | 2 | E | H | 6.1 ± 2.1 |
| 194 | S | W | 5.4 ± 1.5 | 28 | T | H | 6.9 ± 3. |
| 100 | G | M | 5.7 ± 1.8 | 271 | W | H | 5.6 ± 1.8 |
| 202 | G | M | 6. ± 2.2 | 204 | K | P | 6.8 ± 3. |
| 70 | Q | T | 6.7 ± 3. | 84 | S | H | 5.5 ± 1.7 |
| 212 | K | C | 5.5 ± 1.8 | 34 | S | E | 5.1 ± 1.4 |
| 111 | G | K | 5.1 ± 1.4 | 3 | E | I | 5.8 ± 2.1 |
| 131 | K | I | 5.4 ± 1.8 | 47 | L | W | 5.8 ± 2.1 |
| 130 | G | N | 4.8 ± 1.2 | 222 | V | D | 5.3 ± 1.8 |
| 146 | E | C | 4.2 ± .6 | 11 | E | L | 4.1 ± .6 |
| 220 | M | C | 5.1 ± 1.6 | 22 | G | I | 5.6 ± 2.1 |
| 94 | V | Y | 4.9 ± 1.4 | 25 | D | W | 5.2 ± 1.8 |
| 49 | L | S | 5.6 ± 2.1 | 72 | M | A | 5.2 ± 1.8 |
| 56 | M | C | 4.5 ± 1. | 148 | W | H | 4.7 ± 1.3 |
| 262 | W | Y | 5.6 ± 2.2 | 15 | A | C | 4.3 ± .9 |
| 115 | C | N | 4.3 ± .9 | 84 | S | K | 4.1 ± .9 |
| 93 | T | D | 4. ± .6 | 14 | N | C | 3.9 ± .7 |
| 124 | G | F | 4.5 ± 1.2 | 8 | K | F | 4.9 ± 1.8 |
| 132 | L | C | 4.3 ± 1. | 30 | Q | H | 4.1 ± .9 |
| 145 | P | I | 4. ± .8 | 49 | L | S | 5.3 ± 2.2 |
| 258 | R | E | 5.4 ± 2.2 | 38 | P | N | 4.7 ± 1.5 |
| 29 | Q | I | 4.6 ± 1.4 | 15 | A | H | 4.8 ± 1.8 |

TABLE 2A-continued

Single mutants with improved resistance to proteolysis
Single Mutants

| Protease Stability-High | | | Protease Stability-Low | | |
|---|---|---|---|---|---|
| Location | WT | Mutation | Score | Location | WT | Mutation | Score |
| 52 | L | N | 6.2 ± 3. | 243 | H | S | 3.9 ± .9 |
| 113 | L | K | 4.6 ± 1.5 | 230 | P | N | 4.4 ± 1.4 |
| 185 | P | E | 4.7 ± 1.6 | 68 | V | F | 4.1 ± 1.1 |
| 141 | A | L | 3.9 ± .8 | 61 | I | K | 5.1 ± 2.2 |

TABLE 2B

Triple mutants with improved resistance to proteolysis
Triple Mutants
Protease Stability

| Location | WT | Mutations | Score |
|---|---|---|---|
| 62, 64, 66 | W, F, F | Y, S, T | 13.8 ± 5.6 |
| 62, 64, 66 | W, F, F | V, G, D | 11.9 ± 4. |
| 35, 37, 39 | R, S, L | E, G, W | 13.1 ± 5.6 |
| 45, 47, 49 | L, L, L | V, C, R | 13. ± 5.7 |
| 59, 61, 63 | L, I, L | Y, V, S | 11.4 ± 4.1 |
| 52, 54, 56 | L, I, M | E, E, G | 11.3 ± 4.1 |
| 52, 54, 56 | L, I, M | G, A, M | 12.9 ± 5.7 |
| 35, 37, 39 | R, S, L | S, C, S | 12.8 ± 5.7 |
| 45, 47, 49 | L, L, L | I, D, P | 12.8 ± 5.7 |
| 52, 54, 56 | L, I, M | E, V, V | 12.8 ± 5.7 |
| 52, 54, 56 | L, I, M | L, A, R | 12.8 ± 5.7 |
| 86, 88, 90 | K, W, P | G, M, Q | 12.8 ± 5.7 |
| 14, 16, 18 | N, V, Q | H, D, R | 12.5 ± 5.7 |
| 5, 7, 9 | L, V, V | S, R, E | 12.5 ± 5.7 |
| 45, 47, 49 | L, L, L | H, G, V | 12.5 ± 5.7 |
| 52, 54, 56 | L, I, M | Y, G, W | 12.5 ± 5.7 |
| 62, 64, 66 | W, F, F | S, K, S | 12.5 ± 5.7 |
| 76, 78, 80 | Y, C, P | F, S, G | 12.5 ± 5.7 |
| 86, 88, 90 | K, W, P | S, H, K | 12.5 ± 5.7 |
| 5, 7, 9 | L, V, V | E, W, A | 12.4 ± 5.7 |
| 52, 54, 56 | L, I, M | M, G, R | 12.4 ± 5.7 |
| 59, 61, 63 | L, I, L | S, Q, H | 12.4 ± 5.7 |
| 62, 64, 66 | W, F, F | P, W, G | 12.4 ± 5.7 |
| 193, 195, 197 | L, W, H | L, D, S | 12.4 ± 5.7 |

TABLE 2B-continued

Triple mutants with improved resistance to proteolysis
Triple Mutants
Protease Stability

| Location | WT | Mutations | Score |
|---|---|---|---|
| 219, 221, 223 | D, W, M | V, G, W | 12.4 ± 5.7 |
| 59, 61, 63 | L, I, L | M, L, G | 10. ± 3.4 |
| 35, 37, 39 | R, S, L | S, C, R | 12.2 ± 5.7 |
| 45, 47, 49 | L, L, L | G, T, L | 12.2 ± 5.7 |
| 52, 54, 56 | L, I, M | R, V, P | 12.2 ± 5.7 |
| 52, 54, 56 | L, I, M | E, V, R | 12.2 ± 5.7 |
| 52, 54, 56 | L, I, M | Q, E, V | 12.2 ± 5.7 |
| 59, 61, 63 | L, I, L | K, M, A | 12.2 ± 5.7 |
| 59, 61, 63 | L, I, L | S, Q, R | 12.2 ± 5.7 |
| 62, 64, 66 | W, F, F | A, Q, T | 12.2 ± 5.7 |
| 86, 88, 90 | K, W, P | S, S, S | 12.2 ± 5.7 |
| 206, 208, 210 | L, S, E | K, L, R | 10.6 ± 4.1 |
| 206, 208, 210 | L, S, E | G, E, N | 12.2 ± 5.7 |
| 219, 221, 223 | D, W, M | E, G, L | 12.2 ± 5.7 |
| 5, 7, 9 | L, V, V | A, P, A | 12.1 ± 5.7 |
| 52, 54, 56 | L, I, M | S, R, F | 12.1 ± 5.7 |
| 52, 54, 56 | L, I, M | M, G, S | 12.1 ± 5.7 |
| 59, 61, 63 | L, I, L | T, L, G | 12.1 ± 5.7 |
| 59, 61, 63 | L, I, L | A, H, Q | 12.1 ± 5.7 |
| 59, 61, 63 | L, I, L | M, T, A | 12.1 ± 5.7 |
| 62, 64, 66 | W, F, F | V, E, E | 12.1 ± 5.7 |
| 86, 88, 90 | K, W, P | M, A, G | 12.1 ± 5.7 |
| 59, 61, 63 | L, I, L | S, Q, T | 9.7 ± 3.4 |
| 193, 195, 197 | L, W, H | V, G, F | 12. ± 5.7 |
| 206, 208, 210 | L, S, E | K, P, M | 12. ± 5.7 |
| 224, 226, 228 | E, G, L | G, F, A | 12. ± 5.7 |

Example 4

Thermal Stress

Figure 7:
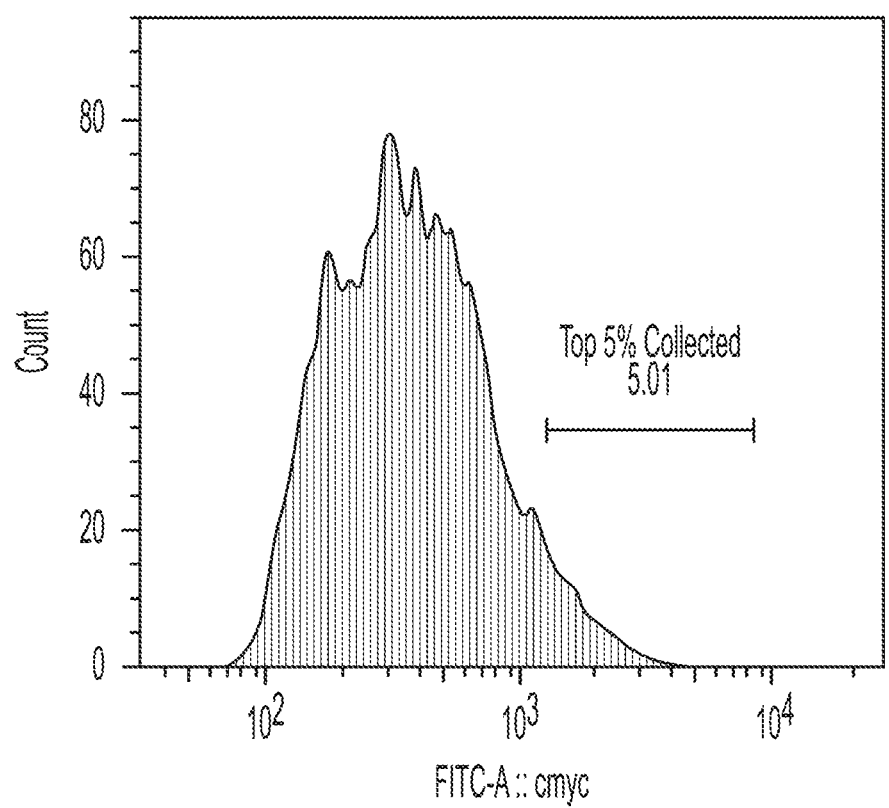
FIG. 7 depicts analysis of CD19 variants by thermal selection using flow cytometry. Yeast displaying CD19 variants with single mutations in tile 1 were induced for CD19 display at 37° C., labeled for displaying with FITC-conjugated anti-MYC, and analyzed by flow cytometry. The top 5% were collected for analysis.
Figures 8A, 8B:
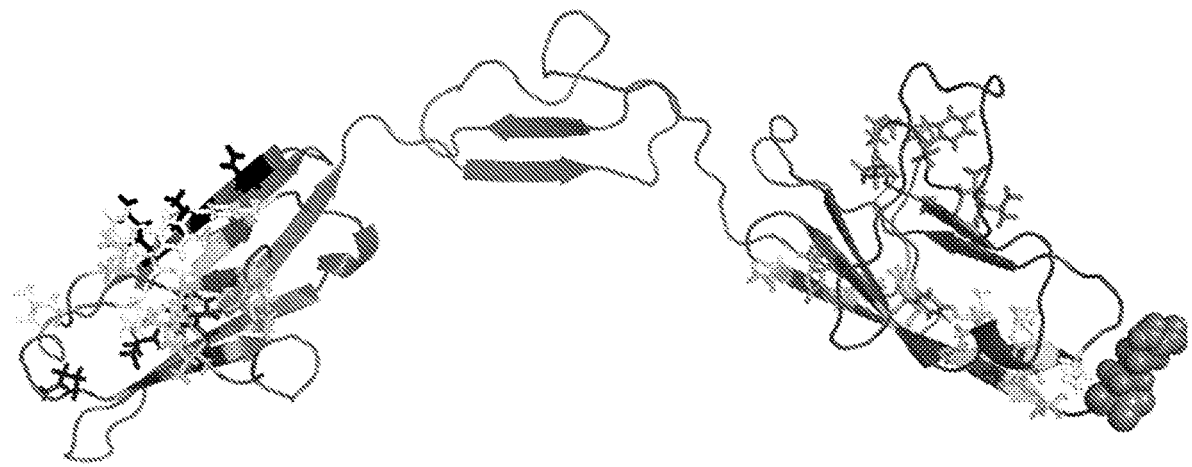
FIG. 8A is a schematic of CD19 with diversified positions shown with side chains and color.
FIG. 8B is a table presenting exemplary sets of sequences permitted in combined library design. For example, (first row) sites 14, 16, and 18, which are N, V, and Q in the wild-type sequence are permitted to be either T, A, and W; E, W, and P; D, W, and R; T, V, and P; or T, W, and P.

The combinatorial libraries were also sorted for the ability of mutants to tolerate thermal stress during induced display. Yeast were induced at 37° C., a condition that has been shown to result in decreased display of protein variants of reduced thermal stability (Shusta et al., J. Mol. Biol. 292: 949-956 (1999); Hackel et al., J. Mol. Biol. 401:84-96 (2010)). CD19 mutants with increased display were selected (FIG. 7) and sequenced (Table 3).

TABLE 3

Mutants with improved expression under thermal stress

| Triple Mutants Thermal Induction | | | | Single Mutants Thermal Induction | | | |
|---|---|---|---|---|---|---|---|
| Location | WT | Mutations | Score | Location | WT | Mutation | Score |
| 247, 249, 251 | L, M, F | K, H, V | 12. ± 6.3 | 189 | S | H | 8.3 ± 3. |
| 253, 255, 256 | L, I, T | E, D, C | 9.5 ± 3.8 | 206 | L | C | 7.6 ± 3. |
| 167, 169, 171 | Q, L, M | M, R, M | 11.8 ± 6.3 | 216 | P | H | 7.6 ± 3. |
| 207, 209, 211 | L, L, L | G, K, W | 11.8 ± 6.3 | 256 | T | M | 6.7 ± 2.2 |
| 247, 249, 251 | L, M, F | K, G, V | 11.8 ± 6.3 | 94 | V | S | 5.4 ± 1.3 |
| 167, 169, 171 | Q, L, M | K, L, Q | 9.9 ± 4.6 | 261 | L | M | 5.6 ± 1.6 |
| 247, 249, 251 | L, M, F | K, A, D | 11.6 ± 6.3 | 213 | D | H | 5.4 ± 1.4 |
| 247, 249, 251 | L, M, F | I, G, T | 11.6 ± 6.3 | 99 | S | Q | 6.8 ± 2.9 |
| 167, 169, 171 | Q, L, M | S, G, M | 9.7 ± 4.6 | 229 | L | K | 5.6 ± 1.8 |
| 167, 169, 171 | Q, L, M | L, W, H | 11.4 ± 6.3 | 262 | W | H | 5.9 ± 2.2 |
| 247, 249, 251 | L, M, F | T, N, I | 11.4 ± 6.3 | 114 | G | E | 6.6 ± 2.9 |
| 247, 249, 251 | L, M, F | N, V, S | 11.4 ± 6.3 | 15 | A | E | 5.8 ± 2.1 |
| 247, 249, 251 | L, M, F | V, G, A | 8.3 ± 3.3 | 209 | L | H | 4.5 ± .9 |
| 253, 255, 256 | L, I, T | I, V, S | 9.5 ± 4.6 | 204 | K | D | 5.7 ± 2.2 |
| 175, 177, 179 | S, L, L | L, E, M | 11.2 ± 6.3 | 148 | W | P | 6.3 ± 2.9 |
| 193, 195, 197 | L, W, H | S, L, S | 11.2 ± 6.3 | 99 | S | P | 6.3 ± 2.9 |
| 207, 209, 211 | L, L, L | Y, P, G | 11.2 ± 6.3 | 207 | L | G | 3.8 ± .5 |
| 224, 226, 228 | E, G, L | A, L, L | 11.2 ± 6.3 | 90 | P | E | 5.4 ± 2.1 |
| 224, 226, 228 | E, G, L | E, L, A | 11.2 ± 6.3 | 206 | L | Q | 4.9 ± 1.6 |
| 253, 255, 256 | L, I, T | Q, C, G | 11.2 ± 6.3 | 138 | Y | E | 4.7 ± 1.5 |
| 253, 255, 256 | L, I, T | C, Q, S | 11.2 ± 6.3 | 99 | S | N | 6.1 ± 2.9 |

TABLE 3-continued

Mutants with improved expression under thermal stress

| Triple Mutants Thermal Induction | | | | Single Mutants Thermal Induction | | | |
|---|---|---|---|---|---|---|---|
| Location | WT | Mutations | Score | Location | WT | Mutation | Score |
| 52, 54, 56 | L, I, M | G, G, M | 8.8 ± 4. | 10 | E | I | 5.2 ± 2.1 |
| 52, 54, 56 | L, I, M | E, W, V | 8.8 ± 4. | 142 | K | L | 4.7 ± 1.7 |
| 175, 177, 179 | S, L, L | R, T, M | 9.3 ± 4.6 | 52 | L | H | 6. ± 2.9 |
| 253, 255, 256 | L, I, T | D, S, W | 9.3 ± 4.6 | 135 | P | W | 5.1 ± 2.1 |
| 167, 169, 171 | Q, L, M | E, S, Y | 11. ± 6.3 | 144 | R | E | 4.3 ± 1.3 |
| 175, 177, 179 | S, L, L | R, T, P | 11. ± 6.3 | 139 | V | K | 5.9 ± 2.9 |
| 193, 195, 197 | L, W, H | P, A, R | 11. ± 6.3 | 209 | L | M | 4. ± 1.1 |
| 207, 209, 211 | L, L, L | L, M, R | 11. ± 6.3 | 259 | P | C | 4. ± 1.1 |
| 224, 226, 228 | E, G, L | T, W, G | 11. ± 6.3 | 52 | L | N | 5.9 ± 3. |
| 247, 249, 251 | L, M, F | S, T, V | 11. ± 6.3 | 131 | K | A | 5.8 ± 2.9 |
| 253, 255, 256 | L, I, T | D, Q, R | 11. ± 6.3 | 198 | V | N | 4.7 ± 1.9 |
| 253, 255, 256 | L, I, T | C, N, E | 11. ± 6.3 | 235 | Q | D | 4.4 ± 1.6 |
| 253, 255, 256 | L, I, T | K, D, D | 11. ± 6.3 | 207 | L | Q | 4. ± 1.3 |
| 253, 255, 256 | L, I, T | Q, G, C | 11. ± 6.3 | 194 | S | W | 4.2 ± 1.5 |
| 45, 47, 49 | L, L, L | G, E, H | 8.6 ± 4.1 | 52 | L | E | 3.9 ± 1.1 |
| 52, 54, 56 | L, I, M | L, E, V | 8.6 ± 4.1 | 209 | L | K | 3.8 ± 1.1 |
| 52, 54, 56 | L, I, M | C, G, V | 8.6 ± 4.1 | 140 | W | P | 5.6 ± 2.9 |
| 193, 195, 197 | L, W, H | A, G, L | 8.3 ± 3.9 | 142 | K | C | 5.5 ± 2.9 |
| 86, 88, 90 | K, W, P | T, T, G | 8.4 ± 4.1 | 7 | V | F | 5.5 ± 3. |
| 167, 169, 171 | Q, L, M | T, M, G | 10.7 ± 6.4 | 12 | G | C | 5.5 ± 3. |
| 175, 177, 179 | S, L, L | M, R, D | 10.7 ± 6.4 | 18 | Q | D | 5.5 ± 3. |
| 193, 195, 197 | L, W, H | Q, C, A | 10.7 ± 6.4 | 204 | K | E | 3.1 ± .6 |
| 193, 195, 197 | L, W, H | D, T, D | 10.7 ± 6.4 | 262 | W | A | 3.4 ± .9 |
| 207, 209, 211 | L, L, L | A, R, M | 10.7 ± 6.4 | 185 | P | W | 3.5 ± 1. |
| 207, 209, 211 | L, L, L | M, T, G | 10.7 ± 6.4 | 196 | T | H | 3.6 ± 1.1 |
| 219, 221, 223 | D, W, M | S, G, S | 10.7 ± 6.4 | 249 | M | K | 3.3 ± .8 |
| 247, 249, 251 | L, M, F | L, A, M | 10.7 ± 6.4 | 105 | W | S | 3.5 ± 1. |
| 247, 249, 251 | L, M, F | F, W, P | 10.7 ± 6.4 | 154 | C | T | 5.4 ± 2.9 |
| 253, 255, 256 | L, I, T | T, E, N | 10.7 ± 6.4 | 138 | Y | P | 4.5 ± 2.1 |

Example 5

Second Generation CD19 ECD Combinatorial Sub-Library

Selection of CD19 variants with improved antibody binding, protease resistance, and/or thermal resistance not only identifies molecules with unique functions, but it also identifies mutants that can be combined to further advance function. The 13 sets of highly beneficial mutations (at 39 sites, of 291 in the CD19 ECD) from the initial CD19 engineering were combined. The initial screen identified the 39 sites with the most benefit from mutation, which constrained the otherwise immense search of sequence space. Moreover, all possible amino acid mutations at 39 sites would entail $20^{39}=10^{50}$ variants. The identification of functional mutations at these sites enabled the combinatorial library to be constrained to $7 \times 10^7$ variants (FIG. 8).

Figure 9:
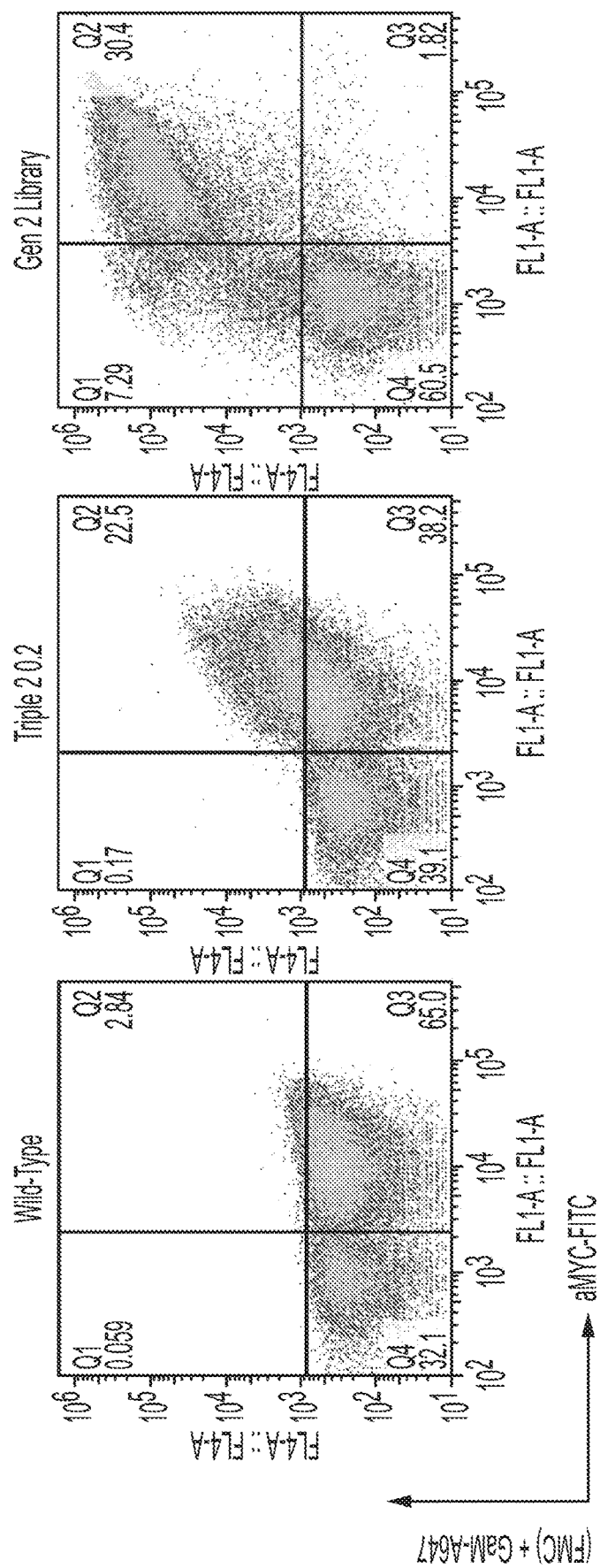
FIG. 9 depicts selection of improved CD19 variants from multi-mutant library using flow cytometry. Yeast displaying the indicated CD19 population (wild-type clone, twice-sorted triple library, or twice-sorted combined library) were incubated with FMC63 and FITC-conjugated anti-MYC antibody (to label the C-terminal epitope to indicate full-length CD19) followed by anti-mouse-AlexaFluor647 and evaluated by flow cytometry.
Figure 15A:
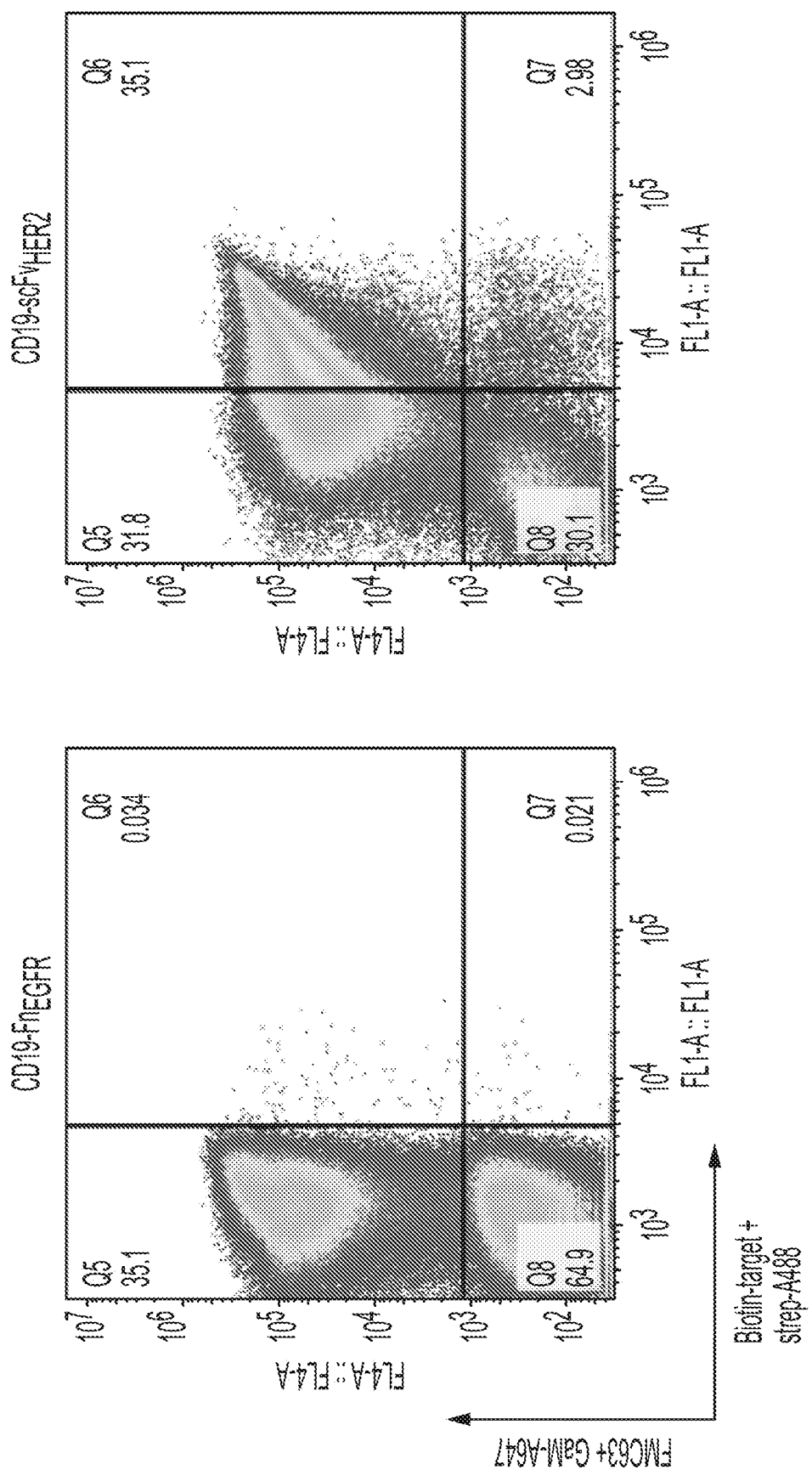
FIG. 15A depicts selection of improved ligand-CD19 variants by flow cytometry. Yeast displaying Fn (anti-EGFR)-CD19 or scFv (anti-HER2)-CD19 populations, which were enriched for target binding and FMC63 binding, were incubated with FMC63 and biotin-conjugated EGFR or HER2 ectodomain followed by anti-mouse-AlexaFluor647 and streptavidin-AlexaFluor488 and evaluated by flow cytometry.
Figure 15B:
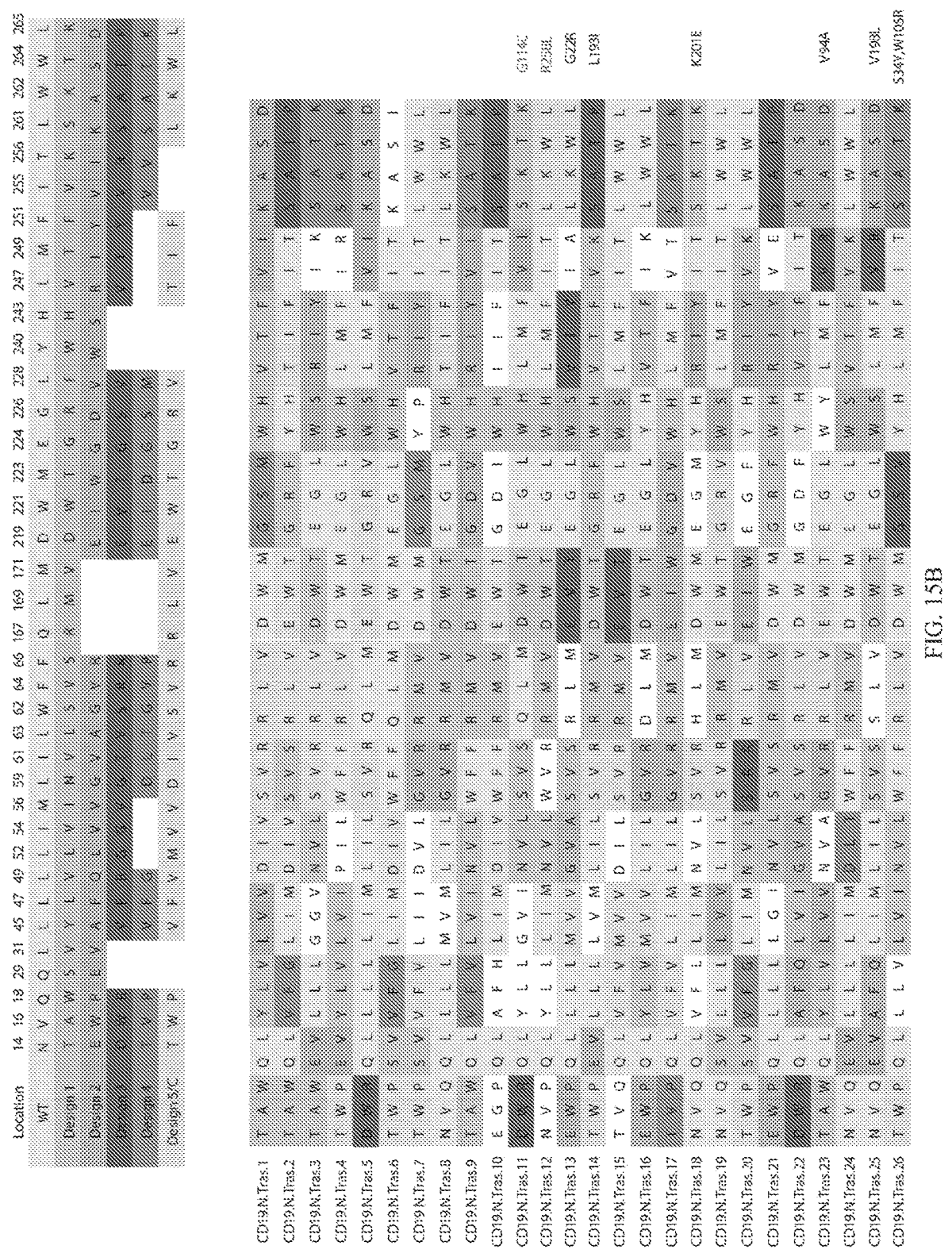
Figure 15C:
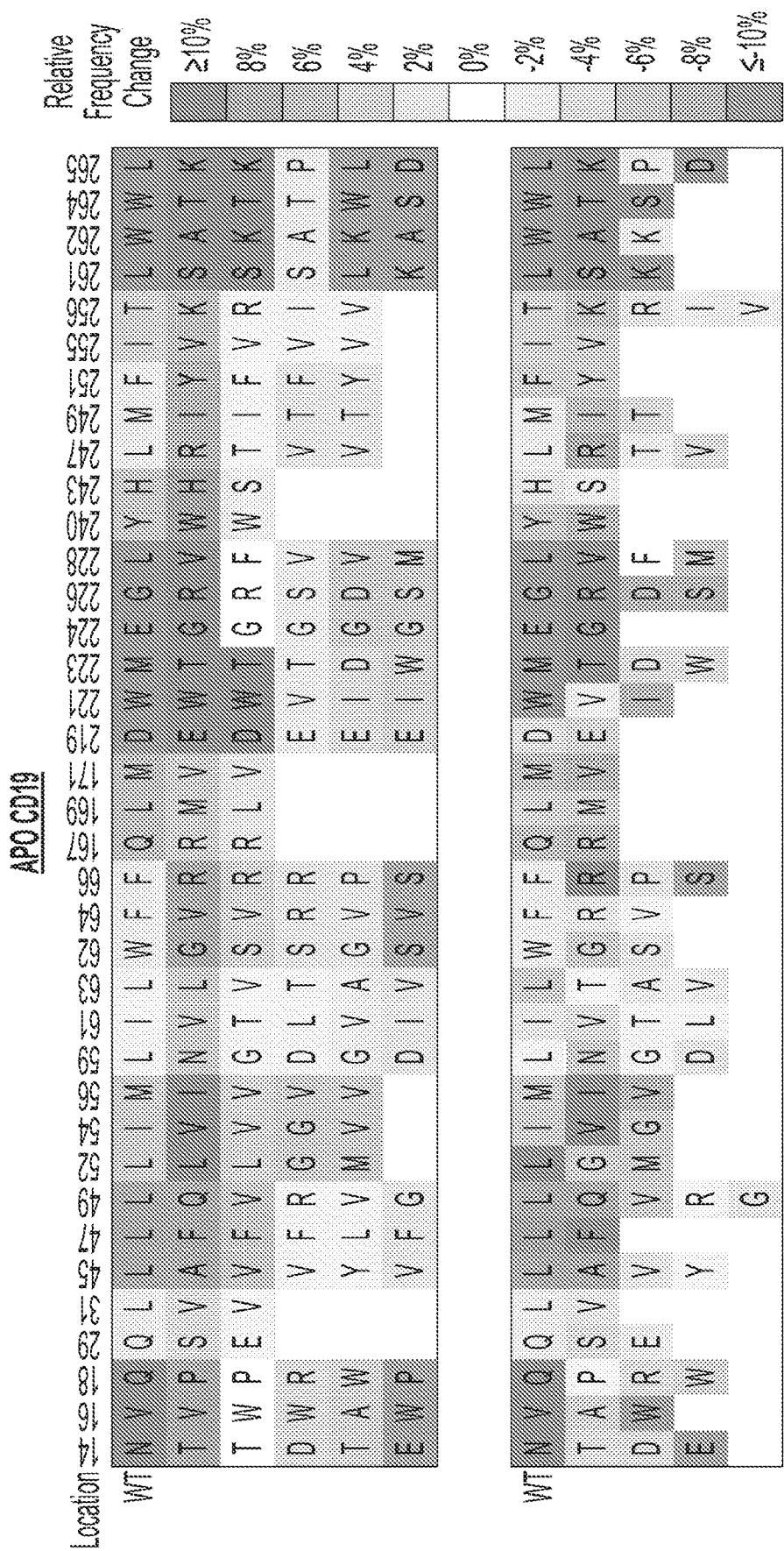
FIG. 15C depicts relative amino acid frequency change of coupled multiple mutations (top of top) or single mutations (bottom of top) identified by deep sequencing. The bottom depicts the relative amino acid frequency change from the unsorted library to the functionally-sorted mutants for three fusion protein contexts ("CT $Fn_{EGFR}$"=CD19-Fn3/EGFR; "CT $scFv_{HER2}$"=CD19-scFv/Her2; "NT $scFv_{HER2}$"=scFv/Her2-CD19)

Analysis of this combinatorial library demonstrated substantially elevated FMC63 binding relative to wild-type CD19 or triple mutants (FIG. 9 and FIG. 15C).

Example 6

Selection of Engineered CD19 Mutants

Figure 10:
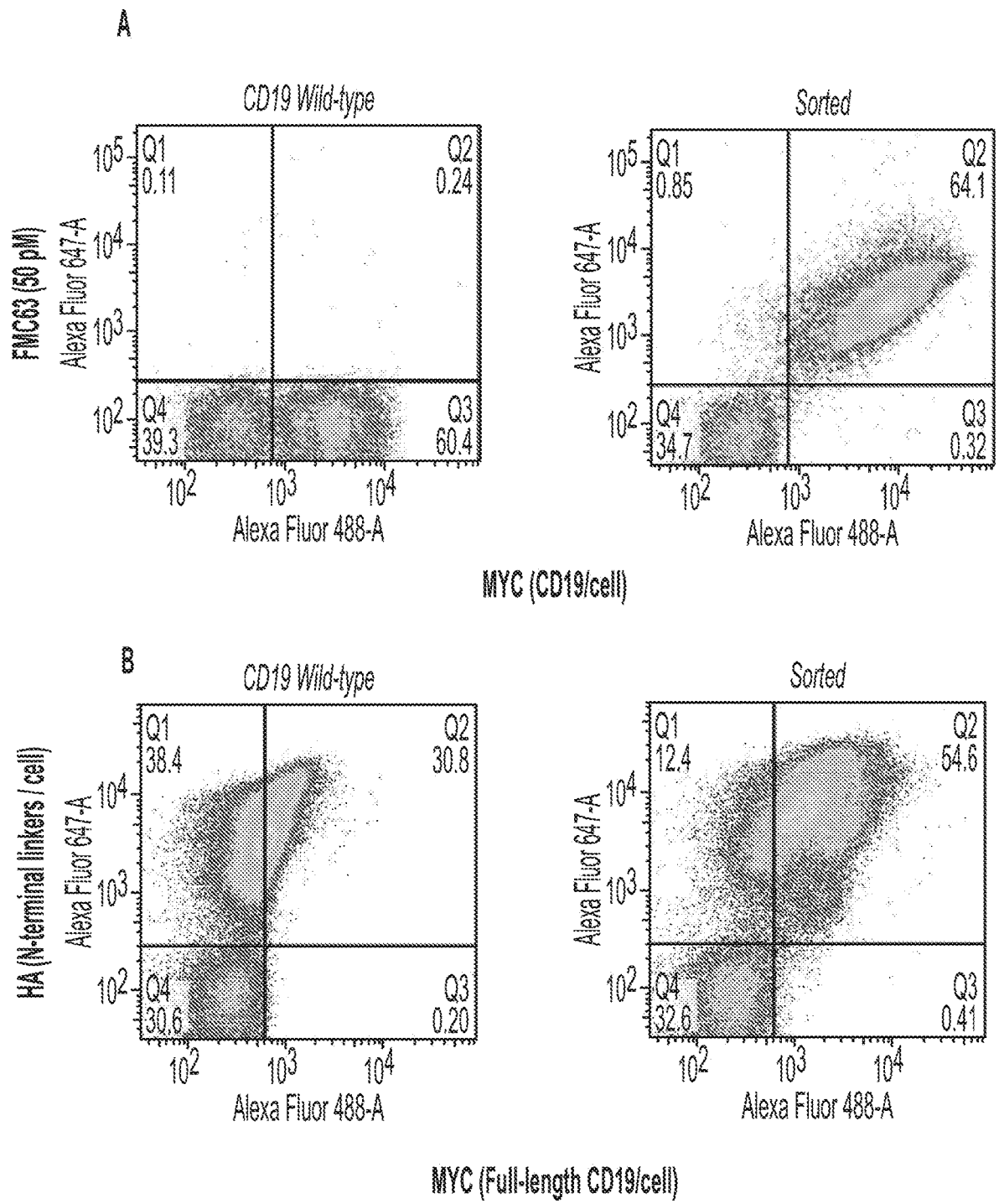
FIG. 10A and FIG. 10B depict characterization of multi-mutants by flow cytometry. Yeast displaying wild-type CD19 or the sorted CD19 population were (i) incubated with FMC63 and FITC-conjugated anti-MYC antibody (to label the C-terminal epitope to indicate full-length CD19) followed by anti-mouse-AlexaFluor647 and evaluated by flow cytometry (FIG. 10A); or (ii) incubated with 0.002 units of proteinase K in PBSA for 10 min. at 37° C.
Figure 11:
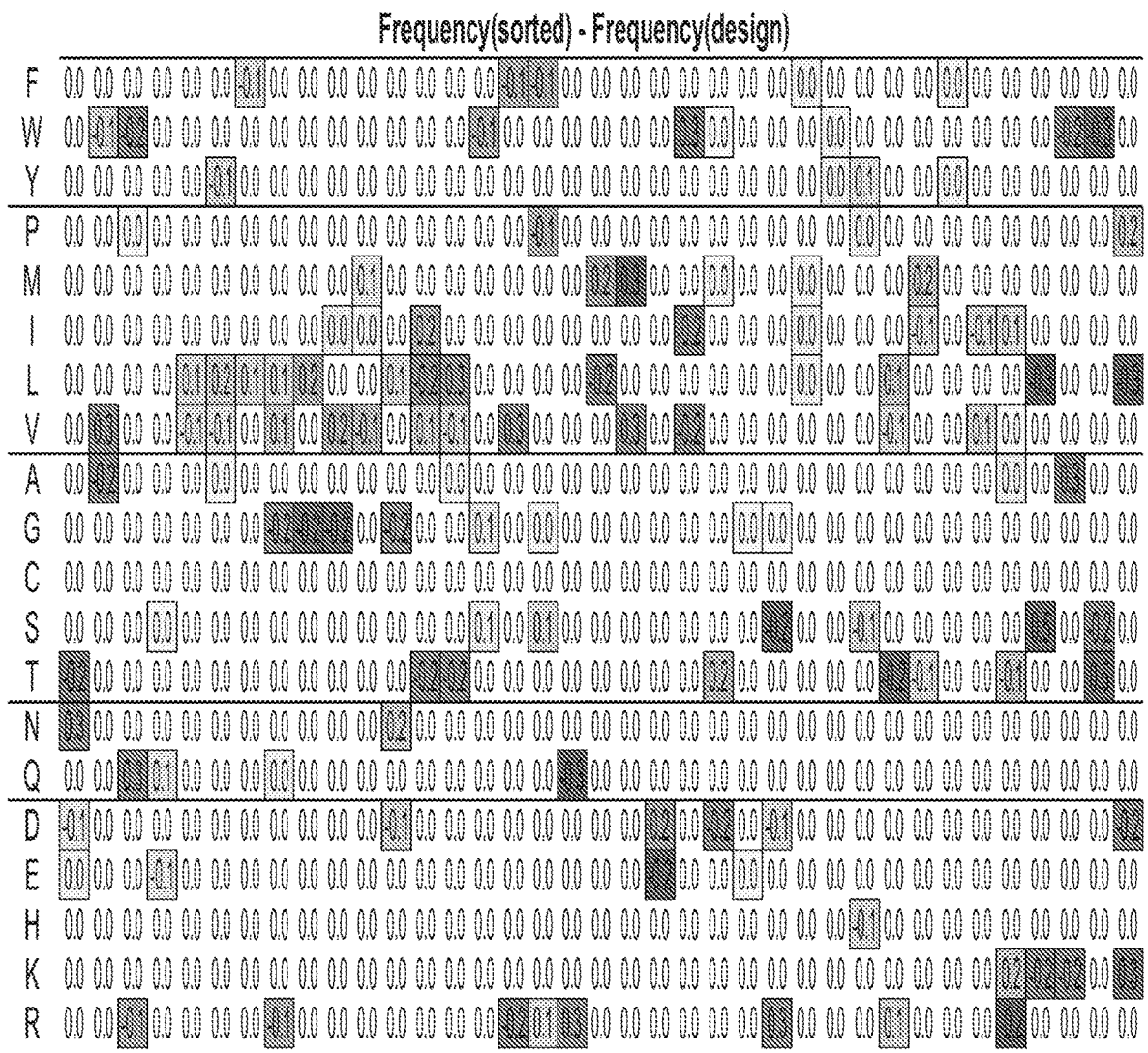
FIG. 11 depicts sequence analysis of improved CD19 variants from multi-mutant library. CD19 variants that emerged from selections for FMC63 binding and protease resistance were sequenced. Amino acids at the diversified positions are indicated for numerous clones. The relative change in frequency from design to sorted population is presented in the lower table.

Selection of CD19 multi-mutants with enhanced protease resistance and FMC63 binding yielded populations with improved FMC63 binding (FIG. 10A) and elevated protease resistance (FIG. 10B).

Example 7

Generation of CD19 Ligand Libraries

CD19 ECD consists of two Ig domains separated by a short linker region (FIG. 12). The CD19 ECD is diversified to generate new binding functionality to a variety of molecular targets. For example, to generate CD19 ligand libraries, the solvent-exposed loops in Ig domain 1, or Ig domain 2, or the beta sheet surface in Ig domain 2, are varied (FIG. 12). Other surfaces and other specific amino acids are also varied. Libraries are constructed at the genetic level (>1×10$^8$ yeast transformants) (Woldring et al., PLoS One 10, e0138956 (2015)).

These mutations are implemented within the context of a stability-engineered CD19 domain (see Example 6). Notably, the example library designs in FIG. 12 are further guided by increasing the frequency of particular amino acids at particular sites observed to improve the structural integrity of CD19 (Examples 2-6) and by decreasing the frequency of amino acids at sites that hinder structural integrity.

Example 8

Discovery and Evolution of CD19-Based Ligands

Libraries are sorted for binders to molecular targets, such as epidermal growth factor receptor (EGFR), using recombinant EGFR ectodomain with magnetic and flow cytometric selections (Hackel et al., J. Mol. Biol. 401:84-96 (2010); Woldring et al., PLoS One 10, e0138956 (2015); Ackerman et al., Biotechnol. Prog. 25:774-783 (2009)), followed by flow cytometric selections using detergent-solubilized EGFR$^+$ cell lysate. Specificity is evolved using depletion sorts against control proteins and EGFR⁻ lysates. Genes of populations enriched for specific binding are isolated from yeast and sequenced to evaluate diversity and integrity of CD19 Ig domains. Genes are evolved using error-prone PCR and loop shuffling (Wrenbeck et al., Nat. Methods 13:928-930 (2016)) followed by more stringent sorting.

Example 9

N-Terminal CD19-Ligand Fusions

Figure 13:
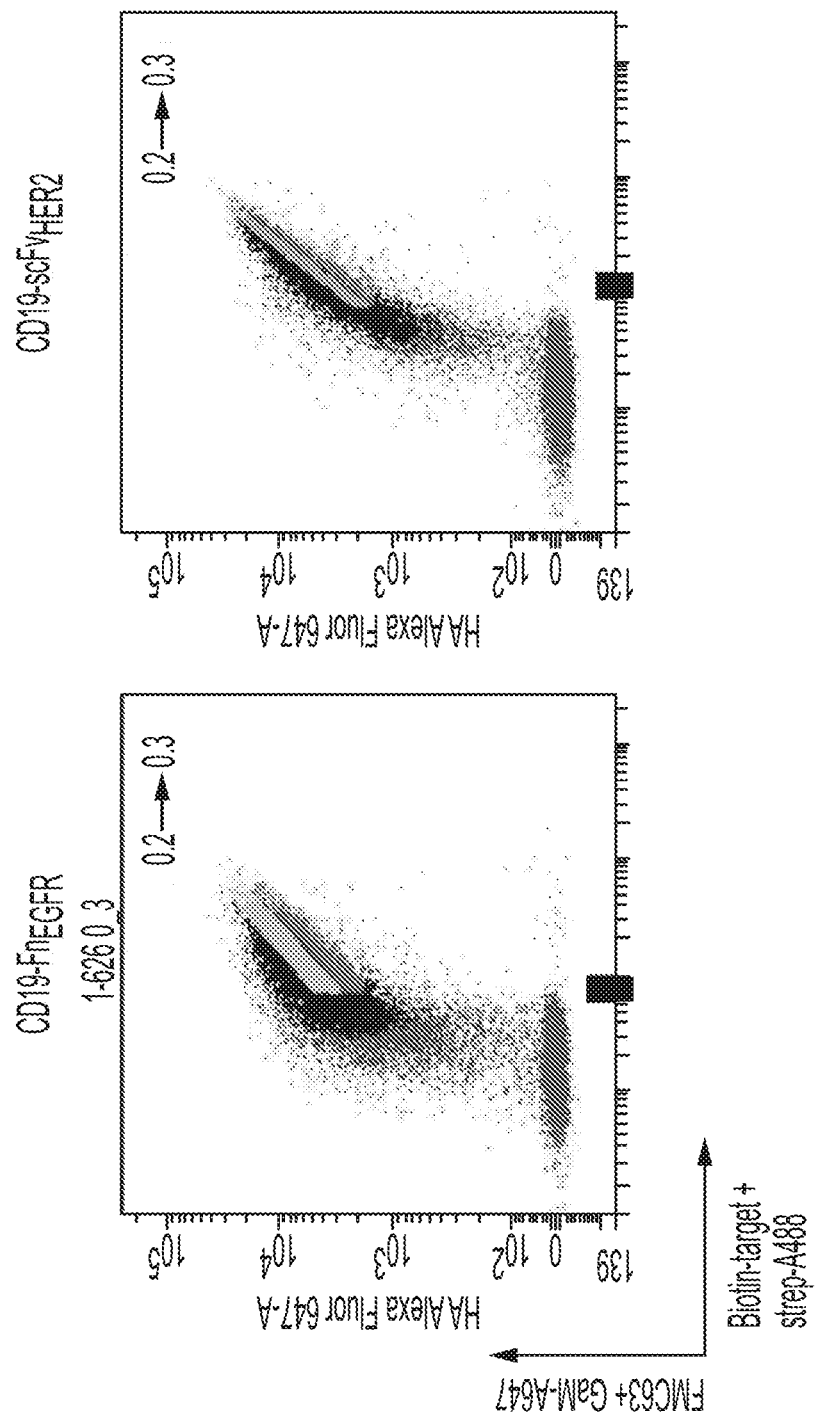
FIG. 13 depicts selection of improved CD19-ligand variants using flow cytometry. Yeast displaying CD19-Fn (anti-EGFR) or CD19-scFv (anti-HER2) populations, which were twice enriched for target binding and FMC63 binding, were incubated with FMC63 and biotin-conjugated EGFR or HER2 ectodomain followed by anti-mouse-AlexaFluor647 and streptavidin-AlexaFluor488 and evaluated by flow cytometry.
Figure 14A:
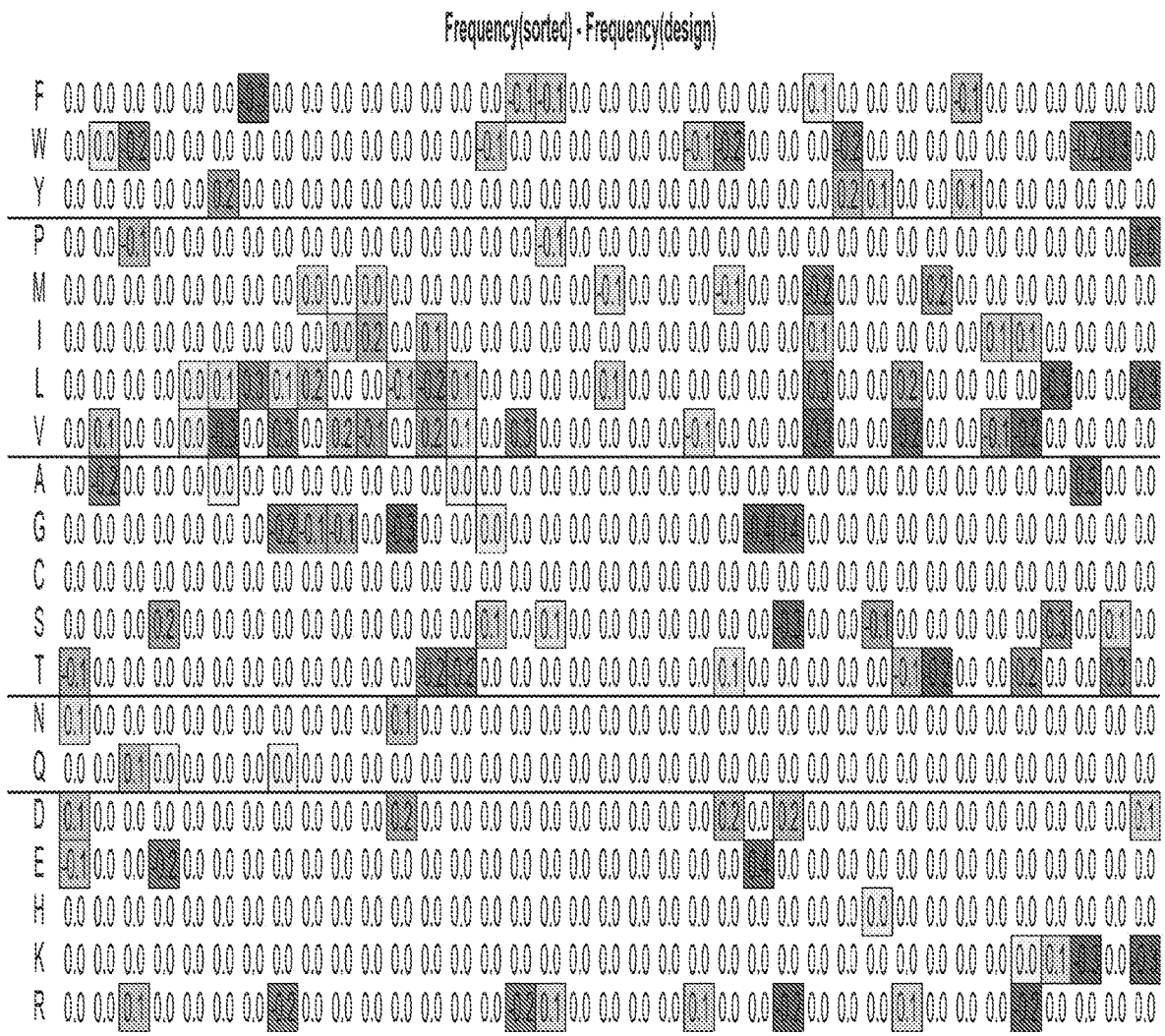
FIG. 14A depicts sequence analysis of CD19/EGFR-binding fibronectin domain variants from multi-mutant library; mutants that emerged from selections for FMC63 binding and EGFR binding were sequenced. Amino acids at the diversified positions are indicated for numerous clones. The relative change in frequency from design to sorted population is presented in the lower table.
Figure 14B:
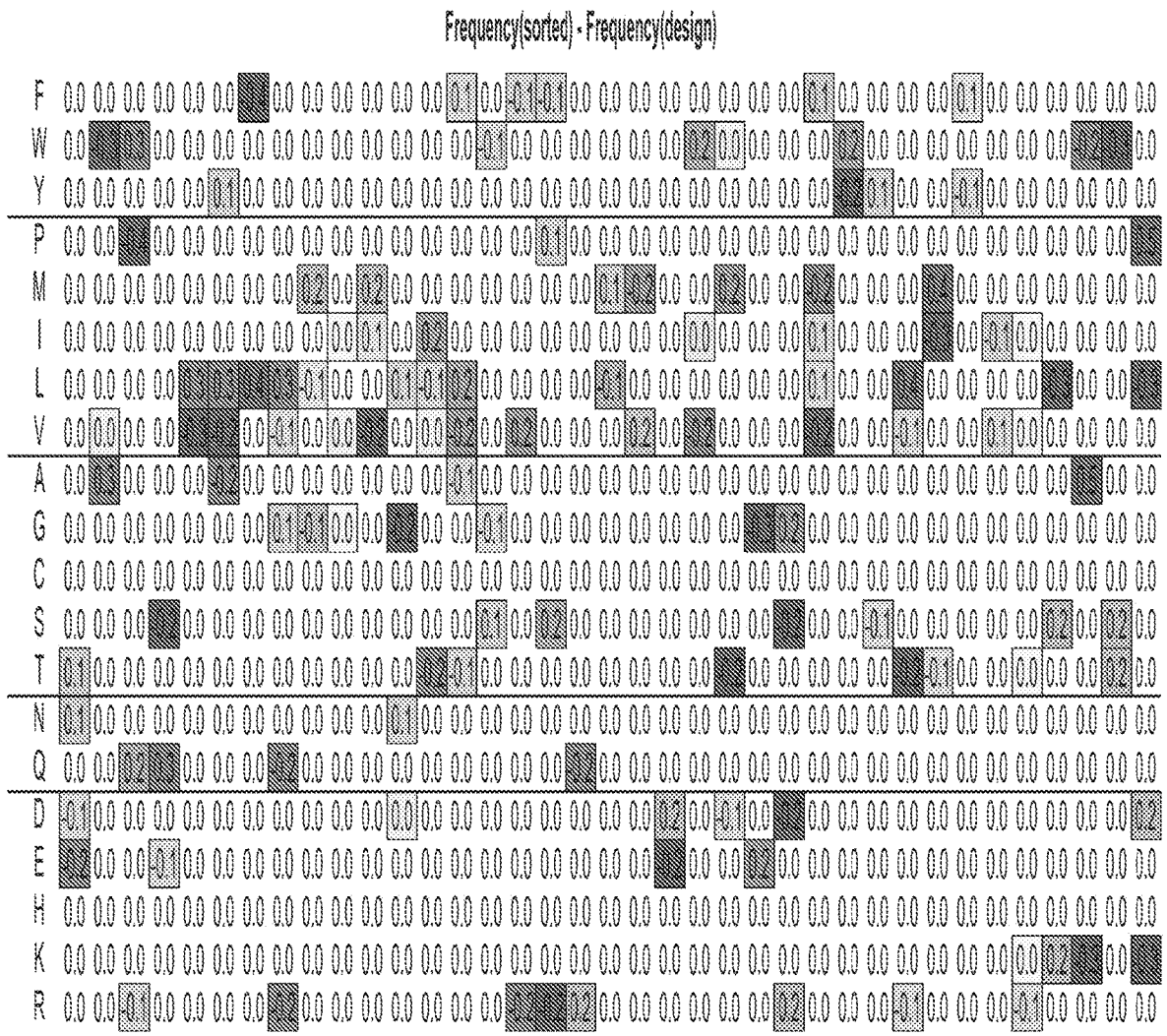
FIG. 14B depicts sequence analysis of CD19/anti-HER2 scFv variants from multi-mutant library; mutants that emerged from selections for FMC63 binding and HER2 binding were sequenced. Amino acids at the diversified positions are indicated for numerous clones. The relative change in frequency from design to sorted population is presented in the lower table.
Figure 14C:
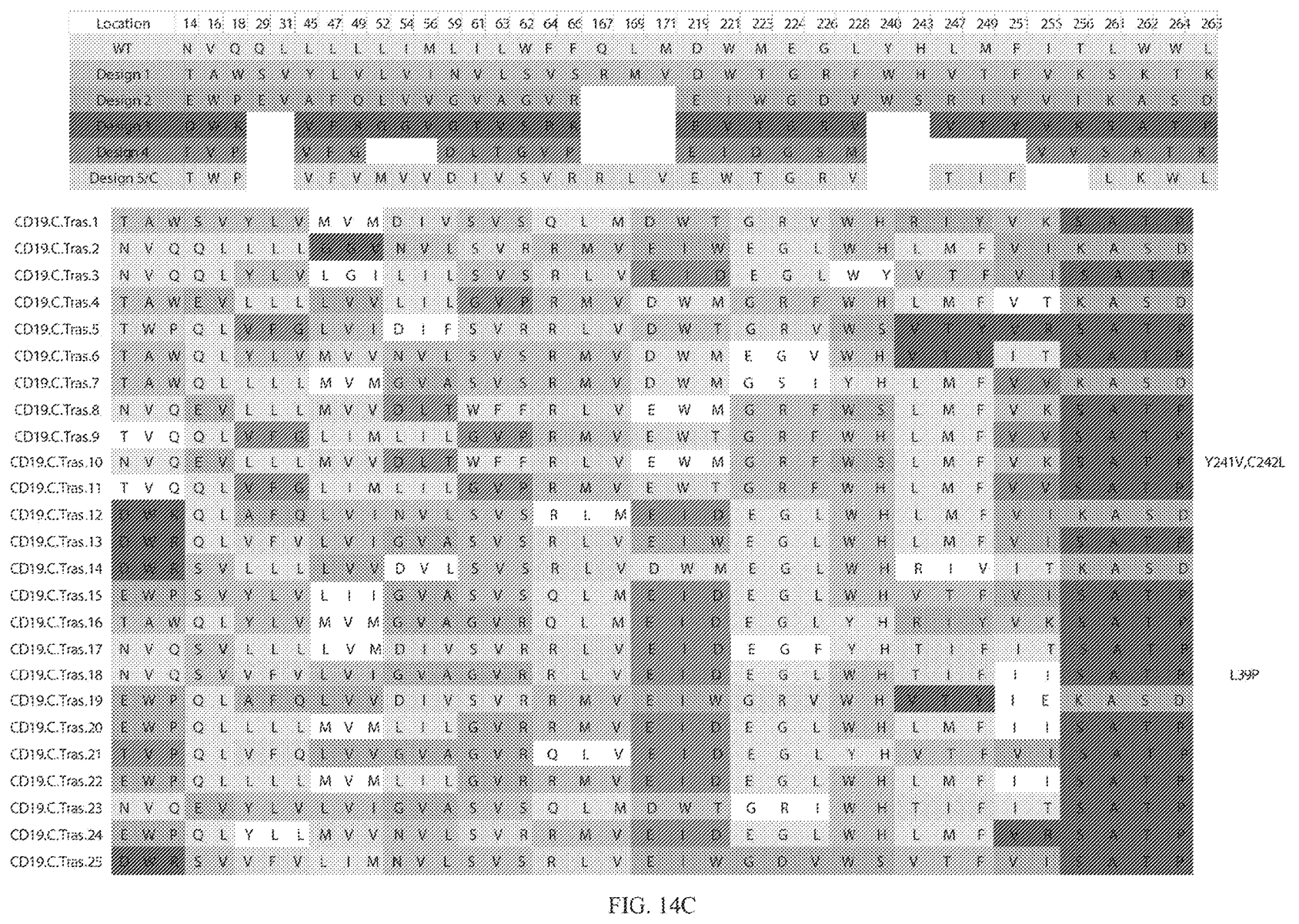
Figure 14D:
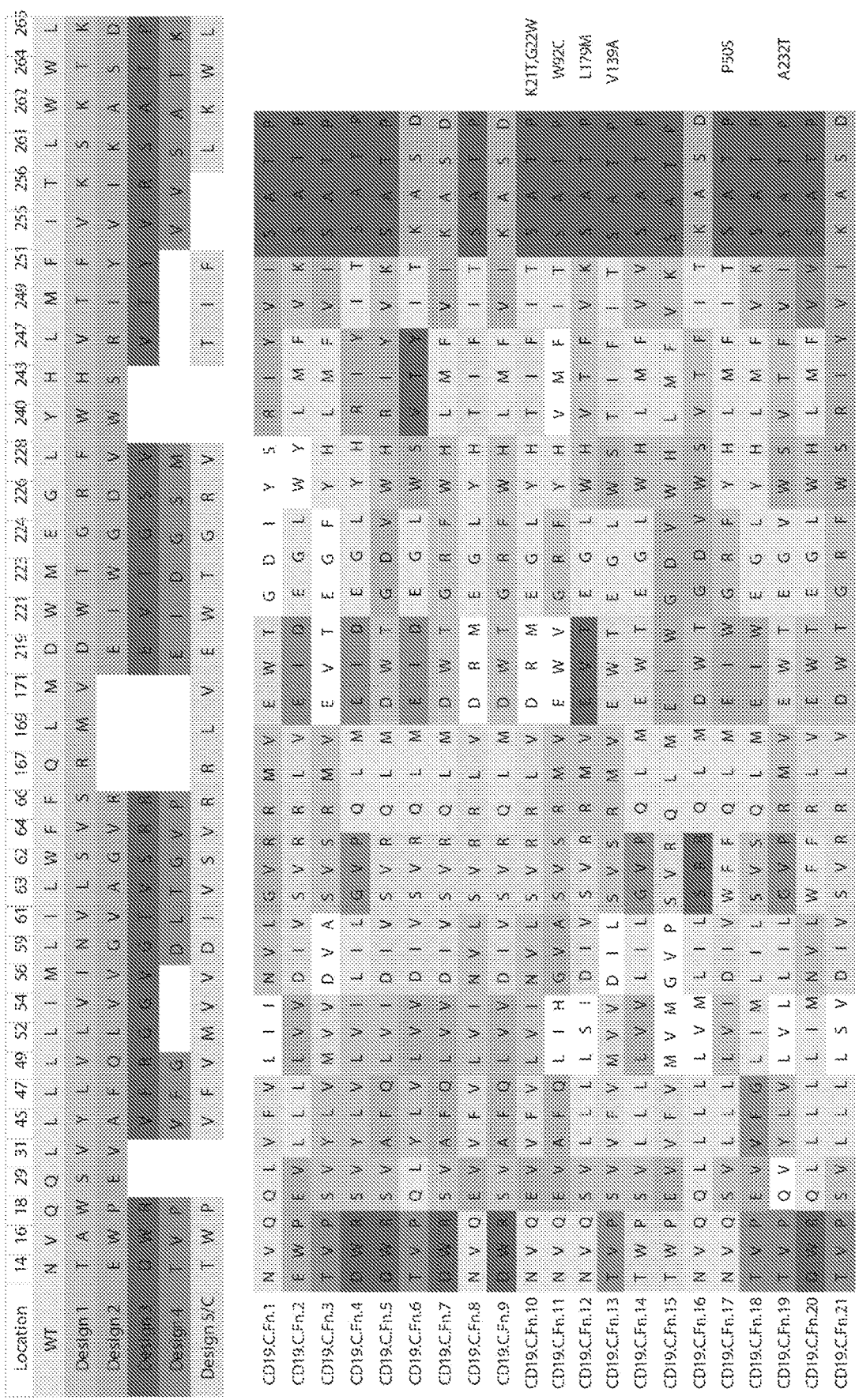
FIG. 14D depicts sequence analysis of CD19/EGFR-binding fibronectin domain variants from multi-mutant library; mutants that emerged from selections for FMC63 binding and EGFR binding were sequenced. Amino acids at the diversified positions are indicated for numerous clones.

The combined mutation library, which provided a focused search of highly functional sequence space (Example 5), was used to identify CD19 mutants with modularity (i.e., ability to function as a member of a protein fusion) in CD19-ligand fusions (with CD19 placed N-terminal to the ligand). The combined mutation library was genetically fused to the N-terminus of either an EGFR-binding fibronectin or a HER2-binding single-chain antibody fragment. The library was sorted twice using a dual-function screen in which mutants were collected that enabled both FMC63 binding and target (EGFR, HER2) binding. After two dual sorts, distinct populations of dually functional CD19-ligand fusions were obtained (FIG. 13). Sequence analysis revealed full-length CD19 variants evolved at the indicated sites (FIG. 14).

Example 10

Ligand-C-Terminal CD19 Fusions

Figure 15C:
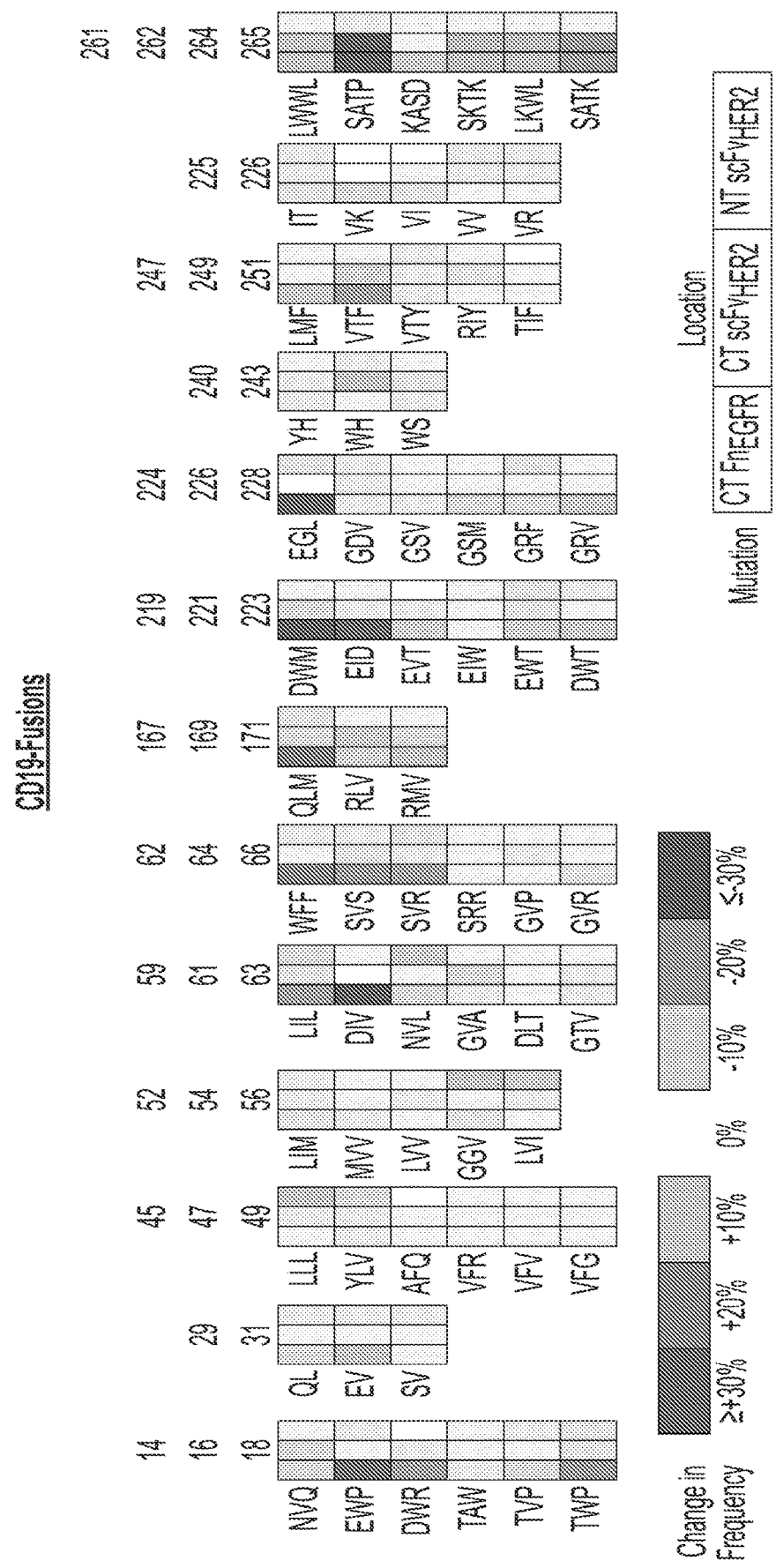

The combined mutation library, which provides a focused search of highly functional sequence space (Example 5), was used to identify CD19 mutants with modularity (i.e., ability to function as a member of a protein fusion) in ligand-CD19 fusions (with CD19 placed C-terminal to the ligand). The combined mutation library was genetically fused to the C-terminus of either an EGFR-binding fibronectin or a HER2-binding single-chain antibody fragment. The library was sorted using a dual-function screen in which mutants were collected that enabled both FMC63 binding and target (EGFR, HER2) binding. After one sort, distinct populations of dually functional ligand-CD19 fusions were obtained (FIG. 15).

Example 11

Function of N-Terminal CD19-Ligand Fusions

Figure 16:
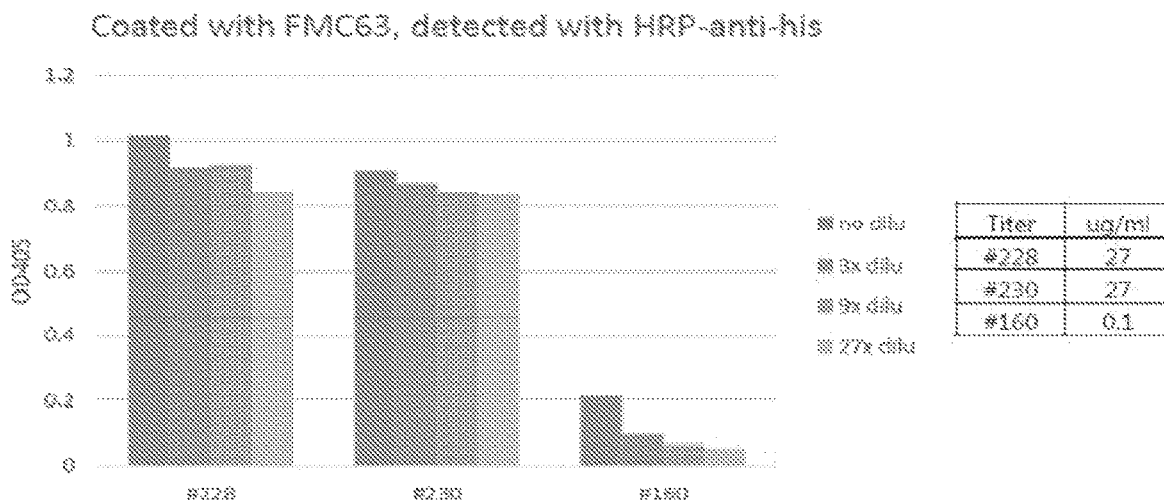
FIG. 16 depicts detection of secreted N-terminal CD19 variant-Fn3/EGFRfusion proteins.

To further demonstrate the ability of a CD19 mutant to function as a member of a fusion protein, e.g., a N-terminal CD19-Ligand fusion, four CD19 mutants identified in Example 9 were further tested. CD19 mutants with the amino acid substitutions corresponding to JRK2, JRK5, JRK14 and JRK15 as shown in FIG. 14 were genetically fused to the N-terminus of an EGFR-binding fibronectin (CD19-Fn3/EGFR; construct #s 227, 228, 229, and 230; SEQ ID Nos 3, 4, 5, and 6, respectively). Transfection of two of these constructs (#228 and #230) into HEK293 cells resulted in increased secretion of the fusion protein into the supernatant relative to a wild type CD19 fused to the N-terminus of an EGFR-binding fibronectin (Construct #160, SEQ ID No. 7) (FIG. 16). All four constructs were analyzed for their ability to bind to EGFR positive cells, and for killing of those cells. All four constructs bound well and all also killed the cells. No significant differences were seen between the four constructs, in secretion level, binding or killing ability (data not shown).

Figure 17:
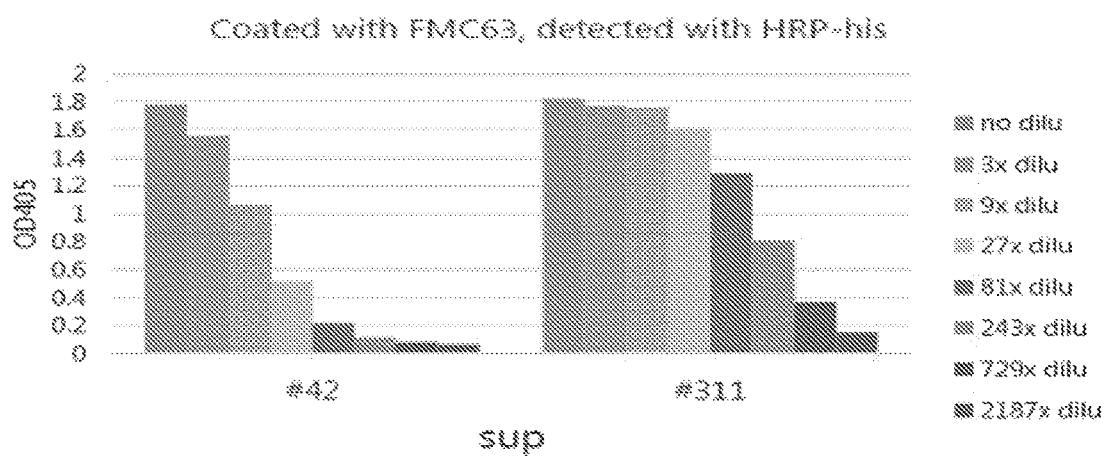
FIG. 17 depicts detection of secreted N-terminal CD19 variant-scFv/Her2 fusion proteins.

Additionally, a fusion protein in which CD19 mutant JRK15 was genetically fused to the N-terminus of a HER2-binding single-chain antibody fragment was tested (CD19-scFv/Her2 Construct #311; SEQ ID NO 8). An increase in secretion of ~8 fold was also seen with CD19 mutant JRK15 placed N-terminal to scFv/Her2, when compared to the wild type CD19-scFv/Her2 fusion protein (#42, SEQ ID NO. 9) (FIG. 17).

Example 12

Function of Ligand-C-Terminal CD19 Fusions

Figure 18:
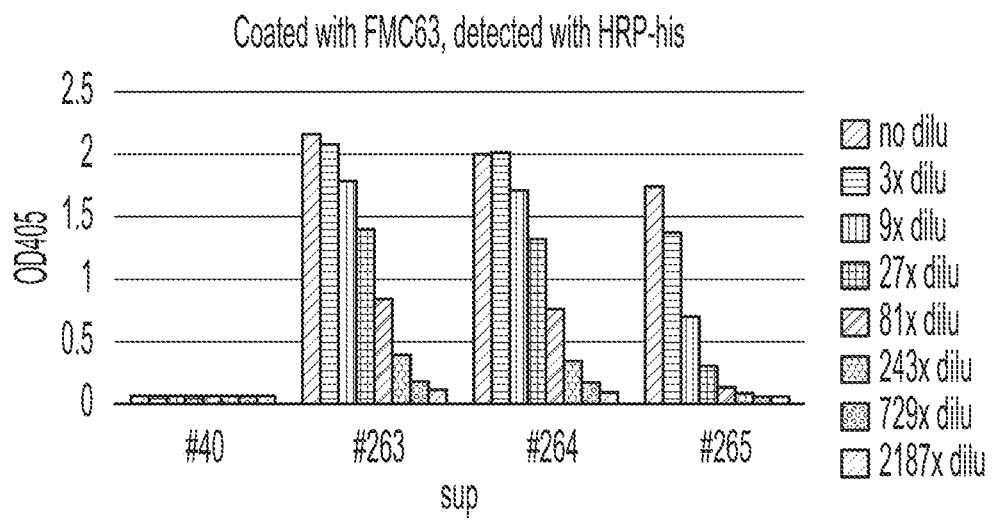
FIG. 18 depicts detection of secreted C-terminal scFv/Her2-CD19 variant fusion proteins.

To further demonstrate a CD19 mutant's ability to function as a member of a protein fusion (e.g., a ligand-C-terminal CD19 fusion), three CD19 mutants were further tested. CD19 mutants were genetically fused to the C-terminus of a HER2-binding single-chain antibody fragment (scFv/Her2-CD19) (construct #s 263, 264, and 265; SEQ ID Nos 10, 11, and 12, respectively). A fusion protein comprising wild type CD19 D1+2 domains fused to the C-terminus of a HER2-binding single-chain antibody fragment (construct #40; SEQ ID NO:38) transfected into HEK293 cells failed to secrete. However, the three constructs with C-terminal CD19 mutants secreted well (FIG. 18).

Figure 19:
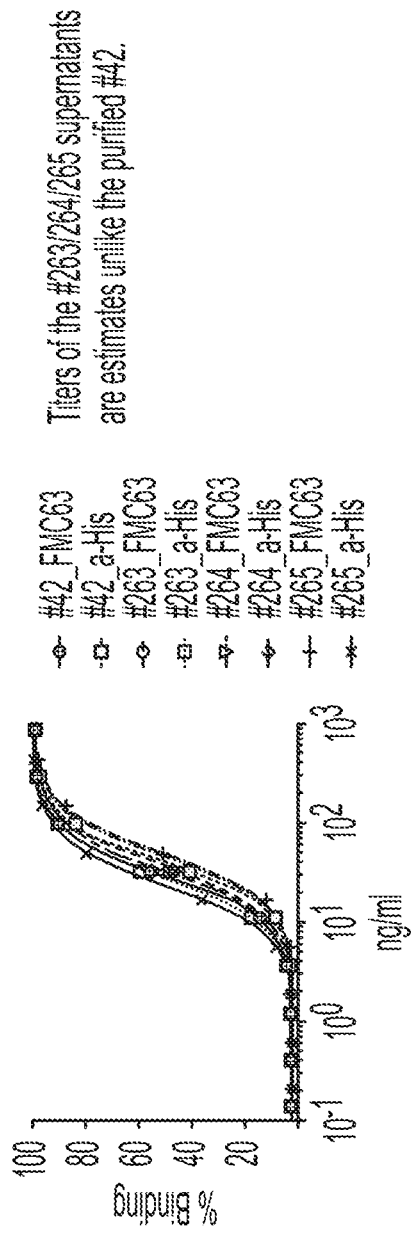
FIG. 19 depicts binding of C-terminal scFv/Her2-CD19variant fusion proteins to Her2 positive cells.
Figure 20:
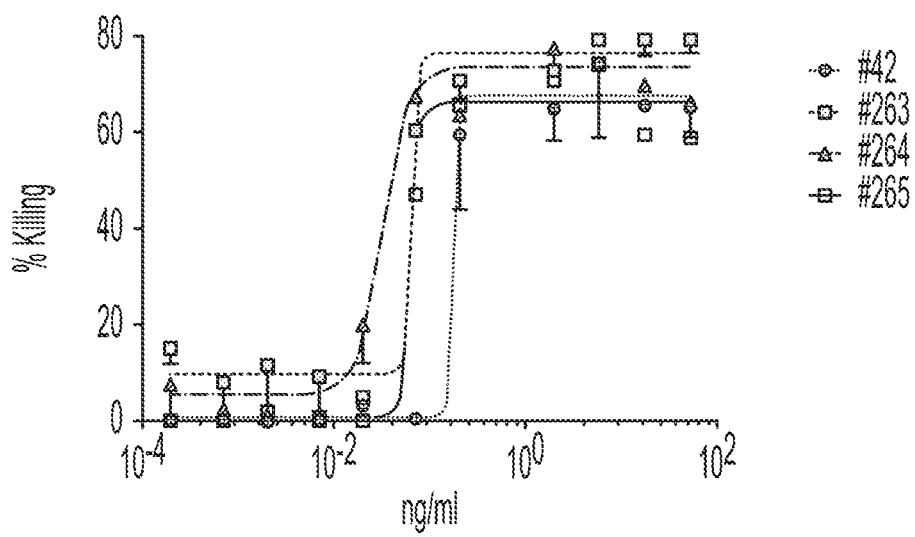
FIG. 20 depicts killing of Her2 positive cells by a CAR19 due to bridging by C-terminal scFv/Her2-CD19 variant fusion proteins.

Each of the scFv/Her2-CD19 fusion proteins (constructs 263, 264, and 265) was purified and titrated for both binding to, and killing of, Her2 positive SKOV3 cells. FIG. 19 shows detection of the three scFv/Her2-CD19 constructs bound to the SKOV3 cells by FACS analysis. The constructs were detected by both anti-His-PE and FMC63-PE antibodies. FIG. 20 shows the ability of each of the three scFv/Her2-CD19 constructs to bridge with CAR19 cells leading to the killing of the Her2 positive SKOV3 cells.

Figure 21:
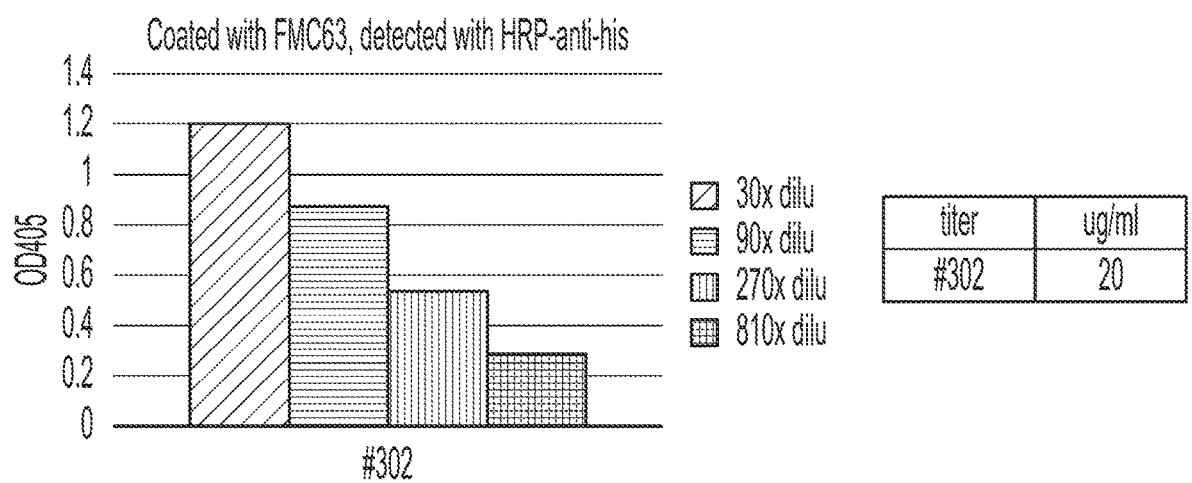
FIG. 21 depicts detection of secreted C-terminal scFv/CD20-CD19 variant fusion proteins.
Figure 22:
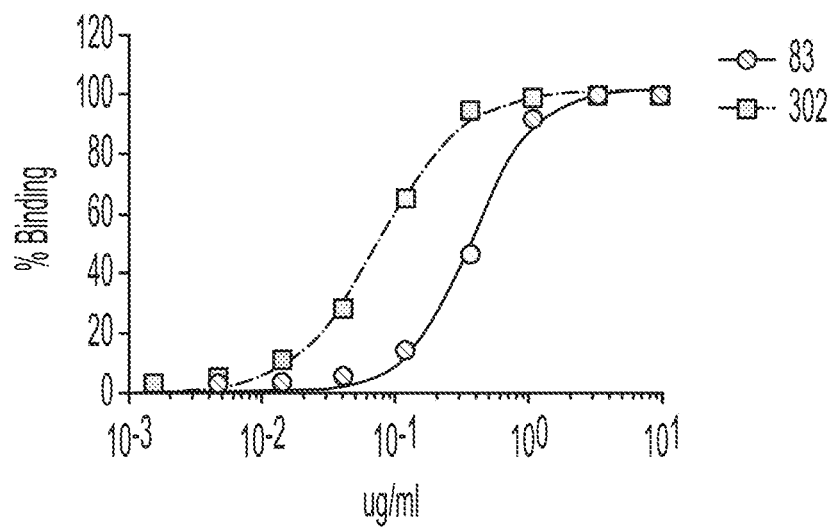
FIG. 22 depicts binding of C-terminal scFv/CD20-CD19 variant fusion proteins to CD20 positive cells.
Figure 23:
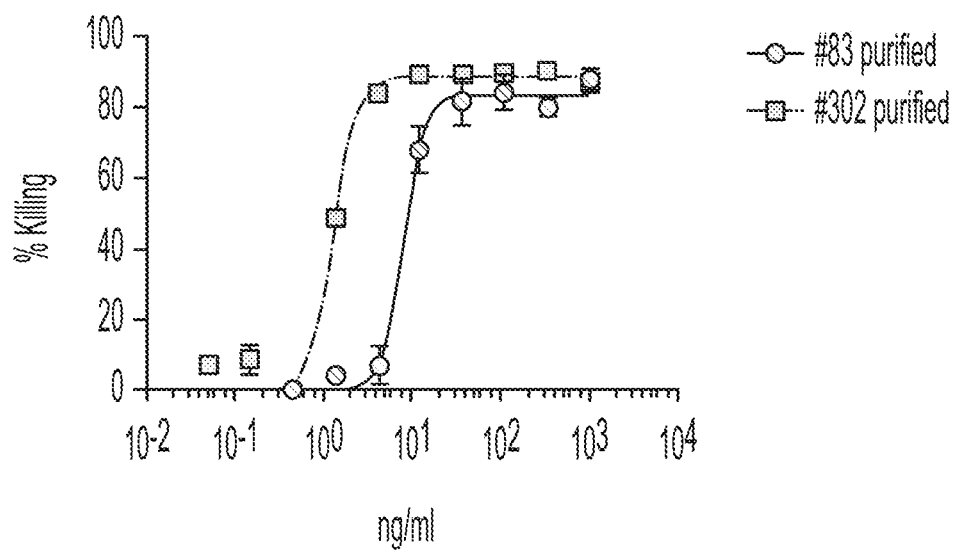
FIG. 23 depicts killing of CD20 positive cells by a CAR19 due to bridging by C-terminal scFv/CD20-CD19 variant fusion proteins.

To provide further evidence of the activity of fusion proteins that include mutant CD19 at the C-terminus, a mutant CD19 was placed C-terminal to the scFv from anti-CD20 mAb Leu16 (construct #302, SEQ ID NO. 13). Good secretion of the fusion protein was observed (FIG. 21). This construct was also tested for its ability to bind and kill 293T cells transfected with CD20. FIG. 22 shows binding of construct #302 to CD20 relative to a fusion protein that included wild type CD19 D1+D2 placed N-terminal to the Leu16 anti-CD20 scFv (construct #83, SEQ ID NO. 14) as detected by FMC63-PE. FIG. 23 shows the ability of construct #302 to bridge with CAR19 cells, leading to the killing of CD20 positive 293T cells. Indeed construct #302 demonstrated increased killing relative to the wild type CD19 D1+D2 fusion protein (construct #83) suggesting that the improved binding shown in FIG. 22 can lead to increased killing.

These data further demonstrate the functional capabilities of fusion proteins that include CD19 mutants at the C-terminus.

Example 13

Function of Masked CD19-Ligand Fusions

Figure 24:
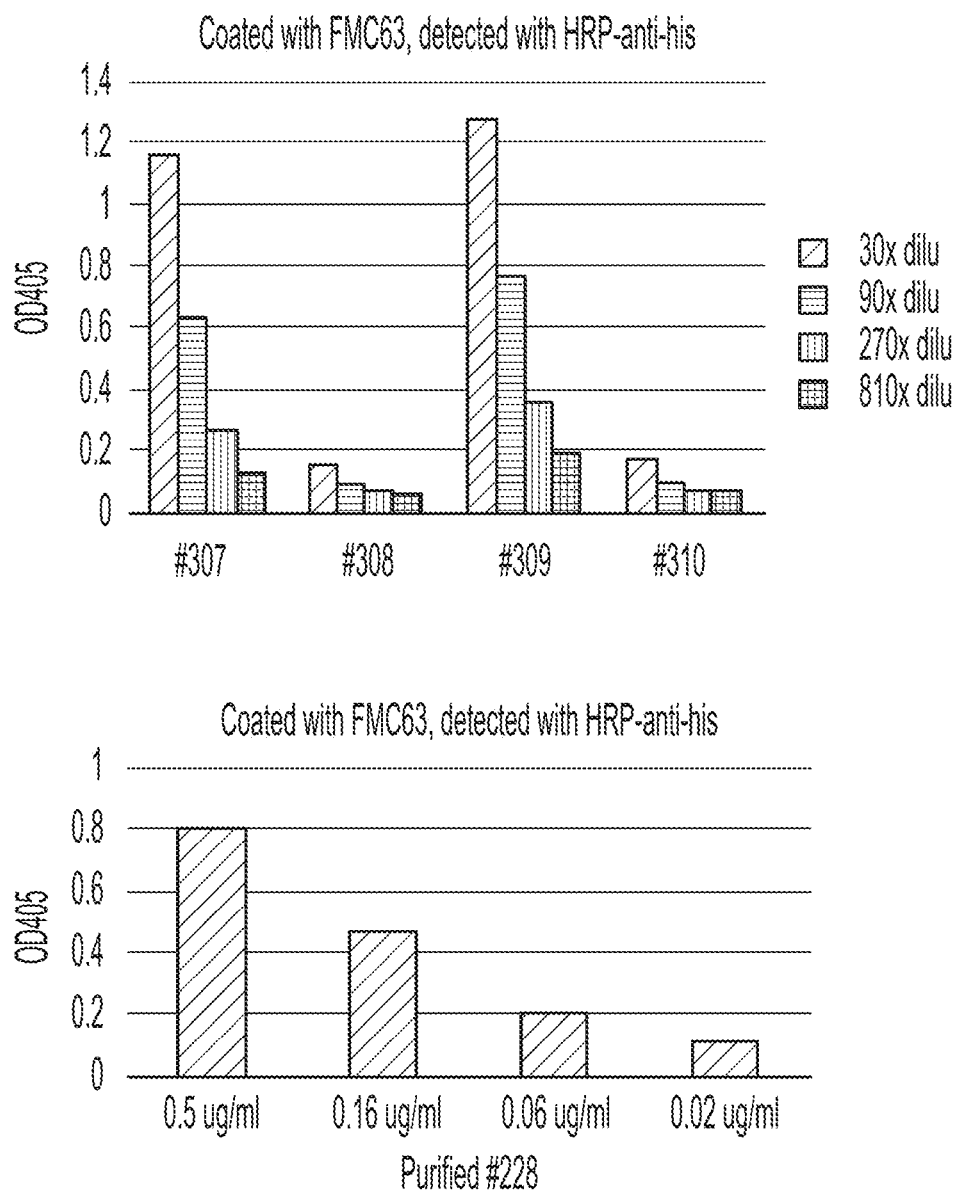
FIG. 24 depicts detection of secreted masked and unmasked C-terminal cetuximab-CD19 variant fusion proteins.

This example further demonstrates the functional capabilities of CD19 mutant proteins by assessing activity of CD19 mutants genetically fused to the C-terminus of an N-terminally masked scFv. A CD19 mutant was fused to the C-terminus of the masked form of the anti-EGFR scFv from Cetuximab that contains a protease substrate cleavable by numerous proteases (e.g., urokinase-type plasminogen activator, uPA), as published (Desnoyers L R et al., Science Translational Medicine (2013)). First, a masked Cetuximab scFv was generated and tested to verify it did not bind EGFR in the absence of proteases, but did so after activation by proteases, e.g. uPA, validating fully the published data (not shown). Next unmasked (construct #307 and #308, SEQ ID NOs. 15 and 16, respectively) and masked (construct #309 and 310, SEQ ID NOs. 17 and 18, respectively) Cetuximab-CD19 constructs were generated. These constructs were well-secreted, whether masked or unmasked, as detected by FMC63 binding and detection by HRP-anti-His in ELISA and shown in FIG. 24.

Figure 25:
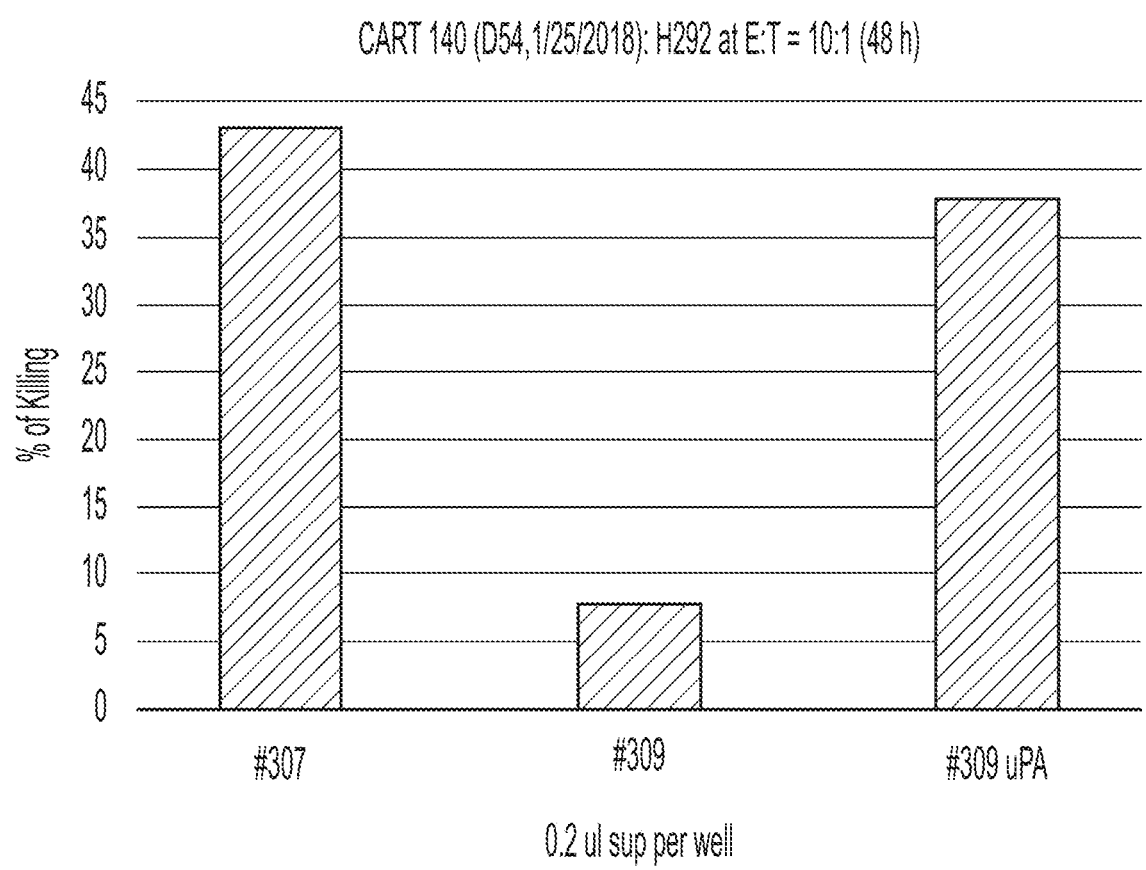
FIG. 25 depicts killing of EGFR positive cells by CAR19 due to bridging by unmasked C-terminal cetuximab-CD19 variant fusion proteins and masked C-terminal cetuximab-CD19 variant fusion proteins in the presence of uPA.
Figure 27:
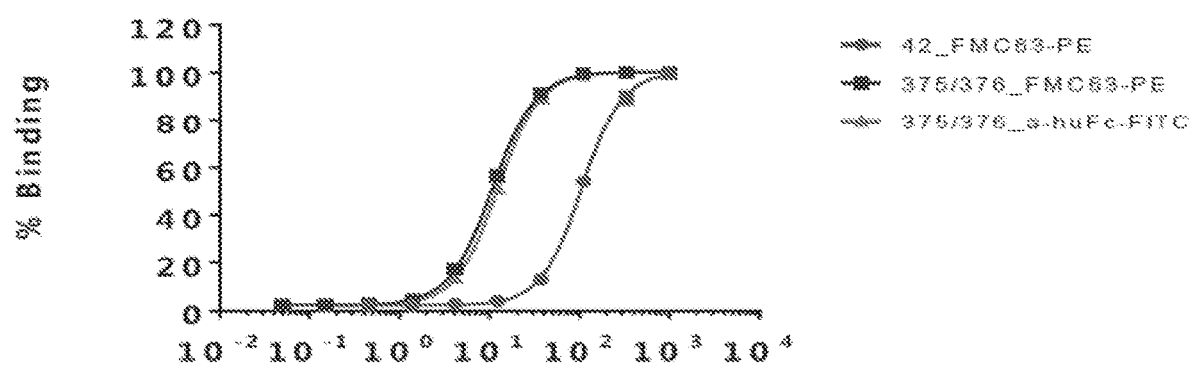
FIG. 27 depicts binding of C-terminal trastuzumab-CD19 variant fusion proteins to Her2 positive cells.
Figure 28:
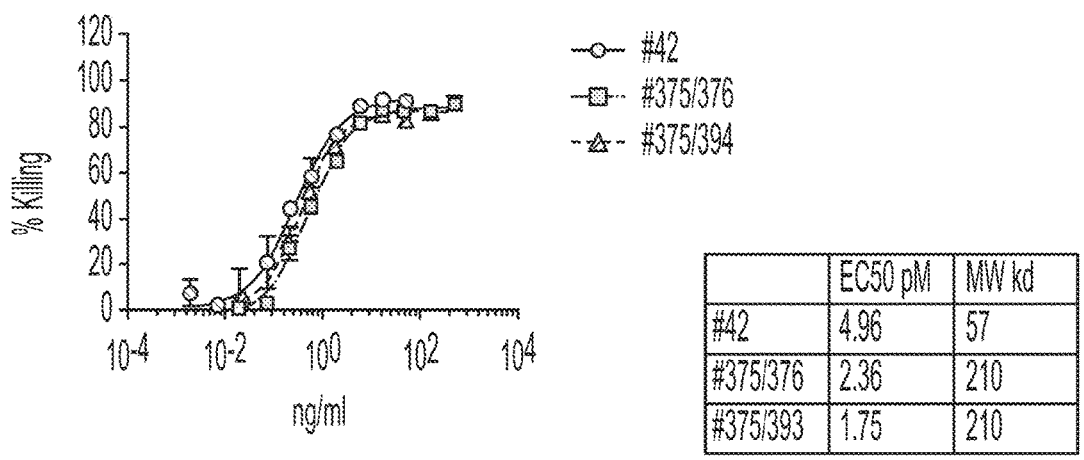
FIG. 28 depicts killing of Her2 positive cells by CAR19 due to bridging by C-terminal trastuzumab-CD19 variant fusion proteins.
Figure 29:
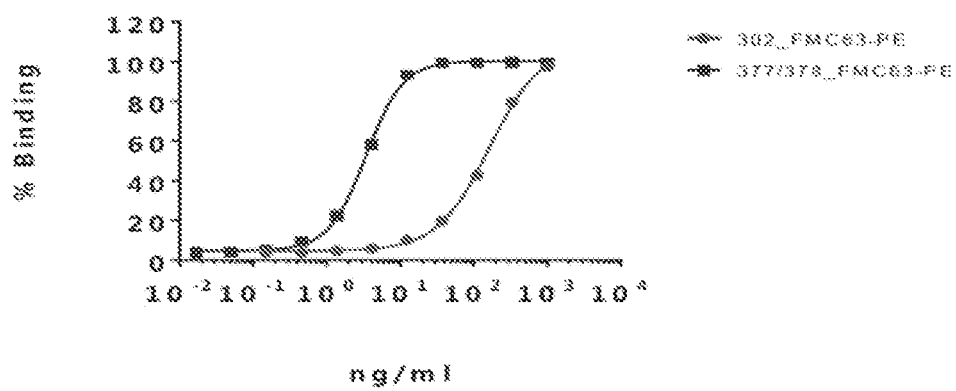
FIG. 29 depicts binding of C-terminal rituximab-CD19 variant fusion proteins to CD20 positive cells.
Figure 30:
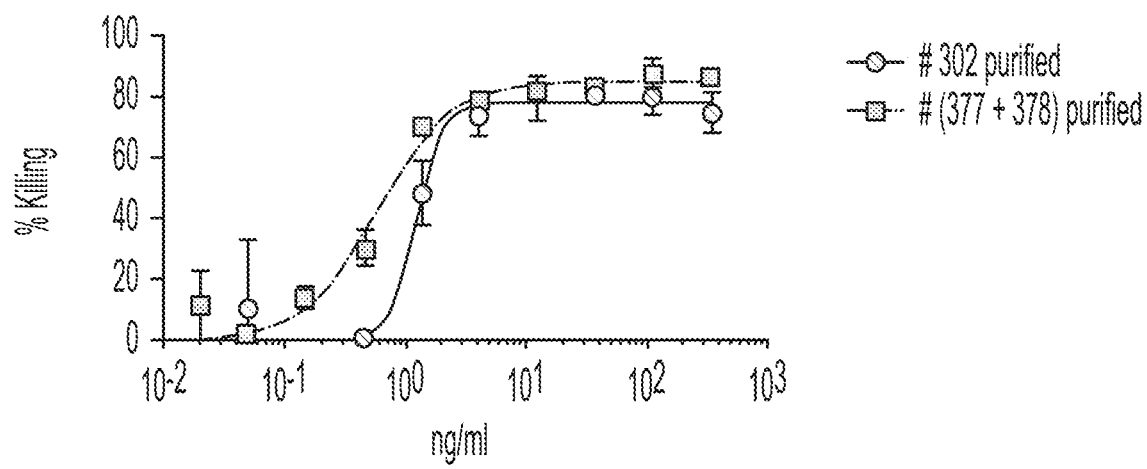
FIG. 30 depicts killing of CD20 positive cells by CAR19 due to bridging by C-terminal rituximab-CD19 variant fusion proteins.
Figure 31:
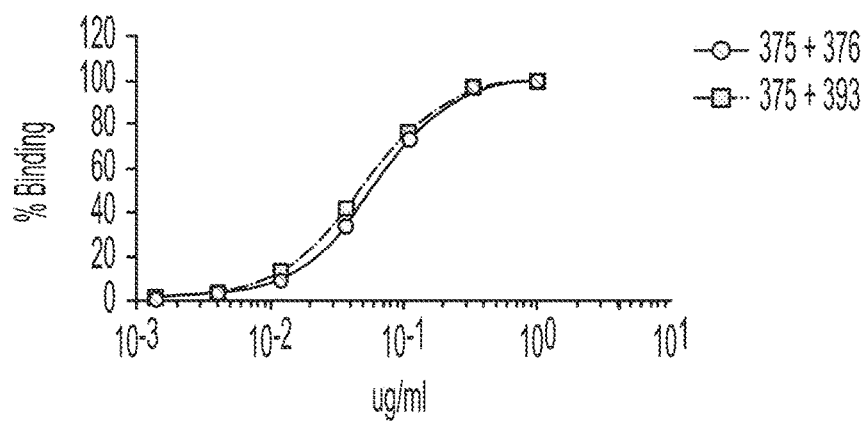
FIG. 31 depicts binding of aglycosyl C-terminal trastuzumab-CD19 variant fusion proteins to Her2 positive cells.
Figure 32:
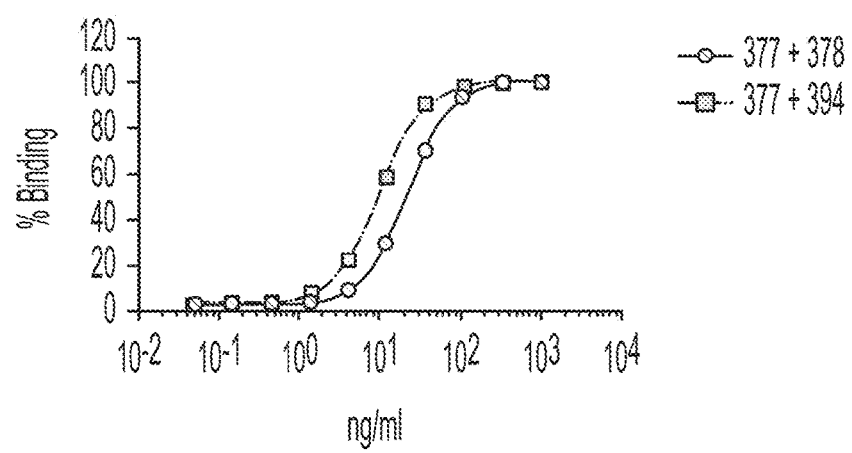
FIG. 32 depicts binding of aglycosyl C-terminal rituximab-CD19 variant fusion proteins to CD20 positive cells.
Figure 33:
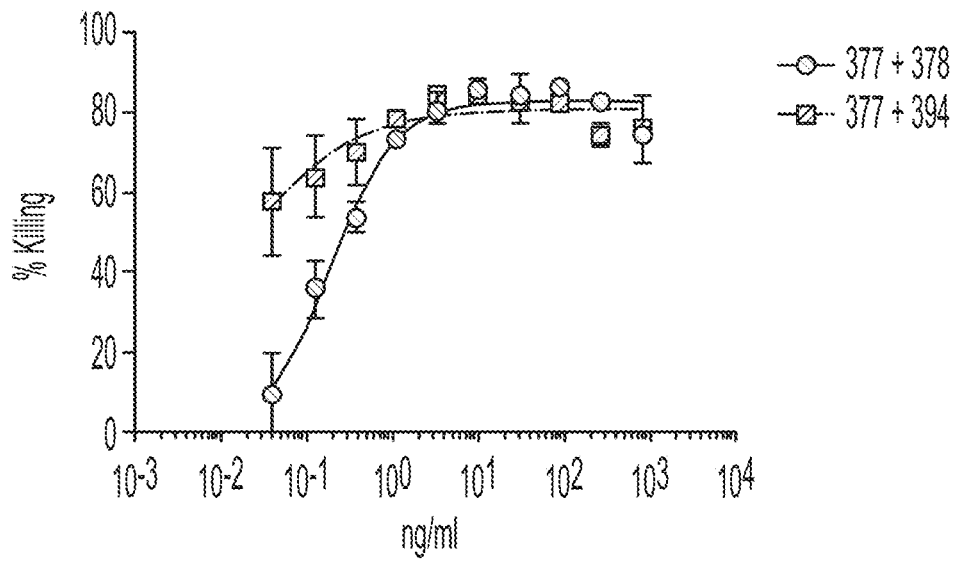
FIG. 33 depicts killing of CD20 positive cells by CAR19 due to bridging by aglycosyl C-terminal rituximab-CD19 variant fusion proteins.
Figure 34:
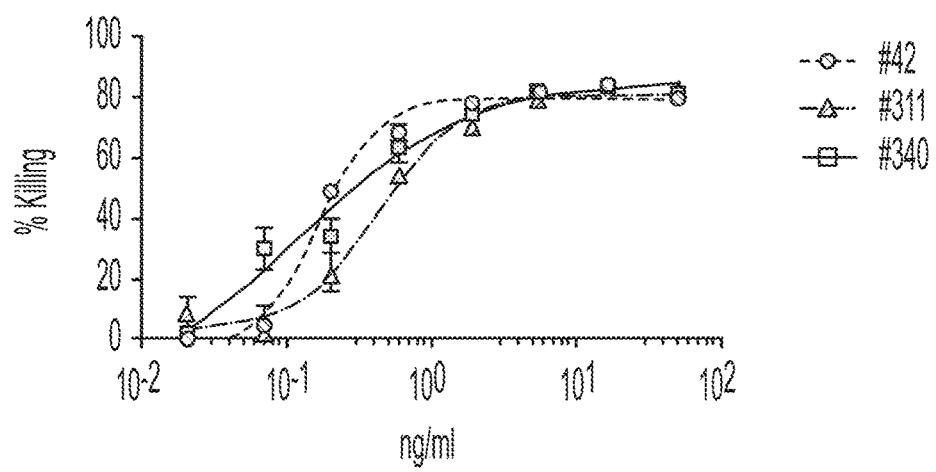
FIG. 34 depicts killing of Her2 positive cells by CAR19 due to bridging by N-terminal truncated CD19 variant-scFv/Her2 fusion proteins.

To demonstrate functionality of the masked construct, masked (construct #309) and unmasked (construct #307) Cetuximab-CD19 constructs were tested for their ability to bridge killing of EGFR positive H292 cells. FIG. 25 shows unmasked scFv/Cetuximab-CD19 construct #307 was capable of bridging killing of EGFR positive cells by CART140 (a CAR19-Tcell). In contrast, masked scFv/Cetuximab-CD19 construct #309 showed significant killing only in the presence of uPA. Thus, this demonstrates CD19 mutant C-terminal fusion with masked antigen binding proteins that were stable and functional.

Example 14

Function of CD19-Multi-Ligand Fusions

This example demonstrates that a CD19 mutant can be placed between two other domains and is not restricted to N- or C-terminal fusions. Specifically, this example demonstrates activity of a CD19 mutant centrally located between two scFvs. A masked scFv/Cetuximab-CD19-scFv/Her2 construct (construct #354, SEQ ID NO. 19) was made to test this concept. FIG. 26 shows construct #354 was secreted well when transfected.

Example 15

Function of Antibody Light Chain-CD19 Fusions

We next assessed whether a fusion protein that includes a mutant CD19 on the light chain of an antibody could produce a functional mAb-CD19 fusion protein. This concept was tested in the context of two fusion proteins. For a first fusion protein, a mutant CD19 was fused C-terminally to the light chain of the Trastuzumab antibody (light chain-CD19 fusion: construct #375, SEQ ID NO. 20; heavy chain: construct #376, SEQ ID NO. 21). For a second fusion protein, a mutant CD19 was fused C-terminally to the light chain of the Rituximab rituximab antibody (light chain-CD19 fusion: construct #377, SEQ ID NO. 22; heavy chain: construct #378, SEQ ID NO. 23).

The trastuzumab-CD19 construct (#375/376) was readily secreted from transfected cells, bound potently to Her2 positive SKOV3 cells as detected in FACS by FMC63-PE and anti-human Fc-FITC (FIG. 27), and potently bridged killing of Her2 positive SKOV3 cells by CART 254 (a CAR19 T-cell) (FIG. 28). The wild type CD19-scFv/Her2 construct is provided for comparison. A construct lacking glyclosylation sites in the heavy chain of the Trastuzumab antibody, described below in Example 16 is also included in FIG. 28.

The Rituximab-CD19 construct (#377/378) was also readily secreted from transfected cells, bound potently to CD20 positive HEK293 cells (FIG. 29), and potently bridged killing of CD20 positive HEK293 cells (FIG. 30). The Leu16scFv-CD19 construct (construct #302, SEQ ID NO. 13) was included for comparison. The Leu16scFv-CD19 construct had a Kd of ~3 nm whereas the Rituximab-based construct, i.e. the full Rituximab mAb, had a Kd of ~16 pM.

Example 16

Aglycosyl mAb-CD19 Fusions

Trastuzumab-CD19 and Rituximab-CD19 constructs were generated in which the CD19 mutant was genetically fused to the C-terminus of the light chain, and a N297A mutation was made in the heavy chain to remove the single glycosylation site. An aglycosyl Trastuzumab-CD19 construct (light chain-CD19 fusion: construct #375, SEQ ID NO. 20; aglycosyl heavy chain: construct #393, SEQ ID NO. 24) demonstrated cell binding that was equivalent to that of a wild type Trastuzumab-CD19 construct (light chain-CD19 fusion: construct #375, SEQ ID NO. 20; heavy chain: construct #376, SEQ ID NO. 21) (FIG. 31). FIG. 28 demonstrates that the wild-type and aglycosyl Trastuzumab-CD19 construct have equivalent EC50s for killing. An aglycosyl Rituximab-CD19 construct (light chain-CD19 fusion: construct #377, SEQ ID NO. 22; aglycosyl heavy chain: construct #394, SEQ ID NO. 25) showed improved binding (~2 fold) relative to a wild type Rituximab-CD19 construct (light chain-CD19 fusion: construct #377, SEQ ID NO. 22; heavy chain: construct #378, SEQ ID NO. 23) (FIG. 32). The observed increase in binding translated to an increase in cell killing by the aglycosyl rituximab-CD19 construct relative to the wild-type construct (FIG. 33).

Example 17

Fusion Proteins with Various CD19 Truncations

Certain CD19 constructs, e.g., construct #42, included a slightly truncated CD19 ECD, with the final 11 amino-acids removed (referred to herein as "D1+D2" or "D1+2"). To assess whether full length CD19 ECD could be used, additional constructs were assessed. Specifically, the activity of wild-type CD19-scFv/Her2 (construct #42, containing "D1+D2" CD19) was compared to NsCD19-scFv/Her2 (i.e., CD19 ECD N term mutant #2-Trastuzumab scFv; construct #311; SEQ ID NO:8) and to a truncated NsCD19-scFv/Her2 (i.e., CD19 D1+2 N term mutant #2-Trastuzumab scFv; construct #340; SEQ ID NO:31). Binding to Her2 positive SKOV3 cells was essentially the same (data not shown), with no difference in secretion or potency, and equivalent killing of Her2 positive SKOV3 cells (FIG. 34). This demonstrates that this truncation is equally effective in the stable CD19 mutants.

Example 18

VHH CD19 Fusions

Fusion proteins of various CD19 mutants and llama VHHs recognizing Clec12A were generated. The VHHs are described by the following clone numbers and sequences noted in the following table:

| Clone | Sequence |
| --- | --- |
| 1B1 | SEQ ID NO: 203 |
| 1G6 | SEQ ID NO: 205 |
| 1B12 | SEQ ID NO: 208 |
| 2C8 | SEQ ID NO: 211 |
| 2F5 | SEQ ID NO: 212 |
| 1A10 | SEQ ID NO: 214 |
| 2H3 | SEQ ID NO: 215 |
| 1H1 | SEQ ID NO: 216 |
| 2F3 | SEQ ID NO: 220 |
| 1B11 | SEQ ID NO: 224 |
| 2C2 | SEQ ID NO: 225 |

Fusion proteins generated and tested included construct #s 186, 289, 290, 291, 292, 293, 320, 321, 323, 327, 328, 329, 330, 331, 333, 334, 335, 337, 338, and 357 (SEQ ID Nos: 52, 39, 40, 41, 42, 43, 44, 26, 45, 28, 46, 47, 27, 48, 49, 50, 51, 30, 29, and 53, respectively).

Figure 35:
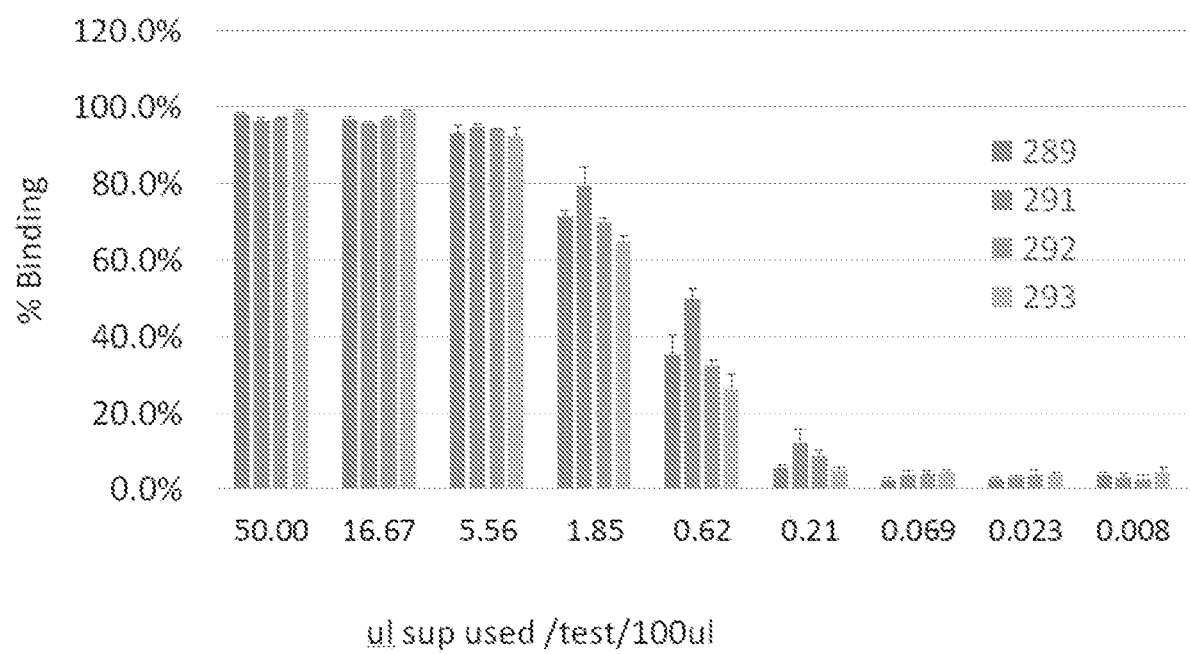
FIG. 35 depicts binding of various CD19 mutant-VHH/Clec12A and VHH/Clec12A-CD19 mutant constructs to U937 cells.
Figure 36:
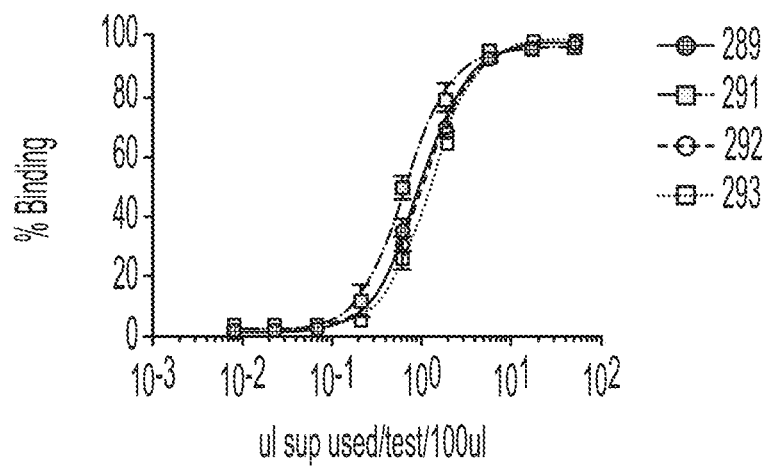
FIG. 36 depicts binding of various CD19 mutant-VHH/Clec12A and VHH/Clec12A-CD19 mutant constructs to U937 cells.
Figure 37:
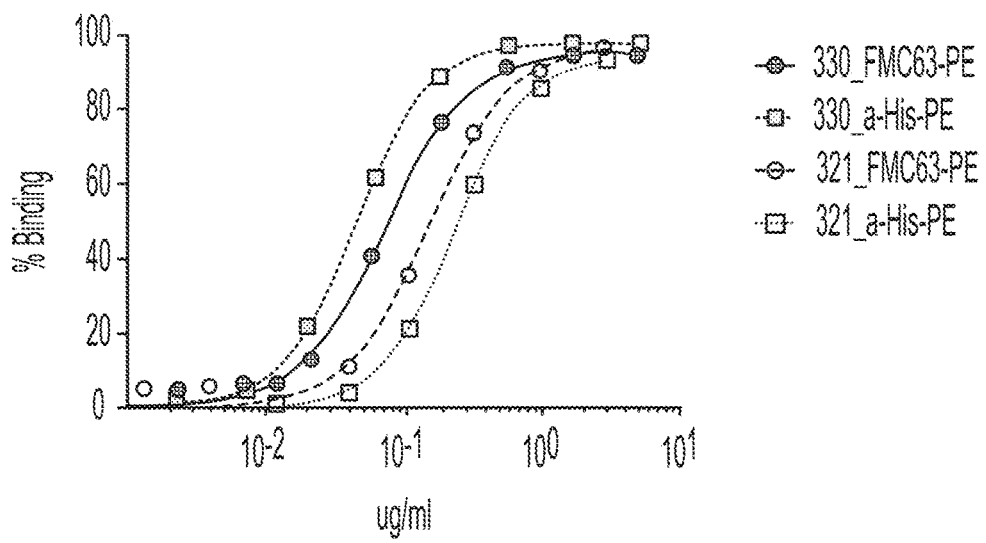
FIG. 37 depicts determination of EC50s of various CD19 mutant-VHH/Clec12A and VHH/Clec12A-CD19 mutant constructs.

Construct #s 289, 291, 292, 293, 321, and 330 (which include CD19 mutant #2 at the N terminus and various VHH at the C terminus) were tested for ability to bind to U937 cells. As shown in FIGS. 35 and 36, construct #s 289, 291, 292, and 293 were able to bind to U937 cells with similar EC50s of between 3 and 5 nM. As shown in FIG. 37, The CD19-VHH1B12/Clec12A (construct #321, SEQ ID NO. 26) and VHH1A10/Clec12A-CD19 (construct #330, SEQ ID NO. 27) constructs both bound in the 1-3 nM range to Clec12A expressing U937 cells.

Figure 38:
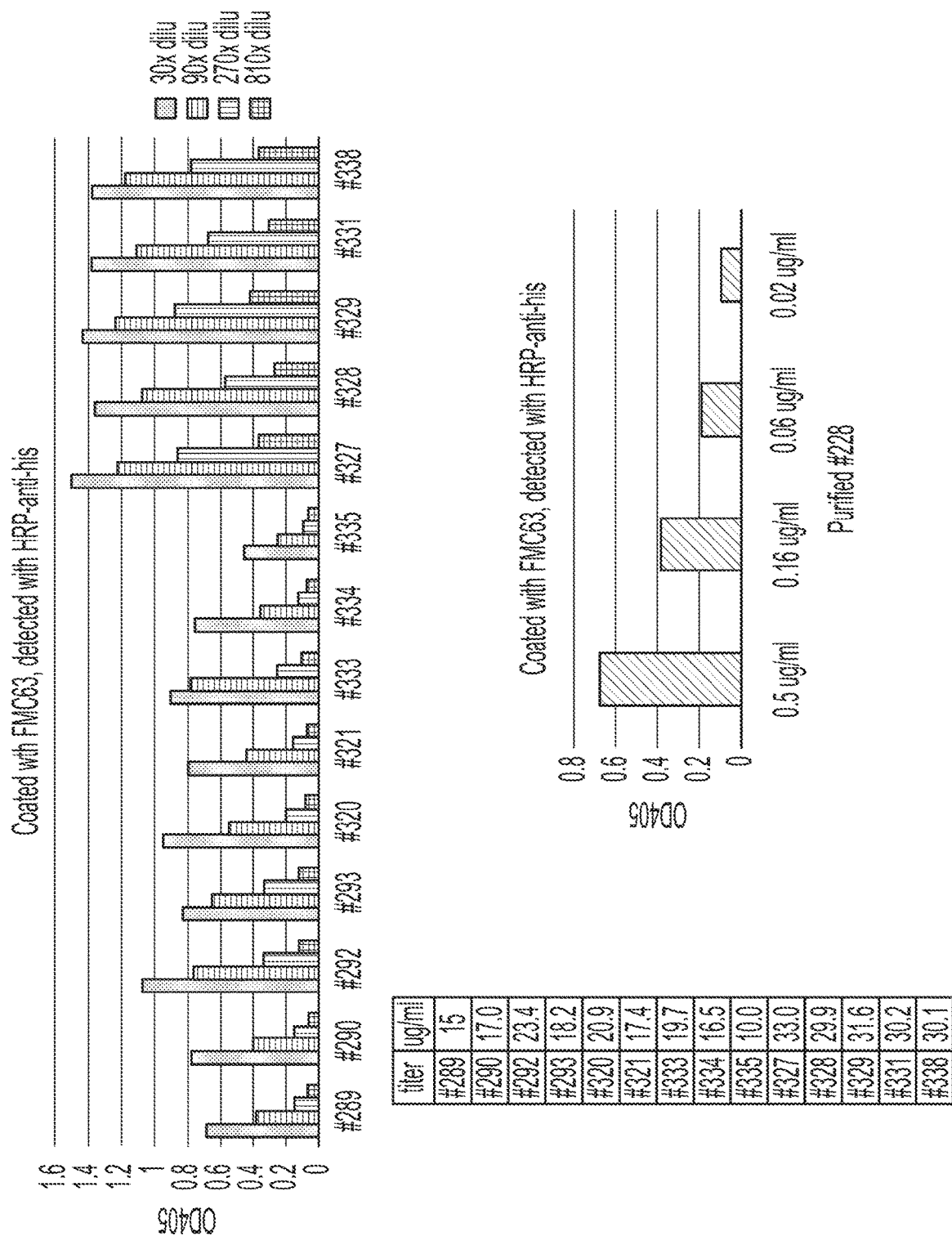
FIG. 38 depicts the titers of various CD19 mutant-VHH/Clec12A and VHH/Clec12A-CD19 mutant constructs.
Figure 40:
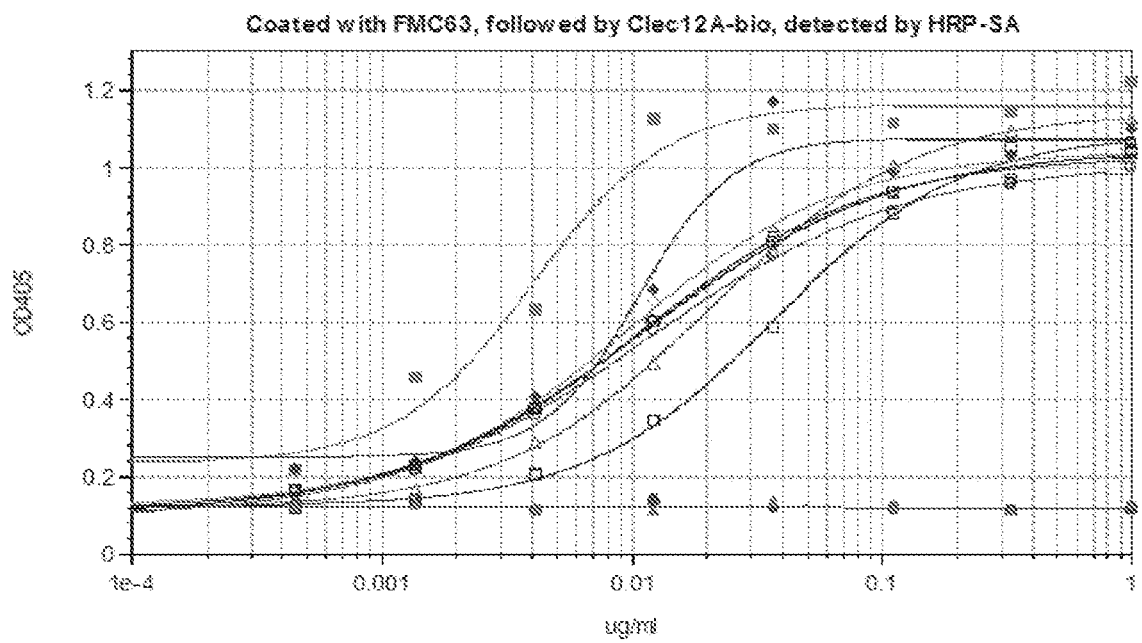
Figure 41:
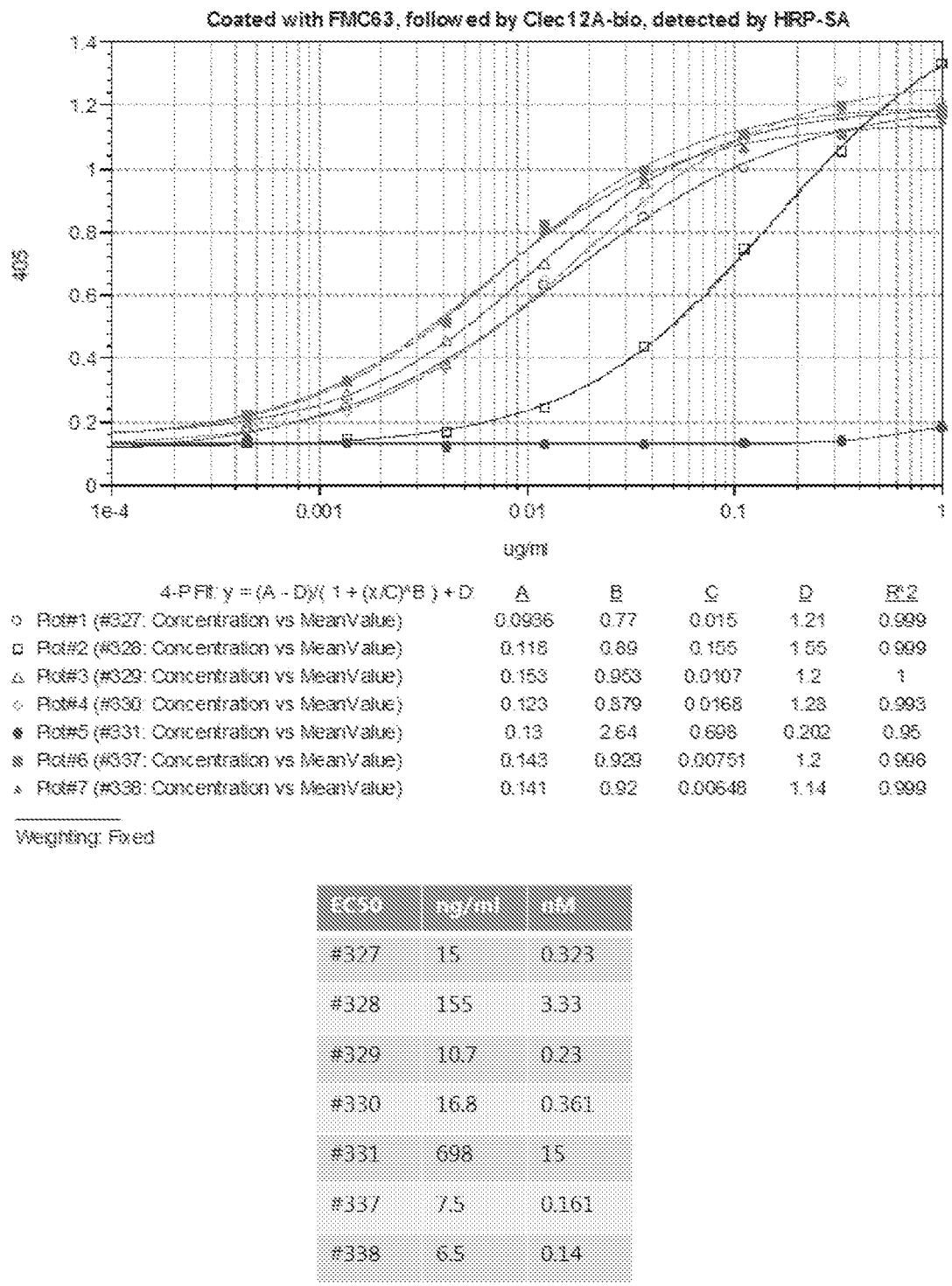

Various constructs that included CD19 mutants at the N terminus and VHH at the C terminus, or constructs that included CD19 mutants at the C terminus and VHH sequences at the N terminus, were assayed for ability to bind to anti-CD19 antibody FMC63 after expression in 293T cells. FIGS. 38 and 39 show the titers of various constructs. These constructs were also assayed for their ability to bind to CLEC12a. The results are depicted in FIGS. 40 and 41.

Figure 42:
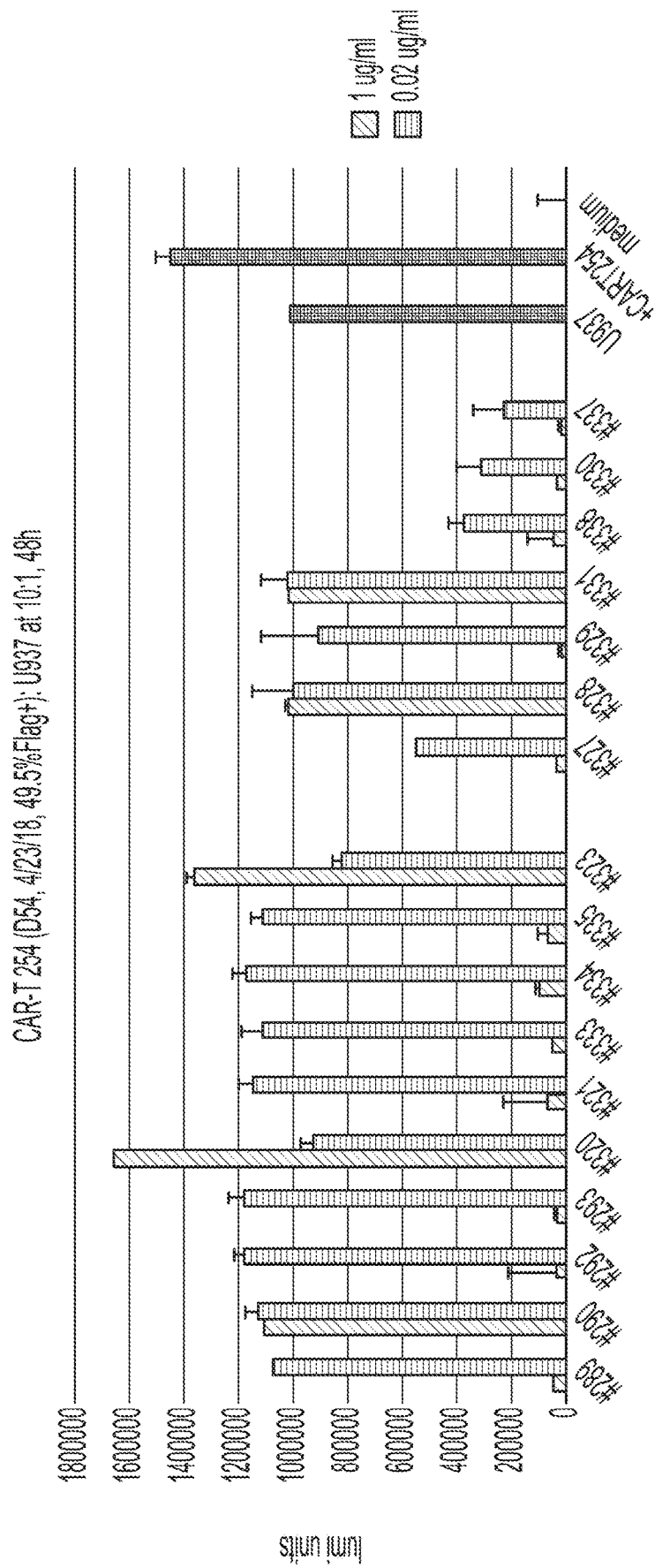
FIG. 42 depicts killing of CLEC12a positive cells by CAR19 due to bridging by various CD19 mutant-VHH/Clec12A and VHH/Clec12A-CD19 mutant constructs.
Figure 43:
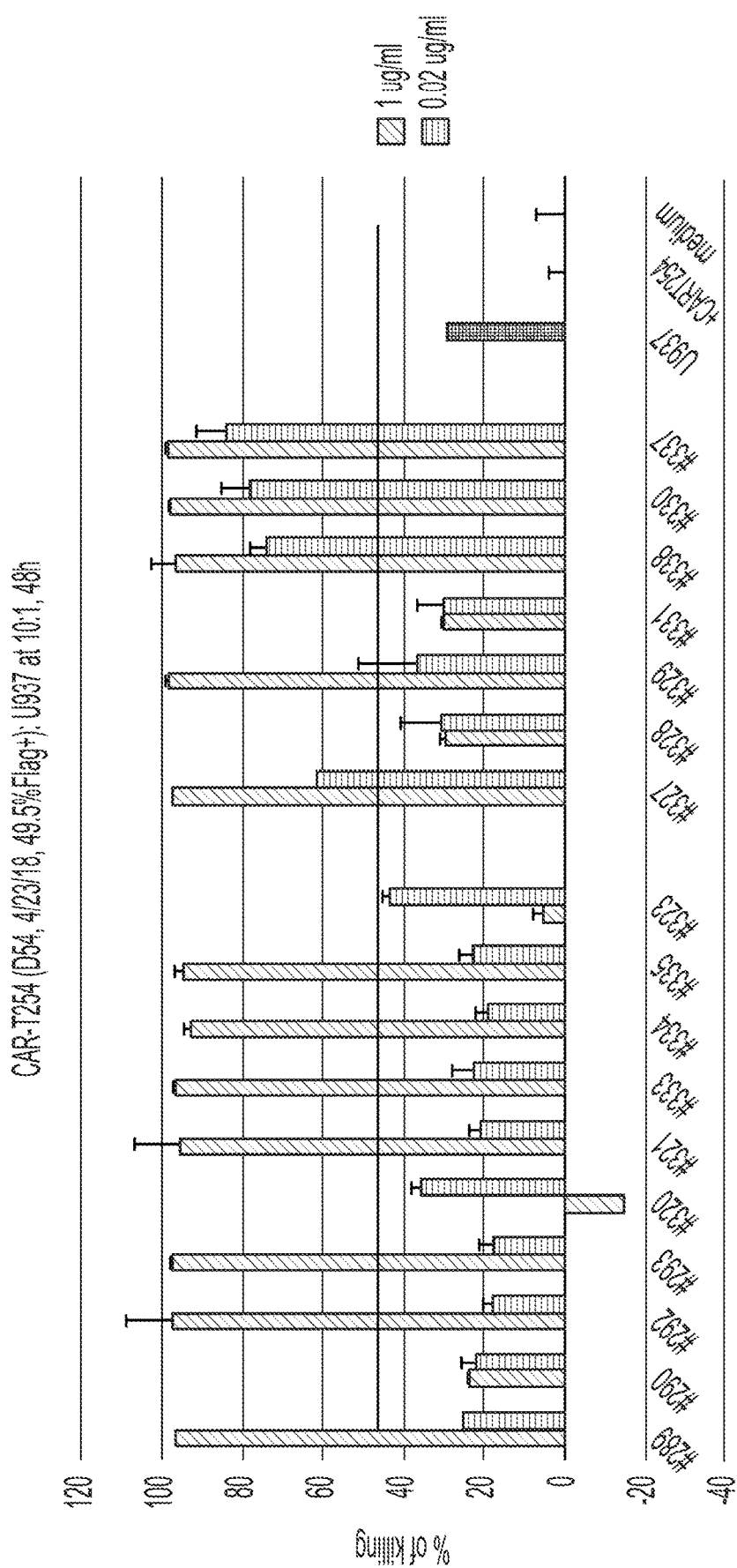
FIG. 43 depicts killing of CLEC12a positive cells by CAR19 due to bridging by various CD19 mutant-VHH/Clec12A and VHH/Clec12A-CD19 mutant constructs.
Figure 44:
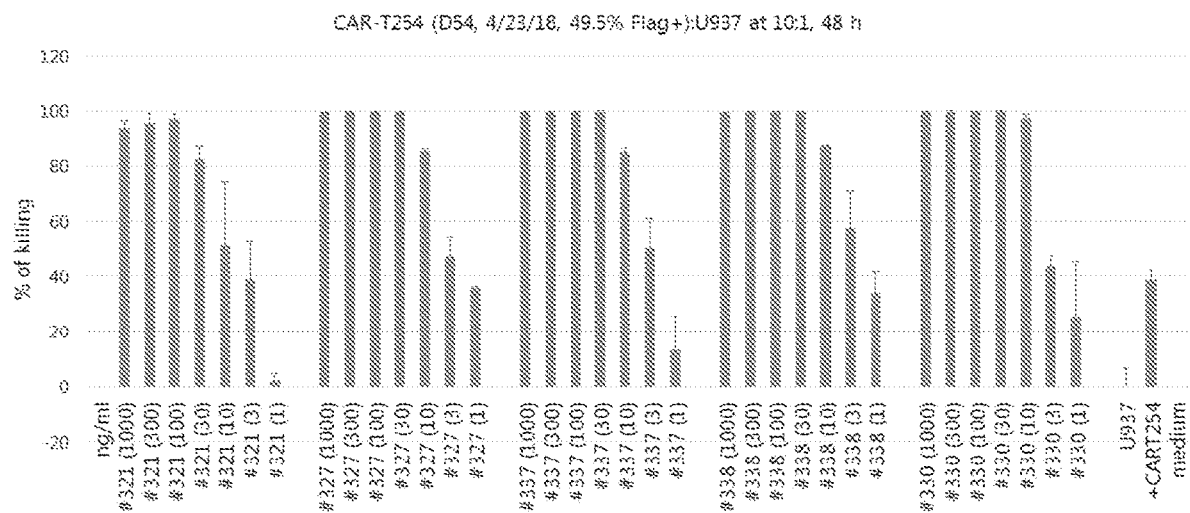
FIG. 44 depicts dose curves of killing of CLEC12a positive cells by CAR19 due to bridging by various CD19 mutant-VHH/Clec12A and VHH/Clec12A-CD19 mutant constructs.
Figure 45:
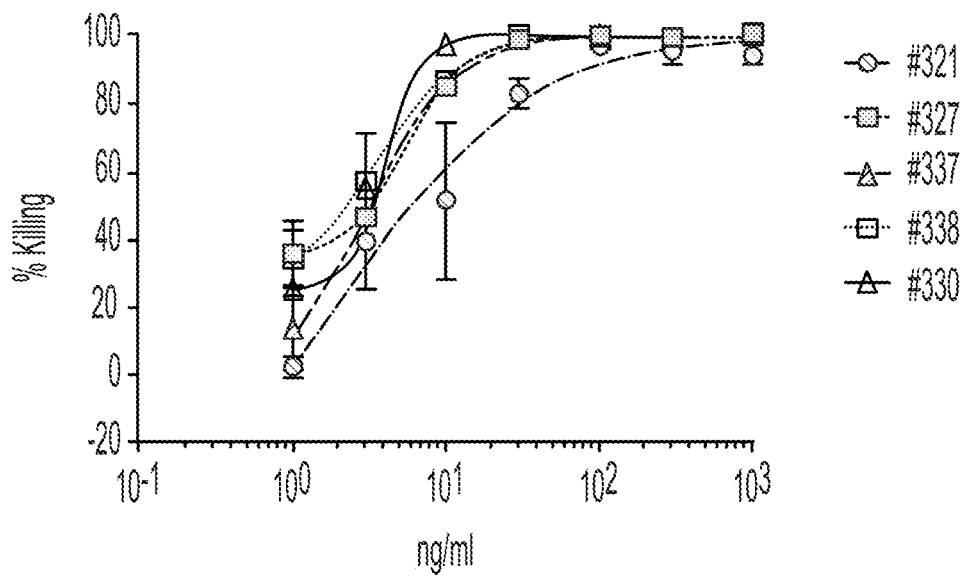
FIG. 45 depicts EC50s of killing of CLEC12a positive cells by CAR19 due to bridging by various CD19 mutant-VHH/Clec12A and VHH/Clec12A-CD19 mutant constructs.

Next, constructs were assayed for their ability to mediate killing of CLEC12a-expressing U937 cells by CAR-T254 cells. Briefly, 1×10$^4$ U937 cells were incubated in wells of a round bottom 96 well plate in RPMI medium. 1 µg/mL and 20 ng/mL constructs were added, for a total of 25 µL per well. CAR-T254 cells were added at a ratio of 1:10 to U937 cells. After 48 hours, cells were spun, lysed, and luciferase levels were measured. FIG. 42 shows luciferase levels, and FIG. 43 shows % of killing for the various constructs, indicating that C terminal fusions were more potent than N terminal fusions. Dose killing curves were performed for four C terminal constructs (#s 327, 337, 338, and 330) and one N-terminal construct (#321). Briefly, 1×10$^4$ U937 cells were incubated in wells of a round bottom 96 well plate in RPMI medium. Constructs were titrated from 1 µg/mL to 1 ng/mL, 25 µL per well. CAR-T254 cells (a CAR19 T-cell) were added at a ratio of 1:10 to U937 cells. After 48 hours, cells were spun, lysed, and luciferase levels were measured. As shown in FIG. 44, maximum U937 cell killing was achieved with all constructs. EC50s were generated, as shown in FIG. 45.

Figure 46B:
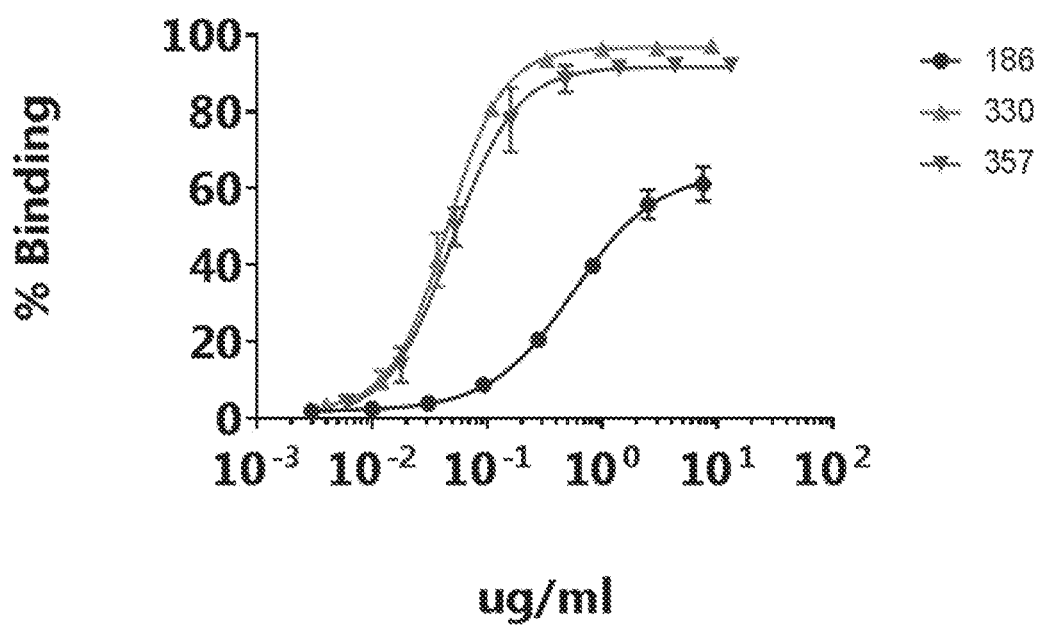
Figure 47B:
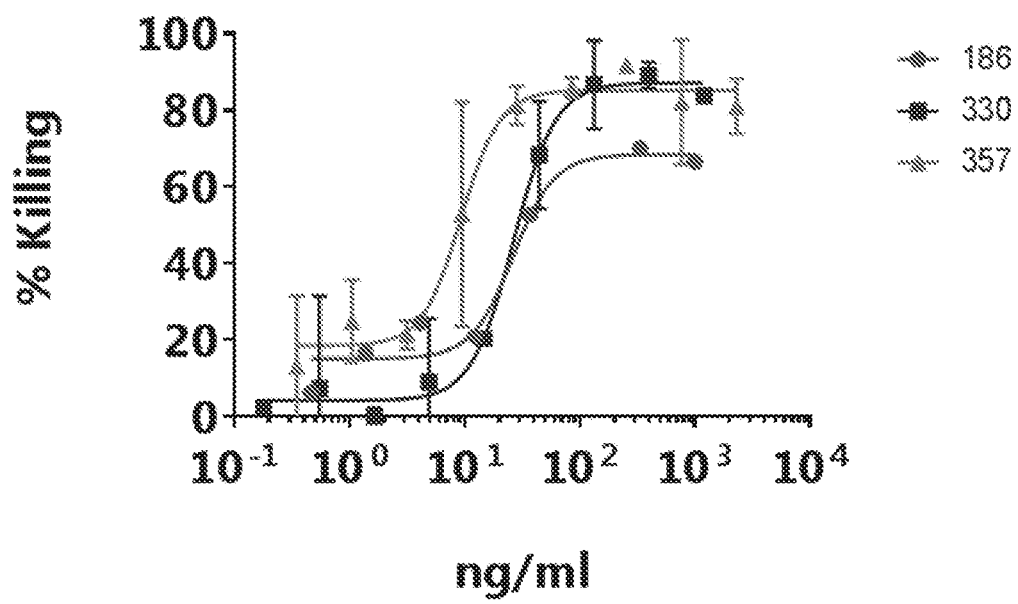

In addition, bispecific constructs were generated and assayed. The bispecific constructs included an anti-CLEC12a scFv described in Wiersma et al., MAbs 7:321-30 (2015). Construct #186 included CD19 domains 1+2 and anti-CLL1 VH and VL domains (described by Wiersma et al.). A bispecific construct (construct #357) was generated that included the VH and VL domains of Construct #186, an anti-CLEC12a VHH (clone 2H3), and CD19 mutant #2. These constructs were assayed for binding to U937 cells. Briefly, U937 cells (5×10$^4$) were Fc blocked, spun, pelleted, 100 µL of 3× serial dilutions of fusion proteins (starting at 7.5 µg/mL) were added, incubated 30 minutes at 4 C, spun, washed twice, to the pellets was added anti-FMC63-PE and incubated for 30 minutes at 4 C. Cells were then spun, washed twice, fixed, and analyzed by FACS. As shown in FIGS. 46A and 46B, the binding EC50 of construct #357 was less than construct #330 (control), which was less then EC50 of construct #186. These constructs were also assayed for their ability to mediate killing of CLEC12a-expressing U937 cells by CAR-T254 cells. Briefly, 1×10$^4$ U937 cells were incubated in wells of a round bottom 96 well plate in RPMI medium. 1×10$^5$ CAR-T254 cells were added at a ratio of 1:10 to U937 cells. 100 µL of 3× serial dilutions of constructs (starting concentrations were 1 µg/mL as final) were used. After a 48 hour incubation, luciferase levels were measured. As shown in FIGS. 47A and 47B, the killing EC50 of construct #357 was much less than construct #186 or #330.

Figure 48:
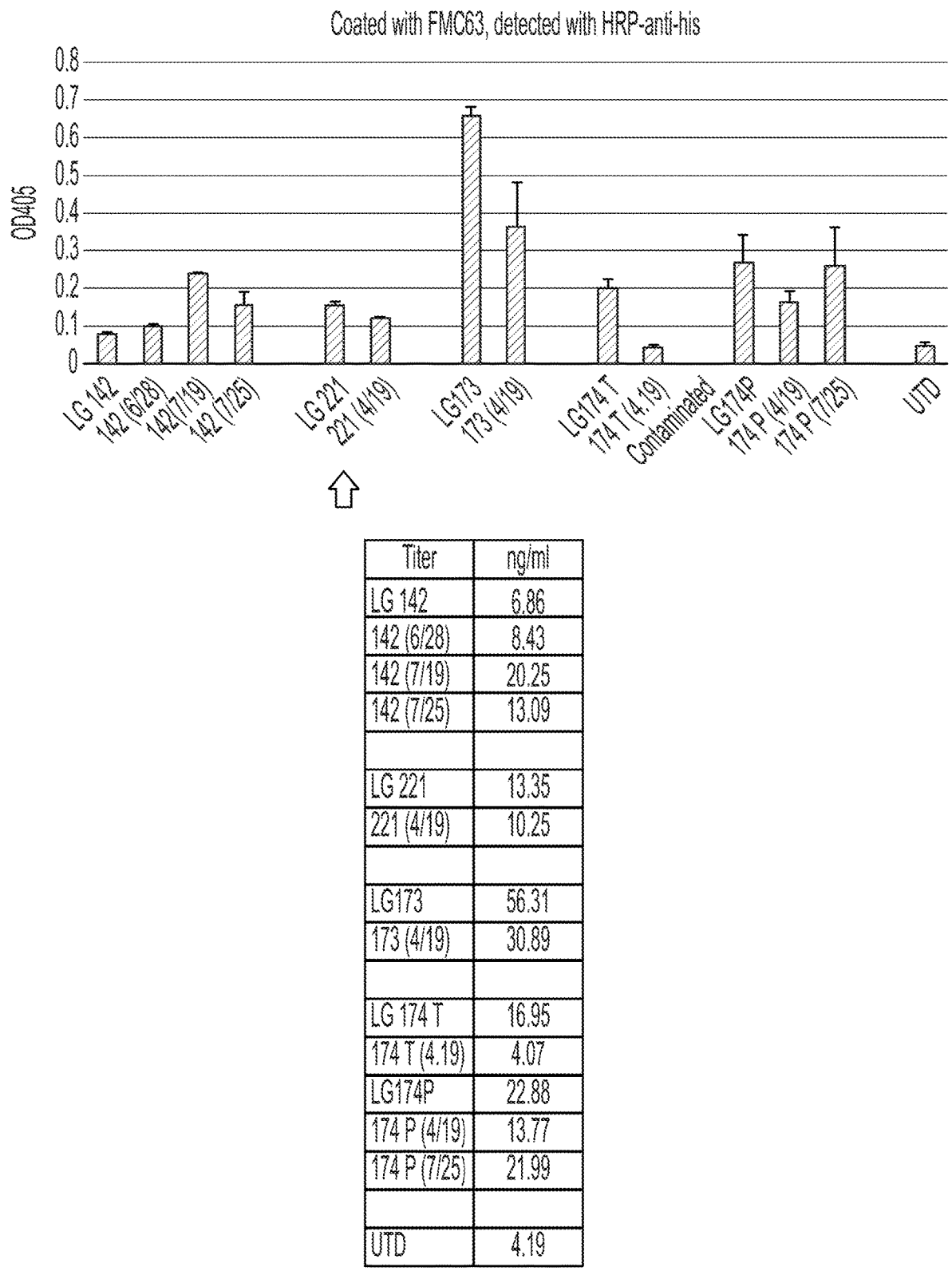
FIG. 48 depicts expression and secretion of fusion constructs from cells infected with a lentiviral vector encoding a fusion protein comprising CAR19; CD19; and an anti-CLEC12a scFv.
Figure 49:
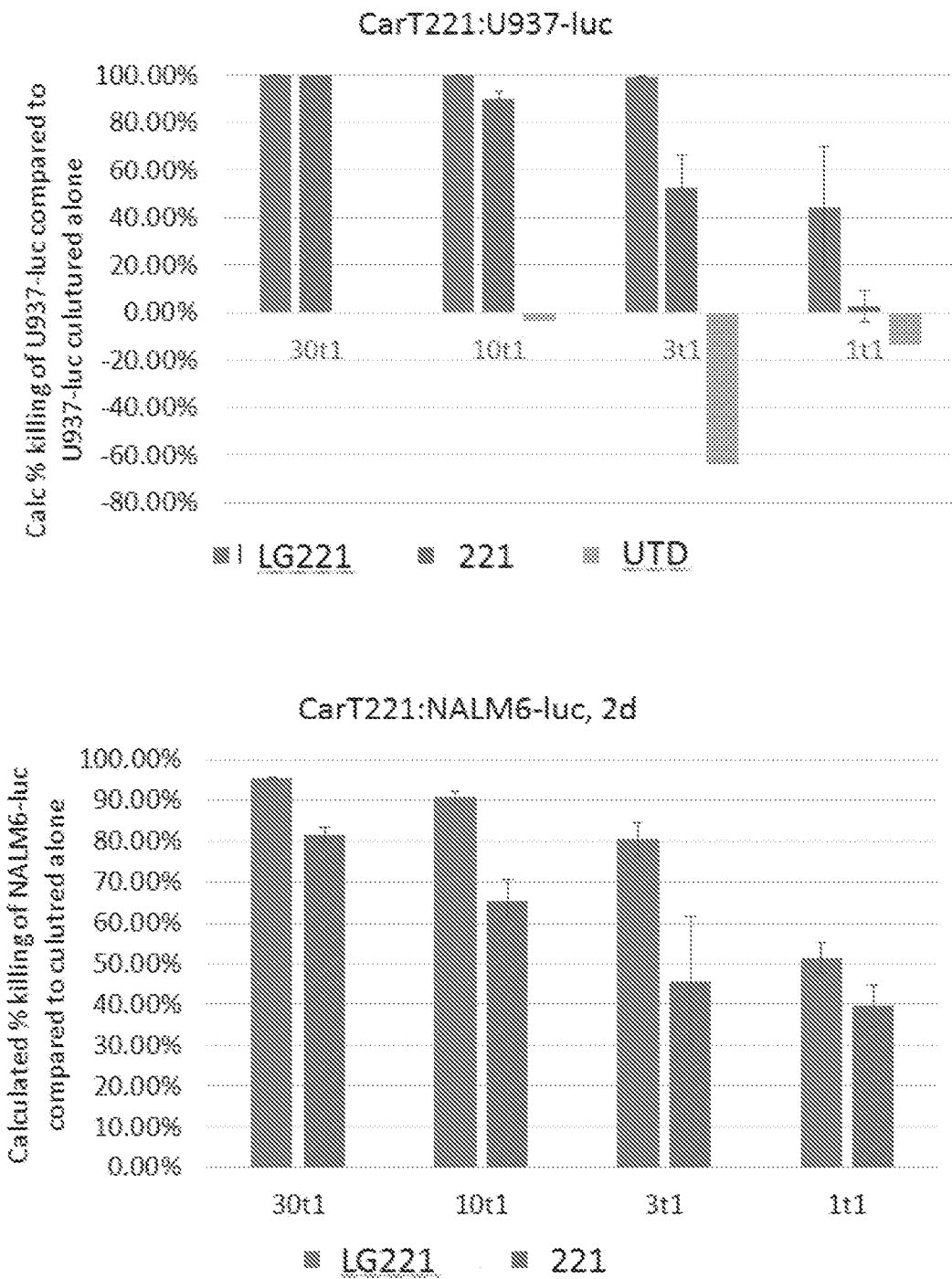

Finally, a lentiviral vector (construct #221) was generated that encoded (i) CD19 CAR and (ii) construct #186. Such lentiviral vector was used to produce CAR T cells expressing CD19 CAR and secreting the fusion protein of construct #186. Such T cells are referred to as "CAR221" cells. Construct #142, 173, and 174 were also generated as controls. As shown in FIG. 48, expression of construct #221 from activated CAR221 cells was low. (Note that "LG142", "LG221", "LG173", and "LG174" are the same constructs #142, 221, 173, and 174, respectfully, but made by a vendor). FIG. 49 demonstrates killing of U937 and NALM6 cells by construct #221 and LG221.

Example 19

CD19 Epitopes

Figure 50:
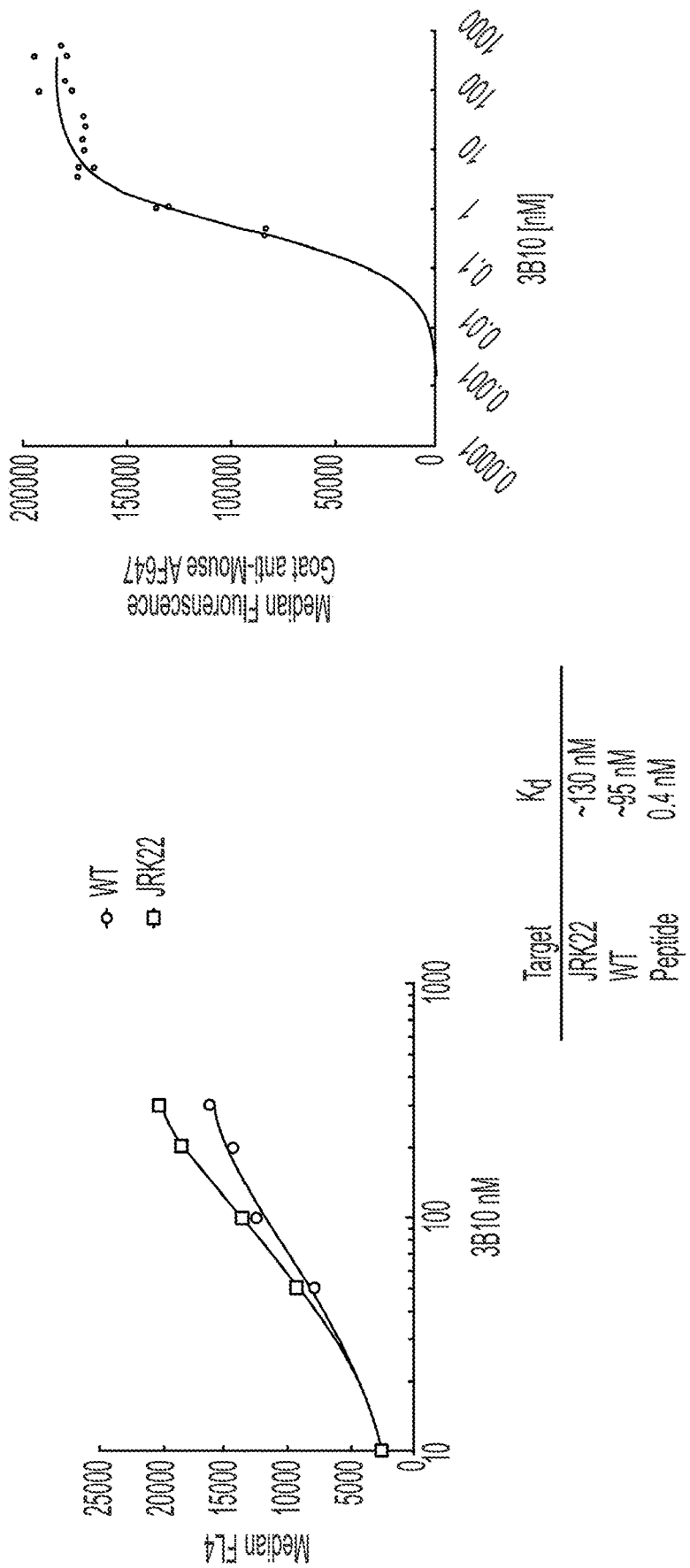

Amino acid positions that were identified (using the systematic mutagenesis library described above) that resulted in loss of FMC63 and 3B10 binding were mapped onto the structure of CD19 (Teplyakov et al., Proteins 86:495-500 (2018)). The epitopes of both mAbs overlap, and are distal from the N- and C-termini, which are close to the plasma membrane. While the FMC63 epitope is not linear, the 3B10 epitope aligns with a linear peptide sequence in CD19, which is consistent with the 3B10 epitope being temperature resistant (described in Example 2; FIG. 3). When this peptide was expressed via yeast display, mAb 3B10 bound well. Surprisingly, mAb 3B10 bound less well to the CD19 ECD expressed on yeast. See FIG. 50.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

Listing of Sequences

SEQ ID NO: 1
CCCGAGGAACCTCTAGTGGTGAAGGTGGAAGAGGGAGATAACGCTGTGCT
GCAGTGCCTCAAGGGGACCTCAGATGGCCCCACTCAGCAGCTGACCTGGT

```
CTCGGGAGTCCCCGCTTAAACCCTTCTTAAAACTCAGCCTGGGGCTGCCA

GGCCTGGGAATCCACATGAGGCCCCTGGCCATCTGGCTTTTCATCTTCAA

CGTCTCTCAACAGATGGGGGGCTTCTACCTGTGCCAGCCGGGGCCCCCT

CTGAGAAGGCCTGGCAGCCTGGCTGGACAGTCAATGTGGAGGGCAGCGGG

GAGCTGTTCCGGTGGAATGTTTCGGACCTAGGTGGCCTGGGCTGTGGCCT

GAAGAACAGGTCCTCAGAGGGCCCCAGCTCCCCTTCCGGGAAGCTCATGA

GCCCCAAGCTGTATGTGTGGGCCAAAGACCGCCCTGAGATCTGGGAGGGA

GAGCCTCCGTGTCTCCCACCGAGGGACAGCCTGAACCAGAGCCTCAGCCA

GGACCTCACCATGGCCCCTGGCTCCACACTCTGGCTGTCCTGTGGGGTAC

CCCCTGACTCTGTGTCCAGGGGCCCCCTCTCCTGGACCCATGTGCACCCC

AAGGGGCCTAAGTCATTGCTGAGCCTAGAGCTGAAGGACGATCGCCCGGC
```

```
CAGAGATATGTGGGTAATGGAGACGGGTCTGTTGTTGCCCCGGGCCACAG

CTCAAGACGCTGGAAAGTATTATTGTCACCGTGGCAACCTGACCATGTCA

TTCCACCTGGAGATCACTGCTCGGCCAGTACTATGGCACTGGCTGCTGAG

GACTGGTGGCTGGAAG
```

SEQ ID NO: 2
PEEPLVVKVEEGDNAVLQCLKGTSDGPTQQLTWSRESPLKPFLKLSLGLP

GLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHP

KGPKSLLSLELKDDRPARDMWVMETGLLLPRATAQDAGKYYCHRGNLTMS

FHLEITARPVLWHWLLRTGGWK

Listing of Construct Amino Acid Sequences

SEQ ID NO: 3
MPPPRLLFFLLFLTPMEVRPEEPLVVKVEEGDDAWLRCLKGTSDGPTSQVTWSRESPLK

PFLKYSLGVPGLGVHIRPLAIGLVIPNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKYYCHRGNRTISYHLEITARPVSAHTPLRTGGWKGGG

GSGGGGSGGGGSGGGGSVSDVPRDLEVVAATPTSLLISWFDYAVTYYRITYGETGGNSP

VQEFTVPGWISTATISGLKPGVDYTITVYAVTDNSHWPFRSTPISTNYRTEIDKPPQHHHH

HH

SEQ ID NO: 4
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSVSDVPRDLEVVAATPTSLLISWFDYAVTYYRITYGETGGNSP

VQEFTVPGWISTATISGLKPGVDYTITVYAVTDNSHWPFRSTPISTNYRTEIDKPPQHHHH

HH

SEQ ID NO: 5
MPPPRLLFFLLFLTPMEVRPEEPLVVKVEEGDTAALWCLKGTSDGPTQQLTWSRESPLK

PFLKLSLGLPGMGVHMRPGAVSAVISNVSQQMGGFYLCQPGPPSEKAWQPGWTVNVE

GSGELFRWNVSDLGGLGCGLKNRSSEGPSSPSGKLMSPKLYVWAKDRPEIWEGEPPCLP

PRDSLNQSLSRDMTVAPGSTLWLSCGVPPDSVSRGPLSWTHVHPKGPKSLLSLELKDDR

PARDMWVMGTSLILPRATAQDAGKYYCHRGNLTMSFHLEVVARPVKAHSDLRTGGW

KGGGGSGGGGSGGGGSGGGGSVSDVPRDLEVVAATPTSLLISWFDYAVTYYRITYGET

GGNSPVQEFTVPGWISTATISGLKPGVDYTITVYAVTDNSHWPFRSTPISTNYRTEIDKPP

QHHHHHH

SEQ ID NO: 6
MPPPRLLFFLLFLTPMEVRPEEPLVVKVEEGDTAALWCLKGTSDGPTQQLTWSRESPLK

PFLKYSLGVPGMGVHVRPNAVSLVISNVSQQMGGFYLCQPGPPSEKAWQPGWTVNVE

```
GSGELFRWNVSDLGGLGCGLKNRSSEGPSSPSGKLMSPKLYVWAKDRPEIWEGEPPCLP

PRDSLNQSLSRDMTVAPGSTLWLScGVPPDSVSRGPLSWTHVHPKGPKSLLSLELKDDR

PARDMWVMETGLVLPRATAQDAGKWYCHRGNVTTSYHLEITARPVSAHTPLRTGGWK

GGGGSGGGGSGGGGSGGGGSVSDVPRDLEVVAATPTSLLISWFDYAVTYYRITYGETG

GNSPVQEFTVPGWISTATISGLKPGVDYTITVYAVTDNSHWPFRSTPISTNYRTEIDKPPQ

HHHHHH

SEQ ID NO: 7
MPPPRLLFFLLFLTPMEVRPEEPLVVKVEEGDNAVLQCLKGTSDGPTQQLTWSRESPLKP

FLKLSLGLPGLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEGEPPCLPPRD

SLNQSLSQDLTMAPGSTLWLSCGVPPDSVSRGPLSWTHVHPKGPKSLLSLELKDDRPAR

DMWVMETGLLLPRATAQDAGKYYCHRGNLTMSFHLEITARPGGGSGGGGSGGGGSG

GGGSVSDVPRDLEVVAATPTSLLISWFDYAVTYYRITYGETGGNSPVQEFTVPGWISTAT

ISGLKPGVDYTITVYAVTDNSHWPFRSTPISTNYRTEIDKPPQHHHHHH

SEQ ID NO: 8
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTGGGGSGGGGSGGGGSDIQMTQSPSSLSASVGDR

VTITCRASQDVNTAVAWYQQKPGKAPKLLIYSASFLYSGVPSRFSGSRSGTDFTLTISSL

QPEDFATYYCQQHYTTPPTFGQGTKVEIKRTHHHHHH

SEQ ID NO: 9
MPPPRLLFFLLFLTPMEVRPEEPLVVKVEEGDNAVLQCLKGTSDGPTQQLTWSRESPLKP

FLKLSLGLPGLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEGEPPCLPPRD

SLNQSLSQDLTMAPGSTLWLSCGVPPDSVSRGPLSWTHVHPKGPKSLLSLELKDDRPAR

DMWVMETGLLLPRATAQDAGKYYCHRGNLTMSFHLEITARPGGGSGGGGSGGGGSG

GGGSEVQLVESGGGLVQPGGSLRLSCAASGFNIKDTYIHWVRQAPGKGLEWVARTYPT

NGYTRYADSVKGRFTISADTSKNTAYLQMNSLRAEDTAVYYCSRWGGDGFYAMDYW

GQGTLVTVSSASTGGGGSGGGGSGGGGSDIQMTQSPSSLSASVGDRVTITCRASQDVNT

AVAWYQQKPGKAPKLLIYSASFLYSGVPSRFSGSRSGTDFTLTISSLQPEDFATYYCQQH

YTTPPTFGQGTKVEIKRTSRGPHHHHHH

SEQ ID NO: 10
MEFGLSWVFLVALFRGVQCEVQLVESGGGLVQPGGSLRLSCAASGFNIKDTYIHWVRQ

APGKGLEWVARIYPTNGYTRYADSVKGRFTISADTSKNTAYLQMNSLRAEDTAVYYCS

RWGGDGFYAMDYWGQGTLVTVSSASTGGGGSGGGGSGGGGSDIQMTQSPSSLSASVG

DRVTITCRASQDVNTAVAWYQQKPGKAPKLLIYSASFLYSGVPSRFSGSRSGTDFTLTIS

SLQPEDFATYYCQQHYTTPPTFGQGTKVEIKRTGGGGSGGGGSGGGGSGGGGS
```

```
-continued
PEEPLVVKVEEGDTAALWCLKGTSDGPTQQLTWSRESPLKPFLKYSLGVPGLGVHVRP

DAISVVIRNVSQQMGGFYLCQPGPPSEKAWQPGWTVNVEGSGELFRWNVSDLGGLGC

GLKNRSSEGPSSPSGKLMSPKLYVWAKDRPEIWEGEPPCLPPRDSLNQSLSRDLTVAPGS

TLWLSCGVPPDSVSRGPLSWTHVHPKGPKSLLSLELKDDRPARDMWVMGTSLMLPRAT

AQDAGKWYCHRGNLTMSFHLEITARPSRHHHHHH

SEQ ID NO: 11
MEFGLSWVFLVALFRGVQCEVQLVESGGGLVQPGGSLRLSCAASGFNIKDTYIHWVRQ

APGKGLEWVARIYPTNGYTRYADSVKGRFTISADTSKNTAYLQMNSLRAEDTAVYYCS

RWGGDGFYAMDYWGQGTLVTVSSASTGGGGSGGGGSGGGGSDIQMTQSPSSLSASVG

DRVTITCRASQDVNTAVAWYQQKPGKAPKLLIYSASFLYSGVPSRFSGSRSGTDFTLTIS

SLQPEDFATYYCQQHYTTPPTFGQGTKVEIKRTGGGGSGGGGSGGGGSGGGGS

PEEPLVVKVEEGDTAALWCLKGTSDGPTQQLTWSRESPLKPFLKYSFGGPGLGIHMRPD

AISVVISNVSQQMGGFYLCQPGPPSEKAWQPGWTVNVEGSGELFRWNVSDLGGLGCGL

KNRSSEGPSSPSGKLMSPKLYVWAKDRPEIWEGEPPCLPPRDSLNQSLSRDLTVAPGSTL

WLSCGVPPDSVSRGPLSWTHVHPKGPKSLLSLELKDDRPAREMWVTGTRLFLPRATAQ

DAGKYYCHRGNLTMSFHLEITARPSRHHHHHH

SEQ ID NO: 12
MEFGLSWVFLVALFRGVQCEVQLVESGGGLVQPGGSLRLSCAASGFNIKDTYIHWVRQ

APGKGLEWVARIYPTNGYTRYADSVKGRFTISADTSKNTAYLQMNSLRAEDTAVYYCS

RWGGDGFYAMDYWGQGTLVTVSSASTGGGGSGGGGSGGGGSDIQMTQSPSSLSASVG

DRVTITCRASQDVNTAVAWYQQKPGKAPKLLIYSASFLYSGVPSRFSGSRSGTDFTLTIS

SLQPEDFATYYCQQHYTTPPTFGQGTKVEIKRTGGGGSGGGGSGGGGSGGGGSPEEPLV

VKVEEGDTAALWCLKGTSDGPTEQVTWSRESPLKPFLKLSLGLPGGGHVRPNAVSLVI

RNVSQQMGGFYLCQPGPPSEKAWQPGWTVNVEGSGELFRWNVSDLGGLGCGLKNRSS

EGPSSPSGKLMSPKLYVWAKDRPEIWEGEPPCLPPRDSLNQSLSRDLTVAPGSTLWLSCG

VPPDSVSRGPLSWTHVHPKGPKSLLSLELKDDRPARDMWVTETGLLLPRATAQDAGKW

YCHRGNLTMSFHLEITARPSRHHHHHH

SEQ ID NO: 13
MMEFGLSWVFLVALFRGVQCQVKLQESGAELVKPGASVKMSCKASGYTFTSYNMHW

VKQTPGQGLEWIGAIYPGNGDTSYNQKFKGKATLTADKSSSTAYMQLSSLTSEDSADY

YCARSNYYGSSYWFFDVWGQGTTVTVSSASTGGGGSGGGGSGGGGSDIELTQSPTILSA

SPGEKVTMTCRASSSVNYMDWYQKKPGSSPKPWIYATSNLASGVPARFSGSGSGTSYSL

TISRVEAEDAATYYCQQWSFNPPTFGGGTKLEIKRAAAGGGGSGGGGSGGGGSGGGGS

PEEPLVVKVEEGDTAALWCLKGTSDGPTQQLTWSRESPLKPFLKYSLGVPGLGVHVRP

DAISVVIRNVSQQMGGFYLCQPGPPSEKAWQPGWTVNVEGSGELFRWNVSDLGGLGC

GLKNRSSEGPSSPSGKLMSPKLYVWAKDRPEIWEGEPPCLPPRDSLNQSLSRDLTVAPGS

TLWLSCGVPPDSVSRGPLSWTHVHPKGPKSLLSLELKDDRPARDMWVMGTSLMLPRAT

AQDAGKWYCHRGNLTMSFHLEITARPSRHHHHHH

SEQ ID NO: 14
MPPPRLLFFLLFLTPMEVRPEEPLVVKVEEGDNAVLQCLKGTSDGPTQQLTWSRESPLKP

FLKLSLGLPGLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEGEPPCLPPRD

SLNQSLSQDLTMAPGSTLWLSCGVPPDSVSRGPLSWTHVHPKGPKSLLSLELKDDRPAR
```

```
-continued
DMWVMETGLLLPRATAQDAGKYYCHRGNLTMSFHLEITARPGGGGSGGGGSGGGGSG

GGGSMAQVKLQESGAELVKPGASVKMSCKASGYTFTSYNMHWVKQTPGQGLEWIGAI

YPGNGDTSYNQKFKGKATLTADKSSSTAYMQLSSLTSEDSADYYCARSNYYGSSYWFF

DVWGQGTTVTVSSGGGGSGGGGSGGGGSDIELTQSPTILSASPGEKVTMTCRASSSVNY

MDWYQKKPGSSPKPWIYATSNLASGVPARFSGSGSGTSYSLTISRVEAEDAATYYCQQ

WSFNPPTFGGGTKLEIKRAAAHHHHHH

SEQ ID NO: 15
MDFGLIFFIVALLKGVQCQILLTQSPVILSVSPGERVSFSCRASQSIGTNIHWYQQRTNGSP

RLLIKYASESISGIPSRFSGSGSGTDFTLSINSVESEDIADYYCQQNNNWPTTFGAGTKLEL

KGSTSGSGKPGSGEGSTKGQVQLKQSGPGLVQPSQSLSITCTVSGFSLTNYGVHWVRQS

PGKGLEWLGVIWSGGNTDYNTPFTSRLSINKDNSKSQVFFKMNSLQSNDTAIYYCARAL

TYYDYEFAYWGQGTLVTVSAGGGGSGGGGSGGGGSGGGGSPEEPLVVKVEEGDTAAL

WCLKGTSDGPTQQLTWSRESPLKPFLKYSLGVPGLGVHVRPDAISVVIRNVSQQMGGFY

LCQPGPPSEKAWQPGWTVNVEGSGELFRWNVSDLGGLGCGLKNRSSEGPSSPSGKLMS

PKLYVWAKDRPEIWEGEPPCLPPRDSLNQSLSRDLTVAPGSTLWLSCGVPPDSVSRGPLS

WTHVHPKGPKSLLSLELKDDRPARDMWVMGTSLMLPRATAQDAGKWYCHRGNLTMS

FHLEITARPSRHHHHHH

SEQ ID NO: 16
MDFGLIFFIVALLKGVQCQILLTQSPVILSVSPGERVSFSCRASQSIGTNIHWYQQRTNGSP

RLLIKYASESISGIPSRFSGSGSGTDFTLSINSVESEDIADYYCQQNNNWPTTFGAGTKLEL

KGSTSGSGKPGSGEGSTKGQVQLKQSGPGLVQPSQSLSITCTVSGFSLTNYGVHWVRQS

PGKGLEWLGVIWSGGNTDYNTPFTSRLSINKDNSKSQVFFKMNSLQSNDTAIYYCARAL

TYYDYEFAYWGQGTLVTVSAGGGGSGGGGSGGGGSGGGGSPEEPLVVKVEEGDTAAL

WCLKGTSDGPTEQVTWSRESPLKPFLKLSLGLPGGGGHVRPNAVSLVIRNVSQQMGGF

YLCQPGPPSEKAWQPGWTVNVEGSGELFRWNVSDLGGLGCGLKNRSSEGPSSPSGKLM

SPKLYVWAKDRPEIWEGEPPCLPPRDSLNQSLSRDLTVAPGSTLWLSCGVPPDSVSRGPL

SWTHVHPKGPKSLLSLELKDDRPARDMWVTETGLLLPRATAQDAGKWYCHRGNLTMS

FHLEITARPSRHHHHHH

SEQ ID NO: 17
MDFGLIFFIVALLKGVQCQGQSGQCISPRGCPDGPYVMYGSSGGSGGSGGSGLSGRSDN

HGSSGTQILLTQSPVILSVSPGERVSFSCRASQSIGTNIHWYQQRTNGSPRLLIKYASESIS

GIPSRFSGSGSGTDFTLSINSVESEDIADYYCQQNNNWPTTFGAGTKLELKGSTSGSGKP

GSGEGSTKGQVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARALTYYDYEFAY

WGQGTLVTVSAGGGGSGGGGSGGGGSGGGGSPEEPLVVKVEEGDTAALWCLKGTSDG

PTQQLTWSRESPLKPFLKYSLGVPGLGVHVRPDAISVVIRNVSQQMGGFYLCQPGPPSEK

AWQPGWTVNVEGSGELFRWNVSDLGGLGCGLKNRSSEGPSSPSGKLMSPKLYVWAKD

RPEIWEGEPPCLPPRDSLNQSLSRDLTVAPGSTLWLSCGVPPDSVSRGPLSWTHVHPKGP

KSLLSLELKDDRPARDMWVMGTSLMLPRATAQDAGKWYCHRGNLTMSFHLEITARPS

RHHHHHH

SEQ ID NO: 18
MDFGLIFFIVALLKGVQCQGQSGQCISPRGCPDGPYVMYGSSGGSGGSGGSGLSGRSDN
```

-continued

HGSSGTQILLTQSPVILSVSPGERVSFSCRASQSIGTNIHWYQQRTNGSPRLLIKYASESIS

GIPSRFSGSGSGTDFTLSINSVESEDIADYYCQQNNNWPTTFGAGTKLELKGSTSGSGKP

GSGEGSTKGQVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARALTYYDYEFAY

WGQGTLVTVSAGGGGSGGGGSGGGGSGGGGSPEEPLVVKVEEGDTAALWCLKGTSDG

PTEQVTWSRESPLKPFLKLSLGLPGGGHVRPNAVSLVIRNVSQQMGGFYLCQPGPPSE

KAWQPGWTVNVEGSGELFRWNVSDLGGLGCGLKNRSSEGPSSPSGKLMSPKLYVWAK

DRPEIWEGEPPCLPPRDSLNQSLSRDLTVAPGSTLWLSCGVPPDSVSRGPLSWTHVHPKG

PKSLLSLELKDDRPARDMWVTETGLLLPRATAQDAGKWYCHRGNLTMSFHLEITARPS

RHHHHHH

SEQ ID NO: 19
MDFGLIFFIVALLKGVQCQGQSGQCISPRGCPDGPYVMYGSSGGSGGSGGSGLSGRSDN

HGSSGTQILLTQSPVILSVSPGERVSFSCRASQSIGTNIHWYQQRTNGSPRLLIKYASESIS

GIPSRFSGSGSGTDFTLSINSVESEDIADYYCQQNNNWPTTFGAGTKLELKGSTSGSGKP

GSGEGSTKGQVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARALTYYDYEFAY

WGQGTLVTVSAGGGGSGGGGSGGGGSGGGGSPEEPLVVKVEEGDTAALWCLKGTSDG

PTQQLTWSRESPLKPFLKYSLGVPGLGVHVRPDAISVVIRNVSQQMGGFYLCQPGPPSEK

AWQPGWTVNVEGSGELFRWNVSDLGGLGCGLKNRSSEGPSSPSGKLMSPKLYVWAKD

RPEIWEGEPPCLPPRDSLNQSLSRDLTVAPGSTLWLSCGVPPDSVSRGPLSWTHVHPKGP

KSLLSLELKDDRPARDMWVMGTSLMLPRATAQDAGKWYCHRGNLTMSFHLEITARPS

RGGGGSGGGGSGGGGSGGGGSEVQLVESGGGLVQPGGSLRLSCAASGFNIKDTYIHWV

RQAPGKGLEWVARTYPTNGYTRYADSVKGRFTISADTSKNTAYLQMNSLRAEDTAVYY

CSRWGGDGFYAMDYWGQGTLVTVSSASTGGGGSGGGGSGGGGSDIQMTQSPSSLSAS

VGDRVTITCRASQDVNTAVAWYQQKPGKAPKLLIYSASFLYSGVPSRFSGSRSGTDFTL

TISSLQPEDFATYYCQQHYTTPPTFGQGTKVEIKRTHHHHHH

SEQ ID NO: 20
MEFGLSWVFLVALFRGVQCDIQMTQSPSSLSASVGDRVTITCRASQDVNTAVAWYQQK

PGKAPKLLIYSASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGECGGGG

SGGGGSGGGGSGGGGSPEEPLVVKVEEGDTAALWCLKGTSDGPTQQLTWSRESPLKPF

LKYSLGVPGLGVHVRPDAISVVIRNVSQQMGGFYLCQPGPPSEKAWQPGWTVNVEGSG

ELFRWNVSDLGGLGCGLKNRSSEGPSSPSGKLMSPKLYVWAKDRPEIWEGEPPCLPPRD

SLNQSLSRDLTVAPGSTLWLSCGVPPDSVSRGPLSWTHVHPKGPKSLLSLELKDDRPAR

DMWVMGTSLMLPRATAQDAGKWYCHRGNLTMSFHLEITARPSRHHHHHH

SEQ ID NO: 21
MEFGLSWVFLVALFRGVQCEVQLVESGGGLVQPGGSLRLSCAASGFNIKDTYIHWVRQ

APGKGLEWVARIYPTNGYTRYADSVKGRFTISADTSKNTAYLQMNSLRAEDTAVYYCS

RWGGDGFYAMDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVD

KKVEPPKSCDKTHTCPPCPAPELLGGPSVFLFPPKPKDTLMISRTPEVTCVVVDVSHEDP

-continued
EVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPG

SEQ ID NO: 22
MEFGLSWVFLVALFRGVQCQIVLSQSPAILSASPGEKVTMTCRASSSVSYIHWFQQKPGS

SPKPWIYATSNLASGVPVRFSGSGSGTSYSLTISRVEAEDAATYYCQQWTSNPPTFGGGT

KLEIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGECGGGGSG

GGGSGGGGSGGGGSPEEPLVVKVEEGDTAALWCLKGTSDGPTQQLTWSRESPLKPFLK

YSLGVPGLGVHVRPDAISVVIRNVSQQMGGFYLCQPGPPSEKAWQPGWTVNVEGSGEL

FRWNVSDLGGLGCGLKNRSSEGPSSPSGKLMSPKLYVWAKDRPEIWEGEPPCLPPRDSL

NQSLSRDLTVAPGSTLWLSCGVPPDSVSRGPLSWTHVHPKGPKSLLSLELKDDRPARDM

WVMGTSLMLPRATAQDAGKWYCHRGNLTMSFHLEITARPSRHHHHHH

SEQ ID NO: 23
MEFGLSWVFLVALFRGVQCQVQLQQPGAELVKPGASVKMSCKASGYTFTSYNMHWV

KQTPGRGLEWIGAIYPGNGDTSYNQKFKGKATLTADKSSSTAYMQLSSLTSEDSAVYYC

ARSTYYGGDWYFNVWGAGTTVTVSAASTKGPSVFPLAPSSKSTSGGTAALGCLVKDYF

PEPVTVSWNSGALTSGVHTFPAVLQSSGLYSLSSVVTVPSSSLGTQTYICNVNHKPSNTK

VDKKAEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSP

G

SEQ ID NO: 24
MEFGLSWVFLVALFRGVQCEVQLVESGGGLVQPGGSLRLSCAASGFNIKDTYIHWVRQ

APGKGLEWVARIYPTNGYTRYADSVKGRFTISADTSKNTAYLQMNSLRAEDTAVYYCS

RWGGDGFYAMDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVD

KKVEPPKSCDKTHTCPPCPAPELLGGPSVFLFPPKPKDTLMISRTPEVTCVVVDVSHEDP

EVKFNWYVDGVEVHNAKTKPREEQYASTYRVVSVLTVLHQDWLNGKEYKCKVSNKA

LPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPG

SEQ ID NO: 25
MEFGLSWVFLVALFRGVQCQVQLQQPGAELVKPGASVKMSCKASGYTFTSYNMHWV

KQTPGRGLEWIGAIYPGNGDTSYNQKFKGKATLTADKSSSTAYMQLSSLTSEDSAVYYC

ARSTYYGGDWYFNVWGAGTTVTVSAASTKGPSVFPLAPSSKSTSGGTAALGCLVKDYF

PEPVTVSWNSGALTSGVHTFPAVLQSSGLYSLSSVVTVPSSSLGTQTYICNVNHKPSNTK

VDKKAEPKSCDKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYKCKVSNK

ALPAPIEKTISKAKGQPREPQVYTLPPSRDQEPGQPDLPGQRLLSQRHRRGVGEQWAAG

EQLQDHASRAGLRRLLLPLQQAHRGQEQVAAGERLLMLRDARGSAQPLHAEEPLPVSG

LVI

-continued

SEQ ID NO: 26
NIPPPRLLFFLLFLTPMEVRPEEPLVVKVEEGDTAVLPCLKGTSDGPTQQLTWSRESPLKP
FLKYSLGVPGLGVHVRPDAISVVIRNVSQQMGGFYLCQPGPPSEKAWQPGWTVNVEGS
GELFRWNVSDLGGLGCGLKNRSSEGPSSPSGKLMSPKLYVWAKDRPEIWEGEPPCLPPR
DSLNQSLSQDLTMAPGSTLWLSCGVPPDSVSRGPLSWTHVHPKGPKSLLSLELKDDRPA
REMIVDETGLLLPRATAQDAGKWYCSRGNVTTSYHLEITARPVKAHSDLRTGGWKGGG
GSGGGGSGGGGSGGGGSQVQLQASGGGLVQAGGSLRLSCAASGSIFAINEINLMGWYR
QAPGKQRELVAACASDGNTYYADSVKGRFTISRDNAEKTVYLQMNNLKPDDTAVYYC
DANSRGNYYSGQGTQVTVSSTSGPGGQGAEQKLISEEDLGAHHHHHHGAS

SEQ ID NO: 27
MEFGLSWVFLVALFRGVQCQVQLQESGGGLVQAGGSLRLSCVASGSIRSINVMGWYRQ
APGKQRELVAACASDGNTYYADSVKGRFTISRDNAEKTVYLQMNNLKPDDTAVYYCD
ANSRGNYYSGQGTQVTVSSTSGPGGQGAGGGGSGGGGSGGGGSGGGGSPEEPLVVKV
EEGDTAALWCLKGTSDGPTQQLTWSRESPLKPFLKYSLGVPGLGVHVRPDAISVVIRNV
SQQMGGFYLCQPGPPSEKAWQPGWTVNVEGSGELFRWNVSDLGGLGCGLKNRSSEGP
SSPSGKLMSPKLYVWAKDRPEIWEGEPPCLPPRDSLNQSLSRDLTVAPGSTLWLSCGVPP
DSVSRGPLSWTHVHPKGPKSLLSLELKDDRPARDMWVMGTSLMLPRATAQDAGKWY
CHRGNLTMSFHLEITARPSRHHHHHH

SEQ ID NO: 28
MEFGLSWVFLVALFRGVQCQVQLQASGGGLVQAGGSLRLSCAASGSIFAINEINLMGW
YRQAPGKQRELVAACASDGNTYYADSVKGRFTISRDNAEKTVYLQMNNLKPDDTAVY
YCDANSRGNYYSGQGTQVTVSSTSGPGGQGAGGGGSGGGGSGGGGSGGGGSPEEPLV
VKVEEGDTAALWCLKGTSDGPTQQLTWSRESPLKPFLKYSLGVPGLGVHVRPDAISVVI
RNVSQQMGGFYLCQPGPPSEKAWQPGWTVNVEGSGELFRWNVSDLGGLGCGLKNRSS
EGPSSPSGKLMSPKLYVWAKDRPEIWEGEPPCLPPRDSLNQSLSRDLTVAPGSTLWLSCG
VPPDSVSRGPLSWTHVHPKGPKSLLSLELKDDRPARDMWVMGTSLMLPRATAQDAGK
WYCHRGNLTMSFHLEITARPSRHHHHHH

SEQ ID NO: 29
MEFGLSWVFLVALFRGVQCQVQLQESGGGLVQAGGSLRLSCAASGSIFAINEINLMGW
YRQAPGKQRELVAACASDGNTYYADSVKGRFTISRDNAEKTVYLQMNNLKPDDTAVY
YCDANSRGNYYSGQGTQVTVSSTSGPGGQGAGGGGSGGGGSGGGGSGGGGSPEEPLV
VKVEEGDTAALWCLKGTSDGPTQQLTWSRESPLKPFLKYSLGVPGLGVHVRPDAISVVI
RNVSQQMGGFYLCQPGPPSEKAWQPGWTVNVEGSGELFRWNVSDLGGLGCGLKNRSS
EGPSSPSGKLMSPKLYVWAKDRPEIWEGEPPCLPPRDSLNQSLSRDLTVAPGSTLWLSCG
VPPDSVSRGPLSWTHVHPKGPKSLLSLELKDDRPARDMWVMGTSLMLPRATAQDAGK
WYCHRGNLTMSFHLEITARPSRHHHHHH

SEQ ID NO: 30
MEFGLSWVFLVALFRGVQCQVQLQESGGGLVQVGESLRLSCVVSGDTRSINLMGWYR
QAPGKQRELVAACASDGNTYYADSVKGRFTISRDNAEKTVYLQMNNLKPDDTAVYYC
DANSRGNYYSGQGTLVTVSSTSGPGGQGAGGGGSGGGGSGGGGSGGGGSPEEPLVVK
VEEGDTAALWCLKGTSDGPTQQLTWSRESPLKPFLKYSLGVPGLGVHVRPDAISVVIRN
VSQQMGGFYLCQPGPPSEKAWQPGWTVNVEGSGELFRWNVSDLGGLGCGLKNRSSEG
PSSPSGKLMSPKLYVWAKDRPEIWEGEPPCLPPRDSLNQSLSRDLTVAPGSTLWLSCGVP

```
PDSVSRGPLSWTHVHPKGPKSLLSLELKDDRPARDMWVMGTSLMLPRATAQDAGKWY

CHRGNLTMSFHLEITARPSRHHHHHH

SEQ ID NO: 31
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPGGGGSGGGGSGGGGSG

GGGSEVQLVESGGGLVQPGGSLRLSCAASGFNIKDTYIHWVRQAPGKGLEWVARTYPT

NGYTRYADSVKGRFTISADTSKNTAYLQMNSLRAEDTAVYYCSRWGGDGFYAMDYW

GQGTLVTVSSASTGGGGSGGGGSGGGGSDIQMTQSPSSLSASVGDRVTITCRASQDVNT

AVAWYQQKPGKAPKLLIYSASFLYSGVPSRFSGSRSGTDFTLTISSLQPEDFATYYCQQH

YTTPPTFGQGTKVEIKRTHHHHHH

SEQ ID NO: 32
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVKLQESGAELVKPGASVKMSCKASGYTFTSYNMHWVKQ

TPGQGLEWIGAIYPGNGDTSYNQKFKGKATLTADKSSSTAYMQLSSLTSEDSADYYCAR

SNYYGSSYWFFDVWGQGTTVTVSSASTGGGGSGGGGSGGGGSDIELTQSPTILSASPGE

KVTMTCRASSSVNYMDWYQKKPGSSPKPWIYATSNLASGVPARFSGSGSGTSYSLTISR

VEAEDAATYYCQQWSFNPPTFGGGTKLEIKRAAAHHHHHH

SEQ ID NO: 33
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSVSDVPRDLEVVAATPTSLLISWCRQRCADSYRITYGETGGNS

PVQEFTVPGSWKTATISGLKPGVDYTITVYVVTHYYGWDRYSHPISINYRTEIDKPSQHH

HHHH

SEQ ID NO: 34
MPPPRLLFFLLFLTPMEVRPEEPLVVKVEEGDTAALWCLKGTSDGPTQQLTWSRESPLK

PFLKYSLGVPGMGVHVRPNAVSLVISNVSQQMGGFYLCQPGPPSEKAWQPGWTVNVE

GSGELFRWNVSDLGGLGCGLKNRSSEGPSSPSGKLMSPKLYVWAKDRPEIWEGEPPCLP

PRDSLNQSLSRDMTVAPGSTLWLSCGVPPDSVSRGPLSWTHVHPKGPKSLLSLELKDDR

PARDMWVMETGLVLPRATAQDAGKWYCHRGNVTTSYHLEITARPVSAHTPLRTGGWK

GGGGSGGGGSGGGGSGGGGSVSDVPRDLEVVAATPTSLLISWCRQRCADSYRITYGET

GGNSPVQEFTVPGSWKTATISGLKPGVDYTITVYVVTHYYGWDRYSHPISINYRTEIDKP

SQHHHHHH
```

SEQ ID NO: 35
MEFGLSWVFLVALFRGVQCEVQLVESGGGLVQPGGSLRLSCAASGFNIKDTYIHWVRQ
APGKGLEWVARIYPTNGYTRYADSVKGRFTISADTSKNTAYLQMNSLRAEDTAVYYCS
RWGGDGFYAMDYWGQGTLVTVSSASTGGGGSGGGGSGGGGSDIQMTQSPSSLSASVG
DRVTITCRASQDVNTAVAWYQQKPGKAPKLLIYSASFLYSGVPSRFSGSRSGTDFTLTIS
SLQPEDFATYYCQQHYTTPPTFGQGTKVEIKRTGGGGSGGGGSGGGGSGGGGSPEEPLV
VKVEEGDTAVLPCLKGTSDGPTQQLTWSRESPLKPFLKYSLGVPGLGVHVRPDAISVVI
RNVSQQMGGFYLCQPGPPSEKAWQPGWTVNVEGSGELFRWNVSDLGGLGCGLKNRSS
EGPSSPSGKLMSPKLYVWAKDRPEIWEGEPPCLPPRDSLNQSLSQDLTMAPGSTLWLSc
GVPPDSVSRGPLSWTHVHPKGPKSLLSLELKDDRPAREMIVDETGLLLPRATAQDAGK
WYCSRGNVTTSYHLEITARPVKAHSDLRTGGWKHHHHHH

SEQ ID NO: 36
MEFGLSWVFLVALFRGVQCQVQLVQSGAEVKKPGASVKVSCKASGYTFTDYYMHWV
RQAPGQGLEWMGRVNPNRRGTTYNQKFEGRVTMTTDTSTSTAYMELRSLRSDDTAVY
YCARANWLDYWGQGTTVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTKVDKR
VESKYGPPCPPCPAPEAAGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLSLG

SEQ ID NO: 37
METDTLLLWVLLLWVPGSTGDIQMTQSPSSLSASVGDRVTITCSVSSSVSSIYLHWYQQ
KPGKAPKLLIYSTSNLASGVPSRFSGSGSGTDFTLTISSLQPEDFATYYCQVYSGYPLTFG
GGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGECDKT
HTSPPSPAPEAAGGPSPEEPLVVKVEEGDNAVLQCLKGTSDGPTQQLTWSRESPLKPFLK
LSLGLPGLGIHMRPLAIWLFIFNVSQQMGGFYLCQPGPPSEKAWQPGWTVNVEGSGELF
RWNVSDLGGLGCGLKNRSSEGPSSPSGKLMSPKLYVWAKDRPEIWEGEPPCLPPRDSLN
QSLSQDLTMAPGSTLWLSCGVPPDSVSRGPLSWTHVHPKGPKSLLSLELKDDRPARDM
WVMETGLLLPRATAQDAGKYYCHRGNLTMSFHLEITARP

SEQ ID NO: 38
MEFGLSWVFLVALFRGVQCEVQLVESGGGLVQPGGSLRLSCAASGFNIKDTYIHWVRQ
APGKGLEWVARIYPTNGYTRYADSVKGRFTISADTSKNTAYLQMNSLRAEDTAVYYCS
RWGGDGFYAMDYWGQGTLVTVSSASTGGGGSGGGGSGGGGSDIQMTQSPSSLSASVG
DRVTITCRASQDVNTAVAWYQQKPGKAPKLLIYSASFLYSGVPSRFSGSRSGTDFTLTIS
SLQPEDFATYYCQQHYTTPPTFGQGTKVEIKRTDKTHTSPPSPAPEAAGGPSPEEPLVVK
VEEGDNAVLQCLKGTSDGPTQQLTWSRESPLKPFLKLSLGLPGLGIHMRPLAIWLFIFNV
SQQMGGFYLCQPGPPSEKAWQPGWTVNVEGSGELFRWNVSDLGGLGCGLKNRSSEGP
SSPSGKLMSPKLYVWAKDRPEIWEGEPPCLPPRDSLNQSLSQDLTMAPGSTLWLSCGVP
PDSVSRGPLSWTHVHPKGPKSLLSLELKDDRPARDMWVMETGLLLPRATAQDAGKYY
CHRGNLTMSFHLEITARPSRGPHHHHHH

SEQ ID NO: 39
MPPPRLLFFLLFLTPMEVRPEEPLVVKVEEGDTAVLPCLKGTSDGPTQQLTWSRESPLKP

-continued

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQQSGGGLVQAGGSLRLSCAASGSIFAINEINLMGWYR

QAPGKQRELVAACASDGNTYYADSVKGRFTISRDNAEKTVYLQMNNLKPDDTAVYYC

DANSRGNYYSGQGTQVTVSSTSGPGGQGAEQKLISEEDLGAHHHHHGAS

SEQ ID NO: 40
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQESGGGLVQPGGSLRLSCAASGFTFNSYAMTWVRQA

PGKGLEWVSDINSGGGSTNYADSVKGRFTISRDNAKNTLYLQMNSLKPEDTAVYYCAT

ELRGSDYYRGPIREYAYWGQGTLVTVSSTSGPGGQGAEQKLISEEDLGAHRHHHHGAS

SEQ ID NO: 41
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQAFGGGLVQPGGSLRLSCVVSGTMFSGKDVNWLRQA

PGKHVEVVATVSSDGGTDYADFVKGRFTISRDDAKNTVNLQMNSLEPEDTANYMCHFL

WGRHYWGQGTQVTVSSTSGPGGQGAEQKLISEEDLGAHHHHHGAS

SEQ ID NO: 42
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQESGGGLVQAGGSLRLSCVASGSIRSINVMGWYRQAP

GKQRELVAACASDGNTYYADSVKGRFTISRDNAEKTVYLQMNNLKPDDTAVYYCDAN

SRGNYYSGQGTQVTVSSTSGPGGQGAEQKLISEEDLGAHHHHHGAS

SEQ ID NO: 43
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQQSGGGLAQTGGSLILSCAASGSIFAINEINLMGWYRQ

APGKQRELVAACASDGNTYYADSVKGRFTISRDNAEKTVYLQMNNLKPDDTAVYYCD

ANSRGNYYSGQGTQVTVSSTSGPGGQGAEQKLISEEDLGAHHHHHGAS

```
                                                       SEQ ID NO: 44
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSAVQLQESGGGLVQAGGSLRLSCAASGSDRSINVMNWYRQA

PGKQRELVAAITSGGTTNYAQSVKGRVTISRDSAKNTVYLQMNSLKPEDTAVYFCKAD

TRWGGMYWGPGTQVTVSSTSGPGGQGAEQKLISEEDLGAHHHHHHGAS

SEQ ID NO: 45
MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQQSGGGLVQAGGSLTLSCAATGRTIDNGAMAWFRQA

PGKQRELVAAINWSGGATFYTDSVKYRFTISRDNVRHTLDLQMTSLKPEDTTIYFCASR

RGVDLRRNSYEYDYWGRGTLVTVSSTSGPGGQGAEQKLISEEDLGAHHHHHHGAS

SEQ ID NO: 46
MEFGLSWVFLVALFRGVQCQVQLQESGGGLVQPGGSLRLSCAASGFTFNSYAMTWVR

QAPGKGLEWVSDINSGGGSTNYADSVKGRFTISRDNAKNTLYLQMNSLKPEDTAVYYC

ATELRGSDYYRGPIREYAYWGQGTLVTVSSTSGPGGQGAGGGGSGGGGSGGGGSGGG

GSPEEPLVVKVEEGDTAALWCLKGTSDGPTQQLTWSRESPLKPFLKYSLGVPGLGVHV

RPDAISVVIRNVSQQMGGFYLCQPGPPSEKAWQPGWTVNVEGSGELFRWNVSDLGGLG

CGLKNRSSEGPSSPSGKLMSPKLYVWAKDRPEIWEGEPPCLPPRDSLNQSLSRDLTVAPG

STLWLSCGVPPDSVSRGPLSWTHVHPKGPKSLLSLELKDDRPARDMWVMGTSLMLPRA

TAQDAGKWYCHRGNLTMSFHLEITARPSRHHHHHH

SEQ ID NO: 47
MEFGLSWVFLVALFRGVQCQVQLQQSGGGLAQTGGSLILSCAASGSIFAINEINLMGWY

RQAPGKQRELVAACASDGNTYYADSVKGRFTISRDNAEKTVYLQMNNLKPDDTAVYY

CDANSRGNYYSGQGTQVTVSSTSGPGGQGAGGGGSGGGGSGGGGSGGGGSPEEPLVV

KVEEGDTAALWCLKGTSDGPTQQLTWSRESPLKPFLKYSLGVPGLGVHVRPDAISVVIR

NVSQQMGGFYLCQPGPPSEKAWQPGWTVNVEGSGELFRWNVSDLGGLGCGLKNRSSE

GPSSPSGKLMSPKLYVWAKDRPEIWEGEPPCLPPRDSLNQSLSRDLTVAPGSTLWLSCG

VPPDSVSRGPLSWTHVHPKGPKSLLSLELKDDRPARDMWVMGTSLMLPRATAQDAGK

WYCHRGNLTMSFHLEITARPSRHHHHHH

SEQ ID NO: 48
MEFGLSWVFLVALFRGVQCQVQLQQSGGGLVQAGGSLTLSCAATGRTIDNGAMAWFR

QAPGKQRELVAAINWSGGATFYTDSVKYRFTISRDNVRHTLDLQMTSLKPEDTTIYFCA

SRRGVDLRRNSYEYDYWGRGTLVTVSSTSGPGGQGAGGGGSGGGGSGGGGSGGGGSP

EEPLVVKVEEGDTAALWCLKGTSDGPTQQLTWSRESPLKPFLKYSLGVPGLGVHVRPD

AISVVIRNVSQQMGGFYLCQPGPPSEKAWQPGWTVNVEGSGELFRWNVSDLGGLGCGL

KNRSSEGPSSPSGKLMSPKLYVWAKDRPEIWEGEPPCLPPRDSLNQSLSRDLTVAPGSTL
```

WLSCGVPPDSVSRGPLSWTHVHPKGPKSLLSLELKDDRPARDMWVMGTSLMLPRATA

QDAGKWYCHRGNLTMSFHLEITARPSRHHHHHH

SEQ ID NO: 49

MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQESGGGLVQVGESLRLSCVVSGDTRSINLMGWYRQA

PGKQRELVAACASDGNTYYADSVKGRFTISRDNAEKTVYLQMNNLKPDDTAVYYCDA

NSRGNYYSGQGTLVTVSSTSGPGGQAEQKLISEEDLGAHHHHHHGAS

SEQ ID NO: 50

MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLQESGGGLVQAGGSLRLSCAASGSIFAINEINLMGWYR

QAPGKQRELVAACASDGNTYYADSVKGRFTISRDNAEKTVYLQMNNLKPDDTAVYYC

DANSRGNYYSGQGTQVTVSSTSGPGGQAEQKLISEEDLGAHHHHHHGAS

SEQ ID NO: 51

MPPPRLLFFLLFLTPMEVRPEEPLVVKVEEGDTAVLPCLKGTSDGPTQQLTWSRESPLKP

FLKYSLGVPGLGVHVRPDAISVVIRNVSQQMGGFYLCQPGPPSEKAWQPGWTVNVEGS

GELFRWNVSDLGGLGCGLKNRSSEGPSSPSGKLMSPKLYVWAKDRPEIWEGEPPCLPPR

DSLNQSLSQDLTMAPGSTLWLSCGVPPDSVSRGPLSWTHVHPKGPKSLLSLELKDDRPA

REMIVDETGLLLPRATAQDAGKWYCSRGNVTTSYHLEITARPVKAHSDLRTGGWKGGG

GSGGGGSGGGGSGGGGSQVQLVESGGGLVQAGGSLRLSCAASGSIFAINEINLMGWYR

QAPGKQRELVAACASDGNTYYADSVKGRFTISRDNAEKTVYLQMNNLKPDDTAVYYC

DANSRGNYYSGQGTLVTVSSTSGPGGQAEQKLISEEDLGAHHHHHHGAS

SEQ ID NO: 52

MPPPRLLFFLLFLTPMEVRPEEPLVVKVEEGDNAVLQCLKGTSDGPTQQLTWSRESPLKP

FLKLSLGLPGLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEGEPPCLPPRD

SLNQSLSQDLTMAPGSTLWLSCGVPPDSVSRGPLSWTHVHPKGPKSLLSLELKDDRPAR

DMWVMETGLLLPRATAQDAGKYYCHRGNLTMSFHLEITARPGGGSGGGGSGGGGSG

GGGSDMAQVQLQESGPGLVKPSETLSLTCVVSGGSISSSNWWSWVRQPPGKGLEWIGEI

YHSGSPDYNPSLKSRVTISVDKSRNQFSLKLSSVTAADTAVYYCAKVSTGGFFDYWGQ

GTLVTVSSGGGGSGGGGSGGGGSEIELTQSPSSLSASVGDRVTITCRASQSISSYLNWYQ

QKPGKAPKLLIYAASSLQSGVPSRFSGSGSGTDFTLTISSLQPEDFATYYCQQSYSTPPTF

GPGTKVEIKRTHHHHHH

SEQ ID NO: 53

MEFGLSWVFLVALFRGVQCDMAQVQLQESGPGLVKPSETLSLTCVVSGGSISSSNWWS

WVRQPPGKGLEWIGEIYHSGSPDYNPSLKSRVTISVDKSRNQFSLKLSSVTAADTAVYY

```
CAKVSTGGFFDYWGQGTLVTVSSGGGGSGGGGSGGGGSEIELTQSPSSLSASVGDRVTI
TCRASQSISSYLNWYQQKPGKAPKLLIYAASSLQSGVPSRFSGSGSGTDFTLTISSLQPED
FATYYCQQSYSTPPTFGPGTKVEIKRTGGGGSGGGGSGGGGSGGGGSQVQLQESGGGL
VQAGGSLRLSCVASGSIRSINVMGWYRQAPGKQRELVAACASDGNTYYADSVKGRFTI
SRDNAEKTVYLQMNNLKPDDTAVYYCDANSRGNYYSGQGTQVTVSSTSGPGGQGAGG
GGSGGGGSGGGGSGGGGSPEEPLVVKVEEGDTAALWCLKGTSDGPTQQLTWSRESPLK
PFLKYSLGVPGLGVHVRPDAISVVIRNVSQQMGGFYLCQPGPPSEKAWQPGWTVNVEG
SGELFRWNVSDLGGLGCGLKNRSSEGPSSPSGKLMSPKLYVWAKDRPEIWEGEPPCLPP
RDSLNQSLSRDLTVAPGSTLWLSCGVPPDSVSRGPLSWTHVHPKGPKSLLSLELKDDRP
ARDMWVMGTSLMLPRATAQDAGKWYCHRGNLTMSFHLEITARPSRHHHHHH
```

SEQ ID NO: 54
```
MRLLVLLWGCLLLPGYEADIQMTQTTSSLSASLGDRVTISCRASQDISKYLNWYQQKPD
GTVKLLIYHTSRLHSGVPSRFSGSGSGTDYSLTISNLEQEDIATYFCQQGNTLPYTFGGGT
KLEITGGGGSGGGGSGGGGSGGGGSEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYY
CAKHYYYGGSYAMDYWGQGTSVTVSSDYKDDDDKIEVMYPPPYLDNEKSNGTIIHVK
GKHLCPSPLFPGPSKPFWVLVVVGGVLACYSLLVTVAFIIFWVRSKRSRLLHSDYMNMT
PRRPGPTRKHYQPYAPPRDFAAYRSKRGRKKLLYIFKQPFMRPVQTTQEEDGCSCRFPE
EEEGGCELRVKFSRSADAPAYQQGQNQLYNELNLGRREEYDVLDKRRGRDPEMGGKP
QRRKNPQEGLYNELQKDKMAEAYSEIGMKGERRRGKGHDGLYQGLSTATKDTYDALH
MQALPPRRAKRSGSGATNFSLLKQAGDVEENPGPMPPPRLLFFLLFLTPMEVRPEEPLVV
KVEEGDNAVLQCLKGTSDGPTQQLTWSRESPLKPFLKLSLGLPGLGIHMRPLAIWLFIFN
VSQQMGGFYLCQPGPPSEKAWQPGWTVNVEGSGELFRWNVSDLGGLGCGLKNRSSEG
PSSPSGKLMSPKLYVWAKDRPEIWEGEPPCLPPRDSLNQSLSQDLTMAPGSTLWLSCGV
PPDSVSRGPLSWTHVHPKGPKSLLSLELKDDRPARDMWVMETGLLLPRATAQDAGKY
YCHRGNLTMSFHLEITARPGGGSGGGGSGGGGSGGGGSDMAQVQLQESGPGLVKPSE
TLSLTCVVSGGSISSSNWWSWVRQPPGKGLEWIGEIYHSGSPDYNPSLKSRVTISVDKSR
NQFSLKLSSVTAADTAVYYCAKVSTGGFFDYWGQGTLVTVSSGGGGSGGGGSGGGGS
EIELTQSPSSLSASVGDRVTITCRASQSISSYLNWYQQKPGKAPKLLIYAASSLQSGVPSR
FSGSGSGTDFTLTISSLQPEDFATYYCQQSYSTPPTFGPGTKVEIKRTHHHHHH
```

SEQ ID NO: 55
```
MRLLVLLWGCLLLPGYEADIQMTQTTSSLSASLGDRVTISCRASQDISKYLNWYQQKPD
GTVKLLIYHTSRLHSGVPSRFSGSGSGTDYSLTISNLEQEDIATYFCQQGNTLPYTFGGGT
KLEITGGGGSGGGGSGGGGSGGGGSEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYY
CAKHYYYGGSYAMDYWGQGTSVTVSSDYKDDDDKIEVMYPPPYLDNEKSNGTIIHVK
GKHLCPSPLFPGPSKPFWVLVVVGGVLACYSLLVTVAFIIFWVRSKRSRLLHSDYMNMT
PRRPGPTRKHYQPYAPPRDFAAYRSKRGRKKLLYIFKQPFMRPVQTTQEEDGCSCRFPE
EEEGGCELRVKFSRSADAPAYQQGQNQLYNELNLGRREEYDVLDKRRGRDPEMGGKP
QRRKNPQEGLYNELQKDKMAEAYSEIGMKGERRRGKGHDGLYQGLSTATKDTYDALH
MQALPPRRAKRSGSGATNFSLLKQAGDVEENPGPMPPPRLLFFLLFLTPMEVRPEEPLVV
```

-continued

KVEEGDNAVLQCLKGTSDGPTQQLTWSRESPLKPFLKLSLGLPGLGIHMRPLAIWLFIFN
VSQQMGGFYLCQPGPPSEKAWQPGWTVNVEGSGELFRWNVSDLGGLGCGLKNRSSEG
PSSPSGKLMSPKLYVWAKDRPEIWEGEPPCLPPRDSLNQSLSQDLTMAPGSTLWLSCGV
PPDSVSRGPLSWTHVHPKGPKSLLSLELKDDRPARDMWVMETGLLLPRATAQDAGKY
YCHRGNLTMSFHLEITARPGGGSGGGGSGGGGSGGGGSEVQLVESGGGLVQPGGSLR
LSCAASGFNIKDTYIHWVRQAPGKGLEWVARIYPTNGYTRYADSVKGRFTISADTSKNT
AYLQMNSLRAEDTAVYYCSRWGGDGFYAMDYWGQGTLVTVSSASTGGGGSGGGGSG
GGGSDIQMTQSPSSLSASVGDRVTITCRASQDVNTAVAWYQQKPGKAPKLLIYSASFLY
SGVPSRFSGSRSGTDFTLTISSLQPEDFATYYCQQHYTTPPTFGQGTKVEIKRTSRHHHHH
H

SEQ ID NO: 56
MRLLVLLWGCLLLPGYEADIQMTQTTSSLSASLGDRVTISCRASQDISKYLNWYQQKPD
GTVKLLIYHTSRLHSGVPSRFSGSGSGTDYSLTISNLEQEDIATYFCQQGNTLPYTFGGGT
KLEITGGGGSGGGGSGGGGSGGGGSEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYY
CAKHYYYGGSYAMDYWGQGTSVTVSSDYKDDDDKIEVMYPPPYLDNEKSNGTIIHVK
GKHLCPSPLFPGPSKPFWVLVVVGGVLACYSLLVTVAFIIFWVRSKRSRLLHSDYMNMT
PRRPGPTRKHYQPYAPPRDFAAYRSKRGRKKLLYIFKQPFMRPVQTTQEEDGCSCRFPE
EEEGGCELRVKFSRSADAPAYQQGQNQLYNELNLGRREEYDVLDKRRGRDPEMGGKP
QRRKNPQEGLYNELQKDKMAEAYSEIGMKGERRRGKGHDGLYQGLSTATKDTYDALH
MQALPPRRAKRSGSGATNFSLLKQAGDVEENPGPMPPPRLLFFLLFLTPMEVRPEEPLVV
KVEEGDNAVLQCLKGTSDGPTQQLTWSRESPLKPFLKLSLGLPGLGIHMRPLAIWLFIFN
VSQQMGGFYLCQPGPPSEKAWQPGWTVNVEGSGELFRWNVSDLGGLGCGLKNRSSEG
PSSPSGKLMSPKLYVWAKDRPEIWEGEPPCLPPRDSLNQSLSQDLTMAPGSTLWLSCGV
PPDSVSRGPLSWTHVHPKGPKSLLSLELKDDRPARDMWVMETGLLLPRATAQDAGKY
YCHRGNLTMSFHLEITARPGGGSGGGGSGGGGSGGGGSEVQLLESGGGQVQPGGSLR
LSCAASGFTFSSYPMSWVRQAPGKGLEWVSAIGGSGGSLPYADSVKGRFTISRDNSKNT
LYLQMNSLRAEDTAVYYCARYWPMDIWGQGTLVTVSSASTGGGGSGGGGSGGGGSG
GGGSEIVLTQSPGTLSLSPGERATLSCRASQSVSSSYLAWYQQKPGQAPRLLMYDASIRA
TGIPDRFSGSGSGTDFTLTISRLEPEDFAVYYCQQYQSWPLTFGQGTKVETKRTHHHHH
H

SEQ ID NO: 57
MRLLVLLWGCLLLPGYEADIQMTQTTSSLSASLGDRVTISCRASQDISKYLNWYQQKPD
GTVKLLIYHTSRLHSGVPSRFSGSGSGTDYSLTISNLEQEDIATYFCQQGNTLPYTFGGGT
KLEITGGGGSGGGGSGGGGSGGGGSEVKLQESGPGLVAPSQSLSVTCTVSGVSLPDYGV
SWIRQPPRKGLEWLGVIWGSETTYYNSALKSRLTIIKDNSKSQVFLKMNSLQTDDTAIYY
CAKHYYYGGSYAMDYWGQGTSVTVSSDYKDDDDKIEVMYPPPYLDNEKSNGTIIHVK
GKHLCPSPLFPGPSKPFWVLVVVGGVLACYSLLVTVAFIIFWVRSKRSRLLHSDYMNMT
PRRPGPTRKHYQPYAPPRDFAAYRSKRGRKKLLYIFKQPFMRPVQTTQEEDGCSCRFPE
EEEGGCELRVKFSRSADAPAYQQGQNQLYNELNLGRREEYDVLDKRRGRDPEMGGKP
QRRKNPQEGLYNELQKDKMAEAYSEIGMKGERRRGKGHDGLYQGLSTATKDTYDALH
MQALPPREGRGSLLTCGDVEENPGPMPPPRLLFFLLFLTPMEVRPEEPLVVKVEEGDNA

-continued

```
VLQCLKGTSDGPTQQLTWSRESPLKPFLKLSLGLPGLGIHMRPLAIWLFIFNVSQQMGGF

YLCQPGPPSEKAWQPGWTVNVEGSGELFRWNVSDLGGLGCGLKNRSSEGPSSPSGKLM

SPKLYVWAKDRPEIWEGEPPCLPPRDSLNQSLSQDLTMAPGSTLWLSCGVPPDSVSRGP

LSWTHVHPKGPKSLLSLELKDDRPARDMWVMETGLLLPRATAQDAGKYYCHRGNLTM

SFHLEITARPGGGGSGGGGSGGGGSGGGGSMAQVKLQESGAELVKPGASVKMSCKASG

YTFTSYNMHWVKQTPGQGLEWIGAIYPGNGDTSYNQKFKGKATLTADKSSSTAYMQLS

SLTSEDSADYYCARSNYYGSSYWFFDVWGQGTTVTVSSGGGGSGGGGSGGGGSDIELT

QSPTILSASPGEKVTMTCRASSSVNYMDWYQKKPGSSPKPWIYATSNLASGVPARFSGS

GSGTSYSLTISRVEAEDAATYYCQQWSFNPPTFGGGTKLEIKRAAAHHHHHH
```

Listing of Construct Nucleotide Sequences

```
                                                SEQ ID NO: 58
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACGACGCCTGGCTGAGGTGC

CTGAAGGGCACCAGCGACGGCCCCACCAGCCAGGTGACCTGGAGCAGGGAGAGCC

CCCTGAAGCCCTTCCTGAAGTACAGCCTGGGCGTGCCCGGCCTGGGCGTGCACATCA

GGCCCCTGGCCATCGGCCTGGTGATCCCCAACGTGAGCCAGCAGATGGGCGGCTTCT

ACCTGTGCCAGCCCGGCCCCCCCAGCGAGAAGGCCTGGCAGCCCGGCTGGACCGTG

AACGTGGAGGGCAGCGGCGAGCTGTTCAGGTGGAACGTGAGCGACCTGGGCGGCCT

GGGCTGCGGCCTGAAGAACAGGAGCAGCGAGGGCCCCAGCAGCCCCAGCGGCAAG

CTGATGAGCCCCAAGCTGTACGTGTGGGCCAAGGACAGGCCCGAGATCTGGGAGGG

CGAGCCCCCCTGCCTGCCCCCCAGGGACAGCCTGAACCAGAGCCTGAGCCAGGACC

TGACCATGGCCCCCGGCAGCACCCTGTGGCTGAGCTGCGGCGTGCCCCCCGACAGC

GTGAGCAGGGGCCCCCTGAGCTGGACCCACGTGCACCCCAAGGGCCCCAAGAGCCT

GCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTACTACTGCCA

CAGGGGCAACAGGACCATCAGCTACCACCTGGAGATCACCGCCAGGCCCGTGAGCG

CCCACACCCCCCTGAGGACCGGCGGCTGGAAGGGAGGAGGTGGGTCTGGAGGTGGA

GGATCTGGTGGAGGTGGGTCTGGAGGAGGTGGGTCTGTGAGCGACGTGCCCAGGGA

CCTGGAGGTGGTGGCCGCCACCCCCACCAGCCTGCTGATCAGCTGGTTCGACTACGC

CGTGACCTACTACAGGATCACCTACGGCGAGACCGGCGGCAACAGCCCCGTGCAGG

AGTTCACCGTGCCCGGCTGGATCAGCACCGCCACCATCAGCGGCCTGAAGCCCGGC

GTGGACTACACCATCACCGTGTACGCCGTGACCGACAACAGCCACTGGCCCTTCAG

GAGCACCCCCATCAGCACCAACTACAGGACCGAGATCGACAAGCCCCCCCAGCATC

ATCACCATCACCAT
                                                SEQ ID NO: 59
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC
```

-continued

```
TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGGTCTGTGAGCGACGTGCCCAGGG

ACCTGGAGGTGGTGGCCGCCACCCCCACCAGCCTGCTGATCAGCTGGTTCGACTACG

CCGTGACCTACTACAGGATCACCTACGGCGAGACCGGCGGCAACAGCCCCGTGCAG

GAGTTCACCGTGCCCGGCTGGATCAGCACCGCCACCATCAGCGGCCTGAAGCCCGG

CGTGGACTACACCATCACCGTGTACGCCGTGACCGACAACAGCCACTGGCCCTTCAG

GAGCACCCCCATCAGCACCAACTACAGGACCGAGATCGACAAGCCCCCCAGCATC

ATCACCATCACCAT
```

SEQ ID NO: 60
```
ATGCCACCTCCTCGCCTCCTCTTCTTCCTCCTCTTCCTCACCCCCATGGAAGTCAGG

CCCGAGGAGCCCCTGGTGGTGAAGGTGGAGGAGGGCGACACCGCCGCCCTGTGGTG

CCTGAAGGGCACCAGCGACGGCCCCACCCAGCAGCTGACCTGGAGCAGGGAGAGCC

CCCTGAAGCCCTTCCTGAAGCTGAGCCTGGGCCTGCCCGGCATGGGCGTGCACATGA

GGCCCGGCGCCGTGAGCGCCGTGATCAGCAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCAGGGAC

ATGACCGTGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGACATGTGGGTGATGGGC

ACCAGCCTGATCCTGCCCAGGGCCACCGCCCAGGACGCCGGCAAGTACTACTGCCA

CAGGGGCAACCTGACCATGAGCTTCCACCTGGAGGTGGTGGCCAGGCCCGTGAAGG

CCCACAGCGACCTGAGGACCGGCGGCTGGAAGGGAGGAGGTGGGTCTGGAGGT

GGAGGATCTGGTGGAGGTGGGTCTGGAGGAGGTGGGTCTGTGAGCGACGTGCCC

AGGGACCTGGAGGTGGTGGCCGCCACCCCCACCAGCCTGCTGATCAGCTGGTTCGA

CTACGCCGTGACCTACTACAGGATCACCTACGGCGAGACCGGCGGCAACAGCCCCG

TGCAGGAGTTCACCGTGCCCGGCTGGATCAGCACCGCCACCATCAGCGGCCTGAAG

CCGGCGTGGACTACACCATCACCGTGTACGCCGTGACCGACAACAGCCACTGGCCC
```

-continued

TTCAGGAGCACCCCCATCAGCACCAACTACAGGACCGAGATCGACAAGCCCCCCA
GCATCATCACCATCACCAT

SEQ ID NO: 61
ATGCCACCTCCTCGCCTCCTCTTCTTCCTCCTCTTCCTCACCCCCATGGAAGTCAGG
CCCGAGGAGCCCCTGGTGGTGAAGGTGGAGGAGGGCGACACCGCCGCCCTGTGGTG
CCTGAAGGGCACCAGCGACGGCCCCACCCAGCAGCTGACCTGGAGCAGGGAGAGCC
CCCTGAAGCCCTTCCTGAAGTACAGCCTGGGCGTGCCCGGCATGGGCGTGCACGTG
AGGCCCAACGCCGTGAGCCTGGTGATCAGCAACGTGAGCCAGCAGATGGGCGGCTT
CTACCTGTGCCAGCCCGGCCCCCCCAGCGAGAAGGCCTGGCAGCCCGGCTGGACCG
TGAACGTGGAGGGCAGCGGCGAGCTGTTCAGGTGGAACGTGAGCGACCTGGGCGGC
CTGGGCTGCGGCCTGAAGAACAGGAGCAGCGAGGGCCCCAGCAGCCCCAGCGGCA
AGCTGATGAGCCCCAAGCTGTACGTGTGGGCCAAGGACAGGCCCGAGATCTGGGAG
GGCGAGCCCCCTGCCTGCCCCCAGGGACAGCCTGAACCAGAGCCTGAGCAGGGA
CATGACCGTGGCCCCCGGCAGCACCCTGTGGCTGAGCTGCGGCGTGCCCCCCGACA
GCGTGAGCAGGGGCCCCCTGAGCTGGACCCACGTGCACCCCAAGGGCCCCAAGAGC
CTGCTGAGCCTGGAGCTGAAGGACGACAGGCCCGCCAGGGACATGTGGGTGATGGA
GACCGGCCTGGTGCTGCCCAGGGCCACCGCCCAGGACGCCGGCAAGTGGTACTGCC
ACAGGGGCAACGTGACCACCAGCTACCACCTGGAGATCACCGCCAGGCCCGTGAGC
GCCCACACCCCCCTGAGGACCGGCGGCTGGAAGGGAGGAGGTGGGTCTGGAGGT
GGAGGATCTGGTGGAGGTGGGTCTGGAGGAGGTGGGTCTGTGAGCGACGTGCCC
AGGGACCTGGAGGTGGTGGCCGCCACCCCCACCAGCCTGCTGATCAGCTGGTTCGA
CTACGCCGTGACCTACTACAGGATCACCTACGGCGAGACCGGCGGCAACAGCCCCG
TGCAGGAGTTCACCGTGCCCGGCTGGATCAGCACCGCCACCATCAGCGGCCTGAAG
CCCGGCGTGGACTACACCATCACCGTGTACGCCGTGACCGACAACAGCCACTGGCC
CTTCAGGAGCACCCCCATCAGCACCAACTACAGGACCGAGATCGACAAGCCCCCC
AGCATCATCACCATCACCAT

SEQ ID NO: 62
ATGCCACCTCCTCGCCTCCTCTTCTTCCTCCTCTTCCTCACCCCCATGGAAGTCAGGC
CCGAGGAACCTCTAGTGGTGAAGGTGGAAGAGGGAGATAACGCTGTGCTGCAGTGC
CTCAAGGGGACCTCAGATGGCCCCACTCAGCAGCTGACCTGGTCTCGGGAGTCCCC
GCTTAAACCCTTCTTAAAACTCAGCCTGGGGCTGCCAGGCCTGGGAATCCACATGAG
GCCCCTGGCCATCTGGCTTTTCATCTTCAACGTCTCTCAACAGATGGGGGGCTTCTAC
CTGTGCCAGCCGGGGCCCCCCTCTGAGAAGGCCTGGCAGCCTGGCTGGACAGTCAA
TGTGGAGGGCAGCGGGGAGCTGTTCCGGTGGAATGTTTCGGACCTAGGTGGCCTGG
GCTGTGGCCTGAAGAACAGGTCCTCAGAGGGCCCCAGCTCCCCTTCCGGGAAGCTC
ATGAGCCCCAAGCTGTATGTGTGGGCCAAAGACCGCCCTGAGATCTGGGAGGGAGA
GCCTCCGTGTCTCCCACCGAGGGACAGCCTGAACCAGAGCCTCAGCCAGGACCTCA
CCATGGCCCCTGGCTCCACACTCTGGCTGTCCTGTGGGGTACCCCCTGACTCTGTGTC
CAGGGGCCCCCTCTCCTGGACCCATGTGCACCCCAAGGGGCCTAAGTCATTGCTGAG
CCTAGAGCTGAAGGACGATCGCCCGGCCAGAGATATGTGGGTAATGGAGACGGGTC
TGTTGTTGCCCCGGGCCACAGCTCAAGACGCTGGAAAGTATTATTGTCACCGTGGCA

-continued

ACCTGACCATGTCATTCCACCTGGAGATCACTGCTCGGCCAGGAGGAGGTGGGTCTG

GAGGTGGAGGATCTGGTGGAGGTGGGTCTGGAGGAGGTGGGTCTGTGAGCGACGTG

CCCAGGGACCTGGAGGTGGTGGCCGCCACCCCCACCAGCCTGCTGATCAGCTGGTTC

GACTACGCCGTGACCTACTACAGGATCACCTACGGCGAGACCGGCGGCAACAGCCC

CGTGCAGGAGTTCACCGTGCCCGGCTGGATCAGCACCGCCACCATCAGCGGCCTGA

AGCCCGGCGTGGACTACACCATCACCGTGTACGCCGTGACCGACAACAGCCACTGG

CCCTTCAGGAGCACCCCCATCAGCACCAACTACAGGACCGAGATCGACAAGCCCCC

CCAGCATCATCACCATCACCAT

SEQ ID NO: 63

ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCGAGGTGCAGCTGGTGGAGT

CTGGTGGTGGTCTTGTTCAACCTGGTGGTTCTCTTCGTCTTTCTTGTGCTGCTTCTGGT

TTTAATATTAAAGATACTTATATTCATTGGGTTCGTCAAGCTCCTGGTAAAGGTCTTG

AATGGGTTGCTCGTATTTATCCTACTAATGGTTATACTCGTTATGCTGATTCTGTTAA

AGGTCGTTTTACTATTTCTGCTGATACTTCTAAAAATACTGCTTATCTTCAAATGAAC

TCTCTTCGTGCTGAAGATACTGCTGTTTATTATTGTTCTCGTTGGGGTGGTGATGGTT

TTTATGCTATGGATTATTGGGGTCAAGGTACTCTTGTCACCGTCTCCTCAGCTAGCAC

CGGGGGAGGTGGGTCTGGAGGTGGAGGATCTGGTGGAGGTGGGTCTGACATCCAGA

TGACCCAGTCTCCTTCTTCTCTTTCTGCTTCTGTTGGTGATCGTGTTACTATTACTTGT

CGTGCTTCTCAAGATGTTAATACTGCTGTTGCTTGGTATCAACAAAAACCTGGTAAA

GCTCCTAAACTTCTTATTTATTCTGCTTCTTTTCTTTATTCTGGTGTTCCTTCTCGTTTT

TCTGGTTCTCGTTCTGGTACTGATTTTACTCTTACTATTTCTTCTCTTCAACCTGAAGA

TTTTGCTACTTATTATTGTCAACAACATTATACTACTCCTCCTACTTTTGGTCAAGGT

ACCAAGGTGGAGATCAAACGTACGCATCATCACCATCACCAT

SEQ ID NO: 64

ATGCCACCTCCTCGCCTCCTCTTCTTCCTCCTCTTCCTCACCCCCATGGAAGTCAGGC

CCGAGGAACCTCTAGTGGTGAAGGTGGAAGAGGGAGATAACGCTGTGCTGCAGTGC

-continued

CTCAAGGGGACCTCAGATGGCCCCACTCAGCAGCTGACCTGGTCTCGGGAGTCCCC

GCTTAAACCCTTCTTAAAACTCAGCCTGGGGCTGCCAGGCCTGGGAATCCACATGAG

GCCCCTGGCCATCTGGCTTTTCATCTTCAACGTCTCTCAACAGATGGGGGGCTTCTAC

CTGTGCCAGCCGGGGCCCCCCTCTGAGAAGGCCTGGCAGCCTGGCTGGACAGTCAA

TGTGGAGGGCAGCGGGGAGCTGTTCCGGTGGAATGTTTCGGACCTAGGTGGCCTGG

GCTGTGGCCTGAAGAACAGGTCCTCAGAGGGCCCCAGCTCCCCTTCCGGGAAGCTC

ATGAGCCCCAAGCTGTATGTGTGGGCCAAAGACCGCCCTGAGATCTGGGAGGGAGA

GCCTCCGTGTCTCCCACCGAGGGACAGCCTGAACCAGAGCCTCAGCCAGGACCTCA

CCATGGCCCCTGGCTCCACACTCTGGCTGTCCTGTGGGGTACCCCCTGACTCTGTGTC

CAGGGGCCCCCTCTCCTGGACCCATGTGCACCCCAAGGGGCCTAAGTCATTGCTGAG

CCTAGAGCTGAAGGACGATCGCCCGGCCAGAGATATGTGGGTAATGGAGACGGGTC

TGTTGTTGCCCCGGGCCACAGCTCAAGACGCTGGAAAGTATTATTGTCACCGTGGCA

ACCTGACCATGTCATTCCACCTGGAGATCACTGCTCGGCCAGGGGGAGGTGGGTCTG

GAGGTGGAGGATCTGGTGGAGGTGGGTCTGGTGGAGGTGGGTCTGAGGTGCAGCTG

GTGGAGTCTGGTGGTGGTCTTGTTCAACCTGGTGGTTCTCTTCGTCTTTCTTGTGCTG

CTTCTGGTTTTAATATTAAAGATACTTATATTCATTGGGTTCGTCAAGCTCCTGGTAA

AGGTCTTGAATGGGTTGCTCGTATTTATCCTACTAATGGTTATACTCGTTATGCTGAT

TCTGTTAAAGGTCGTTTTACTATTTCTGCTGATACTTCTAAAAATACTGCTTATCTTC

AAATGAACTCTCTTCGTGCTGAAGATACTGCTGTTTATTATTGTTCTCGTTGGGGTGG

TGATGGTTTTTATGCTATGGATTATTGGGTCAAGGTACTCTTGTCACCGTCTCCTCA

GCTAGCACCGGGGAGGTGGGTCTGGAGGTGGAGGATCTGGTGGAGGTGGGTCTGA

CATCCAGATGACCCAGTCTCCTTCTTCTCTTTCTGCTTCTGTTGGTGATCGTGTTACTA

TTACTTGTCGTGCTTCTCAAGATGTTAATACTGCTGTTGCTTGGTATCAACAAAAACC

TGGTAAAGCTCCTAAACTTCTTATTTATTCTGCTTCTTTTCTTTATTCTGGTGTTCCTT

CTCGTTTTTCTGGTTCTCGTTCTGGTACTGATTTTACTCTTACTATTTCTTCTCTTCAA

CCTGAAGATTTTGCTACTTATTATTGTCAACAACATTATACTACTCCTCCTACTTTTG

GTCAAGGTACCAAGGTGGAGATCAAACGTACGTCTAGAGGGCCCCATCATCACCAT

CACCAT

SEQ ID NO: 65

ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGTCAAGGTACTCTTGTCA

CCGTCTCCTCAGCTAGCACCGGGGAGGTGGGTCTGGAGGTGGAGGATCTGGTGGA

GGTGGGTCTGACATCCAGATGACCCAGTCTCCTTCTTCTCTTTCTGCTTCTGTTGGTG

ATCGTGTTACTATTACTTGTCGTGCTTCTCAAGATGTTAATACTGCTGTTGCTTGGTA

TCAACAAAAACCTGGTAAAGCTCCTAAACTTCTTATTTATTCTGCTTCTTTTCTTTATT

CTGGTGTTCCTTCTCGTTTTTCTGGTTCTCGTTCTGGTACTGATTTTACTCTTACTATT

-continued

TCTTCTCTTCAACCTGAAGATTTTGCTACTTATTATTGTCAACAACATTATACTACTC

CTCCTACTTTTGGTCAAGGTACCAAGGTGGAGATCAAACGTACGGGAGGAGGTGGG

TCTGGAGGTGGAGGATCTGGTGGAGGTGGGTCTGGAGGAGGTGGATCCCCCGAGGA

ACCTCTAGTGGTGAAGGTGGAAGAGGGAGATACCGCTGCCCTGTGGTGCCTCAAGG

GGACCTCAGATGGCCCCACTCAGCAGCTGACCTGGTCTCGGGAGTCCCCGCTTAAAC

CCTTCTTAAAATACAGCCTGGGGGTGCCAGGCCTGGGAGTGCACGTGAGGCCCGAC

GCCATCAGCGTGGTTATCCGGAACGTCTCTCAACAGATGGGGGGCTTCTACCTGTGC

CAGCCGGGGCCCCCCTCTGAGAAGGCCTGGCAGCCTGGCTGGACAGTCAATGTGGA

GGGCAGCGGGGAGCTGTTCCGGTGGAATGTTTCGGACCTAGGTGGCCTGGGCTGTG

GCCTGAAGAACAGGTCCTCAGAGGGCCCCAGCTCCCCTTCCGGGAAGCTCATGAGC

CCCAAGCTGTATGTGTGGGCCAAAGACCGCCCTGAGATCTGGGAGGGAGAGCCTCC

GTGTCTCCCACCGAGGGACAGCCTGAACCAGAGCCTCAGCCGGGACCTCACCGTTG

CCCCTGGCTCCACACTCTGGCTGTCCTGTGGGGTACCCCCTGACTCTGTGTCCAGGG

GCCCCCTCTCCTGGACCCATGTGCACCCCAAGGGGCCTAAGTCATTGCTGAGCCTAG

AGCTGAAGGACGATCGCCCGGCCAGAGATATGTGGGTAATGGGCACGAGCCTGATG

TTGCCCCGGGCCACAGCTCAAGACGCTGGAAAGTGGTATTGTCACCGTGGCAACCT

GACCATGTCATTCCACCTGGAGATCACTGCTCGGCCATCTAGACATCATCACCATCA

CCAT

SEQ ID NO: 66
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCGGGGGAGGTGGGTCTGGAGGTGGAGGATCTGGTGGA

GGTGGGTCTGACATCCAGATGACCCAGTCTCCTTCTTCTCTTTCTGCTTCTGTTGGTG

ATCGTGTTACTATTACTTGTCGTGCTTCTCAAGATGTTAATACTGCTGTTGCTTGGTA

TCAACAAAAACCTGGTAAAGCTCCTAAACTTCTTATTTATTCTGCTTCTTTTCTTTATT

CTGGTGTTCCTTCTCGTTTTTCTGGTTCTCGTTCTGGTACTGATTTTACTCTTACTATT

TCTTCTCTTCAACCTGAAGATTTTGCTACTTATTATTGTCAACAACATTATACTACTC

CTCCTACTTTTGGTCAAGGTACCAAGGTGGAGATCAAACGTACGGGAGGAGGTGGG

TCTGGAGGTGGAGGATCTGGTGGAGGTGGGTCTGGAGGAGGTGGATCCCCCGAGGA

ACCTCTAGTGGTGAAGGTGGAAGAGGGAGATACCGCTGCCCTGTGGTGCCTCAAGG

GGACCTCAGATGGCCCCACTCAGCAGCTGACCTGGTCTCGGGAGTCCCCGCTTAAAC

CCTTCTTAAAATACAGCTTTGGGGCCCAGGCCTGGGAATCCACATGAGGCCCGAC

GCCATCAGCGTGGTTATCAGCAACGTCTCTCAACAGATGGGGGGCTTCTACCTGTGC

CAGCCGGGGCCCCCCTCTGAGAAGGCCTGGCAGCCTGGCTGGACAGTCAATGTGGA

GGGCAGCGGGGAGCTGTTCCGGTGGAATGTTTCGGACCTAGGTGGCCTGGGCTGTG

GCCTGAAGAACAGGTCCTCAGAGGGCCCCAGCTCCCCTTCCGGGAAGCTCATGAGC

```
CCCAAGCTGTATGTGTGGGCCAAAGACCGCCCTGAGATCTGGGAGGGAGAGCCTCC

GTGTCTCCCACCGAGGGACAGCCTGAACCAGAGCCTCAGCCGGGACCTCACCGTTG

CCCCTGGCTCCACACTCTGGCTGTCCTGTGGGGTACCCCCTGACTCTGTGTCCAGGG

GCCCCCTCTCCTGGACCCATGTGCACCCCAAGGGGCCTAAGTCATTGCTGAGCCTAG

AGCTGAAGGACGATCGCCCGGCCAGAGAGATGTGGGTAACCGGCACGCGGCTGTTT

TTGCCCCGGGCCACAGCTCAAGACGCTGGAAAGTACTATTGTCACCGTGGCAACCTG

ACCATGTCATTCCACCTGGAGATCACTGCTCGGCCATCTAGACATCATCACCATCAC

CAT
```

SEQ ID NO: 67
```
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCGGGGAGGTGGGTCTGGAGGTGGAGGATCTGGTGGA

GGTGGGTCTGACATCCAGATGACCCAGTCTCCTTCTTCTCTTTCTGCTTCTGTTGGTG

ATCGTGTTACTATTACTTGTCGTGCTTCTCAAGATGTTAATACTGCTGTTGCTTGGTA

TCAACAAAAACCTGGTAAAGCTCCTAAACTTCTTATTTATTCTGCTTCTTTTCTTTATT

CTGGTGTTCCTTCTCGTTTTTCTGGTTCTCGTTCTGGTACTGATTTTACTCTTACTATT

TCTTCTCTTCAACCTGAAGATTTTGCTACTTATTATTGTCAACAACATTATACTACTC

CTCCTACTTTTGGTCAAGGTACCAAGGTGGAGATCAAACGTACGGGAGGAGGTGGG

TCTGGAGGTGGAGGATCTGGTGGAGGTGGGTCTGGAGGAGGTGGATCCCCCGAGGA

ACCTCTAGTGGTGAAGGTGGAAGAGGGGAGATACCGCTGCCCTGTGGTGCCTCAAGG

GGACCTCAGATGGCCCCACTGAGCAGGTTACCTGGTCTCGGGAGTCCCCGCTTAAAC

CCTTCTTAAAACTCAGCCTGGGGCTCCCAGGCGGCGGAGGTCACGTGAGGCCCAAC

GCCGTGAGCCTCGTTATCCGGAACGTCTCTCAACAGATGGGGGGCTTCTACCTGTGC

CAGCCGGGGCCCCCCTCTGAGAAGGCCTGGCAGCCTGGCTGGACAGTCAATGTGGA

GGGCAGCGGGGAGCTGTTCCGGTGGAATGTTTCGGACCTAGGTGGCCTGGGCTGTG

GCCTGAAGAACAGGTCCTCAGAGGGCCCCAGCTCCCCTTCCGGGAAGCTCATGAGC

CCCAAGCTGTATGTGTGGGCCAAAGACCGCCCTGAGATCTGGGAGGGAGAGCCTCC

GTGTCTCCCACCGAGGGACAGCCTGAACCAGAGCCTCAGCCGGGACCTCACCGTTG

CCCCTGGCTCCACACTCTGGCTGTCCTGTGGGGTACCCCCTGACTCTGTGTCCAGGG

GCCCCCTCTCCTGGACCCATGTGCACCCCAAGGGGCCTAAGTCATTGCTGAGCCTAG

AGCTGAAGGACGATCGCCCGGCCAGAGATATGTGGGTAACCGAGACGGGTCTGCTC

TTGCCCCGGGCCACAGCTCAAGACGCTGGAAAGTGGTATTGTCACCGTGGCAACCT

GACCATGTCATTCCACCTGGAGATCACTGCTCGGCCATCTAGACATCATCACCATCA

CCAT
```

SEQ ID NO: 68
```
ATGATGGAGTTTGGGCTGAGCTGGGTTTTCCTCGTTGCTCTTTTTAGAGGTGTCCAGT
```

-continued

```
GTCAGGTCAAACTACAGGAGTCAGGGGCTGAGCTGGTGAAGCCTGGGGCCTCAGTG

AAGATGTCCTGCAAGGCTTCTGGCTACACATTTACCAGTTACAATATGCACTGGGTA

AAGCAGACACCTGGACAGGGCCTGGAATGGATTGGAGCTATTTATCCAGGAAATGG

TGATACTTCCTACAATCAGAAGTTCAAAGGCAAGGCCACATTGACTGCAGACAAAT

CCTCCAGCACAGCCTACATGCAGCTCAGCAGCCTGACATCTGAGGACTCTGCGGACT

ATTACTGTGCAAGATCTAATTATTACGGTAGTAGCTACTGGTTCTTCGATGTCTGGG

GCCAAGGGACCACGGTCACCGTCTCCTCAGCCAGCACCGGTGGAGGCGGTTCAGGC

GGAGGTGGCTCTGGCGGTGGCGGATCGGACATCGAGCTCACTCAGTCTCCAACAAT

CCTGTCTGCATCTCCAGGGGAGAAGGTCACAATGACTTGCAGGGCCAGCTCAAGTGT

AAATTACATGGACTGGTACCAGAAGAAGCCAGGATCCTCCCCCAAACCCTGGATTT

ATGCCACATCCAACCTGGCTTCTGGAGTCCCTGCTCGCTTCAGTGGCAGTGGGTCTG

GGACCTCTTACTCTCTCACAATCAGCAGAGTGGAGGCTGAAGATGCTGCCACTTATT

ACTGCCAGCAGTGGAGTTTTAATCCACCCACGTTCGGAGGGGGGACAAAGTTGGAA

ATAAAACGGGCCGCCGCTGGAGGAGGTGGGTCTGGAGGTGGAGGATCTGGTGGAGG

TGGGTCTGGAGGAGGTGGATCCCCCGAGGAACCTCTAGTGGTGAAGGTGGAAGAGG

GAGATACCGCTGCCCTGTGGTGCCTCAAGGGGACCTCAGATGGCCCCACTCAGCAG

CTGACCTGGTCTCGGGAGTCCCCGCTTAAACCCTTCTTAAAATACAGCCTGGGGGTG

CCAGGCCTGGGAGTGCACGTGAGGCCCGACGCCATCAGCGTGGTTATCCGGAACGT

CTCTCAACAGATGGGGGCTTCTACCTGTGCCAGCCGGGGCCCCCCTCTGAGAAGGC

CTGGCAGCCTGGCTGGACAGTCAATGTGGAGGGCAGCGGGGAGCTGTTCCGGTGGA

ATGTTTCGGACCTAGGTGGCCTGGCTGTGGCCTGAAGAACAGGTCCTCAGAGGGC

CCCAGCTCCCCTTCCGGGAAGCTCATGAGCCCCAAGCTGTATGTGTGGGCCAAAGAC

CGCCCTGAGATCTGGGAGGGAGAGCCTCCGTGTCTCCCACCGAGGGACAGCCTGAA

CCAGAGCCTCAGCCGGGACCTCACCGTTGCCCCTGGCTCCACACTCTGGCTGTCCTG

TGGGGTACCCCCTGACTCTGTGTCCAGGGGCCCCCTCTCCTGGACCCATGTGCACCC

CAAGGGGCCTAAGTCATTGCTGAGCCTAGAGCTGAAGGACGATCGCCCGGCCAGAG

ATATGTGGGTAATGGGCACGAGCCTGATGTTGCCCCGGGCCACAGCTCAAGACGCT

GGAAAGTGGTATTGTCACCGTGGCAACCTGACCATGTCATTCCACCTGGAGATCACT

GCTCGGCCATCTAGACATCATCACCATCACCAT
```

SEQ ID NO: 69
```
ATGCCACCTCCTCGCCTCCTCTTCTTCCTCCTCTTCCTCACCCCCATGGAAGTCAGGC

CCGAGGAACCTCTAGTGGTGAAGGTGGAAGAGGGAGATAACGCTGTGCTGCAGTGC

CTCAAGGGGACCTCAGATGGCCCCACTCAGCAGCTGACCTGGTCTCGGGAGTCCCC

GCTTAAACCCTTCTTAAAACTCAGCCTGGGGCTGCCAGGCCTGGGAATCCACATGAG

GCCCCTGGCCATCTGGCTTTTCATCTTCAACGTCTCTCAACAGATGGGGGCTTCTAC

CTGTGCCAGCCGGGGCCCCCCTCTGAGAAGGCCTGGCAGCCTGGCTGGACAGTCAA

TGTGGAGGGCAGCGGGGAGCTGTTCCGGTGGAATGTTTCGGACCTAGGTGGCCTGG

GCTGTGGCCTGAAGAACAGGTCCTCAGAGGGCCCCAGCTCCCCTTCCGGGAAGCTC

ATGAGCCCCAAGCTGTATGTGTGGGCCAAAGACCGCCCTGAGATCTGGGAGGGAGA

GCCTCCGTGTCTCCCACCGAGGGACAGCCTGAACCAGAGCCTCAGCCAGGACCTCA

CCATGGCCCCTGGCTCCACACTCTGGCTGTCCTGTGGGGTACCCCCTGACTCTGTGTC
```

-continued

```
CAGGGGCCCCCTCTCCTGGACCCATGTGCACCCCAAGGGGCCTAAGTCATTGCTGAG

CCTAGAGCTGAAGGACGATCGCCCGGCCAGAGATATGTGGGTAATGGAGACGGGTC

TGTTGTTGCCCCGGGCCACAGCTCAAGACGCTGGAAAGTATTATTGTCACCGTGGCA

ACCTGACCATGTCATTCCACCTGGAGATCACTGCTCGGCCAGGAGGAGGTGGGTCTG

GAGGTGGAGGATCTGGTGGAGGTGGGTCTGGAGGAGGTGGGTCTATGGCCCAGGTC

AAACTACAGGAGTCAGGGGCTGAGCTGGTGAAGCCTGGGGCCTCAGTGAAGATGTC

CTGCAAGGCTTCTGGCTACACATTTACCAGTTACAATATGCACTGGGTAAAGCAGAC

ACCTGGACAGGGCCTGGAATGGATTGGAGCTATTTATCCAGGAAATGGTGATACTTC

CTACAATCAGAAGTTCAAAGGCAAGGCCACATTGACTGCAGACAAATCCTCCAGCA

CAGCCTACATGCAGCTCAGCAGCCTGACATCTGAGGACTCTGCGGACTATTACTGTG

CAAGATCTAATTATTACGGTAGTAGCTACTGGTTCTTCGATGTCTGGGGCCAAGGGA

CCACGGTCACCGTCTCCTCAGGTGGAGGCGGTTCAGGCGGAGGTGGCTCTGGCGGT

GGCGGATCGGACATCGAGCTCACTCAGTCTCCAACAATCCTGTCTGCATCTCCAGGG

GAGAAGGTCACAATGACTTGCAGGGCCAGCTCAAGTGTAAATTACATGGACTGGTA

CCAGAAGAAGCCAGGATCCTCCCCCAAACCCTGGATTTATGCCACATCCAACCTGGC

TTCTGGAGTCCCTGCTCGCTTCAGTGGCAGTGGGTCTGGGACCTCTTACTCTCTCACA

ATCAGCAGAGTGGAGGCTGAAGATGCTGCCACTTATTACTGCCAGCAGTGGAGTTTT

AATCCACCCACGTTCGGAGGGGGGACAAAGTTGGAAATAAAACGGGCCGCCGCTCA

TCATCACCATCACCAT
```

SEQ ID NO: 70

```
ATGGACTTCGGCCTGATCTTCTTCATCGTGGCCCTGCTGAAGGGCGTGCAGTGCCAG

ATCCTGCTGACCCAGAGCCCCGTGATCCTGAGCGTGAGCCCCGGCGAGAGGGTGAG

CTTCAGCTGCAGGGCCAGCCAGAGCATCGGCACCAACATCCACTGGTACCAGCAGA

GGACCAACGGCAGCCCCAGGCTGCTGATCAAGTACGCCAGCGAGAGCATCAGCGGC

ATCCCCAGCAGGTTCAGCGGCAGCGGCAGCGGCACCGACTTCACCCTGAGCATCAA

CAGCGTGGAGAGCGAGGACATCGCCGACTACTACTGCCAGCAGAACAACAACTGGC

CCACCACCTTCGGCGCCGGCACCAAGCTGGAGCTGAAGGGCAGCACCAGCGGCAGC

GGCAAGCCCGGCAGCGGCGAGGGCAGCACCAAGGGCCAGGTGCAGCTGAAGCAGA

GCGGCCCCGGCCTGGTGCAGCCCAGCCAGAGCCTGAGCATCACCTGCACCGTGAGC

GGCTTCAGCCTGACCAACTACGGCGTGCACTGGGTGAGGCAGAGCCCCGGCAAGGG

CCTGGAGTGGCTGGGCGTGATCTGGAGCGGCGGCAACACCGACTACAACACCCCCT

TCACCAGCAGGCTGAGCATCAACAAGGACAACAGCAAGAGCCAGGTGTTCTTCAAG

ATGAACAGCCTGCAGAGCAACGACACCGCCATCTACTACTGCGCCAGGGCCCTGAC

CTACTACGACTACGAGTTCGCCTACTGGGGCCAGGGCACCCTGGTGACCGTGAGCG

CCGGAGGAGGTGGGTCCGGAGGTGGAGGATCTGGTGGAGGTGGGTCTGGAGGAGGT

GGATCCCCCGAGGAACCTCTAGTGGTGAAGGTGGAAGAGGGAGATACCGCTGCCCT

GTGGTGCCTCAAGGGGACCTCAGATGGCCCCACTCAGCAGCTGACCTGGTCTCGGG

AGTCCCGCTTAAACCCTTCTTAAAATACAGCCTGGGGGTGCCAGGCCTGGGAGTGC

ACGTGAGGCCCGACGCCATCAGCGTGGTTATCCGGAACGTCTCTCAACAGATGGGG

GGCTTCTACCTGTGCCAGCCGGGGCCCCCCTCTGAGAAGGCCTGGCAGCCTGGCTGG

ACAGTCAATGTGGAGGGCAGCGGGGAGCTGTTCCGGTGGAATGTTTCGGACCTAGG
```

-continued

TGGCCTGGGCTGTGGCCTGAAGAACAGGTCCTCAGAGGGCCCCAGCTCCCCTTCCGG

GAAGCTCATGAGCCCCAAGCTGTATGTGTGGGCCAAAGACCGCCCTGAGATCTGGG

AGGGAGAGCCTCCGTGTCTCCCACCGAGGGACAGCCTGAACCAGAGCCTCAGCCGG

GACCTCACCGTTGCCCCTGGCTCCACACTCTGGCTGTCCTGTGGGGTACCCCCTGAC

TCTGTGTCCAGGGGCCCCCTCTCCTGGACCCATGTGCACCCCAAGGGGCCTAAGTCA

TTGCTGAGCCTAGAGCTGAAGGACGATCGCCCGGCCAGAGATATGTGGGTAATGGG

CACGAGCCTGATGTTGCCCCGGGCCACAGCTCAAGACGCTGGAAAGTGGTATTGTC

ACCGTGGCAACCTGACCATGTCATTCCACCTGGAGATCACTGCTCGGCCATCTAGAC

ATCATCACCATCACCAT

SEQ ID NO: 71
ATGGACTTCGGCCTGATCTTCTTCATCGTGGCCCTGCTGAAGGGCGTGCAGTGCCAG

ATCCTGCTGACCCAGAGCCCCGTGATCCTGAGCGTGAGCCCCGGCGAGAGGGTGAG

CTTCAGCTGCAGGGCCAGCCAGAGCATCGGCACCAACATCCACTGGTACCAGCAGA

GGACCAACGGCAGCCCCAGGCTGCTGATCAAGTACGCCAGCGAGAGCATCAGCGGC

ATCCCCAGCAGGTTCAGCGGCAGCGGCAGCGGCACCGACTTCACCCTGAGCATCAA

CAGCGTGGAGAGCGAGGACATCGCCGACTACTACTGCCAGCAGAACAACAACTGGC

CCACCACCTTCGGCGCCGGCACCAAGCTGGAGCTGAAGGGCAGCACCAGCGGCAGC

GGCAAGCCCGGCAGCGGCGAGGGCAGCACCAAGGGCCAGGTGCAGCTGAAGCAGA

GCGGCCCCGGCCTGGTGCAGCCCAGCCAGAGCCTGAGCATCACCTGCACCGTGAGC

GGCTTCAGCCTGACCAACTACGGCGTGCACTGGGTGAGGCAGAGCCCCGGCAAGGG

CCTGGAGTGGCTGGGCGTGATCTGGAGCGGCGGCAACACCGACTACAACACCCCCT

TCACCAGCAGGCTGAGCATCAACAAGGACAACAGCAAGAGCCAGGTGTTCTTCAAG

ATGAACAGCCTGCAGAGCAACGACACCGCCATCTACTACTGCGCCAGGGCCCTGAC

CTACTACGACTACGAGTTCGCCTACTGGGGCCAGGGCACCCTGGTGACCGTGAGCG

CCGGAGGAGGTGGGTCCGGAGGTGGAGGATCTGGTGGAGGTGGGTCTGGAGGAGGT

GGATCCCCCGAGGAACCTCTAGTGGTGAAGGTGGAAGAGGGAGATACCGCTGCCCT

GTGGTGCCTCAAGGGGACCTCAGATGGCCCCACTGAGCAGGTTACCTGGTCTCGGG

AGTCCCCGCTTAAACCCTTCTTAAAACTCAGCCTGGGGCTCCCAGGCGGCGGAGGTC

ACGTGAGGCCCAACGCCGTGAGCCTCGTTATCCGGAACGTCTCTCAACAGATGGGG

GGCTTCTACCTGTGCCAGCCGGGGCCCCCCTCTGAGAAGGCCTGGCAGCCTGGCTGG

ACAGTCAATGTGGAGGGCAGCGGGGAGCTGTTCCGGTGGAATGTTTCGGACCTAGG

TGGCCTGGGCTGTGGCCTGAAGAACAGGTCCTCAGAGGGCCCCAGCTCCCCTTCCGG

GAAGCTCATGAGCCCCAAGCTGTATGTGTGGGCCAAAGACCGCCCTGAGATCTGGG

AGGGAGAGCCTCCGTGTCTCCCACCGAGGGACAGCCTGAACCAGAGCCTCAGCCGG

GACCTCACCGTTGCCCCTGGCTCCACACTCTGGCTGTCCTGTGGGGTACCCCCTGAC

TCTGTGTCCAGGGGCCCCCTCTCCTGGACCCATGTGCACCCCAAGGGGCCTAAGTCA

TTGCTGAGCCTAGAGCTGAAGGACGATCGCCCGGCCAGAGATATGTGGGTAACCGA

GACGGGTCTGCTCTTGCCCCGGGCCACAGCTCAAGACGCTGGAAAGTGGTATTGTCA

CCGTGGCAACCTGACCATGTCATTCCACCTGGAGATCACTGCTCGGCCATCTAGACA

TCATCACCATCACCAT

SEQ ID NO: 72
ATGGACTTCGGCCTGATCTTCTTCATCGTGGCCCTGCTGAAGGGCGTGCAGTGCCAG

```
GGCCAGAGCGGCCAGTGCATCAGCCCCAGGGGCTGCCCCGACGGCCCCTACGTGAT

GTACGGCAGCAGCGGCGGCAGCGGCGGCAGCGGCGGCAGCGGCCTGAGCGGCAGG

AGCGACAACCACGGCAGCAGCGGCACCCAGATCCTGCTGACCCAGAGCCCCGTGAT

CCTGAGCGTGAGCCCCGGCGAGAGGGTGAGCTTCAGCTGCAGGGCCAGCCAGAGCA

TCGGCACCAACATCCACTGGTACCAGCAGAGGACCAACGGCAGCCCCAGGCTGCTG

ATCAAGTACGCCAGCGAGAGCATCAGCGGCATCCCCAGCAGGTTCAGCGGCAGCGG

CAGCGGCACCGACTTCACCCTGAGCATCAACAGCGTGGAGAGCGAGGACATCGCCG

ACTACTACTGCCAGCAGAACAACAACTGGCCCACCACCTTCGGCGCCGGCACCAAG

CTGGAGCTGAAGGGCAGCACCAGCGGCAGCGGCAAGCCCGGCAGCGGCGAGGGCA

GCACCAAGGGCCAGGTGCAGCTGAAGCAGAGCGGCCCCGGCCTGGTGCAGCCCAGC

CAGAGCCTGAGCATCACCTGCACCGTGAGCGGCTTCAGCCTGACCAACTACGGCGT

GCACTGGGTGAGGCAGAGCCCCGGCAAGGGCCTGGAGTGGCTGGGCGTGATCTGGA

GCGGCGGCAACACCGACTACAACACCCCCTTCACCAGCAGGCTGAGCATCAACAAG

GACAACAGCAAGAGCCAGGTGTTCTTCAAGATGAACAGCCTGCAGAGCAACGACAC

CGCCATCTACTACTGCGCCAGGGCCCTGACCTACTACGACTACGAGTTCGCCTACTG

GGGCCAGGGCACCCTGGTGACCGTGAGCGCCGGAGGAGGTGGGTCTGGAGGTGGAG

GATCTGGTGGAGGTGGGTCTGGAGGAGGTGGATCCCCCGAGGAACCTCTAGTGGTG

AAGGTGGAAGAGGGAGATACCGCTGCCCTGTGGTGCCTCAAGGGGACCTCAGATGG

CCCCACTCAGCAGCTGACCTGGTCTCGGGAGTCCCCGCTTAAACCCTTCTTAAAATA

CAGCCTGGGGGTGCCAGGCCTGGGAGTGCACGTGAGGCCCGACGCCATCAGCGTGG

TTATCCGGAACGTCTCTCAACAGATGGGGGGCTTCTACCTGTGCCAGCCGGGGCCCC

CCTCTGAGAAGGCCTGGCAGCCTGGCTGGACAGTCAATGTGGAGGGCAGCGGGGAG

CTGTTCCGGTGGAATGTTTCGGACCTAGGTGGCCTGGGCTGTGGCCTGAAGAACAGG

TCCTCAGAGGGCCCCAGCTCCCCTTCCGGGAAGCTCATGAGCCCCAAGCTGTATGTG

TGGGCCAAAGACCGCCCTGAGATCTGGGAGGGAGAGCCTCCGTGTCTCCCACCGAG

GGACAGCCTGAACCAGAGCCTCAGCCGGGACCTCACCGTTGCCCCTGGCTCCACACT

CTGGCTGTCCTGTGGGGTACCCCCTGACTCTGTGTCCAGGGGCCCCCTCTCCTGGAC

CCATGTGCACCCCAAGGGGCCTAAGTCATTGCTGAGCCTAGAGCTGAAGGACGATC

GCCCGGCCAGAGATATGTGGGTAATGGGCACGAGCCTGATGTTGCCCCGGGCCACA

GCTCAAGACGCTGGAAAGTGGTATTGTCACCGTGGCAACCTGACCATGTCATTCCAC

CTGGAGATCACTGCTCGGCCATCTAGACATCATCACCATCACCAT
```
```
                                            SEQ ID NO: 73
ATGGACTTCGGCCTGATCTTCTTCATCGTGGCCCTGCTGAAGGGCGTGCAGTGCCAG

GGCCAGAGCGGCCAGTGCATCAGCCCCAGGGGCTGCCCCGACGGCCCCTACGTGAT

GTACGGCAGCAGCGGCGGCAGCGGCGGCAGCGGCGGCAGCGGCCTGAGCGGCAGG

AGCGACAACCACGGCAGCAGCGGCACCCAGATCCTGCTGACCCAGAGCCCCGTGAT

CCTGAGCGTGAGCCCCGGCGAGAGGGTGAGCTTCAGCTGCAGGGCCAGCCAGAGCA

TCGGCACCAACATCCACTGGTACCAGCAGAGGACCAACGGCAGCCCCAGGCTGCTG

ATCAAGTACGCCAGCGAGAGCATCAGCGGCATCCCCAGCAGGTTCAGCGGCAGCGG

CAGCGGCACCGACTTCACCCTGAGCATCAACAGCGTGGAGAGCGAGGACATCGCCG

ACTACTACTGCCAGCAGAACAACAACTGGCCCACCACCTTCGGCGCCGGCACCAAG
```

-continued

CTGGAGCTGAAGGGCAGCACCAGCGGCAGCGGCAAGCCCGGCAGCGGCGAGGGCA

GCACCAAGGGCCAGGTGCAGCTGAAGCAGAGCGGCCCCGGCCTGGTGCAGCCCAGC

CAGAGCCTGAGCATCACCTGCACCGTGAGCGGCTTCAGCCTGACCAACTACGGCGT

GCACTGGGTGAGGCAGAGCCCCGGCAAGGGCCTGGAGTGGCTGGGCGTGATCTGGA

GCGGCGGCAACACCGACTACAACACCCCCTTCACCAGCAGGCTGAGCATCAACAAG

GACAACAGCAAGAGCCAGGTGTTCTTCAAGATGAACAGCCTGCAGAGCAACGACAC

CGCCATCTACTACTGCGCCAGGGCCCTGACCTACTACGACTACGAGTTCGCCTACTG

GGGCCAGGGCACCCTGGTGACCGTGAGCGCCGGAGGAGGTGGGTCTGGAGGTGGAG

GATCTGGTGGAGGTGGGTCTGGAGGAGGTGGATCCCCCGAGGAACCTCTAGTGGTG

AAGGTGGAAGAGGGAGATACCGCTGCCCTGTGGTGCCTCAAGGGGACCTCAGATGG

CCCCACTGAGCAGGTTACCTGGTCTCGGGAGTCCCCGCTTAAACCCTTCTTAAAACT

CAGCCTGGGGCTCCCAGGCGGCGGAGGTCACGTGAGGCCCAACGCCGTGAGCCTCG

TTATCCGGAACGTCTCTCAACAGATGGGGGGCTTCTACCTGTGCCAGCCGGGGCCCC

CCTCTGAGAAGGCCTGGCAGCCTGGCTGGACAGTCAATGTGGAGGGCAGCGGGGAG

CTGTTCCGGTGGAATGTTTCGGACCTAGGTGGCCTGGGCTGTGGCCTGAAGAACAGG

TCCTCAGAGGGCCCCAGCTCCCCTTCCGGGAAGCTCATGAGCCCCAAGCTGTATGTG

TGGGCCAAAGACCGCCCTGAGATCTGGGAGGGAGAGCCTCCGTGTCTCCCACCGAG

GGACAGCCTGAACCAGAGCCTCAGCCGGGACCTCACCGTTGCCCCTGGCTCCACACT

CTGGCTGTCCTGTGGGGTACCCCCTGACTCTGTGTCCAGGGGCCCCCTCTCCTGGAC

CCATGTGCACCCCAAGGGGCCTAAGTCATTGCTGAGCCTAGAGCTGAAGGACGATC

GCCCGGCCAGAGATATGTGGGTAACCGAGACGGGTCTGCTCTTGCCCCGGGCCACA

GCTCAAGACGCTGGAAAGTGGTATTGTCACCGTGGCAACCTGACCATGTCATTCCAC

CTGGAGATCACTGCTCGGCCATCTAGACATCATCACCATCACCAT

SEQ ID NO: 74
ATGGACTTCGGCCTGATCTTCTTCATCGTGGCCCTGCTGAAGGGCGTGCAGTGCCAG

GGCCAGAGCGGCCAGTGCATCAGCCCCAGGGGCTGCCCCGACGGCCCCTACGTGAT

GTACGGCAGCAGCGGCGGCAGCGGCGGCAGCGGCGGCAGCGGCCTGAGCGGCAGG

AGCGACAACCACGGCAGCAGCGGCACCCAGATCCTGCTGACCCAGAGCCCCGTGAT

CCTGAGCGTGAGCCCCGGCGAGAGGGTGAGCTTCAGCTGCAGGGCCAGCCAGAGCA

TCGGCACCAACATCCACTGGTACCAGCAGAGGACCAACGGCAGCCCCAGGCTGCTG

ATCAAGTACGCCAGCGAGAGCATCAGCGGCATCCCCAGCAGGTTCAGCGGCAGCGG

CAGCGGCACCGACTTCACCCTGAGCATCAACAGCGTGGAGAGCGAGGACATCGCCG

ACTACTACTGCCAGCAGAACAACAACTGGCCCACCACCTTCGGCGCCGGCACCAAG

CTGGAGCTGAAGGGCAGCACCAGCGGCAGCGGCAAGCCCGGCAGCGGCGAGGGCA

GCACCAAGGGCCAGGTGCAGCTGAAGCAGAGCGGCCCCGGCCTGGTGCAGCCCAGC

CAGAGCCTGAGCATCACCTGCACCGTGAGCGGCTTCAGCCTGACCAACTACGGCGT

GCACTGGGTGAGGCAGAGCCCCGGCAAGGGCCTGGAGTGGCTGGGCGTGATCTGGA

GCGGCGGCAACACCGACTACAACACCCCCTTCACCAGCAGGCTGAGCATCAACAAG

GACAACAGCAAGAGCCAGGTGTTCTTCAAGATGAACAGCCTGCAGAGCAACGACAC

CGCCATCTACTACTGCGCCAGGGCCCTGACCTACTACGACTACGAGTTCGCCTACTG

GGGCCAGGGCACCCTGGTGACCGTGAGCGCCGGAGGAGGTGGGTCTGGAGGTGGAG

-continued

```
GATCTGGTGGAGGTGGGTCTGGAGGAGGTGGATCCCCCGAGGAACCTCTAGTGGTG

AAGGTGGAAGAGGGAGATACCGCTGCCCTGTGGTGCCTCAAGGGGACCTCAGATGG

CCCCACTCAGCAGCTGACCTGGTCTCGGGAGTCCCCGCTTAAACCCTTCTTAAAATA

CAGCCTGGGGGTGCCAGGCCTGGGAGTGCACGTGAGGCCCGACGCCATCAGCGTGG

TTATCCGGAACGTCTCTCAACAGATGGGGGGCTTCTACCTGTGCCAGCCGGGGCCCC

CCTCTGAGAAGGCCTGGCAGCCTGGCTGGACAGTCAATGTGGAGGGCAGCGGGGAG

CTGTTCCGGTGGAATGTTTCGGACCTAGGTGGCCTGGGCTGTGGCCTGAAGAACAGG

TCCTCAGAGGGCCCCAGCTCCCCTTCCGGGAAGCTCATGAGCCCCAAGCTGTATGTG

TGGGCCAAAGACCGCCCTGAGATCTGGGAGGGAGAGCCTCCGTGTCTCCCACCGAG

GGACAGCCTGAACCAGAGCCTCAGCCGGGACCTCACCGTTGCCCCTGGCTCCACACT

CTGGCTGTCCTGTGGGTACCCCCTGACTCTGTGTCCAGGGGCCCCCTCTCCTGGAC

CCATGTGCACCCCAAGGGGCCTAAGTCATTGCTGAGCCTAGAGCTGAAGGACGATC

GCCCGGCCAGAGATATGTGGGTAATGGGCACGAGCCTGATGTTGCCCCGGGCCACA

GCTCAAGACGCTGGAAAGTGGTATTGTCACCGTGGCAACCTGACCATGTCATTCCAC

CTGGAGATCACTGCTCGGCCATCTAGAGGAGGAGGTGGGTCTGGAGGTGGAGGATC

TGGTGGAGGTGGGTCTGGAGGAGGTGGATCCGAGGTGCAGCTGGTGGAGTCTGGTG

GTGGTCTTGTTCAACCTGGTGGTTCTCTTCGTCTTTCTTGTGCTGCTTCTGGTTTTAAT

ATTAAAGATACTTATATTCATTGGGTTCGTCAAGCTCCTGGTAAAGGTCTTGAATGG

GTTGCTCGTATTTATCCTACTAATGGTTATACTCGTTATGCTGATTCTGTTAAAGGTC

GTTTTACTATTTCTGCTGATACTTCTAAAAATACTGCTTATCTTCAAATGAACTCTCT

TCGTGCTGAAGATACTGCTGTTTATTATTGTTCTCGTTGGGGTGGTGATGGTTTTTAT

GCTATGGATTATTGGGGTCAAGGTACTCTTGTCACCGTCTCCTCAGCTAGCACCGGG

GGAGGTGGGTCTGGAGGTGGAGGATCTGGTGGAGGTGGGTCTGACATCCAGATGAC

CCAGTCTCCTTCTTCTCTTTCTGCTTCTGTTGGTGATCGTGTTACTATTACTTGTCGTG

CTTCTCAAGATGTTAATACTGCTGTTGCTTGGTATCAACAAAAACCTGGTAAAGCTC

CTAAACTTCTTATTTATTCTGCTTCTTTTCTTTATTCTGGTGTTCCTTCTCGTTTTTCTG

GTTCTCGTTCTGGTACTGATTTTACTCTTACTATTTCTTCTCTTCAACCTGAAGATTTT

GCTACTTATTATTGTCAACAACATTATACTACTCCTCCTACTTTTGGTCAAGGTACCA

AGGTGGAGATCAAACGTACGCATCATCACCATCACCAT
```

SEQ ID NO: 75
```
ATGGAGTTTGGGCTGAGCTGGGTTTTCCTCGTTGCTCTTTTTAGAGGTGTCCAGTGTG

ACATCCAGATGACCCAGAGCCCCAGCAGCCTGAGCGCCAGCGTGGGCGACAGGGTG

ACCATCACCTGCAGGGCCAGCCAGGACGTGAACACCGCCGTGGCCTGGTACCAGCA

GAAGCCCGGCAAGGCCCCCAAGCTGCTGATCTACAGCGCCAGCTTCCTGTACAGCG

GCGTGCCCAGCAGGTTCAGCGGCAGCAGGAGCGGCACCGACTTCACCCTGACCATC

AGCAGCCTGCAGCCCGAGGACTTCGCCACCTACTACTGCCAGCAGCACTACACCAC

CCCCCCCACCTTCGGCCAGGGCACCAAGGTGGAGATCAAGAGGACCGTGGCCGCCC

CCAGCGTGTTCATCTTCCCCCCCAGCGACGAGCAGCTGAAGAGCGGCACCGCCAGC

GTGGTGTGCCTGCTGAACAACTTCTACCCCAGGGAGGCCAAGGTGCAGTGGAAGGT

GGACAACGCCCTGCAGAGCGGCAACAGCCAGGAGAGCGTGACCGAGCAGGACAGC

AAGGACAGCACCTACAGCCTGAGCAGCACCCTGACCCTGAGCAAGGCCGACTACGA
```

```
GAAGCACAAGGTGTACGCCTGCGAGGTGACCCACCAGGGCCTGAGCAGCCCCGTGA

CCAAGAGCTTCAACAGGGGCGAGTGCGGAGGAGGTGGGTCTGGAGGTGGAGGATCT

GGTGGAGGTGGGTCTGGAGGAGGTGGATCCCCCGAGGAACCTCTAGTGGTGAAGGT

GGAAGAGGGAGATACCGCTGCCCTGTGGTGCCTCAAGGGGACCTCAGATGGCCCCA

CTCAGCAGCTGACCTGGTCTCGGGAGTCCCCGCTTAAACCCTTCTTAAAATACAGCC

TGGGGGTGCCAGGCCTGGGAGTGCACGTGAGGCCCGACGCCATCAGCGTGGTTATC

CGGAACGTCTCTCAACAGATGGGGGGCTTCTACCTGTGCCAGCCGGGGCCCCCCTCT

GAGAAGGCCTGGCAGCCTGGCTGGACAGTCAATGTGGAGGGCAGCGGGGAGCTGTT

CCGGTGGAATGTTTCGGACCTAGGTGGCCTGGGCTGTGGCCTGAAGAACAGGTCCTC

AGAGGGCCCCAGCTCCCCTTCCGGGAAGCTCATGAGCCCCAAGCTGTATGTGTGGG

CCAAAGACCGCCCTGAGATCTGGGAGGGAGAGCCTCCGTGTCTCCCACCGAGGGAC

AGCCTGAACCAGAGCCTCAGCCGGGACCTCACCGTTGCCCCTGGCTCCACACTCTGG

CTGTCCTGTGGGGTACCCCCTGACTCTGTGTCCAGGGGCCCCCTCTCCTGGACCCAT

GTGCACCCCAAGGGGCCTAAGTCATTGCTGAGCCTAGAGCTGAAGGACGATCGCCC

GGCCAGAGATATGTGGGTAATGGGCACGAGCCTGATGTTGCCCCGGGCCACAGCTC

AAGACGCTGGAAAGTGGTATTGTCACCGTGGCAACCTGACCATGTCATTCCACCTGG

AGATCACTGCTCGGCCATCTAGACATCATCACCATCACCAT

SEQ ID NO: 76
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCAAGGGTCCTAGCGTTTTTCCATTGGCTCCCAGCAGCA

AGAGCACCAGCGGCGGCACCGCCGCCCTGGGCTGCCTGGTGAAGGACTACTTCCCC

GAGCCCGTGACCGTGAGCTGGAACAGCGGCGCCCTGACCAGCGGCGTGCACACCTT

CCCCGCCGTGCTGCAGAGCAGCGGCCTGTACAGCCTGAGCAGCGTGGTGACCGTGC

CCAGCAGCAGCCTGGGCACCCAGACCTACATCTGCAACGTGAACCACAAGCCCAGC

AACACCAAGGTGGACAAGAAGGTGGAGCCCCCCAAGAGCTGCGACAAAACTCACA

CATGCCCACCGTGCCCAGCACCTGAACTCCTGGGGGACCGTCAGTCTTCCTCTTCC

CCCCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGACGG

CGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAACCATCT

CCAAAGCCAAAGGGCAGCCCCGAGAACCACAGGTGTACACCCTGCCCCCATCCCGA

GACGAGTTGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTACAAGA

CCACGCCTCCCGTGCTGGACTCCGACGGCTCCTTCTTCCTCTACAGCAAGCTCACCG
```

-continued

TGGACAAGAGCAGGTGGCAGCAGGGGAACGTCTTCTCATGCTCCGTGATGCACGAG

GCTCTGCACAACCACTACACGCAGAAGAGCCTCTCCCTGTCTCCGGGT

SEQ ID NO: 77
ATGGAGTTTGGGCTGAGCTGGGTTTTCCTCGTTGCTCTTTTTAGAGGTGTCCAGTGTC

AGATCGTGCTGAGCCAGAGCCCCGCCATCCTGAGCGCCAGCCCCGGCGAGAAGGTG

ACCATGACCTGCAGGGCCAGCAGCAGCGTGAGCTACATCCACTGGTTCCAGCAGAA

GCCCGGCAGCAGCCCCAAGCCCTGGATCTACGCCACCAGCAACCTGGCCAGCGGCG

TGCCCGTGAGGTTCAGCGGCAGCGGCAGCGGCACCAGCTACAGCCTGACCATCAGC

AGGGTGGAGGCCGAGGACGCCGCCACCTACTACTGCCAGCAGTGGACCAGCAACCC

CCCCACCTTCGGCGGCGGCACCAAGCTGGAGATCAAGAGGACCGTGGCCGCCCCCA

GCGTGTTCATCTTCCCCCCCAGCGACGAGCAGCTGAAGAGCGGCACCGCCAGCGTG

GTGTGCCTGCTGAACAACTTCTACCCCAGGGAGGCCAAGGTGCAGTGGAAGGTGGA

CAACGCCCTGCAGAGCGGCAACAGCCAGGAGAGCGTGACCGAGCAGGACAGCAAG

GACAGCACCTACAGCCTGAGCAGCACCCTGACCCTGAGCAAGGCCGACTACGAGAA

GCACAAGGTGTACGCCTGCGAGGTGACCCACCAGGGCCTGAGCAGCCCCGTGACCA

AGAGCTTCAACAGGGGCGAGTGCGGAGGAGGTGGGTCTGGAGGTGGAGGATCTGGT

GGAGGTGGGTCTGGAGGAGGTGGATCCCCCGAGGAACCTCTAGTGGTGAAGGTGGA

AGAGGGAGATACCGCTGCCCTGTGGTGCCTCAAGGGGACCTCAGATGGCCCCACTC

AGCAGCTGACCTGGTCTCGGGAGTCCCCGCTTAAACCCTTCTTAAAATACAGCCTGG

GGGTGCCAGGCCTGGGAGTGCACGTGAGGCCCGACGCCATCAGCGTGGTTATCCGG

AACGTCTCTCAACAGATGGGGGCTTCTACCTGTGCCAGCCGGGCCCCCCTCTGAG

AAGGCCTGGCAGCCTGGCTGGACAGTCAATGTGGAGGGCAGCGGGGAGCTGTTCCG

GTGGAATGTTTCGGACCTAGGTGGCCTGGGCTGTGGCCTGAAGAACAGGTCCTCAG

AGGGCCCCAGCTCCCCTTCCGGGAAGCTCATGAGCCCCAAGCTGTATGTGTGGGCCA

AAGACCGCCCTGAGATCTGGGAGGGAGAGCCTCCGTGTCTCCCACCGAGGGACAGC

CTGAACCAGAGCCTCAGCCGGGACCTCACCGTTGCCCCTGGCTCCACACTCTGGCTG

TCCTGTGGGGTACCCCCTGACTCTGTGTCCAGGGGCCCCCTCTCCTGGACCCATGTG

CACCCCAAGGGGCCTAAGTCATTGCTGAGCCTAGAGCTGAAGGACGATCGCCCGGC

CAGAGATATGTGGGTAATGGGCACGAGCCTGATGTTGCCCCGGGCCACAGCTCAAG

ACGCTGGAAAGTGGTATTGTCACCGTGGCAACCTGACCATGTCATTCCACCTGGAGA

TCACTGCTCGGCCATCTAGACATCATCACCATCACCAT

SEQ ID NO: 78
ATGGAGTTTGGGCTGAGCTGGGTTTTCCTCGTTGCTCTTTTTAGAGGTGTCCAGTGTC

AGGTCCAACTCCAACAGCCCGGTGCAGAGCTGGTGAAGCCCGGCGCCAGCGTGAAG

ATGAGCTGCAAGGCCAGCGGCTACACCTTCACCAGCTACAACATGCACTGGGTGAA

GCAGACCCCCGGCAGGGGCCTGGAGTGGATCGGCGCCATCTACCCCGGCAACGGCG

ACACCAGCTACAACCAGAAGTTCAAGGGCAAGGCCACCCTGACCGCCGACAAGAGC

AGCAGCACCGCCTACATGCAGCTGAGCAGCCTGACCAGCGAGGACAGCGCCGTGTA

CTACTGCGCCAGGAGCACCTACTACGGCGGCGACTGGTACTTCAACGTGTGGGGCG

CTGGCACTACGGTCACGGTGTCTGCTGCCTCCACGAAGGGACCCTCCGTGTTCCCTC

TTGCCCCAAGCAGCAAAAGCACTTCAGGTGGTACGGCCGCCCTGGGCTGCCTGGTG

-continued

AAGGACTACTTCCCCGAGCCCGTGACCGTGAGCTGGAACAGCGGCGCCCTGACCAG

CGGCGTGCACACCTTCCCCGCCGTGCTGCAGAGCAGCGGCCTGTACAGCCTGAGCA

GCGTGGTGACCGTGCCCAGCAGCAGCCTGGGCACCCAGACCTACATCTGCAACGTG

AACCACAAGCCCAGCAACACCAAGGTGGACAAGAAGGCCGAGCCCAAGAGCTGCG

ACAAAACTCACACATGCCCACCGTGCCCAGCACCTGAACTCCTGGGGGGACCGTCA

GTCTTCCTCTTCCCCCCAAAACCCAAGGACACCCTCATGATCTCCCGGACCCCTGAG

GTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCCCATCGA

GAAAACCATCTCCAAAGCCAAAGGGCAGCCCCGAGAACCACAGGTGTACACCCTGC

CCCCATCCCGAGACGAGTTGACCAAGAACCAGGTCAGCCTGACCTGCCTGGTCAAA

GGCTTCTATCCCAGCGACATCGCCGTGGAGTGGGAGAGCAATGGGCAGCCGGAGAA

CAACTACAAGACCACGCCTCCCGTGCTGGACTCCGACGGCTCCTTCTTCCTCTACAG

CAAGCTCACCGTGGACAAGAGCAGGTGGCAGCAGGGGAACGTCTTCTCATGCTCCG

TGATGCACGAGGCTCTGCACAACCACTACACGCAGAAGAGCCTCTCCCTGTCTCCGG

GT

SEQ ID NO: 79
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCAAGGGTCCTAGCGTTTTTCCATTGGCTCCCAGCAGCA

AGAGCACCAGCGGCGGCACCGCCGCCCTGGGCTGCCTGGTGAAGGACTACTTCCCC

GAGCCCGTGACCGTGAGCTGGAACAGCGGCGCCCTGACCAGCGGCGTGCACACCTT

CCCCGCCGTGCTGCAGAGCAGCGGCCTGTACAGCCTGAGCAGCGTGGTGACCGTGC

CCAGCAGCAGCCTGGGCACCCAGACCTACATCTGCAACGTGAACCACAAGCCCAGC

AACACCAAGGTGGACAAGAAGGTGGAGCCCCCAAGAGCTGCGACAAAACTCACA

CATGCCCACCGTGCCCAGCACCTGAACTCCTGGGGGGACCGTCAGTCTTCCTCTTCC

CCCCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGACGG

CGTGGAGGTGCATAATGCCAAGACAAAGCCGCGTGAGGAGCAGTACGCCAGCACGT

ACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTC

CAAAGCCAAAGGGCAGCCCCGAGAACCACAGGTGTACACCCTGCCCCCATCCCGAG

ACGAGTTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGAC

CACGCCTCCCGTGCTGGACTCCGACGGCTCCTTCTTCCTCTACAGCAAGCTCACCGT

-continued

GGACAAGAGCAGGTGGCAGCAGGGGAACGTCTTCTCATGCTCCGTGATGCACGAGG

CTCTGCACAACCACTACACGCAGAAGAGCCTCTCCCTGTCTCCGGGT

SEQ ID NO: 80
ATGGAGTTTGGGCTGAGCTGGGTTTTCCTCGTTGCTCTTTTTAGAGGTGTCCAGTGTC

AGGTCCAACTCCAACAGCCCGGTGCAGAGCTGGTGAAGCCCGGCGCCAGCGTGAAG

ATGAGCTGCAAGGCCAGCGGCTACACCTTCACCAGCTACAACATGCACTGGGTGAA

GCAGACCCCCGGCAGGGGCCTGGAGTGGATCGGCGCCATCTACCCCGGCAACGGCG

ACACCAGCTACAACCAGAAGTTCAAGGGCAAGGCCACCCTGACCGCCGACAAGAGC

AGCAGCACCGCCTACATGCAGCTGAGCAGCCTGACCAGCGAGGACAGCGCCGTGTA

CTACTGCGCCAGGAGCACCTACTACGGCGGCGACTGGTACTTCAACGTGTGGGGCG

CTGGCACTACGGTCACGGTGTCTGCTGCCTCCACGAAGGGACCCTCCGTGTTCCCTC

TTGCCCCAAGCAGCAAAAGCACTTCAGGTGGTACGGCCGCCCTGGGCTGCCTGGTG

AAGGACTACTTCCCCGAGCCCGTGACCGTGAGCTGGAACAGCGGCGCCCTGACCAG

CGGCGTGCACACCTTCCCCGCCGTGCTGCAGAGCAGCGGCCTGTACAGCCTGAGCA

GCGTGGTGACCGTGCCCAGCAGCAGCCTGGGCACCCAGACCTACATCTGCAACGTG

AACCACAAGCCCAGCAACACCAAGGTGGACAAGAAGGCCGAGCCCAAGAGCTGCG

ACAAAACTCACACATGCCCACCGTGCCCAGCACCTGAACTCCTGGGGGGACCGTCA

GTCTTCCTCTTCCCCCCAAAACCCAAGGACACCCTCATGATCTCCCGGACCCCTGAG

GTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGTGAGGAGCAGT

ACGCCAGCACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACACCCTGCC

CCCATCCCGTGACCAAGAACCAGGTCAGCCTGACCTGCCTGGTCAAAGGCTTCTATC

CCAGCGACATCGCCGTGGAGTGGGAGAGCAATGGGCAGCCGGAGAACAACTACAA

GACCACGCCTCCCGTGCTGGACTCCGACGGCTCCTTCTTCCTCTACAGCAAGCTCAC

CGTGGACAAGAGCAGGTGGCAGCAGGGGAACGTCTTCTCATGCTCCGTGATGCACG

AGGCTCTGCACAACCACTACACGCAGAAGAGCCTCTCCCTGTCTCCGGGTTAGTAAT

C

SEQ ID NO: 81
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

-continued

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAAGCGT

CTGGGGGAGGCTTGGTGCAGGCTGGGGGGTCTCTGAGACTCTCCTGTGCAGCCTCAG

GAAGCATCTTCGCTATTAATGAAATCAATCTTATGGGGTGGTACCGCCAGGCTCCAG

GGAAGCAGCGCGAGTTGGTCGCAGCTTGTGCTAGTGATGGCAACACATACTATGCG

GACTCCGTGAAGGGCCGATTCACCATCTCCAGAGACAACGCCGAGAAAACGGTGTA

TCTGCAGATGAACAACCTGAAACCTGACGACACAGCCGTCTATTACTGTGATGCGAA

TTCGAGGGGGAATTATTATTCGGGCCAGGGGACCCAGGTCACCGTTTCCTCAACTAG

TGGCCCGGGAGGCCAAGGCGCAGAACAAAAACTCATCTCAGAAGAGGATCTGGGC

GCACACCATCACCACCATCATGGCGCATCT

SEQ ID NO: 82
ATGGAGTTTGGGCTGAGCTGGGTTTTCCTCGTTGCTCTTTTTAGAGGTGTCCAGTGTC

AGGTGCAGCTGCAGGAGTCTGGGGGAGGCTTGGTGCAGGCTGGGGGGTCCCTTAGA

CTCTCCTGTGTAGCCTCTGGAAGCATCAGAAGTATCAATGTCATGGGCTGGTACCGC

CAGGCTCCAGGGAAGCAGCGCGAGTTGGTCGCAGCTTGTGCTAGTGATGGCAACAC

ATACTATGCGGACTCCGTGAAGGGCCGATTCACCATCTCCAGAGACAACGCCGAGA

AAACGGTGTATCTGCAGATGAACAACCTGAAACCTGACGACACAGCCGTCTATTACT

GTGATGCGAATTCGAGGGGGAATTATTATTCGGGCCAGGGGACCCAGGTCACCGTTT

CCTCAACTAGTGGCCCGGGAGGCCAAGGCGCAGGAGGAGGTGGGTCTGGAGGTGGA

GGATCTGGTGGAGGTGGGTCTGGAGGAGGTGGATCCCCCGAGGAACCTCTAGTGGT

GAAGGTGGAAGAGGGAGATACCGCTGCCCTGTGGTGCCTCAAGGGGACCTCAGATG

GCCCCACTCAGCAGCTGACCTGGTCTCGGGAGTCCCCGCTTAAACCCTTCTTAAAAT

ACAGCCTGGGGGTGCCAGGCCTGGGAGTGCACGTGAGGCCCGACGCCATCAGCGTG

GTTATCCGGAACGTCTCTCAACAGATGGGGGCTTCTACCTGTGCCAGCCGGGGCCC

CCCTCTGAGAAGGCCTGGCAGCCTGGCTGGACAGTCAATGTGGAGGGCAGCGGGA

GCTGTTCCGGTGGAATGTTTCGGACCTAGGTGGCCTGGGCTGTGGCCTGAAGAACAG

GTCCTCAGAGGGCCCCAGCTCCCCTTCCGGGAAGCTCATGAGCCCCAAGCTGTATGT

GTGGGCCAAAGACCGCCCTGAGATCTGGGAGGGAGAGCCTCCGTGTCTCCCACCGA

GGGACAGCCTGAACCAGAGCCTCAGCCGGGACCTCACCGTTGCCCCTGGCTCCACA

CTCTGGCTGTCCTGTGGGGTACCCCCTGACTCTGTGTCCAGGGGCCCCCTCTCCTGG

ACCCATGTGCACCCCAAGGGGCCTAAGTCATTGCTGAGCCTAGAGCTGAAGGACGA

TCGCCCGGCCAGAGATATGTGGGTAATGGGCACGAGCCTGATGTTGCCCCGGGCCA

CAGCTCAAGACGCTGGAAAGTGGTATTGTCACCGTGGCAACCTGACCATGTCATTCC

ACCTGGAGATCACTGCTCGGCCATCTAGACATCATCACCATCACCAT

SEQ ID NO: 83
ATGGAGTTTGGGCTGAGCTGGGTTTTCCTCGTTGCTCTTTTTAGAGGTGTCCAGTGTC

AGGTGCAGTTGCAGGCGTCTGGGGGAGGCTTGGTGCAGGCTGGGGGGTCTCTGAGA

CTCTCCTGTGCAGCCTCAGGAAGCATCTTCGCTATTAATGAAATCAATCTTATGGGG

-continued

TGGTACCGCCAGGCTCCAGGGAAGCAGCGCGAGTTGGTCGCAGCTTGTGCTAGTGA

TGGCAACACATACTATGCGGACTCCGTGAAGGGCCGATTCACCATCTCCAGAGACA

ACGCCGAGAAAACGGTGTATCTGCAGATGAACAACCTGAAACCTGACGACACAGCC

GTCTATTACTGTGATGCGAATTCGAGGGGAATTATTATTCGGGCCAGGGGACCCAG

GTCACCGTTTCCTCAACTAGTGGCCCGGGAGGCCAAGGCGCAGGAGGAGGTGGGTC

TGGAGGTGGAGGATCTGGTGGAGGTGGGTCTGGAGGAGGTGGATCCCCCGAGGAAC

CTCTAGTGGTGAAGGTGGAAGAGGGAGATACCGCTGCCCTGTGGTGCCTCAAGGGG

ACCTCAGATGGCCCCACTCAGCAGCTGACCTGGTCTCGGGAGTCCCCGCTTAAACCC

TTCTTAAAATACAGCCTGGGGGTGCCAGGCCTGGGAGTGCACGTGAGGCCCGACGC

CATCAGCGTGGTTATCCGGAACGTCTCTCAACAGATGGGGGCTTCTACCTGTGCCA

GCCGGGGCCCCCCTCTGAGAAGGCCTGGCAGCCTGGCTGGACAGTCAATGTGGAGG

GCAGCGGGGAGCTGTTCCGGTGGAATGTTTCGGACCTAGGTGGCCTGGGCTGTGGCC

TGAAGAACAGGTCCTCAGAGGGCCCCAGCTCCCCTTCCGGGAAGCTCATGAGCCCC

AAGCTGTATGTGTGGGCCAAAGACCGCCCTGAGATCTGGGAGGGAGAGCCTCCGTG

TCTCCCACCGAGGGACAGCCTGAACCAGAGCCTCAGCCGGGACCTCACCGTTGCCC

CTGGCTCCACACTCTGGCTGTCCTGTGGGGTACCCCCTGACTCTGTGTCCAGGGGCC

CCCTCTCCTGGACCCATGTGCACCCCAAGGGGCCTAAGTCATTGCTGAGCCTAGAGC

TGAAGGACGATCGCCCGGCCAGAGATATGTGGGTAATGGGCACGAGCCTGATGTTG

CCCCGGGCCACAGCTCAAGACGCTGGAAAGTGGTATTGTCACCGTGGCAACCTGAC

CATGTCATTCCACCTGGAGATCACTGCTCGGCCATCTAGACATCATCACCATCACCA

T

SEQ ID NO: 84

ATGGAGTTTGGGCTGAGCTGGGTTTTCCTCGTTGCTCTTTTTAGAGGTGTCCAGTGTC

AGGTGCAGCTGCAGGAGTCTGGGGGAGGCTTGGTGCAGGCTGGGGGGTCTCTGAGA

CTCTCCTGTGCAGCCTCAGGAAGCATCTTCGCTATTAATGAAATCAATCTTATGGGG

TGGTACCGCCAGGCTCCAGGGAAGCAGCGCGAGTTGGTCGCAGCTTGTGCTAGTGA

TGGCAACACATACTATGCGGACTCCGTGAAGGGCCGATTCACCATCTCCAGAGACA

ACGCCGAGAAAACGGTGTATCTGCAGATGAACAACCTGAAACCTGACGACACAGCC

GTCTATTACTGTGATGCGAATTCGAGGGGAATTATTATTCGGGCCAGGGGACCCAG

GTCACCGTCTCCTCAACTAGTGGCCCGGGAGGCCAAGGCGCAGGAGGAGGTGGGTC

TGGAGGTGGAGGATCTGGTGGAGGTGGGTCTGGAGGAGGTGGATCCCCCGAGGAAC

CTCTAGTGGTGAAGGTGGAAGAGGGAGATACCGCTGCCCTGTGGTGCCTCAAGGGG

ACCTCAGATGGCCCCACTCAGCAGCTGACCTGGTCTCGGGAGTCCCCGCTTAAACCC

TTCTTAAAATACAGCCTGGGGGTGCCAGGCCTGGGAGTGCACGTGAGGCCCGACGC

CATCAGCGTGGTTATCCGGAACGTCTCTCAACAGATGGGGGCTTCTACCTGTGCCA

GCCGGGGCCCCCCTCTGAGAAGGCCTGGCAGCCTGGCTGGACAGTCAATGTGGAGG

GCAGCGGGGAGCTGTTCCGGTGGAATGTTTCGGACCTAGGTGGCCTGGGCTGTGGCC

TGAAGAACAGGTCCTCAGAGGGCCCCAGCTCCCCTTCCGGGAAGCTCATGAGCCCC

AAGCTGTATGTGTGGGCCAAAGACCGCCCTGAGATCTGGGAGGGAGAGCCTCCGTG

TCTCCCACCGAGGGACAGCCTGAACCAGAGCCTCAGCCGGGACCTCACCGTTGCCC

CTGGCTCCACACTCTGGCTGTCCTGTGGGGTACCCCCTGACTCTGTGTCCAGGGGCC

-continued
CCCTCTCCTGGACCCATGTGCACCCCAAGGGGCCTAAGTCATTGCTGAGCCTAGAGC
TGAAGGACGATCGCCCGGCCAGAGATATGTGGGTAATGGGCACGAGCCTGATGTTG
CCCCGGGCCACAGCTCAAGACGCTGGAAAGTGGTATTGTCACCGTGGCAACCTGAC
CATGTCATTCCACCTGGAGATCACTGCTCGGCCATCTAGACATCATCACCATCACCA
T SEQ ID NO: 85
ATGGAGTTTGGGCTGAGCTGGGTTTTCCTCGTTGCTCTTTTTAGAGGTGTCCAGTGTC
AGGTGCAGCTGCAGGAGTCTGGGGGAGGCTTGGTGCAGGTCGGGGAGTCTCTGAGA
CTCTCCTGTGTAGTCTCTGGAGATACGAGGAGTATCAATCTCATGGGGTGGTACCGC
CAGGCTCCAGGGAAGCAGCGCGAGTTGGTCGCAGCTTGTGCTAGTGATGGCAACAC
ATACTATGCGGACTCCGTGAAGGGCCGATTCACCATCTCCAGAGACAACGCCGAGA
AAACGGTGTATCTGCAGATGAACAACCTGAAACCTGACGACACAGCCGTCTATTACT
GTGATGCGAATTCGAGGGGGAATTATTATTCGGGCCAGGGGACCCTGGTCACCGTCT
CCTCAACTAGTGGCCCGGGAGGCCAAGGCGCAGGAGGAGGTGGGTCTGGAGGTGGA
GGATCTGGTGGAGGTGGGTCTGGAGGAGGTGGATCCCCCGAGGAACCTCTAGTGGT
GAAGGTGGAAGAGGGAGATACCGCTGCCCTGTGGTGCCTCAAGGGGACCTCAGATG
GCCCCACTCAGCAGCTGACCTGGTCTCGGGAGTCCCCGCTTAAACCCTTCTTAAAAT
ACAGCCTGGGGGTGCCAGGCCTGGGAGTGCACGTGAGGCCCGACGCCATCAGCGTG
GTTATCCGGAACGTCTCTCAACAGATGGGGGGCTTCTACCTGTGCCAGCCGGGGCCC
CCCTCTGAGAAGGCCTGGCAGCCTGGCTGGACAGTCAATGTGGAGGGCAGCGGGGA
GCTGTTCCGGTGGAATGTTTCGGACCTAGGTGGCCTGGGCTGTGGCCTGAAGAACAG
GTCCTCAGAGGGCCCCAGCTCCCCTTCCGGGAAGCTCATGAGCCCCAAGCTGTATGT
GTGGGCCAAAGACCGCCCTGAGATCTGGGAGGGAGAGCCTCCGTGTCTCCCACCGA
GGGACAGCCTGAACCAGAGCCTCAGCCGGGACCTCACCGTTGCCCCTGGCTCCACA
CTCTGGCTGTCCTGTGGGGTACCCCCTGACTCTGTGTCCAGGGGCCCCCTCTCCTGG
ACCCATGTGCACCCCAAGGGGCCTAAGTCATTGCTGAGCCTAGAGCTGAAGGACGA
TCGCCCGGCCAGAGATATGTGGGTAATGGGCACGAGCCTGATGTTGCCCCGGGCCA
CAGCTCAAGACGCTGGAAAGTGGTATTGTCACCGTGGCAACCTGACCATGTCATTCC
ACCTGGAGATCACTGCTCGGCCATCTAGACATCATCACCATCACCAT SEQ ID NO: 86
ATGCCACCTCCTCGCCTCCTCTTCTTCCTCCTCTTCCTCACCCCCATGGAAGTCAGGC
CCGAGGAGCCCCTGGTGGTGAAGGTGGAGGAGGGCGACACCGCCGTGCTGCCCTGC
CTGAAGGGCACCAGCGACGGCCCCACCCAGCAGCTGACCTGGAGCAGGGAGAGCCC
CCTGAAGCCCTTCCTGAAGTACAGCCTGGGCGTGCCCGGCCTGGGCGTGCACGTGA
GGCCCGACGCCATCAGCGTGGTGATCAGGAACGTGAGCCAGCAGATGGGCGGCTTC
TACCTGTGCCAGCCCGGCCCCCCCAGCGAGAAGGCCTGGCAGCCCGGCTGGACCGT
GAACGTGGAGGGCAGCGGCGAGCTGTTCAGGTGGAACGTGAGCGACCTGGGCGGCC
TGGGCTGCGGCCTGAAGAACAGGAGCAGCGAGGGCCCCAGCAGCCCCAGCGGCAA
GCTGATGAGCCCCAAGCTGTACGTGTGGGCCAAGGACAGGCCCGAGATCTGGGAGG
GCGAGCCCCCCTGCCTGCCCCCCAGGGACAGCCTGAACCAGAGCCTGAGCCAGGAC
CTGACCATGGCCCCCGGCAGCACCCTGTGGCTGAGCTGCGGCGTGCCCCCCGACAG
CGTGAGCAGGGGCCCCCTGAGCTGGACCCACGTGCACCCCAAGGGCCCCAAGAGCC

```
TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGGAGGAG

GTGGGTCTGGAGGTGGAGGATCTGGTGGAGGTGGGTCTGGAGGAGGTGGATCCGAG

GTGCAGCTGGTGGAGTCTGGTGGTGGTCTTGTTCAACCTGGTGGTTCTCTTCGTCTTT

CTTGTGCTGCTTCTGGTTTTAATATTAAAGATACTTATATTCATTGGGTTCGTCAAGC

TCCTGGTAAAGGTCTTGAATGGGTTGCTCGTATTTATCCTACTAATGGTTATACTCGT

TATGCTGATTCTGTTAAAGGTCGTTTTACTATTTCTGCTGATACTTCTAAAAATACTG

CTTATCTTCAAATGAACTCTCTTCGTGCTGAAGATACTGCTGTTTATTATTGTTCTCG

TTGGGGTGGTGATGGTTTTTATGCTATGGATTATTGGGGTCAAGGTACTCTTGTCACC

GTCTCCTCAGCTAGCACCGGGGAGGTGGGTCTGGAGGTGGAGGATCTGGTGGAGG

TGGGTCTGACATCCAGATGACCCAGTCTCCTTCTTCTCTTTCTGCTTCTGTTGGTGAT

CGTGTTACTATTACTTGTCGTGCTTCTCAAGATGTTAATACTGCTGTTGCTTGGTATC

AACAAAAACCTGGTAAAGCTCCTAAACTTCTTATTTATTCTGCTTCTTTTCTTTATTCT

GGTGTTCCTTCTCGTTTTTCTGGTTCTCGTTCTGGTACTGATTTTACTCTTACTATTTC

TTCTCTTCAACCTGAAGATTTTGCTACTTATTATTGTCAACAACATTATACTACTCCT

CCTACTTTTGGTCAAGGTACCAAGGTGGAGATCAAACGTACGCATCATCACCATCAC

CAT

SEQ ID NO: 87
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGGTCTCAGGTCAAACTACAGGAGT

CAGGGGCTGAGCTGGTGAAGCCTGGGGCCTCAGTGAAGATGTCCTGCAAGGCTTCT

GGCTACACATTTACCAGTTACAATATGCACTGGGTAAAGCAGACACCTGGACAGGG

CCTGGAATGGATTGGAGCTATTTATCCAGGAAATGGTGATACTTCCTACAATCAGAA

GTTCAAAGGCAAGGCCACATTGACTGCAGACAAATCCTCCAGCACAGCCTACATGC

AGCTCAGCAGCCTGACATCTGAGGACTCTGCGGACTATTACTGTGCAAGATCTAATT
```

```
ATTACGGTAGTAGCTACTGGTTCTTCGATGTCTGGGGCCAAGGGACCACGGTCACCG

TCTCCTCAGCCAGCACCGGTGGAGGCGGTTCAGGCGGAGGTGGCTCTGGCGGTGGC

GGATCGGACATCGAGCTCACTCAGTCTCCAACAATCCTGTCTGCATCTCCAGGGGAG

AAGGTCACAATGACTTGCAGGGCCAGCTCAAGTGTAAATTACATGGACTGGTACCA

GAAGAAGCCAGGATCCTCCCCCAAACCCTGGATTTATGCCACATCCAACCTGGCTTC

TGGAGTCCCTGCTCGCTTCAGTGGCAGTGGGTCTGGGACCTCTTACTCTCTCACAATC

AGCAGAGTGGAGGCTGAAGATGCTGCCACTTATTACTGCCAGCAGTGGAGTTTTAAT

CCACCCACGTTCGGAGGGGGGACAAAGTTGGAAATAAAACGGGCCGCCGCTCATCA

TCACCATCACCAT
```

SEQ ID NO: 88

```
ATGCCACCTCCTCGCCTCCTCTTCTTCCTCCTCTTCCTCACCCCCATG

GAAGTCAGGCCCGAGGAGCCCCTGGTGGTGAAGGTGGAGGAGGGCGACACCGCCG

TGCTGCCCTGCCTGAAGGGCACCAGCGACGGCCCCACCCAGCAGCTGACCTGGAGC

AGGGAGAGCCCCCTGAAGCCCTTCCTGAAGTACAGCCTGGGCGTGCCCGGCCTGGG

CGTGCACGTGAGGCCCGACGCCATCAGCGTGGTGATCAGGAACGTGAGCCAGCAGA

TGGGCGGCTTCTACCTGTGCCAGCCCGGCCCCCCCAGCGAGAAGGCCTGGCAGCCC

GGCTGGACCGTGAACGTGGAGGGCAGCGGCGAGCTGTTCAGGTGGAACGTGAGCGA

CCTGGGCGGCCTGGGCTGCGGCCTGAAGAACAGGAGCAGCGAGGGCCCCAGCAGCC

CCAGCGGCAAGCTGATGAGCCCCAAGCTGTACGTGTGGGCCAAGGACAGGCCCGAG

ATCTGGGAGGGCGAGCCCCCCTGCCTGCCCCCCAGGGACAGCCTGAACCAGAGCCT

GAGCCAGGACCTGACCATGGCCCCCGGCAGCACCCTGTGGCTGAGCTGCGGCGTGC

CCCCCGACAGCGTGAGCAGGGGCCCCCTGAGCTGGACCCACGTGCACCCCAAGGGC

CCCAAGAGCCTGCTGAGCCTGGAGCTGAAGGACGACAGGCCCGCCAGGGAGATGAT

CGTGGACGAGACCGGCCTGCTGCTGCCCAGGGCCACCGCCCAGGACGCCGGCAAGT

GGTACTGCAGCAGGGGCAACGTGACCACCAGCTACCACCTGGAGATCACCGCCAGG

CCCGTGAAGGCCCACAGCGACCTGAGGACCGGCGGCTGGAAGGGAGGAGGTGGGT

CTGGAGGTGGAGGATCTGGTGGAGGTGGGTCTGGAGGAGGTGGGTCTGTGAGCGAC

GTGCCCAGGGACCTGGAGGTGGTGGCCGCCACCCCCACCAGCCTGCTGATCAGCTG

GTGCAGGCAGAGGTGCGCCGACAGCTACAGGATCACCTACGGCGAGACCGGCGGCA

ACAGCCCCGTGCAGGAGTTCACCGTGCCCGGCAGCTGGAAGACCGCCACCATCA

GCGGCCTGAAGCCCGGCGTGGACTACACCATCACCGTGTACGTGGTGACCCACTACT

ACGGCTGGGACAGGTACAGCCACCCCATCAGCATCAACTACAGGACCGAGATCGAC

AAGCCCAGCCAGCATCATCACCATCACCAT
```

SEQ ID NO: 89

```
ATGCCACCTCCTCGCCTCCTCTTCTTCCTCCTCTTCCTCACCCCCATGGAAGTCAGG

CCCGAGGAGCCCCTGGTGGTGAAGGTGGAGGAGGGCGACACCGCCGCCCTGTGGTG

CCTGAAGGGCACCAGCGACGGCCCCACCCAGCAGCTGACCTGGAGCAGGGAGAGCC

CCCTGAAGCCCTTCCTGAAGTACAGCCTGGGCGTGCCCGGCATGGGCGTGCACGTG

AGGCCCAACGCCGTGAGCCTGGTGATCAGCAACGTGAGCCAGCAGATGGGCGGCTT

CTACCTGTGCCAGCCCGGCCCCCCCAGCGAGAAGGCCTGGCAGCCCGGCTGGACCG

TGAACGTGGAGGGCAGCGGCGAGCTGTTCAGGTGGAACGTGAGCGACCTGGGCGGC
```

-continued
```
CTGGGCTGCGGCCTGAAGAACAGGAGCAGCGAGGGCCCCAGCAGCCCCAGCGGCA

AGCTGATGAGCCCCAAGCTGTACGTGTGGGCCAAGGACAGGCCCGAGATCTGGGAG

GGCGAGCCCCCTGCCTGCCCCCCAGGGACAGCCTGAACCAGAGCCTGAGCAGGGA

CATGACCGTGGCCCCCGGCAGCACCCTGTGGCTGAGCTGCGCGTGCCCCCCGACA

GCGTGAGCAGGGGCCCCCTGAGCTGGACCCACGTGCACCCCAAGGGCCCCAAGAGC

CTGCTGAGCCTGGAGCTGAAGGACGACAGGCCCGCCAGGGACATGTGGGTGATGGA

GACCGGCCTGGTGCTGCCCAGGGCCACCGCCCAGGACGCCGGCAAGTGGTACTGCC

ACAGGGGCAACGTGACCACCAGCTACCACCTGGAGATCACCGCCAGGCCCGTGAGC

GCCCACACCCCCTGAGGACCGGCGGCTGGAAGGGAGGAGGTGGGTCTGGAGGT

GGAGGATCTGGTGGAGGTGGGTCTGGAGGAGGTGGGTCTGTGAGCGACGTGCC

CAGGGACCTGGAGGTGGTGGCCGCCACCCCCACCAGCCTGCTGATCAGCTGGTGCA

GGCAGAGGTGCGCCGACAGCTACAGGATCACCTACGGCGAGACCGGCGGCAACAG

CCCCGTGCAGGAGTTCACCGTGCCCGGCAGCTGGAAGACCGCCACCATCA

GCGGCCTGAAGCCCGGCGTGGACTACACCATCACCGTGTACGTGGTGACCCACTACT

ACGGCTGGGACAGGTACAGCCACCCCATCAGCATCAACTACAGGACCGAGATCGAC

AAGCCCAGCCAGCATCATCACCATCACCAT
```

SEQ ID NO: 90
```
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCGGGGGAGGTGGGTCTGGAGGTGGAGGATCTGGTGGA

GGTGGGTCTGACATCCAGATGACCCAGTCTCCTTCTTCTCTTTCTGCTTCTGTTGGTG

ATCGTGTTACTATTACTTGTCGTGCTTCTCAAGATGTTAATACTGCTGTTGCTTGGTA

TCAACAAAAACCTGGTAAAGCTCCTAAACTTCTTATTTATTCTGCTTCTTTTCTTTATT

CTGGTGTTCCTTCTCGTTTTTCTGGTTCTCGTTCTGGTACTGATTTTACTCTTACTATT

TCTTCTCTTCAACCTGAAGATTTTGCTACTTATTATTGTCAACAACATTATACTACTC

CTCCTACTTTTGGTCAAGGTACCAAGGTGGAGATCAAACGTACGGGAGGAGGTGGG

TCTGGAGGTGGAGGATCTGGTGGAGGTGGGTCTGGAGGAGGTGGGTCTCCCGAGGA

GCCCCTGGTGGTGAAGGTGGAGGAGGGCGACACCGCCGTGCTGCCCTGCCTGAAGG

GCACCAGCGACGGCCCCACCCAGCAGCTGACCTGGAGCAGGGAGAGCCCCCTGAAG

CCCTTCCTGAAGTACAGCCTGGGCGTGCCCGGCCTGGGCGTGCACGTGAGGCCCGA

CGCCATCAGCGTGGTGATCAGGAACGTGAGCCAGCAGATGGGCGGCTTCTACCTGT

GCCAGCCCGCCCCCCAGCGAGAAGGCCTGGCAGCCCGGCTGGACCGTGAACGTG

GAGGGCAGCGGCGAGCTGTTCAGGTGGAACGTGAGCGACCTGGGCGGCCTGGGCTG

CGGCCTGAAGAACAGGAGCAGCGAGGGCCCCAGCAGCCCCAGCGGCAAGCTGATG

AGCCCCAAGCTGTACGTGTGGGCCAAGGACAGGCCCGAGATCTGGGAGGGCGAGCC

CCCCTGCCTGCCCCCCAGGGACAGCCTGAACCAGAGCCTGAGCCAGGACCTGACCA
```

-continued

TGGCCCCCGGCAGCACCCTGTGGCTGAGCTGCGGCGTGCCCCCCGACAGCGTGAGC

AGGGGCCCCCTGAGCTGGACCCACGTGCACCCCAAGGGCCCCAAGAGCCTGCTGAG

CCTGGAGCTGAAGGACGACAGGCCCGCCAGGGAGATGATCGTGGACGAGACCGGC

CTGCTGCTGCCCAGGGCCACCGCCCAGGACGCCGGCAAGTGGTACTGCAGCAGGGG

CAACGTGACCACCAGCTACCACCTGGAGATCACCGCCAGGCCCGTGAAGGCCCACA

GCGACCTGAGGACCGGCGGCTGGAAGCATCATCACCATCACCAT

SEQ ID NO: 91
ATGGAGTTTGGGCTGAGCTGGGTTTTCCTCGTTGCTCTTTTTAGAGGTGTCCAGTGTC

AGGTTCAGCTGGTGCAGTCTGGTGCTGAGGTGAAGAAGCCTGGTGCCTCAGTGAAG

GTCTCCTGCAAGGCTTCTGGTTACACATTCACTGACTACTACATGCACTGGGTGCGT

CAGGCCCCTGGTCAAGGTCTTGAGTGGATGGGTCGTGTTAATCCTAACCGGAGGGGT

ACTACCTACAACCAGAAATTCGAGGGCCGTGTCACCATGACCACAGACACATCCAC

GAGCACAGCCTACATGGAGCTGCGTAGCCTGCGTTCTGACGACACGGCCGTGTATTA

CTGTGCGCGTGCGAACTGGCTTGACTACTGGGGCCAGGGCACCACCGTCACCGTCTC

CTCCGCCTCCACCAAGGGCCCATCGGTCTTCCCGCTAGCGCCCTGCTCCAGGAGCAC

CTCCGAGAGCACAGCCGCCCTGGGCTGCCTGGTCAAGGACTACTTCCCCGAACCGGT

GACGGTGTCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCTCCAGCAG

CTTGGGCACGAAGACCTACACCTGCAACGTAGATCACAAGCCCAGCAACACCAAGG

TGGACAAGAGAGTTGAGTCCAAATATGGTCCCCCATGCCCACCCTGCCCAGCACCTG

AGGCCGCCGGGGACCATCAGTCTTCCTGTTCCCCCCAAAACCCAAGGACACTCTCA

TGATCTCCCGGACCCCTGAGGTCACGTGCGTGGTGGTGGACGTGAGCCAGGAAGAC

CCCGAGGTCCAGTTCAACTGGTACGTGGATGGCGTGGAGGTGCATAATGCCAAGAC

AAAGCCGCGGGAGGAGCAGTTCAACAGCACGTACCGTGTGGTCAGCGTCCTCACCG

TCCTGCACCAGGACTGGCTGAACGGCAAGGAGTACAAGTGCAAGGTCTCCAACAAA

GGCCTCCCGTCCTCCATCGAGAAAACCATCTCCAAAGCCAAAGGGCAGCCCCGAGA

GCCACAGGTGTACACCCTGCCCCCATCCCAGGAGGAGATGACCAAGAACCAGGTCA

GCCTGACCTGCCTGGTCAAAGGCTTCTACCCCAGCGACATCGCCGTGGAGTGGGAA

AGCAATGGGCAGCCGGAGAACAACTACAAGACCACGCCTCCCGTGCTGGACTCCGA

CGGCTCCTTCTTCCTCTACAGCAGGCTAACCGTGGACAAGAGCAGGTGGCAGGAGG

GGAATGTCTTCTCATGCTCCGTGATGCATGAGGCTCTGCACAACCACTACACACAGA

AGAGCCTCTCCCTGTCTCTGGGT

SEQ ID NO: 92
ATGGAGACAGACACACTCCTGCTATGGGTACTGCTGCTCTGGGTTCCAGGTTCCACT

GGTGACATCCAGATGACCCAGTCTCCATCCTCCCTGTCTGCATCTGTAGGAGACAGA

GTCACCATCACTTGCAGTGTCAGCTCAAGTGTATCCTCCATTTACTTGCACTGGTATC

AGCAGAAACCAGGGAAAGCCCCTAAGCTCCTGATCTATAGCACATCCAACTTGGCT

TCTGGAGTCCCATCAAGGTTCAGTGGCAGTGGATCTGGGACAGATTTCACTCTCACC

ATCAGCAGTCTGCAACCTGAAGATTTTGCAACTTACTACTGTCAAGTCTACAGTGGT

TACCCGCTCACGTTCGGCGGAGGGACCAAGGTGGAGATCAAACGAACTGTGGCTGC

ACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTG

-continued

```
GATAACGCCCTCCAATCGGGTAACTCCCAGGAGAGTGTCACAGAGCAGGACAGCAA

GGACAGCACCTACAGCCTCAGCAGCACCCTGACGCTGAGCAAAGCAGACTACGAGA

AACACAAAGTCTACGCCTGCGAAGTCACCCATCAGGGCCTGAGCTCGCCCGTCACA

AAGAGCTTCAACAGGGGAGAGTGCGACAAAACTCACACATCGCCACCGTCCCCAGC

ACCTGAAGCCGCGGGGGGACCGTCACCCGAGGAACCTCTAGTGGTGAAGGTGGAAG

AGGGAGATAACGCTGTGCTGCAGTGCCTCAAGGGGACCTCAGATGGCCCCACTCAG

CAGCTGACCTGGTCTCGGGAGTCCCCGCTTAAACCCTTCTTAAAACTCAGCCTGGGG

CTGCCAGGCCTGGGAATCCACATGAGGCCCCTGGCCATCTGGCTTTTCATCTTCAAC

GTCTCTCAACAGATGGGGGGCTTCTACCTGTGCCAGCCGGGGCCCCCCTCTGAGAAG

GCCTGGCAGCCTGGCTGGACAGTCAATGTGGAGGGCAGCGGGGAGCTGTTCCGGTG

GAATGTTTCGGACCTAGGTGGCCTGGGCTGTGGCCTGAAGAACAGGTCCTCAGAGG

GCCCCAGCTCCCCTTCCGGGAAGCTCATGAGCCCCAAGCTGTATGTGTGGGCC

AAAGACCGCCCTGAGATCTGGGAGGGAGAGCCTCCGTGTCTCCCACCGAGGGACAG

CCTGAACCAGAGCCTCAGCCAGGACCTCACCATGGCCCTGGCTCCACACTCT

GGCTGTCCTGTGGGGTACCCCCTGACTCTGTGTCCAGGGGCCCCCTCTC

CTGGACCCATGTGCACCCCAAGGGGCCTAAGTCATTGCTGAGCCTAGAGC

TGAAGGACGATCGCCCGGCCAGAGATATGTGGGTAATGGAGACGGGTCTG

TTGTTGCCCCGGGCCACAGCTCAAGACGCTGGAAAGTATTATTGTCACCG

TGGCAACCTGACCATGTCATTCCACCTGGAGATCACTGCTCGGCCA
```

SEQ ID NO: 93
```
ATGGAGTTTGGGCTGAGCTGGGTTTTCCTCGTTGCTCTTTTTAGAGGTGTCCAGTGTG

AGGTGCAGCTGGTGGAGTCTGGTGGTGGTCTTGTTCAACCTGGTGGTTCTCTTCGTCT

TTCTTGTGCTGCTTCTGGTTTTAATATTAAAGATACTTATATTCATTGGGTTCGTCAA

GCTCCTGGTAAAGGTCTTGAATGGGTTGCTCGTATTTATCCTACTAATGGTTATACTC

GTTATGCTGATTCTGTTAAAGGTCGTTTTACTATTTCTGCTGATACTTCTAAAAATAC

TGCTTATCTTCAAATGAACTCTCTTCGTGCTGAAGATACTGCTGTTTATTATTGTTCT

CGTTGGGGTGGTGATGGTTTTTATGCTATGGATTATTGGGGTCAAGGTACTCTTGTCA

CCGTCTCCTCAGCTAGCACCGGGGGAGGTGGGTCTGGAGGTGGAGGATCTGGTGGA

GGTGGGTCTGACATCCAGATGACCCAGTCTCCTTCTTCTCTTTCTGCTTCTGTTGGTG

ATCGTGTTACTATTACTTGTCGTGCTTCTCAAGATGTTAATACTGCTGTTGCTTGGTA

TCAACAAAAACCTGGTAAAGCTCCTAAACTTCTTATTTATTCTGCTTCTTTTCTTTATT

CTGGTGTTCCTTCTCGTTTTTCTGGTTCTCGTTCTGGTACTGATTTTACTCTTACTATT

TCTTCTCTTCAACCTGAAGATTTTGCTACTTATTATTGTCAACAACATTATACTACTC

CTCCTACTTTTGGTCAAGGTACCAAGGTGGAGATCAAACGTACGGACAAAACTCAC

ACATCGCCACCGTCCCCAGCACCTGAAGCCGCGGGGGGACCGTCACCCGAGGAACC

TCTAGTGGTGAAGGTGGAAGAGGGAGATAACGCTGTGCTGCAGTGCCTCAAGGGGA

CCTCAGATGGCCCCACTCAGCAGCTGACCTGGTCTCGGGAGTCCCCGCTTAAACCCT

TCTTAAAACTCAGCCTGGGGCTGCCAGGCCTGGGAATCCACATGAGGCCCCTGGCC

ATCTGGCTTTTCATCTTCAACGTCTCTCAACAGATGGGGGGCTTCTACCTGTGCCAGC

CGGGGCCCCCCTCTGAGAAGGCCTGGCAGCCTGGCTGGACAGTCAATGTGGAGGGC

AGCGGGGAGCTGTTCCGGTGGAATGTTTCGGACCTAGGTGGCCTGGGCTGTGGCCTG
```

-continued

AAGAACAGGTCCTCAGAGGGCCCCAGCTCCCCTTCCGGGAAGCTCATGAGCCCCAA

GCTGTATGTGTGGGCCAAAGACCGCCCTGAGATCTGGGAGGGAGAGCCTCCGTGTC

TCCCACCGAGGGACAGCCTGAACCAGAGCCTCAGCCAGGACCTCACCATGGCCCCT

GGCTCCACACTCTGGCTGTCCTGTGGGGTACCCCCTGACTCTGTGTCCAGGGGCCCC

CTCTCCTGGACCCATGTGCACCCCAAGGGGCCTAAGTCATTGCTGAGCCTAGAGCTG

AAGGACGATCGCCCGGCCAGAGATATGTGGGTAATGGAGACGGGTCTGTTGTTGCC

CCGGGCCACAGCTCAAGACGCTGGAAAGTATTATTGTCACCGTGGCAACCTGACCA

TGTCATTCCACCTGGAGATCACTGCTCGGCCATCTAGAGGGCCCCATCATCACCATC

ACCAT

SEQ ID NO: 94
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGCAGT

CTGGGGGAGGCTTGGTGCAGGCTGGGGGGTCTCTGAGACTCTCCTGTGCAGCCTCAG

GAAGCATCTTCGCTATTAATGAAATCAATCTTATGGGGTGGTACCGCCAGGCTCCAG

GGAAGCAGCGCGAGTTGGTCGCAGCTTGTGCTAGTGATGGCAACACATACTATGCG

GACTCCGTGAAGGGCCGATTCACCATCTCCAGAGACAACGCCGAGAAAACGGTGTA

TCTGCAGATGAACAACCTGAAACCTGACGACACAGCCGTCTATTACTGTGATGCGAA

TTCGAGGGGGAATTATTATTCGGGCCAGGGGACCCAGGTCACCGTTTCCTCAACTAG

TGGCCCGGGAGGCCAAGGCGCAGAACAAAAACTCATCTCAGAAGAGGATCTGGGC

GCACACCATCACCACCATCATGGCGCATCT

SEQ ID NO: 95
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

```
TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGGAGT

CTGGGGGAGGCTTGGTGCAACCTGGGGGGTCTCTGAGACTCTCCTGTGCAGCCTCTG

GATTCACCTTCAATAGCTATGCTATGACCTGGGTCCGCCAGGCTCCAGGAAAGGGGC

TCGAGTGGGTCTCAGACATTAATAGTGGTGGTGGTAGCACAAACTATGCAGACTCCG

TGAAGGGCCGCTTCACCATCTCCAGAGACAACGCCAAGAACACGCTGTATCTGCAA

ATGAACAGCCTGAAACCTGAGGACACGGCCGTGTATTACTGTGCGACCGAGCTTCG

GGGTAGTGACTACTACCGGGGTCCGATTCGTGAGTATGCCTATTGGGGCCAGGGGA

CCCTGGTCACCGTCTCCTCAACTAGTGGCCCGGGAGGCCAAGGCGCAGAACAAAAA

CTCATCTCAGAAGAGGATCTGGGCGCACACCATCACCACCATCATGGCGCATCT

SEQ ID NO: 96
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGGCGT

TTGGGGGAGGCTTGGTGCAGCCTGGGGGGTCTCTGAGACTCTCCTGCGTAGTTTCTG

GAACAATGTTCAGTGGCAAGGACGTGAACTGGCTTCGCCAGGCTCCAGGGAAGCAC

GTAGAGGTGGTCGCAACAGTTTCCAGTGATGGTGGCACAGATTATGCAGACTTCGTG
```

-continued

AAGGGCCGATTCACCATTTCCAGAGACGACGCCAAGAACACGGTGAATCTGCAAAT

GAACAGCCTGGAACCTGAGGACACAGCCAACTATATGTGCCATTTCTTATGGGCCG

TCACTACTGGGGCCAGGGGACCCAGGTCACCGTTTCCTCAACTAGTGGCCCGGGAG

GCCAAGGCGCAGAACAAAAACTCATCTCAGAAGAGGATCTGGGCGCACACCATCAC

CACCATCATGGCGCATCT

SEQ ID NO: 97
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCGGCAGCACCCTGTGGCTGAGCTGCGGCGTGCCCCCCGACAG

CGTGAGCAGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGGAGT

CTGGGGGAGGCTTGGTGCAGGCTGGGGGGTCCCTTAGACTCTCCTGTGTAGCCTCTG

GAAGCATCAGAAGTATCAATGTCATGGGCTGGTACCGCCAGGCTCCAGGGAAGCAG

CGCGAGTTGGTCGCAGCTTGTGCTAGTGATGGCAACACATACTATGCGGACTCCGTG

AAGGGCCGATTCACCATCTCCAGAGACAACGCCGAGAAAACGGTGTATCTGCAGAT

GAACAACCTGAAACCTGACGACACAGCCGTCTATTACTGTGATGCGAATTCGAGGG

GGAATTATTATTCGGGCCAGGGGACCCAGGTCACCGTTTCCTCAACTAGTGGCCCGG

GAGGCCAAGGCGCAGAACAAAAACTCATCTCAGAAGAGGATCTGGGCGCACACCAT

CACCACCATCATGGCGCATCT

SEQ ID NO: 98
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

-continued

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGTTGCAGCAGT

CTGGGGAGGCTTGGCGCAGACCGGGGGGTCTCTGATACTCTCCTGTGCAGCCTCAG

GAAGCATCTTCGCTATTAATGAAATCAATCTTATGGGGTGGTACCGCCAGGCTCCAG

GGAAGCAGCGCGAGTTGGTCGCAGCTTGTGCTAGTGATGGCAACACATACTATGCG

GACTCCGTGAAGGGCCGATTCACCATCTCCAGAGACAACGCCGAGAAAACGGTGTA

TCTGCAGATGAACAACCTGAAACCTGACGACACAGCCGTCTATTACTGTGATGCGAA

TTCGAGGGGGAATTATTATTCGGGCCAGGGGACCCAGGTCACCGTTTCCTCAACTAG

TGGCCCGGGAGGCCAAGGCGCAGAACAAAAACTCATCTCAGAAGAGGATCTGGGC

GCACACCATCACCACCATCATGGCGCATCT

SEQ ID NO: 99
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCCTGCCTGCCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCGCAGTGCAGCTGCAGGAGT

CTGGGGGAGGCTTGGTGCAGGCTGGGGGGTCTCTGAGACTCTCCTGTGCAGCCTCTG

GAAGCGACCGCAGTATCAATGTCATGAACTGGTACCGCCAGGCTCCAGGGAAGCAG

CGCGAGTTGGTCGCAGCGATTACTAGTGGTGGTACCACAAATTATGCACAGTCCGTG

AAGGGCCGAGTCACCATCTCCAGGGACAGCGCCAAGAACACGGTGTATCTACAGAT

GAACAGCCTGAAACCTGAGGACACAGCCGTCTATTTCTGTAAAGCAGATACGCGTT

GGGGTGGGATGTACTGGGGCCGGGGACCCAGGTCACCGTTTCCTCAACTAGTGGC

CCGGGAGGCCAAGGCGCAGAACAAAAACTCATCTCAGAAGAGGATCTGGGCGCAC

ACCATCACCACCATCATGGCGCATCT

SEQ ID NO: 100
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCCTGCCTGCCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGCAGT

CAGGGGGAGGATTGGTGCAGGCTGGGGGCTCTCTGACACTCTCCTGTGCAGCCACG

GGACGCACAATCGATAACGGCGCCATGGCCTGGTTCCGCCAGGCTCCAGGGAAGCA

GCGTGAGCTTGTAGCTGCCATTAACTGGAGTGGTGGTGCCACATTCTATACAGACTC

CGTCAAGTACCGTTTCACCATCTCCCGAGACAACGTCAGGCACACATTGGATCTGCA

AATGACCAGTCTGAAACCTGAGGACACGACCATTTATTTCTGTGCGTCTCGACGCGG

TGTGGACTTGAGGCGCAATAGTTACGAATATGACTACTGGGGCCGGGGGACCCTGG

TCACCGTCTCCTCAACTAGTGGCCCGGGAGGCCAAGGCGCAGAACAAAAACTCATC

TCAGAAGAGGATCTGGGCGCACACCATCACCACCATCATGGCGCATCT

SEQ ID NO: 101
ATGGAGTTTGGGCTGAGCTGGGTTTTCCTCGTTGCTCTTTTTAGAGGTGTCCAGTGTC

AGGTGCAGCTGCAGGAGTCTGGGGGAGGCTTGGTGCAACCTGGGGGGTCTCTGAGA

CTCTCCTGTGCAGCCTCTGGATTCACCTTCAATAGCTATGCTATGACCTGGGTCCGCC

AGGCTCCAGGAAAGGGGCTCGAGTGGGTCTCAGACATTAATAGTGGTGGTGGTAGC

ACAAACTATGCAGACTCCGTGAAGGGCCGCTTCACCATCTCCAGAGACAACGCCAA

GAACACGCTGTATCTGCAAATGAACAGCCTGAAACCTGAGGACACGGCCGTGTATT

ACTGTGCGACCGAGCTTCGGGGTAGTGACTACTACCGGGGTCCGATTCGTGAGTATG

CCTATTGGGGCCAGGGGACCCTGGTCACCGTCTCCTCAACTAGTGGCCCGGGAGGCC

AAGGCGCAGGAGGAGGTGGGTCTGGAGGTGGAGGATCTGGTGGAGGTGGGTCTGG

AGGAGGTGGATCCCCCGAGGAACCTCTAGTGGTGAAGGTGGAAGAGGGAGATACCG

CTGCCCTGTGGTGCCTCAAGGGGACCTCAGATGGCCCCACTCAGCAGCTGACCTGGT

CTCGGGAGTCCCCGCTTAAACCCTTCTTAAAATACAGCCTGGGGTGCCAGGCCTGG

GAGTGCACGTGAGGCCCGACGCCATCAGCGTGGTTATCCGGAACGTCTCTCAACAG

ATGGGGGGCTTCTACCTGTGCCAGCCGGGGCCCCCCTCTGAGAAGGCCTGGCAGCCT

```
GGCTGGACAGTCAATGTGGAGGGCAGCGGGGAGCTGTTCCGGTGGAATGTTTCGGA

CCTAGGTGGCCTGGGCTGTGGCCTGAAGAACAGGTCCTCAGAGGGCCCCAGCTCCC

CTTCCGGGAAGCTCATGAGCCCCAAGCTGTATGTGTGGGCCAAAGACCGCCCTGAG

ATCTGGGAGGGAGAGCCTCCGTGTCTCCCACCGAGGGACAGCCTGAACCAGAGCCT

CAGCCGGGACCTCACCGTTGCCCCTGGCTCCACACTCTGGCTGTCCTGTGGGGTACC

CCCTGACTCTGTGTCCAGGGGCCCCCTCTCCTGGACCCATGTGCACCCCAAGGGGCC

TAAGTCATTGCTGAGCCTAGAGCTGAAGGACGATCGCCCGGCCAGAGATATGTGGG

TAATGGGCACGAGCCTGATGTTGCCCCGGGCCACAGCTCAAGACGCTGGAAAGTGG

TATTGTCACCGTGGCAACCTGACCATGTCATTCCACCTGGAGATCACTGCTCGGCCA

TCTAGACATCATCACCATCACCAT
```

SEQ ID NO: 102
```
ATGGAGTTTGGGCTGAGCTGGGTTTTCCTCGTTGCTCTTTTTAGAGGTGTCCAGTGTC

AGGTGCAGTTGCAGCAGTCTGGGGGAGGCTTGGCGCAGACCGGGGGGTCTCTGATA

CTCTCCTGTGCAGCCTCAGGAAGCATCTTCGCTATTAATGAAATCAATCTTATGGGG

TGGTACCGCCAGGCTCCAGGGAAGCAGCGCGAGTTGGTCGCAGCTTGTGCTAGTGA

TGGCAACACATACTATGCGGACTCCGTGAAGGGCCGATTCACCATCTCCAGAGACA

ACGCCGAGAAAACGGTGTATCTGCAGATGAACAACCTGAAACCTGACGACACAGCC

GTCTATTACTGTGATGCGAATTCGAGGGGGAATTATTATTCGGGCCAGGGGACCCAG

GTCACCGTTTCCTCAACTAGTGGCCCGGGAGGCCAAGGCGCAGGAGGAGGTGGGTC

TGGAGGTGGAGGATCTGGTGGAGGTGGGTCTGGAGGAGGTGGATCCCCCGAGGAAC

CTCTAGTGGTGAAGGTGGAAGAGGGAGATACCGCTGCCCTGTGGTGCCTCAAGGGG

ACCTCAGATGGCCCCACTCAGCAGCTGACCTGGTCTCGGGAGTCCCCGCTTAAACCC

TTCTTAAAATACAGCCTGGGGGTGCCAGGCCTGGGAGTGCACGTGAGGCCCGACGC

CATCAGCGTGGTTATCCGGAACGTCTCTCAACAGATGGGGGCTTCTACCTGTGCCA

GCCGGGCCCCCCTCTGAGAAGGCCTGGCAGCCTGGCTGGACAGTCAATGTGGAGG

GCAGCGGGGAGCTGTTCCGGTGGAATGTTTCGGACCTAGGTGGCCTGGGCTGTGGCC

TGAAGAACAGGTCCTCAGAGGGCCCCAGCTCCCCTTCCGGGAAGCTCATGAGCCCC

AAGCTGTATGTGTGGGCCAAAGACCGCCCTGAGATCTGGGAGGGAGAGCCTCCGTG

TCTCCCACCGAGGGACAGCCTGAACCAGAGCCTCAGCCGGGACCTCACCGTTGCCC

CTGGCTCCACACTCTGGCTGTCCTGTGGGGTACCCCCTGACTCTGTGTCCAGGGGCC

CCCTCTCCTGGACCCATGTGCACCCCAAGGGGCCTAAGTCATTGCTGAGCCTAGAGC

TGAAGGACGATCGCCCGGCCAGAGATATGTGGGTAATGGGCACGAGCCTGATGTTG

CCCCGGGCCACAGCTCAAGACGCTGGAAAGTGGTATTGTCACCGTGGCAACCTGAC

CATGTCATTCCACCTGGAGATCACTGCTCGGCCATCTAGACATCATCACCATCACCA

T
```

SEQ ID NO: 103
```
ATGGAGTTTGGGCTGAGCTGGGTTTTCCTCGTTGCTCTTTTTAGAGGTGTCCAGTGTC

AGGTGCAGCTGCAGCAGTCAGGGGGAGGATTGGTGCAGGCTGGGGGCTCTCTGACA

CTCTCCTGTGCAGCCACGGGACGCACAATCGATAACGGCGCCATGGCCTGGTTCCGC

CAGGCTCCAGGGAAGCAGCGTGAGCTTGTAGCTGCCATTAACTGGAGTGGTGGTGC

CACATTCTATACAGACTCCGTCAAGTACCGTTTCACCATCTCCCGAGACAACGTCAG

GCACACATTGGATCTGCAAATGACCAGTCTGAAACCTGAGGACACGACCATTTATTT
```

-continued

CTGTGCGTCTCGACGCGGTGTGGACTTGAGGCGCAATAGTTACGAATATGACTACTG

GGGCCGGGGGACCCTGGTCACCGTCTCCTCAACTAGTGGCCCGGGAGGCCAAGGCG

CAGGAGGAGGTGGGTCTGGAGGTGGAGGATCTGGTGGAGGTGGGTCTGGAGGAGGT

GGATCCCCCGAGGAACCTCTAGTGGTGAAGGTGGAAGAGGGAGATACCGCTGCCCT

GTGGTGCCTCAAGGGGACCTCAGATGGCCCCACTCAGCAGCTGACCTGGTCTCGGG

AGTCCCCGCTTAAACCCTTCTTAAAATACAGCCTGGGGGTGCCAGGCCTGGGAGTGC

ACGTGAGGCCCGACGCCATCAGCGTGGTTATCCGGAACGTCTCTCAACAGATGGGG

GGCTTCTACCTGTGCCAGCCGGGGCCCCCCTCTGAGAAGGCCTGGCAGCCTGGCTGG

ACAGTCAATGTGGAGGGCAGCGGGGAGCTGTTCCGGTGGAATGTTTCGGACCTAGG

TGGCCTGGGCTGTGGCCTGAAGAACAGGTCCTCAGAGGGCCCCAGCTCCCCTTCCGG

GAAGCTCATGAGCCCCAAGCTGTATGTGTGGGCCAAAGACCGCCCTGAGATCTGGG

AGGGAGAGCCTCCGTGTCTCCCACCGAGGGACAGCCTGAACCAGAGCCTCAGCCGG

GACCTCACCGTTGCCCCTGGCTCCACACTCTGGCTGTCCTGTGGGGTACCCCCTGAC

TCTGTGTCCAGGGGCCCCCTCTCCTGGACCCATGTGCACCCCAAGGGGCCTAAGTCA

TTGCTGAGCCTAGAGCTGAAGGACGATCGCCCGGCCAGAGATATGTGGGTAATGGG

CACGAGCCTGATGTTGCCCCGGGCCACAGCTCAAGCGCTGGAAAGTGGTATTGTC

ACCGTGGCAACCTGACCATGTCATTCCACCTGGAGATCACTGCTCGGCCATCTAGAC

ATCATCACCATCACCAT

SEQ ID NO: 104
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCCAGGGACAGCCTGAACCAGAGCCTGAGCCAGGAC

CTGACCATGGCCCCCGGCAGCACCCTGTGGCTGAGCTGCGGCGTGCCCCCCGACAG

CGTGAGCAGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAGGAGT

CTGGGGGAGGCTTGGTGCAGGTCGGGGAGTCTCTGAGACTCTCCTGTGTAGTCTCTG

GAGATACGAGGAGTATCAATCTCATGGGGTGGTACCGCCAGGCTCCAGGGAAGCAG

CGCGAGTTGGTCGCAGCTTGTGCTAGTGATGGCAACACATACTATGCGGACTCCGTG

AAGGGCCGATTCACCATCTCCAGAGACAACGCCGAGAAAACGGTGTATCTGCAGAT

GAACAACCTGAAACCTGACGACACAGCCGTCTATTACTGTGATGCGAATTCGAGGG

-continued

```
GGAATTATTATTCGGGCCAGGGGACCCTGGTCACCGTCTCCTCAACTAGTGGCCCGG

GAGGCCAAGGCGCAGAACAAAAACTCATCTCAGAAGAGGATCTGGGCGCACACCAT

CACCACCATCATGGCGCATCT
```

SEQ ID NO: 105
```
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCGGCAGCACCCTGTGGCTGAGCTGCGGCGTGCCCCCCGACAG

CGTGAGCAGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGCAAGAGT

CTGGGGGAGGCTTGGTGCAGGCTGGGGGGTCTCTGAGACTCTCCTGTGCAGCCTCAG

GAAGCATCTTCGCTATTAATGAAATCAATCTTATGGGGTGGTACCGCCAGGCTCCAG

GGAAGCAGCGCGAGTTGGTCGCAGCTTGTGCTAGTGATGGCAACACATACTATGCG

GACTCCGTGAAGGGCCGATTCACCATCTCCAGAGACAACGCCGAGAAAACGGTGTA

TCTGCAGATGAACAACCTGAAACCTGACGACACAGCCGTCTATTACTGTGATGCGAA

TTCGAGGGGAATTATTATTCGGGCCAGGGGACCCAGGTCACCGTCTCCTCAACTAG

TGGCCCGGGAGGCCAAGGCGCAGAACAAAAACTCATCTCAGAAGAGGATCTGGGC

GCACACCATCACCACCATCATGGCGCATCT
```

SEQ ID NO: 106
```
ATGCCACCTCCTCGCCTCCTCTTCTTCCTCCTCTTCCTCACCCCCATGGAAGTCAGGC

CCGAGGAGCCCCTGGTGGTGAAGGTGGAGGAGGGCGACACCGCCGTGCTGCCCTGC

CTGAAGGGCACCAGCGACGGCCCCACCCAGCAGCTGACCTGGAGCAGGGAGAGCCC

CCTGAAGCCCTTCCTGAAGTACAGCCTGGGCGTGCCCGGCCTGGGCGTGCACGTGA

GGCCCGACGCCATCAGCGTGGTGATCAGGAACGTGAGCCAGCAGATGGGCGGCTTC

TACCTGTGCCAGCCCGGCCCCCCCAGCGAGAAGGCCTGGCAGCCCGGCTGGACCGT

GAACGTGGAGGGCAGCGGCGAGCTGTTCAGGTGGAACGTGAGCGACCTGGGCGGCC

TGGGCTGCGGCCTGAAGAACAGGAGCAGCGAGGGCCCCAGCAGCCCCAGCGGCAA

GCTGATGAGCCCCAAGCTGTACGTGTGGGCCAAGGACAGGCCCGAGATCTGGGAGG

GCGAGCCCCCTGCCTGCCCCCAGGGACAGCCTGAACCAGAGCCTGAGCCAGGAC

CTGACCATGGCCCCGGCAGCACCCTGTGGCTGAGCTGCGGCGTGCCCCCCGACAG
```

-continued

CGTGAGCAGGGGCCCCCTGAGCTGGACCCACGTGCACCCCAAGGGCCCCAAGAGCC

TGCTGAGCCTGGAGCTGAAGGACGACAGGCCCGCCAGGGAGATGATCGTGGACGAG

ACCGGCCTGCTGCTGCCCAGGGCCACCGCCCAGGACGCCGGCAAGTGGTACTGCAG

CAGGGGCAACGTGACCACCAGCTACCACCTGGAGATCACCGCCAGGCCCGTGAAGG

CCCACAGCGACCTGAGGACCGGCGGCTGGAAGGGAGGAGGTGGGTCTGGAGGTGG

AGGATCTGGTGGAGGTGGGTCTGGAGGAGGTGGATCCCAGGTGCAGCTGGTGGAGT

CTGGGGGAGGCTTGGTGCAGGCTGGGGGGTCTCTGAGACTCTCCTGTGCAGCCTCAG

GAAGCATCTTCGCTATTAATGAAATCAATCTTATGGGGTGGTACCGCCAGGCTCCAG

GGAAGCAGCGCGAGTTGGTCGCAGCTTGTGCTAGTGATGGCAACACATACTATGCG

GACTCCGTGAAGGGCCGATTCACCATCTCCAGAGACAACGCCGAGAAAACGGTGTA

TCTGCAGATGAACAACCTGAAACCTGACGACACAGCCGTCTATTACTGTGATGCGAA

TTCGAGGGGGAATTATTATTCGGGCCAGGGGACCCTGGTCACCGTCTCCTCAACTAG

TGGCCCGGGAGGCCAAGGCGCAGAACAAAAACTCATCTCAGAAGAGGATCTGGGC

GCACACCATCACCACCATCATGGCGCATCT

SEQ ID NO: 107
ATGCCACCTCCTCGCCTCCTCTTCTTCCTCCTCTTCCTCACCCCCATGGAAGTCAGGC

CCGAGGAACCTCTAGTGGTGAAGGTGGAAGAGGGAGATAACGCTGTGCTGCAGTGC

CTCAAGGGGACCTCAGATGGCCCCACTCAGCAGCTGACCTGGTCTCGGGAGTCCCC

GCTTAAACCCTTCTTAAAACTCAGCCTGGGGCTGCCAGGCCTGGGAATCCACATGAG

GCCCCTGGCCATCTGGCTTTTCATCTTCAACGTCTCTCAACAGATGGGGGGCTTCTAC

CTGTGCCAGCCGGGGCCCCCCTCTGAGAAGGCCTGGCAGCCTGGCTGGACAGTCAA

TGTGGAGGGCAGCGGGGAGCTGTTCCGGTGGAATGTTTCGGACCTAGGTGGCCTGG

GCTGTGGCCTGAAGAACAGGTCCTCAGAGGGCCCCAGCTCCCCTTCCGGGAAGCTC

ATGAGCCCCAAGCTGTATGTGTGGGCCAAAGACCGCCCTGAGATCTGGGAGGGAGA

GCCTCCGTGTCTCCCACCGAGGGACAGCCTGAACCAGAGCCTCAGCCAGGACCTCA

CCATGGCCCCTGGCTCCACACTCTGGCTGTCCTGTGGGGTACCCCCTGACTCTGTGTC

CAGGGGCCCCCTCTCCTGGACCCATGTGCACCCCAAGGGGCCTAAGTCATTGCTGAG

CCTAGAGCTGAAGGACGATCGCCCGGCCAGAGATATGTGGGTAATGGAGACGGGTC

TGTTGTTGCCCCGGGCCACAGCTCAAGACGCTGGAAAGTATTATTGTCACCGTGGCA

ACCTGACCATGTCATTCCACCTGGAGATCACTGCTCGGCCAGGAGGAGGTGGGTCTG

GAGGTGGAGGATCTGGTGGAGGTGGGTCTGGAGGAGGTGGGTCTGACATGGCCCAG

GTGCAGCTGCAGGAGAGCGGCCCCGGCCTGGTGAAGCCCAGCGAGACCCTGAGCCT

GACCTGCGTGGTGAGCGGCGGCAGCATCAGCAGCAGCAACTGGTGGAGCTGGGTGA

GGCAGCCCCCGGCAAGGGCCTGGAGTGGATCGGCGAGATCTACCACAGCGGCAGC

CCCGACTACAACCCCAGCCTGAAGAGCAGGGTGACCATCAGCGTGGACAAGAGCAG

GAACCAGTTCAGCCTGAAGCTGAGCAGCGTGACCGCCGCCGACACCGCCGTGTACT

ACTGCGCCAAGGTGAGCACCGGCGGCTTCTTCGACTACTGGGGCCAGGGCACCCTG

GTGACCGTGAGCAGCGGCGGCGGCGGCAGCGGCGGCGGCGGCAGCGGCGGCGGCG

GCAGCGAGATCGAGCTGACCCAGAGCCCCAGCAGCCTGAGCGCCAGCGTGGGCGAC

AGGGTGACCATCACCTGCAGGGCCAGCCAGAGCATCAGCAGCTACCTGAACTGGTA

CCAGCAGAAGCCCGGCAAGGCCCCCAAGCTGCTGATCTACGCCGCCAGCAGCCTGC

```
AGAGCGGCGTGCCCAGCAGGTTCAGCGGCAGCGGCAGCGGCACCGACTTCACCCTG
ACCATCAGCAGCCTGCAGCCCGAGGACTTCGCCACCTACTACTGCCAGCAGAGCTA
CAGCACCCCCCCCACCTTCGGCCCCGGCACCAAGGTGGAGATCAAGAGGACCCACC
ACCACCACCACCAC
                                             SEQ ID NO: 108
ATGGAGTTTGGGCTGAGCTGGGTTTTCCTCGTTGCTCTTTTTAGAGGTGTCCAGTGTG
ACATGGCCCAGGTGCAGCTGCAGGAGAGCGGCCCCGGCCTGGTGAAGCCCAGCGAG
ACCCTGAGCCTGACCTGCGTGGTGAGCGGCGGCAGCATCAGCAGCAGCAACTGGTG
GAGCTGGGTGAGGCAGCCCCCGGCAAGGGCCTGGAGTGGATCGGCGAGATCTACC
ACAGCGGCAGCCCCGACTACAACCCCAGCCTGAAGAGCAGGGTGACCATCAGCGTG
GACAAGAGCAGGAACCAGTTCAGCCTGAAGCTGAGCAGCGTGACCGCCGCCGACAC
CGCCGTGTACTACTGCGCCAAGGTGAGCACCGGCGGCTTCTTCGACTACTGGGGCCA
GGGCACCCTGGTGACCGTGAGCAGCGGCGGCGGCGGCAGCGGCGGCGGCGGCAGC
GGCGGCGGCGGCAGCGAGATCGAGCTGACCCAGAGCCCCAGCAGCCTGAGCGCCA
GCGTGGGCGACAGGGTGACCATCACCTGCAGGGCCAGCCAGAGCATCAGCAGCTAC
CTGAACTGGTACCAGCAGAAGCCCGGCAAGGCCCCCAAGCTGCTGATCTACGCCGC
CAGCAGCCTGCAGAGCGGCGTGCCCAGCAGGTTCAGCGGCAGCGGCAGCGGCACCG
ACTTCACCCTGACCATCAGCAGCCTGCAGCCCGAGGACTTCGCCACCTACTACTGCC
AGCAGAGCTACAGCACCCCCCCCACCTTCGGCCCCGGCACCAAGGTGGAGATCAAG
AGGACCGGCGGCGGAGGATCTGGCGGAGGTGGAAGCGGAGGCGGAGGAAGCGGTG
GCGGCGGATCTCAGGTGCAGCTGCAGGAGTCTGGGGGAGGCTTGGTGCAGGCTGGG
GGGTCCCTTAGACTCTCCTGTGTAGCCTCTGGAAGCATCAGAAGTATCAATGTCATG
GGCTGGTACCGCCAGGCTCCAGGGAAGCAGCGCGAGTTGGTCGCAGCTTGTGCTAG
TGATGGCAACACATACTATGCGGACTCCGTGAAGGGCCGATTCACCATCTCCAGAG
ACAACGCCGAGAAAACGGTGTATCTGCAGATGAACAACCTGAAACCTGACGACACA
GCCGTCTATTACTGTGATGCGAATTCGAGGGGGAATTATTATTCGGGCCAGGGGACC
CAGGTCACCGTTTCCTCAACTAGTGGCCCGGGAGGCCAAGGTGCAGGAGGAGGGGG
GTCTGGGGGTGGAGGATCTGGTGGAGGTGGGTCTGGAGGAGGTGGATCCCCCGAGG
AACCTCTAGTGGTGAAGGTGGAAGAGGGAGATACCGCTGCCCTGTGGTGCCTCAAG
GGGACCTCAGATGGCCCCACTCAGCAGCTGACCTGGTCTCGGGAGTCCCCGCTTAAA
CCCTTCTTAAAATACAGCCTGGGGGTGCCAGGCCTGGGAGTGCACGTGAGGCCCGA
CGCCATCAGCGTGGTTATCCGGAACGTCTCTCAACAGATGGGGGGCTTCTACCTGTG
CCAGCCGGGGCCCCCCTCTGAGAAGGCCTGGCAGCCTGGCTGGACAGTCAATGTGG
AGGGCAGCGGGGAGCTGTTCCGGTGGAATGTTTCGGACCTAGGTGGCCTGGGCTGT
GGCCTGAAGAACAGGTCCTCAGAGGGCCCCAGCTCCCCTTCCGGGAAGCTCATGAG
CCCCAAGCTGTATGTGTGGGCCAAAGACCGCCCTGAGATCTGGGAGGGAGAGCCTC
CGTGTCTCCCACCGAGGGACAGCCTGAACCAGAGCCTCAGCCGGGACCTCACCGTT
GCCCCTGGCTCCACACTCTGGCTGTCCTGTGGGGTACCCCCTGACTCTGTGTCCAGG
GGCCCCCTCTCCTGGACCCATGTGCACCCCAAGGGGCCTAAGTCATTGCTGAGCCTA
GAGCTGAAGGACGATCGCCCGGCCAGAGATATGTGGGTAATGGGCACGAGCCTGAT
GTTGCCCCGGGCCACAGCTCAAGACGCTGGAAAGTGGTATTGTCACCGTGGCAACC
```

-continued
TGACCATGTCATTCCACCTGGAGATCACTGCTCGGCCATCTAGACATCATCACCATC

ACCAT

SEQ ID NO: 109
ATGAGGCTTCTGGTGCTTCTTTGGGGTTGCTTGCTGTTGCCCGGTTACGAAGCAGAC

ATCCAGATGACACAGACTACATCCTCCCTGTCTGCCTCTCTGGGAGACAGAGTCACC

ATCAGTTGCAGGGCAAGTCAGGACATTAGTAAATATTTAAATTGGTATCAGCAGAA

ACCAGATGGAACTGTTAAACTCCTGATCTACCATACATCAAGATTACACTCAGGAGT

CCCATCAAGGTTCAGTGGCAGTGGGTCTGGAACAGATTATTCTCTCACCATTAGCAA

CCTGGAGCAAGAAGATATTGCCACTTACTTTTGCCAACAAGGTAATACGCTTCCGTA

CACGTTCGGAGGGGGGACTAAGTTGGAAATAACAGGAGGCGGCGGGTCTGGAGGTG

GAGGATCTGGTGGTGGCGGGTCTGGAGGCGGCGGGTCTGAGGTGAAACTGCAGGAG

TCAGGACCTGGCCTGGTGGCGCCCTCACAGAGCCTGTCCGTCACATGCACTGTCTCA

GGGGTCTCATTACCCGACTATGGTGTAAGCTGGATTCGCCAGCCTCCACGAAAGGGT

CTGGAGTGGCTGGGAGTAATATGGGGTAGTGAAACCACATACTACAACTCAGCTCT

CAAATCCAGACTGACCATCATCAAGGACAACTCCAAGAGCCAAGTTTTCTTAAAAAT

GAACAGTCTGCAAACTGATGACACAGCCATTTACTACTGTGCCAAACATTATTACTA

CGGTGGTAGCTATGCTATGGACTACTGGGGTCAAGGAACCTCAGTCACCGTCTCCTC

AGACTACAAAGACGATGACGACAAGATTGAAGTTATGTATCCTCCTCCTTACCTAGA

CAATGAGAAGAGCAATGGAACCATTATCCATGTGAAAGGGAAACACCTTTGTCCAA

GTCCCCTATTTCCCGGACCTTCTAAGCCCTTTTGGGTGCTGGTGGTGGTTGGTGGAGT

CCTGGCTTGCTATAGCTTGCTAGTAACAGTGGCCTTTATTATTTTCTGGGTCCGCAGT

AAGAGGAGCAGGCTCCTGCACAGTGACTACATGAACATGACTCCCCGCCGCCCCGG

GCCCACCCGCAAGCATTACCAGCCCTATGCCCCACCACGCGACTTCGCAGCCTATCG

CTCCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAGGGGCA

CGATGGCCTTTACCAGGGTCTCAGTACAGCCACCAAGGACACCTACGACGCCCTTCA

CATGCAAGCCCTGCCCCCTCGCCGCGCGAAACGCAGCGGCAGCGGCGCGACCAACT

TTAGCCTGCTGAAACAGGCGGGCGATGTGGAAGAAAACCCGGGCCCGATGCCACCT

CCTCGCCTCCTCTTCTTCCTCCTCTTCCTCACCCCCATGGAAGTCAGGCCCGAGGAAC

CTCTAGTGGTGAAGGTGGAAGAGGGAGATAACGCTGTGCTGCAGTGCCTCAAGGGG

ACCTCAGATGGCCCCACTCAGCAGCTGACCTGGTCTCGGGAGTCCCCGCTTAAACCC

TTCTTAAAACTCAGCCTGGGGCTGCCAGGCCTGGGAATCCACATGAGGCCCCTGGCC

ATCTGGCTTTTCATCTTCAACGTCTCTCAACAGATGGGGGGCTTCTACCTGTGCCAGC

CGGGGCCCCCCTCTGAGAAGGCCTGGCAGCCTGGCTGGACAGTCAATGTGGAGGGC

AGCGGGGAGCTGTTCCGGTGGAATGTTTCGGACCTAGGTGGCCTGGGCTGTGGCCTG

AAGAACAGGTCCTCAGAGGGCCCCAGCTCCCCTTCCGGGAAGCTCATGAGCCCCAA

-continued

GCTGTATGTGTGGGCCAAAGACCGCCCTGAGATCTGGGAGGGAGAGCCTCCGTGTC

TCCCACCGAGGGACAGCCTGAACCAGAGCCTCAGCCAGGACCTCACCATGGCCCCT

GGCTCCACACTCTGGCTGTCCTGTGGGGTACCCCCTGACTCTGTGTCCCGCGGCCCC

CTCTCCTGGACCCATGTGCACCCCAAGGGGCCTAAGTCATTGCTGAGCCTAGAGCTG

AAGGACGATCGCCCGGCCAGAGATATGTGGGTAATGGAGACGGGTCTGTTGTTGCC

CCGGGCCACAGCTCAAGACGCTGGAAAGTATTATTGTCACCGTGGCAACCTGACCA

TGTCATTCCACCTGGAGATCACTGCTCGGCCTGGCGGCGGCGGGTCTGGAGGTGGAG

GATCTGGTGGTGGCGGGTCTGGTGGCGGCGGGTCTGACATGGCCCAGGTGCAGCTG

CAGGAGAGCGGCCCCGGCCTGGTGAAGCCCAGCGAGACCCTGAGCCTGACCTGCGT

GGTGAGCGGCGGCAGCATCAGCAGCAGCAACTGGTGGAGCTGGGTGAGGCAGCCCC

CCGGCAAGGGCCTGGAGTGGATCGGCGAGATCTACCACAGCGGCAGCCCCGACTAC

AACCCCAGCCTGAAGAGCAGGGTGACCATCAGCGTGGACAAGAGCAGGAACCAGTT

CAGCCTGAAGCTGAGCAGCGTGACCGCCGCCGACACCGCCGTGTACTACTGCGCCA

AGGTGAGCACCGGCGGCTTCTTCGACTACTGGGGCCAGGGCACCCTGGTGACCGTG

AGCAGCGGCGGCGGCGGCAGCGGCGGCGGCGGCAGCGGCGGCGGCGGCAGCGAGA

TCGAGCTGACCCAGAGCCCCAGCAGCCTGAGCGCCAGCGTGGGCGACAGGGTGACC

ATCACCTGCAGGGCCAGCCAGAGCATCAGCAGCTACCTGAACTGGTACCAGCAGAA

GCCCGGCAAGGCCCCCAAGCTGCTGATCTACGCCGCCAGCAGCCTGCAGAGCGGCG

TGCCCAGCAGGTTCAGCGGCAGCGGCAGCGGCACCGACTTCACCCTGACCATCAGC

AGCCTGCAGCCCGAGGACTTCGCCACCTACTACTGCCAGCAGAGCTACAGCACCCC

CCCCACCTTCGGCCCCGGCACCAAGGTGGAGATCAAGAGGACCCACCACCACCACC

ACCAC

SEQ ID NO: 110
ATGAGGCTTCTGGTGCTTCTTTGGGGTTGCTTGCTGTTGCCCGGTTACGAAGCAGAC

ATCCAGATGACACAGACTACATCCTCCCTGTCTGCCTCTCTGGGAGACAGAGTCACC

ATCAGTTGCAGGGCAAGTCAGGACATTAGTAAATATTTAAATTGGTATCAGCAGAA

ACCAGATGGAACTGTTAAACTCCTGATCTACCATACATCAAGATTACACTCAGGAGT

CCCATCAAGGTTCAGTGGCAGTGGGTCTGGAACAGATTATTCTCTCACCATTAGCAA

CCTGGAGCAAGAAGATATTGCCACTTACTTTTGCCAACAAGGTAATACGCTTCCGTA

CACGTTCGGAGGGGGGACTAAGTTGGAAATAACAGGAGGCGGCGGGTCTGGAGGTG

GAGGATCTGGTGGTGGCGGGTCTGGAGGCGGCGGGTCTGAGGTGAAACTGCAGGAG

TCAGGACCTGGCCTGGTGGCGCCCTCACAGAGCCTGTCCGTCACATGCACTGTCTCA

GGGGTCTCATTACCCGACTATGGTGTAAGCTGGATTCGCCAGCCTCCACGAAAGGGT

CTGGAGTGGCTGGGAGTAATATGGGGTAGTGAAACCACATACTACAACTCAGCTCT

CAAATCCAGACTGACCATCATCAAGGACAACTCCAAGAGCCAAGTTTTCTTAAAAAT

GAACAGTCTGCAAACTGATGACACAGCCATTTACTACTGTGCCAAACATTATTACTA

CGGTGGTAGCTATGCTATGGACTACTGGGGTCAAGGAACCTCAGTCACCGTCTCCTC

AGACTACAAAGACGATGACGACAAGATTGAAGTTATGTATCCTCCTCCTTACCTAGA

CAATGAGAAGAGCAATGGAACCATTATCCATGTGAAAGGGAAACACCTTTGTCCAA

GTCCCCTATTTCCCGGACCTTCTAAGCCCTTTTGGGTGCTGGTGGTGGTTGGTGGAGT

CCTGGCTTGCTATAGCTTGCTAGTAACAGTGGCCTTTATTATTTTCTGGGTCCGCAGT

-continued

```
AAGAGGAGCAGGCTCCTGCACAGTGACTACATGAACATGACTCCCCGCCGCCCCGG

GCCCACCCGCAAGCATTACCAGCCCTATGCCCCACCACGCGACTTCGCAGCCTATCG

CTCCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAGGGGCA

CGATGGCCTTTACCAGGGTCTCAGTACAGCCACCAAGGACACCTACGACGCCCTTCA

CATGCAAGCCCTGCCCCCTCGCCGCGCGAAACGCAGCGGCAGCGGCGCGACCAACT

TTAGCCTGCTGAAACAGGCGGGCGATGTGGAAGAAAACCCGGGCCCGATGCCACCT

CCTCGCCTCCTCTTCTTCCTCCTCTTCCTCACCCCCATGGAAGTCAGGCCCGAGGAAC

CTCTAGTGGTGAAGGTGGAAGAGGGAGATAACGCTGTGCTGCAGTGCCTCAAGGGG

ACCTCAGATGGCCCCACTCAGCAGCTGACCTGGTCTCGGGAGTCCCCGCTTAAACCC

TTCTTAAAACTCAGCCTGGGGCTGCCAGGCCTGGGAATCCACATGAGGCCCCTGGCC

ATCTGGCTTTTCATCTTCAACGTCTCTCAACAGATGGGGGGCTTCTACCTGTGCCAGC

CGGGGCCCCCCTCTGAGAAGGCCTGGCAGCCTGGCTGGACAGTCAATGTGGAGGGC

AGCGGGGAGCTGTTCCGGTGGAATGTTTCGGACCTAGGTGGCCTGGGCTGTGGCCTG

AAGAACAGGTCCTCAGAGGGCCCCAGCTCCCCTTCCGGGAAGCTCATGAGCCCCAA

GCTGTATGTGTGGGCCAAAGACCGCCCTGAGATCTGGGAGGGAGAGCCTCCGTGTC

TCCCACCGAGGGACAGCCTGAACCAGAGCCTCAGCCAGGACCTCACCATGGCCCCT

GGCTCCACACTCTGGCTGTCCTGTGGGGTACCCCCTGACTCTGTGTCCCGCGGCCCC

CTCTCCTGGACCCATGTGCACCCCAAGGGGCCTAAGTCATTGCTGAGCCTAGAGCTG

AAGGACGATCGCCCGGCCAGAGATATGTGGGTAATGGAGACGGGTCTGTTGTTGCC

CCGGGCCACAGCTCAAGACGCTGGAAAGTATTATTGTCACCGTGGCAACCTGACCA

TGTCATTCCACCTGGAGATCACTGCTCGGCCTGGCGGCGGCGGGTCTGGAGGTGGAG

GATCTGGTGGTGGCGGGTCTGGTGGCGGCGGGTCTGAGGTGCAGCTGGTGGAGTCT

GGTGGTGGTCTTGTTCAACCTGGTGGTTCTCTTCGTCTTTCTTGTGCTGCTTCTGGTTT

TAATATTAAAGATACTTATATTCATTGGGTTCGTCAAGCTCCTGGTAAAGGTCTTGA

ATGGGTTGCTCGTATTTATCCTACTAATGGTTATACTCGTTATGCTGATTCTGTTAAA

GGTCGTTTTACTATTTCTGCTGATACTTCTAAAAATACTGCTTATCTTCAAATGAACT

CTCTTCGTGCTGAAGATACTGCTGTTTATTATTGTTCTCGTTGGGGTGGTGATGGTTT

TTATGCTATGGATTATTGGGGTCAAGGTACTCTTGTCACCGTCTCCTCAGCTAGCACC

GGGGGCGGCGGGTCTGGAGGTGGAGGATCTGGTGGCGGCGGGTCTGACATCCAGAT

GACCCAGTCTCCTTCTTCTCTTTCTGCTTCTGTTGGTGATCGTGTTACTATTACTTGTC

GTGCTTCTCAAGATGTTAATACTGCTGTTGCTTGGTATCAACAAAAACCTGGTAAAG

CTCCTAAACTTCTTATTTATTCTGCTTCTTTCTTTATTCTGGTGTTCCTTCTCGTTTTT

CTGGTTCTCGTTCTGGTACTGATTTTACTCTTACTATTTCTTCTCTTCAACCTGAAGAT

TTTGCTACTTATTATTGTCAACAACATTATACTACTCCTCCTACTTTTGGTCAAGGTA

CCAAGGTGGAGATCAAACGTACGTCTAGACATCATCACCATCACCAT
```

-continued

SEQ ID NO: 111

ATGAGGCTTCTGGTGCTTCTTTGGGGTTGCTTGCTGTTGCCCGGTTACGAAGCAGAC

ATCCAGATGACACAGACTACATCCTCCCTGTCTGCCTCTCTGGGAGACAGAGTCACC

ATCAGTTGCAGGGCAAGTCAGGACATTAGTAAATATTTAAATTGGTATCAGCAGAA

ACCAGATGGAACTGTTAAACTCCTGATCTACCATACATCAAGATTACACTCAGGAGT

CCCATCAAGGTTCAGTGGCAGTGGGTCTGGAACAGATTATTCTCTCACCATTAGCAA

CCTGGAGCAAGAAGATATTGCCACTTACTTTTGCCAACAAGGTAATACGCTTCCGTA

CACGTTCGGAGGGGGGACTAAGTTGGAAATAACAGGAGGCGGCGGGTCTGGAGGTG

GAGGATCTGGTGGTGGCGGGTCTGGAGGCGGCGGGTCTGAGGTGAAACTGCAGGAG

TCAGGACCTGGCCTGGTGGCGCCCTCACAGAGCCTGTCCGTCACATGCACTGTCTCA

GGGGTCTCATTACCCGACTATGGTGTAAGCTGGATTCGCCAGCCTCCACGAAAGGGT

CTGGAGTGGCTGGGAGTAATATGGGGTAGTGAAACCACATACTACAACTCAGCTCT

CAAATCCAGACTGACCATCATCAAGGACAACTCCAAGAGCCAAGTTTTCTTAAAAAT

GAACAGTCTGCAAACTGATGACACAGCCATTTACTACTGTGCCAAACATTATTACTA

CGGTGGTAGCTATGCTATGGACTACTGGGGTCAAGGAACCTCAGTCACCGTCTCCTC

AGACTACAAAGACGATGACGACAAGATTGAAGTTATGTATCCTCCTCCTTACCTAGA

CAATGAGAAGAGCAATGGAACCATTATCCATGTGAAAGGGAAACACCTTTGTCCAA

GTCCCCTATTTCCCGGACCTTCTAAGCCCTTTTGGGTGCTGGTGGTGGTTGGTGGAGT

CCTGGCTTGCTATAGCTTGCTAGTAACAGTGGCCTTTATTATTTTCTGGGTCCGCAGT

AAGAGGAGCAGGCTCCTGCACAGTGACTACATGAACATGACTCCCCGCCGCCCCGG

GCCCACCCGCAAGCATTACCAGCCCTATGCCCCACCACGCGACTTCGCAGCCTATCG

CTCCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAGGGGCA

CGATGGCCTTTACCAGGGTCTCAGTACAGCCACCAAGGACACCTACGACGCCCTTCA

CATGCAAGCCCTGCCCCCTCGCCGCGCGAAACGCAGCGGCAGCGGCGCGACCAACT

TTAGCCTGCTGAAACAGGCGGGCGATGTGGAAGAAAACCCGGGCCCGATGCCACCT

CCTCGCCTCCTCTTCTTCCTCCTCTTCCTCACCCCCATGGAAGTCAGGCCCGAGGAAC

CTCTAGTGGTGAAGGTGGAAGAGGGAGATAACGCTGTGCTGCAGTGCCTCAAGGGG

ACCTCAGATGGCCCCACTCAGCAGCTGACCTGGTCTCGGGAGTCCCCGCTTAAACCC

TTCTTAAAACTCAGCCTGGGGCTGCCAGGCCTGGGAATCCACATGAGGCCCCTGGCC

ATCTGGCTTTTCATCTTCAACGTCTCTCAACAGATGGGGGGCTTCTACCTGTGCCAGC

CGGGGCCCCCCTCTGAGAAGGCCTGGCAGCCTGGCTGGACAGTCAATGTGGAGGGC

AGCGGGGAGCTGTTCCGGTGGAATGTTTCGGACCTAGGTGGCCTGGGCTGTGGCCTG

AAGAACAGGTCCTCAGAGGGCCCCAGCTCCCCTTCCGGGAAGCTCATGAGCCCCAA

GCTGTATGTGTGGGCCAAAGACCGCCCTGAGATCTGGGAGGGAGAGCCTCCGTGTC

TCCCACCGAGGGACAGCCTGAACCAGAGCCTCAGCCAGGACCTCACCATGGCCCCT

-continued

```
GGCTCCACACTCTGGCTGTCCTGTGGGGTACCCCCTGACTCTGTGTCCCGCGGCCCC

CTCTCCTGGACCCATGTGCACCCCAAGGGGCCTAAGTCATTGCTGAGCCTAGAGCTG

AAGGACGATCGCCCGGCCAGAGATATGTGGGTAATGGAGACGGGTCTGTTGTTGCC

CCGGGCCACAGCTCAAGACGCTGGAAAGTATTATTGTCACCGTGGCAACCTGACCA

TGTCATTCCACCTGGAGATCACTGCTCGGCCAGGAGGAGGTGGGTCTGGAGGTGGA

GGATCTGGTGGAGGTGGGTCTGGAGGAGGTGGGTCTGAGGTGCAGCTGCTGGAGAG

CGGCGGCGGCCAGGTGCAGCCCGGCGGCAGCCTGAGGCTGAGCTGCGCCGCCAGCG

GCTTCACCTTCAGCAGCTACCCCATGAGCTGGGTGAGGCAGGCCCCCGGCAAGGGC

CTGGAGTGGGTGAGCGCCATCGGCGGCAGCGGCGGCAGCCTGCCCTACGCCGACAG

CGTGAAGGGCAGGTTCACCATCAGCAGGGACAACAGCAAGAACACCCTGTACCTGC

AGATGAACAGCCTGAGGGCCGAGGACACCGCCGTGTACTACTGCGCCAGGTACTGG

CCCATGGACATCTGGGGCCAGGGCACCCTGGTGACCGTGAGCAGCGCCAGCACCGG

CGGCGGCGGCAGCGGCGGCGGCGGCAGCGGCGGCGGCGGCAGCGGCGGCGGCGGC

AGCGAGATCGTGCTGACCCAGAGCCCCGGCACCCTGAGCCTGAGCCCCGGCGAGAG

GGCCACCCTGAGCTGCAGGGCCAGCCAGAGCGTGAGCAGCAGCTACCTGGCCTGGT

ACCAGCAGAAGCCCGGCCAGGCCCCCAGGCTGCTGATGTACGACGCCAGCATCAGG

GCCACCGGCATCCCCGACAGGTTCAGCGGCAGCGGCAGCGGCACCGACTTCACCCT

GACCATCAGCAGGCTGGAGCCCGAGGACTTCGCCGTGTACTACTGCCAGCAGTACC

AGAGCTGGCCCCTGACCTTCGGCCAGGGCACCAAGGTGGAGACCAAGAGGACCCAT

CATCACCATCACCAT
```

SEQ ID NO: 112

```
ATGAGGCTTCTGGTGCTTCTTTGGGGTTGCTTGCTGTTGCCCGGTTACGAAGCAGAC

ATCCAGATGACACAGACTACATCCTCCCTGTCTGCCTCTCTGGGAGACAGAGTCACC

ATCAGTTGCAGGGCAAGTCAGGACATTAGTAAATATTTAAATTGGTATCAGCAGAA

ACCAGATGGAACTGTTAAACTCCTGATCTACCATACATCAAGATTACACTCAGGAGT

CCCATCAAGGTTCAGTGGCAGTGGGTCTGGAACAGATTATTCTCTCACCATTAGCAA

CCTGGAGCAAGAAGATATTGCCACTTACTTTTGCCAACAAGGTAATACGCTTCCGTA

CACGTTCGGAGGGGGGACTAAGTTGGAAATAACAGGAGGCGGCGGGTCTGGAGGTG

GAGGATCTGGTGGTGGCGGGTCTGGAGGCGGCGGGTCTGAGGTGAAACTGCAGGAG

TCAGGACCTGGCCTGGTGGCGCCCTCACAGAGCCTGTCCGTCACATGCACTGTCTCA

GGGGTCTCATTACCCGACTATGGTGTAAGCTGGATTCGCCAGCCTCCACGAAAGGGT

CTGGAGTGGCTGGGAGTAATATGGGGTAGTGAAACCACATACTACAACTCAGCTCT

CAAATCCAGACTGACCATCATCAAGGACAACTCCAAGAGCCAAGTTTTCTTAAAAAT

GAACAGTCTGCAAACTGATGACACAGCCATTTACTACTGTGCCAAACATTATTACTA

CGGTGGTAGCTATGCTATGGACTACTGGGGTCAAGGAACCTCAGTCACCGTCTCCTC

AGACTACAAAGACGATGACGACAAGATTGAAGTTATGTATCCTCCTCCTTACCTAGA

CAATGAGAAGAGCAATGGAACCATTATCCATGTGAAAGGGAAACACCTTTGTCCAA

GTCCCCTATTTCCCGGACCTTCTAAGCCCTTTTGGGTGCTGGTGGTGGTTGGTGGAGT

CCTGGCTTGCTATAGCTTGCTAGTAACAGTGGCCTTTATTATTTTCTGGGTCCGCAGT

AAGAGGAGCAGGCTCCTGCACAGTGACTACATGAACATGACTCCCCGCCGCCCCGG

GCCCACCCGCAAGCATTACCAGCCCTATGCCCCACCACGCGACTTCGCAGCCTATCG
```

-continued

```
CTCCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAGGGGCA

CGATGGCCTTTACCAGGGTCTCAGTACAGCCACCAAGGACACCTACGACGCCCTTCA

CATGCAGGCCCTGCCCCCTCGCGAGGGAAGGGGCAGCCTGCTGACCTGCGGCGACG

TGGAGGAGAACCCCGGCCCTATGCCACCTCCTCGCCTCCTCTTCTTCCTCCTCTTCCT

CACCCCCATGGAAGTCAGGCCCGAGGAACCTCTAGTGGTGAAGGTGGAAGAGGGAG

ATAACGCTGTGCTGCAGTGCCTCAAGGGGACCTCAGATGGCCCCACTCAGCAGCTG

ACCTGGTCTCGGGAGTCCCCGCTTAAACCCTTCTTAAAACTCAGCCTGGGGCTGCCA

GGCCTGGGAATCCACATGAGGCCCCTGGCCATCTGGCTTTTCATCTTCAACGTCTCT

CAACAGATGGGGGGCTTCTACCTGTGCCAGCCGGGGCCCCCCTCTGAGAAGGCCTG

GCAGCCTGGCTGGACAGTCAATGTGGAGGGCAGCGGGGAGCTGTTCCGGTGGAATG

TTTCGGACCTAGGTGGCCTGGGCTGTGGCCTGAAGAACAGGTCCTCAGAGGGCCCC

AGCTCCCCTTCCGGGAAGCTCATGAGCCCCAAGCTGTATGTGTGGGCCAAAGACCG

CCCTGAGATCTGGGAGGGAGAGCCTCCGTGTCTCCCACCGAGGGACAGCCTGAACC

AGAGCCTCAGCCAGGACCTCACCATGGCCCCTGGCTCCACACTCTGGCTGTCCTGTG

GGGTACCCCCTGACTCTGTGTCCAGGGGCCCCCTCTCCTGGACCCATGTGCACCCCA

AGGGGCCTAAGTCATTGCTGAGCCTAGAGCTGAAGGACGATCGCCCGGCCAGAGAT

ATGTGGGTAATGGAGACGGGTCTGTTGTTGCCCCGGGCCACAGCTCAAGACGCTGG

AAAGTATTATTGTCACCGTGGCAACCTGACCATGTCATTCCACCTGGAGATCACTGC

TCGGCCAGGAGGAGGTGGGTCTGGAGGTGGAGGATCTGGTGGAGGTGGGTCTGGAG

GAGGTGGGTCTATGGCCCAGGTCAAACTACAGGAGTCAGGGGCTGAGCTGGTGAAG

CCTGGGGCCTCAGTGAAGATGTCCTGCAAGGCTTCTGGCTACACATTTACCAGTTAC

AATATGCACTGGGTAAAGCAGACACCTGGACAGGGCCTGGAATGGATTGGAGCTAT

TTATCCAGGAAATGGTGATACTTCCTACAATCAGAAGTTCAAAGGCAAGGCCACATT

GACTGCAGACAAATCCTCCAGCACAGCCTACATGCAGCTCAGCAGCCTGACATCTG

AGGACTCTGCGGACTATTACTGTGCAAGATCTAATTATTACGGTAGTAGCTACTGGT

TCTTCGATGTCTGGGGCCAAGGGACCACGGTCACCGTCTCCTCAGGTGGAGGCGGTT

CAGGCGGAGGTGGCTCTGGCGGTGGCGGATCGGACATCGAGCTCACTCAGTCTCCA

ACAATCCTGTCTGCATCTCCAGGGGAGAAGGTCACAATGACTTGCAGGGCCAGCTC

AAGTGTAAATTACATGGACTGGTACCAGAAGAAGCCAGGATCCTCCCCCAAACCCT

GGATTTATGCCACATCCAACCTGGCTTCTGGAGTCCCTGCTCGCTTCAGTGGCAGTG

GGTCTGGGACCTCTTACTCTCTCACAATCAGCAGAGTGGAGGCTGAAGATGCTGCCA

CTTATTACTGCCAGCAGTGGAGTTTTAATCCACCCACGTTCGGAGGGGGGACAAAGT

TGGAAATAAAACGGGCCGCCGCTCATCATCACCATCACCAT
```

VHH Clone Sequences

SEQ ID NO: 203
underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*))
QVQLQESGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTQ VT

VSS*TSQPGGQGAEQKLISEEDLGAHHHHHHGAS*

SEQ ID NO: 204
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*))
QVQLQESGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTLVT

VSS*TSQPGGQGAEQKLISEEDLGAHHHHHHGAS*

SEQ ID NO: 205
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*))
QVQLQQ SGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTQVT

VSS*TSQPGGQGAEQKLISEEDLGAHHHHHHGAS*

SEQ ID NO: 206
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQQ SGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTLVT

VSS*TSQPGGQGAEQKLISEEDLGAHHHHHHGAS*

SEQ ID NO: 207
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQQFGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTLVT

VSS*TSQPGGQGAEQKLISEEDLGAHHHHHHGAS*

SEQ ID NO: 208
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQASGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGTQVT

VSS*TSQPGGQGAEQKLISEEDLGAHHHHHHGAS*

SEQ ID NO: 209
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQEFGGGLVQAGGSLRLS<u>CAASGSIFAINEINLMG</u>WYRQAPGKQRELV<u>AACASDG</u>

<u>NTYYADSVKG</u>RFTISRDNAEKTVYLQMNNLKPDDTAVYYC<u>DANSRGNYY</u>SGQGMVT

VSS*TSQPGGQGAEQKLISEEDLGAHHHHHHGAS*

SEQ ID NO: 210
(underlining denotes CDR1, CDR2, CDR3, sequentially; bolded italics at C- terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQEFGGGLVQAGGSLRLS<u>CAASGSIFAINEINLMG</u>WYRQAPGKQRELV<u>AACASDG</u>

<u>NTYYADSVKGR</u>FTISRDNAEKTVYLQMNNLKPDDTAVYYC<u>DANSRGNYYS</u>GQGTQVT

VSS*TSQPGGQGAEQKLISEEDLGAHHHHHHGAS*

SEQ ID NO: 211
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLVESGGGLVQAGGSLRLS<u>CAASGSIFAINEINLMG</u>WYRQAPGKQRELV<u>AACASDG</u>

<u>NTYYADSVKGR</u>FTISRDNAEKTVYLQMNNLKPDDTAVYYC<u>DANSRGNYYS</u>GQGTINT

VSS*TSQPGGQGAEQKLISEEDLGAHHHHHHGAS*

SEQ ID NO: 212
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQQSGGGLAQTGGSLILS<u>CAASGSIFAINEINLMG</u>WYRQAPGKQRELV<u>AACASDGN</u>

<u>TYYADSVKGR</u>FTISRDNAEKTVYLQMNNLKPDDTAVYYC<u>DANSRGNYYS</u>GQGTQVTV

SS*TSQPGGQGAEQKLISEEDLGAHHHHHHGAS*

SEQ ID NO: 213
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGGLVQPGGSLRLS<u>CAASGSIFAINEINLMG</u>WYRQAPGKQRELV<u>AACASDG</u>

<u>NTYYADSVKGR</u>FTISRDNAEKTVYLQMNNLKPDDTAVYYC<u>DANSRGNYYS</u>GQGTINT

VSS*TSQPGGQGAEQKLISEEDLGAHHHHHHGAS*

SEQ ID NO: 214
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGGLVQVGESLRLS<u>CVVSGDTRSINLMG</u>WYRQAPGKQRELV<u>AACASDGNT</u>

<u>YYADSVKGR</u>FTISRDNAEKTVYLQMNNLKPDDTAVYYC<u>DANSRGNYYS</u>GQGTLVTVS

S*TSQPGGQGAEQKLISEEDLGAHHHHHHGAS*

SEQ ID NO: 215
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGGLVQAGGSLRLS<u>CVASGSIRSINVMG</u>WYRQAPGKQRELV<u>AACASDGNTY</u>

YADSVKGRFTISRDNAEKTVYLQMNNLKPDDTAVYYC<u>DANSRGNYYS</u>GQGTQVTVSS

*TSQPGGQGAEQKLISEEDLGAHHHHHHGAS*

SEQ ID NO: 216
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGGLVQPGGSLRLS<u>CAASGFTFNSYAMTW</u>VRQAPGKGLEW<u>VSDINSGGGST</u>

<u>NYADSVKGR</u>FTISRDNAKNTLYLQMNSLKPEDTAVYYC<u>ATELRGSDYYRGPIREYAYW</u>

GQGTLVTVSS*TSQPGGQGAEQKLISEEDLGAHHHHHHGAS*

SEQ ID NO: 217
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGALVQAGGSLRLS<u>CAASGLTFSNYAMGW</u>FRQAPGKEREFV<u>AAINWSGGT</u>

TDYATSVKGRFTISRDNAKNTVYLQLNSLKPEDTAVYYCAASYRLRITVVVTPDEYHY

WGQGTLVTVSS***TSQPGGQGAEQKLIS*EEDLGAH*HHHHHH*GAS**

SEQ ID NO: 218
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQQSGGGLVQPGGSLRLSCAASGFAFDDYAMIWVRQGPGKGLEWVSSISWNGGG

TYYAESIVGRFTVSRDNAKKMVYLQMNGLKSEDTAMYYCVKLVDSGWYSAYDYWGQ

GTQVTVSS*TSQPGGQGAEQKLISEEDLGAHHHHHHGAS*

SEQ ID NO: 219
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQESGGGLVQAGGSLRLSCVVSGATSNVNAMGWYRQAPGKERELVAAISSGGSTS

YRDSVKGRFTISRDNAKNTLYLQMNSLKPEDTAMYYCAAQDWATEGYEYDYWGQGT

LVTVSS*TSQPGGQGAEQKLISEEDLGAHHHHHHGAS*

SEQ ID NO: 220
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQAFGGGLVQPGGSLRLSCVVSGTMFSGKDVNWLRQAPGKHVEVVATVSSDGGT

DYADFVKGRFTISRDDAKNTVNLQMNSLEPEDTANYMCHFLWGRHYWGQGTQVTVSS

*TSQPGGQGAEQKLISEEDLGAHHHHHHGAS*

SEQ ID NO: 221
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQAFGGGMVQAGESLRLSCVASGNDISGSAMAWYRAHLGAERELVAVDAPRERP

FYIDPVIGRFTISRDDRNKMLYLQMNDLRPDDTATYWCGPSLRTFHGREWYRPPWFTS

WGQGTQVTVSS*TSQPGGQGAEQKLISEEDLGAHHHHHHGAS*

SEQ ID NO: 222
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQQSGGGLVQAGGSLRLSCAASGSIFSINAMGWYRQAPGKRREMVAVVSRFGETT

YTGSVKGRFTISRINRNNTVFLQMNRLKPEDTAVYYCNARIRGNYGSRIDYWGQTQV

TVSS*TSQPGGQGAEQKLISEEDLGAHHHHHHGAS*

SEQ ID NO: 223
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
QVQLQEFGGGLVQLGGSARLSCVVSGNMLDLNTMAWYRQGELVAALGISTYYAESVK

GRFTISRDNAKNTLYLQMNSLKSEDTAVYYCARDYNFESWGQGTLVTVSS*TSGPGGQG*

*AEQKLISEEDLGAHHHHHHGAS*

SEQ ID NO: 224
(underlining denotes CDR1, CDR2, CDR3, sequentially; bolded italics at C-
terminus denotes (i) a linker of 9 amino acids (*TSGPGGQGA*), (ii) a myc-tag
(*EQKLISEEDL*), (iii) a linker of 2 amino acids (*GA*), (iv) a hexa-histidine tag (*HHHHHH*),
and (v) an additional 3 amino acids (*GAS*)):
AVQLQESGGGLVQAGGSLRLSCAASGSDRSINVMNWYRQAPGKQRELVAAITSGGTTN

YAQSVKGRVTISRDSAKNTVYLQMNSLKPEDTAVYFCKADTRWGGMYWGPGTQVTV

SS*TSQPGGQGAEQKLISEEDLGAHHHHHHGAS*

SEQ ID NO: 225

(underlining denotes CDR1, CDR2, CDR3, sequentially; bolded italics at C-terminus denotes (i) a linker of 9 amino acids (*TSGPGGQGA*), (ii) a myc-tag (*EQKLISEEDL*), (iii) a linker of 2 amino acids (*GA*), (iv) a hexa-histidine tag (*HHHHHH*), and (v) an additional 3 amino acids (*GAS*)):

QVQLQQSGGGLVQAGGSLTLSCAAT<u>GRTIDNGAMA</u>WFRQAPGKQRELVAA<u>INWSGGA</u>

<u>TFYTDSVKY</u>RFTISRDNVRHTLDLQMTSLKPEDTTIYFC<u>ASRRGVDLRRNSYEYDY</u>WGR

GTLVTVSS*TSQPGGQGAEQKLISEEDLGAHHHHHHGAS*

---

What is claimed is:

1. A CD19 variant having at least 99% sequence identity to SEQ ID NO:2 wherein, the CD19 variant comprises amino acid substitutions at positions 62/64/66 of the amino acid sequence of SEQ ID NO: 2 selected from the following:

S/V/S; G/V/R; S/R/R; T/V/P; S/R/S; E/R/P; E/W/R; E/V/V; D/L/P; A/R/L; W/S/S; T/R/Q; R/V/R; E/E/V; Y/S/R; D/V/M; W/V/A; TN/F; R/A/F; E/C/S; E/R/R; D/V/R; S/V/A; T/A/S; H/F/R; T/V/R; T/M/S; S/V/R; H/V/S; S/F/N; N/L/P; D/V/S; W/T/A; D/A/S; G/V/K wherein the CD19 variant has improved binding to an anti-CD19 antibody relative to a polypeptide comprising the amino acid sequence of SEQ ID NO:2; or the CD19 variant comprises amino acid substitutions at positions 62/64/66 of the amino acid sequence of SEQ ID NO: 2 selected from the following:

Y/S/T; V/G/D; A/Q/T; V/E/E; wherein the CD19 variant is more resistant to protease cleavage relative to a polypeptide comprising the amino acid sequence of SEQ ID NO:2.

2. The CD19 variant of claim 1, wherein the CD19 variant comprises amino acids S/V/R at positions 62/64/66 of the amino acid sequence of SEQ ID NO: 2.

3. The CD19 variant of claim 1, wherein the CD19 variant comprises amino acids S/V/S at positions 62/64/66 of the amino acid sequence of SEQ ID NO: 2.

4. The CD19 variant of claim 1, wherein the CD19 variant comprises amino acids G/V/R at positions 62/64/66 of the amino acid sequence of SEQ ID NO: 2.

5. The CD19 variant of claim 1, wherein the CD19 variant comprises amino acids S/R/R at positions 62/64/66 of the amino acid sequence of SEQ ID NO: 2.

6. The CD19 variant of claim 1, wherein the CD19 variant comprises amino acids S/R/S at positions 62/64/66 of the amino acid sequence of SEQ ID NO: 2.

7. The CD19 variant of claim 1, wherein the CD19 variant comprises amino acids W/S/S at positions 62/64/66 of the amino acid sequence of SEQ ID NO: 2.

8. The CD19 variant of claim 1, wherein the CD19 variant comprises amino acids Y/S/R at positions 62/64/66 of the amino acid sequence of SEQ ID NO: 2.

9. The CD19 variant of claim 1, wherein the CD19 variant comprises amino acids D/V/R at positions 62/64/66 of the amino acid sequence of SEQ ID NO: 2.

10. The CD19 variant of claim 1, wherein the CD19 variant comprises amino acids T/V/R at positions 62/64/66 of the amino acid sequence of SEQ ID NO: 2.

* * * * *

SEQUENCE LISTING

<160> NUMBER OF SEQ ID NOS: 284

<210> SEQ ID NO 1
<211> LENGTH: 816
<212> TYPE: DNA
<213> ORGANISM: Homo sapiens

<400> SEQUENCE: 1

| | | | | | | |
|---|---|---|---|---|---|---|
| cccgaggaac | ctctagtggt | gaaggtggaa | gagggagata | acgctgtgct | gcagtgcctc | 60 |
| aaggggacct | cagatggccc | cactcagcag | ctgacctggt | ctcgggagtc | cccgcttaaa | 120 |
| cccttcttaa | aactcagcct | ggggctgcca | ggcctgggaa | tccacatgag | gcccctggcc | 180 |
| atctggcttt | tcatcttcaa | cgtctctcaa | cagatggggg | gcttctacct | gtgccagccg | 240 |
| ggcccccct | ctgagaaggc | ctggcagcct | ggctggacag | tcaatgtgga | gggcagcggg | 300 |
| gagctgttcc | ggtggaatgt | ttcggaccta | ggtggcctgg | gctgtggcct | gaagaacagg | 360 |
| tcctcagagg | gccccagctc | cccttccggg | aagctcatga | gccccaagct | gtatgtgtgg | 420 |
| gccaaagacc | gccctgagat | ctgggaggga | gagcctccgt | gtctcccacc | gagggacagc | 480 |
| ctgaaccaga | gcctcagcca | ggacctcacc | atggcccctg | gctccacact | ctggctgtcc | 540 |
| tgtggggtac | cccctgactc | tgtgtccagg | ggccccctct | cctggaccca | tgtgcacccc | 600 |
| aaggggccta | agtcattgct | gagcctagag | ctgaaggacg | atcgcccggc | cagagatatg | 660 |
| tgggtaatgg | agacgggtct | gttgttgccc | cgggccacag | ctcaagacgc | tggaaagtat | 720 |
| tattgtcacc | gtggcaacct | gaccatgtca | ttccacctgg | agatcactgc | tcggccagta | 780 |
| ctatggcact | ggctgctgag | gactggtggc | tggaag | | | 816 |

<210> SEQ ID NO 2
<211> LENGTH: 272
<212> TYPE: PRT
<213> ORGANISM: Homo sapiens

<400> SEQUENCE: 2

```
Pro Glu Glu Pro Leu Val Val Lys Val Glu Glu Gly Asp Asn Ala Val
1               5                   10                  15
Leu Gln Cys Leu Lys Gly Thr Ser Asp Gly Pro Thr Gln Gln Leu Thr
            20                  25                  30
Trp Ser Arg Glu Ser Pro Leu Lys Pro Phe Leu Lys Leu Ser Leu Gly
        35                  40                  45
Leu Pro Gly Leu Gly Ile His Met Arg Pro Leu Ala Ile Trp Leu Phe
    50                  55                  60
Ile Phe Asn Val Ser Gln Gln Met Gly Gly Phe Tyr Leu Cys Gln Pro
65                  70                  75                  80
Gly Pro Pro Ser Glu Lys Ala Trp Gln Pro Gly Trp Thr Val Asn Val
                85                  90                  95
```

```
Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
        130                 135                 140

Pro Glu Ile Trp Glu Gly Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

<210> SEQ ID NO 3
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asp Ala Trp Leu Arg Cys Leu Lys Gly Thr Ser Asp Gly Pro Thr Ser
        35                  40                  45

Gln Val Thr Trp Ser Arg Glu Ser Pro Leu Lys Pro Phe Leu Lys Tyr
    50                  55                  60

Ser Leu Gly Val Pro Gly Leu Gly Val His Ile Arg Pro Leu Ala Ile
65                  70                  75                  80

Gly Leu Val Ile Pro Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190
```

```
Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Tyr Tyr Cys His Arg Gly Asn Arg Thr Ile Ser Tyr His Leu
                260                 265                 270

Glu Ile Thr Ala Arg Pro Val Ser Ala His Thr Pro Leu Arg Thr Gly
                275                 280                 285

Gly Trp Lys Gly Gly Gly Ser Gly Gly Gly Ser Gly Gly Gly
            290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Phe Asp Tyr
                325                 330                 335

Ala Val Thr Tyr Tyr Arg Ile Thr Tyr Gly Glu Thr Gly Gly Asn Ser
                340                 345                 350

Pro Val Gln Glu Phe Thr Val Pro Gly Trp Ile Ser Thr Ala Thr Ile
                355                 360                 365

Ser Gly Leu Lys Pro Gly Val Asp Tyr Thr Ile Thr Val Tyr Ala Val
            370                 375                 380

Thr Asp Asn Ser His Trp Pro Phe Arg Ser Thr Pro Ile Ser Thr Asn
385                 390                 395                 400

Tyr Arg Thr Glu Ile Asp Lys Pro Pro Gln His His His His His
                405                 410                 415

<210> SEQ ID NO 4
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Thr Ala Val Leu Pro Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
        50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
```

```
                130                 135                 140
Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
                195                 200                 205

Arg Gly Pro Leu Ser Trp Thr His Val His Pro Lys Gly Pro Lys Ser
                210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
                260                 265                 270

Glu Ile Thr Ala Arg Pro Val Lys Ala His Ser Asp Leu Arg Thr Gly
                275                 280                 285

Gly Trp Lys Gly Gly Gly Ser Gly Gly Gly Ser Gly Gly Gly
                290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Phe Asp Tyr
                325                 330                 335

Ala Val Thr Tyr Tyr Arg Ile Thr Tyr Gly Glu Thr Gly Gly Asn Ser
                340                 345                 350

Pro Val Gln Glu Phe Thr Val Pro Gly Trp Ile Ser Thr Ala Thr Ile
                355                 360                 365

Ser Gly Leu Lys Pro Gly Val Asp Tyr Thr Ile Thr Val Tyr Ala Val
                370                 375                 380

Thr Asp Asn Ser His Trp Pro Phe Arg Ser Thr Pro Ile Ser Thr Asn
385                 390                 395                 400

Tyr Arg Thr Glu Ile Asp Lys Pro Pro Gln His His His His His His
                405                 410                 415

<210> SEQ ID NO 5
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Thr Ala Ala Leu Trp Cys Leu Lys Gly Thr Ser Asp Gly Pro Thr Gln
                35                  40                  45

Gln Leu Thr Trp Ser Arg Glu Ser Pro Leu Lys Pro Phe Leu Lys Leu
                50                  55                  60

Ser Leu Gly Leu Pro Gly Met Gly Val His Met Arg Pro Gly Ala Val
65              70                  75                  80
```

-continued

```
Ser Ala Val Ile Ser Asn Val Ser Gln Gln Met Gly Gly Phe Tyr Leu
                 85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Arg Asp Met Thr Val Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Gly Thr Ser Leu Ile Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Val Val Ala Arg Pro Val Lys Ala His Ser Asp Leu Arg Thr Gly
        275                 280                 285

Gly Trp Lys Gly Gly Gly Gly Ser Gly Gly Gly Ser Gly Gly Gly Gly
    290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Phe Asp Tyr
                325                 330                 335

Ala Val Thr Tyr Tyr Arg Ile Thr Tyr Gly Glu Thr Gly Gly Asn Ser
            340                 345                 350

Pro Val Gln Glu Phe Thr Val Pro Gly Trp Ile Ser Thr Ala Thr Ile
        355                 360                 365

Ser Gly Leu Lys Pro Gly Val Asp Tyr Thr Ile Thr Val Tyr Ala Val
    370                 375                 380

Thr Asp Asn Ser His Trp Pro Phe Arg Ser Thr Pro Ile Ser Thr Asn
385                 390                 395                 400

Tyr Arg Thr Glu Ile Asp Lys Pro Pro Gln His His His His His
                405                 410                 415

<210> SEQ ID NO 6
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30
```

```
Thr Ala Ala Leu Trp Cys Leu Lys Gly Thr Ser Asp Gly Pro Thr Gln
             35                  40                  45

Gln Leu Thr Trp Ser Arg Glu Ser Pro Leu Lys Pro Phe Leu Lys Tyr
 50                  55                  60

Ser Leu Gly Val Pro Gly Met Gly Val His Val Arg Pro Asn Ala Val
 65                  70                  75                  80

Ser Leu Val Ile Ser Asn Val Ser Gln Gln Met Gly Gly Phe Tyr Leu
                 85                  90                  95

Cys Gln Pro Gly Pro Pro Ser Glu Lys Ala Trp Gln Pro Gly Trp Thr
                100                 105                 110

Val Asn Val Glu Gly Ser Gly Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Arg Asp Met Thr Val Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Val Leu Pro Arg Ala Thr Ala Gln Asp Ala
                245                 250                 255

Gly Lys Trp Tyr Cys His Arg Gly Asn Val Thr Thr Ser Tyr His Leu
            260                 265                 270

Glu Ile Thr Ala Arg Pro Val Ser Ala His Thr Pro Leu Arg Thr Gly
            275                 280                 285

Gly Trp Lys Gly Gly Gly Ser Gly Gly Gly Ser Gly Gly Gly
            290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Phe Asp Tyr
                325                 330                 335

Ala Val Thr Tyr Tyr Arg Ile Thr Tyr Gly Glu Thr Gly Gly Asn Ser
            340                 345                 350

Pro Val Gln Glu Phe Thr Val Pro Gly Trp Ile Ser Thr Ala Thr Ile
            355                 360                 365

Ser Gly Leu Lys Pro Gly Val Asp Tyr Thr Ile Thr Val Tyr Ala Val
370                 375                 380

Thr Asp Asn Ser His Trp Pro Phe Arg Ser Thr Pro Ile Ser Thr Asn
385                 390                 395                 400

Tyr Arg Thr Glu Ile Asp Lys Pro Pro Gln His His His His His
                405                 410                 415

<210> SEQ ID NO 7
<211> LENGTH: 403
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
        260                 265                 270

Glu Ile Thr Ala Arg Pro Gly Gly Gly Ser Gly Gly Gly Gly Ser
    275                 280                 285

Gly Gly Gly Gly Ser Gly Gly Gly Ser Val Ser Asp Val Pro Arg
290                 295                 300

Asp Leu Glu Val Val Ala Ala Thr Pro Thr Ser Leu Leu Ile Ser Trp
305                 310                 315                 320

Phe Asp Tyr Ala Val Thr Tyr Tyr Arg Ile Thr Tyr Gly Glu Thr Gly
            325                 330                 335

Gly Asn Ser Pro Val Gln Glu Phe Thr Val Pro Gly Trp Ile Ser Thr
        340                 345                 350

Ala Thr Ile Ser Gly Leu Lys Pro Gly Val Asp Tyr Thr Ile Thr Val
    355                 360                 365

Tyr Ala Val Thr Asp Asn Ser His Trp Pro Phe Arg Ser Thr Pro Ile
370                 375                 380

Ser Thr Asn Tyr Arg Thr Glu Ile Asp Lys Pro Pro Gln His His His
385                 390                 395                 400

His His His

<210> SEQ ID NO 8
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285

Gly Trp Lys Gly Gly Gly Gly Ser Gly Gly Gly Ser Gly Gly Gly
    290                 295                 300

Gly Ser Gly Gly Gly Ser Glu Val Gln Leu Val Glu Ser Gly Gly
305                 310                 315                 320

Gly Leu Val Gln Pro Gly Gly Ser Leu Arg Leu Ser Cys Ala Ala Ser
                325                 330                 335

Gly Phe Asn Ile Lys Asp Thr Tyr Ile His Trp Val Arg Gln Ala Pro
            340                 345                 350
```

```
Gly Lys Gly Leu Glu Trp Val Ala Arg Ile Tyr Pro Thr Asn Gly Tyr
            355                 360                 365

Thr Arg Tyr Ala Asp Ser Val Lys Gly Arg Phe Thr Ile Ser Ala Asp
            370                 375                 380

Thr Ser Lys Asn Thr Ala Tyr Leu Gln Met Asn Ser Leu Arg Ala Glu
385                 390                 395                 400

Asp Thr Ala Val Tyr Tyr Cys Ser Arg Trp Gly Gly Asp Gly Phe Tyr
                405                 410                 415

Ala Met Asp Tyr Trp Gly Gln Gly Thr Leu Val Thr Val Ser Ser Ala
            420                 425                 430

Ser Thr Gly Gly Gly Ser Gly Gly Gly Ser Gly Gly Gly
            435                 440                 445

Ser Asp Ile Gln Met Thr Gln Ser Pro Ser Ser Leu Ser Ala Ser Val
            450                 455                 460

Gly Asp Arg Val Thr Ile Thr Cys Arg Ala Ser Gln Asp Val Asn Thr
465                 470                 475                 480

Ala Val Ala Trp Tyr Gln Gln Lys Pro Gly Lys Ala Pro Lys Leu Leu
                485                 490                 495

Ile Tyr Ser Ala Ser Phe Leu Tyr Ser Gly Val Pro Ser Arg Phe Ser
            500                 505                 510

Gly Ser Arg Ser Gly Thr Asp Phe Thr Leu Thr Ile Ser Ser Leu Gln
            515                 520                 525

Pro Glu Asp Phe Ala Thr Tyr Tyr Cys Gln Gln His Tyr Thr Thr Pro
            530                 535                 540

Pro Thr Phe Gly Gln Gly Thr Lys Val Glu Ile Lys Arg Thr His His
545                 550                 555                 560

His His His His

<210> SEQ ID NO 9
<211> LENGTH: 555
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140
```

```
Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Gly Gly Gly Ser Gly Gly Gly Ser
        275                 280                 285

Gly Gly Gly Gly Ser Gly Gly Gly Ser Glu Val Gln Leu Val Glu
            290                 295                 300

Ser Gly Gly Gly Leu Val Gln Pro Gly Gly Ser Leu Arg Leu Ser Cys
305                 310                 315                 320

Ala Ala Ser Gly Phe Asn Ile Lys Asp Thr Tyr Ile His Trp Val Arg
            325                 330                 335

Gln Ala Pro Gly Lys Gly Leu Glu Trp Val Ala Arg Ile Tyr Pro Thr
            340                 345                 350

Asn Gly Tyr Thr Arg Tyr Ala Asp Ser Val Lys Gly Arg Phe Thr Ile
            355                 360                 365

Ser Ala Asp Thr Ser Lys Asn Thr Ala Tyr Leu Gln Met Asn Ser Leu
370                 375                 380

Arg Ala Glu Asp Thr Ala Val Tyr Tyr Cys Ser Arg Trp Gly Gly Asp
385                 390                 395                 400

Gly Phe Tyr Ala Met Asp Tyr Trp Gly Gln Gly Thr Leu Val Thr Val
                405                 410                 415

Ser Ser Ala Ser Thr Gly Gly Gly Gly Ser Gly Gly Gly Gly Ser Gly
            420                 425                 430

Gly Gly Ser Asp Ile Gln Met Thr Gln Ser Pro Ser Ser Leu Ser
        435                 440                 445

Ala Ser Val Gly Asp Arg Val Thr Ile Thr Cys Arg Ala Ser Gln Asp
        450                 455                 460

Val Asn Thr Ala Val Ala Trp Tyr Gln Gln Lys Pro Gly Lys Ala Pro
465                 470                 475                 480

Lys Leu Leu Ile Tyr Ser Ala Ser Phe Leu Tyr Ser Gly Val Pro Ser
            485                 490                 495

Arg Phe Ser Gly Ser Arg Ser Gly Thr Asp Phe Thr Leu Thr Ile Ser
            500                 505                 510

Ser Leu Gln Pro Glu Asp Phe Ala Thr Tyr Tyr Cys Gln Gln His Tyr
            515                 520                 525

Thr Thr Pro Pro Thr Phe Gly Gln Gly Thr Lys Val Glu Ile Lys Arg
            530                 535                 540

Thr Ser Arg Gly Pro His His His His His His
545                 550                 555
```

<210> SEQ ID NO 10
<211> LENGTH: 553
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Gly Gly
130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Asp Val Asn Thr Ala Val Ala Trp
            180                 185                 190

Tyr Gln Gln Lys Pro Gly Lys Ala Pro Lys Leu Leu Ile Tyr Ser Ala
        195                 200                 205

Ser Phe Leu Tyr Ser Gly Val Pro Ser Arg Phe Ser Gly Ser Arg Ser
210                 215                 220

Gly Thr Asp Phe Thr Leu Thr Ile Ser Ser Leu Gln Pro Glu Asp Phe
225                 230                 235                 240

Ala Thr Tyr Tyr Cys Gln Gln His Tyr Thr Thr Pro Pro Thr Phe Gly
                245                 250                 255

Gln Gly Thr Lys Val Glu Ile Lys Arg Thr Gly Gly Gly Gly Ser Gly
            260                 265                 270

Gly Gly Ser Gly Gly Gly Ser Gly Gly Gly Ser Pro Glu
        275                 280                 285

Glu Pro Leu Val Val Lys Val Glu Glu Gly Asp Thr Ala Ala Leu Trp
290                 295                 300

Cys Leu Lys Gly Thr Ser Asp Gly Pro Thr Gln Gln Leu Thr Trp Ser
305                 310                 315                 320

Arg Glu Ser Pro Leu Lys Pro Phe Leu Lys Tyr Ser Leu Gly Val Pro
                325                 330                 335

Gly Leu Gly Val His Val Arg Pro Asp Ala Ile Ser Val Val Ile Arg
            340                 345                 350

Asn Val Ser Gln Gln Met Gly Gly Phe Tyr Leu Cys Gln Pro Gly Pro
        355                 360                 365
```

Pro Ser Glu Lys Ala Trp Gln Pro Gly Trp Thr Val Asn Val Glu Gly
        370                 375                 380

Ser Gly Glu Leu Phe Arg Trp Asn Val Ser Asp Leu Gly Gly Leu Gly
385                 390                 395                 400

Cys Gly Leu Lys Asn Arg Ser Ser Glu Gly Pro Ser Ser Pro Ser Gly
                405                 410                 415

Lys Leu Met Ser Pro Lys Leu Tyr Val Trp Ala Lys Asp Arg Pro Glu
            420                 425                 430

Ile Trp Glu Gly Glu Pro Pro Cys Leu Pro Arg Asp Ser Leu Asn
        435                 440                 445

Gln Ser Leu Ser Arg Asp Leu Thr Val Ala Pro Gly Ser Thr Leu Trp
    450                 455                 460

Leu Ser Cys Gly Val Pro Pro Asp Ser Val Ser Arg Gly Pro Leu Ser
465                 470                 475                 480

Trp Thr His Val His Pro Lys Gly Pro Lys Ser Leu Leu Ser Leu Glu
                485                 490                 495

Leu Lys Asp Asp Arg Pro Ala Arg Asp Met Trp Val Met Gly Thr Ser
            500                 505                 510

Leu Met Leu Pro Arg Ala Thr Ala Gln Asp Ala Gly Lys Trp Tyr Cys
        515                 520                 525

His Arg Gly Asn Leu Thr Met Ser Phe His Leu Glu Ile Thr Ala Arg
    530                 535                 540

Pro Ser Arg His His His His His His
545                 550

<210> SEQ ID NO 11
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val

```
            165                 170                 175
Thr Ile Thr Cys Arg Ala Ser Gln Asp Val Asn Thr Ala Val Ala Trp
            180                 185                 190
Tyr Gln Gln Lys Pro Gly Lys Ala Pro Lys Leu Leu Ile Tyr Ser Ala
            195                 200                 205
Ser Phe Leu Tyr Ser Gly Val Pro Ser Arg Phe Ser Gly Ser Arg Ser
            210                 215                 220
Gly Thr Asp Phe Thr Leu Thr Ile Ser Ser Leu Gln Pro Glu Asp Phe
225                 230                 235                 240
Ala Thr Tyr Tyr Cys Gln Gln His Tyr Thr Thr Pro Pro Thr Phe Gly
                245                 250                 255
Gln Gly Thr Lys Val Glu Ile Lys Arg Thr Gly Gly Gly Ser Gly
            260                 265                 270
Gly Gly Gly Ser Gly Gly Gly Ser Gly Gly Gly Ser Pro Glu
            275                 280                 285
Glu Pro Leu Val Val Lys Val Glu Glu Gly Asp Thr Ala Ala Leu Trp
            290                 295                 300
Cys Leu Lys Gly Thr Ser Asp Gly Pro Thr Gln Gln Leu Thr Trp Ser
305                 310                 315                 320
Arg Glu Ser Pro Leu Lys Pro Phe Leu Lys Tyr Ser Phe Gly Gly Pro
                325                 330                 335
Gly Leu Gly Ile His Met Arg Pro Asp Ala Ile Ser Val Val Ile Ser
            340                 345                 350
Asn Val Ser Gln Gln Met Gly Gly Phe Tyr Leu Cys Gln Pro Gly Pro
            355                 360                 365
Pro Ser Glu Lys Ala Trp Gln Pro Gly Trp Thr Val Asn Val Glu Gly
            370                 375                 380
Ser Gly Glu Leu Phe Arg Trp Asn Val Ser Asp Leu Gly Gly Leu Gly
385                 390                 395                 400
Cys Gly Leu Lys Asn Arg Ser Ser Glu Gly Pro Ser Ser Pro Ser Gly
                405                 410                 415
Lys Leu Met Ser Pro Lys Leu Tyr Val Trp Ala Lys Asp Arg Pro Glu
            420                 425                 430
Ile Trp Glu Gly Glu Pro Pro Cys Leu Pro Pro Arg Asp Ser Leu Asn
            435                 440                 445
Gln Ser Leu Ser Arg Asp Leu Thr Val Ala Pro Gly Ser Thr Leu Trp
            450                 455                 460
Leu Ser Cys Gly Val Pro Pro Asp Ser Val Ser Arg Gly Pro Leu Ser
465                 470                 475                 480
Trp Thr His Val His Pro Lys Gly Pro Lys Ser Leu Leu Ser Leu Glu
                485                 490                 495
Leu Lys Asp Asp Arg Pro Ala Arg Glu Met Trp Val Thr Gly Thr Arg
            500                 505                 510
Leu Phe Leu Pro Arg Ala Thr Ala Gln Asp Ala Gly Lys Tyr Tyr Cys
            515                 520                 525
His Arg Gly Asn Leu Thr Met Ser Phe His Leu Glu Ile Thr Ala Arg
            530                 535                 540
Pro Ser Arg His His His His His
545                 550

<210> SEQ ID NO 12
<211> LENGTH: 553
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 12

```
Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Gly Gly
130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Asp Val Asn Thr Ala Val Ala Trp
            180                 185                 190

Tyr Gln Gln Lys Pro Gly Lys Ala Pro Lys Leu Leu Ile Tyr Ser Ala
        195                 200                 205

Ser Phe Leu Tyr Ser Gly Val Pro Ser Arg Phe Ser Gly Ser Arg Ser
210                 215                 220

Gly Thr Asp Phe Thr Leu Thr Ile Ser Ser Leu Gln Pro Glu Asp Phe
225                 230                 235                 240

Ala Thr Tyr Tyr Cys Gln Gln His Tyr Thr Thr Pro Pro Thr Phe Gly
                245                 250                 255

Gln Gly Thr Lys Val Glu Ile Lys Arg Thr Gly Gly Gly Gly Ser Gly
            260                 265                 270

Gly Gly Gly Ser Gly Gly Gly Gly Ser Gly Gly Gly Ser Pro Glu
        275                 280                 285

Glu Pro Leu Val Val Lys Val Glu Glu Gly Asp Thr Ala Ala Leu Trp
290                 295                 300

Cys Leu Lys Gly Thr Ser Asp Gly Pro Thr Glu Gln Val Thr Trp Ser
305                 310                 315                 320

Arg Glu Ser Pro Leu Lys Pro Phe Leu Lys Leu Ser Leu Gly Leu Pro
                325                 330                 335

Gly Gly Gly Gly His Val Arg Pro Asn Ala Val Ser Leu Val Ile Arg
            340                 345                 350

Asn Val Ser Gln Gln Met Gly Gly Phe Tyr Leu Cys Gln Pro Gly Pro
        355                 360                 365

Pro Ser Glu Lys Ala Trp Gln Pro Gly Trp Thr Val Asn Val Glu Gly
370                 375                 380

Ser Gly Glu Leu Phe Arg Trp Asn Val Ser Asp Leu Gly Gly Leu Gly
```

-continued

```
                385                 390                 395                 400
Cys Gly Leu Lys Asn Arg Ser Ser Glu Gly Pro Ser Ser Pro Ser Gly
                    405                 410                 415

Lys Leu Met Ser Pro Lys Leu Tyr Val Trp Ala Lys Asp Arg Pro Glu
                420                 425                 430

Ile Trp Glu Gly Glu Pro Pro Cys Leu Pro Pro Arg Asp Ser Leu Asn
                    435                 440                 445

Gln Ser Leu Ser Arg Asp Leu Thr Val Ala Pro Gly Ser Thr Leu Trp
                450                 455                 460

Leu Ser Cys Gly Val Pro Pro Asp Ser Val Ser Arg Gly Pro Leu Ser
465                 470                 475                 480

Trp Thr His Val His Pro Lys Gly Pro Lys Ser Leu Leu Ser Leu Glu
                    485                 490                 495

Leu Lys Asp Asp Arg Pro Ala Arg Asp Met Trp Val Thr Glu Thr Gly
                500                 505                 510

Leu Leu Leu Pro Arg Ala Thr Ala Gln Asp Ala Gly Lys Trp Tyr Cys
                515                 520                 525

His Arg Gly Asn Leu Thr Met Ser Phe His Leu Glu Ile Thr Ala Arg
                530                 535                 540

Pro Ser Arg His His His His His His
545                 550

<210> SEQ ID NO 13
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Met Glu Phe Gly Leu Ser Trp Val Phe Leu Val Ala Leu Phe Arg
1               5                   10                  15

Gly Val Gln Cys Gln Val Lys Leu Gln Glu Ser Gly Ala Glu Leu Val
                20                  25                  30

Lys Pro Gly Ala Ser Val Lys Met Ser Cys Lys Ala Ser Gly Tyr Thr
            35                  40                  45

Phe Thr Ser Tyr Asn Met His Trp Val Lys Gln Thr Pro Gly Gln Gly
        50                  55                  60

Leu Glu Trp Ile Gly Ala Ile Tyr Pro Gly Asn Gly Asp Thr Ser Tyr
65                  70                  75                  80

Asn Gln Lys Phe Lys Gly Lys Ala Thr Leu Thr Ala Asp Lys Ser Ser
                85                  90                  95

Ser Thr Ala Tyr Met Gln Leu Ser Ser Leu Thr Ser Glu Asp Ser Ala
            100                 105                 110

Asp Tyr Tyr Cys Ala Arg Ser Asn Tyr Tyr Gly Ser Ser Tyr Trp Phe
        115                 120                 125

Phe Asp Val Trp Gly Gln Gly Thr Thr Val Thr Val Ser Ser Ala Ser
    130                 135                 140

Thr Gly Gly Gly Gly Ser Gly Gly Gly Gly Ser Gly Gly Gly Gly Ser
145                 150                 155                 160

Asp Ile Glu Leu Thr Gln Ser Pro Thr Ile Leu Ser Ala Ser Pro Gly
                165                 170                 175

Glu Lys Val Thr Met Thr Cys Arg Ala Ser Ser Ser Val Asn Tyr Met
            180                 185                 190
```

Asp Trp Tyr Gln Lys Lys Pro Gly Ser Ser Pro Lys Pro Trp Ile Tyr
            195                 200                 205

Ala Thr Ser Asn Leu Ala Ser Gly Val Pro Ala Arg Phe Ser Gly Ser
        210                 215                 220

Gly Ser Gly Thr Ser Tyr Ser Leu Thr Ile Ser Arg Val Glu Ala Glu
225                 230                 235                 240

Asp Ala Ala Thr Tyr Tyr Cys Gln Gln Trp Ser Phe Asn Pro Pro Thr
                245                 250                 255

Phe Gly Gly Gly Thr Lys Leu Glu Ile Lys Arg Ala Ala Ala Gly Gly
            260                 265                 270

Gly Gly Ser Gly Gly Gly Gly Ser Gly Gly Gly Gly Ser Gly Gly Gly
        275                 280                 285

Gly Ser Pro Glu Glu Pro Leu Val Val Lys Val Glu Glu Gly Asp Thr
290                 295                 300

Ala Ala Leu Trp Cys Leu Lys Gly Thr Ser Asp Gly Pro Thr Gln Gln
305                 310                 315                 320

Leu Thr Trp Ser Arg Glu Ser Pro Leu Lys Pro Phe Leu Lys Tyr Ser
                325                 330                 335

Leu Gly Val Pro Gly Leu Gly Val His Val Arg Pro Asp Ala Ile Ser
            340                 345                 350

Val Val Ile Arg Asn Val Ser Gln Gln Met Gly Gly Phe Tyr Leu Cys
        355                 360                 365

Gln Pro Gly Pro Pro Ser Glu Lys Ala Trp Gln Pro Gly Trp Thr Val
        370                 375                 380

Asn Val Glu Gly Ser Gly Glu Leu Phe Arg Trp Asn Val Ser Asp Leu
385                 390                 395                 400

Gly Gly Leu Gly Cys Gly Leu Lys Asn Arg Ser Ser Glu Gly Pro Ser
                405                 410                 415

Ser Pro Ser Gly Lys Leu Met Ser Pro Lys Leu Tyr Val Trp Ala Lys
            420                 425                 430

Asp Arg Pro Glu Ile Trp Glu Gly Glu Pro Pro Cys Leu Pro Pro Arg
        435                 440                 445

Asp Ser Leu Asn Gln Ser Leu Ser Arg Asp Leu Thr Val Ala Pro Gly
450                 455                 460

Ser Thr Leu Trp Leu Ser Cys Gly Val Pro Pro Asp Ser Val Ser Arg
465                 470                 475                 480

Gly Pro Leu Ser Trp Thr His Val His Pro Lys Gly Pro Lys Ser Leu
                485                 490                 495

Leu Ser Leu Glu Leu Lys Asp Asp Arg Pro Ala Arg Asp Met Trp Val
            500                 505                 510

Met Gly Thr Ser Leu Met Leu Pro Arg Ala Thr Ala Gln Asp Ala Gly
        515                 520                 525

Lys Trp Tyr Cys His Arg Gly Asn Leu Thr Met Ser Phe His Leu Glu
530                 535                 540

Ile Thr Ala Arg Pro Ser Arg His His His His His
545                 550                 555

<210> SEQ ID NO 14
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Pro Pro Pro Arg Leu Leu Phe Phe Leu Leu Phe Leu Thr Pro Met
1               5                   10                  15

Glu Val Arg Pro Glu Glu Pro Leu Val Lys Val Glu Glu Gly Asp
            20                  25                  30

Asn Ala Val Leu Gln Cys Leu Lys Gly Thr Ser Asp Gly Pro Thr Gln
                35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
            245                 250                 255

Gly Lys Tyr Tyr Cys His Arg Gly Asn Leu Thr Met Ser Phe His Leu
                260                 265                 270

Glu Ile Thr Ala Arg Pro Gly Gly Gly Ser Gly Gly Gly Gly Ser
            275                 280                 285

Gly Gly Gly Gly Ser Gly Gly Gly Ser Met Ala Gln Val Lys Leu
    290                 295                 300

Gln Glu Ser Gly Ala Glu Leu Val Lys Pro Gly Ala Ser Val Lys Met
305                 310                 315                 320

Ser Cys Lys Ala Ser Gly Tyr Thr Phe Thr Ser Tyr Asn Met His Trp
            325                 330                 335

Val Lys Gln Thr Pro Gly Gln Gly Leu Glu Trp Ile Gly Ala Ile Tyr
            340                 345                 350

Pro Gly Asn Gly Asp Thr Ser Tyr Asn Gln Lys Phe Lys Gly Lys Ala
            355                 360                 365

Thr Leu Thr Ala Asp Lys Ser Ser Ser Thr Ala Tyr Met Gln Leu Ser
    370                 375                 380

Ser Leu Thr Ser Glu Asp Ser Ala Asp Tyr Tyr Cys Ala Arg Ser Asn
385                 390                 395                 400

Tyr Tyr Gly Ser Ser Tyr Trp Phe Phe Asp Val Trp Gly Gln Gly Thr
                405                 410                 415
```

```
Thr Val Thr Val Ser Gly Gly Gly Ser Gly Gly Gly Ser
            420             425             430

Gly Gly Gly Gly Ser Asp Ile Glu Leu Thr Gln Ser Pro Thr Ile Leu
            435             440             445

Ser Ala Ser Pro Gly Glu Lys Val Thr Met Thr Cys Arg Ala Ser Ser
450             455             460

Ser Val Asn Tyr Met Asp Trp Tyr Gln Lys Pro Gly Ser Ser Pro
465             470             475             480

Lys Pro Trp Ile Tyr Ala Thr Ser Asn Leu Ala Ser Gly Val Pro Ala
            485             490             495

Arg Phe Ser Gly Ser Gly Ser Gly Thr Ser Tyr Ser Leu Thr Ile Ser
            500             505             510

Arg Val Glu Ala Glu Asp Ala Ala Thr Tyr Tyr Cys Gln Gln Trp Ser
            515             520             525

Phe Asn Pro Pro Thr Phe Gly Gly Gly Thr Lys Leu Glu Ile Lys Arg
            530             535             540

Ala Ala Ala His His His His His His
545             550

<210> SEQ ID NO 15
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Phe Gly Leu Ile Phe Phe Ile Val Ala Leu Leu Lys Gly Val
1               5                   10                  15

Gln Cys Gln Ile Leu Leu Thr Gln Ser Pro Val Ile Leu Ser Val Ser
            20                  25                  30

Pro Gly Glu Arg Val Ser Phe Ser Cys Arg Ala Ser Gln Ser Ile Gly
            35                  40                  45

Thr Asn Ile His Trp Tyr Gln Gln Arg Thr Asn Gly Ser Pro Arg Leu
50                  55                  60

Leu Ile Lys Tyr Ala Ser Glu Ser Ile Ser Gly Ile Pro Ser Arg Phe
65                  70                  75                  80

Ser Gly Ser Gly Ser Gly Thr Asp Phe Thr Leu Ser Ile Asn Ser Val
            85                  90                  95

Glu Ser Glu Asp Ile Ala Asp Tyr Tyr Cys Gln Gln Asn Asn Asn Trp
            100                 105                 110

Pro Thr Thr Phe Gly Ala Gly Thr Lys Leu Glu Leu Lys Gly Ser Thr
            115                 120                 125

Ser Gly Ser Gly Lys Pro Gly Ser Gly Glu Gly Ser Thr Lys Gly Gln
            130                 135                 140

Val Gln Leu Lys Gln Ser Gly Pro Gly Leu Val Gln Pro Ser Gln Ser
145                 150                 155                 160

Leu Ser Ile Thr Cys Thr Val Ser Gly Phe Ser Leu Thr Asn Tyr Gly
            165                 170                 175

Val His Trp Val Arg Gln Ser Pro Gly Lys Gly Leu Glu Trp Leu Gly
            180                 185                 190

Val Ile Trp Ser Gly Gly Asn Thr Asp Tyr Asn Thr Pro Phe Thr Ser
            195                 200                 205

Arg Leu Ser Ile Asn Lys Asp Asn Ser Lys Ser Gln Val Phe Phe Lys
            210                 215                 220
```

```
Met Asn Ser Leu Gln Ser Asn Asp Thr Ala Ile Tyr Tyr Cys Ala Arg
225                 230                 235                 240

Ala Leu Thr Tyr Tyr Asp Tyr Glu Phe Ala Tyr Trp Gly Gln Gly Thr
                245                 250                 255

Leu Val Thr Val Ser Ala Gly Gly Gly Ser Gly Gly Gly Gly Gly Ser
            260                 265                 270

Gly Gly Gly Gly Ser Gly Gly Gly Ser Pro Glu Glu Pro Leu Val
        275                 280                 285

Val Lys Val Glu Glu Gly Asp Thr Ala Ala Leu Trp Cys Leu Lys Gly
    290                 295                 300

Thr Ser Asp Gly Pro Thr Gln Gln Leu Thr Trp Ser Arg Glu Ser Pro
305                 310                 315                 320

Leu Lys Pro Phe Leu Lys Tyr Ser Leu Gly Val Pro Gly Leu Gly Val
                325                 330                 335

His Val Arg Pro Asp Ala Ile Ser Val Val Ile Arg Asn Val Ser Gln
            340                 345                 350

Gln Met Gly Gly Phe Tyr Leu Cys Gln Pro Gly Pro Pro Ser Glu Lys
        355                 360                 365

Ala Trp Gln Pro Gly Trp Thr Val Asn Val Glu Gly Ser Gly Glu Leu
    370                 375                 380

Phe Arg Trp Asn Val Ser Asp Leu Gly Gly Leu Gly Cys Gly Leu Lys
385                 390                 395                 400

Asn Arg Ser Ser Glu Gly Pro Ser Ser Pro Ser Gly Lys Leu Met Ser
                405                 410                 415

Pro Lys Leu Tyr Val Trp Ala Lys Asp Arg Pro Glu Ile Trp Glu Gly
            420                 425                 430

Glu Pro Pro Cys Leu Pro Pro Arg Asp Ser Leu Asn Gln Ser Leu Ser
        435                 440                 445

Arg Asp Leu Thr Val Ala Pro Gly Ser Thr Leu Trp Leu Ser Cys Gly
    450                 455                 460

Val Pro Pro Asp Ser Val Ser Arg Gly Pro Leu Ser Trp Thr His Val
465                 470                 475                 480

His Pro Lys Gly Pro Lys Ser Leu Leu Ser Leu Glu Leu Lys Asp Asp
                485                 490                 495

Arg Pro Ala Arg Asp Met Trp Val Met Gly Thr Ser Leu Met Leu Pro
            500                 505                 510

Arg Ala Thr Ala Gln Asp Ala Gly Lys Trp Tyr Cys His Arg Gly Asn
        515                 520                 525

Leu Thr Met Ser Phe His Leu Glu Ile Thr Ala Arg Pro Ser Arg His
    530                 535                 540

His His His His His
545

<210> SEQ ID NO 16
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Phe Gly Leu Ile Phe Phe Ile Val Ala Leu Leu Lys Gly Val
1               5                   10                  15

Gln Cys Gln Ile Leu Leu Thr Gln Ser Pro Val Ile Leu Ser Val Ser
```

```
                    20                  25                  30
Pro Gly Glu Arg Val Ser Phe Ser Cys Arg Ala Ser Gln Ser Ile Gly
                35                  40                  45

Thr Asn Ile His Trp Tyr Gln Gln Arg Thr Asn Gly Ser Pro Arg Leu
 50                  55                  60

Leu Ile Lys Tyr Ala Ser Glu Ser Ile Ser Ile Pro Ser Arg Phe
 65                  70                  75                  80

Ser Gly Ser Gly Ser Gly Thr Asp Phe Thr Leu Ser Ile Asn Ser Val
                85                  90                  95

Glu Ser Glu Asp Ile Ala Asp Tyr Tyr Cys Gln Gln Asn Asn Asn Trp
               100                 105                 110

Pro Thr Thr Phe Gly Ala Gly Thr Lys Leu Glu Leu Lys Gly Ser Thr
               115                 120                 125

Ser Gly Ser Gly Lys Pro Gly Ser Gly Glu Gly Ser Thr Lys Gly Gln
               130                 135                 140

Val Gln Leu Lys Gln Ser Gly Pro Gly Leu Val Gln Pro Ser Gln Ser
145                 150                 155                 160

Leu Ser Ile Thr Cys Thr Val Ser Gly Phe Ser Leu Thr Asn Tyr Gly
                165                 170                 175

Val His Trp Val Arg Gln Ser Pro Gly Lys Gly Leu Glu Trp Leu Gly
                180                 185                 190

Val Ile Trp Ser Gly Gly Asn Thr Asp Tyr Asn Thr Pro Phe Thr Ser
                195                 200                 205

Arg Leu Ser Ile Asn Lys Asp Asn Ser Lys Ser Gln Val Phe Phe Lys
                210                 215                 220

Met Asn Ser Leu Gln Ser Asn Asp Thr Ala Ile Tyr Tyr Cys Ala Arg
225                 230                 235                 240

Ala Leu Thr Tyr Tyr Asp Tyr Glu Phe Ala Tyr Trp Gly Gln Gly Thr
                245                 250                 255

Leu Val Thr Val Ser Ala Gly Gly Gly Ser Gly Gly Gly Gly Ser
                260                 265                 270

Gly Gly Gly Gly Ser Gly Gly Gly Ser Pro Glu Glu Pro Leu Val
                275                 280                 285

Val Lys Val Glu Glu Gly Asp Thr Ala Ala Leu Trp Cys Leu Lys Gly
                290                 295                 300

Thr Ser Asp Gly Pro Thr Glu Gln Val Thr Trp Ser Arg Glu Ser Pro
305                 310                 315                 320

Leu Lys Pro Phe Leu Lys Leu Ser Leu Gly Leu Pro Gly Gly Gly Gly
                325                 330                 335

His Val Arg Pro Asn Ala Val Ser Leu Val Ile Arg Asn Val Ser Gln
                340                 345                 350

Gln Met Gly Gly Phe Tyr Leu Cys Gln Pro Gly Pro Pro Ser Glu Lys
                355                 360                 365

Ala Trp Gln Pro Gly Trp Thr Val Asn Val Glu Gly Ser Gly Glu Leu
                370                 375                 380

Phe Arg Trp Asn Val Ser Asp Leu Gly Gly Leu Gly Cys Gly Leu Lys
385                 390                 395                 400

Asn Arg Ser Ser Glu Gly Pro Ser Ser Pro Ser Gly Lys Leu Met Ser
                405                 410                 415

Pro Lys Leu Tyr Val Trp Ala Lys Asp Arg Pro Glu Ile Trp Glu Gly
                420                 425                 430

Glu Pro Pro Cys Leu Pro Pro Arg Asp Ser Leu Asn Gln Ser Leu Ser
                435                 440                 445
```

```
Arg Asp Leu Thr Val Ala Pro Gly Ser Thr Leu Trp Leu Ser Cys Gly
        450                 455                 460

Val Pro Pro Asp Ser Val Ser Arg Gly Pro Leu Ser Trp Thr His Val
465                 470                 475                 480

His Pro Lys Gly Pro Lys Ser Leu Leu Ser Leu Glu Leu Lys Asp Asp
                485                 490                 495

Arg Pro Ala Arg Asp Met Trp Val Thr Glu Thr Gly Leu Leu Leu Pro
        500                 505                 510

Arg Ala Thr Ala Gln Asp Ala Gly Lys Trp Tyr Cys His Arg Gly Asn
        515                 520                 525

Leu Thr Met Ser Phe His Leu Glu Ile Thr Ala Arg Pro Ser Arg His
        530                 535                 540

His His His His His
545

<210> SEQ ID NO 17
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Phe Gly Leu Ile Phe Phe Ile Val Ala Leu Leu Lys Gly Val
1               5                   10                  15

Gln Cys Gln Gly Gln Ser Gly Gln Cys Ile Ser Pro Arg Gly Cys Pro
            20                  25                  30

Asp Gly Pro Tyr Val Met Tyr Gly Ser Ser Gly Gly Ser Gly Gly Ser
        35                  40                  45

Gly Gly Ser Gly Leu Ser Gly Arg Ser Asp Asn His Gly Ser Ser Gly
    50                  55                  60

Thr Gln Ile Leu Leu Thr Gln Ser Pro Val Ile Leu Ser Val Ser Pro
65                  70                  75                  80

Gly Glu Arg Val Ser Phe Ser Cys Arg Ala Ser Gln Ser Ile Gly Thr
                85                  90                  95

Asn Ile His Trp Tyr Gln Gln Arg Thr Asn Gly Ser Pro Arg Leu Leu
            100                 105                 110

Ile Lys Tyr Ala Ser Glu Ser Ile Ser Gly Ile Pro Ser Arg Phe Ser
        115                 120                 125

Gly Ser Gly Ser Gly Thr Asp Phe Thr Leu Ser Ile Asn Ser Val Glu
    130                 135                 140

Ser Glu Asp Ile Ala Asp Tyr Tyr Cys Gln Gln Asn Asn Asn Trp Pro
145                 150                 155                 160

Thr Thr Phe Gly Ala Gly Thr Lys Leu Glu Leu Lys Gly Ser Thr Ser
                165                 170                 175

Gly Ser Gly Lys Pro Gly Ser Gly Glu Gly Ser Thr Lys Gly Gln Val
            180                 185                 190

Gln Leu Lys Gln Ser Gly Pro Gly Leu Val Gln Pro Ser Gln Ser Leu
        195                 200                 205

Ser Ile Thr Cys Thr Val Ser Gly Phe Ser Leu Thr Asn Tyr Gly Val
    210                 215                 220

His Trp Val Arg Gln Ser Pro Gly Lys Gly Leu Glu Trp Leu Gly Val
225                 230                 235                 240

Ile Trp Ser Gly Gly Asn Thr Asp Tyr Asn Thr Pro Phe Thr Ser Arg
```

245                 250                 255
Leu Ser Ile Asn Lys Asp Asn Ser Lys Ser Gln Val Phe Phe Lys Met
            260                 265                 270

Asn Ser Leu Gln Ser Asn Asp Thr Ala Ile Tyr Tyr Cys Ala Arg Ala
            275                 280                 285

Leu Thr Tyr Tyr Asp Tyr Glu Phe Ala Tyr Trp Gly Gln Gly Thr Leu
        290                 295                 300

Val Thr Val Ser Ala Gly Gly Gly Ser Gly Gly Gly Ser Gly
305                 310                 315                 320

Gly Gly Gly Ser Gly Gly Gly Ser Pro Glu Glu Pro Leu Val Val
                325                 330                 335

Lys Val Glu Glu Gly Asp Thr Ala Ala Leu Trp Cys Leu Lys Gly Thr
            340                 345                 350

Ser Asp Gly Pro Thr Gln Gln Leu Thr Trp Ser Arg Glu Ser Pro Leu
            355                 360                 365

Lys Pro Phe Leu Lys Tyr Ser Leu Gly Val Pro Gly Leu Gly Val His
            370                 375                 380

Val Arg Pro Asp Ala Ile Ser Val Val Ile Arg Asn Val Ser Gln Gln
385                 390                 395                 400

Met Gly Gly Phe Tyr Leu Cys Gln Pro Gly Pro Pro Ser Glu Lys Ala
                405                 410                 415

Trp Gln Pro Gly Trp Thr Val Asn Val Glu Gly Ser Gly Glu Leu Phe
            420                 425                 430

Arg Trp Asn Val Ser Asp Leu Gly Gly Leu Gly Cys Gly Leu Lys Asn
            435                 440                 445

Arg Ser Ser Glu Gly Pro Ser Ser Pro Ser Gly Lys Leu Met Ser Pro
450                 455                 460

Lys Leu Tyr Val Trp Ala Lys Asp Arg Pro Glu Ile Trp Glu Gly Glu
465                 470                 475                 480

Pro Pro Cys Leu Pro Pro Arg Asp Ser Leu Asn Gln Ser Leu Ser Arg
                485                 490                 495

Asp Leu Thr Val Ala Pro Gly Ser Thr Leu Trp Leu Ser Cys Gly Val
            500                 505                 510

Pro Pro Asp Ser Val Ser Arg Gly Pro Leu Ser Trp Thr His Val His
            515                 520                 525

Pro Lys Gly Pro Lys Ser Leu Leu Ser Leu Glu Leu Lys Asp Asp Arg
            530                 535                 540

Pro Ala Arg Asp Met Trp Val Met Gly Thr Ser Leu Met Leu Pro Arg
545                 550                 555                 560

Ala Thr Ala Gln Asp Ala Gly Lys Trp Tyr Cys His Arg Gly Asn Leu
                565                 570                 575

Thr Met Ser Phe His Leu Glu Ile Thr Ala Arg Pro Ser Arg His His
            580                 585                 590

His His His His
        595

<210> SEQ ID NO 18
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

-continued

Met Asp Phe Gly Leu Ile Phe Phe Ile Val Ala Leu Leu Lys Gly Val
1               5                   10                  15

Gln Cys Gln Gly Gln Ser Gly Gln Cys Ile Ser Pro Arg Gly Cys Pro
            20                  25                  30

Asp Gly Pro Tyr Val Met Tyr Gly Ser Ser Gly Gly Ser Gly Gly Ser
            35                  40                  45

Gly Gly Ser Gly Leu Ser Gly Arg Ser Asp Asn His Gly Ser Ser Gly
            50                  55                  60

Thr Gln Ile Leu Leu Thr Gln Ser Pro Val Ile Leu Ser Val Ser Pro
65                  70                  75                  80

Gly Glu Arg Val Ser Phe Ser Cys Arg Ala Ser Gln Ser Ile Gly Thr
            85                  90                  95

Asn Ile His Trp Tyr Gln Gln Arg Thr Asn Gly Ser Pro Arg Leu Leu
            100                 105                 110

Ile Lys Tyr Ala Ser Glu Ser Ile Ser Gly Ile Pro Ser Arg Phe Ser
            115                 120                 125

Gly Ser Gly Ser Gly Thr Asp Phe Thr Leu Ser Ile Asn Ser Val Glu
            130                 135                 140

Ser Glu Asp Ile Ala Asp Tyr Tyr Cys Gln Gln Asn Asn Asn Trp Pro
145                 150                 155                 160

Thr Thr Phe Gly Ala Gly Thr Lys Leu Glu Leu Lys Gly Ser Thr Ser
            165                 170                 175

Gly Ser Gly Lys Pro Gly Ser Gly Glu Gly Ser Thr Lys Gly Gln Val
            180                 185                 190

Gln Leu Lys Gln Ser Gly Pro Gly Leu Val Gln Pro Ser Gln Ser Leu
            195                 200                 205

Ser Ile Thr Cys Thr Val Ser Gly Phe Ser Leu Thr Asn Tyr Gly Val
            210                 215                 220

His Trp Val Arg Gln Ser Pro Gly Lys Gly Leu Glu Trp Leu Gly Val
225                 230                 235                 240

Ile Trp Ser Gly Gly Asn Thr Asp Tyr Asn Thr Pro Phe Thr Ser Arg
            245                 250                 255

Leu Ser Ile Asn Lys Asp Asn Ser Lys Ser Gln Val Phe Phe Lys Met
            260                 265                 270

Asn Ser Leu Gln Ser Asn Asp Thr Ala Ile Tyr Tyr Cys Ala Arg Ala
            275                 280                 285

Leu Thr Tyr Tyr Asp Tyr Glu Phe Ala Tyr Trp Gly Gln Gly Thr Leu
            290                 295                 300

Val Thr Val Ser Ala Gly Gly Gly Gly Ser Gly Gly Gly Gly Ser Gly
305                 310                 315                 320

Gly Gly Gly Ser Gly Gly Gly Gly Ser Pro Glu Glu Pro Leu Val Val
            325                 330                 335

Lys Val Glu Glu Gly Asp Thr Ala Ala Leu Trp Cys Leu Lys Gly Thr
            340                 345                 350

Ser Asp Gly Pro Thr Glu Gln Val Thr Trp Ser Arg Glu Ser Pro Leu
            355                 360                 365

Lys Pro Phe Leu Lys Leu Ser Leu Gly Leu Pro Gly Gly Gly His
            370                 375                 380

Val Arg Pro Asn Ala Val Ser Leu Val Ile Arg Asn Val Ser Gln Gln
385                 390                 395                 400

Met Gly Gly Phe Tyr Leu Cys Gln Pro Gly Pro Pro Ser Glu Lys Ala
            405                 410                 415

Trp Gln Pro Gly Trp Thr Val Asn Val Glu Gly Ser Gly Glu Leu Phe 420                 425                 430
Arg Trp Asn Val Ser Asp Leu Gly Gly Leu Gly Cys Gly Leu Lys Asn
                435                 440                 445

Arg Ser Ser Glu Gly Pro Ser Ser Pro Ser Gly Lys Leu Met Ser Pro
    450                 455                 460

Lys Leu Tyr Val Trp Ala Lys Asp Arg Pro Glu Ile Trp Glu Gly Glu
465                 470                 475                 480

Pro Pro Cys Leu Pro Arg Asp Ser Leu Asn Gln Ser Leu Ser Arg
                485                 490                 495

Asp Leu Thr Val Ala Pro Gly Ser Thr Leu Trp Leu Ser Cys Gly Val
                500                 505                 510

Pro Pro Asp Ser Val Ser Arg Gly Pro Leu Ser Trp Thr His Val His
                515                 520                 525

Pro Lys Gly Pro Lys Ser Leu Leu Ser Leu Glu Leu Lys Asp Asp Arg
                530                 535                 540

Pro Ala Arg Asp Met Trp Val Thr Glu Thr Gly Leu Leu Pro Arg
545                 550                 555                 560

Ala Thr Ala Gln Asp Ala Gly Lys Trp Tyr Cys His Arg Gly Asn Leu
                565                 570                 575

Thr Met Ser Phe His Leu Glu Ile Thr Ala Arg Pro Ser Arg His His
                580                 585                 590

His His His His
        595

<210> SEQ ID NO 19
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Phe Gly Leu Ile Phe Phe Ile Val Ala Leu Leu Lys Gly Val
1               5                   10                  15

Gln Cys Gln Gly Gln Ser Gly Gln Cys Ile Ser Pro Arg Gly Cys Pro
                20                  25                  30

Asp Gly Pro Tyr Val Met Tyr Gly Ser Ser Gly Gly Ser Gly Gly Ser
            35                  40                  45

Gly Gly Ser Gly Leu Ser Gly Arg Ser Asp Asn His Gly Ser Ser Gly
        50                  55                  60

Thr Gln Ile Leu Leu Thr Gln Ser Pro Val Ile Leu Ser Val Ser Pro
65                  70                  75                  80

Gly Glu Arg Val Ser Phe Ser Cys Arg Ala Ser Gln Ser Ile Gly Thr
                85                  90                  95

Asn Ile His Trp Tyr Gln Gln Arg Thr Asn Gly Ser Pro Arg Leu Leu
                100                 105                 110

Ile Lys Tyr Ala Ser Glu Ser Ile Ser Gly Ile Pro Ser Arg Phe Ser
            115                 120                 125

Gly Ser Gly Ser Gly Thr Asp Phe Thr Leu Ser Ile Asn Ser Val Glu
        130                 135                 140

Ser Glu Asp Ile Ala Asp Tyr Tyr Cys Gln Gln Asn Asn Asn Trp Pro
145                 150                 155                 160

Thr Thr Phe Gly Ala Gly Thr Lys Leu Glu Leu Lys Gly Ser Thr Ser
                165                 170                 175

Gly Ser Gly Lys Pro Gly Ser Gly Glu Ser Thr Lys Gly Gln Val
            180                 185                 190

Gln Leu Lys Gln Ser Gly Pro Gly Leu Val Gln Pro Ser Gln Ser Leu
        195                 200                 205

Ser Ile Thr Cys Thr Val Ser Gly Phe Ser Leu Thr Asn Tyr Gly Val
210                 215                 220

His Trp Val Arg Gln Ser Pro Gly Lys Gly Leu Glu Trp Leu Gly Val
225                 230                 235                 240

Ile Trp Ser Gly Gly Asn Thr Asp Tyr Asn Thr Pro Phe Thr Ser Arg
                245                 250                 255

Leu Ser Ile Asn Lys Asp Asn Ser Lys Ser Gln Val Phe Phe Lys Met
            260                 265                 270

Asn Ser Leu Gln Ser Asn Asp Thr Ala Ile Tyr Tyr Cys Ala Arg Ala
        275                 280                 285

Leu Thr Tyr Tyr Asp Tyr Glu Phe Ala Tyr Trp Gly Gln Gly Thr Leu
    290                 295                 300

Val Thr Val Ser Ala Gly Gly Gly Ser Gly Gly Gly Ser Gly
305                 310                 315                 320

Gly Gly Gly Ser Gly Gly Gly Gly Ser Pro Glu Glu Pro Leu Val Val
                325                 330                 335

Lys Val Glu Glu Gly Asp Thr Ala Ala Leu Trp Cys Leu Lys Gly Thr
            340                 345                 350

Ser Asp Gly Pro Thr Gln Gln Leu Thr Trp Ser Arg Glu Ser Pro Leu
        355                 360                 365

Lys Pro Phe Leu Lys Tyr Ser Leu Gly Val Pro Gly Leu Gly Val His
370                 375                 380

Val Arg Pro Asp Ala Ile Ser Val Val Ile Arg Asn Val Ser Gln Gln
385                 390                 395                 400

Met Gly Gly Phe Tyr Leu Cys Gln Pro Gly Pro Pro Ser Glu Lys Ala
                405                 410                 415

Trp Gln Pro Gly Trp Thr Val Asn Val Glu Gly Ser Gly Glu Leu Phe
            420                 425                 430

Arg Trp Asn Val Ser Asp Leu Gly Gly Leu Gly Cys Gly Leu Lys Asn
        435                 440                 445

Arg Ser Ser Glu Gly Pro Ser Ser Pro Ser Gly Lys Leu Met Ser Pro
450                 455                 460

Lys Leu Tyr Val Trp Ala Lys Asp Arg Pro Glu Ile Trp Glu Gly Glu
465                 470                 475                 480

Pro Pro Cys Leu Pro Pro Arg Asp Ser Leu Asn Gln Ser Leu Ser Arg
                485                 490                 495

Asp Leu Thr Val Ala Pro Gly Ser Thr Leu Trp Leu Ser Cys Gly Val
            500                 505                 510

Pro Pro Asp Ser Val Ser Arg Gly Pro Leu Ser Trp Thr His Val His
        515                 520                 525

Pro Lys Gly Pro Lys Ser Leu Leu Ser Leu Glu Leu Lys Asp Asp Arg
530                 535                 540

Pro Ala Arg Asp Met Trp Val Met Gly Thr Ser Leu Met Leu Pro Arg
545                 550                 555                 560

Ala Thr Ala Gln Asp Ala Gly Lys Trp Tyr Cys His Arg Gly Asn Leu
                565                 570                 575

Thr Met Ser Phe His Leu Glu Ile Thr Ala Arg Pro Ser Arg Gly Gly
            580                 585                 590

Gly Gly Ser Gly Gly Gly Gly Ser Gly Gly Gly Gly Ser Gly Gly Gly

Gly Ser Glu Val Gln Leu Val Glu Ser Gly Gly Leu Val Gln Pro
            610                 615                 620
Gly Gly Ser Leu Arg Leu Ser Cys Ala Ala Ser Gly Phe Asn Ile Lys
625                 630                 635                 640
Asp Thr Tyr Ile His Trp Val Arg Gln Ala Pro Gly Lys Gly Leu Glu
                645                 650                 655
Trp Val Ala Arg Ile Tyr Pro Thr Asn Gly Tyr Thr Arg Tyr Ala Asp
            660                 665                 670
Ser Val Lys Gly Arg Phe Thr Ile Ser Ala Asp Thr Ser Lys Asn Thr
        675                 680                 685
Ala Tyr Leu Gln Met Asn Ser Leu Arg Ala Glu Asp Thr Ala Val Tyr
    690                 695                 700
Tyr Cys Ser Arg Trp Gly Gly Asp Gly Phe Tyr Ala Met Asp Tyr Trp
705                 710                 715                 720
Gly Gln Gly Thr Leu Val Thr Val Ser Ser Ala Ser Thr Gly Gly Gly
                725                 730                 735
Gly Ser Gly Gly Gly Gly Ser Gly Gly Gly Gly Ser Asp Ile Gln Met
            740                 745                 750
Thr Gln Ser Pro Ser Ser Leu Ser Ala Ser Val Gly Asp Arg Val Thr
        755                 760                 765
Ile Thr Cys Arg Ala Ser Gln Asp Val Asn Thr Ala Val Ala Trp Tyr
    770                 775                 780
Gln Gln Lys Pro Gly Lys Ala Pro Lys Leu Leu Ile Tyr Ser Ala Ser
785                 790                 795                 800
Phe Leu Tyr Ser Gly Val Pro Ser Arg Phe Ser Gly Ser Arg Ser Gly
                805                 810                 815
Thr Asp Phe Thr Leu Thr Ile Ser Ser Leu Gln Pro Glu Asp Phe Ala
            820                 825                 830
Thr Tyr Tyr Cys Gln Gln His Tyr Thr Thr Pro Pro Thr Phe Gly Gln
        835                 840                 845
Gly Thr Lys Val Glu Ile Lys Arg Thr His His His His His His
    850                 855                 860

<210> SEQ ID NO 20
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Glu Phe Gly Leu Ser Trp Val Phe Leu Val Ala Leu Phe Arg Gly
1               5                   10                  15
Val Gln Cys Asp Ile Gln Met Thr Gln Ser Pro Ser Ser Leu Ser Ala
            20                  25                  30
Ser Val Gly Asp Arg Val Thr Ile Thr Cys Arg Ala Ser Gln Asp Val
        35                  40                  45
Asn Thr Ala Val Ala Trp Tyr Gln Gln Lys Pro Gly Lys Ala Pro Lys
    50                  55                  60
Leu Leu Ile Tyr Ser Ala Ser Phe Leu Tyr Ser Gly Val Pro Ser Arg
65                  70                  75                  80
Phe Ser Gly Ser Arg Ser Gly Thr Asp Phe Thr Leu Thr Ile Ser Ser
                85                  90                  95

```
Leu Gln Pro Glu Asp Phe Ala Thr Tyr Tyr Cys Gln Gln His Tyr Thr
                100                 105                 110
Thr Pro Pro Thr Phe Gly Gln Gly Thr Lys Val Glu Ile Lys Arg Thr
            115                 120                 125
Val Ala Ala Pro Ser Val Phe Ile Phe Pro Pro Ser Asp Glu Gln Leu
        130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
210                 215                 220
Thr Lys Ser Phe Asn Arg Gly Glu Cys Gly Gly Gly Ser Gly Gly
225                 230                 235                 240
Gly Gly Ser Gly Gly Gly Ser Gly Gly Gly Ser Pro Glu Glu
            245                 250                 255
Pro Leu Val Val Lys Val Glu Glu Gly Asp Thr Ala Ala Leu Trp Cys
        260                 265                 270
Leu Lys Gly Thr Ser Asp Gly Pro Thr Gln Gln Leu Thr Trp Ser Arg
            275                 280                 285
Glu Ser Pro Leu Lys Pro Phe Leu Lys Tyr Ser Leu Gly Val Pro Gly
        290                 295                 300
Leu Gly Val His Val Arg Pro Asp Ala Ile Ser Val Val Ile Arg Asn
305                 310                 315                 320
Val Ser Gln Gln Met Gly Gly Phe Tyr Leu Cys Gln Pro Gly Pro Pro
                325                 330                 335
Ser Glu Lys Ala Trp Gln Pro Gly Trp Thr Val Asn Val Glu Gly Ser
            340                 345                 350
Gly Glu Leu Phe Arg Trp Asn Val Ser Asp Leu Gly Gly Leu Gly Cys
        355                 360                 365
Gly Leu Lys Asn Arg Ser Ser Glu Gly Pro Ser Ser Pro Ser Gly Lys
370                 375                 380
Leu Met Ser Pro Lys Leu Tyr Val Trp Ala Lys Asp Arg Pro Glu Ile
385                 390                 395                 400
Trp Glu Gly Glu Pro Pro Cys Leu Pro Pro Arg Asp Ser Leu Asn Gln
                405                 410                 415
Ser Leu Ser Arg Asp Leu Thr Val Ala Pro Gly Ser Thr Leu Trp Leu
            420                 425                 430
Ser Cys Gly Val Pro Pro Asp Ser Val Ser Arg Gly Pro Leu Ser Trp
        435                 440                 445
Thr His Val His Pro Lys Gly Pro Lys Ser Leu Leu Ser Leu Glu Leu
450                 455                 460
Lys Asp Asp Arg Pro Ala Arg Asp Met Trp Val Met Gly Thr Ser Leu
465                 470                 475                 480
Met Leu Pro Arg Ala Thr Ala Gln Asp Ala Gly Lys Trp Tyr Cys His
                485                 490                 495
Arg Gly Asn Leu Thr Met Ser Phe His Leu Glu Ile Thr Ala Arg Pro
            500                 505                 510
Ser Arg His His His His His His
```

```
                515                 520

<210> SEQ ID NO 21
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350
```

```
Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly
465

<210> SEQ ID NO 22
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Phe Gly Leu Ser Trp Val Phe Leu Val Ala Leu Phe Arg Gly
1               5                   10                  15

Val Gln Cys Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Gly Ser Gly Gly Gly
225                 230                 235                 240
```

Gly Ser Gly Gly Gly Ser Gly Gly Gly Ser Pro Glu Glu Pro
            245                 250                 255

Leu Val Val Lys Val Glu Glu Gly Asp Thr Ala Ala Leu Trp Cys Leu
            260                 265                 270

Lys Gly Thr Ser Asp Gly Pro Thr Gln Gln Leu Thr Trp Ser Arg Glu
            275                 280                 285

Ser Pro Leu Lys Pro Phe Leu Lys Tyr Ser Leu Gly Val Pro Gly Leu
            290                 295                 300

Gly Val His Val Arg Pro Asp Ala Ile Ser Val Val Ile Arg Asn Val
305                 310                 315                 320

Ser Gln Gln Met Gly Gly Phe Tyr Leu Cys Gln Pro Gly Pro Pro Ser
            325                 330                 335

Glu Lys Ala Trp Gln Pro Gly Trp Thr Val Asn Val Glu Gly Ser Gly
            340                 345                 350

Glu Leu Phe Arg Trp Asn Val Ser Asp Leu Gly Gly Leu Gly Cys Gly
            355                 360                 365

Leu Lys Asn Arg Ser Ser Glu Gly Pro Ser Ser Pro Ser Gly Lys Leu
            370                 375                 380

Met Ser Pro Lys Leu Tyr Val Trp Ala Lys Asp Arg Pro Glu Ile Trp
385                 390                 395                 400

Glu Gly Glu Pro Pro Cys Leu Pro Pro Arg Asp Ser Leu Asn Gln Ser
            405                 410                 415

Leu Ser Arg Asp Leu Thr Val Ala Pro Gly Ser Thr Leu Trp Leu Ser
            420                 425                 430

Cys Gly Val Pro Pro Asp Ser Val Ser Arg Gly Pro Leu Ser Trp Thr
            435                 440                 445

His Val His Pro Lys Gly Pro Lys Ser Leu Leu Ser Leu Glu Leu Lys
            450                 455                 460

Asp Asp Arg Pro Ala Arg Asp Met Trp Val Met Gly Thr Ser Leu Met
465                 470                 475                 480

Leu Pro Arg Ala Thr Ala Gln Asp Ala Gly Lys Trp Tyr Cys His Arg
            485                 490                 495

Gly Asn Leu Thr Met Ser Phe His Leu Glu Ile Thr Ala Arg Pro Ser
            500                 505                 510

Arg His His His His His His
        515

<210> SEQ ID NO 23
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Phe Gly Leu Ser Trp Val Phe Leu Val Ala Leu Phe Arg Gly
1               5                   10                  15

Val Gln Cys Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn

```
            65                  70                  75                  80
Gln Lys Phe Lys Gly Lys Ala Thr Leu Thr Ala Asp Lys Ser Ser Ser
                    85                  90                  95
Thr Ala Tyr Met Gln Leu Ser Ser Leu Thr Ser Glu Asp Ser Ala Val
                100                 105                 110
Tyr Tyr Cys Ala Arg Ser Thr Tyr Gly Gly Asp Trp Tyr Phe Asn
            115                 120                 125
Val Trp Gly Ala Gly Thr Thr Val Thr Val Ser Ala Ala Ser Thr Lys
            130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
            210                 215                 220
Val Asn His Lys Pro Ser Asn Thr Lys Val Asp Lys Lys Ala Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
            290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Asp Glu Leu Thr Lys Asn
            370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
            450                 455                 460
Ser Leu Ser Pro Gly
465

<210> SEQ ID NO 24
```

<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Ala
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn

```
                370                 375                 380
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly
465

<210> SEQ ID NO 25
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Phe Gly Leu Ser Trp Val Phe Leu Val Ala Leu Phe Arg Gly
1               5                   10                  15

Val Gln Cys Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255
```

```
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Ala
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Gln Glu Pro Gly Gln
    370                 375                 380

Pro Asp Leu Pro Gly Gln Arg Leu Leu Ser Gln Arg His Arg Arg Gly
385                 390                 395                 400

Val Gly Glu Gln Trp Ala Ala Gly Glu Gln Leu Gln Asp His Ala Ser
                405                 410                 415

Arg Ala Gly Leu Arg Arg Leu Leu Pro Leu Gln Ala His Arg
            420                 425                 430

Gly Gln Glu Gln Val Ala Ala Gly Glu Arg Leu Leu Met Leu Arg Asp
        435                 440                 445

Ala Arg Gly Ser Ala Gln Pro Leu His Ala Glu Glu Pro Leu Pro Val
    450                 455                 460

Ser Gly Leu Val Ile
465

<210> SEQ ID NO 26
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140
```

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
            245                 250                 255

Gly Lys Trp Tyr Cys Ser Arg Gly Asn Val Thr Thr Ser Tyr His Leu
        260                 265                 270

Glu Ile Thr Ala Arg Pro Val Lys Ala His Ser Asp Leu Arg Thr Gly
            275                 280                 285

Gly Trp Lys Gly Gly Gly Ser Gly Gly Gly Ser Gly Gly Gly
290                 295                 300

Gly Ser Gly Gly Gly Ser Gln Val Gln Leu Gln Ala Ser Gly Gly
305                 310                 315                 320

Gly Leu Val Gln Ala Gly Gly Ser Leu Arg Leu Ser Cys Ala Ala Ser
            325                 330                 335

Gly Ser Ile Phe Ala Ile Asn Glu Ile Asn Leu Met Gly Trp Tyr Arg
        340                 345                 350

Gln Ala Pro Gly Lys Gln Arg Glu Leu Val Ala Ala Cys Ala Ser Asp
            355                 360                 365

Gly Asn Thr Tyr Tyr Ala Asp Ser Val Lys Gly Arg Phe Thr Ile Ser
        370                 375                 380

Arg Asp Asn Ala Glu Lys Thr Val Tyr Leu Gln Met Asn Asn Leu Lys
385                 390                 395                 400

Pro Asp Asp Thr Ala Val Tyr Tyr Cys Asp Ala Asn Ser Arg Gly Asn
            405                 410                 415

Tyr Tyr Ser Gly Gln Gly Thr Gln Val Thr Val Ser Ser Thr Ser Gly
        420                 425                 430

Pro Gly Gly Gln Gly Ala Glu Gln Lys Leu Ile Ser Glu Glu Asp Leu
            435                 440                 445

Gly Ala His His His His His Gly Ala Ser
        450                 455

<210> SEQ ID NO 27
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Glu Phe Gly Leu Ser Trp Val Phe Leu Val Ala Leu Phe Arg Gly
1               5                   10                  15

Val Gln Cys Gln Val Gln Leu Gln Glu Ser Gly Gly Gly Leu Val Gln
            20                  25                  30

Ala Gly Gly Ser Leu Arg Leu Ser Cys Val Ala Ser Gly Ser Ile Arg

```
                35                  40                  45
Ser Ile Asn Val Met Gly Trp Tyr Arg Gln Ala Pro Gly Lys Gln Arg
 50                  55                  60

Glu Leu Val Ala Ala Cys Ala Ser Asp Gly Asn Thr Tyr Tyr Ala Asp
 65                  70                  75                  80

Ser Val Lys Gly Arg Phe Thr Ile Ser Arg Asp Asn Ala Glu Lys Thr
                 85                  90                  95

Val Tyr Leu Gln Met Asn Asn Leu Lys Pro Asp Asp Thr Ala Val Tyr
            100                 105                 110

Tyr Cys Asp Ala Asn Ser Arg Gly Asn Tyr Tyr Ser Gly Gln Gly Thr
        115                 120                 125

Gln Val Thr Val Ser Ser Thr Ser Gly Pro Gly Gln Gly Ala Gly
    130                 135                 140

Gly Gly Gly Ser Gly Gly Gly Ser Gly Gly Gly Ser Gly Gly
145                 150                 155                 160

Gly Gly Ser Pro Glu Glu Pro Leu Val Val Lys Val Glu Glu Gly Asp
                165                 170                 175

Thr Ala Ala Leu Trp Cys Leu Lys Gly Thr Ser Asp Gly Pro Thr Gln
            180                 185                 190

Gln Leu Thr Trp Ser Arg Glu Ser Pro Leu Lys Pro Phe Leu Lys Tyr
        195                 200                 205

Ser Leu Gly Val Pro Gly Leu Gly Val His Val Arg Pro Asp Ala Ile
    210                 215                 220

Ser Val Val Ile Arg Asn Val Ser Gln Gln Met Gly Gly Phe Tyr Leu
225                 230                 235                 240

Cys Gln Pro Gly Pro Pro Ser Glu Lys Ala Trp Gln Pro Gly Trp Thr
                245                 250                 255

Val Asn Val Glu Gly Ser Gly Glu Leu Phe Arg Trp Asn Val Ser Asp
            260                 265                 270

Leu Gly Gly Leu Gly Cys Gly Leu Lys Asn Arg Ser Ser Glu Gly Pro
        275                 280                 285

Ser Ser Pro Ser Gly Lys Leu Met Ser Pro Lys Leu Tyr Val Trp Ala
    290                 295                 300

Lys Asp Arg Pro Glu Ile Trp Glu Gly Glu Pro Pro Cys Leu Pro Pro
305                 310                 315                 320

Arg Asp Ser Leu Asn Gln Ser Leu Ser Arg Asp Leu Thr Val Ala Pro
                325                 330                 335

Gly Ser Thr Leu Trp Leu Ser Cys Gly Val Pro Pro Asp Ser Val Ser
            340                 345                 350

Arg Gly Pro Leu Ser Trp Thr His Val His Pro Lys Gly Pro Lys Ser
        355                 360                 365

Leu Leu Ser Leu Glu Leu Lys Asp Asp Arg Pro Ala Arg Asp Met Trp
    370                 375                 380

Val Met Gly Thr Ser Leu Met Leu Pro Arg Ala Thr Ala Gln Asp Ala
385                 390                 395                 400

Gly Lys Trp Tyr Cys His Arg Gly Asn Leu Thr Met Ser Phe His Leu
                405                 410                 415

Glu Ile Thr Ala Arg Pro Ser Arg His His His His His
            420                 425                 430

<210> SEQ ID NO 28
<211> LENGTH: 433
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 28

Met Glu Phe Gly Leu Ser Trp Val Phe Leu Val Ala Leu Phe Arg Gly
1               5                   10                  15

Val Gln Cys Gln Val Gln Leu Gln Ala Ser Gly Gly Gly Leu Val Gln
            20                  25                  30

Ala Gly Gly Ser Leu Arg Leu Ser Cys Ala Ala Ser Gly Ser Ile Phe
        35                  40                  45

Ala Ile Asn Glu Ile Asn Leu Met Gly Trp Tyr Arg Gln Ala Pro Gly
    50                  55                  60

Lys Gln Arg Glu Leu Val Ala Ala Cys Ala Ser Asp Gly Asn Thr Tyr
65                  70                  75                  80

Tyr Ala Asp Ser Val Lys Gly Arg Phe Thr Ile Ser Arg Asp Asn Ala
                85                  90                  95

Glu Lys Thr Val Tyr Leu Gln Met Asn Asn Leu Lys Pro Asp Asp Thr
            100                 105                 110

Ala Val Tyr Tyr Cys Asp Ala Asn Ser Arg Gly Asn Tyr Tyr Ser Gly
        115                 120                 125

Gln Gly Thr Gln Val Thr Val Ser Ser Thr Ser Gly Pro Gly Gly Gln
    130                 135                 140

Gly Ala Gly Gly Gly Ser Gly Gly Gly Gly Ser Gly Gly Gly Gly Gly
145                 150                 155                 160

Ser Gly Gly Gly Ser Pro Glu Glu Pro Leu Val Val Lys Val Glu
                165                 170                 175

Glu Gly Asp Thr Ala Ala Leu Trp Cys Leu Lys Gly Thr Ser Asp Gly
            180                 185                 190

Pro Thr Gln Gln Leu Thr Trp Ser Arg Glu Ser Pro Leu Lys Pro Phe
        195                 200                 205

Leu Lys Tyr Ser Leu Gly Val Pro Gly Leu Gly Val His Val Arg Pro
    210                 215                 220

Asp Ala Ile Ser Val Ile Arg Asn Val Ser Gln Gln Met Gly Gly
225                 230                 235                 240

Phe Tyr Leu Cys Gln Pro Gly Pro Ser Glu Lys Ala Trp Gln Pro
                245                 250                 255

Gly Trp Thr Val Asn Val Glu Gly Ser Gly Glu Leu Phe Arg Trp Asn
            260                 265                 270

Val Ser Asp Leu Gly Gly Leu Gly Cys Gly Leu Lys Asn Arg Ser Ser
        275                 280                 285

Glu Gly Pro Ser Ser Pro Ser Gly Lys Leu Met Ser Pro Lys Leu Tyr
    290                 295                 300

Val Trp Ala Lys Asp Arg Pro Glu Ile Trp Glu Gly Glu Pro Pro Cys
305                 310                 315                 320

Leu Pro Pro Arg Asp Ser Leu Asn Gln Ser Leu Ser Arg Asp Leu Thr
                325                 330                 335

Val Ala Pro Gly Ser Thr Leu Trp Leu Ser Cys Gly Val Pro Pro Asp
            340                 345                 350

Ser Val Ser Arg Gly Pro Leu Ser Trp Thr His Val His Pro Lys Gly
        355                 360                 365

Pro Lys Ser Leu Leu Ser Leu Glu Leu Lys Asp Asp Arg Pro Ala Arg
    370                 375                 380

Asp Met Trp Val Met Gly Thr Ser Leu Met Leu Pro Arg Ala Thr Ala
```

Gln Asp Ala Gly Lys Trp Tyr Cys His Arg Gly Asn Leu Thr Met Ser
    385                 390                 395                 400

Phe His Leu Glu Ile Thr Ala Arg Pro Ser Arg His His His His
            405                 410                 415

His
    420                 425                 430

<210> SEQ ID NO 29
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Glu Phe Gly Leu Ser Trp Val Phe Leu Val Ala Leu Phe Arg Gly
1               5                   10                  15

Val Gln Cys Gln Val Gln Leu Gln Glu Ser Gly Gly Gly Leu Val Gln
            20                  25                  30

Ala Gly Gly Ser Leu Arg Leu Ser Cys Ala Ala Ser Gly Ser Ile Phe
        35                  40                  45

Ala Ile Asn Glu Ile Asn Leu Met Gly Trp Tyr Arg Gln Ala Pro Gly
    50                  55                  60

Lys Gln Arg Glu Leu Val Ala Ala Cys Ala Ser Asp Gly Asn Thr Tyr
65                  70                  75                  80

Tyr Ala Asp Ser Val Lys Gly Arg Phe Thr Ile Ser Arg Asp Asn Ala
                85                  90                  95

Glu Lys Thr Val Tyr Leu Gln Met Asn Asn Leu Lys Pro Asp Asp Thr
            100                 105                 110

Ala Val Tyr Tyr Cys Asp Ala Asn Ser Arg Gly Asn Tyr Tyr Ser Gly
        115                 120                 125

Gln Gly Thr Gln Val Thr Val Ser Ser Thr Ser Gly Pro Gly Gly Gln
    130                 135                 140

Gly Ala Gly Gly Gly Ser Gly Gly Gly Gly Ser Gly Gly Gly Gly Gly
145                 150                 155                 160

Ser Gly Gly Gly Ser Pro Glu Glu Pro Leu Val Val Lys Val Glu
                165                 170                 175

Glu Gly Asp Thr Ala Ala Leu Trp Cys Leu Lys Gly Thr Ser Asp Gly
            180                 185                 190

Pro Thr Gln Gln Leu Thr Trp Ser Arg Glu Ser Pro Leu Lys Pro Phe
        195                 200                 205

Leu Lys Tyr Ser Leu Gly Val Pro Gly Leu Gly Val His Val Arg Pro
    210                 215                 220

Asp Ala Ile Ser Val Val Ile Arg Asn Val Ser Gln Gln Met Gly Gly
225                 230                 235                 240

Phe Tyr Leu Cys Gln Pro Gly Pro Pro Ser Glu Lys Ala Trp Gln Pro
                245                 250                 255

Gly Trp Thr Val Asn Val Glu Gly Ser Gly Glu Leu Phe Arg Trp Asn
            260                 265                 270

Val Ser Asp Leu Gly Gly Leu Gly Cys Gly Leu Lys Asn Arg Ser Ser
        275                 280                 285

Glu Gly Pro Ser Ser Pro Ser Gly Lys Leu Met Ser Pro Lys Leu Tyr
    290                 295                 300

Val Trp Ala Lys Asp Arg Pro Glu Ile Trp Glu Gly Glu Pro Pro Cys

```
                305                 310                 315                 320
Leu Pro Pro Arg Asp Ser Leu Asn Gln Ser Leu Ser Arg Asp Leu Thr
                325                 330                 335

Val Ala Pro Gly Ser Thr Leu Trp Leu Ser Cys Gly Val Pro Pro Asp
                340                 345                 350

Ser Val Ser Arg Gly Pro Leu Ser Trp Thr His Val His Pro Lys Gly
                355                 360                 365

Pro Lys Ser Leu Leu Ser Leu Glu Leu Lys Asp Asp Arg Pro Ala Arg
                370                 375                 380

Asp Met Trp Val Met Gly Thr Ser Leu Met Leu Pro Arg Ala Thr Ala
385                 390                 395                 400

Gln Asp Ala Gly Lys Trp Tyr Cys His Arg Gly Asn Leu Thr Met Ser
                405                 410                 415

Phe His Leu Glu Ile Thr Ala Arg Pro Ser Arg His His His His
                420                 425                 430
His

<210> SEQ ID NO 30
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Glu Phe Gly Leu Ser Trp Val Phe Leu Val Ala Leu Phe Arg Gly
1               5                   10                  15

Val Gln Cys Gln Val Gln Leu Gln Glu Ser Gly Gly Gly Leu Val Gln
                20                  25                  30

Val Gly Glu Ser Leu Arg Leu Ser Cys Val Val Ser Gly Asp Thr Arg
                35                  40                  45

Ser Ile Asn Leu Met Gly Trp Tyr Arg Gln Ala Pro Gly Lys Gln Arg
    50                  55                  60

Glu Leu Val Ala Ala Cys Ala Ser Asp Gly Asn Thr Tyr Tyr Ala Asp
65                  70                  75                  80

Ser Val Lys Gly Arg Phe Thr Ile Ser Arg Asp Asn Ala Glu Lys Thr
                85                  90                  95

Val Tyr Leu Gln Met Asn Asn Leu Lys Pro Asp Asp Thr Ala Val Tyr
                100                 105                 110

Tyr Cys Asp Ala Asn Ser Arg Gly Asn Tyr Tyr Ser Gly Gln Gly Thr
                115                 120                 125

Leu Val Thr Val Ser Ser Thr Ser Gly Pro Gly Gly Gln Gly Ala Gly
                130                 135                 140

Gly Gly Gly Ser Gly Gly Gly Ser Gly Gly Gly Gly Ser Gly Gly
145                 150                 155                 160

Gly Gly Ser Pro Glu Glu Pro Leu Val Val Lys Val Glu Glu Gly Asp
                165                 170                 175

Thr Ala Ala Leu Trp Cys Leu Lys Gly Thr Ser Asp Gly Pro Thr Gln
                180                 185                 190

Gln Leu Thr Trp Ser Arg Glu Ser Pro Leu Lys Pro Phe Leu Lys Tyr
                195                 200                 205

Ser Leu Gly Val Pro Gly Leu Gly Val His Val Arg Pro Asp Ala Ile
                210                 215                 220

Ser Val Val Ile Arg Asn Val Ser Gln Gln Met Gly Gly Phe Tyr Leu
```

```
            225                 230                 235                 240
Cys Gln Pro Gly Pro Ser Glu Lys Ala Trp Gln Pro Gly Trp Thr
            245                 250                 255

Val Asn Val Glu Gly Ser Gly Glu Leu Phe Arg Trp Asn Val Ser Asp
            260                 265                 270

Leu Gly Gly Leu Gly Cys Gly Leu Lys Asn Arg Ser Ser Glu Gly Pro
            275                 280                 285

Ser Ser Pro Ser Gly Lys Leu Met Ser Pro Lys Leu Tyr Val Trp Ala
290                 295                 300

Lys Asp Arg Pro Glu Ile Trp Glu Gly Glu Pro Pro Cys Leu Pro Pro
305                 310                 315                 320

Arg Asp Ser Leu Asn Gln Ser Leu Ser Arg Asp Leu Thr Val Ala Pro
                325                 330                 335

Gly Ser Thr Leu Trp Leu Ser Cys Gly Val Pro Pro Asp Ser Val Ser
            340                 345                 350

Arg Gly Pro Leu Ser Trp Thr His Val His Pro Lys Gly Pro Lys Ser
            355                 360                 365

Leu Leu Ser Leu Glu Leu Lys Asp Asp Arg Pro Ala Arg Asp Met Trp
370                 375                 380

Val Met Gly Thr Ser Leu Met Leu Pro Arg Ala Thr Ala Gln Asp Ala
385                 390                 395                 400

Gly Lys Trp Tyr Cys His Arg Gly Asn Leu Thr Met Ser Phe His Leu
                405                 410                 415

Glu Ile Thr Ala Arg Pro Ser Arg His His His His His His
            420                 425                 430

<210> SEQ ID NO 31
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160
```

```
Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
        260                 265                 270

Glu Ile Thr Ala Arg Pro Gly Gly Gly Ser Gly Gly Gly Ser
    275                 280                 285

Gly Gly Gly Gly Ser Gly Gly Gly Ser Glu Val Gln Leu Val Glu
290                 295                 300

Ser Gly Gly Gly Leu Val Gln Pro Gly Gly Ser Leu Arg Leu Ser Cys
305                 310                 315                 320

Ala Ala Ser Gly Phe Asn Ile Lys Asp Thr Tyr Ile His Trp Val Arg
                325                 330                 335

Gln Ala Pro Gly Lys Gly Leu Glu Trp Val Ala Arg Ile Tyr Pro Thr
        340                 345                 350

Asn Gly Tyr Thr Arg Tyr Ala Asp Ser Val Lys Gly Arg Phe Thr Ile
    355                 360                 365

Ser Ala Asp Thr Ser Lys Asn Thr Ala Tyr Leu Gln Met Asn Ser Leu
370                 375                 380

Arg Ala Glu Asp Thr Ala Val Tyr Tyr Cys Ser Arg Trp Gly Gly Asp
385                 390                 395                 400

Gly Phe Tyr Ala Met Asp Tyr Trp Gly Gln Gly Thr Leu Val Thr Val
                405                 410                 415

Ser Ser Ala Ser Thr Gly Gly Gly Gly Ser Gly Gly Gly Gly Ser Gly
        420                 425                 430

Gly Gly Gly Ser Asp Ile Gln Met Thr Gln Ser Pro Ser Ser Leu Ser
    435                 440                 445

Ala Ser Val Gly Asp Arg Val Thr Ile Thr Cys Arg Ala Ser Gln Asp
450                 455                 460

Val Asn Thr Ala Val Ala Trp Tyr Gln Gln Lys Pro Gly Lys Ala Pro
465                 470                 475                 480

Lys Leu Leu Ile Tyr Ser Ala Ser Phe Leu Tyr Ser Gly Val Pro Ser
                485                 490                 495

Arg Phe Ser Gly Ser Arg Ser Gly Thr Asp Phe Thr Leu Thr Ile Ser
        500                 505                 510

Ser Leu Gln Pro Glu Asp Phe Ala Thr Tyr Tyr Cys Gln Gln His Tyr
    515                 520                 525

Thr Thr Pro Pro Thr Phe Gly Gln Gly Thr Lys Val Glu Ile Lys Arg
530                 535                 540

Thr His His His His His
545                 550
```

<210> SEQ ID NO 32
<211> LENGTH: 567
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 32

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285

Gly Trp Lys Gly Gly Gly Gly Ser Gly Gly Gly Ser Gly Gly Gly
    290                 295                 300

Gly Ser Gly Gly Gly Gly Ser Gln Val Lys Leu Gln Glu Ser Gly Ala
305                 310                 315                 320

Glu Leu Val Lys Pro Gly Ala Ser Val Lys Met Ser Cys Lys Ala Ser
                325                 330                 335

Gly Tyr Thr Phe Thr Ser Tyr Asn Met His Trp Val Lys Gln Thr Pro
            340                 345                 350

Gly Gln Gly Leu Glu Trp Ile Gly Ala Ile Tyr Pro Gly Asn Gly Asp
        355                 360                 365

Thr Ser Tyr Asn Gln Lys Phe Lys Gly Lys Ala Thr Leu Thr Ala Asp
    370                 375                 380

-continued

```
Lys Ser Ser Ser Thr Ala Tyr Met Gln Leu Ser Ser Leu Thr Ser Glu
385                 390                 395                 400

Asp Ser Ala Asp Tyr Tyr Cys Ala Arg Ser Asn Tyr Tyr Gly Ser Ser
                405                 410                 415

Tyr Trp Phe Phe Asp Val Trp Gly Gln Gly Thr Thr Val Thr Val Ser
            420                 425                 430

Ser Ala Ser Thr Gly Gly Gly Ser Gly Gly Gly Ser Gly Gly
        435                 440                 445

Gly Gly Ser Asp Ile Glu Leu Thr Gln Ser Pro Thr Ile Leu Ser Ala
    450                 455                 460

Ser Pro Gly Glu Lys Val Thr Met Thr Cys Arg Ala Ser Ser Ser Val
465                 470                 475                 480

Asn Tyr Met Asp Trp Tyr Gln Lys Lys Pro Gly Ser Ser Pro Lys Pro
                485                 490                 495

Trp Ile Tyr Ala Thr Ser Asn Leu Ala Ser Gly Val Pro Ala Arg Phe
            500                 505                 510

Ser Gly Ser Gly Ser Gly Thr Ser Tyr Ser Leu Thr Ile Ser Arg Val
        515                 520                 525

Glu Ala Glu Asp Ala Ala Thr Tyr Tyr Cys Gln Gln Trp Ser Phe Asn
530                 535                 540

Pro Pro Thr Phe Gly Gly Gly Thr Lys Leu Glu Ile Lys Arg Ala Ala
545                 550                 555                 560

Ala His His His His His His
                565
```

```
<210> SEQ ID NO 33
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Thr Ala Val Leu Pro Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
        50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175
```

```
Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Pro Arg Ala Thr Ala Gln Asp Ala
            245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
            275                 280                 285

Gly Trp Lys Gly Gly Gly Ser Gly Gly Gly Ser Gly Gly Gly
            290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Cys Arg Gln
            325                 330                 335

Arg Cys Ala Asp Ser Tyr Arg Ile Thr Tyr Gly Glu Thr Gly Gly Asn
            340                 345                 350

Ser Pro Val Gln Glu Phe Thr Val Pro Gly Ser Trp Lys Thr Ala Thr
            355                 360                 365

Ile Ser Gly Leu Lys Pro Gly Val Asp Tyr Thr Ile Thr Val Tyr Val
            370                 375                 380

Val Thr His Tyr Tyr Gly Trp Asp Arg Tyr Ser His Pro Ile Ser Ile
385                 390                 395                 400

Asn Tyr Arg Thr Glu Ile Asp Lys Pro Ser Gln His His His His
            405                 410                 415

His

<210> SEQ ID NO 34
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Ala Leu Trp Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
        50                  55                  60

Ser Leu Gly Val Pro Gly Met Gly Val His Val Arg Pro Asn Ala Val
65                  70                  75                  80

Ser Leu Val Ile Ser Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110
```

```
Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Arg Asp Met Thr Val Ala Pro
            180                 185                 190

Gly Ser Thr Leu Trp Leu Ser Cys Gly Val Pro Asp Ser Val Ser
        195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Val Leu Pro Arg Ala Thr Ala Gln Asp Ala
                245                 250                 255

Gly Lys Trp Tyr Cys His Arg Gly Asn Val Thr Thr Ser Tyr His Leu
            260                 265                 270

Glu Ile Thr Ala Arg Pro Val Ser Ala His Thr Pro Leu Arg Thr Gly
        275                 280                 285

Gly Trp Lys Gly Gly Gly Ser Gly Gly Gly Ser Gly Gly Gly
        290                 295                 300

Gly Ser Gly Gly Gly Ser Val Ser Asp Val Pro Arg Asp Leu Glu
305                 310                 315                 320

Val Val Ala Ala Thr Pro Thr Ser Leu Leu Ile Ser Trp Cys Arg Gln
                325                 330                 335

Arg Cys Ala Asp Ser Tyr Arg Ile Thr Tyr Gly Glu Thr Gly Gly Asn
            340                 345                 350

Ser Pro Val Gln Glu Phe Thr Val Pro Gly Ser Trp Lys Thr Ala Thr
        355                 360                 365

Ile Ser Gly Leu Lys Pro Gly Val Asp Tyr Thr Ile Thr Val Tyr Val
        370                 375                 380

Val Thr His Tyr Tyr Gly Trp Asp Arg Tyr Ser His Pro Ile Ser Ile
385                 390                 395                 400

Asn Tyr Arg Thr Glu Ile Asp Lys Pro Ser Gln His His His His
                405                 410                 415

His

<210> SEQ ID NO 35
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45
```

```
Lys Asp Thr Tyr Ile His Trp Val Arg Gln Ala Pro Gly Lys Gly Leu
 50                  55                  60
Glu Trp Val Ala Arg Ile Tyr Pro Thr Asn Gly Tyr Thr Arg Tyr Ala
 65                  70                  75                  80
Asp Ser Val Lys Gly Arg Phe Thr Ile Ser Ala Asp Thr Ser Lys Asn
                 85                  90                  95
Thr Ala Tyr Leu Gln Met Asn Ser Leu Arg Ala Glu Asp Thr Ala Val
                100                 105                 110
Tyr Tyr Cys Ser Arg Trp Gly Asp Gly Phe Tyr Ala Met Asp Tyr
            115                 120                 125
Trp Gly Gln Gly Thr Leu Val Thr Val Ser Ser Ala Ser Thr Gly Gly
            130                 135                 140
Gly Gly Ser Gly Gly Gly Ser Gly Gly Gly Ser Asp Ile Gln
145                 150                 155                 160
Met Thr Gln Ser Pro Ser Ser Leu Ser Ala Ser Val Gly Asp Arg Val
                165                 170                 175
Thr Ile Thr Cys Arg Ala Ser Gln Asp Val Asn Thr Ala Val Ala Trp
                180                 185                 190
Tyr Gln Gln Lys Pro Gly Lys Ala Pro Lys Leu Leu Ile Tyr Ser Ala
            195                 200                 205
Ser Phe Leu Tyr Ser Gly Val Pro Ser Arg Phe Ser Gly Ser Arg Ser
210                 215                 220
Gly Thr Asp Phe Thr Leu Thr Ile Ser Ser Leu Gln Pro Glu Asp Phe
225                 230                 235                 240
Ala Thr Tyr Tyr Cys Gln Gln His Tyr Thr Thr Pro Pro Thr Phe Gly
            245                 250                 255
Gln Gly Thr Lys Val Glu Ile Lys Arg Thr Gly Gly Gly Gly Ser Gly
            260                 265                 270
Gly Gly Ser Gly Gly Gly Ser Gly Gly Gly Ser Pro Glu
            275                 280                 285
Glu Pro Leu Val Val Lys Val Glu Glu Gly Asp Thr Ala Val Leu Pro
    290                 295                 300
Cys Leu Lys Gly Thr Ser Asp Gly Pro Thr Gln Gln Leu Thr Trp Ser
305                 310                 315                 320
Arg Glu Ser Pro Leu Lys Pro Phe Leu Lys Tyr Ser Leu Gly Val Pro
                325                 330                 335
Gly Leu Gly Val His Val Arg Pro Asp Ala Ile Ser Val Val Ile Arg
                340                 345                 350
Asn Val Ser Gln Gln Met Gly Gly Phe Tyr Leu Cys Gln Pro Gly Pro
            355                 360                 365
Pro Ser Glu Lys Ala Trp Gln Pro Gly Trp Thr Val Asn Val Glu Gly
370                 375                 380
Ser Gly Glu Leu Phe Arg Trp Asn Val Ser Asp Leu Gly Gly Leu Gly
385                 390                 395                 400
Cys Gly Leu Lys Asn Arg Ser Ser Glu Gly Pro Ser Ser Pro Ser Gly
                405                 410                 415
Lys Leu Met Ser Pro Lys Leu Tyr Val Trp Ala Lys Asp Arg Pro Glu
            420                 425                 430
Ile Trp Glu Gly Glu Pro Pro Cys Leu Pro Pro Arg Asp Ser Leu Asn
            435                 440                 445
Gln Ser Leu Ser Gln Asp Leu Thr Met Ala Pro Gly Ser Thr Leu Trp
450                 455                 460
```

```
Leu Ser Cys Gly Val Pro Pro Asp Ser Val Ser Arg Gly Pro Leu Ser
465                 470                 475                 480

Trp Thr His Val His Pro Lys Gly Pro Lys Ser Leu Leu Ser Leu Glu
                485                 490                 495

Leu Lys Asp Asp Arg Pro Ala Arg Glu Met Ile Val Asp Glu Thr Gly
            500                 505                 510

Leu Leu Leu Pro Arg Ala Thr Ala Gln Asp Ala Gly Lys Trp Tyr Cys
        515                 520                 525

Ser Arg Gly Asn Val Thr Thr Ser Tyr His Leu Glu Ile Thr Ala Arg
    530                 535                 540

Pro Val Lys Ala His Ser Asp Leu Arg Thr Gly Gly Trp Lys His His
545                 550                 555                 560

His His His His

<210> SEQ ID NO 36
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Glu Phe Gly Leu Ser Trp Val Phe Leu Val Ala Leu Phe Arg Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Met His Trp Val Arg Gln Ala Pro Gly Gln Gly Leu
    50                  55                  60

Glu Trp Met Gly Arg Val Asn Pro Asn Arg Arg Gly Thr Thr Tyr Asn
65                  70                  75                  80

Gln Lys Phe Glu Gly Arg Val Thr Met Thr Thr Asp Thr Ser Thr Ser
                85                  90                  95

Thr Ala Tyr Met Glu Leu Arg Ser Leu Arg Ser Asp Thr Ala Val
            100                 105                 110

Tyr Tyr Cys Ala Arg Ala Asn Trp Leu Asp Tyr Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Ala Ala Gly Gly Pro Ser Val Phe Leu
                245                 250                 255
```

```
Phe Pro Pro Lys Pro Lys Asp Thr Leu Met Ile Ser Arg Thr Pro Glu
                260                 265                 270

Val Thr Cys Val Val Val Asp Val Ser Gln Glu Asp Pro Glu Val Gln
            275                 280                 285

Phe Asn Trp Tyr Val Asp Gly Val Glu Val His Asn Ala Lys Thr Lys
        290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Arg Leu Thr Val Asp Lys Ser Arg Trp Gln
        420                 425                 430

Glu Gly Asn Val Phe Ser Cys Ser Val Met His Glu Ala Leu His Asn
                435                 440                 445

His Tyr Thr Gln Lys Ser Leu Ser Leu Ser Leu Gly
    450                 455                 460

<210> SEQ ID NO 37
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Ser Val Ser Ser Ser
        35                  40                  45

Val Ser Ser Ile Tyr Leu His Trp Tyr Gln Gln Lys Pro Gly Lys Ala
    50                  55                  60

Pro Lys Leu Leu Ile Tyr Ser Thr Ser Asn Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Val Tyr
            100                 105                 110

Ser Gly Tyr Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160
```

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Asp Lys Thr His Thr
225                 230                 235                 240

Ser Pro Pro Ser Pro Ala Pro Glu Ala Ala Gly Gly Pro Ser Pro Glu
                245                 250                 255

Glu Pro Leu Val Val Lys Val Glu Glu Gly Asp Asn Ala Val Leu Gln
            260                 265                 270

Cys Leu Lys Gly Thr Ser Asp Gly Pro Thr Gln Gln Leu Thr Trp Ser
        275                 280                 285

Arg Glu Ser Pro Leu Lys Pro Phe Leu Lys Leu Ser Leu Gly Leu Pro
    290                 295                 300

Gly Leu Gly Ile His Met Arg Pro Leu Ala Ile Trp Leu Phe Ile Phe
305                 310                 315                 320

Asn Val Ser Gln Gln Met Gly Gly Phe Tyr Leu Cys Gln Pro Gly Pro
                325                 330                 335

Pro Ser Glu Lys Ala Trp Gln Pro Gly Trp Thr Val Asn Val Glu Gly
            340                 345                 350

Ser Gly Glu Leu Phe Arg Trp Asn Val Ser Asp Leu Gly Gly Leu Gly
        355                 360                 365

Cys Gly Leu Lys Asn Arg Ser Ser Glu Gly Pro Ser Ser Pro Ser Gly
    370                 375                 380

Lys Leu Met Ser Pro Lys Leu Tyr Val Trp Ala Lys Asp Arg Pro Glu
385                 390                 395                 400

Ile Trp Glu Gly Glu Pro Pro Cys Leu Pro Pro Arg Asp Ser Leu Asn
                405                 410                 415

Gln Ser Leu Ser Gln Asp Leu Thr Met Ala Pro Gly Ser Thr Leu Trp
            420                 425                 430

Leu Ser Cys Gly Val Pro Pro Asp Ser Val Ser Arg Gly Pro Leu Ser
        435                 440                 445

Trp Thr His Val His Pro Lys Gly Pro Lys Ser Leu Leu Ser Leu Glu
    450                 455                 460

Leu Lys Asp Asp Arg Pro Ala Arg Asp Met Trp Val Met Glu Thr Gly
465                 470                 475                 480

Leu Leu Leu Pro Arg Ala Thr Ala Gln Asp Ala Gly Lys Tyr Tyr Cys
                485                 490                 495

His Arg Gly Asn Leu Thr Met Ser Phe His Leu Glu Ile Thr Ala Arg
            500                 505                 510

Pro

<210> SEQ ID NO 38
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Glu Phe Gly Leu Ser Trp Val Phe Leu Val Ala Leu Phe Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Gly Gly
            130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Asp Val Asn Thr Ala Val Ala Trp
            180                 185                 190

Tyr Gln Gln Lys Pro Gly Lys Ala Pro Lys Leu Leu Ile Tyr Ser Ala
        195                 200                 205

Ser Phe Leu Tyr Ser Gly Val Pro Ser Arg Phe Ser Gly Ser Arg Ser
    210                 215                 220

Gly Thr Asp Phe Thr Leu Thr Ile Ser Ser Leu Gln Pro Glu Asp Phe
225                 230                 235                 240

Ala Thr Tyr Tyr Cys Gln Gln His Tyr Thr Thr Pro Pro Thr Phe Gly
                245                 250                 255

Gln Gly Thr Lys Val Glu Ile Lys Arg Thr Asp Lys Thr His Thr Ser
            260                 265                 270

Pro Pro Ser Pro Ala Pro Glu Ala Ala Gly Gly Pro Ser Pro Glu Glu
        275                 280                 285

Pro Leu Val Val Lys Val Glu Glu Gly Asp Asn Ala Val Leu Gln Cys
    290                 295                 300

Leu Lys Gly Thr Ser Asp Gly Pro Thr Gln Gln Leu Thr Trp Ser Arg
305                 310                 315                 320

Glu Ser Pro Leu Lys Pro Phe Leu Lys Leu Ser Leu Gly Leu Pro Gly
                325                 330                 335

Leu Gly Ile His Met Arg Pro Leu Ala Ile Trp Leu Phe Ile Phe Asn
            340                 345                 350

Val Ser Gln Gln Met Gly Gly Phe Tyr Leu Cys Gln Pro Gly Pro Pro
        355                 360                 365

Ser Glu Lys Ala Trp Gln Pro Gly Trp Thr Val Asn Val Glu Gly Ser
    370                 375                 380

Gly Glu Leu Phe Arg Trp Asn Val Ser Asp Leu Gly Gly Leu Gly Cys
385                 390                 395                 400

Gly Leu Lys Asn Arg Ser Ser Glu Gly Pro Ser Ser Pro Ser Gly Lys
                405                 410                 415
```

```
Leu Met Ser Pro Lys Leu Tyr Val Trp Ala Lys Asp Arg Pro Glu Ile
            420                 425                 430

Trp Glu Gly Glu Pro Pro Cys Leu Pro Pro Arg Asp Ser Leu Asn Gln
                435                 440                 445

Ser Leu Ser Gln Asp Leu Thr Met Ala Pro Gly Ser Thr Leu Trp Leu
    450                 455                 460

Ser Cys Gly Val Pro Pro Asp Ser Val Ser Arg Gly Pro Leu Ser Trp
465                 470                 475                 480

Thr His Val His Pro Lys Gly Pro Lys Ser Leu Leu Ser Leu Glu Leu
                485                 490                 495

Lys Asp Asp Arg Pro Ala Arg Asp Met Trp Val Met Glu Thr Gly Leu
                500                 505                 510

Leu Leu Pro Arg Ala Thr Ala Gln Asp Ala Gly Lys Tyr Tyr Cys His
            515                 520                 525

Arg Gly Asn Leu Thr Met Ser Phe His Leu Glu Ile Thr Ala Arg Pro
        530                 535                 540

Ser Arg Gly Pro His His His His His His
545                 550

<210> SEQ ID NO 39
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Thr Ala Val Leu Pro Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220
```

Leu Leu Ser Leu Glu Leu Lys Asp Asp Arg Pro Ala Arg Glu Met Ile
225                 230                 235                 240

Val Asp Glu Thr Gly Leu Leu Pro Arg Ala Thr Ala Gln Asp Ala
            245                 250                 255

Gly Lys Trp Tyr Cys Ser Arg Gly Asn Val Thr Thr Ser Tyr His Leu
        260                 265                 270

Glu Ile Thr Ala Arg Pro Val Lys Ala His Ser Asp Leu Arg Thr Gly
            275                 280                 285

Gly Trp Lys Gly Gly Gly Ser Gly Gly Gly Ser Gly Gly Gly
        290                 295                 300

Gly Ser Gly Gly Gly Ser Gln Val Gln Leu Gln Gln Ser Gly Gly
305                 310                 315                 320

Gly Leu Val Gln Ala Gly Gly Ser Leu Arg Leu Ser Cys Ala Ala Ser
            325                 330                 335

Gly Ser Ile Phe Ala Ile Asn Glu Ile Asn Leu Met Gly Trp Tyr Arg
            340                 345                 350

Gln Ala Pro Gly Lys Gln Arg Glu Leu Val Ala Ala Cys Ala Ser Asp
        355                 360                 365

Gly Asn Thr Tyr Tyr Ala Asp Ser Val Lys Gly Arg Phe Thr Ile Ser
        370                 375                 380

Arg Asp Asn Ala Glu Lys Thr Val Tyr Leu Gln Met Asn Asn Leu Lys
385                 390                 395                 400

Pro Asp Asp Thr Ala Val Tyr Tyr Cys Asp Ala Asn Ser Arg Gly Asn
            405                 410                 415

Tyr Tyr Ser Gly Gln Gly Thr Gln Val Thr Val Ser Ser Thr Ser Gly
            420                 425                 430

Pro Gly Gly Gln Gly Ala Glu Gln Lys Leu Ile Ser Glu Glu Asp Leu
            435                 440                 445

Gly Ala His His His His His His Gly Ala Ser
    450                 455

<210> SEQ ID NO 40
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp

```
            115                 120                 125
Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285

Gly Trp Lys Gly Gly Gly Ser Gly Gly Gly Ser Gly Gly Gly
    290                 295                 300

Gly Ser Gly Gly Gly Ser Gln Val Gln Leu Gln Glu Ser Gly Gly
305                 310                 315                 320

Gly Leu Val Gln Pro Gly Gly Ser Leu Arg Leu Ser Cys Ala Ala Ser
                325                 330                 335

Gly Phe Thr Phe Asn Ser Tyr Ala Met Thr Trp Val Arg Gln Ala Pro
            340                 345                 350

Gly Lys Gly Leu Glu Trp Val Ser Asp Ile Asn Ser Gly Gly Gly Ser
        355                 360                 365

Thr Asn Tyr Ala Asp Ser Val Lys Gly Arg Phe Thr Ile Ser Arg Asp
    370                 375                 380

Asn Ala Lys Asn Thr Leu Tyr Leu Gln Met Asn Ser Leu Lys Pro Glu
385                 390                 395                 400

Asp Thr Ala Val Tyr Tyr Cys Ala Thr Glu Leu Arg Gly Ser Asp Tyr
                405                 410                 415

Tyr Arg Gly Pro Ile Arg Glu Tyr Ala Tyr Trp Gly Gln Gly Thr Leu
            420                 425                 430

Val Thr Val Ser Ser Thr Ser Gly Pro Gly Gly Gln Gly Ala Glu Gln
        435                 440                 445

Lys Leu Ile Ser Glu Glu Asp Leu Gly Ala His His His His His
    450                 455                 460

Gly Ala Ser
465

<210> SEQ ID NO 41
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41
```

```
Met Pro Pro Pro Arg Leu Leu Phe Phe Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
                35                  40                  45

Gln Leu Thr Trp Ser Arg Glu Ser Pro Leu Lys Pro Phe Leu Lys Tyr
        50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
            275                 280                 285

Gly Trp Lys Gly Gly Gly Ser Gly Gly Gly Ser Gly Gly Gly
            290                 295                 300

Gly Ser Gly Gly Gly Ser Gln Val Gln Leu Gln Ala Phe Gly Gly
305                 310                 315                 320

Gly Leu Val Gln Pro Gly Gly Ser Leu Arg Leu Ser Cys Val Val Ser
                325                 330                 335

Gly Thr Met Phe Ser Gly Lys Asp Val Asn Trp Leu Arg Gln Ala Pro
            340                 345                 350

Gly Lys His Val Glu Val Val Ala Thr Val Ser Ser Asp Gly Gly Thr
            355                 360                 365

Asp Tyr Ala Asp Phe Val Lys Gly Arg Phe Thr Ile Ser Arg Asp Asp
370                 375                 380

Ala Lys Asn Thr Val Asn Leu Gln Met Asn Ser Leu Glu Pro Glu Asp
385                 390                 395                 400

Thr Ala Asn Tyr Met Cys His Phe Leu Trp Gly Arg His Tyr Trp Gly
                405                 410                 415

Gln Gly Thr Gln Val Thr Val Ser Ser Thr Ser Gly Pro Gly Gly Gln
```

```
                    420                 425                 430
Gly Ala Glu Gln Lys Leu Ile Ser Glu Glu Asp Leu Gly Ala His His
                435                 440                 445

His His His His Gly Ala Ser
        450                 455

<210> SEQ ID NO 42
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285

Gly Trp Lys Gly Gly Gly Ser Gly Gly Gly Ser Gly Gly Gly
    290                 295                 300

Gly Ser Gly Gly Gly Ser Gln Val Gln Leu Gln Glu Ser Gly Gly
305                 310                 315                 320
```

Gly Leu Val Gln Ala Gly Gly Ser Leu Arg Leu Ser Cys Val Ala Ser
              325                 330                 335

Gly Ser Ile Arg Ser Ile Asn Val Met Gly Trp Tyr Arg Gln Ala Pro
          340                 345                 350

Gly Lys Gln Arg Glu Leu Val Ala Ala Cys Ala Ser Asp Gly Asn Thr
          355                 360                 365

Tyr Tyr Ala Asp Ser Val Lys Gly Arg Phe Thr Ile Ser Arg Asp Asn
370                 375                 380

Ala Glu Lys Thr Val Tyr Leu Gln Met Asn Asn Leu Lys Pro Asp Asp
385                 390                 395                 400

Thr Ala Val Tyr Tyr Cys Asp Ala Asn Ser Arg Gly Asn Tyr Tyr Ser
              405                 410                 415

Gly Gln Gly Thr Gln Val Thr Val Ser Ser Thr Ser Gly Pro Gly Gly
              420                 425                 430

Gln Gly Ala Glu Gln Lys Leu Ile Ser Glu Glu Asp Leu Gly Ala His
              435                 440                 445

His His His His His Gly Ala Ser
      450                 455

<210> SEQ ID NO 43
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
              20                  25                  30

Thr Ala Val Leu Pro Cys Leu Lys Gly Thr Ser Asp Gly Pro Thr Gln
          35                  40                  45

Gln Leu Thr Trp Ser Arg Glu Ser Pro Leu Lys Pro Phe Leu Lys Tyr
50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
              85                  90                  95

Cys Gln Pro Gly Pro Pro Ser Glu Lys Ala Trp Gln Pro Gly Trp Thr
          100                 105                 110

Val Asn Val Glu Gly Ser Gly Glu Leu Phe Arg Trp Asn Val Ser Asp
      115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
              165                 170                 175

Arg Asp Ser Leu Asn Gln Ser Leu Ser Gln Asp Leu Thr Met Ala Pro
          180                 185                 190

Gly Ser Thr Leu Trp Leu Ser Cys Gly Val Pro Pro Asp Ser Val Ser
      195                 200                 205

Arg Gly Pro Leu Ser Trp Thr His Val His Pro Lys Gly Pro Lys Ser
210                 215                 220

```
Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
            245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
            275                 280                 285

Gly Trp Lys Gly Gly Gly Ser Gly Gly Gly Ser Gly Gly Gly
        290                 295                 300

Gly Ser Gly Gly Gly Ser Gln Val Gln Leu Gln Gln Ser Gly Gly
305                 310                 315                 320

Gly Leu Ala Gln Thr Gly Gly Ser Leu Ile Leu Ser Cys Ala Ala Ser
            325                 330                 335

Gly Ser Ile Phe Ala Ile Asn Glu Ile Asn Leu Met Gly Trp Tyr Arg
            340                 345                 350

Gln Ala Pro Gly Lys Gln Arg Glu Leu Val Ala Ala Cys Ala Ser Asp
            355                 360                 365

Gly Asn Thr Tyr Tyr Ala Asp Ser Val Lys Gly Arg Phe Thr Ile Ser
            370                 375                 380

Arg Asp Asn Ala Glu Lys Thr Val Tyr Leu Gln Met Asn Asn Leu Lys
385                 390                 395                 400

Pro Asp Asp Thr Ala Val Tyr Tyr Cys Asp Ala Asn Ser Arg Gly Asn
            405                 410                 415

Tyr Tyr Ser Gly Gln Gly Thr Gln Val Thr Val Ser Ser Thr Ser Gly
            420                 425                 430

Pro Gly Gly Gln Gly Ala Glu Gln Lys Leu Ile Ser Glu Glu Asp Leu
            435                 440                 445

Gly Ala His His His His His His Gly Ala Ser
    450                 455
```

<210> SEQ ID NO 44
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
```

115                 120                 125
Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
        180                 185                 190

Gly Ser Thr Leu Trp Leu Ser Cys Gly Val Pro Pro Asp Ser Val Ser
                195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
        260                 265                 270

Glu Ile Thr Ala Arg Pro Val Lys Ala His Ser Asp Leu Arg Thr Gly
                275                 280                 285

Gly Trp Lys Gly Gly Gly Ser Gly Gly Gly Ser Gly Gly Gly
        290                 295                 300

Gly Ser Gly Gly Gly Gly Ser Ala Val Gln Leu Gln Glu Ser Gly Gly
305                 310                 315                 320

Gly Leu Val Gln Ala Gly Gly Ser Leu Arg Leu Ser Cys Ala Ala Ser
                325                 330                 335

Gly Ser Asp Arg Ser Ile Asn Val Met Asn Trp Tyr Arg Gln Ala Pro
        340                 345                 350

Gly Lys Gln Arg Glu Leu Val Ala Ala Ile Thr Ser Gly Gly Thr Thr
        355                 360                 365

Asn Tyr Ala Gln Ser Val Lys Gly Arg Val Thr Ile Ser Arg Asp Ser
370                 375                 380

Ala Lys Asn Thr Val Tyr Leu Gln Met Asn Ser Leu Lys Pro Glu Asp
385                 390                 395                 400

Thr Ala Val Tyr Phe Cys Lys Ala Asp Thr Arg Trp Gly Gly Met Tyr
                405                 410                 415

Trp Gly Pro Gly Thr Gln Val Thr Val Ser Ser Thr Ser Gly Pro Gly
        420                 425                 430

Gly Gln Gly Ala Glu Gln Lys Leu Ile Ser Glu Glu Asp Leu Gly Ala
        435                 440                 445

His His His His His His Gly Ala Ser
        450                 455

<210> SEQ ID NO 45
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Pro Pro Pro Arg Leu Leu Phe Phe Leu Leu Phe Leu Thr Pro Met
1               5                   10                  15

-continued

Glu Val Arg Pro Glu Pro Leu Val Val Lys Val Glu Glu Gly Asp
            20              25              30

Thr Ala Val Leu Pro Cys Leu Lys Gly Thr Ser Asp Gly Pro Thr Gln
                35              40              45

Gln Leu Thr Trp Ser Arg Glu Ser Pro Leu Lys Pro Phe Leu Lys Tyr
 50              55              60

Ser Leu Gly Val Pro Gly Leu Gly Val His Val Arg Pro Asp Ala Ile
 65              70              75              80

Ser Val Val Ile Arg Asn Val Ser Gln Gln Met Gly Gly Phe Tyr Leu
                85              90              95

Cys Gln Pro Gly Pro Pro Ser Glu Lys Ala Trp Gln Pro Gly Trp Thr
                100             105             110

Val Asn Val Glu Gly Ser Gly Glu Leu Phe Arg Trp Asn Val Ser Asp
            115             120             125

Leu Gly Gly Leu Gly Cys Gly Leu Lys Asn Arg Ser Ser Glu Gly Pro
    130             135             140

Ser Ser Pro Ser Gly Lys Leu Met Ser Pro Lys Leu Tyr Val Trp Ala
145             150             155             160

Lys Asp Arg Pro Glu Ile Trp Glu Gly Glu Pro Pro Cys Leu Pro Pro
                165             170             175

Arg Asp Ser Leu Asn Gln Ser Leu Ser Gln Asp Leu Thr Met Ala Pro
                180             185             190

Gly Ser Thr Leu Trp Leu Ser Cys Gly Val Pro Pro Asp Ser Val Ser
            195             200             205

Arg Gly Pro Leu Ser Trp Thr His Val His Pro Lys Gly Pro Lys Ser
    210             215             220

Leu Leu Ser Leu Glu Leu Lys Asp Asp Arg Pro Ala Arg Glu Met Ile
225             230             235             240

Val Asp Glu Thr Gly Leu Leu Pro Arg Ala Thr Ala Gln Asp Ala
            245             250             255

Gly Lys Trp Tyr Cys Ser Arg Gly Asn Val Thr Thr Ser Tyr His Leu
                260             265             270

Glu Ile Thr Ala Arg Pro Val Lys Ala His Ser Asp Leu Arg Thr Gly
    275             280             285

Gly Trp Lys Gly Gly Gly Gly Ser Gly Gly Gly Ser Gly Gly Gly
    290             295             300

Gly Ser Gly Gly Gly Ser Gln Val Gln Leu Gln Gln Ser Gly Gly
305             310             315             320

Gly Leu Val Gln Ala Gly Gly Ser Leu Thr Leu Ser Cys Ala Ala Thr
                325             330             335

Gly Arg Thr Ile Asp Asn Gly Ala Met Ala Trp Phe Arg Gln Ala Pro
                340             345             350

Gly Lys Gln Arg Glu Leu Val Ala Ala Ile Asn Trp Ser Gly Gly Ala
    355             360             365

Thr Phe Tyr Thr Asp Ser Val Lys Tyr Arg Phe Thr Ile Ser Arg Asp
    370             375             380

Asn Val Arg His Thr Leu Asp Leu Gln Met Thr Ser Leu Lys Pro Glu
385             390             395             400

Asp Thr Thr Ile Tyr Phe Cys Ala Ser Arg Arg Gly Val Asp Leu Arg
                405             410             415

Arg Asn Ser Tyr Glu Tyr Asp Tyr Trp Gly Arg Gly Thr Leu Val Thr
                420             425             430

Val Ser Ser Thr Ser Gly Pro Gly Gly Gln Gly Ala Glu Gln Lys Leu

```
                435                 440                 445
Ile Ser Glu Glu Asp Leu Gly Ala His His His His His Gly Ala
    450                 455                 460

Ser
465

<210> SEQ ID NO 46
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Glu Phe Gly Leu Ser Trp Val Phe Leu Val Ala Leu Phe Arg Gly
1               5                   10                  15

Val Gln Cys Gln Val Gln Leu Gln Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ser Tyr Ala Met Thr Trp Val Arg Gln Ala Pro Gly Lys Gly Leu
    50                  55                  60

Glu Trp Val Ser Asp Ile Asn Ser Gly Gly Ser Thr Asn Tyr Ala
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Lys Pro Glu Asp Thr Ala Val
            100                 105                 110

Tyr Tyr Cys Ala Thr Glu Leu Arg Gly Ser Asp Tyr Tyr Arg Gly Pro
        115                 120                 125

Ile Arg Glu Tyr Ala Tyr Trp Gly Gln Gly Thr Leu Val Thr Val Ser
    130                 135                 140

Ser Thr Ser Gly Pro Gly Gly Gln Ala Gly Gly Gly Ser Gly
145                 150                 155                 160

Gly Gly Gly Ser Gly Gly Gly Ser Gly Gly Gly Ser Pro Glu
                165                 170                 175

Glu Pro Leu Val Val Lys Val Glu Glu Gly Asp Thr Ala Ala Leu Trp
            180                 185                 190

Cys Leu Lys Gly Thr Ser Asp Gly Pro Thr Gln Gln Leu Thr Trp Ser
        195                 200                 205

Arg Glu Ser Pro Leu Lys Pro Phe Leu Lys Tyr Ser Leu Gly Val Pro
    210                 215                 220

Gly Leu Gly Val His Val Arg Pro Asp Ala Ile Ser Val Val Ile Arg
225                 230                 235                 240

Asn Val Ser Gln Gln Met Gly Gly Phe Tyr Leu Cys Gln Pro Gly Pro
                245                 250                 255

Pro Ser Glu Lys Ala Trp Gln Pro Gly Trp Thr Val Asn Val Glu Gly
            260                 265                 270

Ser Gly Glu Leu Phe Arg Trp Asn Val Ser Asp Leu Gly Gly Leu Gly
        275                 280                 285

Cys Gly Leu Lys Asn Arg Ser Ser Glu Gly Pro Ser Ser Pro Ser Gly
    290                 295                 300

Lys Leu Met Ser Pro Lys Leu Tyr Val Trp Ala Lys Asp Arg Pro Glu
305                 310                 315                 320
```

```
Ile Trp Glu Gly Glu Pro Pro Cys Leu Pro Pro Arg Asp Ser Leu Asn
                325                 330                 335

Gln Ser Leu Ser Arg Asp Leu Thr Val Ala Pro Gly Ser Thr Leu Trp
            340                 345                 350

Leu Ser Cys Gly Val Pro Pro Asp Ser Val Ser Arg Gly Pro Leu Ser
            355                 360                 365

Trp Thr His Val His Pro Lys Gly Pro Lys Ser Leu Leu Ser Leu Glu
        370                 375                 380

Leu Lys Asp Asp Arg Pro Ala Arg Asp Met Trp Val Met Gly Thr Ser
385                 390                 395                 400

Leu Met Leu Pro Arg Ala Thr Ala Gln Asp Ala Gly Lys Trp Tyr Cys
                405                 410                 415

His Arg Gly Asn Leu Thr Met Ser Phe His Leu Glu Ile Thr Ala Arg
            420                 425                 430

Pro Ser Arg His His His His His His
            435                 440

<210> SEQ ID NO 47
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Phe Gly Leu Ser Trp Val Phe Leu Val Ala Leu Phe Arg Gly
1               5                   10                  15

Val Gln Cys Gln Val Gln Leu Gln Gln Ser Gly Gly Gly Leu Ala Gln
                20                  25                  30

Thr Gly Gly Ser Leu Ile Leu Ser Cys Ala Ala Ser Gly Ser Ile Phe
            35                  40                  45

Ala Ile Asn Glu Ile Asn Leu Met Gly Trp Tyr Arg Gln Ala Pro Gly
        50                  55                  60

Lys Gln Arg Glu Leu Val Ala Ala Cys Ala Ser Asp Gly Asn Thr Tyr
65                  70                  75                  80

Tyr Ala Asp Ser Val Lys Gly Arg Phe Thr Ile Ser Arg Asp Asn Ala
                85                  90                  95

Glu Lys Thr Val Tyr Leu Gln Met Asn Asn Leu Lys Pro Asp Asp Thr
            100                 105                 110

Ala Val Tyr Tyr Cys Asp Ala Asn Ser Arg Gly Asn Tyr Tyr Ser Gly
        115                 120                 125

Gln Gly Thr Gln Val Thr Val Ser Ser Thr Ser Gly Pro Gly Gly Gln
130                 135                 140

Gly Ala Gly Gly Gly Ser Gly Gly Gly Ser Gly Gly Gly Gly Gly Gly
145                 150                 155                 160

Ser Gly Gly Gly Gly Ser Pro Glu Glu Pro Leu Val Val Lys Val Glu
                165                 170                 175

Glu Gly Asp Thr Ala Ala Leu Trp Cys Leu Lys Gly Thr Ser Asp Gly
            180                 185                 190

Pro Thr Gln Gln Leu Thr Trp Ser Arg Glu Ser Pro Leu Lys Pro Phe
        195                 200                 205

Leu Lys Tyr Ser Leu Gly Val Pro Gly Leu Gly Val His Val Arg Pro
    210                 215                 220

Asp Ala Ile Ser Val Val Ile Arg Asn Val Ser Gln Gln Met Gly Gly
225                 230                 235                 240
```

```
Phe Tyr Leu Cys Gln Pro Gly Pro Ser Glu Lys Ala Trp Gln Pro
                245                 250                 255

Gly Trp Thr Val Asn Val Gly Ser Gly Glu Leu Phe Arg Trp Asn
            260                 265                 270

Val Ser Asp Leu Gly Gly Leu Gly Cys Gly Leu Lys Asn Arg Ser Ser
            275                 280                 285

Glu Gly Pro Ser Ser Pro Ser Gly Lys Leu Met Ser Pro Lys Leu Tyr
            290                 295                 300

Val Trp Ala Lys Asp Arg Pro Glu Ile Trp Glu Gly Pro Pro Cys
305                 310                 315                 320

Leu Pro Pro Arg Asp Ser Leu Asn Gln Ser Leu Ser Arg Asp Leu Thr
                325                 330                 335

Val Ala Pro Gly Ser Thr Leu Trp Leu Ser Cys Gly Val Pro Pro Asp
            340                 345                 350

Ser Val Ser Arg Gly Pro Leu Ser Trp Thr His Val His Pro Lys Gly
            355                 360                 365

Pro Lys Ser Leu Leu Ser Leu Glu Leu Lys Asp Asp Arg Pro Ala Arg
            370                 375                 380

Asp Met Trp Val Met Gly Thr Ser Leu Met Leu Pro Arg Ala Thr Ala
385                 390                 395                 400

Gln Asp Ala Gly Lys Trp Tyr Cys His Arg Gly Asn Leu Thr Met Ser
            405                 410                 415

Phe His Leu Glu Ile Thr Ala Arg Pro Ser Arg His His His His
                420                 425                 430
His

<210> SEQ ID NO 48
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Glu Phe Gly Leu Ser Trp Val Phe Leu Val Ala Leu Phe Arg Gly
1               5                   10                  15

Val Gln Cys Gln Val Gln Leu Gln Gln Ser Gly Gly Gly Leu Val Gln
                20                  25                  30

Ala Gly Gly Ser Leu Thr Leu Ser Cys Ala Ala Thr Gly Arg Thr Ile
            35                  40                  45

Asp Asn Gly Ala Met Ala Trp Phe Arg Gln Ala Pro Gly Lys Gln Arg
    50                  55                  60

Glu Leu Val Ala Ala Ile Asn Trp Ser Gly Ala Thr Phe Tyr Thr
65                  70                  75                  80

Asp Ser Val Lys Tyr Arg Phe Thr Ile Ser Arg Asp Asn Val Arg His
                85                  90                  95

Thr Leu Asp Leu Gln Met Thr Ser Leu Lys Pro Glu Asp Thr Thr Ile
                100                 105                 110

Tyr Phe Cys Ala Ser Arg Arg Gly Val Asp Leu Arg Arg Asn Ser Tyr
            115                 120                 125

Glu Tyr Asp Tyr Trp Gly Arg Gly Thr Leu Val Thr Val Ser Ser Thr
            130                 135                 140

Ser Gly Pro Gly Gly Gln Gly Ala Gly Gly Gly Ser Gly Gly Gly
145                 150                 155                 160
```

Gly Ser Gly Gly Gly Ser Gly Gly Gly Ser Pro Glu Glu Pro
                165                 170                 175

Leu Val Val Lys Val Glu Glu Gly Asp Thr Ala Ala Leu Trp Cys Leu
            180                 185                 190

Lys Gly Thr Ser Asp Gly Pro Thr Gln Gln Leu Thr Trp Ser Arg Glu
            195                 200                 205

Ser Pro Leu Lys Pro Phe Leu Lys Tyr Ser Leu Gly Val Pro Gly Leu
        210                 215                 220

Gly Val His Val Arg Pro Asp Ala Ile Ser Val Val Ile Arg Asn Val
225                 230                 235                 240

Ser Gln Gln Met Gly Gly Phe Tyr Leu Cys Gln Pro Gly Pro Pro Ser
                245                 250                 255

Glu Lys Ala Trp Gln Pro Gly Trp Thr Val Asn Val Glu Gly Ser Gly
            260                 265                 270

Glu Leu Phe Arg Trp Asn Val Ser Asp Leu Gly Gly Leu Gly Cys Gly
        275                 280                 285

Leu Lys Asn Arg Ser Ser Glu Gly Pro Ser Ser Pro Ser Gly Lys Leu
        290                 295                 300

Met Ser Pro Lys Leu Tyr Val Trp Ala Lys Asp Arg Pro Glu Ile Trp
305                 310                 315                 320

Glu Gly Glu Pro Pro Cys Leu Pro Pro Arg Asp Ser Leu Asn Gln Ser
                325                 330                 335

Leu Ser Arg Asp Leu Thr Val Ala Pro Gly Ser Thr Leu Trp Leu Ser
            340                 345                 350

Cys Gly Val Pro Pro Asp Ser Val Ser Arg Gly Pro Leu Ser Trp Thr
        355                 360                 365

His Val His Pro Lys Gly Pro Lys Ser Leu Leu Ser Leu Glu Leu Lys
        370                 375                 380

Asp Asp Arg Pro Ala Arg Asp Met Trp Val Met Gly Thr Ser Leu Met
385                 390                 395                 400

Leu Pro Arg Ala Thr Ala Gln Asp Ala Gly Lys Trp Tyr Cys His Arg
                405                 410                 415

Gly Asn Leu Thr Met Ser Phe His Leu Glu Ile Thr Ala Arg Pro Ser
            420                 425                 430

Arg His His His His His His
        435

<210> SEQ ID NO 49
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile

```
                65                  70                  75                  80
            Ser Val Val Ile Arg Asn Val Ser Gln Gln Met Gly Gly Phe Tyr Leu
                            85                  90                  95
            Cys Gln Pro Gly Pro Ser Glu Lys Ala Trp Gln Pro Gly Trp Thr
                        100                 105                 110
            Val Asn Val Glu Gly Ser Gly Glu Leu Phe Arg Trp Asn Val Ser Asp
                        115                 120                 125
            Leu Gly Gly Leu Gly Cys Gly Leu Lys Asn Arg Ser Ser Glu Gly Pro
                130                 135                 140
            Ser Ser Pro Ser Gly Lys Leu Met Ser Pro Lys Leu Tyr Val Trp Ala
            145                 150                 155                 160
            Lys Asp Arg Pro Glu Ile Trp Glu Gly Glu Pro Pro Cys Leu Pro Pro
                            165                 170                 175
            Arg Asp Ser Leu Asn Gln Ser Leu Ser Gln Asp Leu Thr Met Ala Pro
                        180                 185                 190
            Gly Ser Thr Leu Trp Leu Ser Cys Gly Val Pro Pro Asp Ser Val Ser
                        195                 200                 205
            Arg Gly Pro Leu Ser Trp Thr His Val His Pro Lys Gly Pro Lys Ser
                210                 215                 220
            Leu Leu Ser Leu Glu Leu Lys Asp Asp Arg Pro Ala Arg Glu Met Ile
            225                 230                 235                 240
            Val Asp Glu Thr Gly Leu Leu Leu Pro Arg Ala Thr Ala Gln Asp Ala
                            245                 250                 255
            Gly Lys Trp Tyr Cys Ser Arg Gly Asn Val Thr Thr Ser Tyr His Leu
                        260                 265                 270
            Glu Ile Thr Ala Arg Pro Val Lys Ala His Ser Asp Leu Arg Thr Gly
                        275                 280                 285
            Gly Trp Lys Gly Gly Gly Ser Gly Gly Gly Ser Gly Gly Gly Gly
                290                 295                 300
            Gly Ser Gly Gly Gly Ser Gln Val Gln Leu Gln Glu Ser Gly Gly
            305                 310                 315                 320
            Gly Leu Val Gln Val Gly Glu Ser Leu Arg Leu Ser Cys Val Val Ser
                            325                 330                 335
            Gly Asp Thr Arg Ser Ile Asn Leu Met Gly Trp Tyr Arg Gln Ala Pro
                        340                 345                 350
            Gly Lys Gln Arg Glu Leu Val Ala Ala Cys Ala Ser Asp Gly Asn Thr
                        355                 360                 365
            Tyr Tyr Ala Asp Ser Val Lys Gly Arg Phe Thr Ile Ser Arg Asp Asn
                370                 375                 380
            Ala Glu Lys Thr Val Tyr Leu Gln Met Asn Asn Leu Lys Pro Asp Asp
            385                 390                 395                 400
            Thr Ala Val Tyr Tyr Cys Asp Ala Asn Ser Arg Gly Asn Tyr Tyr Ser
                            405                 410                 415
            Gly Gln Gly Thr Leu Val Thr Val Ser Ser Thr Ser Gly Pro Gly Gly
                        420                 425                 430
            Gln Gly Ala Glu Gln Lys Leu Ile Ser Glu Glu Asp Leu Gly Ala His
                        435                 440                 445
            His His His His Gly Ala Ser
                450                 455

<210> SEQ ID NO 50
<211> LENGTH: 459
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 50

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Thr Ala Val Leu Pro Cys Leu Lys Gly Thr Ser Asp Gly Pro Thr Gln
        35                  40                  45

Gln Leu Thr Trp Ser Arg Glu Ser Pro Leu Lys Pro Phe Leu Lys Tyr
    50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285

Gly Trp Lys Gly Gly Gly Gly Ser Gly Gly Gly Gly Ser Gly Gly Gly
    290                 295                 300

Gly Ser Gly Gly Gly Gly Ser Gln Val Gln Leu Gln Glu Ser Gly Gly
305                 310                 315                 320

Gly Leu Val Gln Ala Gly Gly Ser Leu Arg Leu Ser Cys Ala Ala Ser
            325                 330                 335

Gly Ser Ile Phe Ala Ile Asn Glu Ile Asn Leu Met Gly Trp Tyr Arg
        340                 345                 350

Gln Ala Pro Gly Lys Gln Arg Glu Leu Val Ala Ala Cys Ala Ser Asp
    355                 360                 365

Gly Asn Thr Tyr Tyr Ala Asp Ser Val Lys Gly Arg Phe Thr Ile Ser
370                 375                 380

Arg Asp Asn Ala Glu Lys Thr Val Tyr Leu Gln Met Asn Asn Leu Lys

-continued

```
                385                 390                 395                 400
Pro Asp Asp Thr Ala Val Tyr Tyr Cys Asp Ala Asn Ser Arg Gly Asn
                    405                 410                 415

Tyr Tyr Ser Gly Gln Gly Thr Gln Val Thr Val Ser Ser Thr Ser Gly
                420                 425                 430

Pro Gly Gly Gln Gly Ala Glu Gln Lys Leu Ile Ser Glu Glu Asp Leu
                435                 440                 445

Gly Ala His His His His His His Gly Ala Ser
            450                 455

<210> SEQ ID NO 51
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Thr Ala Val Leu Pro Cys Leu Lys Gly Thr Ser Asp Gly Pro Thr Gln
            35                  40                  45

Gln Leu Thr Trp Ser Arg Glu Ser Pro Leu Lys Pro Phe Leu Lys Tyr
        50                  55                  60

Ser Leu Gly Val Pro Gly Leu Gly Val His Val Arg Pro Asp Ala Ile
65                  70                  75                  80

Ser Val Val Ile Arg Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Glu Met Ile
225                 230                 235                 240

Val Asp Glu Thr Gly Leu Leu Leu Pro Arg Ala Thr Ala Gln Asp Ala
                245                 250                 255

Gly Lys Trp Tyr Cys Ser Arg Gly Asn Val Thr Thr Ser Tyr His Leu
            260                 265                 270

Glu Ile Thr Ala Arg Pro Val Lys Ala His Ser Asp Leu Arg Thr Gly
        275                 280                 285
```

Gly Trp Lys Gly Gly Gly Ser Gly Gly Gly Ser Gly Gly Gly
            290                 295                 300

Gly Ser Gly Gly Gly Ser Gln Val Gln Leu Val Glu Ser Gly Gly
305                 310                 315                 320

Gly Leu Val Gln Ala Gly Gly Ser Leu Arg Leu Ser Cys Ala Ala Ser
                325                 330                 335

Gly Ser Ile Phe Ala Ile Asn Glu Ile Asn Leu Met Gly Trp Tyr Arg
                340                 345                 350

Gln Ala Pro Gly Lys Gln Arg Glu Leu Val Ala Ala Cys Ala Ser Asp
            355                 360                 365

Gly Asn Thr Tyr Tyr Ala Asp Ser Val Lys Gly Arg Phe Thr Ile Ser
370                 375                 380

Arg Asp Asn Ala Glu Lys Thr Val Tyr Leu Gln Met Asn Asn Leu Lys
385                 390                 395                 400

Pro Asp Asp Thr Ala Val Tyr Tyr Cys Asp Ala Asn Ser Arg Gly Asn
                405                 410                 415

Tyr Tyr Ser Gly Gln Gly Thr Leu Val Thr Val Ser Ser Thr Ser Gly
            420                 425                 430

Pro Gly Gly Gln Gly Ala Glu Gln Lys Leu Ile Ser Glu Glu Asp Leu
            435                 440                 445

Gly Ala His His His His His His Gly Ala Ser
450                 455

<210> SEQ ID NO 52
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Gly Gly Gly Ser Gly Gly Gly Ser
            275                 280                 285

Gly Gly Gly Gly Ser Gly Gly Gly Ser Asp Met Ala Gln Val Gln
            290                 295                 300

Leu Gln Glu Ser Gly Pro Gly Leu Val Lys Pro Ser Glu Thr Leu Ser
305                 310                 315                 320

Leu Thr Cys Val Val Ser Gly Gly Ser Ile Ser Ser Asn Trp Trp
            325                 330                 335

Ser Trp Val Arg Gln Pro Pro Gly Lys Gly Leu Glu Trp Ile Gly Glu
            340                 345                 350

Ile Tyr His Ser Gly Ser Pro Asp Tyr Asn Pro Ser Leu Lys Ser Arg
            355                 360                 365

Val Thr Ile Ser Val Asp Lys Ser Arg Asn Gln Phe Ser Leu Lys Leu
            370                 375                 380

Ser Ser Val Thr Ala Ala Asp Thr Ala Val Tyr Tyr Cys Ala Lys Val
385                 390                 395                 400

Ser Thr Gly Gly Phe Phe Asp Tyr Trp Gly Gln Gly Thr Leu Val Thr
            405                 410                 415

Val Ser Ser Gly Gly Gly Gly Ser Gly Gly Gly Gly Ser Gly Gly Gly
            420                 425                 430

Gly Ser Glu Ile Glu Leu Thr Gln Ser Pro Ser Ser Leu Ser Ala Ser
            435                 440                 445

Val Gly Asp Arg Val Thr Ile Thr Cys Arg Ala Ser Gln Ser Ile Ser
450                 455                 460

Ser Tyr Leu Asn Trp Tyr Gln Gln Lys Pro Gly Lys Ala Pro Lys Leu
465                 470                 475                 480

Leu Ile Tyr Ala Ala Ser Ser Leu Gln Ser Gly Val Pro Ser Arg Phe
            485                 490                 495

Ser Gly Ser Gly Ser Gly Thr Asp Phe Thr Leu Thr Ile Ser Ser Leu
            500                 505                 510

Gln Pro Glu Asp Phe Ala Thr Tyr Tyr Cys Gln Gln Ser Tyr Ser Thr
            515                 520                 525

Pro Pro Thr Phe Gly Pro Gly Thr Lys Val Glu Ile Lys Arg Thr His
            530                 535                 540

His His His His His
545

<210> SEQ ID NO 53
<211> LENGTH: 695
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 53

Met Glu Phe Gly Leu Ser Trp Val Phe Leu Val Ala Leu Phe Arg Gly
1               5                   10                  15

Val Gln Cys Asp Met Ala Gln Val Gln Leu Gln Glu Ser Gly Pro Gly
                20                  25                  30

Leu Val Lys Pro Ser Glu Thr Leu Ser Leu Thr Cys Val Val Ser Gly
            35                  40                  45

Gly Ser Ile Ser Ser Ser Asn Trp Trp Ser Trp Val Arg Gln Pro Pro
        50                  55                  60

Gly Lys Gly Leu Glu Trp Ile Gly Glu Ile Tyr His Ser Gly Ser Pro
65                  70                  75                  80

Asp Tyr Asn Pro Ser Leu Lys Ser Arg Val Thr Ile Ser Val Asp Lys
                85                  90                  95

Ser Arg Asn Gln Phe Ser Leu Lys Leu Ser Ser Val Thr Ala Ala Asp
                100                 105                 110

Thr Ala Val Tyr Tyr Cys Ala Lys Val Ser Thr Gly Gly Phe Phe Asp
            115                 120                 125

Tyr Trp Gly Gln Gly Thr Leu Val Thr Val Ser Ser Gly Gly Gly Gly
130                 135                 140

Ser Gly Gly Gly Gly Ser Gly Gly Gly Gly Ser Glu Ile Glu Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Ile Ser Ser Tyr Leu Asn Trp Tyr Gln
            180                 185                 190

Gln Lys Pro Gly Lys Ala Pro Lys Leu Leu Ile Tyr Ala Ala Ser Ser
        195                 200                 205

Leu Gln Ser Gly Val Pro Ser Arg Phe Ser Gly Ser Gly Ser Gly Thr
210                 215                 220

Asp Phe Thr Leu Thr Ile Ser Ser Leu Gln Pro Glu Asp Phe Ala Thr
225                 230                 235                 240

Tyr Tyr Cys Gln Gln Ser Tyr Ser Thr Pro Pro Thr Phe Gly Pro Gly
            245                 250                 255

Thr Lys Val Glu Ile Lys Arg Thr Gly Gly Gly Ser Gly Gly Gly
                260                 265                 270

Gly Ser Gly Gly Gly Gly Ser Gly Gly Gly Gly Ser Gln Val Gln Leu
            275                 280                 285

Gln Glu Ser Gly Gly Gly Leu Val Gln Ala Gly Gly Ser Leu Arg Leu
        290                 295                 300

Ser Cys Val Ala Ser Gly Ser Ile Arg Ser Ile Asn Val Met Gly Trp
305                 310                 315                 320

Tyr Arg Gln Ala Pro Gly Lys Gln Arg Glu Leu Val Ala Ala Cys Ala
                325                 330                 335

Ser Asp Gly Asn Thr Tyr Tyr Ala Asp Ser Val Lys Gly Arg Phe Thr
            340                 345                 350

Ile Ser Arg Asp Asn Ala Glu Lys Thr Val Tyr Leu Gln Met Asn Asn
        355                 360                 365

Leu Lys Pro Asp Asp Thr Ala Val Tyr Tyr Cys Asp Ala Asn Ser Arg
370                 375                 380

Gly Asn Tyr Tyr Ser Gly Gln Gly Thr Gln Val Thr Val Ser Ser Thr
385                 390                 395                 400

Ser Gly Pro Gly Gly Gln Gly Ala Gly Gly Gly Ser Gly Gly Gly
            405                 410                 415
```

Gly Ser Gly Gly Gly Ser Gly Gly Gly Ser Pro Glu Glu Pro
             420                 425             430

Leu Val Val Lys Val Glu Gly Asp Thr Ala Ala Leu Trp Cys Leu
         435                 440             445

Lys Gly Thr Ser Asp Gly Pro Thr Gln Gln Leu Thr Trp Ser Arg Glu
     450                 455                 460

Ser Pro Leu Lys Pro Phe Leu Lys Tyr Ser Leu Gly Val Pro Gly Leu
465             470                 475                 480

Gly Val His Val Arg Pro Asp Ala Ile Ser Val Val Ile Arg Asn Val
             485                 490                 495

Ser Gln Gln Met Gly Gly Phe Tyr Leu Cys Gln Pro Gly Pro Pro Ser
             500                 505                 510

Glu Lys Ala Trp Gln Pro Gly Trp Thr Val Asn Val Glu Gly Ser Gly
         515                 520                 525

Glu Leu Phe Arg Trp Asn Val Ser Asp Leu Gly Gly Leu Gly Cys Gly
         530                 535                 540

Leu Lys Asn Arg Ser Ser Glu Gly Pro Ser Pro Ser Gly Lys Leu
545             550                 555                 560

Met Ser Pro Lys Leu Tyr Val Trp Ala Lys Asp Arg Pro Glu Ile Trp
             565                 570                 575

Glu Gly Glu Pro Pro Cys Leu Pro Pro Arg Asp Ser Leu Asn Gln Ser
         580                 585                 590

Leu Ser Arg Asp Leu Thr Val Ala Pro Gly Ser Thr Leu Trp Leu Ser
     595                 600                 605

Cys Gly Val Pro Pro Asp Ser Val Ser Arg Gly Pro Leu Ser Trp Thr
     610                 615                 620

His Val His Pro Lys Gly Pro Lys Ser Leu Leu Ser Leu Glu Leu Lys
625             630                 635                 640

Asp Asp Arg Pro Ala Arg Asp Met Trp Val Met Gly Thr Ser Leu Met
             645                 650                 655

Leu Pro Arg Ala Thr Ala Gln Asp Ala Gly Lys Trp Tyr Cys His Arg
             660                 665                 670

Gly Asn Leu Thr Met Ser Phe His Leu Glu Ile Thr Ala Arg Pro Ser
             675                 680                 685

Arg His His His His His His
     690                 695

<210> SEQ ID NO 54
<211> LENGTH: 1111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Arg Leu Leu Val Leu Leu Trp Gly Cys Leu Leu Pro Gly Tyr
1               5                   10                  15

Glu Ala Asp Ile Gln Met Thr Gln Thr Thr Ser Ser Leu Ser Ala Ser
             20                  25                  30

Leu Gly Asp Arg Val Thr Ile Ser Cys Arg Ala Ser Gln Asp Ile Ser
         35                  40                  45

Lys Tyr Leu Asn Trp Tyr Gln Gln Lys Pro Asp Gly Thr Val Lys Leu
     50                  55                  60

Leu Ile Tyr His Thr Ser Arg Leu His Ser Gly Val Pro Ser Arg Phe

```
                65                  70                  75                  80
        Ser Gly Ser Gly Ser Gly Thr Asp Tyr Ser Leu Thr Ile Ser Asn Leu
                        85                  90                  95

Glu Gln Glu Asp Ile Ala Thr Tyr Phe Cys Gln Gln Gly Asn Thr Leu
                       100                 105                 110

Pro Tyr Thr Phe Gly Gly Gly Thr Lys Leu Glu Ile Thr Gly Gly Gly
                       115                 120                 125

Gly Ser Gly Gly Gly Gly Ser Gly Gly Gly Ser Gly Gly Gly Gly
                130                 135                 140

Ser Glu Val Lys Leu Gln Glu Ser Gly Pro Gly Leu Val Ala Pro Ser
        145                 150                 155                 160

Gln Ser Leu Ser Val Thr Cys Thr Val Ser Gly Val Ser Leu Pro Asp
                        165                 170                 175

Tyr Gly Val Ser Trp Ile Arg Gln Pro Pro Arg Lys Gly Leu Glu Trp
                        180                 185                 190

Leu Gly Val Ile Trp Gly Ser Glu Thr Thr Tyr Tyr Asn Ser Ala Leu
                        195                 200                 205

Lys Ser Arg Leu Thr Ile Ile Lys Asp Asn Ser Lys Ser Gln Val Phe
        210                 215                 220

Leu Lys Met Asn Ser Leu Gln Thr Asp Asp Thr Ala Ile Tyr Tyr Cys
        225                 230                 235                 240

Ala Lys His Tyr Tyr Tyr Gly Gly Ser Tyr Ala Met Asp Tyr Trp Gly
                        245                 250                 255

Gln Gly Thr Ser Val Thr Val Ser Ser Asp Tyr Lys Asp Asp Asp Asp
                        260                 265                 270

Lys Ile Glu Val Met Tyr Pro Pro Pro Tyr Leu Asp Asn Glu Lys Ser
                        275                 280                 285

Asn Gly Thr Ile Ile His Val Lys Gly Lys His Leu Cys Pro Ser Pro
                        290                 295                 300

Leu Phe Pro Gly Pro Ser Lys Pro Phe Trp Val Leu Val Val Val Gly
        305                 310                 315                 320

Gly Val Leu Ala Cys Tyr Ser Leu Leu Val Thr Val Ala Phe Ile Ile
                        325                 330                 335

Phe Trp Val Arg Ser Lys Arg Ser Arg Leu Leu His Ser Asp Tyr Met
                        340                 345                 350

Asn Met Thr Pro Arg Arg Pro Gly Pro Thr Arg Lys His Tyr Gln Pro
                        355                 360                 365

Tyr Ala Pro Pro Arg Asp Phe Ala Ala Tyr Arg Ser Lys Arg Gly Arg
                        370                 375                 380

Lys Lys Leu Leu Tyr Ile Phe Lys Gln Pro Phe Met Arg Pro Val Gln
        385                 390                 395                 400

Thr Thr Gln Glu Glu Asp Gly Cys Ser Cys Arg Phe Pro Glu Glu Glu
                        405                 410                 415

Glu Gly Gly Cys Glu Leu Arg Val Lys Phe Ser Arg Ser Ala Asp Ala
                        420                 425                 430

Pro Ala Tyr Gln Gln Gly Gln Asn Gln Leu Tyr Asn Glu Leu Asn Leu
                        435                 440                 445

Gly Arg Arg Glu Glu Tyr Asp Val Leu Asp Lys Arg Gly Arg Asp
                450                 455                 460

Pro Glu Met Gly Gly Lys Pro Gln Arg Arg Lys Asn Pro Gln Glu Gly
        465                 470                 475                 480

Leu Tyr Asn Glu Leu Gln Lys Asp Lys Met Ala Glu Ala Tyr Ser Glu
                        485                 490                 495
```

```
Ile Gly Met Lys Gly Glu Arg Arg Gly Lys Gly His Asp Gly Leu
            500                 505                 510
Tyr Gln Gly Leu Ser Thr Ala Thr Lys Asp Thr Tyr Asp Ala Leu His
        515                 520                 525
Met Gln Ala Leu Pro Pro Arg Ala Lys Arg Ser Gly Ser Gly Ala
        530                 535                 540
Thr Asn Phe Ser Leu Leu Lys Gln Ala Gly Asp Val Glu Glu Asn Pro
545                 550                 555                 560
Gly Pro Met Pro Pro Arg Leu Leu Phe Phe Leu Leu Phe Leu Thr
                565                 570                 575
Pro Met Glu Val Arg Pro Glu Glu Pro Leu Val Val Lys Val Glu Glu
            580                 585                 590
Gly Asp Asn Ala Val Leu Gln Cys Leu Lys Gly Thr Ser Asp Gly Pro
            595                 600                 605
Thr Gln Gln Leu Thr Trp Ser Arg Glu Ser Pro Leu Lys Pro Phe Leu
            610                 615                 620
Lys Leu Ser Leu Gly Leu Pro Gly Leu Gly Ile His Met Arg Pro Leu
625                 630                 635                 640
Ala Ile Trp Leu Phe Ile Phe Asn Val Ser Gln Gln Met Gly Gly Phe
                645                 650                 655
Tyr Leu Cys Gln Pro Gly Pro Pro Ser Glu Lys Ala Trp Gln Pro Gly
            660                 665                 670
Trp Thr Val Asn Val Glu Gly Ser Gly Glu Leu Phe Arg Trp Asn Val
            675                 680                 685
Ser Asp Leu Gly Gly Leu Gly Cys Gly Leu Lys Asn Arg Ser Ser Glu
            690                 695                 700
Gly Pro Ser Ser Pro Ser Gly Lys Leu Met Ser Pro Lys Leu Tyr Val
705                 710                 715                 720
Trp Ala Lys Asp Arg Pro Glu Ile Trp Glu Gly Glu Pro Pro Cys Leu
                725                 730                 735
Pro Pro Arg Asp Ser Leu Asn Gln Ser Leu Ser Gln Asp Leu Thr Met
            740                 745                 750
Ala Pro Gly Ser Thr Leu Trp Leu Ser Cys Gly Val Pro Pro Asp Ser
            755                 760                 765
Val Ser Arg Gly Pro Leu Ser Trp Thr His Val His Pro Lys Gly Pro
            770                 775                 780
Lys Ser Leu Leu Ser Leu Glu Leu Lys Asp Asp Arg Pro Ala Arg Asp
785                 790                 795                 800
Met Trp Val Met Glu Thr Gly Leu Leu Leu Pro Arg Ala Thr Ala Gln
                805                 810                 815
Asp Ala Gly Lys Tyr Tyr Cys His Arg Gly Asn Leu Thr Met Ser Phe
            820                 825                 830
His Leu Glu Ile Thr Ala Arg Pro Gly Gly Gly Ser Gly Gly Gly
            835                 840                 845
Gly Ser Gly Gly Gly Gly Ser Gly Gly Gly Gly Ser Asp Met Ala Gln
            850                 855                 860
Val Gln Leu Gln Glu Ser Gly Pro Gly Leu Val Lys Pro Ser Glu Thr
865                 870                 875                 880
Leu Ser Leu Thr Cys Val Val Ser Gly Gly Ser Ile Ser Ser Ser Asn
                885                 890                 895
Trp Trp Ser Trp Val Arg Gln Pro Pro Gly Lys Gly Leu Glu Trp Ile
                900                 905                 910
```

-continued

```
Gly Glu Ile Tyr His Ser Gly Ser Pro Asp Tyr Asn Pro Ser Leu Lys
            915                 920                 925

Ser Arg Val Thr Ile Ser Val Asp Lys Ser Arg Asn Gln Phe Ser Leu
    930                 935                 940

Lys Leu Ser Ser Val Thr Ala Ala Asp Thr Ala Val Tyr Tyr Cys Ala
945                 950                 955                 960

Lys Val Ser Thr Gly Gly Phe Phe Asp Tyr Trp Gly Gln Gly Thr Leu
                965                 970                 975

Val Thr Val Ser Ser Gly Gly Gly Ser Gly Gly Gly Gly Ser Gly
                980                 985                 990

Gly Gly Ser Glu Ile Glu Leu Thr Gln Ser Pro Ser Ser Leu Ser
            995                1000                1005

Ala Ser Val Gly Asp Arg Val Thr Ile Thr Cys Arg Ala Ser Gln
        1010                1015                1020

Ser Ile Ser Ser Tyr Leu Asn Trp Tyr Gln Gln Lys Pro Gly Lys
        1025                1030                1035

Ala Pro Lys Leu Leu Ile Tyr Ala Ala Ser Ser Leu Gln Ser Gly
        1040                1045                1050

Val Pro Ser Arg Phe Ser Gly Ser Gly Ser Gly Thr Asp Phe Thr
        1055                1060                1065

Leu Thr Ile Ser Ser Leu Gln Pro Glu Asp Phe Ala Thr Tyr Tyr
        1070                1075                1080

Cys Gln Gln Ser Tyr Ser Thr Pro Pro Thr Phe Gly Pro Gly Thr
        1085                1090                1095

Lys Val Glu Ile Lys Arg Thr His His His His His His
        1100                1105                1110
```

<210> SEQ ID NO 55
<211> LENGTH: 1115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Arg Leu Leu Val Leu Leu Trp Gly Cys Leu Leu Pro Gly Tyr
1               5                   10                  15

Glu Ala Asp Ile Gln Met Thr Gln Thr Thr Ser Ser Leu Ser Ala Ser
                20                  25                  30

Leu Gly Asp Arg Val Thr Ile Ser Cys Arg Ala Ser Gln Asp Ile Ser
            35                  40                  45

Lys Tyr Leu Asn Trp Tyr Gln Gln Lys Pro Asp Gly Thr Val Lys Leu
50                  55                  60

Leu Ile Tyr His Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Glu Gln Glu Asp Ile Ala Thr Tyr Phe Cys Gln Gln Gly Asn Thr Leu
            100                 105                 110

Pro Tyr Thr Phe Gly Gly Gly Thr Lys Leu Glu Ile Thr Gly Gly Gly
        115                 120                 125

Gly Ser Gly Gly Gly Gly Ser Gly Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160
```

-continued

```
Gln Ser Leu Ser Val Thr Cys Thr Val Ser Gly Val Ser Leu Pro Asp
                165                 170                 175
Tyr Gly Val Ser Trp Ile Arg Gln Pro Pro Arg Lys Gly Leu Glu Trp
            180                 185                 190
Leu Gly Val Ile Trp Gly Ser Glu Thr Thr Tyr Tyr Asn Ser Ala Leu
        195                 200                 205
Lys Ser Arg Leu Thr Ile Ile Lys Asp Asn Ser Lys Ser Gln Val Phe
    210                 215                 220
Leu Lys Met Asn Ser Leu Gln Thr Asp Asp Thr Ala Ile Tyr Tyr Cys
225                 230                 235                 240
Ala Lys His Tyr Tyr Tyr Gly Gly Ser Tyr Ala Met Asp Tyr Trp Gly
                245                 250                 255
Gln Gly Thr Ser Val Thr Val Ser Ser Asp Tyr Lys Asp Asp Asp Asp
            260                 265                 270
Lys Ile Glu Val Met Tyr Pro Pro Pro Tyr Leu Asp Asn Glu Lys Ser
        275                 280                 285
Asn Gly Thr Ile Ile His Val Lys Gly Lys His Leu Cys Pro Ser Pro
    290                 295                 300
Leu Phe Pro Gly Pro Ser Lys Pro Phe Trp Val Leu Val Val Val Gly
305                 310                 315                 320
Gly Val Leu Ala Cys Tyr Ser Leu Leu Val Thr Val Ala Phe Ile Ile
                325                 330                 335
Phe Trp Val Arg Ser Lys Arg Ser Arg Leu Leu His Ser Asp Tyr Met
            340                 345                 350
Asn Met Thr Pro Arg Arg Pro Gly Pro Thr Arg Lys His Tyr Gln Pro
        355                 360                 365
Tyr Ala Pro Pro Arg Asp Phe Ala Ala Tyr Arg Ser Lys Arg Gly Arg
    370                 375                 380
Lys Lys Leu Leu Tyr Ile Phe Lys Gln Pro Phe Met Arg Pro Val Gln
385                 390                 395                 400
Thr Thr Gln Glu Glu Asp Gly Cys Ser Cys Arg Phe Pro Glu Glu Glu
                405                 410                 415
Glu Gly Gly Cys Glu Leu Arg Val Lys Phe Ser Arg Ser Ala Asp Ala
            420                 425                 430
Pro Ala Tyr Gln Gln Gly Gln Asn Gln Leu Tyr Asn Glu Leu Asn Leu
        435                 440                 445
Gly Arg Arg Glu Glu Tyr Asp Val Leu Asp Lys Arg Arg Gly Arg Asp
    450                 455                 460
Pro Glu Met Gly Gly Lys Pro Gln Arg Arg Lys Asn Pro Gln Glu Gly
465                 470                 475                 480
Leu Tyr Asn Glu Leu Gln Lys Asp Lys Met Ala Glu Ala Tyr Ser Glu
                485                 490                 495
Ile Gly Met Lys Gly Glu Arg Arg Arg Gly Lys Gly His Asp Gly Leu
            500                 505                 510
Tyr Gln Gly Leu Ser Thr Ala Thr Lys Asp Thr Tyr Asp Ala Leu His
        515                 520                 525
Met Gln Ala Leu Pro Pro Arg Arg Ala Lys Arg Ser Gly Ser Gly Ala
    530                 535                 540
Thr Asn Phe Ser Leu Leu Lys Gln Ala Gly Asp Val Glu Glu Asn Pro
545                 550                 555                 560
Gly Pro Met Pro Pro Pro Arg Leu Leu Phe Phe Leu Leu Phe Leu Thr
                565                 570                 575
```

```
Pro Met Glu Val Arg Pro Glu Pro Leu Val Lys Val Glu Glu
            580                 585                 590

Gly Asp Asn Ala Val Leu Gln Cys Leu Lys Gly Thr Ser Asp Gly Pro
            595                 600                 605

Thr Gln Gln Leu Thr Trp Ser Arg Glu Ser Pro Leu Lys Pro Phe Leu
            610                 615                 620

Lys Leu Ser Leu Gly Leu Pro Gly Leu Gly Ile His Met Arg Pro Leu
625                 630                 635                 640

Ala Ile Trp Leu Phe Ile Phe Asn Val Ser Gln Gln Met Gly Gly Phe
                645                 650                 655

Tyr Leu Cys Gln Pro Gly Pro Pro Ser Glu Lys Ala Trp Gln Pro Gly
            660                 665                 670

Trp Thr Val Asn Val Glu Gly Ser Gly Glu Leu Phe Arg Trp Asn Val
            675                 680                 685

Ser Asp Leu Gly Gly Leu Gly Cys Gly Leu Lys Asn Arg Ser Ser Glu
            690                 695                 700

Gly Pro Ser Ser Pro Ser Gly Lys Leu Met Ser Pro Lys Leu Tyr Val
705                 710                 715                 720

Trp Ala Lys Asp Arg Pro Glu Ile Trp Glu Gly Glu Pro Pro Cys Leu
                725                 730                 735

Pro Pro Arg Asp Ser Leu Asn Gln Ser Leu Ser Gln Asp Leu Thr Met
            740                 745                 750

Ala Pro Gly Ser Thr Leu Trp Leu Ser Cys Gly Val Pro Pro Asp Ser
            755                 760                 765

Val Ser Arg Gly Pro Leu Ser Trp Thr His Val His Pro Lys Gly Pro
770                 775                 780

Lys Ser Leu Leu Ser Leu Glu Leu Lys Asp Asp Arg Pro Ala Arg Asp
785                 790                 795                 800

Met Trp Val Met Glu Thr Gly Leu Leu Leu Pro Arg Ala Thr Ala Gln
                805                 810                 815

Asp Ala Gly Lys Tyr Tyr Cys His Arg Gly Asn Leu Thr Met Ser Phe
            820                 825                 830

His Leu Glu Ile Thr Ala Arg Pro Gly Gly Gly Gly Ser Gly Gly Gly
            835                 840                 845

Gly Ser Gly Gly Gly Ser Gly Gly Gly Ser Glu Val Gln Leu
850                 855                 860

Val Glu Ser Gly Gly Gly Leu Val Gln Pro Gly Gly Ser Leu Arg Leu
865                 870                 875                 880

Ser Cys Ala Ala Ser Gly Phe Asn Ile Lys Asp Thr Tyr Ile His Trp
                885                 890                 895

Val Arg Gln Ala Pro Gly Lys Gly Leu Glu Trp Val Ala Arg Ile Tyr
            900                 905                 910

Pro Thr Asn Gly Tyr Thr Arg Tyr Ala Asp Ser Val Lys Gly Arg Phe
            915                 920                 925

Thr Ile Ser Ala Asp Thr Ser Lys Asn Thr Ala Tyr Leu Gln Met Asn
            930                 935                 940

Ser Leu Arg Ala Glu Asp Thr Ala Val Tyr Tyr Cys Ser Arg Trp Gly
945                 950                 955                 960

Gly Asp Gly Phe Tyr Ala Met Asp Tyr Trp Gly Gln Gly Thr Leu Val
                965                 970                 975

Thr Val Ser Ser Ala Ser Thr Gly Gly Gly Ser Gly Gly Gly Gly
            980                 985                 990

Ser Gly Gly Gly Gly Ser Asp Ile  Gln Met Thr Gln Ser  Pro Ser Ser
```

```
                995                 1000                1005
Leu Ser Ala Ser Val Gly Asp Arg Val Thr Ile Thr Cys Arg Ala
        1010                1015                1020

Ser Gln Asp Val Asn Thr Ala Val Ala Trp Tyr Gln Gln Lys Pro
        1025                1030                1035

Gly Lys Ala Pro Lys Leu Leu Ile Tyr Ser Ala Ser Phe Leu Tyr
        1040                1045                1050

Ser Gly Val Pro Ser Arg Phe Ser Gly Ser Arg Ser Gly Thr Asp
        1055                1060                1065

Phe Thr Leu Thr Ile Ser Ser Leu Gln Pro Glu Asp Phe Ala Thr
        1070                1075                1080

Tyr Tyr Cys Gln Gln His Tyr Thr Thr Pro Pro Thr Phe Gly Gln
        1085                1090                1095

Gly Thr Lys Val Glu Ile Lys Arg Thr Ser Arg His His His His
        1100                1105                1110

His His
    1115

<210> SEQ ID NO 56
<211> LENGTH: 1114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Arg Leu Leu Val Leu Leu Trp Gly Cys Leu Leu Pro Gly Tyr
1               5                   10                  15

Glu Ala Asp Ile Gln Met Thr Gln Thr Thr Ser Ser Leu Ser Ala Ser
            20                  25                  30

Leu Gly Asp Arg Val Thr Ile Ser Cys Arg Ala Ser Gln Asp Ile Ser
        35                  40                  45

Lys Tyr Leu Asn Trp Tyr Gln Gln Lys Pro Asp Gly Thr Val Lys Leu
    50                  55                  60

Leu Ile Tyr His Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Glu Gln Glu Asp Ile Ala Thr Tyr Phe Cys Gln Gln Gly Asn Thr Leu
            100                 105                 110

Pro Tyr Thr Phe Gly Gly Gly Thr Lys Leu Glu Ile Thr Gly Gly Gly
        115                 120                 125

Gly Ser Gly Gly Gly Gly Ser Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
        195                 200                 205

Lys Ser Arg Leu Thr Ile Ile Lys Asp Asn Ser Lys Ser Gln Val Phe
    210                 215                 220
```

```
Leu Lys Met Asn Ser Leu Gln Thr Asp Asp Thr Ala Ile Tyr Tyr Cys
225                 230                 235                 240

Ala Lys His Tyr Tyr Gly Gly Ser Tyr Ala Met Asp Tyr Trp Gly
                245                 250                 255

Gln Gly Thr Ser Val Thr Val Ser Ser Asp Tyr Lys Asp Asp Asp Asp
                260                 265                 270

Lys Ile Glu Val Met Tyr Pro Pro Pro Tyr Leu Asp Asn Glu Lys Ser
                275                 280                 285

Asn Gly Thr Ile Ile His Val Lys Gly Lys His Leu Cys Pro Ser Pro
290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
                355                 360                 365

Tyr Ala Pro Pro Arg Asp Phe Ala Ala Tyr Arg Ser Lys Arg Gly Arg
370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Arg Val Lys Phe Ser Arg Ser Ala Asp Ala
                420                 425                 430

Pro Ala Tyr Gln Gln Gly Gln Asn Gln Leu Tyr Asn Glu Leu Asn Leu
                435                 440                 445

Gly Arg Arg Glu Glu Tyr Asp Val Leu Asp Lys Arg Arg Gly Arg Asp
                450                 455                 460

Pro Glu Met Gly Gly Lys Pro Gln Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Arg Gly Lys Gly His Asp Gly Leu
                500                 505                 510

Tyr Gln Gly Leu Ser Thr Ala Thr Lys Asp Thr Tyr Asp Ala Leu His
                515                 520                 525

Met Gln Ala Leu Pro Pro Arg Arg Ala Lys Arg Ser Gly Ser Gly Ala
                530                 535                 540

Thr Asn Phe Ser Leu Leu Lys Gln Ala Gly Asp Val Glu Glu Asn Pro
545                 550                 555                 560

Gly Pro Met Pro Pro Pro Arg Leu Leu Phe Phe Leu Leu Phe Leu Thr
                565                 570                 575

Pro Met Glu Val Arg Pro Glu Glu Pro Leu Val Val Lys Val Glu Glu
                580                 585                 590

Gly Asp Asn Ala Val Leu Gln Cys Leu Lys Gly Thr Ser Asp Gly Pro
                595                 600                 605

Thr Gln Gln Leu Thr Trp Ser Arg Glu Ser Pro Leu Lys Pro Phe Leu
                610                 615                 620

Lys Leu Ser Leu Gly Leu Pro Gly Leu Gly Ile His Met Arg Pro Leu
625                 630                 635                 640

Ala Ile Trp Leu Phe Ile Phe Asn Val Ser Gln Gln Met Gly Gly Phe
```

-continued

```
                645                 650                 655
Tyr Leu Cys Gln Pro Gly Pro Ser Glu Lys Ala Trp Gln Pro Gly
            660                 665                 670

Trp Thr Val Asn Val Glu Gly Ser Gly Glu Leu Phe Arg Trp Asn Val
            675                 680                 685

Ser Asp Leu Gly Gly Leu Gly Cys Gly Leu Lys Asn Arg Ser Ser Glu
    690                 695                 700

Gly Pro Ser Ser Pro Ser Gly Lys Leu Met Ser Pro Lys Leu Tyr Val
705                 710                 715                 720

Trp Ala Lys Asp Arg Pro Glu Ile Trp Glu Gly Glu Pro Pro Cys Leu
                725                 730                 735

Pro Pro Arg Asp Ser Leu Asn Gln Ser Leu Ser Gln Asp Leu Thr Met
            740                 745                 750

Ala Pro Gly Ser Thr Leu Trp Leu Ser Cys Gly Val Pro Pro Asp Ser
            755                 760                 765

Val Ser Arg Gly Pro Leu Ser Trp Thr His Val His Pro Lys Gly Pro
    770                 775                 780

Lys Ser Leu Leu Ser Leu Glu Leu Lys Asp Asp Arg Pro Ala Arg Asp
785                 790                 795                 800

Met Trp Val Met Glu Thr Gly Leu Leu Leu Pro Arg Ala Thr Ala Gln
                805                 810                 815

Asp Ala Gly Lys Tyr Tyr Cys His Arg Gly Asn Leu Thr Met Ser Phe
            820                 825                 830

His Leu Glu Ile Thr Ala Arg Pro Gly Gly Gly Gly Ser Gly Gly Gly
            835                 840                 845

Gly Ser Gly Gly Gly Gly Ser Gly Gly Gly Gly Ser Glu Val Gln Leu
    850                 855                 860

Leu Glu Ser Gly Gly Gly Gln Val Gln Pro Gly Gly Ser Leu Arg Leu
865                 870                 875                 880

Ser Cys Ala Ala Ser Gly Phe Thr Phe Ser Ser Tyr Pro Met Ser Trp
                885                 890                 895

Val Arg Gln Ala Pro Gly Lys Gly Leu Glu Trp Val Ser Ala Ile Gly
            900                 905                 910

Gly Ser Gly Gly Ser Leu Pro Tyr Ala Asp Ser Val Lys Gly Arg Phe
    915                 920                 925

Thr Ile Ser Arg Asp Asn Ser Lys Asn Thr Leu Tyr Leu Gln Met Asn
    930                 935                 940

Ser Leu Arg Ala Glu Asp Thr Ala Val Tyr Tyr Cys Ala Arg Tyr Trp
945                 950                 955                 960

Pro Met Asp Ile Trp Gly Gln Gly Thr Leu Val Thr Val Ser Ser Ala
                965                 970                 975

Ser Thr Gly Gly Gly Gly Ser Gly Gly Gly Gly Ser Gly Gly Gly Gly
            980                 985                 990

Ser Gly Gly Gly Gly Ser Glu Ile Val Leu Thr Gln Ser Pro Gly Thr
    995                 1000                1005

Leu Ser Leu Ser Pro Gly Glu Arg Ala Thr Leu Ser Cys Arg Ala
    1010                1015                1020

Ser Gln Ser Val Ser Ser Ser Tyr Leu Ala Trp Tyr Gln Gln Lys
    1025                1030                1035

Pro Gly Gln Ala Pro Arg Leu Leu Met Tyr Asp Ala Ser Ile Arg
    1040                1045                1050

Ala Thr Gly Ile Pro Asp Arg Phe Ser Gly Ser Gly Ser Gly Thr
    1055                1060                1065
```

```
Asp Phe Thr Leu Thr Ile Ser Arg Leu Glu Pro Glu Asp Phe Ala
    1070                1075                1080

Val Tyr Tyr Cys Gln Gln Tyr Gln Ser Trp Pro Leu Thr Phe Gly
        1085                1090                1095

Gln Gly Thr Lys Val Glu Thr Lys Arg Thr His His His His His
    1100                1105                1110

His
```

<210> SEQ ID NO 57
<211> LENGTH: 1106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Arg Leu Leu Val Leu Leu Trp Gly Cys Leu Leu Pro Gly Tyr
1                 5                  10                 15

Glu Ala Asp Ile Gln Met Thr Gln Thr Thr Ser Ser Leu Ser Ala Ser
            20                  25                  30

Leu Gly Asp Arg Val Thr Ile Ser Cys Arg Ala Ser Gln Asp Ile Ser
        35                  40                  45

Lys Tyr Leu Asn Trp Tyr Gln Gln Lys Pro Asp Gly Thr Val Lys Leu
    50                  55                  60

Leu Ile Tyr His Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Glu Gln Glu Asp Ile Ala Thr Tyr Phe Cys Gln Gln Gly Asn Thr Leu
            100                 105                 110

Pro Tyr Thr Phe Gly Gly Gly Thr Lys Leu Glu Ile Thr Gly Gly Gly
        115                 120                 125

Gly Ser Gly Gly Gly Gly Ser Gly Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
        195                 200                 205

Lys Ser Arg Leu Thr Ile Ile Lys Asp Asn Ser Lys Ser Gln Val Phe
    210                 215                 220

Leu Lys Met Asn Ser Leu Gln Thr Asp Asp Thr Ala Ile Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Ser Val Thr Val Ser Ser Asp Tyr Lys Asp Asp Asp Asp
            260                 265                 270

Lys Ile Glu Val Met Tyr Pro Pro Pro Tyr Leu Asp Asn Glu Lys Ser
        275                 280                 285

Asn Gly Thr Ile Ile His Val Lys Gly Lys His Leu Cys Pro Ser Pro
    290                 295                 300
```

-continued

```
Leu Phe Pro Gly Pro Ser Lys Pro Phe Trp Val Leu Val Val Gly
305                 310                 315                 320

Gly Val Leu Ala Cys Tyr Ser Leu Leu Val Thr Val Ala Phe Ile Ile
            325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Lys Arg Gly Arg
        370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
450                 455                 460

Pro Glu Met Gly Gly Lys Pro Gln Arg Arg Lys Asn Pro Gln Glu Gly
465                 470                 475                 480

Leu Tyr Asn Glu Leu Gln Lys Asp Lys Met Ala Glu Ala Tyr Ser Glu
            485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg Glu Gly Arg Gly Ser Leu Leu Thr Cys
530                 535                 540

Gly Asp Val Glu Glu Asn Pro Gly Pro Met Pro Pro Arg Leu Leu
545                 550                 555                 560

Phe Phe Leu Leu Phe Leu Thr Pro Met Glu Val Arg Pro Glu Glu Pro
                565                 570                 575

Leu Val Val Lys Val Glu Glu Gly Asp Asn Ala Val Leu Gln Cys Leu
            580                 585                 590

Lys Gly Thr Ser Asp Gly Pro Thr Gln Gln Leu Thr Trp Ser Arg Glu
            595                 600                 605

Ser Pro Leu Lys Pro Phe Leu Lys Leu Ser Leu Gly Leu Pro Gly Leu
        610                 615                 620

Gly Ile His Met Arg Pro Leu Ala Ile Trp Leu Phe Ile Phe Asn Val
625                 630                 635                 640

Ser Gln Gln Met Gly Gly Phe Tyr Leu Cys Gln Pro Gly Pro Pro Ser
            645                 650                 655

Glu Lys Ala Trp Gln Pro Gly Trp Thr Val Asn Val Glu Gly Ser Gly
            660                 665                 670

Glu Leu Phe Arg Trp Asn Val Ser Asp Leu Gly Gly Leu Gly Cys Gly
        675                 680                 685

Leu Lys Asn Arg Ser Ser Glu Gly Pro Ser Ser Pro Ser Gly Lys Leu
        690                 695                 700

Met Ser Pro Lys Leu Tyr Val Trp Ala Lys Asp Arg Pro Glu Ile Trp
705                 710                 715                 720
```

```
Glu Gly Glu Pro Pro Cys Leu Pro Pro Arg Asp Ser Leu Asn Gln Ser
                725                 730                 735

Leu Ser Gln Asp Leu Thr Met Ala Pro Gly Ser Thr Leu Trp Leu Ser
        740                 745                 750

Cys Gly Val Pro Pro Asp Ser Val Ser Arg Gly Pro Leu Ser Trp Thr
            755                 760                 765

His Val His Pro Lys Gly Pro Lys Ser Leu Leu Ser Leu Glu Leu Lys
        770                 775                 780

Asp Asp Arg Pro Ala Arg Asp Met Trp Val Met Glu Thr Gly Leu Leu
785                 790                 795                 800

Leu Pro Arg Ala Thr Ala Gln Asp Ala Gly Lys Tyr Tyr Cys His Arg
            805                 810                 815

Gly Asn Leu Thr Met Ser Phe His Leu Glu Ile Thr Ala Arg Pro Gly
            820                 825                 830

Gly Gly Gly Ser Gly Gly Gly Ser Gly Gly Gly Ser Gly Gly
            835                 840                 845

Gly Gly Ser Met Ala Gln Val Lys Leu Gln Glu Ser Gly Ala Glu Leu
        850                 855                 860

Val Lys Pro Gly Ala Ser Val Lys Met Ser Cys Lys Ala Ser Gly Tyr
865                 870                 875                 880

Thr Phe Thr Ser Tyr Asn Met His Trp Val Lys Gln Thr Pro Gly Gln
            885                 890                 895

Gly Leu Glu Trp Ile Gly Ala Ile Tyr Pro Gly Asn Gly Asp Thr Ser
            900                 905                 910

Tyr Asn Gln Lys Phe Lys Gly Lys Ala Thr Leu Thr Ala Asp Lys Ser
        915                 920                 925

Ser Ser Thr Ala Tyr Met Gln Leu Ser Ser Leu Thr Ser Glu Asp Ser
        930                 935                 940

Ala Asp Tyr Tyr Cys Ala Arg Ser Asn Tyr Tyr Gly Ser Ser Tyr Trp
945                 950                 955                 960

Phe Phe Asp Val Trp Gly Gln Gly Thr Thr Val Thr Val Ser Ser Gly
            965                 970                 975

Gly Gly Gly Ser Gly Gly Gly Gly Ser Gly Gly Gly Gly Ser Asp Ile
            980                 985                 990

Glu Leu Thr Gln Ser Pro Thr Ile  Leu Ser Ala Ser Pro  Gly Glu Lys
        995                 1000                1005

Val Thr Met Thr Cys Arg Ala  Ser Ser Ser Val Asn  Tyr Met Asp
       1010                 1015                1020

Trp Tyr Gln Lys Lys Pro Gly  Ser Ser Pro Lys Pro  Trp Ile Tyr
       1025                 1030                1035

Ala Thr Ser Asn Leu Ala Ser  Gly Val Pro Ala Arg  Phe Ser Gly
       1040                 1045                1050

Ser Gly Ser Gly Thr Ser Tyr  Ser Leu Thr Ile Ser  Arg Val Glu
       1055                 1060                1065

Ala Glu Asp Ala Ala Thr Tyr  Tyr Cys Gln Gln Trp  Ser Phe Asn
       1070                 1075                1080

Pro Pro Thr Phe Gly Gly Gly  Thr Lys Leu Glu Ile  Lys Arg Ala
       1085                 1090                1095

Ala Ala His His His His His  His
       1100                 1105

<210> SEQ ID NO 58
<211> LENGTH: 1248
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 58

| | | | | | |
|---|---|---|---|---|---|
| atgccacctc | ctcgcctcct | cttcttcctc | ctcttcctca | cccccatgga | agtcaggccc | 60 |
| gaggagcccc | tggtggtgaa | ggtggaggag | ggcgacgacg | cctggctgag | gtgcctgaag | 120 |
| ggcaccagcg | acggccccac | cagccaggtg | acctggagca | gggagagccc | cctgaagccc | 180 |
| ttcctgaagt | acagcctggg | cgtgcccggc | ctgggcgtgc | acatcaggcc | cctggccatc | 240 |
| ggcctggtga | tccccaacgt | gagccagcag | atgggcggct | ctacctgtg | ccagcccggc | 300 |
| cccccagcg | agaaggcctg | gcagcccggc | tggaccgtga | acgtggaggg | cagcggcgag | 360 |
| ctgttcaggt | ggaacgtgag | cgacctgggc | ggcctgggct | gcggcctgaa | gaacaggagc | 420 |
| agcgagggcc | ccagcagccc | cagcggcaag | ctgatgagcc | caagctgta | cgtgtgggcc | 480 |
| aaggacaggc | ccgagatctg | ggagggcgag | ccccccctgcc | tgcccccag | ggacagcctg | 540 |
| aaccagagcc | tgagccagga | cctgaccatg | gcccccggca | gcaccctgtg | gctgagctgc | 600 |
| ggcgtgcccc | ccgacagcgt | gagcagggc | cccctgagct | ggaccacgt | gcaccccaag | 660 |
| ggccccaaga | gcctgctgag | cctggagctg | aaggacgaca | ggcccgccag | ggagatgatc | 720 |
| gtggacgaga | ccgcctgct | gctgcccagg | gccaccgccc | aggacgccgg | caagtactac | 780 |
| tgccacaggg | gcaacaggac | catcagctac | cacctggaga | tcaccgccag | gcccgtgagc | 840 |
| gcccacaccc | ccctgaggac | cggcggctgg | aagggaggag | gtgggtctgg | aggtggagga | 900 |
| tctggtggag | gtgggtctgg | aggaggtggg | tctgtgagcg | acgtgcccag | ggacctggag | 960 |
| gtggtggccg | ccaccccac | cagcctgctg | atcagctggt | tcgactacgc | cgtgaccctac | 1020 |
| tacaggatca | cctacggcga | gaccggcggc | aacagcccccg | tgcaggagtt | caccgtgccc | 1080 |
| ggctggatca | gcaccgccac | catcagcggc | ctgaagcccg | cgtggacta | caccatcacc | 1140 |
| gtgtacgccg | tgaccgacaa | cagccactgg | cccttcagga | gcaccccat | cagcaccaac | 1200 |
| tacaggaccg | agatcgacaa | gccccccag | catcatcacc | atcaccat | | 1248 |

<210> SEQ ID NO 59
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

| | | | | | |
|---|---|---|---|---|---|
| atgccacctc | ctcgcctcct | cttcttcctc | ctcttcctca | cccccatgga | agtcaggccc | 60 |
| gaggagcccc | tggtggtgaa | ggtggaggag | ggcgacaccg | ccgtgctgcc | ctgcctgaag | 120 |
| ggcaccagcg | acggccccac | ccagcagctg | acctggagca | gggagagccc | cctgaagccc | 180 |
| ttcctgaagt | acagcctggg | cgtgcccggc | ctgggcgtgc | acgtgaggcc | cgacgccatc | 240 |
| agcgtggtga | tcaggaacgt | gagccagcag | atgggcggct | ctacctgtg | ccagcccggc | 300 |
| cccccagcg | agaaggcctg | gcagcccggc | tggaccgtga | acgtggaggg | cagcggcgag | 360 |
| ctgttcaggt | ggaacgtgag | cgacctgggc | ggcctgggct | gcggcctgaa | gaacaggagc | 420 |
| agcgagggcc | ccagcagccc | cagcggcaag | ctgatgagcc | caagctgta | cgtgtgggcc | 480 |
| aaggacaggc | ccgagatctg | ggagggcgag | ccccccctgcc | tgcccccag | ggacagcctg | 540 |
| aaccagagcc | tgagccagga | cctgaccatg | gcccccggca | gcaccctgtg | gctgagctgc | 600 |

```
ggcgtgcccc ccgacagcgt gagcaggggc cccctgagct ggaccacgt gcacccaag      660 ggccccaaga gcctgctgag cctggagctg aaggacgaca ggcccgccag ggagatgatc    720
gtggacgaga ccggcctgct gctgcccagg ccaccgccc aggacgccgg caagtggtac     780
tgcagcaggg gcaacgtgac caccagctac cacctggaga tcaccgccag gcccgtgaag    840
gcccacagcg acctgaggac cggcggctgg aagggaggag gtgggtctgg aggtggagga    900
tctggtggag gtgggtctgg aggaggtggg tctgtgagcg acgtgcccag ggacctggag    960
gtggtggccg ccaccccac cagcctgctg atcagctggt tcgactacgc cgtgacctac    1020
tacaggatca cctacggcga gaccggcggc aacagccccg tgcaggagtt caccgtgccc    1080
ggctggatca gcaccgccac catcagcggc ctgaagcccg gcgtggacta caccatcacc    1140
gtgtacgccc tgaccgacaa cagccactgg cccttcagga gcacccccat cagcaccaac    1200
tacaggaccg agatcgacaa gcccccccag catcatcacc atcaccat                 1248
```

<210> SEQ ID NO 60
<211> LENGTH: 1247
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgccacctc ctcgcctcct cttcttcctc ctcttcctca cccccatgga agtcaggccc     60
gaggagcccc tggtggtgaa ggtggaggag ggcgacaccg ccgccctgtg gtgcctgaag    120
ggcaccagcg acggccccac ccagcagctg acctggagca gggagagccc cctgaagccc    180
ttcctgaagc tgagcctggg cctgcccggc atgggcgtgc acatgaggcc cggcgccgtg    240
agcgccgtga tcagcaacgt gagccagcag atgggcggct ctacctgtg ccagcccggc    300 ccccccagcg agaaggcctg gcagcccggc tggaccgtga acgtggaggg cagcggcgag    360
ctgttcaggt ggaacgtgag cgacctgggc ggcctgggct gcggcctgaa gaacaggagc    420
agcgagggcc ccagcagccc cagcggcaag ctgatgagcc caagctgta cgtgtgggcc    480 aaggacaggc ccgagatctg ggagggcgag ccccctgcc tgccccccag ggacagcctg    540
aaccagagcc tgagcaggga catgaccgtg gcccccggca gcaccctgtg gctgagctgc    600
ggcgtgcccc ccgacagcgt gagcaggggc cccctgagct ggaccacgt gcacccaag     660 ggccccaaga gcctgctgag cctggagctg aaggacgaca ggcccgccag gacatgtgg    720 gtgatgggca ccagcctgat cctgcccagg ccaccgccc aggacgccgg caagtactac     780
tgccacaggg gcaacctgac catgagcttc cacctggagg tggtggccag gcccgtgaag    840
gcccacagcg acctgaggac cggcggctgg aagggaggag gtgggtctgg aggtggagga    900
tctggtggag gtgggtctgg aggaggtggg tctgtgagcg acgtgcccag ggacctggag    960
gtggtggccg ccaccccac cagcctgctg atcagctggt tcgactacgc cgtgacctac    1020
tacaggatca cctacggcga gaccggcggc aacagccccg tgcaggagtt caccgtgccc    1080
ggctggatca gcaccgccac catcagcggc ctgaagccgg cgtggactac accatcaccg    1140
tgtacgccgt gaccgacaac agccactggc ccttcaggag cacccccatc agcaccaact    1200
acaggaccga gatcgacaag cccccccagc atcatcacca tcaccat                  1247
```

<210> SEQ ID NO 61
<211> LENGTH: 1248

| <212> TYPE: DNA
| <213> ORGANISM: Artificial Sequence
| <220> FEATURE:
| <223> OTHER INFORMATION: Description of Artificial Sequence: Synthetic
|       polynucleotide

<400> SEQUENCE: 61

| atgccacctc ctcgcctcct cttcttcctc ctcttcctca cccccatgga agtcaggccc | 60 |
| gaggagcccc tggtggtgaa ggtggaggag ggcgacaccg ccgccctgtg gtgcctgaag | 120 |
| ggcaccagcg acggccccac ccagcagctg acctggagca gggagagccc cctgaagccc | 180 |
| ttcctgaagt acagcctggg cgtgcccggc atgggcgtgc acgtgaggcc caacgccgtg | 240 |
| agcctggtga tcagcaacgt gagccagcag atgggcggct ctacctgtgt ccagcccggc | 300 |
| ccccccagcg agaaggcctg gcagcccggc tggaccgtga acgtggaggg cagcggcgag | 360 |
| ctgttcaggt ggaacgtgag cgacctgggc ggcctgggct gcggcctgaa gaacaggagc | 420 |
| agcgagggcc ccagcagccc cagcggcaag ctgatgagcc caagctgta cgtgtgggcc | 480 |
| aaggacaggc ccgagatctg ggaggcgag ccccctgcc tgcccccag ggacagcctg | 540 |
| aaccagagcc tgagcaggga catgaccgtg gccccggca gcaccctgtg gctgagctgc | 600 |
| ggcgtgcccc ccgacagcgt gagcaggggc ccctgagct ggaccacgt gcaccccaag | 660 |
| ggccccaaga gcctgctgag cctggagctg aaggacgaca ggcccgccag ggacatgtgg | 720 |
| gtgatggaga ccggcctggt gctgcccagg gccaccgccc aggacgccgg caagtggtac | 780 |
| tgccacaggg gcaacgtgac caccagctac acctggaga tcaccgccag gcccgtgagc | 840 |
| gcccacaccc ccctgaggac cggcggctgg aagggaggag gtgggtctgg aggtggagga | 900 |
| tctggtggag gtgggtctgg aggaggtggg tctgtgagcg acgtgcccag ggacctggag | 960 |
| gtggtggccg ccaccccac cagcctgctg atcagctggt cgactacgc cgtgaccta | 1020 |
| tacaggatca cctacggcga ccggcggc aacagccccg tgcaggagtt caccgtgccc | 1080 |
| ggctggatca gcaccgccac catcagcggc ctgaagcccg cgtggacta ccatcacc | 1140 |
| gtgtacgccg tgaccgacaa cagccactgg cccttcagga gcacccccat cagcaccaac | 1200 |
| tacaggaccg agatcgacaa gccccccag catcatcacc atcaccat | 1248 |

<210> SEQ ID NO 62
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| atgccacctc ctcgcctcct cttcttcctc ctcttcctca cccccatgga agtcaggccc | 60 |
| gaggaacctc tagtggtgaa ggtggaagag ggagataacg ctgtgctgca gtgcctcaag | 120 |
| gggacctcag atgccccac tcagcagctg acctggtctc gggagtcccc gcttaaaccc | 180 |
| ttcttaaaac tcagcctggg gctgccaggc ctgggaatcc acatgaggcc cctggccatc | 240 |
| tggcttttca tcttcaacgt ctctcaacag atgggggct tctacctgtg ccagccgggg | 300 |
| ccccctctg agaaggcctg gcagcctggc tggacagtga atgtgaggg cagcggggag | 360 |
| ctgttccggt ggaatgtttc ggacctaggt ggcctgggct gtggcctgaa gaacaggtcc | 420 |
| tcagagggcc ccagctcccc ttccgggaag ctcatgagcc caagctgta tgtgtgggcc | 480 |
| aaagaccgcc ctgagatctg ggagggagag cctccgtgtc tcccaccgag ggacagcctg | 540 |

-continued

| | |
|---|---|
| aaccagagcc tcagccagga cctcaccatg cccctggct ccacactctg ctgtcctgt | 600 |
| ggggtacccc ctgactctgt gtccaggggc ccctctcct ggacccatgt gcacccaag | 660 |
| gggcctaagt cattgctgag cctagagctg aaggacgatc gcccggccag agatatgtgg | 720 |
| gtaatggaga cgggtctgtt gttgccccgg ccacagctc aagacgctgg aaagtattat | 780 |
| tgtcaccgtg caacctgac catgtcattc cacctggaga tcactgctcg gccaggagga | 840 |
| ggtgggtctg gaggtggagg atctggtgga ggtgggtctg gaggaggtgg gtctgtgagc | 900 |
| gacgtgccca gggacctgga ggtggtggcc gccacccca ccagcctgct gatcagctgg | 960 |
| ttcgactacg ccgtgaccta ctacaggatc acctacggcg agaccggcgg caacagcccc | 1020 |
| gtgcaggagt tcaccgtgcc cggctggatc agcaccgcca ccatcagcgg cctgaagccc | 1080 |
| ggcgtggact acaccatcac cgtgtacgcc gtgaccgaca cagccactg gccccttcagg | 1140 |
| agcaccccca tcagcaccaa ctacaggacc gagatcgaca agccccccca gcatcatcac | 1200 |
| catcaccat | 1209 |

<210> SEQ ID NO 63
<211> LENGTH: 1692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | |
|---|---|
| atgccacctc ctcgcctcct cttcttcctc ctcttcctca cccccatgga agtcaggccc | 60 |
| gaggagcccc tggtggtgaa ggtggaggag ggcgacaccg ccgtgctgcc ctgcctgaag | 120 |
| ggcaccagcg acggcccac ccagcagctg acctggagca gggagagccc cctgaagccc | 180 |
| ttcctgaagt acagcctggg cgtgcccggc ctgggcgtgc acgtgaggcc cgacgccatc | 240 |
| agcgtggtga tcaggaacgt gagccagcag atgggcggct tctacctgtg ccagcccggc | 300 |
| cccccagcg agaaggcctg gcagcccggc tggaccgtga acgtggaggg cagcggcgag | 360 |
| ctgttcaggt ggaacgtgag cgacctgggc ggcctgggct gcggcctgaa gaacaggagc | 420 |
| agcgagggcc ccagcagccc cagcggcaag ctgatgagcc caagctgta cgtgtgggcc | 480 |
| aaggacaggc ccgagatctg ggagggcgag ccccctgcc tgcccccag ggacagcctg | 540 |
| aaccagagcc tgagccagga cctgaccatg ccccccggca gcaccctgtg ctgagctgc | 600 |
| ggcgtgcccc ccgacagcgt gagcaggggc cccctgagct ggacccacgt gcacccaag | 660 |
| ggccccaaga gcctgctgag cctggagctg aaggacgaca gcccgccag ggagatgatc | 720 |
| gtggacgaga ccggcctgct gctgcccagg ccaccgccc aggacgccgg caagtggtac | 780 |
| tgcagcaggg gcaacgtgac caccagctac cacctggaga tcaccgccag gcccgtgaag | 840 |
| gcccacagcg acctgaggac cggcggctgg aagggaggag gtgggtctgg aggtggagga | 900 |
| tctggtggag gtgggtctgg aggaggtgga tccgaggtgc agctggtgga gtctggtggt | 960 |
| ggtcttgttc aacctggtgg ttctcttcgt cttctcttgtg ctgcttctgg tttaatatt | 1020 |
| aaagatactt atattcattg ggttcgtcaa gctcctggta aaggtcttga atgggttgct | 1080 |
| cgtatttatc ctactaatgg ttatactcgt tatgctgatt ctgttaaagg tcgtttact | 1140 |
| atttctgctg atacttctaa aaatactgct tatcttcaaa tgaactctct tcgtgctgaa | 1200 |
| gatactgctg tttattattg ttctcgttgg ggtggtgatg gttttatgc tatggattat | 1260 |
| tgggtcaag gtactcttgt caccgtctcc tcagctagca ccggggagg tgggtctgga | 1320 |

```
ggtggaggat ctggtggagg tgggtctgac atccagatga cccagtctcc ttcttctctt    1380
tctgcttctg ttggtgatcg tgttactatt acttgtcgtg cttctcaaga tgttaatact    1440
gctgttgctt ggtatcaaca aaaacctggt aaagctccta aacttcttat ttattctgct    1500
tcttttcttt attctggtgt tccttctcgt ttttctggtt ctcgttctgg tactgatttt    1560
actcttacta tttcttctct caacctgaa  gattttgcta cttattattg tcaacaacat    1620
tatactactc ctcctacttt tggtcaaggt accaaggtgg agatcaaacg tacgcatcat    1680
caccatcacc at                                                        1692
```

<210> SEQ ID NO 64
<211> LENGTH: 1665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctgggaatcc acatgaggcc cctgccatc      240 tggcttttca tcttcaacgt ctctcaacag atggggggct ctacctgtg  ccagccgggg    300 ccccctctg  agaaggcctg gcagcctggc tggacagtca atgtggaggg cagcggggag    360
ctgttccggt ggaatgtttc ggacctaggt ggcctgggct gtggcctgaa gaacaggtcc    420
tcagagggcc ccagctcccc ttccgggaag ctcatgagcc caagctgta  tgtgtgggcc    480 aaagaccgcc ctgagatctg ggaggagag  cctccgtgtc tcccaccgag ggacagcctg    540
aaccagagcc tcagccagga cctcaccatg gccctggct  ccacactctg gctgtcctgt    600
ggggtacccc ctgactctgt gtccaggggc cccctctcct ggacccatgt gcaccccaag    660
gggcctaagt cattgctgag cctagagctg aaggacgatc gcccggccag agatatgtgg    720
gtaatggaga cgggtctgtt gttgccccgg gccacagctc aagacgctgg aaagtattat    780
tgtcaccgtg gcaacctgac catgtcattc cacctggaga tcactgctcg gccaggggga    840
ggtgggtctg gaggtggagg atctggtgga ggtgggtctg gtggaggtgg gtctgaggtg    900
cagctggtgg agtctggtgg tggtcttgtt caacctggtg gttctcttcg tctttcttgt    960
gctgcttctg gttttaatat taaagatact tatattcatt gggttcgtca agctcctggt    1020
aaaggtcttg aatgggttgc tcgtatttat cctactaatg ttatactcg  ttatgctgat    1080 tctgttaaag gtcgttttac tatttctgct gatacttcta aaaatactgc ttatcttcaa    1140
atgaactctc ttcgtgctga agatactgct gtttattatt gttctcgttg gggtggtgat    1200 ggttttatg  ctatggatta ttggggtcaa ggtactcttg tcaccgtctc ctcagctagc    1260
accgggggag gtgggtctgg aggtggagga tctggtggag gtgggtctga catccagatg    1320
acccagtctc cttcttctct ttctgcttct gttggtgatc gtgttactat tacttgtcgt    1380
gcttctcaag atgttaatac tgctgttgct tggtatcaac aaaaacctgg taaagctcct    1440
aaacttctta tttattctgc ttcttttctt tattctggtg ttccttctcg tttttctggt    1500
tctcgttctg gtactgattt tactcttact atttcttctc ttcaacctga agattttgct    1560
acttattatt gtcaacaaca ttatactact cctcctactt ttggtcaagg taccaaggtg    1620
```
gagatcaaac gtacgtctag agggccccat catcaccatc accat 1665

<210> SEQ ID NO 65
<211> LENGTH: 1659
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 65

| | |
|---|---|
| atggagtttg ggctgagctg ggttttcctc gttgctcttt ttagaggtgt ccagtgtgag | 60 |
| gtgcagctgg tggagtctgg tggtggtctt gttcaacctg gtggttctct tcgtctttct | 120 |
| tgtgctgctt ctggttttaa tattaaagat acttatattc attgggttcg tcaagctcct | 180 |
| ggtaaaggtc ttgaatgggt tgctcgtatt tatcctacta atggttatac tcgttatgct | 240 |
| gattctgtta aggtcgtttt tactatttct gctgatactt ctaaaaatac tgcttatctt | 300 |
| caaatgaact ctcttcgtgc tgaagatact gctgtttatt attgttctcg ttggggtggt | 360 |
| gatggttttt atgctatgga ttattgggt caaggtactc ttgtcaccgt ctcctcagct | 420 |
| agcaccgggg gaggtgggtc tggaggtgga ggatctggtg gaggtgggtc tgacatccag | 480 |
| atgacccagt ctccttcttc tctttctgct tctgttggtg atcgtgttac tattacttgt | 540 |
| cgtgcttctc aagatgttaa tactgctgtt gcttggtatc aacaaaaacc tggtaaagct | 600 |
| cctaaacttc ttatttattc tgcttctttt ctttattctg gtgttccttc tcgttttttct | 660 |
| ggttctcgtt ctggtactga ttttactctt actatttctt ctcttcaacc tgaagatttt | 720 |
| gctacttatt attgtcaaca acattatact actcctccta cttttggtca aggtaccaag | 780 |
| gtggagatca acgtacgggg aggaggtggg tctggaggtg gaggatctgg tggaggtggg | 840 |
| tctggaggag gtggatcccc cgaggaacct ctagtggtga aggtggaaga gggagatacc | 900 |
| gctgccctgt ggtgcctcaa ggggacctca gatggcccca ctcagcagct gacctggtct | 960 |
| cgggagtccc cgcttaaacc cttcttaaaa tacagcctgg gggtgccagg cctgggagtg | 1020 |
| cacgtgaggc ccgacgccat cagcgtggtt atccggaacg tctctcaaca gatgggggc | 1080 |
| ttctacctgt gccagccggg gccccccctct gagaaggcct ggcagcctgg ctggacagtc | 1140 |
| aatgtggagg gcagcgggga gctgttccgg tggaatgttt cggacctagg tggcctgggc | 1200 |
| tgtggcctga gaacaggtc ctcagagggc cccagctccc cttccgggaa gctcatgagc | 1260 |
| cccaagctgt atgtgtgggc caaagaccgc cctgagatct gggaggagag gcctccgtgt | 1320 |
| ctcccaccga gggacagcct gaaccagagc ctcagccggg acctcaccgt tgcccctggc | 1380 |
| tccacactct ggctgtcctg tggggtaccc cctgactctg tgtccagggg cccctctcc | 1440 |
| tggaccatg tgcaccccaa ggggcctaag tcattgctga cctagagct gaaggacgat | 1500 |
| cgcccggcca gagatatgtg ggtaatgggc acgagcctga tgttgccccg gccacagct | 1560 |
| caagacgctg gaaagtggta ttgtcaccgt ggcaacctga ccatgtcatt ccacctggag | 1620 |
| atcactgctc ggccatctag acatcatcac catcaccat | 1659 |

<210> SEQ ID NO 66
<211> LENGTH: 1659
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 66

```
atggagtttg ggctgagctg ggttttcctc gttgctcttt ttagaggtgt ccagtgtgag      60
gtgcagctgg tggagtctgg tggtggtctt gttcaacctg gtggttctct tcgtctttct     120
tgtgctgctt ctggttttaa tattaaagat acttatattc attgggttcg tcaagctcct     180
ggtaaaggtc ttgaatgggt tgctcgtatt tatcctacta atggttatac tcgttatgct     240
gattctgtta aaggtcgttt tactatttct gctgatactt ctaaaaatac tgcttatctt     300
caaatgaact ctcttcgtgc tgaagatact gctgtttatt attgttctcg ttggggtggt     360
gatggttttt atgctatgga ttattggggt caaggtactc ttgtcaccgt ctcctcagct     420
agcaccgggg gaggtgggtc tggaggtgga ggatctggtg gaggtgggtc tgacatccag     480
atgacccagt ctccttcttc tctttctgct tctgttggtg atcgtgttac tattacttgt     540
cgtgcttctc aagatgttaa tactgctgtt gcttggtatc aacaaaaacc tggtaaagct     600
cctaaacttc ttatttattc tgcttctttt ctttattctg gtgttccttc tcgttttttct     660 ggttctcgtt ctggtactga ttttactctt actatttctt ctcttcaacc tgaagatttt     720
gctacttatt attgtcaaca acattatact actcctccta cttttggtca aggtaccaag     780
gtggagatca aacgtacggg aggaggtggg tctggaggtg aggatctggt ggaggtgggt     840 ctggaggag gtggatcccc cgaggaacct ctagtggtga aggtggaaga gggagatacc     900
gctgccctgt ggtgcctcaa ggggacctca gatggcccca ctcagcagct gacctggtct    960
cgggagtccc gcttaaaacc cttcttaaaa tacagctttg ggggcccagg cctgggaatc    1020
cacatgaggc ccgacgccat cagcgtggtt atcagcaacg tctctcaaca gatgggggc     1080 ttctacctgt gccagccggg gcccccctct gagaaggcct ggcagcctgg ctggacagtc    1140
aatgtggagg gcagcgggga gctgttccgg tggaatgttt cggacctagg tggcctgggc    1200
tgtggcctga agaacaggtc ctcagagggc cccagctccc cttccgggaa gctcatgagc    1260
cccaagctgt atgtgtgggc caaagaccgc cctgagatct ggagggaga gcctccgtgt    1320 ctcccaccga gggacagcct gaaccagagc ctcagccggg acctcaccgt tgcccctggc    1380
tccacactct ggctgtcctg tgggataccc cctgactctg tgtccagggg cccctctcc    1440 tggacccatg tgcaccccaa ggggcctaag tcattgctga cctagagct gaaggacgat    1500 cgcccggcca gagagatgtg ggtaaccggc acgcggctgt ttttgccccg ggccacagct    1560
caagacgctg gaaagtacta ttgtcaccgt ggcaacctga ccatgtcatt ccacctggag    1620
atcactgctc ggccatctag acatcatcac catcaccat                           1659
```

<210> SEQ ID NO 67
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
atggagtttg ggctgagctg ggttttcctc gttgctcttt ttagaggtgt ccagtgtgag      60
gtgcagctgg tggagtctgg tggtggtctt gttcaacctg gtggttctct tcgtctttct     120
tgtgctgctt ctggttttaa tattaaagat acttatattc attgggttcg tcaagctcct     180
ggtaaaggtc ttgaatgggt tgctcgtatt tatcctacta atggttatac tcgttatgct     240
gattctgtta aaggtcgttt tactatttct gctgatactt ctaaaaatac tgcttatctt     300
caaatgaact ctcttcgtgc tgaagatact gctgtttatt attgttctcg ttggggtggt     360
```

```
gatggttttt atgctatgga ttattggggt caaggtactc ttgtcaccgt ctcctcagct    420
agcaccgggg gaggtgggtc tggaggtgga ggatctggtg gaggtgggtc tgacatccag    480
atgacccagt ctccttcttc tctttctgct tctgttggtg atcgtgttac tattacttgt    540
cgtgcttctc aagatgttaa tactgctgtt gcttggtatc aacaaaaacc tggtaaagct    600
cctaaacttc ttatttattc tgcttctttt ctttattctg gtgttccttc tcgttttttct   660 ggttctcgtt ctggtactga ttttactctt actatttctt ctcttcaacc tgaagatttt    720
gctacttatt attgtcaaca acattatact actcctccta cttttggtca aggtaccaag    780
gtggagatca aacgtacggg aggaggtggg tctggaggtg aggatctggt ggaggtgggg   840
tctggaggag gtggatcccc cgaggaacct ctagtggtga aggtggaaga gggagatacc    900
gctgccctgt ggtgcctcaa ggggacctca gatggcccca ctgagcaggt tacctggtct    960
cgggagtccc cgcttaaacc cttcttaaaa ctcagcctgg ggctcccagg cggcggaggt    1020
cacgtgaggc ccaacgccgt gagcctcgtt atccggaacg tctctcaaca gatgggggc    1080 ttctacctgt gccagccggg gccccctct gagaaggcct ggcagcctgg ctggacagtc    1140
aatgtggagg gcagcgggga gctgttccgg tggaatgttt cggacctagg tggcctgggc    1200
tgtggcctga agaacaggtc ctcagagggc cccagctccc cttccgggaa gctcatgagc    1260
cccaagctgt atgtgtgggc caaagaccgc cctgagatct gggagggaga gcctccgtgt    1320
ctcccaccga gggacagcct gaaccagagc ctcagccggg acctcaccgt tgccctggc    1380 tccacactct ggctgtcctg tggggtaccc cctgactctg tgtccagggg ccccctctcc    1440
tggacccatg tgcaccccaa ggggcctaag tcattgctga gcctagagct gaaggacgat    1500
cgcccggcca gagatatgtg ggtaaccgag acgggtctgc tcttgccccg ggccacagct    1560
caagacgctg gaaagtggta ttgtcaccgt ggcaacctga ccatgtcatt ccacctggag    1620
atcactgctc ggccatctag acatcatcac catcaccat                          1659
```

<210> SEQ ID NO 68
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
atgatggagt ttgggctgag ctgggttttc ctcgttgctc ttttagagg tgtccagtgt     60 caggtcaaac tacaggagtc aggggctgag ctggtgaagc ctggggcctc agtgaagatg    120
tcctgcaagg cttctggcta cacatttacc agttacaata tgcactgggt aaagcagaca    180
cctggacagg gcctggaatg gattggagct atttatccag gaaatggtga tacttcctac    240
aatcagaagt tcaaaggcaa ggccacattg actgcagaca atcctccag cacagcctac    300 atgcagctca gcagcctgac atctgaggac tctgcggact attactgtgc aagatctaat    360
tattacggta gtagctactg gttcttcgat gtctggggcc aagggaccac ggtcaccgtc    420
tcctcagcca gcaccggtgg aggcggttca ggcggaggtg gctctggcgg tggcggatcg    480
gacatcgagc tcactcagtc tccaacaatc ctgtctgcat ctccagggga aaggtcaca    540 atgacttgca gggccagctc aagtgtaaat tacatggact ggtaccagaa gaagccagga    600
tcctccccca aacctggat ttatgccaca tccaacctgg cttctggagt ccctgctcgc    660
ttcagtggca gtgggtctgg gacctcttac tctctcacaa tcagcagagt ggaggctgaa    720
```

```
gatgctgcca cttattactg ccagcagtgg agttttaatc cacccacgtt cggaggggg       780 acaaagttgg aaataaaacg ggccgccgct ggaggaggtg ggtctggagg tggaggatct      840
ggtggaggtg ggtctggagg aggtggatcc cccgaggaac ctctagtggt gaaggtggaa      900
gagggagata ccgctgccct gtggtgcctc aaggggacct cagatggccc cactcagcag      960
ctgacctggt ctcgggagtc cccgcttaaa cccttcttaa aatacagcct gggggtgcca     1020
ggcctgggag tgcacgtgag gcccgacgcc atcagcgtgg ttatccggaa cgtctctcaa     1080
cagatggggg gcttctacct gtgccagccg ggcccccct ctgagaaggc ctggcagcct      1140
ggctggacag tcaatgtgga gggcagcggg agctgttcc ggtggaatgt ttcggaccta      1200
ggtggcctgg gctgtggcct gaagaacagg tcctcagagg gccccagctc cccttccggg     1260
aagctcatga gccccaagct gtatgtgtgg gccaaagacc gccctgagat ctgggaggga     1320
gagcctccgt gtctcccacc gagggacagc ctgaaccaga gcctcagccg ggacctcacc     1380 gttgccctg ctccacact ctggctgtcc tgtggggtac cccctgactc tgtgtccagg      1440 ggcccctct cctggaccca tgtgcacccc aaggggccta agtcattgct gagcctagag      1500
ctgaaggacg atcgcccggc cagagatatg tgggtaatgg gcacgagcct gatgttgccc     1560
cgggccacag ctcaagacgc tggaaagtgg tattgtcacc gtggcaacct gaccatgtca     1620
ttccacctgg agatcactgc tcggccatct agacatcatc accatcacca t              1671
```

<210> SEQ ID NO 69
<211> LENGTH: 1659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
atgccacctc ctcgcctcct cttcttcctc ctcttcctca cccccatgga agtcaggccc       60
gaggaacctc tagtggtgaa ggtggaagag ggagataacg ctgtgctgca gtgcctcaag      120
gggacctcag atggcccac tcagcagctg acctggtctc gggagtcccc gcttaaaccc       180
ttcttaaaac tcagcctggg gctgccaggc ctgggaatcc acatgaggcc cctggccatc      240
tggcttttca tcttcaacgt ctctcaacag atggggggct ctacctgtg ccagccgggg      300 cccccctctg agaaggcctg gcagcctggc tggacagtca atgtggaggg cagcggggag      360
ctgttccggt ggaatgtttc ggacctaggg gcctgggtg tggcctgaa gaacaggtcc       420 tcagagggcc ccagctcccc ttccgggaag ctcatgagcc caagctgta tgtgtgggcc      480 aaagaccgcc ctgagatctg ggaggagag cctccgtgtc tcccaccgag gacagcctg       540 aaccagagcc tcagccagga cctcaccatg gcccctggct ccacactctg gctgtcctgt      600 ggggtaccc ctgactctgt gtccaggggc ccctctcct ggacccatgt gcaccccaag       660 ggcctaagt cattgctgag cctagagctg aaggacgatc gcccggccag agatatgtgg      720
gtaatggaga cgggtctgtt gttgccccgg gccacagctc aagacgctgg aaagtattat      780
tgtcaccgtg gcaacctgac catgtcattc cacctggaga tcactgctcg gccaggagga      840
ggtgggtctg gaggtggagg atctggtgga ggtgggtctg gaggaggtgg gtctatggcc      900
caggtcaaac tacaggagtc aggggctgag ctggtgaagc ctggggcctc agtgaagatg      960
tcctgcaagg cttctggcta cacatttacc agttacaata tgcactgggt aaagcagaca     1020
cctggacagg gcctggaatg gattggagct atttatccag gaaatggtga tacttcctac     1080
```

```
aatcagaagt tcaaaggcaa ggccacattg actgcagaca atcctccag cacagcctac    1140 atgcagctca gcagcctgac atctgaggac tctgcggact attactgtgc aagatctaat    1200
tattacggta gtagctactg gttcttcgat gtctggggcc aagggaccac ggtcaccgtc    1260
tcctcaggtg gaggcggttc aggcggaggt ggctctggcg gtggcggatc ggacatcgag    1320
ctcactcagt ctccaacaat cctgtctgca tctccagggg agaaggtcac aatgacttgc    1380
agggccagct caagtgtaaa ttacatggac tggtaccaga agaagccagg atcctccccc    1440
aaaccctgga tttatgccac atccaacctg gcttctggag tccctgctcg cttcagtggc    1500
agtgggtctg ggacctctta ctctctcaca atcagcagag tggaggctga agatgctgcc    1560
acttattact gccagcagtg gagttttaat ccacccacgt tcggaggggg gacaaagttg    1620
gaaataaaac gggccgccgc tcatcatcac catcaccat                           1659
```

<210> SEQ ID NO 70
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
atggacttcg gcctgatctt cttcatcgtg gccctgctga agggcgtgca gtgccagatc    60
ctgctgaccc agagccccgt gatcctgagc gtgagccccg gcgagagggt gagcttcagc    120
tgcagggcca gccagagcat cggcaccaac atccactggt accagcagag gaccaacggc    180
agccccaggc tgctgatcaa gtacgccagc gagagcatca gcggcatccc cagcaggttc    240
agcggcagcg gcagcggcac cgacttcacc ctgagcatca cagcgtgga gagcgaggac    300 atcgccgact actactgcca gcagaacaac aactggccca ccacttcgg cgccggcacc    360 aagctggagc tgaagggcag caccagcggc agcggcaagc ccggcagcgg cgagggcagc    420
accaagggcc aggtgcagct gaagcagagc ggccccggcc tggtgcagcc cagccagagc    480
ctgagcatca cctgcaccgt gagcggcttc agcctgacca actacggcgt gcactgggtg    540
aggcagagcc ccggcaaggg cctggagtgg ctgggcgtga tctggagcgg cggcaacacc    600
gactacaaca ccccccttcac cagcaggctg agcatcaaca aggacaacag caagagccag    660
gtgttcttca gatgaacag cctgcagagc aacgacaccg ccatctacta ctgcgccagg    720
gccctgacct actacgacta cgagttcgcc tactgggggcc agggcaccct ggtgaccgtg    780
agcgccggag gaggtgggtc cggaggtgga ggatctggtg gaggtgggtc tggaggaggt    840 ggatccccccg aggaacctct agtggtgaag gtggaagagg gagataccgc tgccctgtgg    900
tgcctcaagg ggacctcaga tggccccact cagcagctga cctggtctcg ggagtcccccg    960 cttaaaccct tcttaaaata cagcctgggg gtgccaggcc tgggagtgca cgtgaggccc    1020
gacgccatca gcgtggttat ccggaacgtc tctcaacaga tgggggggctt ctacctgtgc    1080 cagccggggc cccctctga aaggcctgg cagcctggct ggacagtcaa tgtggagggc    1140 agcgggagc tgttccggtg gaatgtttcg gacctaggtg gcctgggctg tggcctgaag    1200
aacaggtcct cagagggccc cagctcccct tccgggaagc tcatgagccc caagctgtat    1260
gtgtgggcca agaccgccc tgagatctgg gagggagagc ctccgtgtct cccaccgagg    1320
gacagcctga accagagcct cagccgggac ctcaccgttg cccctggctc cacactctgg    1380
ctgtcctgtg gggtaccccc tgactctgtg tccaggggcc ccctctcctg gacccatgtg    1440
```

<210> SEQ ID NO 71
<211> LENGTH: 1647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
atggacttcg gcctgatctt cttcatcgtg gccctgctga agggcgtgca gtgccagatc      60
ctgctgaccc agagccccgt gatcctgagc gtgagcccg gcgagagggt gagcttcagc     120
tgcagggcca gccagagcat cggcaccaac atccactggt accagcagag gaccaacggc     180
agccccaggc tgctgatcaa gtacgccagc gagagcatca gcggcatccc cagcaggttc     240
agcggcagcg gcagcggcac cgacttcacc ctgagcatca cagcgtgga gagcgaggac     300
atcgccgact actactgcca gcagaacaac aactggccca ccccttcgg cgccggcacc     360
aagctggagc tgaagggcag caccagcggc agcggcaagc ccggcagcgg cgagggcagc     420
accaagggcc aggtgcagct gaagcagagc ggccccggcc tggtgcagcc cagccagagc     480
ctgagcatca cctgcaccgt gagcggcttc agcctgacca actacggcgt gcactgggtg     540
aggcagagcc ccggcaaggg cctggagtgg ctgggcgtga tctggagcgg cggcaacacc     600
gactacaaca ccccccttcac cagcaggctg agcatcaaca aggacaacag caagagccag     660
gtgttcttca agatgaacag cctgcagagc aacgacaccg ccatctacta ctgcgccagg     720
gccctgacct actacgacta cgagttcgcc tactgggccc agggcacccc tgtgaccgtg     780
agcgccggag gaggtgggtc cggaggtgga ggatctggtg gaggtgggtc tggaggaggt     840
ggatccccg aggaacctct agtggtgaag gtggaagagg gagataccgc tgccctgtgg     900
tgcctcaagg ggacctcaga tggccccact gagcaggtta cctggtctcg ggagtccccg     960
cttaaaccct tcttaaaact cagcctgggg ctcccaggcg gcggaggtca cgtgaggccc    1020
aacgccgtga gcctcgttat ccggaacgtc tctcaacaga tgggggggctt ctacctgtgc    1080
cagccggggc ccccctctga aaggcctgg cagcctggct ggacagtcaa tgtggagggc    1140
agcggggagc tgttccggtg gaatgtttcg gacctaggtg gcctgggctg tggcctgaag    1200
aacaggtcct cagagggccc cagctcccct tccgggaagc tcatgagccc caagctgtat    1260
gtgtgggcca aagaccgccc tgagatctgg gagggagagc ctccgtgtct cccaccgagg    1320
gacagcctga accagagcct cagccgggac ctcaccgttg ccctggctc cacactctgg    1380
ctgtcctgtg gggtaccccc tgactctgtg tccaggggcc ccctctcctg gacccatgtg    1440
cacccccaagg ggcctaagtc attgctgagc ctagagctga aggacgatcg cccggccaga    1500
gatatgtggg taaccgagac gggtctgctc ttgccccggg ccacagctca agacgctgga    1560
aagtggtatt gtcaccgtgg caacctgacc atgtcattcc acctggagat cactgctcgg    1620
ccatctagac atcatcacca tcaccat                                       1647
```

<210> SEQ ID NO 72
<211> LENGTH: 1788

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
atggacttcg gcctgatctt cttcatcgtg gccctgctga agggcgtgca gtgccagggc      60
cagagcggcc agtgcatcag ccccaggggc tgccccgacg gcccctacgt gatgtacggc     120
agcagcggcg gcagcggcgg cagcggcggc agcggcctga gcggcaggag cgacaaccac     180
ggcagcagcg gcacccagat cctgctgacc cagagccccg tgatcctgag cgtgagcccc     240
ggcgagaggg tgagcttcag ctgcagggcc agccagagca tcggcaccaa catccactgg     300
taccagcaga ggaccaacgg cagccccagg ctgctgatca gtacgccag cgagagcatc      360
agcggcatcc ccagcaggtt cagcggcagc ggcagcggca ccgacttcac cctgagcatc     420
aacagcgtgg agagcgagga catcgccgac tactactgcc agcagaacaa caactggccc     480
accaccttcg gcgccggcac caagctggag ctgaagggca gcaccagcgg cagcggcaag     540
cccggcagcg gcgagggcag caccaagggc caggtgcagc tgaagcagag cggccccggc     600
ctggtgcagc ccagccagag cctgagcatc acctgcaccg tgagcggctt cagcctgacc     660
aactacggcg tgcactgggt gaggcagagc cccggcaagg gcctggagtg gctgggcgtg     720
atctggagcg gcggcaacac cgactacaac acccccttca ccagcaggct gagcatcaac     780
aaggacaaca gcaagagcca ggtgttcttc aagatgaaca gcctgcagag caacgacacc     840
gccatctact actgcgccag ggccctgacc tactacgact acgagttcgc ctactggggc     900
cagggcaccc tggtgaccgt gagcgccgga ggaggtgggt ctggaggtgg aggatctggt     960
ggaggtgggt ctggaggagg tggatccccc gaggaacctc tagtggtgaa ggtggaagag    1020
ggagataccg ctgccctgtg gtgcctcaag gggacctcag atggccccac tcagcagctg    1080
acctggtctc gggagtcccc gcttaaaccc ttcttaaaat acagcctggg ggtgccaggc    1140
ctgggagtgc acgtgaggcc cgacgccatc agcgtggtta tccggaacgt ctctcaacag    1200
atgggggggct tctacctgtg ccagccgggg ccccctctg agaaggcctg gcagcctggc    1260
tggacagtca atgtggaggg cagcggggag ctgttccggt ggaatgtttc ggacctaggt    1320
ggcctgggct gtggcctgaa gaacaggtcc tcagagggcc ccagctcccc ttccgggaag    1380
ctcatgagcc ccaagctgta tgtgtgggcc aaagaccgcc ctgagatctg ggaggagag     1440
cctccgtgtc tcccaccgag ggacagcctg aaccagagcc tcagccggga cctcaccgtt    1500
gccccttggct ccacactctg gctgtcctgt gggtacccc ctgactctgt gtccaggggc    1560
cccctctcct ggacccatgt gcaccccaag gggcctaagt cattgctgag cctagagctg    1620
aaggacgatc gcccggccag agatatgtgg gtaatgggca cgagcctgat gttgccccgg    1680
gccacagctc aagacgctgg aaagtggtat tgtcaccgtg gcaacctgac catgtcattc    1740
cacctggaga tcactgctcg gccatctaga catcatcacc atcaccat               1788
```

<210> SEQ ID NO 73
<211> LENGTH: 1788
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| atggacttcg gcctgatctt cttcatcgtg ccctgctga agggcgtgca gtgccagggc | 60 |
| cagagcggcc agtgcatcag ccccaggggc tgccccgacg ccccctacgt gatgtacggc | 120 |
| agcagcggcg gcagcggcgg cagcggcggc agcggcctga gcggcaggag cgacaaccac | 180 |
| ggcagcagcg gcacccagat cctgctgacc cagagcccg tgatcctgag cgtgagcccc | 240 |
| ggcgagaggg tgagcttcag ctgcagggcc agccagagca tcggcaccaa catccactgg | 300 |
| taccagcaga ggaccaacgg cagccccagg ctgctgatca gtacgccag cgagagcatc | 360 |
| agcggcatcc ccagcaggtt cagcggcagc ggcagcggca ccgacttcac cctgagcatc | 420 |
| aacagcgtgg agagcgagga catcgccgac tactactgcc agcagaacaa caactggccc | 480 |
| accaccttcg gcgccggcac caagctggag ctgaagggca gcaccagcgg cagcggcaag | 540 |
| cccggcagcg gcgagggcag caccaagggc caggtgcagc tgaagcagag cggcccggc | 600 |
| ctggtgcagc ccagccagag cctgagcatc acctgcaccg tgagcggctt cagcctgacc | 660 |
| aactacggcg tgcactgggt gaggcagagc cccggcaagg gcctggagtg gctgggcgtg | 720 |
| atctggagcg gcggcaacac cgactacaac acccccttca ccagcaggct gagcatcaac | 780 |
| aaggacaaca gcaagagcca ggtgttcttc aagatgaaca gcctgcagag caacgacacc | 840 |
| gccatctact actgcgccag ggccctgacc tactacgact acgagttcgc ctactggggc | 900 |
| cagggcaccc tggtgaccgt gagcgccgga ggaggtgggt ctggaggtgg aggatctggt | 960 |
| ggaggtgggt ctggaggagg tggatccccc gaggaacctc tagtggtgaa ggtggaagag | 1020 |
| ggagataccg ctgccctgtg gtgcctcaag ggacctcag atggcccac tgagcaggtt | 1080 |
| acctggtctc gggagtcccc gcttaaaccc ttcttaaaac tcagcctggg gctcccaggc | 1140 |
| ggcggaggtc acgtgaggcc caacgccgtg agcctcgtta ccggaacgt ctctcaacag | 1200 |
| atggggggct tctacctgtg ccagccgggg ccccctctg agaaggcctg gcagcctggc | 1260 |
| tggacagtca atgtggaggg cagcggggag ctgttccggt ggaatgtttc ggacctaggt | 1320 |
| ggcctgggct gtggcctgaa gaacaggtcc tcagagggcc ccagctcccc ttccgggaag | 1380 |
| ctcatgagcc ccaagctgta tgtgtgggcc aaagaccgcc ctgagatctg ggaggagag | 1440 |
| cctccgtgtc tcccaccgag ggacagcctg aaccagagcc tcagccggga cctcaccgtt | 1500 |
| gccctggct ccacactctg gctgtcctgt ggggtacccc ctgactctgt gtccaggggc | 1560 |
| cccctctcct ggacccatgt gcacccaag gggcctaagt cattgctgag cctagagctg | 1620 |
| aaggacgatc gccggccag agatatgtgg gtaaccgaga cgggtctgct cttgccccgg | 1680 |
| gccacagctc aagacgctgg aaagtggtat tgtcaccgtg gcaacctgac catgtcattc | 1740 |
| cacctggaga tcactgctcg gccatctaga catcatcacc atcaccat | 1788 |

<210> SEQ ID NO 74
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

| | |
|---|---|
| atggacttcg gcctgatctt cttcatcgtg ccctgctga agggcgtgca gtgccagggc | 60 |
| cagagcggcc agtgcatcag ccccaggggc tgccccgacg ccccctacgt gatgtacggc | 120 |
| agcagcggcg gcagcggcgg cagcggcggc agcggcctga gcggcaggag cgacaaccac | 180 |
| ggcagcagcg gcacccagat cctgctgacc cagagcccg tgatcctgag cgtgagcccc | 240 |

```
ggcgagaggg tgagcttcag ctgcagggcc agccagagca tcggcaccaa catccactgg      300
taccagcaga ggaccaacgg cagccccagg ctgctgatca agtacgccag cgagagcatc      360
agcggcatcc ccagcaggtt cagcggcagc ggcagcggca ccgacttcac cctgagcatc      420
aacagcgtgg agagcgagga catcgccgac tactactgcc agcagaacaa caactggccc      480
accaccttcg gcgccggcac caagctggag ctgaagggca gcaccagcgg cagcggcaag      540
cccggcagcg gcgagggcag caccaagggc caggtgcagc tgaagcagag cggcccggc       600 ctggtgcagc ccagccagag cctgagcatc acctgcaccg tgagcggctt cagcctgacc      660
aactacggcg tgcactgggt gaggcagagc cccggcaagg gcctgagtg gctgggcgtg       720 atctggagcg gcggcaacac cgactacaac acccccttca ccagcaggct gagcatcaac      780
aaggacaaca gcaagagcca ggtgttcttc aagatgaaca gcctgcagag caacgacacc      840
gccatctact actgcgccag ggccctgacc tactacgact acgagttcgc ctactggggc      900
cagggcaccc tggtgaccgt gagcgccgga ggaggtgggt ctggaggtgg aggatctggt      960
ggaggtgggt ctggaggagg tggatccccc gaggaacctc tagtggtgaa ggtggaagag     1020
ggagataccg ctgccctgtg gtgcctcaag gggacctcag atggcccac tcagcagctg      1080 acctggtctc gggagtcccc gcttaaaccc ttcttaaaat acagcctggg ggtgccaggc     1140
ctgggagtgc acgtgaggcc cgacgccatc agcgtggtta ccggaacgt ctctcaacag      1200 atgggggct tctacctgtg ccagccgggg ccccccctctg agaaggcctg gcagcctggc     1260
tggacagtca atgtggaggg cagcggggag ctgttccggt ggaatgtttc ggacctaggt     1320
ggcctgggct gtgcctgaa gaacaggtcc tcagagggcc ccagctcccc ttccgggaag      1380
ctcatgagcc ccaagctgta tgtgtgggcc aaagaccgcc ctgagatctg ggagggagag     1440
cctccgtgtc tcccaccgag ggacagcctg aaccagagcc tcagccggga cctcaccgtt     1500
gcccctggct ccacactctg gctgtcctgt gggtacccc ctgactctgt gtccaggggc      1560
cccctctcct ggacccatgt gcaccccaag gggcctaagt cattgctgag cctagagctg     1620
aaggacgatc gcccggccag agatatgtgg gtaatgggca cgagcctgat gttgcccgg      1680 gccacagctc aagacgctgg aaagtggtat tgtcaccgtg gcaacctgac catgtcattc     1740
cacctggaga tcactgctcg gccatctaga ggaggaggtg ggtctggagg tggaggatct     1800
ggtggaggtg gtctggagg aggtggatcc gaggtgcagc tggtggagtc tggtggtggt     1860
cttgttcaac ctggtggttc tcttcgtctt tcttgtgctg cttctggttt taatattaaa     1920
gatacttata ttcattgggt tcgtcaagct cctggtaaag tcttgaatg ggttgctcgt      1980 atttatccta ctaatggtta tactcgttat gctgattctg ttaaaggtcg ttttactatt     2040
tctgctgata cttctaaaaa tactgcttat cttcaaatga actctcttcg tgctgaagat     2100
actgctgttt attattgttc tcgttggggt ggtgatggtt tttatgctat ggattattgg     2160
ggtcaaggta ctcttgtcac cgtctcctca gctagcaccg ggagggtgg gtctggaggt     2220 ggaggatctg gtgaggtgg gtctgacatc cagatgaccc agtctccttc ttctctttct     2280
gcttctgttg gtgatcgtgt tactattact tgtcgtgctt ctcaagatgt taatactgct     2340 gttgcttgg atcaacaaaa acctggtaaa gctcctaaac ttcttatta ttctgcttct      2400 tttctttatt ctggtgttcc ttctcgtttt tctggttctc gttctggtac tgattttact     2460
cttactattt cttctcttca acctgaagat tttgctactt attattgtca acaacattat     2520
actactcctc ctacttttgg tcaaggtacc aaggtggaga tcaaacgtac gcatcatcac     2580
catcaccat                                                             2589
```

<210> SEQ ID NO 75
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atggagtttg ggctgagctg ggttttcctc gttgctcttt ttagaggtgt ccagtgtgac    60
atccagatga cccagagccc cagcagcctg agcgccagcg tgggcgacag ggtgaccatc   120
acctgcaggg ccagccagga cgtgaacacc gccgtggcct ggtaccagca gaagcccggc   180
aaggccccca gctgctgat ctacagcgcc agcttcctgt acagcggcgt gcccagcagg   240
ttcagcggca gcaggagcgg caccgacttc accctgacca tcagcagcct gcagcccgag   300
gacttcgcca cctactactg ccagcagcac tacaccaccc cccccacctt cggccagggc   360
accaaggtgg agatcaagag gaccgtggcc gcccccagcg tgttcatctt cccccccagc   420
gacgagcagc tgaagagcgg caccgccagc gtggtgtgcc tgctgaacaa cttctacccc   480
agggaggcca aggtgcagtg gaaggtggac aacgccctgc agagcggcaa cagccaggag   540
agcgtgaccg agcaggacag caaggacagc acctacagcc tgagcagcac cctgaccctg   600
agcaaggccg actacgagaa gcacaaggtg tacgcctgcg aggtgaccca ccagggcctg   660
agcagccccg tgaccaagag cttcaacagg ggcgagtgcg aggaggtgg gtctggaggt   720 ggaggatctg gtgaggtgg gtctggagga ggtggatccc ccgaggaacc tctagtggtg   780
aaggtggaag agggagatac cgctgccctg tggtgcctca aggggacctc agatggcccc   840
actcagcagc tgacctggtc tcgggagtcc ccgcttaaac ccttcttaaa atacagcctg   900
ggggtgccag gctgggagt gcacgtgagg cccgacgcca tcagcgtggt tatccggaac   960
gtctctcaac agatggggg cttctacctg tgccagccgg ggccccctc tgagaaggcc  1020 tggcagcctg gctggacagt caatgtggag ggcagcgggg agctgttccg gtggaatgtt  1080
tcggacctag gtggcctggg ctgtggcctg aagaacaggt cctcagaggg ccccagctcc  1140
ccttccggga agctcatgag ccccaagctg tatgtgtggg ccaaagaccg ccctgagatc  1200
tgggagggag agcctccgtg tctcccaccg agggacagcc tgaaccagag cctcagccgg  1260
gacctcaccg ttgcccctgg ctccacactc tggctgtcct gtggggtacc ccctgactct  1320
gtgtccaggg gcccctctc ctggacccat gtgcaccca aggggcctaa gtcattgctg  1380
agcctagagc tgaaggacga tcgcccggcc agagatatgt gggtaatggg cacgagcctg  1440
atgttgcccc gggccacagc tcaagacgct ggaaagtggt attgtcaccg tggcaacctg  1500
accatgtcat tccacctgga gatcactgct cggccatcta gacatcatca ccatcaccat  1560
```

<210> SEQ ID NO 76
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
atggagtttg ggctgagctg ggttttcctc gttgctcttt ttagaggtgt ccagtgtgag    60
gtgcagctgg tggagtctgg tggtggtctt gttcaacctg gtggttctct tcgtctttct   120
```

| | |
|---|---:|
| tgtgctgctt ctggttttaa tattaaagat acttatattc attgggttcg tcaagctcct | 180 |
| ggtaaaggtc ttgaatgggt tgctcgtatt tatcctacta atggttatac tcgttatgct | 240 |
| gattctgtta aaggtcgttt tactatttct gctgatactt ctaaaaatac tgcttatctt | 300 |
| caaatgaact ctcttcgtgc tgaagatact gctgtttatt attgttctcg ttggggtggt | 360 |
| gatggttttt atgctatgga ttattggggt caaggtactc ttgtcaccgt ctcctcagct | 420 |
| agcaccaagg gtcctagcgt ttttccattg gctcccagca gcaagagcac cagcggcggc | 480 |
| accgccgccc tgggctgcct ggtgaaggac tacttccccg agcccgtgac cgtgagctgg | 540 |
| aacagcggcg ccctgaccag cggcgtgcac accttccccg ccgtgctgca gagcagcggc | 600 |
| ctgtacagcc tgagcagcgt ggtgaccgtg cccagcagca gcctgggcac ccagacctac | 660 |
| atctgcaacg tgaaccacaa gcccagcaac accaaggtgg acaagaaggt ggagccccc | 720 |
| aagagctgcg acaaaactca cacatgccca ccgtgcccag cacctgaact cctgggggga | 780 |
| ccgtcagtct tcctcttccc cccaaaaccc aaggacaccc tcatgatctc ccggacccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag gcagccccg agaaccacag gtgtacaccc tgcccccatc ccgagacgag | 1140 |
| ttgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctac agcaagctca ccgtggacaa gagcaggtgg | 1320 |
| cagcagggga acgtcttctc atgctccgtg atgcacgagg ctctgcacaa ccactacacg | 1380 |
| cagaagagcc tctccctgtc tccgggt | 1407 |

<210> SEQ ID NO 77
<211> LENGTH: 1557
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 77

| | |
|---|---:|
| atggagtttg ggctgagctg ggttttcctc gttgctcttt ttagaggtgt ccagtgtcag | 60 |
| atcgtgctga ccagagcccc gccatcctg agcgccagcc ccggcgagaa ggtgaccatg | 120 |
| acctgcaggg ccagcagcag cgtgagctac atccactggt tccagcagaa gcccggcagc | 180 |
| agccccaagc cctggatcta cgccaccagc aacctggcca gcggcgtgcc cgtgaggttc | 240 |
| agcggcagcg gcagcggcac cagctacagc ctgaccatca gcagggtgga ggccgaggac | 300 |
| gccgccacct actactgcca gcagtggacc agcaaccccc ccaccttcgg cggcggcacc | 360 |
| aagctggaga tcaagaggac cgtggccgcc cccagcgtgt tcatcttccc ccccagcgac | 420 |
| gagcagctga agagcggcac cgccagcgtg gtgtgcctgc tgaacaactt ctaccccagg | 480 |
| gaggccaagg tgcagtggaa ggtggacaac gccctgcaga gcggcaacag ccaggagagc | 540 |
| gtgaccgagc aggacagcaa ggacagcacc tacagcctga gcagcaccct gaccctgagc | 600 |
| aaggccgact acgagaagca caaggtgtac gcctgcgagg tgacccacca gggcctgagc | 660 |
| agccccgtga ccaagagctt caacaggggc gagtgcggag gaggtgggtc tggaggtgga | 720 |

```
ggatctggtg gaggtgggtc tggaggaggt ggatcccccg aggaacctct agtggtgaag    780
gtggaagagg gagataccgc tgccctgtgg tgcctcaagg ggacctcaga tggccccact    840
cagcagctga cctggtctcg ggagtcccca cttaaaccct tcttaaaata cagcctgggg    900
gtgccaggcc tgggagtgca cgtgaggccc gacgccatca gcgtggttat ccggaacgtc    960
tctcaacaga tgggggctt ctacctgtgc cagccggggc ccccctctga aaggcctgg    1020
cagcctggct ggacagtcaa tgtggagggc agcggggagc tgttccggtg gaatgtttcg   1080
gacctaggtg gcctgggctg tggcctgaag aacaggtcct cagagggccc cagctcccct   1140
tccgggaagc tcatgagccc caagctgtat gtgtgggcca agaccgccc tgagatctgg   1200
gagggagagc ctccgtgtct cccaccgagg acagcctga accagagcct cagccgggac   1260
ctcaccgttg cccctggctc cacactctgg ctgtcctgtg gggtaccccc tgactctgtg   1320
tccaggggcc ccctctcctg gacccatgtg caccccaagg ggcctaagtc attgctgagc   1380
ctagagctga aggacgatcg cccggccaga gatatgtggg taatgggcac gagcctgatg   1440
ttgccccggg ccacagctca agacgctgga aagtggtatt gtcaccgtgg caacctgacc   1500
atgtcattcc acctggagat cactgctcgg ccatctagac atcatcacca tcaccat      1557

<210> SEQ ID NO 78
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
atggagtttg ggctgagctg ggttttcctc gttgctcttt ttagaggtgt ccagtgtcag     60
gtccaactcc aacagcccgg tgcagagctg gtgaagcccg gcgccagcgt gaagatgagc    120
tgcaaggcca gcggctacac cttcaccagc tacaacatgc actgggtgaa gcagaccccc    180
ggcaggggcc tggagtggat cggcgccatc taccccggca acggcgacac cagctacaac    240
cagaagttca agggcaaggc caccctgacc gccgacaaga gcagcagcac cgcctacatg    300
cagctgagca gcctgaccag cgaggacagc gccgtgtact actgcgccag gagcacctac    360
tacggcggcg actggtactt caacgtgtgg ggcgctggca ctacggtcac ggtgtctgct    420
gcctccacga agggacccte cgtgttccct cttgccccaa gcagcaaaag cacttcaggt    480
ggtacggccg ccctgggctg cctggtgaag gactacttcc ccgagcccgt gaccgtgagc    540
tggaacagcg gcgccctgac cagcggcgtg cacaccttcc ccgccgtgct gcagagcagc    600
ggcctgtaca gcctgagcag cgtggtgacc gtgcccagca gcagcctggg cacccagacc    660
tacatctgca acgtgaacca caagcccagc aacaccaagg tggacaagaa ggccgagccc    720
aagagctgcg acaaaactca cacatgccca ccgtgcccag cacctgaact cctggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gcagccccg agaaccacag gtgtacaccc tgcccccatc ccgagacgag   1140
ttgaccaaga accaggtcag cctgacctgc ctggtcaaag gcttctatcc cagcgacatc   1200
```

```
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcacgagg ctctgcacaa ccactacacg    1380
cagaagagcc tctccctgtc tccgggt                                        1407
```

<210> SEQ ID NO 79
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atggagtttg ggctgagctg ggttttcctc gttgctcttt ttagaggtgt ccagtgtgag     60
gtgcagctgg tggagtctgg tggtggtctt gttcaacctg gtggttctct tcgtctttct    120
tgtgctgctt ctggttttaa tattaaagat acttatattc attgggttcg tcaagctcct    180
ggtaaaggtc ttgaatgggt tgctcgtatt tatcctacta atggttatac tcgttatgct    240
gattctgtta aaggtcgttt tactatttct gctgatactt ctaaaaatac tgcttatctt    300
caaatgaact ctcttcgtgc tgaagatact gctgtttatt attgttctcg ttggggtggt    360
gatggttttt atgctatgga ttattggggt caaggtactc ttgtcaccgt ctcctcagct    420
agcaccaagg gtcctagcgt ttttccattg gctcccagca gcaagagcac cagcggcggc    480
accgccgccc tgggctgcct ggtgaaggac tacttcccg agcccgtgac cgtgagctgg    540
aacagcggcg ccctgaccag cggcgtgcac accttcccg ccgtgctgca gagcagcggc    600
ctgtacagcc tgagcagcgt ggtgaccgtg cccagcagca gcctgggcac ccagacctac    660
atctgcaacg tgaaccacaa gcccagcaac accaaggtgg acaagaaggt ggagcccccc    720
aagagctgcg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgtgagga gcagtacgcc    960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgagacgag    1140
ttgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcacgagg ctctgcacaa ccactacacg    1380
cagaagagcc tctccctgtc tccgggt                                        1407
```

<210> SEQ ID NO 80
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
atggagtttg ggctgagctg ggttttcctc gttgctcttt ttagaggtgt ccagtgtcag     60
```

```
gtccaactcc aacagcccgg tgcagagctg gtgaagcccg cgccagcgt gaagatgagc    120 tgcaaggcca gcggctacac cttcaccagc tacaacatgc actgggtgaa gcagacccc    180 ggcaggggcc tggagtggat cggcgccatc taccccggca acggcgacac cagctacaac    240
cagaagttca agggcaaggc caccctgacc gccgacaaga gcagcagcac cgcctacatg    300
cagctgagca gcctgaccag cgaggacagc gccgtgtact actgcgccag gagcacctac    360
tacggcggcg actggtactt caacgtgtgg ggcgctggca ctacggtcac ggtgtctgct    420
gcctccacga agggaccctc cgtgttccct cttgccccaa gcagcaaaag cacttcaggt    480
ggtacggccg ccctgggctg cctggtgaag gactacttcc ccgagcccgt gaccgtgagc    540
tggaacagcg gcgccctgac cagcggcgtg cacaccttcc ccgccgtgct gcagagcagc    600
ggcctgtaca gcctgagcag cgtggtgacc gtgcccagca gcagcctggg cacccagacc    660
tacatctgca acgtgaacca caagcccagc aacaccaagg tggacaagaa ggccgagccc    720
aagagctgcg acaaaactca cacatgccca ccgtgcccag cacctgaact cctggggggga    780 ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgtgagga gcagtacgcc    960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgtgaccaa    1140
gaaccaggtc agcctgacct gcctggtcaa aggcttctat cccagcgaca tcgccgtgga    1200
gtgggagagc aatgggcagc cggagaacaa ctacaagacc acgcctcccg tgctggactc    1260
cgacggctcc ttcttcctct acagcaagct caccgtggac aagagcaggt ggcagcaggg    1320
gaacgtcttc tcatgctccg tgatgcacga ggctctgcac aaccactaca cgcagaagag    1380
cctctccctg tctccgggtt agtaatc                                       1407

<210> SEQ ID NO 81
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
atgccacctc ctcgcctcct cttcttcctc ctcttcctca cccccatgga agtcaggccc     60
gaggagcccc tggtggtgaa ggtggaggag ggcgacaccg ccgtgctgcc ctgcctgaag    120
ggcaccagcg acggccccac ccagcagctg acctggagca gggagagccc cctgaagccc    180
ttcctgaagt acagcctggg cgtgcccggc ctgggcgtgc acgtgaggcc cgacgccatc    240
agcgtggtga tcaggaacgt gagccagcag atgggcggct ctacctgtg ccagcccggc    300 cccccagcg agaaggcctg gcagcccggc tggaccgtga acgtggaggg cagcggcgag    360
ctgttcaggt ggaacgtgag cgacctgggc ggcctgggct cgggcctgaa gaacaggagc    420
agcgagggcc ccagcagccc cagcggcaag ctgatgagcc caagctgta cgtgtgggcc    480 aaggacaggc ccgagatctg ggagggcgag ccccccgcc tgcccccag ggacagcctg    540 aaccagagcc tgagccagga cctgaccatg gccccggca gcaccctgtg gctgagctgc    600
ggcgtgcccc ccgacagcgt gagcaggggc cccctgagct ggacccacgt gcaccccaag    660
```

```
ggcccaaga gcctgctgag cctggagctg aaggacgaca ggcccgccag ggagatgatc    720
gtggacgaga ccggcctgct gctgcccagg gccaccgccc aggacgccgg caagtggtac    780
tgcagcaggg gcaacgtgac caccagctac cacctggaga tcaccgccag gcccgtgaag    840
gcccacagcg acctgaggac cggcggctgg aagggaggag gtgggtctgg aggtggagga    900
tctggtggag gtgggtctgg aggaggtgga tcccaggtgc agctgcaagc gtctggggga    960
ggcttggtgc aggctggggg gtctctgaga ctctcctgtg cagcctcagg aagcatcttc   1020
gctattaatg aaatcaatct tatggggtgg taccgccagg ctccagggaa gcagcgcgag   1080
ttggtcgcag cttgtgctag tgatggcaac acatactatg cggactccgt gaagggccga   1140
ttcaccatct ccagagacaa cgccgagaaa cggtgtatc tgcagatgaa caacctgaaa   1200
cctgacgaca cagccgtcta ttactgtgat gcgaattcga gggggaatta ttattcgggc   1260
caggggaccc aggtcaccgt ttcctcaact agtggcccgg gaggccaagg cgcagaacaa   1320
aaactcatct cagaagagga tctgggcgca caccatcacc accatcatgg cgcatct      1377
```

<210> SEQ ID NO 82
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atggagtttg gctgagctg ggttttcctc gttgctcttt ttagaggtgt ccagtgtcag     60
gtgcagctgc aggagtctgg gggaggcttg gtgcaggctg ggggtccct tagactctcc    120 tgtgtagcct ctggaagcat cagaagtatc aatgtcatgg gctggtaccg ccaggctcca    180
gggaagcagc gcgagttggt cgcagcttgt gctagtgatg gcaacacata ctatgcggac    240
tccgtgaagg gccgattcac catctccaga gacaacgccg agaaacggt gtatctgcag    300 atgaacaacc tgaaacctga cgacacagcc gtctattact gtgatgcgaa ttcgaggggg   360
aattattatt cgggccaggg gacccaggtc accgtttcct caactagtgg cccgggaggc   420
caaggcgcag aggaggtgg gtctggaggt ggaggatctg gtggaggtgg gtctggagga   480
ggtggatccc ccgaggaacc tctagtggtg aaggtggaag agggagatac cgctgccctg    540
tggtgcctca agggggacctc agatggcccc actcagcagc tgacctggtc tcgggagtcc    600
ccgcttaaac ccttcttaaa atacagcctg ggggtgccag gctgggagt gcacgtgagg   660 cccgacgcca tcagcgtggt tatccggaac gtctctcaac agatgggggg cttctacctg    720
tgccagccgg gccccccctc tgagaaggcc tggcagcctg gctggacagt caatgtggag   780
ggcagcgggg agctgttccg gtggaatgtt tcggacctag gtggcctggg ctgtggcctg   840
aagaacaggt cctcagaggg ccccagctcc ccttccggga agctcatgag ccccaagctg    900
tatgtgtggg ccaaagaccg ccctgagatc tgggaggag agcctccgtg tctcccaccg    960
agggacagcc tgaaccagag cctcagccgg gacctcaccg ttgcccctgg ctccacactc   1020
tggctgtcct gtggggtacc ccctgactct gtgtccaggg gccccctctc ctggacccat   1080
gtgcacccca agggcctaa gtcattgctg agcctagagc tgaaggacga tcgcccggcc   1140
agagatatgt gggtaatggg cacgagcctg atgttgcccc gggccacagc tcaagacgct   1200
ggaaagtggt attgtcaccg tggcaacctg accatgtcat tccacctgga gatcactgct   1260
cggccatcta gacatcatca ccatcaccat                                     1290
```

<210> SEQ ID NO 83
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
atggagtttg ggctgagctg ggttttcctc gttgctcttt ttagaggtgt ccagtgtcag      60
gtgcagttgc aggcgtctgg gggaggcttg gtgcaggctg gggggtctct gagactctcc     120
tgtgcagcct caggaagcat cttcgctatt aatgaaatca atcttatggg gtggtaccgc     180
caggctccag ggaagcagcg cgagttggtc gcagcttgtg ctagtgatgg caacacatac     240
tatgcggact ccgtgaaggg ccgattcacc atctccagag acaacgccga aaacggtg       300 tatctgcaga tgaacaacct gaaacctgac gacacagccg tctattactg tgatgcgaat     360
tcgaggggga attattattc gggccagggg acccaggtca ccgtttcctc aactagtggc     420 ccggaggcc aaggcgcagg aggaggtggg tctggaggtg gaggatctgg tggaggtggg     480
tctggaggag gtggatcccc cgaggaacct ctagtggtga aggtggaaga gggagatacc     540
gctgccctgt ggtgcctcaa ggggacctca gatggcccca ctcagcagct gacctggtct     600
cgggagtccc cgcttaaacc cttcttaaaa tacagcctgg gggtgccagg cctgggagtg     660
cacgtgaggc ccgacgccat cagcgtggtt atccggaacg tctctcaaca gatgggggc      720 ttctacctgt gccagccggg gccccctct gagaaggcct ggcagcctgg ctggacagtc      780
aatgtggagg gcagcgggga gctgttccgg tggaatgttt cggacctagg tggcctgggc     840
tgtggcctga agaacaggtc ctcagagggc cccagctccc cttccgggaa gctcatgagc     900
cccaagctgt atgtgtgggc caaagaccgc cctgagatct gggagggaga gcctccgtgt     960
ctcccaccga gggacagcct gaaccagagc ctcagccggg acctcaccgt tgcccctggc    1020
tccacactct ggctgtcctg tggggtaccc cctgactctg tgtccagggg cccctctcc    1080 tggacccatg tgcaccccaa ggggcctaag tcattgctga cctagagct gaaggacgat    1140 cgcccggcca gagatatgtg ggtaatgggc acgagcctga tgttgccccg ggccacagct    1200
caagacgctg gaaagtggta ttgtcaccgt ggcaacctga ccatgtcatt ccacctggag    1260
atcactgctc ggccatctag acatcatcac catcaccat                           1299
```

<210> SEQ ID NO 84
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
atggagtttg ggctgagctg ggttttcctc gttgctcttt ttagaggtgt ccagtgtcag      60
gtgcagctgc aggagtctgg gggaggcttg gtgcaggctg gggggtctct gagactctcc     120
tgtgcagcct caggaagcat cttcgctatt aatgaaatca atcttatggg gtggtaccgc     180
caggctccag ggaagcagcg cgagttggtc gcagcttgtg ctagtgatgg caacacatac     240
tatgcggact ccgtgaaggg ccgattcacc atctccagag acaacgccga aaacggtg       300 tatctgcaga tgaacaacct gaaacctgac gacacagccg tctattactg tgatgcgaat     360
```

```
tcgagggga   attattattc   gggccagggg   acccaggtca   ccgtctcctc   aactagtggc      420
ccgggaggcc   aaggcgcagg   aggaggtggg   tctggaggtg   gaggatctgg   tggaggtggg      480
tctggaggag   gtggatcccc   cgaggaacct   ctagtggtga   aggtggaaga   gggagatacc      540
gctgccctgt   ggtgcctcaa   ggggacctca   gatggcccca   ctcagcagct   gacctggtct      600
cgggagtccc   cgcttaaacc   cttcttaaaa   tacagcctgg   gggtgccagg   cctgggagtg      660
cacgtgaggc   ccgacgccat   cagcgtggtt   atccggaacg   tctctcaaca   gatggggggc      720
ttctacctgt   gccagccggg   gcccccctct   gagaaggcct   ggcagcctgg   ctggacagtc      780
aatgtggagg   gcagcgggga   gctgttccgg   tggaatgttt   cggacctagg   tggcctgggc      840
tgtggcctga   agaacaggtc   ctcagagggc   cccagctccc   cttccgggaa   gctcatgagc      900
cccaagctgt   atgtgtgggc   caaagaccgc   cctgagatct   gggagggaga   gcctccgtgt      960
ctcccaccga   gggacagcct   gaaccagagc   ctcagccggg   acctcaccgt   tgcccctggc     1020
tccacactct   ggctgtcctg   tggggtaccc   cctgactctg   tgtccagggg   ccccctctcc     1080
tggacccatg   tgcaccccaa   ggggcctaag   tcattgctga   gctagagct    gaaggacgat     1140 cgcccggcca   gagatatgtg   ggtaatgggc   acgagcctga   tgttgccccg   ggccacagct     1200
caagacgctg   gaaagtggta   ttgtcaccgt   ggcaacctga   ccatgtcatt   ccacctggag     1260
atcactgctc   ggccatctag   acatcatcac   catcaccat                               1299
```

<210> SEQ ID NO 85
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atggagtttg   ggctgagctg   ggttttcctc   gttgctcttt   ttagaggtgt   ccagtgtcag       60
gtgcagctgc   aggagtctgg   gggaggcttg   gtgcaggtcg   gggagtctct   gagactctcc      120
tgtgtagtct   ctggagatac   gaggagtatc   aatctcatgg   ggtggtaccg   ccaggctcca      180
gggaagcagc   gcgagttggt   cgcagcttgt   gctagtgatg   gcaacacata   ctatgcggac      240
tccgtgaagg   gccgattcac   catctccaga   gacaacgccg   agaaaacggt   gtatctgcag      300
atgaacaacc   tgaaacctga   cgacacagcc   gtctattact   gtgatgcgaa   ttcgaggggg      360
aattattatt   cgggccaggg   gaccctggtc   accgtctcct   caactagtgg   cccgggaggc      420
caaggcgcag   gaggaggtgg   gtctggaggt   ggaggatctg   gtggaggtgg   gtctggagga      480
ggtggatccc   ccgaggaacc   tctagtggtg   aaggtggaag   agggagatac   cgctgccctg      540
tggtgcctca   ggggacctc    agatggcccc   actcagcagc   tgacctggtc   tcgggagtcc      600
ccgcttaaac   ccttcttaaa   atacagcctg   ggggtgccag   gcctgggagt   gcacgtgagg      660
cccgacgcca   tcagcgtggt   tatccggaac   gtctctcaac   agatgggggg   cttctacctg      720
tgccagccgg   ggcccccctc   tgagaaggcc   tggcagcctg   gctggacagt   caatgtggag      780
ggcagcgggg   agctgttccg   gtggaatgtt   tcggacctag   gtggcctggg   ctgtggcctg      840
aagaacaggt   cctcagaggg   ccccagctcc   ccttccggga   agctcatgag   ccccaagctg      900
tatgtgtggg   ccaaagaccg   ccctgagatc   tgggagggag   agcctccgtg   tctcccaccg      960
agggacagcc   tgaaccagag   cctcagccgg   gacctcaccg   ttgccctgg    ctccacactc     1020 tggctgtcct   gtggggtacc   ccctgactct   gtgtccaggg   gccccctctc   ctggacccat     1080
```

```
gtgcacccca agggccctaa gtcattgctg agcctagagc tgaaggacga tcgcccggcc    1140
agagatatgt gggtaatggg cacgagcctg atgttgcccc gggccacagc tcaagacgct    1200
ggaaagtggt attgtcaccg tggcaacctg accatgtcat tccacctgga gatcactgct    1260
cggccatcta gacatcatca ccatcaccat                                     1290
```

<210> SEQ ID NO 86
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
atgccacctc ctcgcctcct cttcttcctc ctcttcctca ccccatgga agtcaggccc       60 gaggagcccc tggtggtgaa ggtggaggag ggcgacaccg ccgtgctgcc ctgcctgaag      120
ggcaccagcg acggcccac ccagcagctg acctggagca gggagagccc cctgaagccc      180
ttcctgaagt acagcctggg cgtgcccggc ctgggcgtgc acgtgaggcc cgacgccatc      240
agcgtggtga tcaggaacgt gagccagcag atgggcggct ctacctgtg ccagcccggc       300 cccccagcg agaaggcctg gcagcccggc tggaccgtga acgtggaggg cagcggcgag       360
ctgttcaggt ggaacgtgag cgacctgggc ggcctgggct gcggcctgaa gaacaggagc      420
agcgagggcc ccagcagccc cagcggcaag ctgatgagcc caagctgta cgtgtgggcc       480 aaggacaggc ccgagatctg ggagggcgag ccccccctgcc tgcccccag ggacagcctg      540 aaccagagcc tgagccagga cctgaccatg gccccggca gcaccctgtg gctgagctgc      600
ggcgtgcccc ccgacagcgt gagcaggggc cccctgagct ggaccccacgt gcaccccaag      660 ggcccccaaga gcctgctgag cctggagctg aaggacgaca ggcccgccag ggagatgatc      720
gtggacgaga ccggcctgct gctgcccagg gccaccgccc aggacgccgg caagtggtac      780
tgcagcaggg gcaacgtgac caccagctac acctggaga tcaccgccag gcccggagga       840
ggtgggtctg gaggtggagg atctggtgga ggtgggtctg gaggaggtgg atccgaggtg      900
cagctggtgg agtctggtgg tggtcttgtt caacctggtg gttctcttcg tctttcttgt      960
gctgcttctg gttttaatat taagatact tatattcatt gggttcgtca agctcctggt      1020
aaaggtcttg aatgggttgc tcgtatttat cctactaatg ttatactcg ttatgctgat      1080 tctgttaaag tcgttttac tatttctgct gatacttcta aaaatactgc ttatcttcaa      1140
atgaactctc ttcgtgctga agatactgct gtttattat gttctcgttg gggtggtgat      1200 ggttttttatg ctatggatta ttggggtcaa ggtactcttg tcaccgtctc ctcagctagc      1260
accgggggag gtgggtctgg aggtggagga tctggtggag gtgggtctga catccagatg      1320
acccagtctc cttcttctct ttctgcttct gttggtgatc gtgttactat tacttgtcgt      1380
gcttctcaag atgttaatac tgctgttgct tggtatcaac aaaaacctgg taaagctcct      1440
aaacttctta tttattctgc ttcttttctt tattctggtg ttccttctcg ttttttctggt      1500 tctcgttctg gtactgattt tactcttact atttcttctc ttcaacctga agattttgct      1560
acttattatt gtcaacaaca ttatactact cctcctactt ttggtcaagg taccaaggtg      1620
gagatcaaac gtacgcatca tcaccatcac cat                                 1653
```

<210> SEQ ID NO 87
<211> LENGTH: 1701
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 87

```
atgccacctc ctcgcctcct cttcttcctc ctcttcctca cccccatgga agtcaggccc    60
gaggagcccc tggtggtgaa ggtggaggag ggcgacaccg ccgtgctgcc ctgcctgaag   120
ggcaccagcg acggcccac ccagcagctg acctggagca gggagagccc cctgaagccc   180
ttcctgaagt acagcctggg cgtgcccggc ctgggcgtgc acgtgaggcc cgacgccatc   240
agcgtggtga tcaggaacgt gagccagcag atgggcggct tctacctgtg ccagcccggc   300
cccccagcg agaaggcctg gcagcccggc tggaccgtga acgtggaggg cagcggcgag   360
ctgttcaggt ggaacgtgag cgacctgggc ggcctgggct gcggcctgaa gaacaggagc   420
agcgagggcc ccagcagccc cagcggcaag ctgatgagcc caagctgta cgtgtgggcc   480
aaggacaggc ccgagatctg ggagggcgag ccccccctgcc tgcccccag ggacagcctg   540
aaccagagcc tgagccagga cctgaccatg gccccggca gcaccctgtg gctgagctgc   600
ggcgtgcccc ccgacagcgt gagcagggc cccctgagct ggacccacgt gcaccccaag   660
ggccccaaga gcctgctgag cctggagctg aaggacgaca ggcccgccag ggagatgatc   720
gtggacgaga ccgccctgct gctgcccagg gccaccgccc aggacgccgg caagtggtac   780
tgcagcaggg gcaacgtgac caccagctac cacctggaga tcaccgccag gcccgtgaag   840
gcccacagcg acctgaggac cggcggctgg aagggaggag gtgggtctgg aggtggagga   900
tctggtggag gtgggtctgg aggaggtggg tctcaggtca aactacagga gtcagggct   960
gagctggtga agcctggggc ctcagtgaag atgtcctgca aggcttctgg ctacacattt  1020
accagttaca atatgcactg ggtaaagcag acacctggac agggcctgga atggattgga  1080
gctatttatc caggaaatgg tgatacttcc tacaatcaga gttcaaagg caaggccaca  1140
ttgactgcag acaaatcctc cagcacagcc tacatgcagc tcagcagcct gacatctgag  1200
gactctgcgg actattactg tgcaagatct aattattacg gtagtagcta ctggttcttc  1260
gatgtctggg gccaagggac cacggtcacc gtctcctcag ccagcaccgg tggaggcggt  1320
tcaggcggag gtggctctgg cggtggcgga tcggacatcg agctcactca gtctccaaca  1380
atcctgtctg catctccagg ggagaaggtc acaatgactt gcagggccag ctcaagtgta  1440
aattacatgg actggtacca gaagaagcca ggatcctccc ccaaaccctg gatttatgcc  1500
acatccaacc tggcttctgg agtccctgct cgcttcagtg gcagtgggtc tgggaccct  1560
tactctctca caatcagcag agtggaggct gaagatgctg ccacttatta ctgccagcag  1620
tggagtttta atccacccac gttcggaggg gggacaaagt tggaaataaa acgggccgcc  1680
gctcatcatc accatcacca t                                             1701
```

<210> SEQ ID NO 88
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
atgccacctc ctcgcctcct cttcttcctc ctcttcctca cccccatgga agtcaggccc    60
gaggagcccc tggtggtgaa ggtggaggag ggcgacaccg ccgtgctgcc ctgcctgaag   120
```

| | |
|---|---|
| ggcaccagcg acggccccac ccagcagctg acctggagca gggagagccc cctgaagccc | 180 |
| ttcctgaagt acagcctggg cgtgcccggc ctgggcgtgc acgtgaggcc cgacgccatc | 240 |
| agcgtggtga tcaggaacgt gagccagcag atgggcggct tctacctgtg ccagcccggc | 300 |
| ccccccagcg agaaggcctg gcagcccggc tggaccgtga acgtggaggg cagcggcgag | 360 |
| ctgttcaggt ggaacgtgag cgacctgggc ggcctgggct gcggcctgaa gaacaggagc | 420 |
| agcgagggcc ccagcagccc cagcggcaag ctgatgagcc ccaagctgta cgtgtgggcc | 480 |
| aaggacaggc ccgagatctg ggagggcgag ccccctgcc tgcccccag gacagcctg | 540 |
| aaccagagcc tgagcagga cctgaccatg gcccccggca gcaccctgtg gctgagctgc | 600 |
| ggcgtgcccc ccgacagcgt gagcagggc cccctgagct ggacccacgt gcaccccaag | 660 |
| ggccccaaga gcctgctgag cctggagctg aaggacgaca ggcccgccag ggagatgatc | 720 |
| gtggacgaga ccggcctgct gctgcccagg gccaccgccc aggacgccgg caagtggtac | 780 |
| tgcagcaggg gcaacgtgac caccagctac cacctggaga tcaccgccag gcccgtgaag | 840 |
| gcccacagcg acctgaggac cggcggctgg aagggaggag gtgggtctgg aggtggagga | 900 |
| tctggtggag gtgggtctgg aggaggtggg tctgtgagcg acgtgcccag ggacctggag | 960 |
| gtggtggccg ccaccccac cagcctgctg atcagctggt gcaggcagag gtgcgccgac | 1020 |
| agctacagga tcacctacgg cgagaccggc ggcaacagcc ccgtgcagga gttcaccgtg | 1080 |
| cccggcagct ggaagaccgc caccatcagc ggcctgaagc ccggcgtgga ctacaccatc | 1140 |
| accgtgtacg tggtgaccca ctactacggc tgggacaggt acagccaccc catcagcatc | 1200 |
| aactacagga ccgagatcga caagcccagc cagcatcatc accatcacca t | 1251 |

<210> SEQ ID NO 89
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| | |
|---|---|
| atgccacctc ctcgcctcct cttcttcctc ctcttcctca cccccatgga agtcaggccc | 60 |
| gaggagcccc tggtggtgaa ggtggaggag ggcgacaccg ccgccctgtg gtgcctgaag | 120 |
| ggcaccagcg acggccccac ccagcagctg acctggagca gggagagccc cctgaagccc | 180 |
| ttcctgaagt acagcctggg cgtgcccggc atgggcgtgc acgtgaggcc caacgccgtg | 240 |
| agcctggtga tcagcaacgt gagccagcag atgggcggct tctacctgtg ccagcccggc | 300 |
| ccccccagcg agaaggcctg gcagcccggc tggaccgtga acgtggaggg cagcggcgag | 360 |
| ctgttcaggt ggaacgtgag cgacctgggc ggcctgggct gcggcctgaa gaacaggagc | 420 |
| agcgagggcc ccagcagccc cagcggcaag ctgatgagcc ccaagctgta cgtgtgggcc | 480 |
| aaggacaggc ccgagatctg ggagggcgag ccccctgcc tgcccccag gacagcctg | 540 |
| aaccagagcc tgagcaggga catgaccgtg gcccccggca gcaccctgtg gctgagctgc | 600 |
| ggcgtgcccc ccgacagcgt gagcagggc cccctgagct ggacccacgt gcaccccaag | 660 |
| ggccccaaga gcctgctgag cctggagctg aaggacgaca ggcccgccag ggacatgtgg | 720 |
| gtgatggaga ccggcctggt gctgcccagg gccaccgccc aggacgccgg caagtggtac | 780 |
| tgccacaggg gcaacgtgac caccagctac cacctggaga tcaccgccag gcccgtgagc | 840 |
| gcccacaccc ccctgaggac cggcggctgg aagggaggag gtgggtctgg aggtggagga | 900 |

-continued

```
tctggtggag gtgggtctgg aggaggtggg tctgtgagcg acgtgcccag ggacctggag      960
gtggtggccg ccaccccac cagcctgctg atcagctggt gcaggcagag gtgcgccgac     1020
agctacagga tcacctacgg cgagaccggc ggcaacagcc ccgtgcagga gttcaccgtg     1080
cccggcagct ggaagaccgc caccatcagc ggcctgaagc ccggcgtgga ctacaccatc     1140
accgtgtacg tggtgaccca ctactacggc tgggacaggt acagccaccc catcagcatc     1200
aactacagga ccgagatcga caagcccagc cagcatcatc accatcacca t              1251
```

<210> SEQ ID NO 90
<211> LENGTH: 1692
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
atggagtttg ggctgagctg ggttttcctc gttgctcttt ttagaggtgt ccagtgtgag       60
gtgcagctgg tggagtctgg tggtggtctt gttcaacctg gtggttctct tcgtctttct      120
tgtgctgctt ctggttttaa tattaaagat acttatattc attgggttcg tcaagctcct      180
ggtaaaggtc ttgaatgggt tgctcgtatt tatcctacta atggttatac tcgttatgct      240
gattctgtta aaggtcgttt tactatttct gctgatactt ctaaaaatac tgcttatctt      300
caaatgaact ctcttcgtgc tgaagatact gctgtttatt attgttctcg ttggggtggt      360
gatggttttt atgctatgga ttattggggt caaggtactc ttgtcaccgt ctcctcagct      420
agcaccgggg gaggtgggtc tggaggtgga ggatctggtg gaggtgggtc tgacatccag      480
atgacccagt ctccttcttc tctttctgct tctgttggtg atcgtgttac tattacttgt      540
cgtgcttctc aagatgttaa tactgctgtt gcttggtatc aacaaaaacc tggtaaagct      600
cctaaacttc ttatttattc tgcttctttt ctttattctg gtgttccttc tcgtttttct      660
ggttctcgtt ctggtactga ttttactctt actatttctt ctcttcaacc tgaagatttt      720
gctacttatt attgtcaaca acattatact actcctccta cttttggtca aggtaccaag      780
gtggagatca aacgtacggg aggaggtggg tctggaggtg gaggatctgg tggaggtggg      840
tctggaggag gtgggtctcc cgaggagccc ctggtggtga aggtggagga gggcgacacc      900
gccgtgctgc cctgcctgaa gggcaccagc gacggcccca cccagcagct gacctggagc      960
agggagagcc ccctgaagcc cttcctgaag tacagcctgg gcgtgcccgg cctgggcgtg     1020
cacgtgaggc ccgacgccat cagcgtggtg atcaggaacg tgagccagca gatgggcggc     1080
ttctacctgt gccagcccgg cccccccagc gagaaggcct ggcagccggg ctggaccgtg     1140
aacgtggagg cagcggcga gctgttcagg tggaacgtga gcgacctggg cggcctgggc     1200
tgcggcctga gaacaggag cagcgaggc cccagcagcc cagcggcaa gctgatgagc     1260 cccaagctgt acgtgtgggc caaggacagg cccgagatct gggagggcga gccccctgc      1320 ctgcccccca gggacagcct gaaccagagc ctgagccagg acctgaccat ggcccccggc      1380
agcaccctgt ggctgagctg cggcgtgccc ccgacagcg tgagcagggg cccctgagc      1440 tggacccacg tgcaccccaa gggccccaag agcctgctga gcctggagct gaaggacgac      1500
aggcccgcca gggagatgat cgtggacgag accggcctgc tgctgcccag gccaccgcc      1560 caggacgccg gcaagtggta ctgcagcagg ggcaacgtga ccaccagcta ccacctggag      1620
atcaccgcca ggcccgtgaa ggcccacagc gacctgagga ccggcggctg gaagcatcat      1680
```
caccatcacc at                                                         1692

<210> SEQ ID NO 91
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atggagtttg ggctgagctg ggttttcctc gttgctcttt ttagaggtgt ccagtgtcag    60
gttcagctgg tgcagtctgg tgctgaggtg aagaagcctg gtgcctcagt gaaggtctcc   120
tgcaaggctt ctggttacac attcactgac tactacatgc actgggtgcg tcaggcccct   180
ggtcaaggtc ttgagtggat gggtcgtgtt aatcctaacc ggaggggtac tacctacaac   240
cagaaattcg agggccgtgt caccatgacc acagacacat ccacgagcac agcctacatg   300
gagctgcgta gcctgcgttc tgacgacacg gccgtgtatt actgtgcgcg tgcgaactgg   360
cttgactact ggggccaggg caccaccgtc accgtctcct ccgcctccac caagggccca   420
tcggtcttcc cgctagcgcc ctgctccagg agcacctccg agagcacagc cgccctgggc   480
tgcctggtca aggactactt ccccgaaccg gtgacggtgt cgtggaactc aggcgccctg   540
accagcggcg tgcacacctt cccggctgtc ctacagtcct caggactcta ctccctcagc   600
agcgtggtga ccgtgccctc agcagcttgg gcacgaaga cctacacctg caacgtagat   660
cacaagccca gcaacaccaa ggtggacaag agagttgagt ccaaatatgg tcccccatgc   720
ccaccctgcc cagcacctga ggccgccggg ggaccatcag tcttcctgtt ccccccaaaa   780
cccaaggaca ctctcatgat ctcccggacc cctgaggtca cgtgcgtggt ggtggacgtg   840
agccaggaag accccgaggt ccagttcaac tggtacgtgg atggcgtgga ggtgcataat   900
gccaagacaa agccgcggga ggagcagttc aacagcacgt accgtgtggt cagcgtcctc   960
accgtcctgc accaggactg gctgaacggc aaggagtaca agtgcaaggt ctccaacaaa  1020
ggcctcccgt cctccatcga gaaaaccatc tccaaagcca agggcagccc cgagagcca   1080 caggtgtaca ccctgccccc atcccaggag gagatgacca gaaccaggt cagcctgacc   1140 tgcctggtca aaggcttcta ccccagcgac atcgccgtgg agtgggaaag caatgggcag  1200
ccggagaaca actacaagac cacgcctccc gtgctggact ccgacggctc cttcttcctc  1260
tacagcaggc taaccgtgga caagagcagg tggcaggagg gaatgtcttt ctcatgctcc  1320
gtgatgcatg aggctctgca caaccactac acacagaaga gcctctccct gtctctgggt  1380

<210> SEQ ID NO 92
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atggagacag acacactcct gctatgggta ctgctgctct gggttccagg ttccactggt    60
gacatccaga tgacccagtc tccatcctcc ctgtctgcat ctgtaggaga cagagtcacc   120
atcacttgca gtgtcagctc aagtgtatcc tccatttact tgcactggta tcagcagaaa   180
ccagggaaag cccctaagct cctgatctat agcacatcca acttggcttc tggagtccca   240

-continued

```
tcaaggttca gtggcagtgg atctgggaca gatttcactc tcaccatcag cagtctgcaa    300
cctgaagatt ttgcaactta ctactgtcaa gtctacagtg gttacccgct cacgttcggc    360
ggagggacca aggtggagat caaacgaact gtggctgcac atctgtcttc atcttcccg    420 ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgcgacaa aactcacaca    720
tcgccaccgt ccccagcacc tgaagccgcg ggggaccgt cacccgagga acctctagtg    780
gtgaaggtgg aagagggaga taacgctgtg ctgcagtgcc tcaaggggac ctcagatggc    840
cccactcagc agctgacctg gtctcgggag tccccgctta aacccttctt aaaactcagc    900
ctggggctgc aggcctggga atccacatg aggcccctgg ccatctggct tttcatcttc    960
aacgtctctc aacagatggg gggcttctac ctgtgccagc cggggccccc ctctgagaag   1020
gcctggcagc ctggctggac agtcaatgtg gagggcagcg gggagctgtt ccggtggaat   1080
gtttcggacc taggtggcct gggctgtggc ctgaagaaca ggtcctcaga gggccccagc   1140 tcccccttccg ggaagctcat gagccccaag ctgtatgtgt gggccaaaga ccgccctgag   1200
atctgggagg gagagcctcc gtgtctccca ccgagggaca gctgaaacca gagcctcagc   1260
caggacctca ccatggcccc tggctccaca ctctggctgt cctgtggggt accccctgac   1320
tctgtgtcca ggggcccct ctcctggacc catgtgcacc ccaagggggcc taagtcattg   1380 ctgagcctag agctgaagga cgatcgcccg ccagagata tgtgggtaat ggagacgggt   1440
ctgttgttgc ccgggccac agctcaagac gctggaaagt attattgtca ccgtggcaac   1500
ctgaccatgt cattccacct ggagatcact gctcggcca                          1539
```

<210> SEQ ID NO 93
<211> LENGTH: 1662
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atggagtttg gctgagctg ggttttcctc gttgctcttt ttagaggtgt ccagtgtgag     60
gtgcagctgg tggagtctgg tggtggtctt gttcaacctg gtggttctct tcgtctttct    120
tgtgctgctt ctggttttaa tattaaagat acttatattc attgggttcg tcaagctcct   180
ggtaaaggtc ttgaatgggt tgctcgtatt tatcctacta atggttatac cgttatgct   240 gattctgtta aggtcgtttt actatttct gctgatactt ctaaaaatac tgcttatctt   300
caaatgaact ctcttcgtgc tgaagatact gctgtttatt attgttctcg ttggggtggt   360
gatggttttt atgctatgga ttattgggt caaggtactc ttgtcaccgt ctcctcagct   420
agcaccgggg gaggtgggtc tggaggtgga ggatctggtg gaggtgggtc tgacatccag   480
atgacccagt ctccttcttc tctttctgct tctgttggtg atcgtgttac tattacttgt   540
cgtgcttctc aagatgttaa tactgctgtt gcttggtatc aacaaaaacc tggtaaagct   600
cctaaacttc ttatttattc tgcttctttt cttattctg gtgttccttc tcgttttct   660 ggttctcgtt ctggtactga ttttactctt actatttctt ctcttcaacc tgaagatttt   720
```

```
gctacttatt attgtcaaca acattatact actcctccta cttttggtca aggtaccaag    780
gtggagatca aacgtacgga caaaactcac acatcgccac cgtccccagc acctgaagcc    840 gcgggggggac cgtcacccga ggaacctcta gtggtgaagg tggaagaggg agataacgct   900
gtgctgcagt gcctcaaggg gacctcagat ggccccactc agcagctgac ctggtctcgg    960
gagtccccgc ttaaaccctt cttaaaactc agcctggggc tgccaggcct gggaatccac   1020
atgaggcccc tggccatctg gcttttcatc ttcaacgtct ctcaacagat gggggggcttc  1080 tacctgtgcc agccggggcc cccctctgag aaggcctggc agcctggctg acagtcaat   1140 gtggagggca gcggggagct gttccggtgg aatgtttcgg acctaggtgg cctgggctgt   1200
ggcctgaaga acaggtcctc agagggcccc agctccccctt ccgggaagct catgagcccc  1260
aagctgtatg tgtgggccaa agaccgcccct gagatctggg agggagagcc tccgtgtctc  1320
ccaccgaggg acagcctgaa ccagagcctc agccaggacc tcaccatggc ccctggctcc  1380
acactctggc tgtcctgtgg ggtaccccct gactctgtgt ccaggggccc cctctcctgg  1440
acccatgtgc accccaaggg gcctaagtca ttgctgagcc tagagctgaa ggacgatcgc  1500
ccggccagag atatgtgggt aatggagacg ggtctgttgt tgccccgggc cacagctcaa  1560
gacgctggaa agtattattg tcaccgtggc aacctgacca tgtcattcca cctggagatc  1620
actgctcggc catctagagg gccccatcat caccatcacc at                      1662
```

<210> SEQ ID NO 94
<211> LENGTH: 1377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
atgccacctc ctcgcctcct cttcttcctc ctcttcctca cccccatgga agtcaggccc     60
gaggagcccc tggtggtgaa ggtggaggag ggcgacaccg ccgtgctgcc ctgcctgaag    120
ggcaccagcg acggccccac ccagcagctg acctggagca gggagagccc cctgaagccc    180
ttcctgaagt acagcctggg cgtgcccggc ctgggcgtgc acgtgaggcc cgacgccatc    240
agcgtggtga tcaggaacgt gagccagcag atgggcggct tctacctgtg ccagcccggc    300
ccccccagcg agaaggcctg gcagcccggc tggaccgtga acgtgagggg cagcggcgag    360
ctgttcaggt ggaacgtgag cgacctgggc ggcctgggct gcggcctgaa gaacaggagc    420
agcgagggcc ccagcagccc cagcggcaag ctgatgagcc caagctgta  cgtgtgggcc    480 aaggacaggc ccgagatctg ggagggcgag cccccctgcc tgcccccag  ggacagcctg    540 aaccagagcc tgagccagga cctgaccatg gcccccggca gcaccctgtg gctgagctgc    600
ggcgtgcccc ccgacagcgt gagcaggggc cccctgagct ggacccacgt gcaccccaag    660 ggcccccaaga gcctgctgag cctggagctg aaggacgaca gcccgccag ggagatgatc    720 gtggacgaga ccggcctgct gctgcccagg gccaccgccc aggacgccgg caagtggtac    780
tgcagcaggg gcaacgtgac caccagctac cacctggaga tcaccgccag gcccgtgaag    840
gcccacagcg acctgaggac cggcggctgg aaggaggag  gtgggtctgg aggtggagga    900
tctggtggag gtgggtctgg aggaggtgga tcccaggtgc agctgcagca gtctggggga    960
ggcttggtgc aggctggggg gtctctgaga ctctcctgtg cagcctcagg aagcatcttc   1020
gctattaatg aaatcaatct tatggggtgg taccgccagc ctccagggaa gcagcgcgag   1080
```

```
ttggtcgcag cttgtgctag tgatggcaac acatactatg cggactccgt gaagggccga   1140
ttcaccatct ccagagacaa cgccgagaaa acggtgtatc tgcagatgaa caacctgaaa   1200
cctgacgaca cagccgtcta ttactgtgat gcgaattcga gggggaatta ttattcgggc   1260
caggggaccc aggtcaccgt tcctcaact agtggcccgg gaggccaagg cgcagaacaa    1320
aaactcatct cagaagagga tctgggcgca caccatcacc accatcatgg cgcatct     1377
```

<210> SEQ ID NO 95
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
atgccacctc ctcgcctcct cttcttcctc ctcttcctca cccccatgga agtcaggccc     60
gaggagcccc tggtggtgaa ggtggaggag ggcgacaccg ccgtgctgcc ctgcctgaag    120
ggcaccagcg acggcccac ccagcagctg acctggagca gggagagccc cctgaagccc    180
ttcctgaagt acagcctggg cgtgcccggc ctgggcgtgc acgtgaggcc cgacgccatc    240
agcgtggtga tcaggaacgt gagccagcag atgggcggct ctacctgtg ccagcccggc    300 ccccccagcg agaaggcctg gcagcccggc tggaccgtga acgtggaggg cagcggcgag    360
ctgttcaggt ggaacgtgag cgacctgggc ggcctgggct gcggcctgaa gaacaggagc    420
agcgagggcc ccagcagccc cagcggcaag ctgatgagcc caagctgta cgtgtgggcc    480 aaggacaggc ccgagatctg ggagggcgag ccccctgcc tgccccccag ggacagcctg    540
aaccagagcc tgagccagga cctgaccatg gcccccggca gcaccctgtg gctgagctgc    600
ggcgtgcccc ccgacagcgt gagcagggc cccctgagct ggaccacgt gcaccccaag     660 ggccccaaga gcctgctgag cctggagctg aaggacgaca ggcccgccag ggagatgatc    720
gtggacgaga ccggcctgct gctgcccagg gccaccgccc aggacgccgg caagtggtac    780
tgcagcaggg gcaacgtgac caccagctac cacctggaga tcaccgccag gcccgtgaag    840
gcccacagcg acctgaggac cggcggctgg aaggaggag gtgggtctgg aggtggagga    900
tctggtggag gtgggtctgg aggaggtgga tcccaggtgc agctgcagga gtctggggga    960
ggcttggtgc aacctggggg gtctctgaga ctctcctgtg cagcctctgg attcaccttc   1020
aatagctatg ctatgacctg ggtccgccag gctccaggaa agggctcga gtgggtctca   1080 gacattaata gtggtggtgg tagcacaaac tatgcagact ccgtgaaggg ccgcttcacc   1140
atctccagag acaacgccaa gaacacgctg tatctgcaaa tgaacagcct gaaacctgag   1200
gacacggccg tgtattactg tgcgaccgag cttcgggta gtgactacta ccggggtccg   1260
attcgtgagt atgcctattg gggccagggg accctggtca ccgtctcctc aactagtggc   1320 ccggaggcc aaggcgcaga acaaaaactc atctcagaag aggatctggg cgcacaccat   1380
caccaccatc atggcgcatc t                                            1401
```

<210> SEQ ID NO 96
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
atgccacctc ctcgcctcct cttcttcctc ctcttcctca cccccatgga agtcaggccc    60
gaggagcccc tggtggtgaa ggtggaggag ggcgacaccg ccgtgctgcc ctgcctgaag   120
ggcaccagcg acggcccac ccagcagctg acctggagca gggagagccc cctgaagccc   180
ttcctgaagt acagcctggg cgtgcccggc ctgggcgtgc acgtgaggcc cgacgccatc   240
agcgtggtga tcaggaacgt gagccagcag atgggcggct tctacctgtg ccagcccggc   300
ccccccagcg agaaggcctg gcagcccggc tggaccgtga acgtggaggg cagcggcgag   360
ctgttcaggt ggaacgtgag cgacctgggc ggcctgggct gcggcctgaa gaacaggagc   420
agcgagggcc ccagcagccc cagcggcaag ctgatgagcc caagctgta cgtgtgggcc   480
aaggacaggc ccgagatctg ggagggcgag cccccctgcc tgcccccag ggacagcctg   540
aaccagagcc tgagccagga cctgaccatg gcccccggca gcaccctgtg gctgagctgc   600
ggcgtgcccc ccgacagcgt gagcaggggc cccctgagct ggacccacgt gcaccccaag   660
ggccccaaga gcctgctgag cctggagctg aaggacgaca ggcccgccag ggagatgatc   720
gtggacgaga ccggcctgct gctgcccagg gccaccgccc aggacgccgg caagtggtac   780
tgcagcaggg gcaacgtgac caccagctac cacctggaga tcaccgccag gcccgtgaag   840
gcccacagcg acctgaggac cggcggctgg aagggaggag gtgggtctgg aggtggagga   900
tctggtggag gtgggtctgg aggaggtgga tcccaggtgc agctgcaggc gtttggggga   960
ggcttggtgc agcctggggg gtctctgaga ctctcctgcg tagtttctgg aacaatgttc  1020
agtggcaagg acgtgaactg gcttcgccag gctccaggga agcacgtaga ggtggtcgca  1080
acagtttcca gtgatggtgg cacagattat gcagacttcg tgaagggccg attcaccatt  1140
tccagagacg acgccaagaa cacggtgaat ctgcaaatga acagcctgga acctgaggac  1200
acagccaact atatgtgcca tttcttatgg ggccgtcact actggggcca ggggacccag  1260
gtcaccgttt cctcaactag tggcccggga ggccaaggcg cagaacaaaa actcatctca  1320
gaagaggatc tgggcgcaca ccatcaccac catcatggcg catct            1365
```

<210> SEQ ID NO 97
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
atgccacctc ctcgcctcct cttcttcctc ctcttcctca cccccatgga agtcaggccc    60
gaggagcccc tggtggtgaa ggtggaggag ggcgacaccg ccgtgctgcc ctgcctgaag   120
ggcaccagcg acggcccac ccagcagctg acctggagca gggagagccc cctgaagccc   180
ttcctgaagt acagcctggg cgtgcccggc ctgggcgtgc acgtgaggcc cgacgccatc   240
agcgtggtga tcaggaacgt gagccagcag atgggcggct tctacctgtg ccagcccggc   300
ccccccagcg agaaggcctg gcagcccggc tggaccgtga acgtggaggg cagcggcgag   360
ctgttcaggt ggaacgtgag cgacctgggc ggcctgggct gcggcctgaa gaacaggagc   420
agcgagggcc ccagcagccc cagcggcaag ctgatgagcc caagctgta cgtgtgggcc   480
aaggacaggc ccgagatctg ggagggcgag cccccctgcc tgcccccag ggacagcctg   540
aaccagagcc tgagccagga cctgaccatg gcccccggca gcaccctgtg gctgagctgc   600
ggcgtgcccc ccgacagcgt gagcaggggc cccctgagct ggacccacgt gcaccccaag   660
```

```
ggcccaaga gcctgctgag cctggagctg aaggacgaca ggcccgccag ggagatgatc    720
gtggacgaga ccggcctgct gctgcccagg gccaccgccc aggacgccgg caagtggtac    780
tgcagcaggg gcaacgtgac caccagctac cacctggaga tcaccgccag gcccgtgaag    840
gcccacagcg acctgaggac cggcggctgg aagggaggag gtgggtctgg aggtggagga    900
tctggtggag gtgggtctgg aggaggtgga tcccaggtgc agctgcagga gtctggggga    960
ggcttggtgc aggctggggg gtcccttaga ctctcctgtg tagcctctgg aagcatcaga   1020
agtatcaatg tcatgggctg gtaccgccag gctccaggga agcagcgcga gttggtcgca   1080
gcttgtgcta gtgatggcaa cacatactat gcggactccg tgaagggccg attcaccatc   1140
tccagagaca acgccgagaa aacggtgtat ctgcagatga acaacctgaa acctgacgac   1200
acagccgtct attactgtga tgcgaattcg agggggaatt attattcggg ccaggggacc   1260
caggtcaccg tttcctcaac tagtggcccg ggaggccaag gcgcagaaca aaaactcatc   1320
tcagaagagg atctgggcgc acaccatcac caccatcatg gcgcatct                 1368
```

<210> SEQ ID NO 98
<211> LENGTH: 1377
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 98

```
atgccacctc ctcgcctcct cttcttcctc ctcttcctca cccccatgga agtcaggccc     60
gaggagcccc tggtggtgaa ggtggaggag ggcgacaccg ccgtgctgcc ctgcctgaag    120
ggcaccagcg acgcccccac ccagcagctg acctggagca gggagagccc cctgaagccc    180
ttcctgaagt acagcctggg cgtgcccggc ctgggcgtgc acgtgaggcc cgacgccatc    240
agcgtggtga tcaggaacgt gagccagcag atgggcggct tctacctgtg ccagcccggc    300
ccccccagcg agaaggcctg gcagcccggc tggaccgtga acgtggaggg cagcggcgag    360
ctgttcaggt ggaacgtgag cgacctgggc ggcctgggct gcggcctgaa gaacaggagc    420
agcgagggcc ccagcagccc cagcggcaag ctgatgagcc ccaagctgta cgtgtgggcc    480
aaggacaggc ccgagatctg ggagggcgag ccccccctgcc tgcccccag ggacagcctg    540 aaccagagcc tgagccagga cctgaccatg gcccccggca gcaccctgtg gctgagctgc    600
ggcgtgcccc ccgacagcgt gagcaggggc cccctgagct ggaccacgt gcaccccaag    660 ggccccaaga gcctgctgag cctggagctg aaggacgaca ggcccgccag ggagatgatc    720
gtggacgaga ccggcctgct gctgcccagg gccaccgccc aggacgccgg caagtggtac    780
tgcagcaggg gcaacgtgac caccagctac cacctggaga tcaccgccag gcccgtgaag    840
gcccacagcg acctgaggac cggcggctgg aagggaggag gtgggtctgg aggtggagga    900
tctggtggag gtgggtctgg aggaggtgga tcccaggtgc agttgcagca gtctggggga    960
ggcttggcgc agaccggggg gtctctgata ctctcctgtg cagcctcagg aagcatcttc   1020
gctattaatg aaatcaatct tatggggtgg taccgccagg ctccaggaa gcagcgcgag   1080 ttggtcgcag cttgtgctag tgatggcaac acatactatg cggactccgt gaagggccga   1140
ttcaccatct ccagagacaa cgccgagaaa acggtgtatc tgcagatgaa caacctgaaa   1200
cctgacgaca cagccgtcta ttactgtgat gcgaattcga gggggaatta ttattcgggc   1260
caggggaccc aggtcaccgt ttcctcaact agtggcccgg gaggccaagg cgcagaacaa   1320
```
aaactcatct cagaagagga tctgggcgca caccatcacc accatcatgg cgcatct    1377

<210> SEQ ID NO 99
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
atgccacctc ctcgcctcct cttcttcctc ctcttcctca ccccatgga agtcaggccc    60
gaggagcccc tggtggtgaa ggtggaggag ggcgacaccg ccgtgctgcc ctgcctgaag   120
ggcaccagcg acgcccccac ccagcagctg acctggagca gggagagccc cctgaagccc   180
ttcctgaagt acagcctggg cgtgcccggc ctgggcgtgc acgtgaggcc cgacgccatc   240
agcgtggtga tcaggaacgt gagccagcag atgggcggct tctacctgtg ccagcccggc   300
ccccccagcg agaaggcctg gcagcccggc tggaccgtga acgtggaggg cagcggcgag   360
ctgttcaggt ggaacgtgag cgacctgggc ggcctgggct gcggcctgaa gacaggagc   420
agcgagggcc ccagcagccc cagcggcaag ctgatgagcc ccaagctgta cgtgtgggcc   480
aaggacaggc ccgagatctg ggagggcgag ccccctgcc tgcccccag gacagcctg      540
aaccagagcc tgagccagga cctgaccatg gccccggca gcaccctgtg gctgagctgc   600
ggcgtgcccc ccgacagcgt gagcagggc cccctgagct ggacccacgt gcaccccaag   660
ggcccccaaga gcctgctgag cctggagctg aaggacgaca ggcccgccag ggagatgatc   720
gtggacgaga ccggcctgct gctgcccagg gccaccgccc aggacgccgg caagtggtac   780
tgcagcaggg gcaacgtgac caccagctac cacctggaga tcaccgccag gcccgtgaag   840
gcccacagcg acctgaggac cggcggctgg aaggaggag tgggtctgg aggtggagga    900
tctggtggag gtgggtctgg aggaggtgga tccgcagtgc agctgcagga gtctggggga   960
ggcttggtgc aggctggggg gtctctgaga ctctcctgtg cagcctctgg aagcgaccgc  1020
agtatcaatg tcatgaactg gtaccgccag gctccaggga agcagcgcga gttggtcgca  1080
gcgattacta gtggtggtac cacaaattat gcacagtccg tgaagggccg agtcaccatc  1140
tccagggaca cgccaagaa cacggtgtat ctacagatga acagcctgaa acctgaggac  1200
acagccgtct atttctgtaa agcagatacg cgttggggtg gatgtactg gggcccgggg  1260
acccaggtca ccgtttcctc aactagtggc cgggaggcc aaggcgcaga caaaaactc   1320
atctcagaag aggatctggg cgcacaccat caccaccatc atggcgcatc t          1371

<210> SEQ ID NO 100
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
atgccacctc ctcgcctcct cttcttcctc ctcttcctca ccccatgga agtcaggccc    60
gaggagcccc tggtggtgaa ggtggaggag ggcgacaccg ccgtgctgcc ctgcctgaag   120
ggcaccagcg acgcccccac ccagcagctg acctggagca gggagagccc cctgaagccc   180
ttcctgaagt acagcctggg cgtgcccggc ctgggcgtgc acgtgaggcc cgacgccatc   240

| | |
|---|---|
| agcgtggtga tcaggaacgt gagccagcag atgggcggct tctacctgtg ccagcccggc | 300 |
| cccccagcg agaaggcctg gcagcccggc tggaccgtga acgtggaggg cagcggcgag | 360 |
| ctgttcaggt ggaacgtgag cgacctgggc ggcctgggct gcggcctgaa gaacaggagc | 420 |
| agcgagggcc ccagcagccc cagcggcaag ctgatgagcc caagctgta cgtgtgggcc | 480 |
| aaggacaggc ccgagatctg ggagggcgag cccccctgcc tgcccccag gacagcctg | 540 |
| aaccagagcc tgagccagga cctgaccatg gcccccggca gcaccctgtg gctgagctgc | 600 |
| ggcgtgcccc ccgacagcgt gagcaggggc cccctgagct ggacccacgt gcaccccaag | 660 |
| ggccccaaga gcctgctgag cctggagctg aaggacgaca ggcccgccag ggagatgatc | 720 |
| gtggacgaga ccggcctgct gctgcccagg gccaccgccc aggacgccgg caagtggtac | 780 |
| tgcagcaggg gcaacgtgac caccagctac cacctggaga tcaccgccag gcccgtgaag | 840 |
| gcccacagcg acctgaggac cggcggctgg aagggaggag gtgggtctgg aggtggagga | 900 |
| tctggtggag gtgggtctgg aggaggtgga tcccaggtgc agctgcagca gtcaggggga | 960 |
| ggattggtgc aggctggggg ctctctgaca ctctcctgtg cagccacggg acgcacaatc | 1020 |
| gataacggcg ccatggcctg gttccgccag gctccaggga agcagcgtga gcttgtagct | 1080 |
| gccattaact ggagtggtgg tgccacattc tatacagact ccgtcaagta ccgtttcacc | 1140 |
| atctcccgag acaacgtcag gcacacattg gatctgcaaa tgaccagtct gaaacctgag | 1200 |
| gacacgacca tttatttctg tgcgtctcga cgcggtgtgg acttgaggcg caatagttac | 1260 |
| gaatatgact actggggccg ggggaccctg gtcaccgtct cctcaactag tggcccggga | 1320 |
| ggccaaggcg cagaacaaaa actcatctca gaagaggatc tgggcgcaca ccatcaccac | 1380 |
| catcatggcg catct | 1395 |

<210> SEQ ID NO 101
<211> LENGTH: 1323
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

| | |
|---|---|
| atggagtttg ggctgagctg ggttttcctc gttgctcttt ttagaggtgt ccagtgtcag | 60 |
| gtgcagctgc aggagtctgg gggaggcttg gtgcaacctg gggggtctct gagactctcc | 120 |
| tgtgcagcct ctggattcac cttcaatagc tatgctatga cctgggtccg ccaggctcca | 180 |
| ggaaagggc tcgagtgggt ctcagacatt aatagtggtg gtggtagcac aaactatgca | 240 |
| gactccgtga agggccgctt caccatctcc agagacaacg ccaagaacac gctgtatctg | 300 |
| caaatgaaca gcctgaaacc tgaggacacg gccgtgtatt actgtgcgac cgagcttcgg | 360 |
| ggtagtgact actaccgggg tccgattcgt gagtatgcct attggggcca ggggaccctg | 420 |
| gtcaccgtct cctcaactag tggcccggga ggccaaggcg caggaggagg tgggtctgga | 480 |
| ggtggaggat ctggtggagg tgggtctgga ggaggtggat cccccgagga acctctagtg | 540 |
| gtgaaggtgg aagagggaga taccgctgcc ctgtggtgcc tcaagggac ctcagatggc | 600 |
| cccactcagc agctgacctg gtctcgggag tccccgctta aacccttctt aaaatacagc | 660 |
| ctggggtgc caggcctggg agtgcacgtg aggcccgacg ccatcagcgt ggttatccgg | 720 |
| aacgtctctc aacagatggg gggcttctac ctgtgccagc cggggccccc ctctgagaag | 780 |
| gcctggcagc ctggctggac agtcaatgtg agggcagcg gggagctgtt ccggtggaat | 840 |

```
gtttcggacc taggtggcct gggctgtggc ctgaagaaca ggtcctcaga gggccccagc    900
tccccttccg ggaagctcat gagcccaag ctgtatgtgt gggccaaaga ccgccctgag    960
atctgggagg gagagcctcc gtgtctccca ccgagggaca gcctgaacca gagcctcagc   1020
cgggacctca ccgttgcccc tggctccaca ctctggctgt cctgtggggt accccctgac   1080
tctgtgtcca ggggccccct ctcctggacc catgtgcacc ccaaggggcc taagtcattg   1140
ctgagcctag agctgaagga cgatcgcccg gccagagata tgtgggtaat gggcacgagc   1200
ctgatgttgc cccgggccac agctcaagac gctggaaagt ggtattgtca ccgtggcaac   1260
ctgaccatgt cattccacct ggagatcact gctcggccat ctagacatca tcaccatcac   1320
cat                                                                 1323

<210> SEQ ID NO 102
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atggagtttg ggctgagctg ggttttcctc gttgctcttt ttagaggtgt ccagtgtcag     60
gtgcagttgc agcagtctgg gggaggcttg gcgcagaccg gggggtctct gatactctcc    120
tgtgcagcct caggaagcat cttcgctatt aatgaaatca atcttatggg gtggtaccgc    180
caggctccag ggaagcagcg cgagttggtc gcagcttgtg ctagtgatgg caacacatac    240
tatgcggact ccgtgaaggg ccgattcacc atctccagag acaacgccga gaaaacggtg    300
tatctgcaga tgaacaacct gaaacctgac gacacagccg tctattactg tgatgcgaat    360 tcgagggga attattattc gggccagggg acccaggtca ccgtttcctc aactagtggc    420 ccggaggcc aaggcgcagg aggaggtggg tctggaggtg aggatctgg tggaggtggg    480 tctggaggag gtgatcccc cgaggaacct ctagtggtga aggtggaaga gggagatacc    540
gctgccctgt ggtgcctcaa ggggacctca gatggcccca ctcagcagct gacctggtct    600
cgggagtccc cgcttaaacc cttcttaaaa tacagcctgg gggtgccagg cctgggagtg    660
cacgtgaggc ccgacgccat cagcgtggtt atccggaacg tctctcaaca gatgggggc    720 ttctacctgt gccagccggg gccccctct gagaaggcct ggcagcctgg ctggacagtc    780
aatgtggagg gcagcgggga gctgttccgg tggaatgttt cggacctagg tggcctgggc    840 tgtggctga gaacaggtc ctcagagggc ccagctccc cttccgggaa gctcatgagc    900
cccaagctgt atgtgtgggc caaagaccgc cctgagatct gggagggaga gcctccgtgt    960
ctcccaccga gggacagcct gaaccagagc ctcagccggg acctcaccgt tgcccctggc   1020
tccacactct ggctgtcctg tgggtaccc cctgactctg tgtccagggg cccctctcc   1080 tggacccatg tgcaccccaa ggggcctaag tcattgctga gcctagagct gaaggacgat   1140
cgcccggcca gagatatgtg gtaatgggc acgagcctga tgttgccccg gccacagct   1200 caagacgctg gaaagtggta ttgtcaccgt ggcaacctga ccatgtcatt ccacctggag   1260
atcactgctc ggccatctag acatcatcac catcaccat                          1299

<210> SEQ ID NO 103
<211> LENGTH: 1317
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 103

| | | | | | |
|---|---|---|---|---|---|
| atggagtttg | ggctgagctg | ggttttcctc | gttgctcttt | ttagaggtgt | ccagtgtcag | 60 |
| gtgcagctgc | agcagtcagg | gggaggattg | gtgcaggctg | ggggctctct | gacactctcc | 120 |
| tgtgcagcca | cgggacgcac | aatcgataac | ggcgccatgg | cctggttccg | ccaggctcca | 180 |
| gggaagcagc | gtgagcttgt | agctgccatt | aactggagtg | gtggtgccac | attctataca | 240 |
| gactccgtca | agtaccgttt | caccatctcc | cgagacaacg | tcaggcacac | attggatctg | 300 |
| caaatgacca | gtctgaaacc | tgaggacacg | accatttatt | tctgtgcgtc | tcgacgcggt | 360 |
| gtggacttga | ggcgcaatag | ttacgaatat | gactactggg | gccggggac | cctggtcacc | 420 |
| gtctcctcaa | ctagtggccc | gggaggccaa | ggcgcaggag | gaggtgggtc | tggaggtgga | 480 |
| ggatctggtg | gaggtgggtc | tggaggaggt | ggatccccg | aggaacctct | agtggtgaag | 540 |
| gtggaagagg | gagataccgc | tgccctgtgg | tgcctcaagg | ggacctcaga | tggccccact | 600 |
| cagcagctga | cctggtctcg | ggagtccccg | cttaaaccct | tcttaaaata | cagcctgggg | 660 |
| gtgccaggcc | tggagtgca | cgtgaggccc | gacgccatca | gcgtggttat | ccggaacgtc | 720 |
| tctcaacaga | tgggggggctt | ctacctgtgc | cagccggggc | ccccctctga | aaggcctgg | 780 |
| cagcctggct | ggacagtcaa | tgtggagggc | agcggggagc | tgttccggtg | gaatgtttcg | 840 |
| gacctaggtg | gcctgggctg | tggcctgaag | aacaggtcct | cagagggccc | cagctcccct | 900 |
| tccgggaagc | tcatgagccc | caagctgtat | gtgtgggcca | agaccgccc | tgagatctgg | 960 |
| gagggagagc | ctccgtgtct | cccaccgagg | gacagcctga | accagagcct | cagccgggac | 1020 |
| ctcaccgttg | ccctggctc | cacactctgg | ctgtcctgtg | gggtaccccc | tgactctgtg | 1080 |
| tccaggggcc | ccctctcctg | gacccatgtg | caccccaagg | ggcctaagtc | attgctgagc | 1140 |
| ctagagctga | aggacgatcg | cccggccaga | gatatgtggg | taatgggcac | gagcctgatg | 1200 |
| ttgccccggg | ccacagctca | agacgctgga | aagtggtatt | gtcaccgtgg | caacctgacc | 1260 |
| atgtcattcc | acctggagat | cactgctcgg | ccatctagac | atcatcacca | tcaccat | 1317 |

<210> SEQ ID NO 104
<211> LENGTH: 1368
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 104

| | | | | | |
|---|---|---|---|---|---|
| atgccacctc | ctcgcctcct | cttcttcctc | ctcttcctca | ccccatgga | agtcaggccc | 60 |
| gaggagcccc | tggtggtgaa | ggtggaggag | ggcgacaccg | ccgtgctgcc | ctgcctgaag | 120 |
| ggcaccagcg | acggcccac | ccagcagctg | acctggagca | gggagagccc | cctgaagccc | 180 |
| ttcctgaagt | acagcctggg | cgtgcccggc | ctggcgtgc | acgtgaggcc | cgacgccatc | 240 |
| agcgtggtga | tcaggaacgt | gagccagcag | atgggcggct | tctacctgtg | ccagcccggc | 300 |
| ccccccagcg | agaaggcctg | gcagcccggc | tggaccgtga | acgtggaggg | cagcggcgag | 360 |
| ctgttcaggt | ggaacgtgag | cgacctgggc | ggcctgggct | gcggcctgaa | gaacaggagc | 420 |
| agcgagggcc | ccagcagccc | cagcggcaag | ctgatgagcc | caagctgta | cgtgtgggcc | 480 |
| aaggacaggc | ccgagatctg | ggagggcgag | cccccctgcc | tgcccccag | ggacagcctg | 540 |
| aaccagagcc | tgagccagga | cctgaccatg | gcccccggca | gcacccctgtg | gctgagctgc | 600 |

-continued

```
ggcgtgcccc ccgacagcgt gagcagdggc cccctgagct ggacccacgt gcacccaag       660
ggccccaaga gcctgctgag cctggagctg aaggacgaca ggcccgccag ggagatgatc       720
gtggacgaga ccggcctgct gctgcccagg gccaccgccc aggacgccgg caagtggtac       780
tgcagcaggg gcaacgtgac caccagctac cacctggaga tcaccgccag gcccgtgaag       840
gcccacagcg acctgaggac cggcggctgg aagggaggag gtgggtctgg aggtggagga       900
tctggtggag gtgggtctgg aggaggtgga tcccaggtgc agctgcagga gtctggggga       960
ggcttggtgc aggtcgggga gtctctgaga ctctcctgtg tagtctctgg agatacgagg      1020
agtatcaatc tcatggggtg gtaccgccag gctccaggga gcagcgcga gttggtcgca      1080
gcttgtgcta gtgatggcaa cacatactat gcggactccg tgaagggccg attcaccatc      1140
tccagagaca cgccgagaaa acggtgtat ctgcagatga caacctgaa acctgacgac      1200
acagccgtct attactgtga tgcgaattcg agggggaatt attattcggg ccaggggacc      1260
ctggtcaccg tctcctcaac tagtggcccg ggaggccaag cgcagaaca aaaactcatc      1320
tcagaagagg atctgggcgc acaccatcac caccatcatg gcgcatct                   1368
```

<210> SEQ ID NO 105
<211> LENGTH: 1377
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 105

```
atgccacctc ctcgcctcct cttcttcctc ctcttcctca cccccatgga agtcaggccc        60
gaggagcccc tggtggtgaa ggtggaggag ggcgacaccg ccgtgctgcc ctgcctgaag       120
ggcaccagcg acggccccac ccagcagctg acctggagca gggagagccc cctgaagccc       180
ttcctgaagt acagcctggg cgtgcccggc ctggcgtgc acgtgaggcc cgacgccatc       240
agcgtggtga tcaggaacgt gagccagcag atgggcggct ctacctgtg ccagcccggc       300
cccccagcg agaaggcctg gcagcccggc tggaccgtga acgtggaggg cagcggcgag       360
ctgttcaggt ggaacgtgag cgacctgggc ggcctgggct gcggcctgaa gaacaggagc       420
agcgagggcc ccagcagccc cagcggcaag ctgatgagcc caagctgta cgtgtgggcc       480
aaggacaggc ccgagatctg ggagggcgag ccccctgcc tgcccccag ggacagcctg        540
aaccagagcc tgagccagga cctgaccatg gccccggca gcaccctgtg ctgagctgc       600
ggcgtgcccc ccgacagcgt gagcagdggc cccctgagct ggacccacgt gcacccaag       660
ggccccaaga gcctgctgag cctggagctg aaggacgaca ggcccgccag ggagatgatc       720
gtggacgaga ccggcctgct gctgcccagg gccaccgccc aggacgccgg caagtggtac       780
tgcagcaggg gcaacgtgac caccagctac cacctggaga tcaccgccag gcccgtgaag       840
gcccacagcg acctgaggac cggcggctgg aagggaggag gtgggtctgg aggtggagga       900
tctggtggag gtgggtctgg aggaggtgga tcccaggtgc agctgcaaga gtctggggga       960
ggcttggtgc aggctggggg gtctctgaga ctctcctgtg cagcctcagg aagcatcttc      1020
gctattaatg aaatcaatct tatggggtgg taccgccagg ctccagggaa gcagcgcgag      1080
ttggtcgcag cttgtgctag tgatggcaac acatactatg cggactccgt gaagggccga      1140
ttcaccatct ccagagacaa cgccgagaaa acggtgtatc tgcagatgaa caacctgaaa      1200
cctgacgaca cagccgtcta ttactgtgat gcgaattcga gggggaatta ttattcgggc      1260
```

```
caggggaccc aggtcaccgt ctcctcaact agtggcccgg gaggccaagg cgcagaacaa    1320
aaactcatct cagaagagga tctgggcgca caccatcacc accatcatgg cgcatct       1377
```

<210> SEQ ID NO 106
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
atgccacctc ctcgcctcct cttcttcctc ctcttcctca cccccatgga agtcaggccc      60
gaggagcccc tggtggtgaa ggtggaggag ggcgacaccg ccgtgctgcc ctgcctgaag     120
ggcaccagcg acgccccac ccagcagctg acctggagca gggagagccc cctgaagccc      180
ttcctgaagt acagcctggg cgtgcccggc ctgggcgtgc acgtgaggcc cgacgccatc     240
agcgtggtga tcaggaacgt gagccagcag atgggcggct ctacctgtg ccagcccggc      300 ccccccagcg agaaggcctg gcagcccggc tggaccgtga acgtggaggg cagcggcgag     360
ctgttcaggt ggaacgtgag cgacctgggc ggcctgggct gcggcctgaa gaacaggagc     420
agcgagggcc ccagcagccc cagcggcaag ctgatgagcc caagctgta cgtgtgggcc      480 aaggacaggc ccgagatctg ggagggcgag ccccccctgcc tgcccccag ggacagcctg     540 aaccagagcc tgagccagga cctgaccatg gccccggca gcaccctgtg gctgagctgc     600
ggcgtgcccc ccgacagcgt gagcaggggc cccctgagct ggaccacgt gcaccccaag     660 ggccccaaga gcctgctgag cctggagctg aaggacgaca ggcccgccag ggagatgatc     720
gtggacgaga ccgcctgct gctgcccagg gccaccgccc aggacgccgg caagtggtac     780
tgcagcaggg gcaacgtgac caccagctac cacctggaga tcaccgccag gcccgtgaag     840
gcccacagcg acctgaggac cggcggctgg aagggaggag gtgggtctgg aggtggagga     900
tctggtggag gtgggtctgg aggaggtgga tcccaggtgc agctggtgga gtctggggga     960
ggcttggtgc aggctggggg gtctctgaga ctctcctgtg cagcctcagg aagcatcttc    1020
gctattaatg aaatcaatct tatggggtgg taccgccagg ctccagggaa gcagcgcgag    1080
ttggtcgcag cttgtgctag tgatggcaac acatactatg cggactccgt gaagggccga    1140
ttcaccatct ccagagacaa cgccgagaaa acggtgtatc tgcagatgaa caacctgaaa    1200
cctgacgaca cagccgtcta ttactgtgat gcgaattcga gggggaatta ttattcgggc    1260
caggggaccc tggtcaccgt ctcctcaact agtggcccgg gaggccaagg cgcagaacaa    1320
aaactcatct cagaagagga tctgggcgca caccatcacc accatcatgg cgcatct       1377
```

<210> SEQ ID NO 107
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
```

-continued

| | |
|---|---|
| ttcttaaaac tcagcctggg gctgccaggc ctgggaatcc acatgaggcc cctggccatc | 240 |
| tggcttttca tcttcaacgt ctctcaacag atgggggct tctacctgtg ccagccgggg | 300 |
| ccccctctg agaaggcctg gcagcctggc tggacagtca atgtggaggg cagcggggag | 360 |
| ctgttccggt ggaatgtttc ggacctaggt ggcctgggt gtggcctgaa gaacaggtcc | 420 |
| tcagagggcc ccagctcccc ttccgggaag ctcatgagcc caagctgta tgtgtgggcc | 480 |
| aaagaccgcc ctgagatctg ggagggagag cctccgtgtc tcccaccgag ggacagcctg | 540 |
| aaccagagcc tcagccagga cctcaccatg gccctggct ccacactctg gctgtcctgt | 600 |
| ggggtacccc ctgactctgt gtccaggggc cccctctcct ggacccatgt gcaccccaag | 660 |
| gggcctaagt cattgctgag cctagagctg aaggacgatc gcccggccag agatatgtgg | 720 |
| gtaatggaga cgggtctgtt gttgccccgg ccacagctc aagacgctgg aaagtattat | 780 |
| tgtcaccgtg gcaacctgac catgtcattc cacctggaga tcactgctcg gccaggagga | 840 |
| ggtgggtctg gaggtggagg atctggtgga ggtgggtctg gaggaggtgg gtctgacatg | 900 |
| gcccaggtgc agctgcagga gagcggcccc ggcctggtga gcccagcga gaccctgagc | 960 |
| ctgacctgcg tggtgagcgg cggcagcatc agcagcagca actggtggag ctgggtgagg | 1020 |
| cagccccccg gcaagggcct ggagtggatc ggcgagatct accacagcgg cagccccgac | 1080 |
| tacaaccca gcctgaagag cagggtgacc atcagcgtgg acaagagcag gaaccagttc | 1140 |
| agcctgaagc tgagcagcgt gaccgccgcc gacaccgccg tgtactactg cgccaaggtg | 1200 |
| agcaccggcg gcttcttcga ctactggggc cagggcaccc tggtgaccgt gagcagcggc | 1260 |
| ggcggcggca gcggcggcgg cggcagcggc ggcggcggca gcgagatcga gctgacccag | 1320 |
| agccccagca gcctgagcgc cagcgtgggc gacagggtga ccatcacctg cagggccagc | 1380 |
| cagagcatca gcagctacct gaactggtac cagcagaagc ccggcaaggc ccccaagctg | 1440 |
| ctgatctacg ccgccagcag cctgcagagc ggcgtgccca gcaggttcag cggcagcggc | 1500 |
| agcggcaccg acttcaccct gaccatcagc agcctgcagc ccgaggactt cgccacctac | 1560 |
| tactgccagc agagctacag caccccccc accttcggcc ccggcaccaa ggtggagatc | 1620 |
| aagaggaccc accaccacca ccaccac | 1647 |

<210> SEQ ID NO 108
<211> LENGTH: 2085
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 108

| | |
|---|---|
| atggagtttg gctgagctg gttttcctc gttgctcttt ttagaggtgt ccagtgtgac | 60 |
| atggcccagg tgcagctgca ggagagcggc cccggcctgg tgaagcccag cgagaccctg | 120 |
| agcctgacct gcgtggtgag cggcggcagc atcagcagca gcaactggtg gagctgggtg | 180 |
| aggcagcccc ccggcaaggg cctggagtgg atcggcgaga tctaccacag cggcagcccc | 240 |
| gactacaacc ccagcctgaa gagcagggtg accatcagcg tggacaagag caggaaccag | 300 |
| ttcagcctga gctgagcag cgtgaccgcc gccgacaccg ccgtgtacta ctgcgccaag | 360 |
| gtgagcaccg gcggcttctt cgactactgg ggccagggca ccctggtgac cgtgagcagc | 420 |
| ggcggcggcg gcagcggcgg cggcggcagc ggcggcggcg gcagcgagat cgagctgacc | 480 |
| cagagcccca gcagcctgag cgccagcgtg ggcgacaggg tgaccatcac ctgcagggcc | 540 |

| | |
|---|---|
| agccagagca tcagcagcta cctgaactgg taccagcaga agcccggcaa ggcccccaag | 600 |
| ctgctgatct acgccgccag cagcctgcag agcggcgtgc ccagcaggtt cagcggcagc | 660 |
| ggcagcggca ccgacttcac cctgaccatc agcagcctgc agcccgagga cttcgccacc | 720 |
| tactactgcc agcagagcta cagcaccccc cccaccttcg gccccggcac caaggtggag | 780 |
| atcaagagga ccggcggcgg aggatctggc ggaggtggaa gcggaggcgg aggaagcggt | 840 |
| ggcggcggat ctcaggtgca gctgcaggag tctgggggag gcttggtgca ggctgggggg | 900 |
| tcccttagac tctcctgtgt agcctctgga agcatcagaa gtatcaatgt catgggctgg | 960 |
| taccgccagg ctccagggaa gcagcgcgag ttggtcgcag cttgtgctag tgatggcaac | 1020 |
| acatactatg cggactccgt gaagggccga ttcaccatct ccagagacaa cgccgagaaa | 1080 |
| acggtgtatc tgcagatgaa caacctgaaa cctgacgaca cagccgtcta ttactgtgat | 1140 |
| gcgaattcga gggggaatta ttattcgggc caggggaccc aggtcaccgt tcctcaact | 1200 |
| agtggcccgg gaggccaagg tgcaggagga ggggggtctg ggggtggagg atctggtgga | 1260 |
| ggtgggtctg gaggaggtgg atcccccgag gaacctctag tggtgaaggt ggaagaggga | 1320 |
| gataccgctg ccctgtggtg cctcaagggg acctcagatg gccccactca gcagctgacc | 1380 |
| tggtctcggg agtccccgct taaacccttc ttaaaataca gctgggggt gccaggcctg | 1440 |
| ggagtgcacg tgaggcccga cgccatcagc gtggttatcc ggaacgtctc tcaacagatg | 1500 |
| gggggcttct acctgtgcca gccggggccc ccctctgaga aggcctggca gcctggctgg | 1560 |
| acagtcaatg tggagggcag cggggagctg ttccggtgga atgtttcgga cctaggtggc | 1620 |
| ctgggctgtg gcctgaagaa caggtcctca gagggcccca gctcccttc cgggaagctc | 1680 |
| atgagcccca gctgtatgt gtgggccaaa gaccgccctg agatctggga gggagagcct | 1740 |
| ccgtgtctcc caccgaggga cagcctgaac cagagcctca gccgggacct caccgttgcc | 1800 |
| cctggctcca cactctggct gtcctgtggg gtaccccctg actctgtgtc caggggcccc | 1860 |
| ctctcctgga cccatgtgca ccccaagggg cctaagtcat tgctgagcct agagctgaag | 1920 |
| gacgatcgcc cggccagaga tatgtgggta atgggcacga gcctgatgtt gccccgggcc | 1980 |
| acagctcaag acgctggaaa gtggtattgt caccgtggca acctgaccat gtcattccac | 2040 |
| ctggagatca ctgctcggcc atctagacat catcaccatc accat | 2085 |

<210> SEQ ID NO 109
<211> LENGTH: 3333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

| | |
|---|---|
| atgaggcttc tggtgcttct ttggggttgc ttgctgttgc ccggttacga agcagacatc | 60 |
| cagatgacac agactacatc ctccctgtct gcctctctgg agacagagt caccatcagt | 120 |
| tgcagggcaa gtcaggacat tagtaaatat ttaaattggt atcagcagaa accagatgga | 180 |
| actgttaaac tcctgatcta ccatacatca agattacact caggagtccc atcaaggttc | 240 |
| agtggcagtg gtctggaac agattattct ctcaccatta gcaacctgga gcaagaagat | 300 |
| attgccactt acttttgcca acaaggtaat acgcttccgt acacgttcgg aggggggact | 360 |
| aagttggaaa taacaggagg cggcgggtct ggaggtggag gatctggtgg tggcgggtct | 420 |
| ggaggcggcg gtctgaggt gaaactgcag gagtcaggac ctggcctggt ggcgcccta | 480 |

```
cagagcctgt ccgtcacatg cactgtctca ggggtctcat tacccgacta tggtgtaagc    540
tggattcgcc agcctccacg aaagggtctg gagtggctgg gagtaatatg gggtagtgaa    600
accacatact acaactcagc tctcaaatcc agactgacca tcatcaagga caactccaag    660
agccaagttt tcttaaaaat gaacagtctg caaactgatg acacagccat ttactactgt    720
gccaaacatt attactacgg tggtagctat gctatggact actggggtca aggaacctca    780
gtcaccgtct cctcagacta caaagacgat gacgacaaga ttgaagttat gtatcctcct    840
ccttacctag acaatgagaa gagcaatgga accattatcc atgtgaaagg aaacaccttt    900
tgtccaagtc ccctatttcc cggaccttct aagcccttt gggtgctggt ggtggttggt    960
ggagtcctgg cttgctatag cttgctagta acagtggcct ttattatttt ctgggtccgc   1020
agtaagagga gcaggctcct gcacagtgac tacatgaaca tgactccccg ccgcccggg   1080 cccacccgca agcattacca gccctatgcc ccaccacgcg acttcgcagc ctatcgctcc   1140
aaacggggca gaaagaaact cctgtatata ttcaaacaac catttatgag accagtacaa   1200
actactcaag aggaagatgg ctgtagctgc cgatttccag aagaagaaga aggaggatgt   1260
gaactgagag tgaagttcag caggagcgca gacgcccccg cgtaccagca gggccagaac   1320
cagctctata cgagctcaa tctaggacga agagaggagt acgatgtttt ggacaagaga   1380
cgtggccggg accctgagat ggggggaaag ccgcagagaa ggaagaaccc tcaggaaggc   1440
ctgtacaatg aactgcagaa agataagatg cggaggcct acagtgagat tgggatgaaa   1500
ggcgagcgcc ggaggggcaa ggggcacgat ggcctttacc agggtctcag tacagccacc   1560
aaggacacct acgacgccct tcacatgcaa gccctgcccc ctcgccgcgc gaaacgcagc   1620
ggcagcggcg cgaccaactt tagcctgctg aaacaggcgg gcgatgtgga agaaaacccg   1680
ggcccgatgc cacctcctcg cctcctcttc ttcctcctct tcctcacccc catggaagtc   1740
aggcccgagg aacctctagt ggtgaaggtg aagagggag ataacgctgt gctgcagtgc   1800
ctcaagggga cctcagatgg ccccactcag cagctgacct ggtctcggga gtccccgctt   1860
aaacccttct taaaactcag cctggggctg ccaggcctgg aatccacat gaggcccctg   1920 gccatctggc ttttcatctt caacgtctct caacagatgg ggggcttcta cctgtgccag   1980
ccggggcccc cctctgagaa ggcctggcag cctggctgga cagtcaatgt ggagggcagc   2040
ggggagctgt tccggtggaa tgtttcggac ctaggtggcc tgggctgtgg cctgaagaac   2100
aggtcctcag agggccccag ctcccttcc gggaagctca tgagcccaa gctgtatgtg   2160 tgggccaaag accgccctga gatctgggag ggagagcctc cgtgtctccc accgagggac   2220
agcctgaacc agagcctcag ccaggacctc accatggccc ctggctccac actctggctg   2280
tcctgtgggg tacccctga ctctgtgtcc cgcggccccc tctcctggac ccatgtgcac   2340
cccaaggggc ctaagtcatt gctgagccta gagctgaagg acgatcgccc ggccagagat   2400
atgtgggtaa tggagacggg tctgttgttg ccccgggcca cagctcaaga cgctggaaag   2460
tattattgtc accgtggcaa cctgaccatg tcattccacc tggagatcac tgctcggcct   2520
ggcggcggcg ggtctggagg tggaggatct ggtggtggcg ggtctggtgg cggcgggtct   2580
gacatggccc aggtgcagct gcaggagagc ggccccggcc tggtgaagcc agcgagacc   2640 ctgagcctga cctgcgtggt gagcggcggc agcatcagca gcaactg gtggagctgg   2700 gtgaggcagc cccccggcaa gggcctggag tggatcggcg agatctacca cagcggcagc   2760
cccgactaca accccagcct gaagagcagg gtgaccatca gcgtggacaa gagcaggaac   2820
cagttcagcc tgaagctgag cagcgtgacc gccgccgaca ccgccgtgta ctactgcgcc   2880
```

```
aaggtgagca ccggcggctt cttcgactac tggggccagg gcaccctggt gaccgtgagc    2940
agcggcggcg gcggcagcgg cggcggcggc agcggcggcg gcggcagcga gatcgagctg    3000
acccagagcc ccagcagcct gagcgccagc gtgggcgaca gggtgaccat cacctgcagg    3060
gccagccaga gcatcagcag ctacctgaac tggtaccagc agaagcccgg caaggccccc    3120
aagctgctga tctacgccgc cagcagcctg cagagcggcg tgcccagcag gttcagcggc    3180
agcggcagcg gcaccgactt cacccTGacc atcagcagcc tgcagcccga ggacttcgcc    3240
acctactact gccagcagag ctacagcacc ccccccacct tcggcccgg caccaaggtg     3300 gagatcaaga ggacccacca ccaccaccac cac                                 3333
```

<210> SEQ ID NO 110
<211> LENGTH: 3345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
atgaggcttc tggtgcttct ttggggttgc ttgctgttgc ccggttacga agcagacatc      60
cagatgacac agactacatc ctccctgtct gcctctctgg agacagagt caccatcagt      120 tgcagggcaa gtcaggacat tagtaaatat ttaaattggt atcagcagaa accagatgga     180
actgttaaac tcctgatcta ccatacatca agattacact caggagtccc atcaaggttc     240
agtggcagtg gtctggaac agattattct ctcaccatta gcaacctgga gcaagaagat      300
attgccactt acttttgcca acaaggtaat acgcttccgt acacgttcgg aggggggact     360
aagttggaaa taacaggagg cggcgggtct ggaggtggag gatctggtgg tggcgggtct     420
ggaggcggcg gtctgaggt gaaactgcag gagtcaggac ctggcctggt ggcgccctca      480
cagagcctgt ccgtcacatg cactgtctca ggggtctcat acccgactac tggtgtaagc     540
tggattcgcc agcctccacg aaagggtctg gagtggctgg gagtaatatg gggtagtgaa     600
accacatact caactcagc tctcaaatcc agactgacca tcatcaagga caactccaag      660
agccaagttt tcttaaaaat gaacagtctg caaactgatg acacagccat ttactactgt     720
gccaaacatt attactacgg tggtagctat gctatggact actggggtca aggaaccTca    780
gtcaccgtct cctcagacta caaagacgat gacgacaaga ttgaagttat gtatcctcct    840
ccttacctag acaatgagaa gagcaatgga accattatcc atgtgaaagg aaacaccctt    900
tgtccaagtc ccctatttcc cggaccttct aagccctttt gggtgctggt ggtggttggt    960
ggagtcctgg cttgctatag cttgctagta acagtggcct ttattatttt ctgggtccgc    1020
agtaagagga gcaggctcct gcacagtgac tacatgaaca tgactccccg ccgcccggg     1080 cccacccgca gcattaccag ccctatgcc ccaccgcgc acttcgcagc ctatcgctcc      1140 aaacgggca gaaagaaact cctgtatata ttcaaacaac catttatgag accagtacaa    1200
actactcaag aggaagatgg ctgtagctgc cgatttccag aagaagaaga aggaggatgt    1260
gaactgagag tgaagttcag caggagcgca gacgcccccg cgtaccagca gggccagaac    1320
cagctctata acgagctcaa tctaggacga agagaggagt acgatgtttt ggacaagaga   1380
cgtggccggg accctgagat ggggggaaag ccgcagagaa ggaagaaccc tcaggaaggc   1440
ctgtacaatg aactgcagaa agataagatg gcggaggcct acagtgagat tgggatgaaa    1500
ggcgagcgcc ggaggggcaa ggggcacgat ggcctttacc agggtctcag tacagccacc   1560
```

```
aaggacacct acgacgccct tcacatgcaa gccctgcccc ctcgccgcgc gaaacgcagc    1620
ggcagcggcg cgaccaactt tagcctgctg aaacaggcgg gcgatgtgga agaaaacccg    1680
ggcccgatgc cacctcctcg cctcctcttc ttcctcctct tcctcacccc catggaagtc    1740
aggcccgagg aacctctagt ggtgaaggtg aagagggga taacgctgt gctgcagtgc     1800 ctcaagggga cctcagatgg ccccactcag cagctgacct ggtctcggga gtccccgctt    1860
aaacccttct taaaactcag cctggggctg ccaggcctgg gaatccacat gaggcccctg    1920
gccatctggc ttttcatctt caacgtctct caacagatgg ggggcttcta cctgtgccag    1980
ccggggcccc cctctgagaa ggcctggcag cctggctgga cagtcaatgt ggagggcagc    2040
ggggagctgt tccggtggaa tgtttcggac ctaggtggcc tgggctgtgg cctgaagaac    2100
aggtcctcag agggccccag ctccccttcc gggaagctca tgagcccaa gctgtatgtg     2160 tgggccaaag accgccctga gatctgggag ggagagcctc cgtgtctccc accgagggac    2220
agcctgaacc agagcctcag ccaggacctc accatggccc ctggctccac actctggctg    2280
tcctgtgggg taccccctga ctctgtgtcc cgcggccccc tctcctggac ccatgtgcac    2340
cccaaggggc ctaagtcatt gctgagccta gagctgaagg acgatcgccc ggccagagat    2400
atgtgggtaa tggagacggg tctgttgttg ccccgggcca cagctcaaga cgctggaaag    2460
tattattgtc accgtggcaa cctgaccatg tcattccacc tggagatcac tgctcggcct    2520
ggcggcggcg ggtctggagg tggaggatct ggtggtggcg ggtctggtgg cggcgggtct    2580
gaggtgcagc tggtggagtc tggtggtggt cttgttcaac ctggtggttc tcttcgtctt    2640
tcttgtgctg cttctggttt taatattaaa gatacttata ttcattgggt tcgtcaagct    2700
cctggtaaag gtcttgaatg ggttgctcgt atttatccta ctaatggtta tactcgttat    2760
gctgattctg ttaaaggtcg ttttactatt tctgctgata cttctaaaaa tactgcttat    2820
cttcaaatga actctcttcg tgctgaagat actgctgttt attattgttc tcgttggggt    2880
ggtgatggtt tttatgctat ggattattgg ggtcaaggta ctcttgtcac cgtctcctca    2940
gctagcaccg ggggcggcgg gtctggaggt ggaggatctg gtggcggcgg gtctgacatc    3000
cagatgaccc agtctcctcc ttctctttct gcttctgttg gtgatcgtgt tactattact    3060
tgtcgtgctt ctcaagatgt taatactgct gttgcttggt atcaacaaaa acctggtaaa    3120
gctcctaaac ttcttatta ttctgcttct tttctttatt ctggtgttcc ttctcgtttt     3180
tctggttctc gttctggtac tgattttact cttactattt cttctcttca acctgaagat    3240
tttgctactt attattgtca acaacattat actactcctc ctacttttgg tcaaggtacc    3300
aaggtggaga tcaaacgtac gtctagacat catcaccatc accat                    3345
```

<210> SEQ ID NO 111
<211> LENGTH: 3342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
atgaggcttc tggtgcttct ttggggttgc ttgctgttgc ccggttacga agcagacatc     60
cagatgacac agactacatc ctccctgtct gcctctctgg agacagagt caccatcagt    120 tgcagggcaa gtcaggacat tagtaaatat ttaaattggt atcagcagaa accagatgga    180
actgttaaac tcctgatcta ccatacatca agattacact caggagtccc atcaaggttc    240
```

```
agtggcagtg ggtctggaac agattattct ctcaccatta gcaacctgga gcaagaagat    300
attgccactt acttttgcca acaaggtaat acgcttccgt acacgttcgg aggggggact    360
aagttggaaa taacaggagg cggcgggtct ggaggtggag gatctggtgg tggcgggtct    420
ggaggcggcg ggtctgaggt gaaactgcag gagtcaggac ctggcctggt ggcgccctca    480
cagagcctgt ccgtcacatg cactgtctca ggggtctcat tacccgacta tggtgtaagc    540
tggattcgcc agcctccacg aaagggtctg gagtggctgg gagtaatatg gggtagtgaa    600
accacatact acaactcagc tctcaaatcc agactgacca tcatcaagga caactccaag    660
agccaagttt tcttaaaaat gaacagtctg caaactgatg acacagccat ttactactgt    720
gccaaacatt attactacgg tggtagctat gctatggact actggggtca aggaacctca    780
gtcaccgtct cctcagacta caaagacgat gacgacaaga ttgaagttat gtatcctcct    840
ccttacctag acaatgagaa gagcaatgga accattatcc atgtgaaagg gaaacacctt    900
tgtccaagtc ccctatttcc cggaccttct aagccctttt gggtgctggt ggtggttggt    960
ggagtcctgg cttgctatag cttgctagta acagtggcct ttattatttt ctgggtccgc   1020
agtaagagga gcaggctcct gcacagtgac tacatgaaca tgactccccg ccgccccggg   1080
cccacccgca agcattacca gccctatgcc ccaccacgcg acttcgcagc ctatcgctcc   1140
aaacggggca gaaagaaact cctgtatata ttcaaacaac catttatgag accagtacaa   1200
actactcaag aggaagatgg ctgtagctgc cgatttccag aagaagaaga aggaggatgt   1260
gaactgagag tgaagttcag caggagcgca gacgcccccg cgtaccagca gggccagaac   1320
cagctctata acgagctcaa tctaggacga agagaggagt acgatgtttt ggacaagaga   1380
cgtggccggg accctgagat ggggggaaag ccgcagagaa ggaagaaccc tcaggaaggc   1440
ctgtacaatg aactgcagaa agataagatg gcggaggcct acagtgagat tgggatgaaa   1500
ggcgagcgcc ggaggggcaa ggggcacgat ggcctttacc agggtctcag tacagccacc   1560
aaggacacct acgacgccct tcacatgcaa gccctgcccc ctcgccgcgc gaaacgcagc   1620
ggcagcggcg cgaccaactt tagcctgctg aaacaggcgg gcgatgtgga agaaaacccg   1680
ggccccgatg cacctcctcg cctcctcttc ttcctcctct tcctcacccc catggaagtc   1740
aggcccgagg aacctctagt ggtgaaggtg gaagagggag ataacgctgt gctgcagtgc   1800
ctcaaggga cctcagatgg ccccactcag cagctgacct ggtctcggga gtccccgctt   1860
aaacccttct taaaactcag cctgggggctg ccaggcctgg gaatccacat gaggcccctg   1920
gccatctggc ttttcatctt caacgtctct caacagatgg ggggcttcta cctgtgccag   1980
ccggggcccc cctctgagaa ggcctggcag cctggctgga cagtcaatgt ggagggcagc   2040
ggggagctgt tccggtggaa tgtttcggac ctaggtggcc tgggctgtgg cctgaagaac   2100
aggtcctcag agggcccag ctccccttcc gggaagctca tgagcccaa gctgtatgtg   2160
tgggccaaag accgccctga gatctgggag ggagagcctc cgtgtctccc accgagggac   2220
agcctgaacc agagcctcag ccaggacctc accatggccc ctggctccac actctggctg   2280
tcctgtgggg taccccctga ctctgtgtcc cgcggccccc tctcctggac ccatgtgcac   2340
cccaaggggc ctaagtcatt gctgagccta gagctgaagg acgatcgccc ggccagagat   2400
atgtgggtaa tggagacggg tctgttgttg ccccggggcca cagctcaaga cgctggaaag   2460
tattattgtc accgtggcaa cctgaccatg tcattccacc tggagatcac tgctcggcca   2520
ggaggaggtg ggtctggagg tggaggatct ggtggaggtg ggtctggagg aggtgggtct   2580
```

| | | |
|---|---|---|
| gaggtgcagc tgctggagag cggcggcggc caggtgcagc ccggcggcag cctgaggctg | 2640 | |
| agctgcgccg ccagcggctt caccttcagc agctacccca tgagctgggt gaggcaggcc | 2700 | |
| cccggcaagg gcctggagtg ggtgagcgcc atcggcggca gcggcggcag cctgccctac | 2760 | |
| gccgacagcg tgaagggcag gttcaccatc agcagggaca cagcaagaa cccctgtac | 2820 | |
| ctgcagatga acagcctgag ggccgaggac accgccgtgt actactgcgc caggtactgg | 2880 | |
| cccatggaca tctggggcca gggcaccctg gtgaccgtga gcagcgccag caccggcggc | 2940 | |
| ggcggcagcg gcggcggcgg cagcggcggc ggcggcagcg gcggcggcgg cagcgagatc | 3000 | |
| gtgctgaccc agagccccgg caccctgagc ctgagcccg gcgagagggc caccctgagc | 3060 | |
| tgcagggcca gccagagcgt gagcagcagc tacctggcct ggtaccagca gaagcccggc | 3120 | |
| caggcccca ggctgctgat gtacgacgcc agcatcaggg ccaccggcat ccccgacagg | 3180 | |
| ttcagcggca gcggcagcgg caccgacttc accctgacca tcagcaggct ggagcccgag | 3240 | |
| gacttcgccg tgtactactg ccagcagtac cagagctggc ccctgacctt cggccagggc | 3300 | |
| accaaggtgg agaccaagag gacccatcat caccatcacc at | 3342 | |

<210> SEQ ID NO 112
<211> LENGTH: 3318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

| | | |
|---|---|---|
| atgaggcttc tggtgcttct ttggggttgc ttgctgttgc ccggttacga agcagacatc | 60 | |
| cagatgacac agactacatc ctccctgtct gcctctctgg agacagagt caccatcagt | 120 | |
| tgcagggcaa gtcaggacat tagtaaatat ttaaattggt atcagcagaa accagatgga | 180 | |
| actgttaaac tcctgatcta ccatacatca agattacact caggagtccc atcaaggttc | 240 | |
| agtggcagtg ggtctggaac agattattct ctcaccatta gcaacctgga gcaagaagat | 300 | |
| attgccactt actttgcca acaaggtaat acgcttccgt acacgttcgg agggggact | 360 | |
| aagttggaaa taacaggagg cggcgggtct ggaggtggag gatctggtgg tggcgggtct | 420 | |
| ggaggcggcg gtctgaggt gaaactgcag gagtcaggac ctggcctggt ggcgccctca | 480 | |
| cagagcctgt ccgtcacatg cactgtctca ggggtctcat acccgactac tggtgtaagc | 540 | |
| tggattcgcc agcctccacg aaagggtctg agtggctgg agtaatatg gggtagtgaa | 600 | |
| accacatact caactcagc tctcaaatcc agactgacca tcatcaagga caactccaag | 660 | |
| agccaagttt tcttaaaaat gaacagtctg caaactgatg acacagccat ttactactgt | 720 | |
| gccaaacatt attactacgg tggtagctat gctatggact actggggtca aggaaccctca | 780 | |
| gtcaccgtct cctcagacta caaagacgat gacgacaaga ttgaagttat gtatcctcct | 840 | |
| ccttacctag acaatgagaa gagcaatgga accattatcc atgtgaaagg aaacaccctt | 900 | |
| tgtccaagtc ccctattcc cggaccttct aagccctttt gggtgctggt ggtggttggt | 960 | |
| ggagtcctgg cttgctatag cttgctagta acagtggcct ttattattt ctgggtccgc | 1020 | |
| agtaagagga gcaggctcct gcacagtgac tacatgaaca tgactccccg ccgcccgggg | 1080 | |
| cccacccgca agcattacca gcctatgcc ccaccacgcg acttcgcagc ctatcgctcc | 1140 | |
| aaacggggca gaagaaaact cctgtatata ttcaaacaac catttatgag accagtacaa | 1200 | |
| actactcaag aggaagatgg ctgtagctgc cgatttccag aagaagaaga aggaggatgt | 1260 | |

| | |
|---|---|
| gaactgagag tgaagttcag caggagcgca gacgccccg cgtaccagca gggccagaac | 1320 |
| cagctctata acgagctcaa tctaggacga agagaggagt acgatgtttt ggacaagaga | 1380 |
| cgtggccggg accctgagat ggggggaaag ccgcagagaa ggaagaaccc tcaggaaggc | 1440 |
| ctgtacaatg aactgcagaa agataagatg cggaggcct acagtgagat tgggatgaaa | 1500 |
| ggcgagcgcc ggaggggcaa ggggcacgat ggcctttacc agggtctcag tacagccacc | 1560 |
| aaggacacct acgacgccct tcacatgcag gccctgcccc ctcgcgaggg aaggggcagc | 1620 |
| ctgctgacct gcggcgacgt ggaggagaac cccggcccta tgccacctcc tcgcctcctc | 1680 |
| ttcttcctcc tcttcctcac ccccatgaa gtcaggcccg aggaacctct agtggtgaag | 1740 |
| gtggaagagg gagataacgc tgtgctgcag tgcctcaagg ggacctcaga tggccccact | 1800 |
| cagcagctga cctggtctcg ggagtccccg cttaaaccct tcttaaaact cagcctgggg | 1860 |
| ctgccaggcc tgggaatcca catgaggccc ctggccatct ggcttttcat cttcaacgtc | 1920 |
| tctcaacaga tggggggctt ctacctgtgc cagccggggc cccctctga aaggcctgg | 1980 |
| cagcctggct ggacagtcaa tgtggaggc agcggggagc tgttccggtg gaatgtttcg | 2040 |
| gacctaggtg gcctgggctg tggcctgaag aacaggtcct cagagggccc cagctcccct | 2100 |
| tccgggaagc tcatgagccc caagctgtat gtgtgggcca agaccgccc tgagatctgg | 2160 |
| gagggagagc ctccgtgtct cccaccgagg acagcctga accagagcct cagccaggac | 2220 |
| ctcaccatgg cccctggctc cacactctgg ctgtcctgtg gggtaccccc tgactctgtg | 2280 |
| tccaggggcc ccctctcctg gacccatgtg caccccaagg ggcctaagtc attgctgagc | 2340 |
| ctagagctga aggacgatcg cccggccaga gatatgtggg taatgagac gggtctgttg | 2400 |
| ttgccccggg ccacagctca agacgctgga agtattatt gtcaccgtgg caacctgacc | 2460 |
| atgtcattcc acctggagat cactgctcgg ccaggaggag gtgggtctgg aggtggagga | 2520 |
| tctggtggag gtgggtctgg aggaggtggg tctatggccc aggtcaaact acaggagtca | 2580 |
| ggggctgagc tggtgaagcc tgggcctca gtgaagatgt cctgcaaggc ttctggctac | 2640 |
| acatttacca gttacaatat gcactgggta aagcagacac ctggacaggg cctggaatgg | 2700 |
| attggagcta tttatccagg aaatggtgat acttcctaca atcagaagtt caaaggcaag | 2760 |
| gccacattga ctgcagacaa atcctccagc acagcctaca tgcagctcag cagcctgaca | 2820 |
| tctgaggact ctgcggacta ttactgtgca agatctaatt attacggtag tagctactgg | 2880 |
| ttcttcgatg tctggggcca agggaccacg gtcaccgtct cctcaggtgg aggcggttca | 2940 |
| ggcggaggtg gctctggcgg tggcggatcg gacatcgagc tcactcagtc tccaacaatc | 3000 |
| ctgtctgcat ctccagggga gaaggtcaca atgacttgca gggccagctc aagtgtaaat | 3060 |
| tacatggact ggtaccagaa gaagccagga tcctccccca aaccctggat ttatgccaca | 3120 |
| tccaacctgg cttctggagt ccctgctcgc ttcagtggca gtgggtctgg gacctcttac | 3180 |
| tctctcacaa tcagcagagt ggaggctgaa gatgctgcca cttattactg ccagcagtgg | 3240 |
| agttttaatc cacccacgtt cggaggggg acaaagttgg aaataaaacg ggccgccgct | 3300 |
| catcatcacc atcaccat | 3318 |

<210> SEQ ID NO 113

<400> SEQUENCE: 113

000

<210> SEQ ID NO 114

```
<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125
```

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

-continued

<210> SEQ ID NO 148
<400> SEQUENCE: 148
000

<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159

<400> SEQUENCE: 159

000

<210> SEQ ID NO 160
<400> SEQUENCE: 160

000

<210> SEQ ID NO 161
<400> SEQUENCE: 161

000

<210> SEQ ID NO 162
<400> SEQUENCE: 162

000

<210> SEQ ID NO 163
<400> SEQUENCE: 163

000

<210> SEQ ID NO 164
<400> SEQUENCE: 164

000

<210> SEQ ID NO 165
<400> SEQUENCE: 165

000

<210> SEQ ID NO 166
<400> SEQUENCE: 166

000

<210> SEQ ID NO 167
<400> SEQUENCE: 167

000

<210> SEQ ID NO 168
<400> SEQUENCE: 168

000

<210> SEQ ID NO 169
<400> SEQUENCE: 169

000

<210> SEQ ID NO 170
<400> SEQUENCE: 170

000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179
<400> SEQUENCE: 179
000

<210> SEQ ID NO 180
<400> SEQUENCE: 180
000

<210> SEQ ID NO 181
<400> SEQUENCE: 181
000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

```
<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 204
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 205
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 206
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 207
<211> LENGTH: 148
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 207

Gln Val Gln Leu Gln Gln Phe Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His
    130                 135                 140

His Gly Ala Ser
145

<210> SEQ ID NO 208
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gln Val Gln Leu Gln Ala Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His
    130                 135                 140

His Gly Ala Ser
145

<210> SEQ ID NO 209
```

<211> LENGTH: 148
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

```
Gln Val Gln Leu Gln Glu Phe Gly Gly Gly Leu Val Gln Ala Gly Gly
1               5                   10                  15
Ser Leu Arg Leu Ser Cys Ala Ala Ser Gly Ser Ile Phe Ala Ile Asn
            20                  25                  30
Glu Ile Asn Leu Met Gly Trp Tyr Arg Gln Ala Pro Gly Lys Gln Arg
        35                  40                  45
Glu Leu Val Ala Ala Cys Ala Ser Asp Gly Asn Thr Tyr Tyr Ala Asp
    50                  55                  60
Ser Val Lys Gly Arg Phe Thr Ile Ser Arg Asp Asn Ala Glu Lys Thr
65                  70                  75                  80
Val Tyr Leu Gln Met Asn Asn Leu Lys Pro Asp Asp Thr Ala Val Tyr
                85                  90                  95
Tyr Cys Asp Ala Asn Ser Arg Gly Asn Tyr Tyr Ser Gly Gln Gly Thr
            100                 105                 110
Leu Val Thr Val Ser Ser Thr Ser Gly Pro Gly Gly Gln Gly Ala Glu
        115                 120                 125
Gln Lys Leu Ile Ser Glu Glu Asp Leu Gly Ala His His His His
    130                 135                 140
His Gly Ala Ser
145
```

<210> SEQ ID NO 210
<211> LENGTH: 148
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

```
Gln Val Gln Leu Gln Glu Phe Gly Gly Gly Leu Val Gln Ala Gly Gly
1               5                   10                  15
Ser Leu Arg Leu Ser Cys Ala Ala Ser Gly Ser Ile Phe Ala Ile Asn
            20                  25                  30
Glu Ile Asn Leu Met Gly Trp Tyr Arg Gln Ala Pro Gly Lys Gln Arg
        35                  40                  45
Glu Leu Val Ala Ala Cys Ala Ser Asp Gly Asn Thr Tyr Tyr Ala Asp
    50                  55                  60
Ser Val Lys Gly Arg Phe Thr Ile Ser Arg Asp Asn Ala Glu Lys Thr
65                  70                  75                  80
Val Tyr Leu Gln Met Asn Asn Leu Lys Pro Asp Asp Thr Ala Val Tyr
                85                  90                  95
Tyr Cys Asp Ala Asn Ser Arg Gly Asn Tyr Tyr Ser Gly Gln Gly Thr
            100                 105                 110
Gln Val Thr Val Ser Ser Thr Ser Gly Pro Gly Gly Gln Gly Ala Glu
        115                 120                 125
Gln Lys Leu Ile Ser Glu Glu Asp Leu Gly Ala His His His His
    130                 135                 140
His Gly Ala Ser
145
```

<210> SEQ ID NO 211
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 212
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Gln Gln Ser Gly Gly Gly Leu Ala Gln Thr Gly Gly
1               5                   10                  15

Ser Leu Ile Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

```
His Gly Ala Ser
145

<210> SEQ ID NO 213
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145

<210> SEQ ID NO 214
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Gln Glu Ser Gly Gly Gly Leu Val Gln Val Gly Glu
1               5                   10                  15

Ser Leu Arg Leu Ser Cys Val Val Ser Gly Asp Thr Arg Ser Ile Asn
            20                  25                  30

Leu Met Gly Trp Tyr Arg Gln Ala Pro Gly Lys Gln Arg Glu Leu Val
        35                  40                  45

Ala Ala Cys Ala Ser Asp Gly Asn Thr Tyr Tyr Ala Asp Ser Val Lys
    50                  55                  60

Gly Arg Phe Thr Ile Ser Arg Asp Asn Ala Glu Lys Thr Val Tyr Leu
65                  70                  75                  80

Gln Met Asn Asn Leu Lys Pro Asp Asp Thr Ala Val Tyr Tyr Cys Asp
                85                  90                  95

Ala Asn Ser Arg Gly Asn Tyr Tyr Ser Gly Gln Gly Thr Leu Val Thr
            100                 105                 110

Val Ser Ser Thr Ser Gly Pro Gly Gly Gln Gly Ala Glu Gln Lys Leu
        115                 120                 125
```

Ile Ser Glu Glu Asp Leu Gly Ala His His His His His Gly Ala
    130                 135                 140

Ser
145

<210> SEQ ID NO 215
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Ile Arg Ser Ile Asn
            20                  25                  30

Val Met Gly Trp Tyr Arg Gln Ala Pro Gly Lys Gln Arg Glu Leu Val
        35                  40                  45

Ala Ala Cys Ala Ser Asp Gly Asn Thr Tyr Tyr Ala Asp Ser Val Lys
    50                  55                  60

Gly Arg Phe Thr Ile Ser Arg Asp Asn Ala Glu Lys Thr Val Tyr Leu
65                  70                  75                  80

Gln Met Asn Asn Leu Lys Pro Asp Asp Thr Ala Val Tyr Tyr Cys Asp
                85                  90                  95

Ala Asn Ser Arg Gly Asn Tyr Tyr Ser Gly Gln Gly Thr Gln Val Thr
            100                 105                 110

Val Ser Ser Thr Ser Gly Pro Gly Gly Gln Gly Ala Glu Gln Lys Leu
        115                 120                 125

Ile Ser Glu Glu Asp Leu Gly Ala His His His His His Gly Ala
    130                 135                 140

Ser
145

<210> SEQ ID NO 216
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Thr Trp Val Arg Gln Ala Pro Gly Lys Gly Leu Glu Trp Val
        35                  40                  45

Ser Asp Ile Asn Ser Gly Gly Gly Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Glu Leu Arg Gly Ser Asp Tyr Tyr Arg Gly Pro Ile Arg Glu
            100                 105                 110

```
Tyr Ala Tyr Trp Gly Gln Gly Thr Leu Val Thr Val Ser Ser Thr Ser
        115                 120                 125

Gly Pro Gly Gly Gln Gly Ala Glu Gln Lys Leu Ile Ser Glu Glu Asp
    130                 135                 140

Leu Gly Ala His His His His His Gly Ala Ser
145                 150                 155

<210> SEQ ID NO 217
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Gln Glu Ser Gly Gly Ala Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Gly Thr Thr Asp Tyr Ala Thr Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Tyr Arg Leu Arg Ile Thr Val Val Val Thr Pro Asp Glu
            100                 105                 110

Tyr His Tyr Trp Gly Gln Gly Thr Leu Val Thr Val Ser Ser Thr Ser
        115                 120                 125

Gly Pro Gly Gly Gln Gly Ala Glu Gln Lys Leu Ile Ser Glu Glu Asp
    130                 135                 140

Leu Gly Ala His His His His His Gly Ala Ser
145                 150                 155

<210> SEQ ID NO 218
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Met Ile Trp Val Arg Gln Gly Pro Gly Lys Gly Leu Glu Trp Val
        35                  40                  45

Ser Ser Ile Ser Trp Asn Gly Gly Thr Tyr Tyr Ala Glu Ser Ile
    50                  55                  60

Val Gly Arg Phe Thr Val Ser Arg Asp Asn Ala Lys Lys Met Val Tyr
65                  70                  75                  80

Leu Gln Met Asn Gly Leu Lys Ser Glu Asp Thr Ala Met Tyr Tyr Cys
                85                  90                  95
```

Val Lys Leu Val Asp Ser Gly Trp Tyr Ser Ala Tyr Asp Tyr Trp Gly
            100                 105                 110

Gln Gly Thr Gln Val Thr Val Ser Ser Thr Ser Gly Pro Gly Gly Gln
        115                 120                 125

Gly Ala Glu Gln Lys Leu Ile Ser Glu Glu Asp Leu Gly Ala His His
    130                 135                 140

His His His His Gly Ala Ser
145                 150

<210> SEQ ID NO 219
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Gln Glu Ser Gly Gly Leu Val Gln Ala Gly Gly
1               5                   10                  15

Ser Leu Arg Leu Ser Cys Val Val Ser Gly Ala Thr Ser Asn Val Asn
            20                  25                  30

Ala Met Gly Trp Tyr Arg Gln Ala Pro Gly Lys Glu Arg Glu Leu Val
        35                  40                  45

Ala Ala Ile Ser Ser Gly Gly Ser Thr Ser Tyr Arg Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Gln Asp Trp Ala Thr Glu Gly Tyr Glu Tyr Asp Tyr Trp Gly Gln
            100                 105                 110

Gly Thr Leu Val Thr Val Ser Ser Thr Ser Gly Pro Gly Gly Gln Gly
        115                 120                 125

Ala Glu Gln Lys Leu Ile Ser Glu Glu Asp Leu Gly Ala His His His
    130                 135                 140

His His His Gly Ala Ser
145                 150

<210> SEQ ID NO 220
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Gln Ala Phe Gly Gly Gly Leu Val Gln Pro Gly Gly
1               5                   10                  15

Ser Leu Arg Leu Ser Cys Val Val Ser Gly Thr Met Phe Ser Gly Lys
            20                  25                  30

Asp Val Asn Trp Leu Arg Gln Ala Pro Gly Lys His Val Glu Val Val
        35                  40                  45

Ala Thr Val Ser Ser Asp Gly Gly Thr Asp Tyr Ala Asp Phe Val Lys
    50                  55                  60

Gly Arg Phe Thr Ile Ser Arg Asp Asp Ala Lys Asn Thr Val Asn Leu
65                  70                  75                  80

```
Gln Met Asn Ser Leu Glu Pro Glu Asp Thr Ala Asn Tyr Met Cys His
                85                  90                  95

Phe Leu Trp Gly Arg His Tyr Trp Gly Gln Gly Thr Gln Val Thr Val
            100                 105                 110

Ser Ser Thr Ser Gly Pro Gly Gly Gln Gly Ala Glu Gln Lys Leu Ile
        115                 120                 125

Ser Glu Glu Asp Leu Gly Ala His His His His His Gly Ala Ser
    130                 135                 140

<210> SEQ ID NO 221
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Ala Phe Gly Gly Gly Met Val Gln Ala Gly Glu
1               5                   10                  15

Ser Leu Arg Leu Ser Cys Val Ala Ser Gly Asn Asp Ile Ser Gly Ser
            20                  25                  30

Ala Met Ala Trp Tyr Arg Ala His Leu Gly Ala Glu Arg Glu Leu Val
        35                  40                  45

Ala Val Asp Ala Pro Arg Glu Arg Pro Phe Tyr Ile Asp Pro Val Ile
    50                  55                  60

Gly Arg Phe Thr Ile Ser Arg Asp Asp Arg Asn Lys Met Leu Tyr Leu
65                  70                  75                  80

Gln Met Asn Asp Leu Arg Pro Asp Asp Thr Ala Thr Tyr Trp Cys Gly
                85                  90                  95

Pro Ser Leu Arg Thr Phe His Gly Arg Glu Trp Tyr Arg Pro Pro Trp
            100                 105                 110

Phe Thr Ser Trp Gly Gln Gly Thr Gln Val Thr Val Ser Ser Thr Ser
        115                 120                 125

Gly Pro Gly Gly Gln Gly Ala Glu Gln Lys Leu Ile Ser Glu Glu Asp
    130                 135                 140

Leu Gly Ala His His His His His Gly Ala Ser
145                 150                 155

<210> SEQ ID NO 222
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Arg Arg Glu Met Val
        35                  40                  45

Ala Val Val Ser Arg Phe Gly Glu Thr Thr Tyr Thr Gly Ser Val Lys
    50                  55                  60

Gly Arg Phe Thr Ile Ser Arg Ile Asn Arg Asn Asn Thr Val Phe Leu
65                  70                  75                  80
```

Gln Met Asn Arg Leu Lys Pro Glu Asp Thr Ala Val Tyr Tyr Cys Asn
                85                  90                  95

Ala Arg Ile Arg Gly Asn Tyr Gly Ser Arg Ile Asp Tyr Trp Gly Gln
            100                 105                 110

Gly Thr Gln Val Thr Val Ser Ser Thr Ser Gly Pro Gly Gly Gln Gly
        115                 120                 125

Ala Glu Gln Lys Leu Ile Ser Glu Glu Asp Leu Gly Ala His His His
    130                 135                 140

His His His Gly Ala Ser
145                 150

<210> SEQ ID NO 223
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Gln Glu Phe Gly Gly Gly Leu Val Gln Leu Gly Gly
1               5                   10                  15

Ser Ala Arg Leu Ser Cys Val Val Ser Gly Asn Met Leu Asp Leu Asn
            20                  25                  30

Thr Met Ala Trp Tyr Arg Gln Gly Glu Leu Val Ala Ala Leu Gly Ile
        35                  40                  45

Ser Thr Tyr Tyr Ala Glu Ser Val Lys Gly Arg Phe Thr Ile Ser Arg
    50                  55                  60

Asp Asn Ala Lys Asn Thr Leu Tyr Leu Gln Met Asn Ser Leu Lys Ser
65                  70                  75                  80

Glu Asp Thr Ala Val Tyr Tyr Cys Ala Arg Asp Tyr Asn Phe Glu Ser
                85                  90                  95

Trp Gly Gln Gly Thr Leu Val Thr Val Ser Ser Thr Ser Gly Pro Gly
            100                 105                 110

Gly Gln Gly Ala Glu Gln Lys Leu Ile Ser Glu Glu Asp Leu Gly Ala
        115                 120                 125

His His His His His His Gly Ala Ser
    130                 135

<210> SEQ ID NO 224
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Ala Val Gln Leu Gln Glu Ser Gly Gly Gly Leu Val Gln Ala Gly Gly
1               5                   10                  15

Ser Leu Arg Leu Ser Cys Ala Ala Ser Gly Ser Asp Arg Ser Ile Asn
            20                  25                  30

Val Met Asn Trp Tyr Arg Gln Ala Pro Gly Lys Gln Arg Glu Leu Val
        35                  40                  45

Ala Ala Ile Thr Ser Gly Gly Thr Thr Asn Tyr Ala Gln Ser Val Lys
    50                  55                  60

Gly Arg Val Thr Ile Ser Arg Asp Ser Ala Lys Asn Thr Val Tyr Leu
65                  70                  75                  80

Gln Met Asn Ser Leu Lys Pro Glu Asp Thr Ala Val Tyr Phe Cys Lys
                85                  90                  95

Ala Asp Thr Arg Trp Gly Gly Met Tyr Trp Gly Pro Gly Thr Gln Val
            100                 105                 110

Thr Val Ser Ser Thr Ser Gly Pro Gly Gly Gln Gly Ala Glu Gln Lys
        115                 120                 125

Leu Ile Ser Glu Glu Asp Leu Gly Ala His His His His His His Gly
    130                 135                 140

Ala Ser
145

<210> SEQ ID NO 225
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Gln Gln Ser Gly Gly Gly Leu Val Gln Ala Gly Gly
1               5                   10                  15

Ser Leu Thr Leu Ser Cys Ala Ala Thr Gly Arg Thr Ile Asp Asn Gly
            20                  25                  30

Ala Met Ala Trp Phe Arg Gln Ala Pro Gly Lys Gln Arg Glu Leu Val
        35                  40                  45

Ala Ala Ile Asn Trp Ser Gly Gly Ala Thr Phe Tyr Thr Asp Ser Val
    50                  55                  60

Lys Tyr Arg Phe Thr Ile Ser Arg Asp Asn Val Arg His Thr Leu Asp
65                  70                  75                  80

Leu Gln Met Thr Ser Leu Lys Pro Glu Asp Thr Thr Ile Tyr Phe Cys
                85                  90                  95

Ala Ser Arg Arg Gly Val Asp Leu Arg Arg Asn Ser Tyr Glu Tyr Asp
            100                 105                 110

Tyr Trp Gly Arg Gly Thr Leu Val Thr Val Ser Ser Thr Ser Gly Pro
        115                 120                 125

Gly Gly Gln Gly Ala Glu Gln Lys Leu Ile Ser Glu Glu Asp Leu Gly
    130                 135                 140

Ala His His His His His His Gly Ala Ser
145                 150

<210> SEQ ID NO 226
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Thr Ser Gly Pro Gly Gly Gln Gly Ala Glu Gln Lys Leu Ile Ser Glu
1               5                   10                  15

Glu Asp Leu Gly Ala His His His His His Gly Ala Ser
            20                  25                  30

<210> SEQ ID NO 227
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 227

Thr Ser Gly Pro Gly Gly Gln Gly Ala
1               5

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Glu Gln Lys Leu Ile Ser Glu Glu Asp Leu
1               5                   10

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 229

His His His His His His
1               5

<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Cys Ala Ala Ser Gly Ser Ile Phe Ala Ile Asn Glu Ile
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Cys Val Val Ser Gly Asp Thr Arg Ser Ile
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Val Ala Ser Gly Ser Ile Arg Ser Ile
1               5                   10
```

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Ala Ala Ser Gly Phe Thr Phe Asn Ser Tyr Ala
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Ala Ala Ser Gly Leu Thr Phe Ser Asn Tyr Ala
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Ala Ala Ser Gly Phe Ala Phe Asp Asp Tyr Ala
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Val Val Ser Gly Ala Thr Ser Asn Val Asn Ala
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Cys Val Val Ser Gly Thr Met Phe Ser Gly Lys Asp
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 238

Cys Val Ala Ser Gly Asn Asp Ile Ser Gly Ser Ala
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Cys Ala Ala Ser Gly Ser Ile Phe Ser Ile Asn Ala
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Cys Val Val Ser Gly Asn Met Leu Asp Leu Asn Thr
1               5                   10

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Ser Asp Arg Ser Ile Asn Val
1               5

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Arg Thr Ile Asp Asn Gly Ala
1               5

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Val Ala Ala Cys Ala Ser Asp Gly Asn Thr Tyr
1               5                   10

<210> SEQ ID NO 244
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 244

Trp Val Ser Asp Ile Asn Ser Gly Gly Gly Ser Thr Asn
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Ile Asn Trp Ser Gly Gly Thr Thr Asp
1               5                   10

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Trp Val Ser Ser Ile Ser Trp Asn Gly Gly Gly Thr Tyr
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Leu Val Ala Ala Ile Ser Ser Gly Gly Ser Thr Ser
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Ala Thr Val Ser Ser Asp Gly Gly Thr Asp
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Val Ala Val Asp Ala Pro Arg Glu Arg Pro Phe
1               5                   10
```

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Val Ala Val Val Ser Arg Phe Gly Glu Thr Thr
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Leu Val Ala Ala Leu Gly Ile Ser Thr Tyr
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Thr Ser Gly Gly Thr Thr
1               5

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ile Asn Trp Ser Gly Gly Ala Thr
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Ala Asn Ser Arg Gly Asn Tyr Tyr
1               5

<210> SEQ ID NO 255
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Thr Glu Leu Arg Gly Ser Asp Tyr Tyr Arg Gly Pro Ile Arg Glu
1               5                   10                  15

Tyr Ala Tyr

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Ala Ser Tyr Arg Leu Arg Ile Thr Val Val Thr Pro Asp Glu
1               5                   10                  15

Tyr His Tyr

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Val Lys Leu Val Asp Ser Gly Trp Tyr Ser Ala Tyr Asp Tyr
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Ala Gln Asp Trp Ala Thr Glu Gly Tyr Glu Tyr Asp Tyr
1               5                   10

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

His Phe Leu Trp Gly Arg His Tyr
1               5

<210> SEQ ID NO 260
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Pro Ser Leu Arg Thr Phe His Gly Arg Glu Trp Tyr Arg Pro Pro
1               5                   10                  15

```
Trp Phe Thr Ser
            20

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asn Ala Arg Ile Arg Gly Asn Tyr Gly Ser Arg Ile Asp Tyr
1               5                   10

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Arg Asp Tyr Asn Phe Glu Ser
1               5

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Ala Asp Thr Arg Trp Gly Gly Met Tyr
1               5                   10

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Ser Arg Arg Gly Val Asp Leu Arg Arg Asn Ser Tyr Glu Tyr Asp
1               5                   10                  15

Tyr

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Ser Ile Phe Ala Ile Asn Glu Ile Asn Leu
1               5                   10

<210> SEQ ID NO 266
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Asp Thr Arg Ser Ile Asn Leu
1               5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Ser Ile Arg Ser Ile Asn Val
1               5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Asn Ser Tyr Ala
1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Leu Thr Phe Ser Asn Tyr Ala
1               5

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Phe Ala Phe Asp Asp Tyr Ala
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Ala Thr Ser Asn Val Asn Ala
```

```
1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Thr Met Phe Ser Gly Lys Asp
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Asn Asp Ile Ser Gly Ser Ala
1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gly Ser Ile Phe Ser Ile Asn Ala
1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gly Asn Met Leu Asp Leu Asn Thr
1               5

<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Ala Ser Asp Gly Asn Thr
1               5

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 277

Ile Asn Ser Gly Gly Gly Ser Thr
1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ile Asn Trp Ser Gly Gly Thr Thr
1               5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ile Ser Trp Asn Gly Gly Gly Thr
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ile Ser Ser Gly Gly Ser Thr
1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Val Ser Ser Asp Gly Gly Thr
1               5

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Val Asp Ala Pro Arg Glu Arg Pro
1               5

<210> SEQ ID NO 283

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Val Ser Arg Phe Gly Glu Thr
1               5

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Leu Gly Ile Ser Thr
1               5
```

UNITED STATES PATENT AND TRADEMARK OFFICE
CERTIFICATE OF CORRECTION

| | | |
|---|---|---|
| PATENT NO. | : 11,891,426 B2 | Page 1 of 1 |
| APPLICATION NO. | : 16/954002 | |
| DATED | : February 6, 2024 | |
| INVENTOR(S) | : Roy Lobb et al. | |

It is certified that error appears in the above-identified patent and that said Letters Patent is hereby corrected as shown below:

On the Title Page

Item (71), Line 2, please replace Regents of The University of Minnesota, Minneapolis, MN (US) with Regents of the University of Minnesota, Minneapolis, MN (US).

Item (73), Line 2, please replace Regents of The University of Minnesota, Minneapolis, MN (US) with Regents of the University of Minnesota, Minneapolis, MN (US).

Signed and Sealed this
Twenty-second Day of July, 2025

Coke Morgan Stewart
*Acting Director of the United States Patent and Trademark Office*